(12) United States Patent
Kubo et al.

(10) Patent No.: US 11,230,726 B2
(45) Date of Patent: Jan. 25, 2022

(54) GENE INVOLVED IN SYNTHESIS OF CYCLIC PEPTIDE COMPOUND, METHOD FOR PRODUCING CYCLIC PEPTIDE COMPOUND USING THE SAME, AND TRANSFORMANT COMPRISING THE SAME

(71) Applicants: NATIONAL INSTITUTE OF ADVANCED INDUSTRIAL SCIENCE AND TECHNOLOGY, Tokyo (JP); TOHOKU UNIVERSITY, Sendai (JP); KUMIAI CHEMICAL INDUSTRY CO., LTD., Tokyo (JP)

(72) Inventors: Takashi Kubo, Sapporo (JP); Masayuki Machida, Sapporo (JP); Maiko Umemura, Sapporo (JP); Keietsu Abe, Sendai (JP); Akira Yoshimi, Sendai (JP); Tomonori Fujioka, Tokyo (JP); Shigenari Yamaguchi, Tokyo (JP); Kiyoshi Kawai, Tokyo (JP)

(73) Assignees: NATIONAL INSTITUTE OF ADVANCED INDUSTRIAL SCIENCE AND TECHNOLOGY, Tokyo (JP); TOHOKU UNIVERSITY, Sendai (JP); KUMIAI CHEMICAL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 16/476,000

(22) PCT Filed: Dec. 27, 2017

(86) PCT No.: PCT/JP2017/046858
§ 371 (c)(1),
(2) Date: Jul. 3, 2019

(87) PCT Pub. No.: WO2018/128140
PCT Pub. Date: Jul. 12, 2018

(65) Prior Publication Data
US 2019/0316164 A1    Oct. 17, 2019

(30) Foreign Application Priority Data
Jan. 5, 2017    (JP) .............................. JP2017-000770

(51) Int. Cl.
| C12N 1/16 | (2006.01) |
| C12N 1/20 | (2006.01) |
| C12P 21/04 | (2006.01) |
| C12P 21/02 | (2006.01) |
| C07K 7/64 | (2006.01) |
| C12N 15/80 | (2006.01) |
| A61K 38/10 | (2006.01) |

(52) U.S. Cl.
CPC .............. *C12P 21/02* (2013.01); *C07K 7/64* (2013.01); *C12N 15/80* (2013.01); *A61K 38/10* (2013.01)

(58) Field of Classification Search
CPC . A61K 38/10; C07K 7/64; C12N 1/16; C12N 1/20; C12P 21/02
USPC .............. 435/69.7, 468, 252.3, 252.7, 320.1; 536/23.2
See application file for complete search history.

(56) References Cited

FOREIGN PATENT DOCUMENTS

| JP | 8-504165 A | 5/1996 |
| JP | 9-157168 A | 6/1997 |
| WO | WO 93/12659 A1 | 7/1993 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Brakhage et al., "Fungal secondary metabolites—Strategies to activate silent gene clusters", Fungal Genetics and Biology, vol. 48, 2011, pp. 15-22 (8 pages).
Georgianna et al., "Beyond aflatoxin: four distinct expression patterns and functional roles associated with Aspergillus flavus secondary metabolism gene clusters", Molecular Plant Pathology, vol. 11, No. 2, 2010, pp. 213-226 (14 pages).
Machida et al., "Genome sequencing and analysis of Aspergillus oryzae", Nature, vol. 438, No. 22, Dec. 29, 2005, pp. 1157-1161 (5 pages).
Yamaguchi et al., "The identification of biosynthetic gene cluster for the antimicrobial cyclic peptide produced by Curvularia clavata". Annual Meeting of the Japan Society for Bioscience, Biotechnology, and Agrochemistry, 2017, 3 pages (with translation).
Yoshimi et al., "Heterologous production of the antifungal cyclic peptide, KK-1, in Aspergillus oryzae", Annual Meeting of the Japan Society of Bioscience, Biotechnology, and Agrochemistry, 2017, 4 pages (with translation).

* cited by examiner

*Primary Examiner* — Robert B Mondesi
*Assistant Examiner* — Mohammad Y Meah
(74) *Attorney, Agent, or Firm* — Birch, Stewart, Kolasch & Birch, LLP

(57) ABSTRACT

This invention is intended to identify a gene cluster involved in biosynthesis of a cyclic peptide compound produced by a filamentous fungus of the *Curvularia* species and to establish a system for synthesizing such cyclic peptide compound. The gene is composed of a first module to a tenth module and encodes a protein having activity of synthesizing a nonribosomal peptide constituting a basic peptide backbone of a cyclic peptide compound produced by a filamentous fungus of the *Curvularia* species.

9 Claims, 27 Drawing Sheets
Specification includes a Sequence Listing.

Fig. 4

| Gene ID | Annotation |
|---|---|
| TRAF01000135000015 | similar to ubiquinol-cytochrome-c reductase [Alternaria alternata] |
| TRAF01000135000014 | |
| TRAF01000135000013 | kinesin light chain 3 [Pyrenophora tritici-repentis Pt-1C-BFP] |
| TRAF01000135000012 | kinesin light chain 3 [Pyrenophora tritici-repentis Pt-1C-BFP] |
| TRAF01000135000011 | transposase [Aspergillus niger CBS 513.88] |
| TRAF01000135000010 | hypothetical protein BcDW1_6707 [Botryotinia fuckeliana BcDW1] |
| TRAF01000135000009 | similar to kinesin light chain [Botryotinia fuckeliana T4] |
| TRAF01000135000008 | hypothetical protein COCC4DRAFT_76928 [Bipolaris maydis ATCC 48331] |
| TRAF01000135000007 | related to HETEROKARYON incompatibility protein [Fusarium fujikuroi IMI 58289] |
| TRAF01000135000006 | Ankyrin repeat protein [Aspergillus fumigatus A1163] |
| TRAF01000135000005 | hypothetical protein COCSADRAFT_42061 [Bipolaris sorokiniana ND90Pr] |
| TRAF01000135000004 | kinesin, putative [Talaromyces marneffei ATCC 18224] |
| TRAF01000135000003 | |
| TRAF01000135000002 | O-methyltransferase, putative [Talaromyces marneffei ATCC 18224] |
| TRAF01000135000001_J3G | Nonribosomal peptide synthetase (NRPS) |
| TRAF01000068000002 | amidase [Mycosphaerella populorum SO2202] |
| TRAF01000068000003 | hypothetical protein MYCGRDRAFT_97764 [Zymoseptoria tritici IPO323] |
| TRAF01000068000004 | hypothetical protein ARB_03427 [Arthroderma benhamiae CBS 112371] |
| TRAF01000068000005 | putative transcriptional regulator protein [Neofusicoccum parvum UCRNP2] |
| TRAF01000068000006 | leptomycin B resistance protein pmd1 [Pyrenophora tritici-repentis Pt-1C-BFP] |
| TRAF01000068000007 | putative d-lactate dehydrogenase protein [Togninia minima UCRPA7] |
| TRAF01000068000008 | pyrroline-5-carboxylate reductase-like protein [Chaetomium thermophilum var. thermophilum DSM 1495] |
| TRAF01000068000009 | alpha/beta-Hydrolase [Glarea lozoyensis ATCC 20868] |
| TRAF01000068000010 | hypothetical protein COCSADRAFT_343231, partial [Bipolaris sorokiniana ND90Pr] |
| TRAF01000068000011 | GDP-mannose transporter [Trichophyton equinum CBS 127.97] |
| TRAF01000068000012 | hypothetical protein PTT_11656 [Pyrenophora teres f. teres 0-1] |
| TRAF01000068000013 | hypothetical protein SETTUDRAFT_24621 [Setosphaeria turcica Et28A] |
| TRAF01000068000014 | histone H3, putative [Perkinsus marinus ATCC 50983] |
| TRAF01000068000015 | SNF2-related protein [Macrophomina phaseolina MS6] |

Putative biosynthetic cluster (about 75 kb) — brackets rows TRAF01000135000002 through TRAF01000068000009

Fig. 24
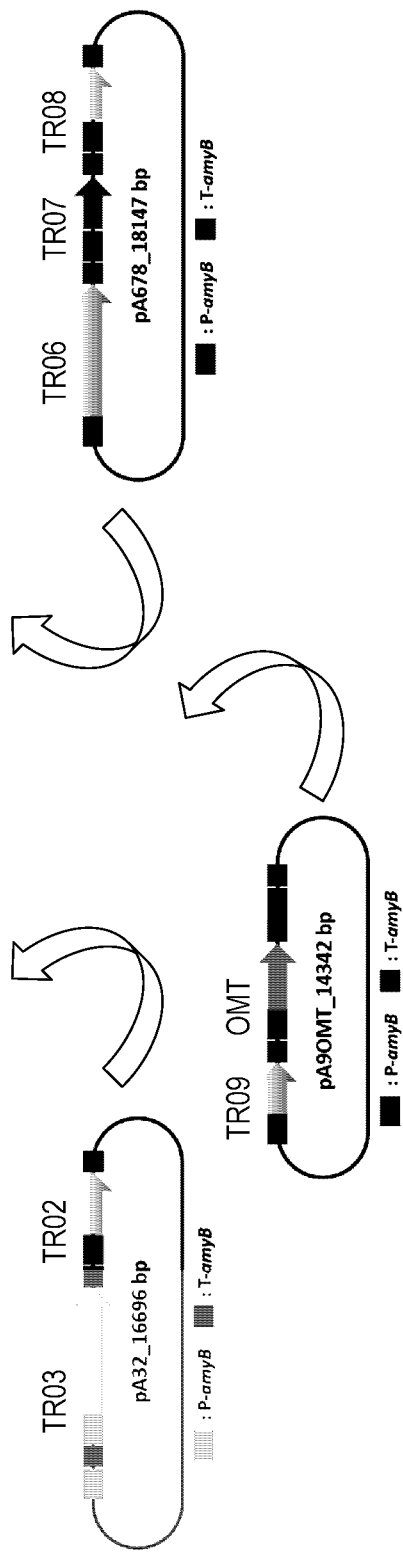

Fig. 26
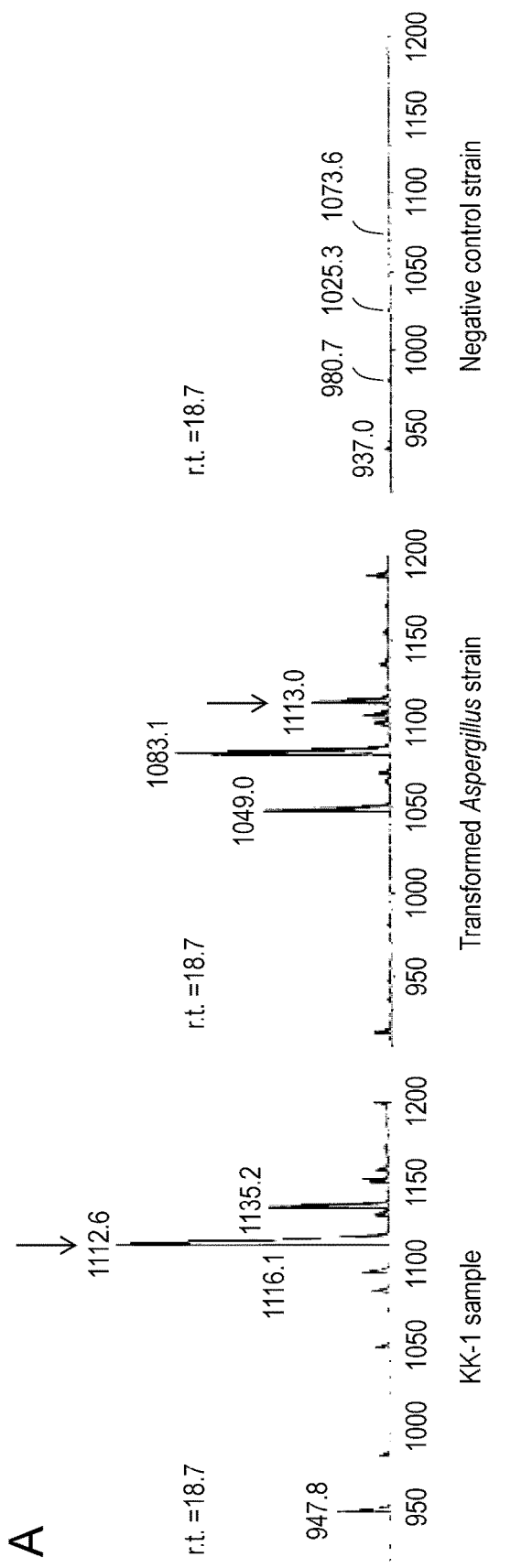
A
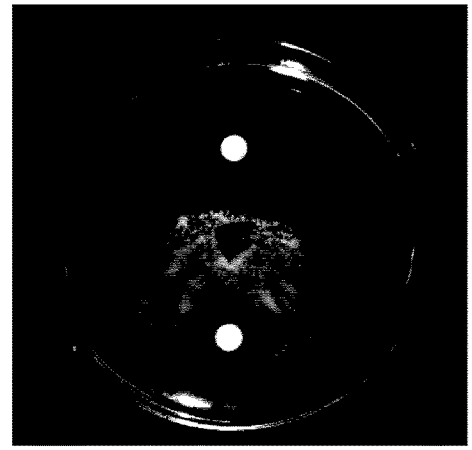
B

SEQUENCE LISTING

<160> NUMBER OF SEQ ID NOS: 151

<210> SEQ ID NO 1
<211> LENGTH: 393
<212> TYPE: PRT
<213> ORGANISM: Curvularia clavata

<400> SEQUENCE: 1

```
Leu Thr Phe Ala Glu Leu Asp Ser Phe Ser Cys Leu Ala Gln His
1               5                   10                  15

Ile Gln Ser Leu Glu Leu Gly Asp Ala Lys Ala Ile Pro Leu Cys Phe
        20                  25                  30

Glu Lys Ser Lys Trp Ala Ile Val Gly Met Leu Gly Val Leu Lys Ala
            35                  40                  45

Gly Arg Ala Phe Thr Leu Ile Asp Pro Ser Asn Pro Pro Ala Arg Ala
        50                  55                  60

Arg Gln Ile Cys Arg Gln Thr Ala Ala Thr Ile Ser Ile Ala Ser Pro
65                  70                  75                  80

Tyr Gln Cys Asp Met Met Arg Ala Leu Val Pro Asp Cys Ile Val Val
                85                  90                  95

Asp Asp Asp Phe Phe Lys Ser Leu Ala Phe Asp Thr Asp Gln Phe Gln
            100                 105                 110

Pro Thr Ala Thr Pro Gln Thr Leu Ala Tyr Ile Leu Phe Thr Ser Gly
        115                 120                 125

Ser Thr Gly Glu Pro Lys Gly Ser Met Met Glu His His Gly Phe Val
    130                 135                 140

Ser Cys Cys Leu Glu Phe Gly Ala Ala Leu Gly Ile Asn Ser Asn Thr
145                 150                 155                 160

Arg Ala Leu Gln Phe Ala Ser Tyr Ala Phe Gly Ala Cys Leu Leu Glu
                165                 170                 175

Ile Leu Thr Thr Leu Met His Gly Gly Thr Val Cys Ile Pro Ser Asp
            180                 185                 190

Asp Glu Arg Ile Asn Asp Ala Pro Gly Phe Ile Arg Arg Ala Asn Val
        195                 200                 205

Asn Trp Ala Ile Leu Thr Pro Ser Phe Ile Gly Ala Ile Gln Pro Thr
    210                 215                 220

Thr Val Pro Asn Leu Lys Thr Leu Val Leu Val Gly Glu Ala Met Pro
225                 230                 235                 240

Ser Asp Ile Arg Asp Val Trp Ala Ser His Val Gln Leu Lys Asn Ala
                245                 250                 255

Tyr Gly Gln Ser Glu Ser Ala Thr Ile Cys Ser Val Thr Glu Val Thr
            260                 265                 270

Pro Ala Thr Val Glu Ala His Asn Ile Gly His Ala Val Gly Ala Arg
        275                 280                 285

Phe Trp Ile Thr Asp Pro Asn Asn Pro Asn Lys Leu Ala Pro Ile Gly
    290                 295                 300

Cys Val Gly Glu Leu Leu Val Glu Ser Pro Gly Ile Ala Arg Gly Tyr
305                 310                 315                 320

Leu Ile Pro Leu Pro Ala Asp Ala Thr Pro Phe Ile Asp Thr Leu Pro
                325                 330                 335

Asp Trp Tyr Pro Arg Thr Gln Pro Leu Asp Asn Phe Lys Phe Tyr Arg
            340                 345                 350

Thr Gly Asp Leu Val Cys Tyr Arg Ser Asp Gly Thr Val Val Tyr Leu
        355                 360                 365
```

```
Gly Arg Arg Asp Ser Gln Ile Lys Ile Arg Gly Gln Arg Val Glu Ile
    370                 375                 380

Gly Glu Val Glu Thr Cys Leu Arg Gln
385                 390

<210> SEQ ID NO 2
<211> LENGTH: 69
<212> TYPE: PRT
<213> ORGANISM: Curvularia clavata

<400> SEQUENCE: 2

Ile Thr Leu Glu Arg Ile Trp Phe Gln Ser Leu Gly Leu Lys Pro Asn
1               5                   10                  15

Ser Thr Arg His Lys Ser Asn Phe Phe Asn Leu Gly Gly Asp Ser Ile
                20                  25                  30

Ala Ala Ile Arg Met Val Asn Met Ala Arg Ala Ala Gly Leu Leu Leu
            35                  40                  45

Ser Ile Ser Asp Ile Phe Gln Asn Pro Ser Leu Ala Gly Leu Ile Asn
        50                  55                  60

Val Met Gln Gln Ser
65

<210> SEQ ID NO 3
<211> LENGTH: 298
<212> TYPE: PRT
<213> ORGANISM: Curvularia clavata

<400> SEQUENCE: 3

Gly Pro Val Glu Gln Ser Phe Ala Gln Gly Arg Leu Trp Phe Leu Asp
1               5                   10                  15

Gln Leu Thr Thr Gly Ala Ser Trp Tyr Leu Met Pro Leu Ala Val Arg
                20                  25                  30

Ile His Gly Pro Leu Arg Val Gln Ala Leu Ser Ser Ala Leu His Ala
            35                  40                  45

Leu Glu Gln Arg His Glu Thr Leu Arg Thr Thr Phe Glu Gln Gln Asp
        50                  55                  60

Gly Met Gly Val Gln Ile Val His Pro Ser Ser Lys Arg Glu Leu Arg
65                  70                  75                  80

Val Ile Asp Val Ser Gly Lys Gln Asn Gly Gly Tyr Asp Gln Val Leu
                85                  90                  95

Lys Arg Glu Gln Thr Thr Pro Ile Asp Leu Ala Lys Glu Pro Gly Trp
            100                 105                 110

Arg Ala Ala Leu Leu Arg Val Gly Asp Glu His Ile Leu Ser Ile
        115                 120                 125

Val Ile His His Ile Ile Tyr Asp Gly Trp Ser Leu Gly Val Leu Arg
130                 135                 140

Glu Glu Leu Gly Asp Leu Tyr Ala Ala Ala Leu Arg Gly Pro Asp Pro
145                 150                 155                 160

Leu Ala His Met Ala Pro Leu Pro Ile Gln Tyr Arg Asp Phe Ser Val
                165                 170                 175

Trp Gln Lys Gln Pro Gln Gln Val Ala Gln His Gln Gln Leu Val
            180                 185                 190

Tyr Trp Thr Lys Gln Leu Glu Asp Ser Ala Pro Ala Glu Leu Leu Thr
        195                 200                 205

Asp Phe Pro Arg Pro Ala Glu Leu Ser Gly Arg Ala Gly Glu Val Arg
210                 215                 220
```

```
Phe Thr Ile Glu Gly Ser Val Phe Asp Ser Leu Leu Ala Phe Arg Arg
225                 230                 235                 240

Val His Gln Thr Thr Ser Phe Ala Val Leu Leu Ala Val Phe Arg Ala
                245                 250                 255

Ala His Tyr Arg Leu Thr Gly Thr Glu Asp Ala Thr Ile Gly Thr Pro
            260                 265                 270

Ile Ala Asn Arg Thr Arg Ala Glu Val Glu Lys Leu Ile Gly Phe Phe
        275                 280                 285

Val Asn Thr Gln Cys Met Arg Ile Ala Val
    290                 295
```

<210> SEQ ID NO 4
<211> LENGTH: 398
<212> TYPE: PRT
<213> ORGANISM: Curvularia clavata

<400> SEQUENCE: 4

```
Leu Thr Tyr Ala Gln Leu Asp Gln Glu Ser Asp Lys Ile Ala Val Trp
1               5                   10                  15

Leu Arg Lys Arg Asn Ile Pro Ala Glu Thr Leu Ile Ala Leu Leu Ala
            20                  25                  30

Pro Arg Ser Cys Asp Ser Val Ala Ala Phe Leu Gly Ile Leu Lys Ala
        35                  40                  45

Asn Leu Ala Tyr Leu Pro Leu Asp Val Asn Val Pro Ala Ala Arg Ile
    50                  55                  60

Glu Ala Ile Leu Ser Thr Val Ala Gly His Lys Leu Val Leu Leu Gly
65                  70                  75                  80

Arg Asp Val Pro Leu Leu Gly Thr Gln Leu Ala Asp Leu Glu Leu Val
                85                  90                  95

Arg Ile Gly Glu Ala Leu Arg Gly Ser Ser Gly Ser Val Ala Ala
            100                 105                 110

Asp Lys Ala Ile Arg Pro Thr Ala Thr Ser Leu Ala Tyr Val Ile Phe
        115                 120                 125

Thr Ser Gly Ser Thr Gly Gln Pro Lys Gly Ile Met Val Pro His Arg
130                 135                 140

Ser Leu Val Asn Val Ile Lys Gln Arg Pro Ala Tyr Gly Asn Val Ala
145                 150                 155                 160

His Met Thr Asn Leu Ala Phe Asp Pro Ser Leu Phe Glu Met Cys Thr
                165                 170                 175

Ala Leu Phe Asn Gly Asn Thr Leu Ile Cys Ile Asp Thr Leu Val Ala
            180                 185                 190

Leu Asp Ala Thr Gln Leu Pro Thr Ile Phe Lys Gln Glu Ala Ile Arg
        195                 200                 205

Val Ala Met Met Thr Pro Ala Leu Leu Thr Arg Leu Leu Ala Gln Ala
    210                 215                 220

Thr Asp Ala Leu His Glu Leu Glu Ala Leu Tyr Val Leu Gly Asp Arg
225                 230                 235                 240

Phe Pro Pro Lys Asp Ala Ala Arg Ala Ser Glu Leu Val Lys Thr Ala
                245                 250                 255

Val Tyr Asn Ala Tyr Gly Pro Ser Glu Asn Ser Ile Cys Thr Thr Leu
            260                 265                 270

Phe His Ala Ala Thr Gly Ala Met Cys Thr Asn Gly Val Pro Val Gly
        275                 280                 285

Arg Val Ile Asn Asn Ser Gly Val Tyr Val Met Asp Pro Lys Gln Ser
    290                 295                 300
```

Leu Val Ser Tyr Gly Val Met Gly Glu Leu Val Ala Gly Glu Gly
305                 310                 315                 320

Leu Ala Ile Gly Tyr Thr Lys Pro Glu Leu Asn Glu Gly Arg Phe Leu
            325                 330                 335

Thr Leu Thr Met Asp Gly Lys Pro Val Arg Ala Phe Arg Thr Gly Asp
            340                 345                 350

Arg Val Arg Tyr Arg Pro Thr Asp Gly Gln Leu Glu Phe Phe Gly Arg
        355                 360                 365

Met Asp Phe Gln Ile Lys Ile Arg Gly His Arg Val Glu Leu Ala Glu
        370                 375                 380

Val Glu Arg Val Leu Asn Arg His Pro Ala Ile Lys Asp Ala
385                 390                 395

<210> SEQ ID NO 5
<211> LENGTH: 69
<212> TYPE: PRT
<213> ORGANISM: Curvularia clavata

<400> SEQUENCE: 5

Ile Glu Ala Val Leu Cys Glu Glu Phe Ala His Ile Leu Gly Val Glu
1               5                   10                  15

Ile Gly Val Thr Asp Asn Phe Phe Asp Leu Gly Gly His Ser Leu Met
            20                  25                  30

Ala Thr Thr Leu Ala Ala Arg Leu Ala Arg Arg Leu Asn Ala Ser Ile
        35                  40                  45

Ser Val Lys Asp Val Phe Asp Gln Pro Ile Val Ala Asn Leu Ala Ala
    50                  55                  60

Thr Ile Lys Arg Gly
65

<210> SEQ ID NO 6
<211> LENGTH: 297
<212> TYPE: PRT
<213> ORGANISM: Curvularia clavata

<400> SEQUENCE: 6

Gly Pro Val Glu Gln Ser Phe Ala Gln Gly Arg Leu Trp Phe Leu Asp
1               5                   10                  15

Gln Leu Asn Leu Gly Ala Ala Trp Tyr His Met Pro Leu Ala Val Arg
            20                  25                  30

Leu Arg Gly Pro Leu His Leu Glu Ala Leu Thr Ala Ala Leu His Ala
        35                  40                  45

Leu Glu Glu Arg His Glu Thr Leu Arg Thr Val Phe Glu Glu Gln Asp
    50                  55                  60

Gly Val Gly Met Gln Ile Val Arg Pro Ser Ser Lys Thr Pro Leu Arg
65                  70                  75                  80

Ile Ile Asp Val Ser Thr Lys Glu Arg Gly Tyr Ala Glu Leu Leu Lys
                85                  90                  95

Gln Glu Gln Thr Thr Pro Phe Asp Leu Ala Thr Glu Leu Gly Trp Arg
            100                 105                 110

Val Ala Leu Leu Arg Gln Gly Lys Asp His Ile Leu Ser Ile Val
        115                 120                 125

Ile His His Ile Ile Ser Asp Gly Trp Ser Leu Asp Ile Leu Cys Glu
    130                 135                 140

Glu Leu Gly Gln Phe Tyr Ala Ala Val Leu Arg Gly Gln Asp Pro Leu
145                 150                 155                 160

Ala Gln Ile Ser Pro Leu Pro Ile Gln Tyr Arg Asp Phe Ser Leu Trp
            165                 170                 175

Gln Lys Gln Pro Glu Gln Val Ala Glu His His Arg Gln Leu Glu Tyr
        180                 185                 190

Trp Thr Thr Gln Leu Glu Gly Ser Val Pro Ala Glu Leu Leu Thr Asp
            195                 200                 205

Leu Pro Arg Pro Thr Ile Gln Ser Gly Lys Ala Gly Val Ile Pro Ile
        210                 215                 220

Thr Val Asn Gly Pro Val Tyr Glu Arg Leu Arg Ala Phe Ser Arg Ala
225                 230                 235                 240

His Gln Thr Thr Ala Phe Ala Val Leu Leu Ala Ala Phe Arg Ala Thr
            245                 250                 255

His Tyr Arg Leu Ser Gly Val Ala Asp Ala Thr Ile Gly Thr Pro Ile
            260                 265                 270

Ala Asn Arg Asn Arg Pro Glu Leu Glu Asn Met Ile Gly Phe Phe Val
        275                 280                 285

Asn Ala Gln Cys Met Arg Ile Thr Val
    290                 295

<210> SEQ ID NO 7
<211> LENGTH: 402
<212> TYPE: PRT
<213> ORGANISM: Curvularia clavata

<400> SEQUENCE: 7

Leu Thr Tyr Ala Gln Leu Asn Glu Gln Ser Asp Lys Val Ala Ala Trp
1               5                   10                  15

Leu His Gln Cys Asn Leu Pro Thr Glu Thr Leu Val Ala Val Leu Ala
            20                  25                  30

Pro Arg Ser Cys Gln Thr Val Ala Phe Leu Gly Ile Leu Lys Ala
        35                  40                  45

Asn Leu Ala Tyr Leu Pro Leu Asp Val Asn Val Pro Ala Ala Arg Ile
    50                  55                  60

Glu Ala Ile Leu Ser Glu Val Ser Gly His Ile Leu Val Leu Leu Gly
65                  70                  75                  80

Ser His Val Ser Ala Pro Lys Ile Glu Leu Ala Asp Val Glu Phe Val
            85                  90                  95

Lys Ile Asp Asn Thr Val Glu His Asn Leu Pro Gly Arg Ile Gly Ser
            100                 105                 110

Ala Pro Ser Ala Thr Ser Leu Ala Tyr Val Ile Phe Thr Ser Gly Ser
        115                 120                 125

Thr Gly Lys Pro Lys Gly Val Lys Val Glu His Arg Gly Ile Val Arg
    130                 135                 140

Leu Val Lys Glu Ser Asn Val Val Ala Lys Met Pro Gln Ala Ala Arg
145                 150                 155                 160

Ile Ala His Leu Ser Asn Ile Ala Phe Asp Ala Ala Thr Trp Glu Leu
            165                 170                 175

Tyr Ala Ala Leu Leu Asn Gly Gly Thr Leu Val Cys Ile Asn Tyr Leu
            180                 185                 190

Thr Thr Leu Asp Ser Lys Ala Leu Glu Ala Val Phe Glu Gln Glu Lys
        195                 200                 205

Ile Gln Ala Ala Met Leu Pro Pro Ala Leu Leu Lys Gln Tyr Leu Val
    210                 215                 220

Asn Ile Pro Ala Ala Ile Gly Ala Leu Glu Val Val Leu Val Ala Gly

```
                225                 230                 235                 240
Asp Arg Phe Asp Arg Arg Asp Ala Ala Thr Gln Ala Leu Val Gly
                    245                 250                 255

Ala Gly Val Tyr Asn Ala Tyr Gly Pro Thr Glu Asn Thr Thr Leu Ser
                    260                 265                 270

Thr Ile Tyr Asn Val Val Gln Gly Asp Ala Asn Val Asn Gly Val Pro
                275                 280                 285

Ile Gly Arg Pro Val Ser Asn Ser Gly Ala Tyr Ile Met Asn Met Asn
            290                 295                 300

Gln Glu Leu Val Pro Ile Gly Val Ile Gly Glu Leu Val Val Gly
305                 310                 315                 320

Asp Gly Val Ala Arg Gly Tyr Thr Asp Pro Ala Leu Asp Val Asn Arg
                    325                 330                 335

Phe Val Asn Val Thr Ile Glu Gly Gln Thr Met Arg Ala Tyr Arg Thr
                340                 345                 350

Gly Asp Arg Ala Arg Tyr Arg Pro Lys Asp Ala Gln Ile Glu Phe Phe
                355                 360                 365

Gly Arg Met Asp Gln Gln Ile Lys Ile Arg Gly His Arg Ile Glu Pro
            370                 375                 380

Ala Glu Val Glu His Ala Leu Leu Asn Asn Asp Leu Leu Gln Asp Ala
385                 390                 395                 400

Ala Val
```

<210> SEQ ID NO 8
<211> LENGTH: 224
<212> TYPE: PRT
<213> ORGANISM: Curvularia clavata

<400> SEQUENCE: 8

```
Asp Gly Ser Ala Ile Asp Lys Ala Glu Met Gln Glu Trp Leu Asp Asp
1               5                   10                  15

Thr Met Gln Thr Ile Leu Asp Gly Arg Pro Ala Gly Arg Val Leu Glu
                20                  25                  30

Ile Gly Thr Gly Thr Gly Met Ile Leu Phe Asn Leu Gly Glu Gly Leu
            35                  40                  45

Gln Ser Tyr Val Gly Leu Glu Pro Ser Thr Ser Ala Ala Ala Phe Val
        50                  55                  60

Asn Arg Arg Ile Gln Thr Leu Pro Ala Phe Ala Gly Lys Ala Glu Val
65                  70                  75                  80

His Val Gly Thr Ala Thr Asp Ile Ser Gln Leu Gln Asp Leu Arg Pro
                85                  90                  95

Glu Val Val Val Ile Asn Ser Val Ala Gln Tyr Phe Pro Ser Pro Glu
            100                 105                 110

Tyr Leu Ser Lys Val Leu Tyr Ala Leu Ala Gln Ile Pro Gly Val Lys
        115                 120                 125

Arg Leu Phe Phe Gly Asp Met Arg Ser Tyr Ala Ile Asn Asp Gln Phe
    130                 135                 140

Leu Ala Ala Arg Ala Leu His Asn Ile Gly Ser Lys Ala Thr Lys Ser
145                 150                 155                 160

Ala Ile Arg Ser Lys Met Val Asp Leu Glu Asn Ser Glu Glu Glu Leu
                165                 170                 175

Leu Val Asp Pro Thr Phe Phe Thr Asn Leu Ala Thr Glu Leu Pro Glu
            180                 185                 190

Val Glu His Val Glu Ile Leu Pro Lys Arg Met Gln Ala Thr Asn Glu
```

```
            195                 200                 205
Leu Ser Ala Tyr Arg Tyr Ala Ala Val Val His Ile Arg Asp Ser Ser
    210                 215                 220

<210> SEQ ID NO 9
<211> LENGTH: 69
<212> TYPE: PRT
<213> ORGANISM: Curvularia clavata

<400> SEQUENCE: 9

Thr Glu Ala Val Leu Cys Glu Glu Phe Thr Asp Val Leu Gly Leu Glu
1               5                   10                  15

Val Gly Ile Thr Asp Asn Phe Phe Asp Leu Gly Gly His Ser Leu Met
            20                  25                  30

Ala Thr Lys Leu Ala Ala Arg Ile Ser Arg Arg Leu Asp Ala Arg Val
        35                  40                  45

Ser Val Lys Asp Val Phe Asp Gln Pro Val Ile Val Asp Leu Ala Ala
    50                  55                  60

Ser Ile Arg Arg Gly
65

<210> SEQ ID NO 10
<211> LENGTH: 295
<212> TYPE: PRT
<213> ORGANISM: Curvularia clavata

<400> SEQUEN

```
                225                 230                 235                 240
Thr Thr Thr Phe Ala Val Leu Leu Ala Ala Phe Arg Ala Thr His Tyr
                245                 250                 255

Arg Leu Thr Gly Ala Glu Asp Ala Thr Val Gly Thr Pro Ile Ala Asn
                260                 265                 270

Arg Asn Arg Pro Glu Leu Glu Asn Leu Val Gly Phe Phe Val Asn Thr
                275                 280                 285

Gln Cys Met Arg Ile Ser Val
                290                 295

<210> SEQ ID NO 11
<211> LENGTH: 404
<212> TYPE: PRT
<213> ORGANISM: Curvularia clavata

<400> SEQUENCE: 11

Leu Thr Tyr Ala Gln Leu Asp Glu Gln Ser Asp Glu Val Ala Val Trp
1               5                   10                  15

Leu His Gln Arg Lys Leu Pro Ala Glu Ser Leu Val Ala Val Leu Ala
                20                  25                  30

Pro Arg Ser Cys Glu Thr Ile Ile Thr Phe Phe Gly Ile Leu Lys Ala
            35                  40                  45

Asn Leu Ala Tyr Leu Pro Leu Asp Ile Asn Val Pro Ala Ala Arg Ile
        50                  55                  60

Gln Ala Ile Leu Ser Ser Val Ala Gly Lys Lys Ile Leu Leu Leu Gly
65                  70                  75                  80

Ser Asp Gln Ala Gln Pro Glu Ile Arg Leu Asp Asp Val Glu Phe Val
                85                  90                  95

Gln Ile Asn Glu Thr Ile Asp His Asn Met Ala Lys Asp Asn Thr Thr
            100                 105                 110

Arg Ser Gly Pro Leu Ala Thr Ser Leu Ala Tyr Val Ile Phe Thr Ser
        115                 120                 125

Gly Ser Thr Gly Gln Pro Lys Gly Val Lys Val Glu His Arg Gly Ile
    130                 135                 140

Val Arg Leu Val Lys Asn Ser Asn Val Val Ala Lys Met Pro Glu Ala
145                 150                 155                 160

Ala Cys Val Ala His Leu Ser Asn Leu Ala Phe Asp Ala Ala Thr Trp
                165                 170                 175

Glu Ile Tyr Ala Ala Leu Leu Asn Gly Gly Ser Leu Ile Cys Ile Asp
            180                 185                 190

Tyr Phe Thr Thr Leu Asp Ser Lys Val Leu Glu Ala Val Phe Glu Arg
        195                 200                 205

Glu Gln Ile Arg Ala Ala Met Phe Pro Pro Ala Leu Leu Lys Gln Cys
    210                 215                 220

Leu Leu Asn Ile Pro Thr Thr Ile Ser Ala Leu Asp Val Ile Leu Ala
225                 230                 235                 240

Ala Gly Asp Arg Phe Asp Arg Arg Asp Ala Ile Ala Ala Gln Ala Leu
                245                 250                 255

Val Gly Gly Val Tyr Asn Ala Tyr Gly Pro Thr Glu Asn Thr Thr
            260                 265                 270

Leu Ser Thr Ile Tyr Asn Val Val Asp Gly Asp Thr Asn Val Asn Gly
        275                 280                 285

Ile Pro Ile Gly Leu Pro Val Ser Asn Ser Gly Val Tyr Val Met Asp
    290                 295                 300
```

```
Pro Asn Gln Gln Leu Val Pro Leu Gly Val Met Gly Glu Leu Val Val
305                 310                 315                 320

Val Gly Asp Gly Val Ala Arg Gly Tyr Thr Asp Pro Ala Leu Asp Val
                325                 330                 335

Asp Arg Phe Ile Lys Val Glu Ile Asp Gly Gln Ile Val Arg Ala Tyr
            340                 345                 350

Arg Thr Gly Asp Arg Val Arg His Arg Pro Lys Asp Gly Gln Ile Glu
        355                 360                 365

Phe Phe Gly Arg Met Asp Gln Gln Val Lys Ile Arg Gly His Arg Ile
    370                 375                 380

Glu Leu Ala Glu Val Glu His Val Ile Leu Asp Asn Ser Leu Val Gln
385                 390                 395                 400

Asp Ala Ala Val
```

<210> SEQ ID NO 12
<211> LENGTH: 69
<212> TYPE: PRT
<213> ORGANISM: Curvularia clavata

<400> SEQUENCE: 12

```
Ile Glu Thr Ile Leu Cys Glu Glu Tyr Ala Glu Val Leu Gly Val Glu
1               5                   10                  15

Val Gly Val Met Asp Asn Phe Phe Asp Leu Gly Gly His Ser Leu Met
            20                  25                  30

Ala Thr Lys Leu Ala Ala Arg Ala Thr Arg Arg Leu Asp Ala Lys Leu
        35                  40                  45

Ser Val Lys Asp Ile Phe Asp Tyr Pro Ile Leu Ala Asn Leu Ala Ala
    50                  55                  60

Ala Val Gln Arg Gly
65
```

<210> SEQ ID NO 13
<211> LENGTH: 298
<212> TYPE: PRT
<213> ORGANISM: Curvularia clavata

<400> SEQUENCE: 13

```
Gly Pro Val Glu Gln Ser Phe Ala Gln Gly Arg Leu Trp Phe Leu Asp
1               5                   10                  15

Gln Leu Asn Val Gly Ser Asn Trp Tyr Leu Gln Pro Ile Ala Ile Arg
            20                  25                  30

Ile Arg Gly Ser Leu Asn Ile Asn Ala Leu Thr Thr Ala Leu His Ala
        35                  40                  45

Leu Glu Gln Arg His Glu Thr Leu Arg Thr Thr Phe Glu Glu Glu Asp
    50                  55                  60

Gly Val Gly Met Gln Val Val Gln Glu Tyr Asp Pro Ile Glu Leu Arg
65                  70                  75                  80

Ile Met Asp Ile Ala Ala Asp Tyr Asp Gly Asp Tyr Thr Glu Ala Leu
            85                  90                  95

Lys Gly Glu Gln Thr Thr Pro Phe Asp Leu Glu Ser Glu Pro Gly Trp
        100                 105                 110

Arg Val Ser Leu Leu Arg Met Asn Asp Asn Asp His Ile Leu Ser Leu
    115                 120                 125

Val Leu His His Ile Ile Ser Asp Gly Trp Ser Val Asp Val Leu Arg
130                 135                 140

Gln Glu Leu Lys Gln Phe Tyr Ala Ala Ala Leu Gln Gly Leu Asp Pro
```

```
              145                 150                 155                 160
Leu Ser Gly Ala Asp Pro Leu Pro Ile Gln Tyr Arg Asp Phe Ser Leu
                165                 170                 175

Trp Gln Lys Gln Pro Glu Gln Val Ala Glu His Glu Arg Gln Leu Lys
                180                 185                 190

Tyr Trp Val Glu Gln Leu Ala Asp Asn Ser Pro Ala Thr Leu Leu Ala
                195                 200                 205

Asp Arg Pro Arg Pro Ser Val Leu Ser Gly Gln Ala Gly Ser Val Pro
            210                 215                 220

Leu Ser Ile Glu Gly Gln Val Tyr Glu Lys Leu Gln Ala Phe Cys Arg
225                 230                 235                 240

Ala His Gln Thr Thr Ser Phe Ser Val Leu Leu Ala Ala Phe Arg Ala
                245                 250                 255

Ala His Phe Arg Leu Thr Gly Val Asp Asp Ala Thr Ile Gly Ile Pro
                260                 265                 270

Ile Ala Asn Arg Asn Arg Pro Glu Leu Glu His Leu Ile Gly Phe Phe
                275                 280                 285

Val Asn Arg Gln Cys Met Arg Ile Thr Val
            290                 295

<210> SEQ ID NO 14
<211> LENGTH: 403
<212> TYPE: PRT
<213> ORGANISM: Curvularia clavata

<400> SEQUENCE: 14

Leu Thr Tyr Ala Gln Leu Asp Gln Gln Ser Asp Glu Ile Ala Thr Trp
1               5                   10                  15

Leu Arg Asn Lys Lys Met Ala Pro Glu Thr Leu Val Gly Val Leu Ala
                20                  25                  30

Pro Arg Ser Cys Gln Thr Ile Val Ala Phe Leu Gly Val Leu Lys Ala
                35                  40                  45

Asn Leu Ala Tyr Leu Pro Leu Asp Val Asn Ala Pro Met Ala Arg Val
            50                  55                  60

Glu Thr Ile Met Ser Ser Val Pro Gly Ser Lys Leu Leu Leu Leu Gly
65                  70                  75                  80

Ser Asp Val Pro Ala Gln Glu Ile Gln Leu Gln Asn Val Glu Leu Val
                85                  90                  95

Arg Ile Glu Asp Thr Leu Gly His Ala Ala Ser Ala Gly Thr Ala Thr
                100                 105                 110

Thr Glu Pro Ser Pro Thr Ser Leu Ala Tyr Val Ile Phe Thr Ser Gly
                115                 120                 125

Ser Thr Gly Lys Pro Lys Gly Val Met Val Glu His Arg Ser Val Ile
            130                 135                 140

Arg Leu Val Arg Lys Glu Ser Asn Ser Met Ser Lys Met Ser Ser Arg
145                 150                 155                 160

Ala Arg Val Ala His Leu Thr Asn Ile Ala Phe Asp Val Ser Ala Trp
                165                 170                 175

Glu Val Tyr Ala Thr Leu Leu Asn Gly Gly Thr Leu Val Cys Val Asp
                180                 185                 190

Tyr Phe Thr Ser Phe Asp Ala Lys Ala Leu Gly Leu Leu Phe Glu Arg
                195                 200                 205

Glu Gln Ile Thr Ala Ala Met Ile Thr Pro Thr Leu Leu Lys Gln Cys
            210                 215                 220
```

```
Ile Thr Ile Val Pro Glu Ala Leu Arg Lys Leu Ser Val Leu Tyr Thr
225                 230                 235                 240

Gly Gly Asp Arg Phe Asp Arg Arg Asp Ala Ile Ala Thr Lys Ala Leu
            245                 250                 255

Val Lys Gly Pro Val Tyr Asn Ala Trp Gly Pro Thr Glu Thr Thr Ile
        260                 265                 270

Val Ser Thr Ile Tyr Glu Leu Ala Asp Asp Gln Phe Thr Asn Gly
    275                 280                 285

Val Pro Ile Gly Lys Ala Val Ser Asn Ser Trp Ala Tyr Val Met Asp
    290                 295                 300

Leu Asn Gln Gln Leu Val Pro Val Gly Val Met Gly Glu Ala Val Val
305                 310                 315                 320

Ile Gly Asp Gly Leu Ala Arg Gly Tyr Thr Asp Pro Ala Leu Asp Cys
            325                 330                 335

Asn Arg Phe Val His Ile Thr Ile Asp Gly Lys Arg Val Arg Ala Tyr
            340                 345                 350

Arg Thr Gly Asp Arg Ala Arg Tyr Arg Pro Lys Asp Gly Glu Ile Glu
        355                 360                 365

Phe Phe Gly Arg Met Asp Arg Gln Leu Lys Ile Arg Gly His Arg Ile
370                 375                 380

Glu Pro Ala Glu Ile Glu His Ala Met Leu Gly His Asn Asp Ile Val
385                 390                 395                 400

Asp Val Ala

<210> SEQ ID NO 15
<211> LENGTH: 224
<212> TYPE: PRT
<213> ORGANISM: Curvularia clavata

<400> SEQUENCE: 15

Asp Gly Gly Ala Ile Asp Gln Ala Glu Met Gln Glu Trp Leu Asp Asp
1               5                   10                  15

Thr Ile Gln Thr Ile Val Asp Gly Gln Pro Ala Gly His Val Phe Glu
            20                  25                  30

Ile Gly Thr Gly Thr Gly Met Ile Met Phe Gly Leu Gly Lys Gln Gly
        35                  40                  45

Leu Gln Ser Tyr Val Gly Leu Glu Pro Ser Thr Ser Ala Thr Thr Tyr
    50                  55                  60

Val Asn Arg Lys Ile Lys Thr Ala Pro Thr Val Ala Gly Lys Ala Lys
65                  70                  75                  80

Val Tyr Val Gly Thr Ala Met Glu Ala Ala Gln Leu Asn Gly Leu His
                85                  90                  95

Pro Glu Val Val Ile Asn Ser Val Ala Gln Tyr Phe Pro Thr Pro
            100                 105                 110

Glu Tyr Leu Leu Glu Val Val Gly Ile Leu Thr Gln Met Pro Gly Val
    115                 120                 125

Lys Arg Leu Phe Phe Gly Asp Ile Arg Ser Tyr Ala Thr Asn Arg Lys
130                 135                 140

Phe Leu Ala Ala Arg Ala Leu His Met Leu Gly Ser Asn Ala Lys Lys
145                 150                 155                 160

His Asp Ile Arg Arg Lys Met Ala Glu Leu Asp Glu Phe Glu Glu Glu
                165                 170                 175

Leu Ile Val Asp Pro Ser Phe Phe Thr Gly Leu Val Ser Arg Leu Pro
            180                 185                 190
```

Gly Gln Val Lys His Val Glu Ile Leu Pro Lys Gln Met Ile Ala Thr
            195                 200                 205

Asn Glu Leu Ser Ala Tyr Arg Tyr Ala Ala Val Val His Leu Ala Leu
    210                 215                 220

<210> SEQ ID NO 16
<211> LENGTH: 69
<212> TYPE: PRT
<213> ORGANISM: Curvularia clavata

<400> SEQUENCE: 16

Val Glu Ala Val Leu Cys Glu Glu Phe Ser Glu Val Leu Gly Val Glu
1               5                   10                  15

Val Gly Val Thr Asp Asn Phe Phe Asp Leu Gly Gly His Ser Leu Met
            20                  25                  30

Ala Thr Lys Leu Ala Ala Arg Thr Gly Arg Arg Leu Asp Ala Lys Val
        35                  40                  45

Ser Val Lys Asp Val Phe Asp His Pro Val Leu Ala Asp Leu Ala Ala
    50                  55                  60

Ala Ile Gln Arg Gly
65

<210> SEQ ID NO 17
<211> LENGTH: 298
<212> TYPE: PRT
<213> ORGANISM: Curvularia clavata

<400> SEQUENCE: 17

Gly Pro Val Glu Gln Ser Tyr Ala Gln Gly Arg Leu Trp Phe Leu Glu
1               5                   10                  15

Gln Leu Asn Phe Lys Ala Thr Trp Tyr Leu Leu Pro Leu Ala Val Arg
            20                  25                  30

Ile Arg Gly Pro Leu Asn Ile Lys Ala Leu Thr Thr Ala Leu His Ala
        35                  40                  45

Leu Glu Gln Arg His Glu Thr Leu Arg Thr Thr Phe Ile Glu Arg Asp
    50                  55                  60

Gly Val Gly Lys Gln Ala Val Gln Pro Phe Gln Pro Lys Glu Leu Glu
65                  70                  75                  80

Ile Val Asp Ile Ala Ala Asp His Gln Gly Asp Tyr Leu Lys Val Leu
                85                  90                  95

Arg Asp Glu Gln Thr Thr Met Phe Asn Leu Ala Thr Gln Pro Gly Trp
            100                 105                 110

Arg Val Thr Leu His Arg Val Asp Gln Asn Thr His Asn Leu Ser Ile
        115                 120                 125

Val Met His His Ile Ile Ser Asp Gly Trp Ser Val Asp Val Leu Arg
    130                 135                 140

His Glu Leu Arg Gln Phe Tyr Ala Ala Ala Leu Arg Gly Gln Asp Pro
145                 150                 155                 160

Leu Ala His Ile Ser Pro Leu Pro Ile Gln Tyr Arg Asp Phe Ser Leu
                165                 170                 175

Trp Gln Lys Gln Pro Asp Gln Ile Ile Glu His Ala Lys Gln Leu Glu
            180                 185                 190

Tyr Trp Thr Lys Gln Leu Ala Asp Ser Ser Pro Ala Glu Leu Pro Thr
        195                 200                 205

Asp Leu Pro Arg Pro Ala Val Leu Ser Gly Lys Ala Gly Glu Val Ala
    210                 215                 220

```
Leu Ser Val Lys Gly Pro Leu Tyr Glu Arg Leu Gln Ala Phe Cys Lys
225                 230                 235                 240

Thr His Gln Thr Thr Ala Phe Ala Thr Leu Leu Ala Ala Phe Arg Ala
            245                 250                 255

Thr His His Arg Leu Thr Gly Ala Glu Asp Ala Thr Ile Gly Thr Pro
            260                 265                 270

Ile Ala Asn Arg Asn Arg Pro Glu Leu Glu Asn Leu Ile Gly Phe Phe
            275                 280                 285

Val Asn Ala Gln Cys Met Arg Ile Thr Ile
            290                 295

<210> SEQ ID NO 18
<211> LENGTH: 402
<212> TYPE: PRT
<213> ORGANISM: Curvularia clavata

<400> SEQUENCE: 18

Leu Thr Tyr Ala Gln Leu Asn Glu Gln Ser Asp Lys Val Ala Ala Trp
1               5                   10                  15

Leu His Gln Cys Asn Leu Pro Thr Glu Thr Leu Val Ala Val Leu Ala
            20                  25                  30

Pro Arg Ser Cys Gln Thr Val Val Ala Phe Leu Gly Ile Leu Lys Ala
        35                  40                  45

Asn Leu Ala Tyr Leu Pro Leu Asp Val Asn Val Pro Ala Ala Arg Ile
    50                  55                  60

Glu Ala Ile Leu Ser Glu Val Ser Gly His Ile Leu Val Leu Leu Gly
65                  70                  75                  80

Ser His Val Ser Ala Pro Lys Ile Glu Leu Ala Asp Val Glu Phe Val
                85                  90                  95

Lys Ile Asp Asn Thr Val Glu His Asn Leu Pro Gly Arg Ile Gly Ser
            100                 105                 110

Ala Pro Ser Ala Thr Ser Leu Ala Tyr Val Ile Phe Thr Ser Gly Ser
        115                 120                 125

Thr Gly Lys Pro Lys Gly Val Lys Val Glu His Arg Gly Ile Val Arg
    130                 135                 140

Leu Val Lys Glu Ser Asn Val Val Ala Lys Met Pro Gln Ala Ala Arg
145                 150                 155                 160

Ile Ala His Leu Ser Asn Ile Ala Phe Asp Ala Ala Thr Trp Glu Leu
                165                 170                 175

Tyr Ala Ala Leu Leu Asn Gly Gly Thr Leu Val Cys Ile Asn Tyr Leu
            180                 185                 190

Thr Thr Leu Asp Ser Lys Ala Leu Glu Ala Val Phe Glu Gln Glu Lys
        195                 200                 205

Ile Gln Ala Ala Met Leu Pro Pro Ala Leu Leu Lys Gln Tyr Leu Val
    210                 215                 220

Asn Ile Pro Ala Ala Ile Gly Ala Leu Glu Val Val Leu Val Ala Gly
225                 230                 235                 240

Asp Arg Phe Asp Arg Arg Asp Ala Ala Thr Gln Ala Leu Val Gly
                245                 250                 255

Ala Gly Val Tyr Asn Ala Tyr Gly Pro Thr Glu Asn Thr Thr Leu Ser
            260                 265                 270

Thr Ile Tyr Asn Val Val Gln Gly Asp Ala Asn Val Asn Gly Val Pro
        275                 280                 285

Ile Gly Arg Pro Val Ser Asn Ser Gly Ala Tyr Ile Met Asn Met Asn
    290                 295                 300
```

Gln Glu Leu Val Pro Ile Gly Val Ile Gly Glu Leu Val Val Gly
305                 310                 315                 320

Asp Gly Val Ala Arg Gly Tyr Thr Asp Pro Ala Leu Asp Val Asn Arg
            325                 330                 335

Phe Val Asn Val Thr Ile Glu Gly Gln Thr Met Arg Ala Tyr Arg Thr
            340                 345                 350

Gly Asp Arg Ala Arg Tyr Arg Pro Lys Asp Ala Gln Ile Glu Phe Phe
            355                 360                 365

Gly Arg Met Asp Gln Gln Ile Lys Ile Arg Gly His Arg Ile Glu Pro
370                 375                 380

Ala Glu Val Glu His Ala Leu Leu Asn Asn Asp Leu Leu Gln Asp Ala
385                 390                 395                 400

Ala Val

<210> SEQ ID NO 19
<211> LENGTH: 222
<212> TYPE: PRT
<213> ORGANISM: Curvularia clavata

<400> SEQUENCE: 19

Asp Gly Ser Ala Ile Asp Lys Ala Glu Met Gln Glu Trp Leu Asp Asp
1               5                   10                  15

Thr Met Gln Thr Ile Leu Asp Gly Arg Pro Ala Gly Arg Val Leu Glu
            20                  25                  30

Ile Gly Thr Gly Thr Gly Met Ile Leu Phe Asn Leu Gly Glu Gly Leu
        35                  40                  45

Gln Ser Tyr Val Gly Leu Glu Pro Ser Thr Ser Ala Ala Ala Phe Val
50                  55                  60

Asn Arg Arg Ile Gln Thr Leu Pro Ala Phe Ala Gly Lys Ala Glu Val
65                  70                  75                  80

His Val Gly Thr Ala Thr Asp Ile Ser Gln Leu Gln Asp Leu Arg Pro
            85                  90                  95

Glu Val Val Val Ile Asn Ser Val Ala Gln Tyr Phe Pro Ser Pro Glu
            100                 105                 110

Tyr Leu Ser Lys Val Leu Tyr Ala Leu Ala Gln Ile Pro Gly Val Lys
        115                 120                 125

Arg Leu Phe Phe Gly Asp Met Arg Ser Tyr Ala Ile Asn Asp Gln Phe
130                 135                 140

Leu Ala Ala Arg Ala Leu His Asn Ile Gly Ser Lys Ala Thr Lys Ser
145                 150                 155                 160

Ala Ile Arg Ser Lys Met Val Asp Leu Glu Asn Ser Glu Glu Glu Leu
            165                 170                 175

Leu Val Asp Pro Thr Phe Phe Thr Asn Leu Ala Thr Glu Leu Pro Glu
            180                 185                 190

Val Glu His Val Glu Ile Leu Pro Lys Arg Met Gln Ala Thr Asn Glu
        195                 200                 205

Leu Ser Ala Tyr Arg Tyr Ala Ala Val Val His Ile Arg Asp
210                 215                 220

<210> SEQ ID NO 20
<211> LENGTH: 69
<212> TYPE: PRT
<213> ORGANISM: Curvularia clavata

<400> SEQUENCE: 20

```
Ile Glu Ala Ala Leu Cys Glu Val Phe Val Asp Leu Leu Gly Thr Glu
  1               5                  10                  15

Val Ser Ile Thr Asp Asn Phe Phe Asn Leu Gly Gly His Ser Leu Met
             20                  25                  30

Ala Thr Lys Leu Ala Ala Arg Ile Ser Arg Arg Leu Asp Ala Arg Ile
         35                  40                  45

Ser Val Lys Asp Val Phe Asp Tyr Pro Val Leu Ala Asp Leu Ala Gly
     50                  55                  60

Ala Val Gln Arg Gly
 65
```

<210> SEQ ID NO 21
<211> LENGTH: 295
<212> TYPE: PRT
<213> ORGANISM: Curvularia clavata

<400> SEQUENCE: 21

```
Gly Pro Val Glu Gln Ser Phe Ala Gln Gly Arg Leu Trp Phe Leu Asp
  1               5                  10                  15

Gln Leu Asn Ala Gly Ser Leu Trp Tyr Ile Gln Pro Ile Ala Val Arg
             20                  25                  30

Val Arg Gly Ser Leu Asn Ile Gly Ala Leu Thr Thr Ala Leu Asn Ala
         35                  40                  45

Leu Glu Lys Arg His Glu Pro Leu Arg Thr Thr Phe Glu Glu His Asp
     50                  55                  60

Gly Ile Gly Val Gln Val Val Gln Pro His Gln Pro Lys Lys Leu Arg
 65                  70                  75                  80

Ile Val Asp Thr Val Ala Asn Tyr Gln Gly Asp Phe Ile Arg Ala Leu
                 85                  90                  95

Arg Lys Glu Gln Gln Thr Leu Phe Asn Leu Ala Thr Glu Pro Gly Trp
            100                 105                 110

Arg Val Ser Leu Leu Arg Ile Gly Glu Asp Asp Asn Ile Leu Ser Ile
            115                 120                 125

Val Met His His Ile Ile Ser Asp Gly Trp Ser Val Asp Ile Leu Arg
            130                 135                 140

Gln Asp Leu Lys Leu Phe Tyr Ala Ala Ala Leu Lys Ser Gln Glu Pro
145                 150                 155                 160

Gln Val Asp Ala Leu Pro Ile Gln Tyr Arg Asp Phe Ala Phe Trp Gln
                165                 170                 175

Lys Gln Pro Glu Gln Val Ala Glu His Gln Arg Gln Leu Asp Tyr Trp
            180                 185                 190

Ile Glu Gln Leu Lys Asp Ser Lys Pro Ala Glu Leu Ile Thr Asp Phe
            195                 200                 205

Pro Arg Pro Glu Val Leu Ser Gly Thr Ala Gly Ile Val Gln Leu Ala
            210                 215                 220

Val Asp Gly Gln Val Tyr Glu Gly Leu Arg Ala Phe Cys Arg Ile His
225                 230                 235                 240

Gln Thr Thr Ser Phe Val Val Leu Ala Ala Phe Arg Ala His
                245                 250                 255

Tyr Arg Leu Thr Gly Thr Glu Asp Ala Thr Ile Gly Ser Pro Ile Ala
            260                 265                 270

Asn Arg Asn Arg Pro Glu Leu Glu Ser Leu Ile Gly Phe Phe Val Asn
            275                 280                 285

Thr Gln Cys Met Arg Ile Met
            290                 295
```

<210> SEQ ID NO 22
<211> LENGTH: 406
<212> TYPE: PRT
<213> ORGANISM: Curvularia clavata

<400> SEQUENCE: 22

```
Leu Thr Tyr Ala Gln Leu Asp Glu Glu Ser Asn Lys Val Ala Thr Trp
1               5                   10                  15

Leu Ser Gln Arg Gln Leu Ala Pro Glu Thr Leu Val Gly Val Leu Ala
            20                  25                  30

Pro Arg Ser Cys Pro Thr Ile Val Thr Phe Phe Gly Ile Leu Lys Ala
        35                  40                  45

Ser Leu Ala Tyr Leu Pro Leu Asp Val Asn Val Pro Ser Ala Arg Ile
    50                  55                  60

Glu Ala Ile Leu Ser Ala Val Pro Asp His Lys Leu Val Phe Leu Gly
65                  70                  75                  80

Ala Asp Val Pro Asp Pro Glu Ala Pro Leu Val Asn Val Glu Leu Val
                85                  90                  95

Arg Ile Asp Asp Ile Leu Arg Gln Ser Ile His Ala Ser Asn Ala Gly
            100                 105                 110

Leu Leu Ala Asn His Pro Leu Ala Thr Ser Leu Ala Tyr Val Met Phe
        115                 120                 125

Thr Ser Gly Ser Thr Gly Lys Pro Lys Gly Val Met Val Glu His Arg
    130                 135                 140

Ser Ile Val Arg Leu Val Lys Glu Thr Asn Leu Val Pro Ala Val Glu
145                 150                 155                 160

Ala Val Ser Ser Val Ala His Ile Ser Asn Val Ala Phe Asp Ala Ala
                165                 170                 175

Thr Trp Glu Ile Tyr Ala Ala Leu Leu Asn Gly Gly Thr Thr Val Cys
            180                 185                 190

Ile Asp His Ile Thr Val Leu Asp Pro Ala Lys Leu Ala Leu Val Phe
        195                 200                 205

Ser Ser Glu Lys Ile Lys Ala Ala Phe Phe Ser Thr Ala Leu Leu Lys
    210                 215                 220

Gln Arg Leu Tyr Glu Glu Pro Ser Thr Ile Thr Gly Leu Asp Leu Leu
225                 230                 235                 240

Tyr Ala Gly Gly Glu Arg Met Arg Pro Gln Asp Ala Leu Lys Thr Arg
                245                 250                 255

Glu Leu Val Arg Gly Ser Phe Cys His Val Tyr Gly Pro Thr Glu Asn
            260                 265                 270

Thr Thr Phe Ser Thr Val Tyr Pro Met Gly Val Glu Glu Arg Cys Val
        275                 280                 285

Asn Gly Leu Pro Ile Gly Arg Ala Val Ser His Ser Gly Ala Val Ile
    290                 295                 300

Met Asp Ala Asn Gln Arg Leu Val Pro Leu Gly Val Met Gly Glu Leu
305                 310                 315                 320

Val Val Thr Gly Asp Gly Leu Ala Arg Gly Tyr Thr Asp Pro Ala Leu
                325                 330                 335

Asn Arg Asp Arg Phe Val Glu Val Asn Ile His Gly Gln Val Leu Arg
            340                 345                 350

Ala Tyr Arg Thr Gly Asp Gln Ala Arg Tyr Arg Pro Lys Asp Gly Gln
        355                 360                 365

Ile Glu Phe Ser Gly Arg Met Asp Arg Gln Leu Lys Ile Arg Gly His
```

```
    370                 375                 380

Arg Ile Glu Pro Ala Glu Val Glu His Ala Ile Leu Ser His Asp Asp
385                 390                 395                 400

Ile Arg Asn Ala Val Val
                405

<210> SEQ ID NO 23
<211> LENGTH: 221
<212> TYPE: PRT
<213> ORGANISM: Curvularia clavata

<400> SEQUENCE: 23

Asp Gly Thr Ala Ile Asp Lys Ala Glu Met Gln Glu Trp Leu Asp Asp
1               5                   10                  15

Thr Met Arg Thr Leu His Asp Gly Arg Asp Pro Gly His Val Leu Glu
            20                  25                  30

Val Gly Thr Gly Thr Gly Met Ile Leu Phe Asn Leu Gly Lys Gly Leu
        35                  40                  45

Gln Ser Tyr Val Gly Leu Glu Pro Ser Thr Ser Ala Ala Ala Phe Val
    50                  55                  60

Asn Arg Lys Ile Glu Thr Ile Ser Ser Leu Ala Gly Lys Ala Lys Val
65                  70                  75                  80

Glu Ile Gly Thr Ala Thr Asp Val Gly Gln Leu Lys Asn Leu Arg Ser
                85                  90                  95

Asp Leu Val Val Ile Asn Ser Val Ala Gln Tyr Phe Pro Ser Pro Glu
            100                 105                 110

Tyr Leu Val Glu Ala Val Thr Ala Leu Val His Ile Pro Gly Val Lys
        115                 120                 125

Arg Leu Phe Phe Gly Asp Met Arg Ser Tyr Ala Met Asn Lys Gln Phe
    130                 135                 140

Leu Val Ala Arg Ala Leu Arg Thr Leu Gly Ala Lys Ala Asn Lys Asp
145                 150                 155                 160

Asp Val Arg Arg Lys Met Val Glu Leu Glu Glu Phe Glu Glu Glu Leu
                165                 170                 175

Leu Val Asp Pro Ala Phe Phe Thr Gly Leu Ala Asn Trp Leu Ser Glu
            180                 185                 190

Val Glu His Val Glu Ile Leu Pro Lys Gln Met Thr Ser Thr Asn Glu
        195                 200                 205

Leu Ser Ser Tyr Arg Tyr Ala Ala Ile Val His Leu Arg
    210                 215                 220

<210> SEQ ID NO 24
<211> LENGTH: 69
<212> TYPE: PRT
<213> ORGANISM: Curvularia clavata

<400> SEQUENCE: 24

Ile Glu Ala Leu Leu Cys Glu Glu Phe Ala Glu Val Leu Gly Val Glu
1               5                   10                  15

Val Gly Ile Asn Asp Asp Phe Phe Asp Leu Gly Gly His Ser Leu Met
            20                  25                  30

Ala Thr Lys Leu Ala Ala Arg Ser Ser Arg Arg Phe Asp Ala Lys Val
        35                  40                  45

Ser Val Lys Asp Val Phe Asp His Pro Ile Leu Ala Asp Leu Ala Ala
    50                  55                  60

Ser Ile Gln Arg Gly

<210> SEQ ID NO 25
<211> LENGTH: 298
<212> TYPE: PRT
<213> ORGANISM: Curvularia clavata

<400> SEQUENCE: 25

```
Gly Pro Val Glu Gln Ser Phe Ala Gln Gly Arg Leu Trp Phe Leu Glu
1               5                   10                  15

Gln Leu Asn Val Ser Ser Thr Trp Tyr Leu Gln Pro Ile Ala Val Arg
            20                  25                  30

Met Arg Gly Pro Leu Lys Ile Glu Ala Leu Ala Ala Ala Phe His Ala
        35                  40                  45

Leu Glu Glu Arg His Glu Thr Leu Arg Thr Thr Phe Glu Glu His Asp
    50                  55                  60

Gly Ile Gly Met Gln Val Val Gln Pro His Arg Pro Lys Glu Leu Arg
65                  70                  75                  80

Val Ile Asp Val Gln Ala Glu His Asp Gly Asp Tyr Thr Gln Ala Leu
                85                  90                  95

His Thr Glu Gln Thr Thr Thr Phe Asn Leu Glu Thr Glu Pro Gly Trp
            100                 105                 110

Arg Val Ser Val Phe Arg Leu Asn Glu Asp Asp Asn Ile Leu Ser Ile
        115                 120                 125

Val Met His His Ile Ile Ser Asp Gly Trp Ser Phe Asp Ile Leu Arg
    130                 135                 140

Lys Glu Ile Arg Glu Phe Tyr Asn Ala Ala Leu Lys Gly Lys Asp Pro
145                 150                 155                 160

Leu Ala Gln Met Ser Pro Leu His Ile Gln Tyr Arg Asp Phe Ser Val
                165                 170                 175

Trp Gln Lys Gln Leu Asn Gln Ile Thr Glu His Lys Arg Gln Leu Asp
            180                 185                 190

Tyr Trp Thr Lys Asn Leu Ala Asp Asn Thr Pro Ala Glu Leu Pro Thr
        195                 200                 205

Asp Leu Pro Arg Pro Ala Val Leu Ser Gly Lys Ala Gly Val Ile Gln
    210                 215                 220

Leu Ser Ile Thr Gly Pro Val Tyr Asp Arg Leu Arg Ala Phe Cys Arg
225                 230                 235                 240

Val His Gln Thr Thr Leu Phe Thr Val Leu Leu Thr Val Phe Arg Ala
                245                 250                 255

Thr His Tyr Arg Leu Thr Gly Ala Glu Asp Ala Thr Ile Gly Thr Pro
            260                 265                 270

Ile Ala Asn Arg Asn Arg Pro Glu Leu Glu Asn Leu Ile Gly Phe Phe
        275                 280                 285

Val Asn Thr Gln Cys Met Arg Ile Thr Val
    290                 295
```

<210> SEQ ID NO 26
<211> LENGTH: 405
<212> TYPE: PRT
<213> ORGANISM: Curvularia clavata

<400> SEQUENCE: 26

```
Leu Thr Tyr Ala Gln Leu Asp Leu His Ser Asp Glu Leu Ala Ser Trp
1               5                   10                  15

Leu Arg Gln Lys Lys Met Ala Pro Glu Thr Leu Val Gly Val Leu Ala
```

```
                20                  25                  30
Pro Arg Ser Cys Gln Thr Ile Val Thr Phe Leu Gly Ile Leu Lys Ala
            35                  40                  45
Ser Leu Ala Tyr Leu Pro Leu Asp Val Lys Val Pro Val Ala Arg Ile
 50                  55                  60
Glu Ala Ile Leu Ser Ser Ile Ser Gly Gln Lys Leu Ile Leu Leu Gly
 65                  70                  75                  80
Gln Asp Val Pro Val Pro Glu Ile Gln Leu Pro Asp Val Asp Val Val
                85                  90                  95
Pro Ile Ser Glu Ile Leu Gly Arg Ser Val Pro Ser Arg Ala Thr Asp
            100                 105                 110
Lys Ser Leu Gly Pro Leu Ala Arg Asn Leu Ala Tyr Val Leu Phe Thr
            115                 120                 125
Ser Gly Ser Thr Gly Lys Pro Lys Gly Val Met Ile Glu His Arg Ser
            130                 135                 140
Ile Val Arg Leu Val Lys Glu Thr Asn Leu Ile Ser Lys Leu Pro Asn
145                 150                 155                 160
Ala Pro Arg Thr Ala His Leu Thr Asn Leu Val Phe Asp Asn Ser Ala
                165                 170                 175
Trp Glu Ile Tyr Ser Thr Leu Leu Asn Gly Gly Thr Leu Val Cys Ile
            180                 185                 190
Asp Tyr Ala Thr Val Leu Asp Ser Lys Ala Leu Glu Thr Val Phe Lys
            195                 200                 205
Glu Gln Arg Ile Gln Thr Ser Leu Met Pro Pro Ala Leu Leu Lys Glu
            210                 215                 220
Cys Leu Ala Asn Met Pro Thr Met Phe Asp Asp Val Glu Val Leu Tyr
225                 230                 235                 240
Ala Leu Gly Asp Arg Phe Asp Lys Gln Asp Ala Met Lys Ala Arg Ser
                245                 250                 255
Ile Val Lys Thr Ala Val Tyr Asn Ala Tyr Gly Pro Thr Glu Asn Thr
            260                 265                 270
Val Ile Ser Thr Ile Tyr Glu Ile Ala Lys Asp Asp Ser Phe Val Asn
            275                 280                 285
Gly Val Pro Ile Gly Arg Ser Ile Ser Asn Ser Gly Ala Phe Ile Met
            290                 295                 300
Asp Ser Arg Gln Gln Leu Val Pro Val Gly Val Leu Gly Glu Leu Val
305                 310                 315                 320
Val Ser Gly Asp Gly Leu Ala Arg Gly Tyr Thr Asp Pro Thr Leu Asp
                325                 330                 335
Val Asn Arg Phe Val Glu Val Thr Val Asp Gly Gln His Val Arg Val
            340                 345                 350
Tyr Arg Thr Gly Asp Arg Val Arg Phe Arg Pro Lys Asp Gly Gln Ile
            355                 360                 365
Glu Phe Phe Ser Arg Met Asp Gln Gln Val Lys Ile Arg Gly His Arg
            370                 375                 380
Ile Glu Pro Ala Glu Val Glu His Val Ile Leu Thr Asn Lys Ile Ile
385                 390                 395                 400
Arg Asp Ala Ala Val
            405

<210> SEQ ID NO 27
<211> LENGTH: 69
<212> TYPE: PRT
<213> ORGANISM: Curvularia clavata
```

<400> SEQUENCE: 27

Met Glu Arg Ile Leu Cys Glu Glu Phe Ala Asp Val Leu Gly Val Glu
1               5                   10                  15

Val Gly Ile Thr Asp Asn Phe Phe Asp Phe Gly Gly His Ser Leu Met
            20                  25                  30

Ala Thr Lys Leu Ala Ala Arg Ile Ser Arg Arg Val Asn Ala Arg Val
        35                  40                  45

Ser Val Lys Ser Val Phe Asp His Pro Val Leu Val Asp Leu Ala Ser
    50                  55                  60

Thr Ile Lys Gln Asp
65

<210> SEQ ID NO 28
<211> LENGTH: 299
<212> TYPE: PRT
<213> ORGANISM: Curvularia clavata

<400> SEQUENCE: 28

Gly Pro Val Glu Gln Ser Phe Ala Gln Gly Arg Leu Trp Phe Leu Asp
1               5                   10                  15

Gln Leu Asn Phe Gly Ala Ser Trp Tyr Leu Met Pro Leu Ala Leu Arg
            20                  25                  30

Leu Gln Gly Ser Leu His Val Lys Ser Leu Thr Thr Ala Leu Phe Ala
        35                  40                  45

Leu Glu Gln Arg His Glu Thr Leu Arg Thr Thr Phe Glu Glu Gln Asp
    50                  55                  60

Gly Val Gly Ile Gln Ile Val His Pro Ala Asn Lys Lys Asp Leu Arg
65                  70                  75                  80

Ile Leu Asp Val Ser Lys Glu Gln Asn Ser Asp Tyr Ala Lys Val Leu
                85                  90                  95

His Lys Glu Arg Thr Ile Pro Ile Asp Leu Thr Ser Glu Pro Gly Trp
            100                 105                 110

Arg Val Ser Leu Ile Arg Leu Gly Glu Asp Asp His Ile Leu Ser Ile
        115                 120                 125

Val Met His His Ile Ile Ser Asp Gly Trp Ser Val Asp Val Leu Arg
    130                 135                 140

Gln Glu Leu Lys Gln Phe Tyr Thr Ala Ala Leu Lys Gly Gln Asp Pro
145                 150                 155                 160

Leu Ala Gln Ile Asp Ala Leu Pro Ile Gln Tyr Arg Asp Phe Ser Leu
                165                 170                 175

Trp Gln Lys Leu Pro Asp Gln Val Ala Glu His Gln Arg Gln Leu Glu
            180                 185                 190

Tyr Trp Ala Glu Gln Leu Ala Asp Asn Thr Pro Ala Glu Leu Leu Thr
        195                 200                 205

Asp Leu Pro Arg Pro Asp Val Leu Ser Gly Lys Ala Gly Ala Val Gln
    210                 215                 220

Leu Thr Ile Asp Gly Pro Val Phe Asp Gln Leu Gln Ala Phe Cys Arg
225                 230                 235                 240

Ala His Gln Thr Thr Met Phe Thr Val Leu Leu Ala Val Phe Arg Thr
                245                 250                 255

Thr His Tyr Arg Leu Thr Gly Ala Thr Asp Ala Thr Ile Gly Thr Pro
            260                 265                 270

Ile Ala Asn Arg Asn Arg Pro Glu Leu Glu Arg Leu Val Gly Phe Phe
        275                 280                 285

```
Val Asn Thr Gln Cys Ile Arg Ile Thr Val Asp
    290                 295

<210> SEQ ID NO 29
<211> LENGTH: 403
<212> TYPE: PRT
<213> ORGANISM: Curvularia clavata

<400> SEQUENCE: 29

Leu Thr Tyr Ser Gln Leu Asp Asp Gln Ser Asp Lys Ile Thr Ala Trp
1               5                   10                  15

Leu Leu Gln Arg Lys Ile Pro Ala Glu Ser Leu Val Ala Val Tyr Ala
            20                  25                  30

Pro Arg Thr Cys Gln Thr Ile Ile Thr Phe Phe Gly Ile Leu Lys Ala
        35                  40                  45

Asn Leu Ala Tyr Leu Pro Leu Asp Ile Asn Val Pro Ala Ala Arg Ile
    50                  55                  60

Glu Ala Ile Leu Ser Thr Ile Ser Gly His Lys Leu Val Leu Leu Gly
65                  70                  75                  80

Ser Gln Val Ser Ala Pro Ala Val Gln Leu Lys Asp Val Glu Tyr Val
                85                  90                  95

Trp Ile Asp Glu Ala Met Ala Glu Thr Val Arg Thr Cys Thr Ser Pro
            100                 105                 110

Glu Pro Ser Ala Thr Ser Leu Ala Tyr Val Ile Phe Thr Ser Gly Ser
        115                 120                 125

Thr Gly Leu Pro Lys Gly Val Lys Val Glu His Arg Gly Val Val Arg
    130                 135                 140

Leu Val Lys Gln Ser Asn Val Val Ala Lys Met Pro Gln Ala Ala Arg
145                 150                 155                 160

Val Ala His Leu Ser Asn Ile Ala Phe Asp Ala Ala Thr Trp Glu Ile
                165                 170                 175

Tyr Ala Ala Leu Leu Asn Gly Gly Ser Leu Ile Cys Ile Asp Tyr Phe
            180                 185                 190

Thr Thr Leu Asp Ser Lys Glu Leu Glu Ala Val Phe Ala Arg Glu Lys
        195                 200                 205

Ile Gln Ala Ala Met Leu Pro Pro Ala Leu Leu Lys Gln Cys Leu Val
    210                 215                 220

Asn Ile Pro Ala Thr Ile Ser Ala Leu Asp Val Leu Ala Ala Gly
225                 230                 235                 240

Asp Arg Phe Asp Arg Arg Asp Ala Ala Ala Thr Gln Ala Leu Val Gly
                245                 250                 255

Gly Cys Val Tyr Asn Ala Tyr Gly Pro Thr Glu Asn Thr Thr Leu Ser
            260                 265                 270

Thr Ile Tyr Asn Val Val Lys Gly Asp Ala Asn Val Asn Gly Val Pro
        275                 280                 285

Ile Gly Arg Pro Val Ser Asn Ser Gly Ala Tyr Ile Met Asp Pro Asn
    290                 295                 300

Gln Gln Leu Val Pro Lys Gly Val Met Gly Glu Leu Ile Val Val Gly
305                 310                 315                 320

Asp Gly Val Ala Arg Gly Tyr Thr Asp Pro Ala Leu Asp Val Asn Arg
                325                 330                 335

Phe Ile Glu Ile Ala Ile Asp Gly Asp Gln Ala Val Arg Ala Tyr Arg
            340                 345                 350

Thr Gly Asp Arg Ala Arg Tyr Arg Pro Lys Asp Gly Gln Ile Glu Phe
```

```
                355                 360                 365
Phe Gly Arg Met Asp Gln Gln Ile Lys Ile Arg Gly His Arg Ile Glu
    370                 375                 380

Pro Ala Glu Val Glu His Ala Val Leu Asp Asn Ser Met Val Gln Asp
385                 390                 395                 400

Ala Ala Val

<210> SEQ ID NO 30
<211> LENGTH: 225
<212> TYPE: PRT
<213> ORGANISM: Curvularia clavata

<400> SEQUENCE: 30

Asp Gly Ser Ala Ile Asp Lys Asp Glu Met Gln Glu Trp Leu Asp Asp
1               5                   10                  15

Thr Met Ser Thr Leu Leu Asp Gly Arg Gln Pro Gly His Val Leu Glu
            20                  25                  30

Ile Gly Thr Gly Thr Gly Met Ile Leu Phe Asn Leu Ala Glu Arg Met
        35                  40                  45

Gly Leu Lys Ser Tyr Val Gly Leu Asp Pro Ser Glu Lys Ala Thr Ser
50                  55                  60

Phe Val Lys Gln Ala Ile Lys Ser Arg Pro Ser Leu Ala Gly Lys Ala
65                  70                  75                  80

Glu Val His Val Gly Thr Ala Thr Asp Val Ala Arg Met Arg Asp Leu
                85                  90                  95

His Pro Glu Val Val Ile Asn Ser Val Ala Gln Tyr Phe Pro Ser
            100                 105                 110

Pro Glu Tyr Leu Ala Asp Val Val Gly Ala Leu Val Arg Ile Pro Gly
        115                 120                 125

Val Lys Arg Leu Phe Phe Gly Asp Ile Arg Ser Tyr Ala Thr Asn Asn
130                 135                 140

His Phe Leu Ala Ala Arg Ala Leu His Lys Leu Gly Glu Lys Ala Thr
145                 150                 155                 160

Arg Asp Thr Val Arg Ser Lys Met Ala Glu Leu Glu Gly Tyr Glu Glu
                165                 170                 175

Glu Leu Leu Val Asp Pro Thr Phe Phe Thr Ser Leu Thr Ala Lys Leu
            180                 185                 190

His Gly Gln Val Glu His Val Glu Ile Leu Pro Lys Arg Met Gln Ala
        195                 200                 205

Thr Asn Glu Leu Ser Ala Tyr Arg Tyr Ala Ala Ile Val Tyr Ile Arg
    210                 215                 220

Asp
225

<210> SEQ ID NO 31
<211> LENGTH: 69
<212> TYPE: PRT
<213> ORGANISM: Curvularia clavata

<400> SEQUENCE: 31

Val Glu Ala Val Leu Cys Glu Glu Phe Thr Asp Val Leu Gly Val Glu
1               5                   10                  15

Val Gly Ile Thr Asp Asn Phe Phe Asp Leu Gly Gly His Ser Leu Met
            20                  25                  30

Ala Thr Lys Leu Ala Ala Arg Ile Ser Lys His Leu Asp Ala Arg Val
        35                  40                  45
```

```
Ser Val Lys Asp Val Phe Asp Tyr Pro Val Val Ala Asp Leu Ala Ala
 50                  55                  60

Ser Ile Glu Arg Asn
 65
```

<210> SEQ ID NO 32
<211> LENGTH: 296
<212> TYPE: PRT
<213> ORGANISM: Curvularia clavata

<400> SEQUENCE: 32

```
Gly Pro Val Glu Gln Ser Phe Ala Gln Gly Arg Leu Trp Phe Leu Asp
  1               5                  10                  15

Gln Leu Asn Met Gly Val Ser Glu Leu Tyr Leu Met Pro Leu Ala Leu
             20                  25                  30

Arg Leu Arg Gly Pro Leu Arg Val Asp Ala Phe Ala Ala Ala Val Ser
         35                  40                  45

Ala Leu Glu Ala Arg His Glu Thr Leu Arg Thr Thr Phe Met Asp His
 50                  55                  60

Asp Gly Val Gly Met Gln Val Ile Leu Pro Ser Asn Ser Lys Lys Leu
 65                  70                  75                  80

Arg Val Ile Asp Ala Ser Glu Asn Asp Tyr Ile Asp Ile Leu Arg Gln
                 85                  90                  95

Glu Arg Thr Ala Pro Phe Asn Leu Thr Thr Glu Pro Gly Phe Arg Ile
            100                 105                 110

Ala Leu Leu Gln Leu Gly Gln Thr Asp Phe Ile Leu Ser Ile Val Met
        115                 120                 125

His His Ile Ile Tyr Asp Gly Trp Ser Ile Asp Val Leu Cys Arg Glu
130                 135                 140

Leu Gly Arg Phe Tyr Ser Ala Ala Leu Gln Gly Gln Asp Pro Leu Ala
145                 150                 155                 160

Gln Val Ser Pro Leu Pro Ile Gln Tyr Arg Asp Phe Ser Ile Trp Gln
                165                 170                 175

Lys Arg Pro Glu Gln Val Ala Glu His Glu Arg Gln Leu Gln Tyr Trp
            180                 185                 190

Thr Glu Gln Leu Ala Asp Ser Ser Pro Ala Glu Leu Leu Thr Asp Leu
        195                 200                 205

Pro Arg Pro Leu Val Pro Thr Gly Lys Ala Gly Ile Val Gln Leu Thr
210                 215                 220

Ile Glu Gly Ala Val Tyr Glu Arg Leu Arg Ala Phe Cys Arg Val His
225                 230                 235                 240

Gln Thr Thr Ser Phe Ala Val Leu Leu Ala Ala Phe Arg Ala Thr His
                245                 250                 255

Tyr Arg Leu Thr Gly Ala Glu Asp Ala Thr Ile Gly Ser Pro Ile Ala
            260                 265                 270

Asn Arg Asn Arg Pro Glu Leu Glu Ser Leu Ile Gly Phe Phe Val Asn
        275                 280                 285

Thr Gln Cys Ile Arg Val Thr Ile
        290                 295
```

<210> SEQ ID NO 33
<211> LENGTH: 405
<212> TYPE: PRT
<213> ORGANISM: Curvularia clavata

<400> SEQUENCE: 33

```
Leu Thr Tyr Ala Gln Leu Asp Glu Lys Ser Asp Gln Leu Ala Ala Trp
1               5                   10                  15

Leu Cys Gln His Asn Ile Pro Ala Glu Thr Ile Val Gly Val Leu Ala
            20                  25                  30

Pro Arg Ser Cys Glu Thr Ile Ile Ala Phe Leu Gly Ile Leu Lys Ala
        35                  40                  45

Asn Leu Ala Tyr Leu Pro Leu Asp Asp Asn Val Pro Ala Ala Arg Ile
    50                  55                  60

Glu Thr Ile Leu Ser Ala Val Pro Gly His Thr Leu Val Leu Leu Gly
65                  70                  75                  80

Ser His Val Ala Ala Pro Ser Ile Gly Leu Ala Asp Ala Glu Phe Val
                85                  90                  95

Asn Ile Asn His Thr Leu Gly His Ser Leu Gln Leu Asn Ser Thr Cys
                100                 105                 110

Ala Lys Leu Gln Pro Ser Ala Thr Ser Leu Ala Tyr Val Ile Phe Thr
            115                 120                 125

Ser Gly Ser Thr Gly Lys Pro Lys Gly Val Met Ile Glu His Arg Ser
        130                 135                 140

Ile Val Arg Leu Val Lys Asn Ser Asn Thr Leu Ala Lys Leu Pro Arg
145                 150                 155                 160

Ala Ala Arg Val Ala His Gln Phe Asn Leu Ala Phe Asp Ala Ala Asn
                165                 170                 175

Tyr Glu Ile Tyr Gly Thr Leu Leu Asn Gly Gly Ala Leu Ile Cys Val
            180                 185                 190

Asp Tyr Ser Thr Leu Leu Asp Ile Asp Ala Leu Val Ala Met Phe Lys
        195                 200                 205

Arg Glu Lys Ile Thr Ala Ser Ser Leu Ser Pro Gly Leu Leu Lys Gln
    210                 215                 220

Cys Val Asn Ser Ala Pro Glu Met Leu Lys Ala Leu Gln Val Ile Tyr
225                 230                 235                 240

Thr Gly Gly Asp Arg Leu Asp Gly Arg Asp Ala Ile Glu Leu Gln Ala
                245                 250                 255

Leu Val Pro Gly Gly Val Tyr Asn Met Tyr Gly Pro Thr Glu Asn Thr
            260                 265                 270

Val Ile Ser Thr Leu Tyr Asn Leu Gly Asp Lys His Ser Tyr Val Asn
        275                 280                 285

Gly Val Pro Ile Gly Thr Thr Val Ser Asn Ser Gly Ala Tyr Val Met
    290                 295                 300

Asp Ala Leu Gln Gln Leu Val Pro Val Gly Val Met Gly Glu Leu Val
305                 310                 315                 320

Val Thr Gly Asp Gly Leu Ala Arg Gly Tyr Thr Asp Pro Glu Leu Asp
                325                 330                 335

Arg Asn Arg Phe Ile Lys Val Asn Ile Asp Gly Gln Val Val Arg Ala
            340                 345                 350

Tyr Arg Thr Gly Asp Arg Val Arg Tyr Arg Arg Ile Asp Gly Gln Leu
        355                 360                 365

Glu Phe Phe Gly Arg Met Asp Gln Gln Ile Lys Ile Arg Gly Phe Arg
    370                 375                 380

Ile Glu Thr Ala Glu Val Glu Asn Ala Met Leu Ser His Ser Ala Val
385                 390                 395                 400

Arg Asn Ala Ala Val
                405
```

<210> SEQ ID NO 34
<211> LENGTH: 67
<212> TYPE: PRT
<213> ORGANISM: Curvularia clavata

<400> SEQUENCE: 34

```
Leu Glu Ala Ser Leu Cys Lys Glu Phe Ala Glu Val Leu Gly Val Glu
1               5                   10                  15

Val Gly Ile Thr Asp Asn Phe Phe Asp Leu Gly Gly His Ser Leu Leu
            20                  25                  30

Ala Thr Lys Leu Ala Ala Arg Ile Ser Arg Arg Leu Asp Thr Arg Val
        35                  40                  45

Ser Val Lys Asp Val Phe Asp Gln Pro Val Pro Ala Asp Leu Ala Leu
    50                  55                  60

Lys Val Ser
65
```

<210> SEQ ID NO 35
<211> LENGTH: 277
<212> TYPE: PRT
<213> ORGANISM: Curvularia clavata

<400> SEQUENCE: 35

```
Val Asp Val Tyr Pro Val Thr Trp Ile Gln Lys His Phe Leu Val Asp
1               5                   10                  15

Pro Ala Thr Gly Leu Pro Arg Thr Pro Ser Leu Phe Phe Val Asp Phe
            20                  25                  30

Pro Ala Asn Ala Asp Cys Asp Lys Ile Cys Asn Ala Ser Arg Ser Leu
        35                  40                  45

Ile Gln Leu Phe Asp Ile Phe Arg Thr Val Phe Val Gln Ala Ala Gly
    50                  55                  60

Asn Phe Tyr Gln Val Val Leu Glu Glu Leu Asp Ile Pro Ile Ser Val
65                  70                  75                  80

Ile Glu Thr Glu Asp Ile Ser Thr Ala Thr Arg Val Leu Lys Glu Gln
                85                  90                  95

Asp Gln Gln Asn Pro Leu Gln Phe Gly Gln Gly Phe Leu Arg Phe Ala
            100                 105                 110

Val Val Lys Thr Arg Ser Ala Val Arg Leu Val Leu Arg Ile Ser His
        115                 120                 125

Cys Leu Tyr Asp Gly Leu Ser Phe Glu His Val Val Gln Ser Leu His
    130                 135                 140

Ala Leu Tyr Asn Gly Asp Arg Ile Pro Thr Gln Pro Lys Phe Val Gln
145                 150                 155                 160

Tyr Val Gln His Leu Thr Asp Ser Arg Lys Glu Gly Tyr Asp Phe Trp
                165                 170                 175

Leu Ser Val Leu Glu Glu Ser Ser Met Thr Val Val Glu Thr Gly Arg
            180                 185                 190

Arg Ala Gln Gln Leu Ser Ser Pro Glu Gly Ala Trp Phe Val Glu Lys
        195                 200                 205

Ile Ile Lys Ala Val Ile Pro Ala Asn Ser Asp Gly Ile Thr Gln Ala
    210                 215                 220

Thr Val Phe Thr Thr Ala Ser Thr Ile Leu Leu Ala Arg Met Thr Gly
225                 230                 235                 240

Ser Ser Asp Ile Thr Phe Ser Arg Leu Val Ser Gly Arg Gln Ser Leu
                245                 250                 255
```

```
Pro Ile Asn Asp Gln His Ile Val Gly Pro Cys Thr Asn Ile Val Pro
            260                 265                 270

Val Arg Ile Arg Met
        275

<210> SEQ ID NO 36
<211> LENGTH: 39126
<212> TYPE: DNA
<213> ORGANISM: Curvularia clavata
<220> FEATURE:
<221> NAME/KEY: CDS
<222> LOCATION: (1)..(39126)

<400> SEQUENCE: 36 atg gcc agc gac atc aat act cat cca gag gga gcg acc aag ttt tgg      48
Met Ala Ser Asp Ile Asn Thr His Pro Glu Gly Ala Thr Lys Phe Trp
1               5                   10                  15 cag caa cac ttt gac ggc ttg aac gcc tct gtg ttt cct gct ctg tcc      96
Gln Gln His Phe Asp Gly Leu Asn Ala Ser Val Phe Pro Ala Leu Ser
            20                  25                  30 tcc cat ttg act gtc ccg cgt ccc aac gcg cag aca gca cat cgc att    144
Ser His Leu Thr Val Pro Arg Pro Asn Ala Gln Thr Ala His Arg Ile
        35                  40                  45 tcc tat tca acc ttg gcg aag caa aaa tgg gac aac acc agc ctt tgc    192
Ser Tyr Ser Thr Leu Ala Lys Gln Lys Trp Asp Asn Thr Ser Leu Cys
    50                  55                  60 cga gct gcg ctc gca ata ctg ctt gcc cgc tat tcg aat gca tct gaa    240
Arg Ala Ala Leu Ala Ile Leu Leu Ala Arg Tyr Ser Asn Ala Ser Glu
65                  70                  75                  80 gca ctc ttc ggc gtc ttg gta gaa cag ttt ctc ccg tcc aac ggt gaa    288
Ala Leu Phe Gly Val Leu Val Glu Gln Phe Leu Pro Ser Asn Gly Glu
                85                  90                  95 cag gca tcg aca gag gaa tca cca caa agc atc ctt ccc atc cgc atc    336
Gln Ala Ser Thr Glu Glu Ser Pro Gln Ser Ile Leu Pro Ile Arg Ile
            100                 105                 110 cga ctt gac ctt gag gaa gct ggg ttg ggc ctt ttg caa gct atc aat    384
Arg Leu Asp Leu Glu Glu Ala Gly Leu Gly Leu Leu Gln Ala Ile Asn
        115                 120                 125 acc cta gat gca tct ctg cgc gag tgg aag cat atc ggt ctt gac gcc    432
Thr Leu Asp Ala Ser Leu Arg Glu Trp Lys His Ile Gly Leu Asp Ala
    130                 135                 140 att cgt ggc acg gga gag tac ggg tct gcc gga tgc gag ttc cag aca    480
Ile Arg Gly Thr Gly Glu Tyr Gly Ser Ala Gly Cys Glu Phe Gln Thr
145                 150                 155                 160 gta ctt gct gtc act act gga aag acg cca cga acg cat aga ctc gcg    528
Val Leu Ala Val Thr Thr Gly Lys Thr Pro Arg Thr His Arg Leu Ala
                165                 170                 175 tct tgc act gat cgc gcc ctt ttg ctc gat tgc cga atg gac gac gat    576
Ser Cys Thr Asp Arg Ala Leu Leu Leu Asp Cys Arg Met Asp Asp Asp
            180                 185                 190 tcg gcc aca ctt ctc gca cgc tat gat ccc agt gtg att gat gac ctc    624
Ser Ala Thr Leu Leu Ala Arg Tyr Asp Pro Ser Val Ile Asp Asp Leu
        195                 200                 205 cag gtc gcc cgt ttc cta aaa cag ctc ggg cac gtg att gag caa ttg    672
Gln Val Ala Arg Phe Leu Lys Gln Leu Gly His Val Ile Glu Gln Leu
    210                 215                 220 cgt gtc cag gca gtc gat cta cct ctc tgg gaa ctt ggt att gtc acg    720
Arg Val Gln Ala Val Asp Leu Pro Leu Trp Glu Leu Gly Ile Val Thr
225                 230                 235                 240 caa gaa gat agc gca gag att caa aaa tgg aac tcg cag caa ctc caa    768
Gln Glu Asp Ser Ala Glu Ile Gln Lys Trp Asn Ser Gln Gln Leu Gln
```

```
                    245                 250                 255
ttc agc cag gaa tgc ata cac gac gtg ttc gcc aac agg gtg gtt gat      816
Phe Ser Gln Glu Cys Ile His Asp Val Phe Ala Asn Arg Val Val Asp
            260                 265                 270 acg ccg cag aaa atc gcc gta tcc gct tgg aac ggc gag cta acg ttt      864
Thr Pro Gln Lys Ile Ala Val Ser Ala Trp Asn Gly Glu Leu Thr Phe
        275                 280                 285 gct gaa ctt gac agc ttc tcc tca tgc ctc gcc cag cac atc caa tcg      912
Ala Glu Leu Asp Ser Phe Ser Ser Cys Leu Ala Gln His Ile Gln Ser
    290                 295                 300 ctt gaa ttg ggc gat gca aaa gcg ata ccg ctt tgc ttt gag aag tca      960
Leu Glu Leu Gly Asp Ala Lys Ala Ile Pro Leu Cys Phe Glu Lys Ser
305                 310                 315                 320 aaa tgg gct atc gtc ggg atg ctc ggt gtg ctc aag gct ggc cga gca     1008
Lys Trp Ala Ile Val Gly Met Leu Gly Val Leu Lys Ala Gly Arg Ala
                325                 330                 335 ttc aca ctg att gac cca tct aac cca ccc gct agg gct cgt caa atc     1056
Phe Thr Leu Ile Asp Pro Ser Asn Pro Pro Ala Arg Ala Arg Gln Ile
            340                 345                 350 tgt cga caa aca gcc gcc acc att tcc atc gcg tct cca tac cag tgc     1104
Cys Arg Gln Thr Ala Ala Thr Ile Ser Ile Ala Ser Pro Tyr Gln Cys
        355                 360                 365 gat atg atg cgc gct ctg gtg ccc gac tgc atc gtg gtc gac gac gac     1152
Asp Met Met Arg Ala Leu Val Pro Asp Cys Ile Val Val Asp Asp Asp
    370                 375                 380 ttt ttc aag tca ttg gcg ttt gat aca gat caa ttc cag cct acg gca     1200
Phe Phe Lys Ser Leu Ala Phe Asp Thr Asp Gln Phe Gln Pro Thr Ala
385                 390                 395                 400 acg ccg cag aca ttg gcc tac atc ctc ttc act tct ggt agt acc gga     1248
Thr Pro Gln Thr Leu Ala Tyr Ile Leu Phe Thr Ser Gly Ser Thr Gly
                405                 410                 415 gag cca aaa ggc agt atg atg gag cat cac gga ttt gtg tct tgc tgt     1296
Glu Pro Lys Gly Ser Met Met Glu His His Gly Phe Val Ser Cys Cys
            420                 425                 430 ctc gaa ttt ggt gcg gcg ctg ggc atc aac agc aac aca cgc gct ctt     1344
Leu Glu Phe Gly Ala Ala Leu Gly Ile Asn Ser Asn Thr Arg Ala Leu
        435                 440                 445 caa ttt gcc tct tat gct ttc ggt gct tgc ctg cta gag att ttg acc     1392
Gln Phe Ala Ser Tyr Ala Phe Gly Ala Cys Leu Leu Glu Ile Leu Thr
    450                 455                 460 acc cta atg cac ggc ggc acg gtc tgc atc cca tct gat gat gaa cgc     1440
Thr Leu Met His Gly Gly Thr Val Cys Ile Pro Ser Asp Asp Glu Arg
465                 470                 475                 480 ata aat gat gca ccc ggg ttt atc aga cgc gca aac gtt aac tgg gca     1488
Ile Asn Asp Ala Pro Gly Phe Ile Arg Arg Ala Asn Val Asn Trp Ala
                485                 490                 495 att ctc act cct tct ttc att ggc gcc atc cag ccc acc acc gta cct     1536
Ile Leu Thr Pro Ser Phe Ile Gly Ala Ile Gln Pro Thr Thr Val Pro
            500                 505                 510 aac ctc aag acg ctg gta ttg gtg gga gaa gcc atg ccg tca gac ata     1584
Asn Leu Lys Thr Leu Val Leu Val Gly Glu Ala Met Pro Ser Asp Ile
        515                 520                 525 cgc gat gtc tgg gcc tcg cac gtt cag ctt aaa aat gcc tat ggc cag     1632
Arg Asp Val Trp Ala Ser His Val Gln Leu Lys Asn Ala Tyr Gly Gln
    530                 535                 540 agc gag agc gca acg atc tgt agc gta acg gaa gtc act ccc gcg acg     1680
Ser Glu Ser Ala Thr Ile Cys Ser Val Thr Glu Val Thr Pro Ala Thr
545                 550                 555                 560 gtg gag gcg cac aat atc ggt cac gct gtg ggc gcc cga ttc tgg att     1728
```

-continued

| | | |
|---|---|---|
| Val Glu Ala His Asn Ile Gly His Ala Val Gly Ala Arg Phe Trp Ile<br>                        565                            570                          575 | |
| acc gac ccc aat aat ccc aac aaa ctt gcg cca atc ggc tgc gta ggc<br>Thr Asp Pro Asn Asn Pro Asn Lys Leu Ala Pro Ile Gly Cys Val Gly<br>                  580                            585                        590 | 1776 |
| gag ctg ctt gtt gaa agt cct ggc atc gcg cgt gga tat ctg att cct<br>Glu Leu Leu Val Glu Ser Pro Gly Ile Ala Arg Gly Tyr Leu Ile Pro<br>            595                            600                        605 | 1824 |
| ctg cca gcg gac gca aca cct ttc att gac acg ctt cct gat tgg tac<br>Leu Pro Ala Asp Ala Thr Pro Phe Ile Asp Thr Leu Pro Asp Trp Tyr<br>     610                           615                        620 | 1872 |
| cca agg acg cag ccg ctc gac aac ttc aag ttc tac aga act ggc gat<br>Pro Arg Thr Gln Pro Leu Asp Asn Phe Lys Phe Tyr Arg Thr Gly Asp<br>625                        630                            635                        640 | 1920 |
| ctt gtc tgc tac cga tcc gac ggc acc gtg gtg tat ctg ggg cga cga<br>Leu Val Cys Tyr Arg Ser Asp Gly Thr Val Val Tyr Leu Gly Arg Arg<br>                        645                            650                        655 | 1968 |
| gac tcg caa att aag atc cga gga cag cgc gtc gaa atc ggc gaa gta<br>Asp Ser Gln Ile Lys Ile Arg Gly Gln Arg Val Glu Ile Gly Glu Val<br>                  660                            665                        670 | 2016 |
| gaa aca tgc ttg cga caa cag ctt ccc agt caa ctg gta cca gtt gtc<br>Glu Thr Cys Leu Arg Gln Gln Leu Pro Ser Gln Leu Val Pro Val Val<br>            675                            680                        685 | 2064 |
| gaa gct gtc agt ctg tcg ggc atg tcc aag agc atg acg ctg att gcc<br>Glu Ala Val Ser Leu Ser Gly Met Ser Lys Ser Met Thr Leu Ile Ala<br>     690                           695                        700 | 2112 |
| ttt ctg gtt ggc gaa aac acc att ctg gaa gag gac gtt tac gtt ttg<br>Phe Leu Val Gly Glu Asn Thr Ile Leu Glu Glu Asp Val Tyr Val Leu<br>705                        710                            715                        720 | 2160 |
| gag ggc agt gcc gcg cag cgc atc agt tcg aaa ctg cga cag att gta<br>Glu Gly Ser Ala Ala Gln Arg Ile Ser Ser Lys Leu Arg Gln Ile Val<br>                        725                            730                        735 | 2208 |
| ccc ggg tac tgc att ccg tct cac tat att cgc atc aac cat ctt ccc<br>Pro Gly Tyr Cys Ile Pro Ser His Tyr Ile Arg Ile Asn His Leu Pro<br>                  740                            745                        750 | 2256 |
| act acc gcc act gga aag tgt gat cgg aaa gca ctt cga gcc atc ggt<br>Thr Thr Ala Thr Gly Lys Cys Asp Arg Lys Ala Leu Arg Ala Ile Gly<br>            755                            760                        765 | 2304 |
| acc aaa ttg ctt agg gaa gcc gtg gag ggc atg gcg tca cag gag gaa<br>Thr Lys Leu Leu Arg Glu Ala Val Glu Gly Met Ala Ser Gln Glu Glu<br>     770                           775                        780 | 2352 |
| cag gag agt gct tcg tta atg acc gaa ggg att aca ctg gaa cgc atc<br>Gln Glu Ser Ala Ser Leu Met Thr Glu Gly Ile Thr Leu Glu Arg Ile<br>785                        790                            795                        800 | 2400 |
| tgg ttc cag agc ctg ggt ctc aag ccc aac tcc acg aga cac aaa tct<br>Trp Phe Gln Ser Leu Gly Leu Lys Pro Asn Ser Thr Arg His Lys Ser<br>                        805                            810                        815 | 2448 |
| aac ttc ttc aat ctg ggc ggc gac tcc att gcg gca atc cgg atg gtg<br>Asn Phe Phe Asn Leu Gly Gly Asp Ser Ile Ala Ala Ile Arg Met Val<br>                  820                            825                        830 | 2496 |
| aac atg gca cgg gca gca ggc ttg ttg ctg agc atc tcc gat atc ttt<br>Asn Met Ala Arg Ala Ala Gly Leu Leu Leu Ser Ile Ser Asp Ile Phe<br>            835                            840                        845 | 2544 |
| cag aac ccc tca ctg gcg ggg ctc atc aat gtg atg cag cag agc tcg<br>Gln Asn Pro Ser Leu Ala Gly Leu Ile Asn Val Met Gln Gln Ser Ser<br>     850                           855                        860 | 2592 |
| act gca caa gac gct att ccc gcc acc gag tac agc ggg ccg gtc gag<br>Thr Ala Gln Asp Ala Ile Pro Ala Thr Glu Tyr Ser Gly Pro Val Glu<br>865                        870                            875                        880 | 2640 |

-continued

| | |
|---|---|
| cag tcg ttt gca cag ggc cgt ttg tgg ttc ttg gat cag ctc acg acc<br>Gln Ser Phe Ala Gln Gly Arg Leu Trp Phe Leu Asp Gln Leu Thr Thr<br>                     885                   890                 895 | 2688 |
| ggc gca tcg tgg tac cta atg cca ctt gcg gtc cgc att cac ggg ccg<br>Gly Ala Ser Trp Tyr Leu Met Pro Leu Ala Val Arg Ile His Gly Pro<br>                   900                   905                   910 | 2736 |
| ctc cgc gtc caa gcc ctt tcc agc gcc ctg cat gct ttg gag cag cgc<br>Leu Arg Val Gln Ala Leu Ser Ser Ala Leu His Ala Leu Glu Gln Arg<br>                   915                   920                   925 | 2784 |
| cac gag acg cta cga acg acg ttc gag cag caa gac ggt atg ggc gtg<br>His Glu Thr Leu Arg Thr Thr Phe Glu Gln Gln Asp Gly Met Gly Val<br>                   930                   935                   940 | 2832 |
| cag att gtc cac cca agc agc aag agg gag ctg cgc gtc atc gac gtg<br>Gln Ile Val His Pro Ser Ser Lys Arg Glu Leu Arg Val Ile Asp Val<br>945                   950                   955                   960 | 2880 |
| tcg ggt aag cag aac ggc ggc tac gat cag gtg ttg aag cga gag cag<br>Ser Gly Lys Gln Asn Gly Gly Tyr Asp Gln Val Leu Lys Arg Glu Gln<br>                   965                   970                   975 | 2928 |
| aca aca ccc atc gac ttg gcc aaa gag ccc gga tgg aga gcc gcg ctg<br>Thr Thr Pro Ile Asp Leu Ala Lys Glu Pro Gly Trp Arg Ala Ala Leu<br>                   980                   985                   990 | 2976 |
| cta cga gtg ggc gac gat gag cac atc ctc tcg att gtc atc cac cac<br>Leu Arg Val Gly Asp Asp Glu His Ile Leu Ser Ile Val Ile His His<br>                   995                  1000               1005 | 3024 |
| atc ata tac gac ggt tgg tcg ctg ggc gta ctg cgt gag gaa ctc<br>Ile Ile Tyr Asp Gly Trp Ser Leu Gly Val Leu Arg Glu Glu Leu<br>1010                1015                1020 | 3069 |
| ggc gac ctt tat gcg gcg gcg ctg cga ggt ccc gat cca ctc gca<br>Gly Asp Leu Tyr Ala Ala Ala Leu Arg Gly Pro Asp Pro Leu Ala<br>1025                1030                1035 | 3114 |
| cac atg gcc ccg ctc ccg atc cag tac cgc gac ttc tct gtt tgg<br>His Met Ala Pro Leu Pro Ile Gln Tyr Arg Asp Phe Ser Val Trp<br>1040                1045                1050 | 3159 |
| cag aag cag cca cag caa gtg gcg cag cac caa caa cag ctc gtg<br>Gln Lys Gln Pro Gln Gln Val Ala Gln His Gln Gln Gln Leu Val<br>1055                1060                1065 | 3204 |
| tac tgg aca aag cag ctt gaa gac agc gcg cct gca gag ctg ctt<br>Tyr Trp Thr Lys Gln Leu Glu Asp Ser Ala Pro Ala Glu Leu Leu<br>1070                1075                1080 | 3249 |
| acc gac ttc ccc cgc cct gcc gag tta tct ggc cgt gcc ggt gag<br>Thr Asp Phe Pro Arg Pro Ala Glu Leu Ser Gly Arg Ala Gly Glu<br>1085                1090                1095 | 3294 |
| gtt cgt ttc act atc gaa ggc agt gtc ttc gac agc ctg ctc gct<br>Val Arg Phe Thr Ile Glu Gly Ser Val Phe Asp Ser Leu Leu Ala<br>1100                1105                1110 | 3339 |
| ttt cgt cgc gtc cac cag acg aca tca ttt gcg gtg cta cta gcc<br>Phe Arg Arg Val His Gln Thr Thr Ser Phe Ala Val Leu Leu Ala<br>1115                1120                1125 | 3384 |
| gtc ttc cgt gct gcc cac tat cgt ctc acc ggc aca gag gac gcc<br>Val Phe Arg Ala Ala His Tyr Arg Leu Thr Gly Thr Glu Asp Ala<br>1130                1135                1140 | 3429 |
| aca atc ggc acg ccc atc gct aat cgt act cgt gct gag gtc gag<br>Thr Ile Gly Thr Pro Ile Ala Asn Arg Thr Arg Ala Glu Val Glu<br>1145                1150                1155 | 3474 |
| aag ctc atc ggt ttc ttt gtc aac acg cag tgt atg cgc att gct<br>Lys Leu Ile Gly Phe Phe Val Asn Thr Gln Cys Met Arg Ile Ala<br>1160                1165                1170 | 3519 |
| gtc gcc gac gat gac acc ttc gca tcg ctc gtc agt caa gtc tgg<br>Val Ala Asp Asp Asp Thr Phe Ala Ser Leu Val Ser Gln Val Trp<br>1175                1180                1185 | 3564 |

```
tcc gtc gcg act gcc gca ttc gag cat cag gat gtc ccc ttc gag    3609
Ser Val Ala Thr Ala Ala Phe Glu His Gln Asp Val Pro Phe Glu
    1190            1195                1200 cgt atc gtg tcg gcg ctc ctg ccc ggc gcc aga gac aca tct cgc    3654
Arg Ile Val Ser Ala Leu Leu Pro Gly Ala Arg Asp Thr Ser Arg
    1205            1210                1215 aac ccg ctg gcc cag ctc ctg ttt gcg ctc cat ctg gag cag gac    3699
Asn Pro Leu Ala Gln Leu Leu Phe Ala Leu His Leu Glu Gln Asp
    1220            1225                1230 ctc gac aag atc aat ctc gag ggc ttg gcc tgc gag act gta ccc    3744
Leu Asp Lys Ile Asn Leu Glu Gly Leu Ala Cys Glu Thr Val Pro
    1235            1240                1245 acg cca atg gcg act cgc ttc gac gtc gag ttc cat ctc ttc cag    3789
Thr Pro Met Ala Thr Arg Phe Asp Val Glu Phe His Leu Phe Gln
    1250            1255                1260 gaa gac gac aga ctg aac ggc gtc gtc aac ttc tcc acg gac ctc    3834
Glu Asp Asp Arg Leu Asn Gly Val Val Asn Phe Ser Thr Asp Leu
    1265            1270                1275 ttc gag ccc cag acc atc cac agc ctg gtc tct gtc ttt cag gag    3879
Phe Glu Pro Gln Thr Ile His Ser Leu Val Ser Val Phe Gln Glu
    1280            1285                1290 atc ctg cgc cgc ggc ctc gac caa cca cag acg cct att gca cat    3924
Ile Leu Arg Arg Gly Leu Asp Gln Pro Gln Thr Pro Ile Ala His
    1295            1300                1305 ctc cag ctg act gat ggg ctt gaa gag ctt cgc aat gcc ggc ctg    3969
Leu Gln Leu Thr Asp Gly Leu Glu Glu Leu Arg Asn Ala Gly Leu
    1310            1315                1320 ctg gac atc aag agg atc gac tac ccg cgc gag gcg agc gtt gta    4014
Leu Asp Ile Lys Arg Ile Asp Tyr Pro Arg Glu Ala Ser Val Val
    1325            1330                1335 gac atg ttc caa aag cag gta gcc gct tgc cct aac gtg act gcc    4059
Asp Met Phe Gln Lys Gln Val Ala Ala Cys Pro Asn Val Thr Ala
    1340            1345                1350 gtc aaa gat tcg acc tcg cag ctc acg tat gct caa ctg gat cag    4104
Val Lys Asp Ser Thr Ser Gln Leu Thr Tyr Ala Gln Leu Asp Gln
    1355            1360                1365 gag tct gac aag ata gcc gtt tgg ctg cgc aaa cgc aac att cca    4149
Glu Ser Asp Lys Ile Ala Val Trp Leu Arg Lys Arg Asn Ile Pro
    1370            1375                1380 gcc gag aca ttg att gcg ctg cta gca cct cga tcc tgt gac tcc    4194
Ala Glu Thr Leu Ile Ala Leu Leu Ala Pro Arg Ser Cys Asp Ser
    1385            1390                1395 gtg gct gcc ttc ctc ggt att ctc aaa gcc aat ctg gcc tat ctc    4239
Val Ala Ala Phe Leu Gly Ile Leu Lys Ala Asn Leu Ala Tyr Leu
    1400            1405                1410 cct ctg gat gtt aat gtc ccc gct gct cgt atc gag gca atc ctg    4284
Pro Leu Asp Val Asn Val Pro Ala Ala Arg Ile Glu Ala Ile Leu
    1415            1420                1425 tca acc gta gca ggt cac aaa ctg gtc ttg ctc gga cga gat gtg    4329
Ser Thr Val Ala Gly His Lys Leu Val Leu Leu Gly Arg Asp Val
    1430            1435                1440 cct ctg cta ggt acg cag ctg gcc gac ctc gag ctt gtc cgt atc    4374
Pro Leu Leu Gly Thr Gln Leu Ala Asp Leu Glu Leu Val Arg Ile
    1445            1450                1455 ggc gag gcg ctg cgt ggc tcg agt tca ggg agt gtc gcc gcc gac    4419
Gly Glu Ala Leu Arg Gly Ser Ser Ser Gly Ser Val Ala Ala Asp
    1460            1465                1470 aag gct att cga cct aca gca aca agc ctg gcc tac gtt atc ttc    4464
Lys Ala Ile Arg Pro Thr Ala Thr Ser Leu Ala Tyr Val Ile Phe
```

```
                   1475                1480                1485
acg tct gga tct act ggc cag cca aag ggt atc atg gtt cct cat       4509
Thr Ser Gly Ser Thr Gly Gln Pro Lys Gly Ile Met Val Pro His
    1490                1495                1500 cgc agc ttg gtc aac gtg atc aag cag cga cct gcc tat gga aat       4554
Arg Ser Leu Val Asn Val Ile Lys Gln Arg Pro Ala Tyr Gly Asn
    1505                1510                1515 gtc gct cac atg aca aat ctc gcc ttt gat ccc tcc ctg ttc gag       4599
Val Ala His Met Thr Asn Leu Ala Phe Asp Pro Ser Leu Phe Glu
    1520                1525                1530 atg tgc act gcc ttg ttc aat ggc aat acg ctg att tgc atc gac       4644
Met Cys Thr Ala Leu Phe Asn Gly Asn Thr Leu Ile Cys Ile Asp
    1535                1540                1545 aca ttg gta gca ctc gat gca act cag ctt cct acc atc ttc aag       4689
Thr Leu Val Ala Leu Asp Ala Thr Gln Leu Pro Thr Ile Phe Lys
    1550                1555                1560 cag gaa gca att cgt gtc gca atg atg acg ccg gcc ttg ctc acc       4734
Gln Glu Ala Ile Arg Val Ala Met Met Thr Pro Ala Leu Leu Thr
    1565                1570                1575 aga ctc cta gcc cag gct act gac gca ctg cat gaa cta gag gca       4779
Arg Leu Leu Ala Gln Ala Thr Asp Ala Leu His Glu Leu Glu Ala
    1580                1585                1590 ctt tat gtt ctg gga gat cga ttc cct cca aaa gat gct gcc aga       4824
Leu Tyr Val Leu Gly Asp Arg Phe Pro Pro Lys Asp Ala Ala Arg
    1595                1600                1605 gca agt gaa ctt gtc aaa acg gcc gta tac aat gcc tac gga ccg       4869
Ala Ser Glu Leu Val Lys Thr Ala Val Tyr Asn Ala Tyr Gly Pro
    1610                1615                1620 agt gag aac tcc atc tgc aca act ctc ttc cat gct gcc act ggc       4914
Ser Glu Asn Ser Ile Cys Thr Thr Leu Phe His Ala Ala Thr Gly
    1625                1630                1635 gcc atg tgt acc aat ggt gtg cct gtt ggc cga gta atc aac aac       4959
Ala Met Cys Thr Asn Gly Val Pro Val Gly Arg Val Ile Asn Asn
    1640                1645                1650 tcg ggc gta tat gtt atg gat cca aag cag tcg ctt gtt tcc tac       5004
Ser Gly Val Tyr Val Met Asp Pro Lys Gln Ser Leu Val Ser Tyr
    1655                1660                1665 ggc gtc atg ggt gag ctc gtc gtc gct ggc gaa ggc ctt gca att       5049
Gly Val Met Gly Glu Leu Val Val Ala Gly Glu Gly Leu Ala Ile
    1670                1675                1680 gga tat acc aag cca gaa ctc aac gaa ggc cgc ttt ctg acg ctt       5094
Gly Tyr Thr Lys Pro Glu Leu Asn Glu Gly Arg Phe Leu Thr Leu
    1685                1690                1695 aca atg gac gga aaa cct gta aga gcg ttt cgt acc gga gat cgt       5139
Thr Met Asp Gly Lys Pro Val Arg Ala Phe Arg Thr Gly Asp Arg
    1700                1705                1710 gtt cga tac cgg ccg aca gat ggt caa ctg gaa ttt ttt ggc cgc       5184
Val Arg Tyr Arg Pro Thr Asp Gly Gln Leu Glu Phe Phe Gly Arg
    1715                1720                1725 atg gac ttc caa att aag atc cga ggt cat cgt gtc gag ttg gct       5229
Met Asp Phe Gln Ile Lys Ile Arg Gly His Arg Val Glu Leu Ala
    1730                1735                1740 gaa gtg gaa cga gtt ttg aac agg cac cct gcc atc aaa gac gcc       5274
Glu Val Glu Arg Val Leu Asn Arg His Pro Ala Ile Lys Asp Ala
    1745                1750                1755 atc aca ctg ctg agg cag cac ggc tcc tca gca caa gac aca gag       5319
Ile Thr Leu Leu Arg Gln His Gly Ser Ser Ala Gln Asp Thr Glu
    1760                1765                1770 ctt gtc agt ttt att gtg cta gga gag cag aag cct gta aag ccc       5364
```

|   |   |   |   |   |   |   |   |   |   |   |   |   |   |
|---|---|---|---|---|---|---|---|---|---|---|---|---|---|
| Leu | Val | Ser | Phe | Ile | Val | Leu | Gly | Glu | Gln | Lys | Pro | Val | Lys | Pro |
| 1775 |  |  |  |  | 1780 |  |  |  |  | 1785 |  |  |  |  |

```
cat cga aac gcc acc gac cat ggc gga atg gag att gag caa ttg         5409
His Arg Asn Ala Thr Asp His Gly Gly Met Glu Ile Glu Gln Leu
1790            1795                1800 gac caa aag cta gaa gca aac ctg cgt gcc atg atg cag gct acg         5454
Asp Gln Lys Leu Glu Ala Asn Leu Arg Ala Met Met Gln Ala Thr
1805            1810                1815 ctg ccc tca tac atg gtt ccc tcg aga atc ata gtg cta gac cat         5499
Leu Pro Ser Tyr Met Val Pro Ser Arg Ile Ile Val Leu Asp His
1820            1825                1830 atg ccg ctc gac aag aat gga aag gtt gac cga cga gga ttg aca         5544
Met Pro Leu Asp Lys Asn Gly Lys Val Asp Arg Arg Gly Leu Thr
1835            1840                1845 gga ctg acg ctg agc cca gcc atg gaa aca agc tcg cgt gtt gtt         5589
Gly Leu Thr Leu Ser Pro Ala Met Glu Thr Ser Ser Arg Val Val
1850            1855                1860 gtg gca gca cgg aac gag atc gag gcc gta ctg tgc gag gag ttt         5634
Val Ala Ala Arg Asn Glu Ile Glu Ala Val Leu Cys Glu Glu Phe
1865            1870                1875 gct cac atc ctt ggt gtt gaa att ggc gtc act gat aac ttc ttc         5679
Ala His Ile Leu Gly Val Glu Ile Gly Val Thr Asp Asn Phe Phe
1880            1885                1890 gac ctc ggc gga cat tca ctc atg gct act act ctc gct gct cgc         5724
Asp Leu Gly Gly His Ser Leu Met Ala Thr Thr Leu Ala Ala Arg
1895            1900                1905 ctc gct cgc cgt ctt aat gct agc att tcc gtc aag gat gtc ttc         5769
Leu Ala Arg Arg Leu Asn Ala Ser Ile Ser Val Lys Asp Val Phe
1910            1915                1920 gat cag cct att gtc gct aat ctc gcc gcc aca atc aag cga ggc         5814
Asp Gln Pro Ile Val Ala Asn Leu Ala Ala Thr Ile Lys Arg Gly
1925            1930                1935 tcg acc cct cac aat gca atc cct cca act aaa tac tct ggg ccg         5859
Ser Thr Pro His Asn Ala Ile Pro Pro Thr Lys Tyr Ser Gly Pro
1940            1945                1950 gtt gaa cag tcc ttc gca caa ggt cgt ctc tgg ttt ctg gac caa         5904
Val Glu Gln Ser Phe Ala Gln Gly Arg Leu Trp Phe Leu Asp Gln
1955            1960                1965 ctg aac ctt ggg gct gcc tgg tat cat atg cct ctt gca gtg cgt         5949
Leu Asn Leu Gly Ala Ala Trp Tyr His Met Pro Leu Ala Val Arg
1970            1975                1980 ttg cgc ggg cct ctc cat ctt gag gca ctc act gca gcg ctg cat         5994
Leu Arg Gly Pro Leu His Leu Glu Ala Leu Thr Ala Ala Leu His
1985            1990                1995 gcc ctt gag gag cgc cac gag acg tta cgg aca gta ttt gag gaa         6039
Ala Leu Glu Glu Arg His Glu Thr Leu Arg Thr Val Phe Glu Glu
2000            2005                2010 caa gat ggt gtg ggc atg cag atc gtc cgg cca agc agc aag acg         6084
Gln Asp Gly Val Gly Met Gln Ile Val Arg Pro Ser Ser Lys Thr
2015            2020                2025 ccg ctg cga ata atc gac gtg tcc act aaa gag cga ggt tat gcc         6129
Pro Leu Arg Ile Ile Asp Val Ser Thr Lys Glu Arg Gly Tyr Ala
2030            2035                2040 gag ttg ctc aag cag gag caa aca aca cca ttc gat cta gcc aca         6174
Glu Leu Leu Lys Gln Glu Gln Thr Thr Pro Phe Asp Leu Ala Thr
2045            2050                2055 gag tta ggg tgg agg gtg gct ctg ctg agg caa ggg aag gat gac         6219
Glu Leu Gly Trp Arg Val Ala Leu Leu Arg Gln Gly Lys Asp Asp
2060            2065                2070
```

```
cat att ctg tca att gtc att cac cac atc att tcc gac ggt tgg    6264
His Ile Leu Ser Ile Val Ile His His Ile Ile Ser Asp Gly Trp
    2075            2080                2085 tct ctc gat atc ttg tgc gag gaa ctt ggt cag ttc tac gcc gct    6309
Ser Leu Asp Ile Leu Cys Glu Glu Leu Gly Gln Phe Tyr Ala Ala
    2090            2095                2100 gtg ctc cgt ggc cag gac cca tta gcc caa ata agc cct ctg cct    6354
Val Leu Arg Gly Gln Asp Pro Leu Ala Gln Ile Ser Pro Leu Pro
    2105            2110                2115 atc cag tat cgc gat ttc tct ctg tgg cag aag cag cct gag caa    6399
Ile Gln Tyr Arg Asp Phe Ser Leu Trp Gln Lys Gln Pro Glu Gln
    2120            2125                2130 gtt gct gag cac cac cgg caa ctc gag tac tgg acc acc cag ctc    6444
Val Ala Glu His His Arg Gln Leu Glu Tyr Trp Thr Thr Gln Leu
    2135            2140                2145 gag ggc agc gta cct gca gag ctt cta acc gat ctt cct cga cca    6489
Glu Gly Ser Val Pro Ala Glu Leu Leu Thr Asp Leu Pro Arg Pro
    2150            2155                2160 acc ata cag tcc ggc aag gca ggc gtc atc cca ata acc gtc aac    6534
Thr Ile Gln Ser Gly Lys Ala Gly Val Ile Pro Ile Thr Val Asn
    2165            2170                2175 ggc cct gta tac gag cgt cta cgg gcc ttc tct cga gct cat caa    6579
Gly Pro Val Tyr Glu Arg Leu Arg Ala Phe Ser Arg Ala His Gln
    2180            2185                2190 acg acc gct ttt gcg gta ctg ttg gcc gcc ttt cga gca act cat    6624
Thr Thr Ala Phe Ala Val Leu Leu Ala Ala Phe Arg Ala Thr His
    2195            2200                2205 tac cgt ctc tct gga gtc gca gac gct acc atc ggc acg cca atc    6669
Tyr Arg Leu Ser Gly Val Ala Asp Ala Thr Ile Gly Thr Pro Ile
    2210            2215                2220 gcc aac cgt aat cga cct gaa ctg gag aat atg ata ggc ttt ttc    6714
Ala Asn Arg Asn Arg Pro Glu Leu Glu Asn Met Ile Gly Phe Phe
    2225            2230                2235 gta aat gcc cag tgt atg cgt atc act gtc gag caa gac gat act    6759
Val Asn Ala Gln Cys Met Arg Ile Thr Val Glu Gln Asp Asp Thr
    2240            2245                2250 ttt gag aca ctt gtc cgc cag atc cga ttt acg gca act gcc gcc    6804
Phe Glu Thr Leu Val Arg Gln Ile Arg Phe Thr Ala Thr Ala Ala
    2255            2260                2265 ttt gcc aac caa gat gta ccc ttt gag cat atc gtc tca gcc ctt    6849
Phe Ala Asn Gln Asp Val Pro Phe Glu His Ile Val Ser Ala Leu
    2270            2275                2280 atg cct gac tca cgc gat aca tcg cgg aat ccg cta gtg cag ctc    6894
Met Pro Asp Ser Arg Asp Thr Ser Arg Asn Pro Leu Val Gln Leu
    2285            2290                2295 atg ttc gca ctc cac gcg tac aaa gat ctc ggc aag att gag ctt    6939
Met Phe Ala Leu His Ala Tyr Lys Asp Leu Gly Lys Ile Glu Leu
    2300            2305                2310 gaa ggt tat gtt gca gag cct gtg cat aca act ctg tca acc cgc    6984
Glu Gly Tyr Val Ala Glu Pro Val His Thr Thr Leu Ser Thr Arg
    2315            2320                2325 ttc gat ctc gaa ttc cac atg ttc cag gag aca aat cac ctc agc    7029
Phe Asp Leu Glu Phe His Met Phe Gln Glu Thr Asn His Leu Ser
    2330            2335                2340 ggc tac gta ctg tat gca aca gac ttg ttc gag cct gag agc att    7074
Gly Tyr Val Leu Tyr Ala Thr Asp Leu Phe Glu Pro Glu Ser Ile
    2345            2350                2355 gag ggg atg gtt tcc att ttt aaa gaa atc ctc gct cga gct ctt    7119
Glu Gly Met Val Ser Ile Phe Lys Glu Ile Leu Ala Arg Ala Leu
    2360            2365                2370
```

```
gac caa ccc caa acc cca ctg gcg ctt cta ccg ctc acc gat ggg    7164
Asp Gln Pro Gln Thr Pro Leu Ala Leu Leu Pro Leu Thr Asp Gly
    2375            2380                2385 ctg gct gaa ctt cgc agg agg ggg ctg ctt gag att gaa agg ccc    7209
Leu Ala Glu Leu Arg Arg Arg Gly Leu Leu Glu Ile Glu Arg Pro
    2390            2395                2400 agc tat cct cgc gag tcg agc gtt gtt gac gtc ttc tgt agc cag    7254
Ser Tyr Pro Arg Glu Ser Ser Val Val Asp Val Phe Cys Ser Gln
    2405            2410                2415 gta gcg gct tct ccc aac gca acc gct gtg aag gac tcg att tca    7299
Val Ala Ala Ser Pro Asn Ala Thr Ala Val Lys Asp Ser Ile Ser
    2420            2425                2430 cag ctc act tac gct cag cta aat gag caa tct gac aag gtc gct    7344
Gln Leu Thr Tyr Ala Gln Leu Asn Glu Gln Ser Asp Lys Val Ala
    2435            2440                2445 gct tgg cta cac cag tgc aac ctt cca act gaa act ttg gtc gct    7389
Ala Trp Leu His Gln Cys Asn Leu Pro Thr Glu Thr Leu Val Ala
    2450            2455                2460 gtg cta gcg cct cga tct tgc caa aca gtt gtg gcc ttc ttg ggt    7434
Val Leu Ala Pro Arg Ser Cys Gln Thr Val Val Ala Phe Leu Gly
    2465            2470                2475 att ctg aag gcc aac cta gca tat ctt ccc cta gac gtc aat gtt    7479
Ile Leu Lys Ala Asn Leu Ala Tyr Leu Pro Leu Asp Val Asn Val
    2480            2485                2490 ccg gca gct cgc att gag gca att ctc tca gaa gtc tct ggc cac    7524
Pro Ala Ala Arg Ile Glu Ala Ile Leu Ser Glu Val Ser Gly His
    2495            2500                2505 ata ctt gtc tta ctt gga tct cat gtt tct gct ccc aag att gag    7569
Ile Leu Val Leu Leu Gly Ser His Val Ser Ala Pro Lys Ile Glu
    2510            2515                2520 ctc gct gat gtc gaa ttc gtc aaa att gac aac aca gtc gag cac    7614
Leu Ala Asp Val Glu Phe Val Lys Ile Asp Asn Thr Val Glu His
    2525            2530                2535 aat ttg ccg ggc cgc att gga tct gct cca tct gcc acg agc ctc    7659
Asn Leu Pro Gly Arg Ile Gly Ser Ala Pro Ser Ala Thr Ser Leu
    2540            2545                2550 gcc tat gtt att ttc aca tct gga tcg act ggc aag ccc aaa ggt    7704
Ala Tyr Val Ile Phe Thr Ser Gly Ser Thr Gly Lys Pro Lys Gly
    2555            2560                2565 gtt aag gta gag cac cgc ggt att gtc cgc ctc gtt aaa gag agc    7749
Val Lys Val Glu His Arg Gly Ile Val Arg Leu Val Lys Glu Ser
    2570            2575                2580 aat gta gta gca aaa atg cca caa gct gcg cgc att gct cac ttg    7794
Asn Val Val Ala Lys Met Pro Gln Ala Ala Arg Ile Ala His Leu
    2585            2590                2595 tca aac att gcc ttt gac gcg gct acg tgg gaa tta tat gct gcg    7839
Ser Asn Ile Ala Phe Asp Ala Ala Thr Trp Glu Leu Tyr Ala Ala
    2600            2605                2610 ttg ctc aac ggc ggc acc ctc gtc tgt atc aac tat tta acc acg    7884
Leu Leu Asn Gly Gly Thr Leu Val Cys Ile Asn Tyr Leu Thr Thr
    2615            2620                2625 ctg gat agt aaa gca ctc gag gcc gtg ttt gag cag gaa aag atc    7929
Leu Asp Ser Lys Ala Leu Glu Ala Val Phe Glu Gln Glu Lys Ile
    2630            2635                2640 caa gcg gct atg ctt cca cca gca ctg ctc aaa cag tat ttg gtt    7974
Gln Ala Ala Met Leu Pro Pro Ala Leu Leu Lys Gln Tyr Leu Val
    2645            2650                2655 aac att ccc gca gct atc ggt gca cta gaa gtg gtc ctt gtc gct    8019
Asn Ile Pro Ala Ala Ile Gly Ala Leu Glu Val Val Leu Val Ala
```

-continued

| | | |
|---|---|---|
| ggt gac cgt ttc gat cga cgc gat gct gca gcc acg cag gct ctt<br>Gly Asp Arg Phe Asp Arg Arg Asp Ala Ala Ala Thr Gln Ala Leu<br>2675                      2680                      2685 | 8064 |
| gtt gga gca ggc gtg tat aac gcc tat gga ccg acg gag aat aca<br>Val Gly Ala Gly Val Tyr Asn Ala Tyr Gly Pro Thr Glu Asn Thr<br>2690                      2695                      2700 | 8109 |
| aca ctc agc act atc tac aat gtc gtt cag ggc gat gcc aat gtg<br>Thr Leu Ser Thr Ile Tyr Asn Val Val Gln Gly Asp Ala Asn Val<br>2705                      2710                      2715 | 8154 |
| aat ggc gtc ccg att gga cgc cct gtc agc aac tct ggc gcc tac<br>Asn Gly Val Pro Ile Gly Arg Pro Val Ser Asn Ser Gly Ala Tyr<br>2720                      2725                      2730 | 8199 |
| atc atg aat atg aat cag gaa ctc gtt cct att ggc gtc ata ggc<br>Ile Met Asn Met Asn Gln Glu Leu Val Pro Ile Gly Val Ile Gly<br>2735                      2740                      2745 | 8244 |
| gag ctg gtc gta gta gga gac ggt gtc gcc cga gga tac acc gac<br>Glu Leu Val Val Val Gly Asp Gly Val Ala Arg Gly Tyr Thr Asp<br>2750                      2755                      2760 | 8289 |
| cca gcc ttg gac gtc aac cgc ttc gtc aac gtc act att gaa ggc<br>Pro Ala Leu Asp Val Asn Arg Phe Val Asn Val Thr Ile Glu Gly<br>2765                      2770                      2775 | 8334 |
| caa act atg agg gct tat agg act ggc gat cgt gcc cgc tat agg<br>Gln Thr Met Arg Ala Tyr Arg Thr Gly Asp Arg Ala Arg Tyr Arg<br>2780                      2785                      2790 | 8379 |
| ccc aaa gac gca cag att gaa ttc ttt ggc cga atg gat caa cag<br>Pro Lys Asp Ala Gln Ile Glu Phe Phe Gly Arg Met Asp Gln Gln<br>2795                      2800                      2805 | 8424 |
| atc aag att cga ggc cat cgt att gag cca gct gag gtc gag cat<br>Ile Lys Ile Arg Gly His Arg Ile Glu Pro Ala Glu Val Glu His<br>2810                      2815                      2820 | 8469 |
| gcg ttg ctc aac aat gac ttg ctt cag gac gct gca gtc att atc<br>Ala Leu Leu Asn Asn Asp Leu Leu Gln Asp Ala Ala Val Ile Ile<br>2825                      2830                      2835 | 8514 |
| cga aag caa caa aat gat gag ctg gag atg gtt gct ttt gta gaa<br>Arg Lys Gln Gln Asn Asp Glu Leu Glu Met Val Ala Phe Val Glu<br>2840                      2845                      2850 | 8559 |
| gca aac agc aat aag tcg atc gaa caa gag gcg agc aac caa gta<br>Ala Asn Ser Asn Lys Ser Ile Glu Gln Glu Ala Ser Asn Gln Val<br>2855                      2860                      2865 | 8604 |
| gaa gac tgg ggc gct caa ttc gag agc aac gtc tac gcc gag atc<br>Glu Asp Trp Gly Ala Gln Phe Glu Ser Asn Val Tyr Ala Glu Ile<br>2870                      2875                      2880 | 8649 |
| gag gca atc gat gcc tct gct gtt ggt aac gac ttc atg ggt tgg<br>Glu Ala Ile Asp Ala Ser Ala Val Gly Asn Asp Phe Met Gly Trp<br>2885                      2890                      2895 | 8694 |
| act tcc atg tac gac ggc agc gcg atc gac aag gct gag atg cag<br>Thr Ser Met Tyr Asp Gly Ser Ala Ile Asp Lys Ala Glu Met Gln<br>2900                      2905                      2910 | 8739 |
| gaa tgg ctc gat gat act atg cag aca ata ctt gat ggt cga cca<br>Glu Trp Leu Asp Asp Thr Met Gln Thr Ile Leu Asp Gly Arg Pro<br>2915                      2920                      2925 | 8784 |
| gcc ggc cgc gtt ctc gaa atc ggc act ggc acg ggt atg atc ctc<br>Ala Gly Arg Val Leu Glu Ile Gly Thr Gly Thr Gly Met Ile Leu<br>2930                      2935                      2940 | 8829 |
| ttc aat ctt ggt gaa ggg tta cag agc tat gtc ggt ctc gaa cca<br>Phe Asn Leu Gly Glu Gly Leu Gln Ser Tyr Val Gly Leu Glu Pro<br>2945                      2950                      2955 | 8874 |
| tct acc tcg gcg gct gcg ttc gtc aat cgc agg att cag aca ctt | 8919 |

```
Ser Thr Ser Ala Ala Ala Phe Val Asn Arg Arg Ile Gln Thr Leu
    2960            2965                2970 cca gct ttc gct ggt aaa gct gaa gtt cac gtg ggt aca gcg aca              8964
Pro Ala Phe Ala Gly Lys Ala Glu Val His Val Gly Thr Ala Thr
    2975            2980                2985 gat ata agc caa ctt caa gat ctc cgc ccg gaa gta gtg gtt atc              9009
Asp Ile Ser Gln Leu Gln Asp Leu Arg Pro Glu Val Val Val Ile
    2990            2995                3000 aac tcg gtg gct cag tac ttc cca tcg cct gag tac ttg tct aag              9054
Asn Ser Val Ala Gln Tyr Phe Pro Ser Pro Glu Tyr Leu Ser Lys
    3005            3010                3015 gtt ttg tac gca cta gcc caa att cct ggc gtc aag cgt ttg ttc              9099
Val Leu Tyr Ala Leu Ala Gln Ile Pro Gly Val Lys Arg Leu Phe
    3020            3025                3030 ttt gga gac atg cga tct tac gcc atc aac gac cag ttc ctt gca              9144
Phe Gly Asp Met Arg Ser Tyr Ala Ile Asn Asp Gln Phe Leu Ala
    3035            3040                3045 gct cgc gcc tta cac aac ata ggt agc aag gct act aag agc gcc              9189
Ala Arg Ala Leu His Asn Ile Gly Ser Lys Ala Thr Lys Ser Ala
    3050            3055                3060 att cga agc aag atg gtc gat ctg gaa aac tct gag gaa gaa ttg              9234
Ile Arg Ser Lys Met Val Asp Leu Glu Asn Ser Glu Glu Glu Leu
    3065            3070                3075 ctc gtc gac cca acc ttc ttc acc aac cta gcg acc gag ctt cca              9279
Leu Val Asp Pro Thr Phe Phe Thr Asn Leu Ala Thr Glu Leu Pro
    3080            3085                3090 gag gtt gag cat gtt gag att ctg cca aaa cgc atg cag gct acc              9324
Glu Val Glu His Val Glu Ile Leu Pro Lys Arg Met Gln Ala Thr
    3095            3100                3105 aac gaa ctt agc gcc tat cgt tat gca gct gtg gtg cac atc cgt              9369
Asn Glu Leu Ser Ala Tyr Arg Tyr Ala Ala Val Val His Ile Arg
    3110            3115                3120 gat tca tcg gaa cga gct cag acc gtg cat gcc atc aaa tcg agc              9414
Asp Ser Ser Glu Arg Ala Gln Thr Val His Ala Ile Lys Ser Ser
    3125            3130                3135 gca tgg gtc gac ttc agc aaa tct cag atg gac cgc aag gcc ctc              9459
Ala Trp Val Asp Phe Ser Lys Ser Gln Met Asp Arg Lys Ala Leu
    3140            3145                3150 atc agt ctt ctt caa agc tcg gta aac acc gag gct gtt gct atc              9504
Ile Ser Leu Leu Gln Ser Ser Val Asn Thr Glu Ala Val Ala Ile
    3155            3160                3165 ggc aat atc ccc tac agc aag act atc atg gcg cga cat gtc gtc              9549
Gly Asn Ile Pro Tyr Ser Lys Thr Ile Met Ala Arg His Val Val
    3170            3175                3180 caa tcg ctt gac gaa gac aat gca gac aag gac att gcg caa gat              9594
Gln Ser Leu Asp Glu Asp Asn Ala Asp Lys Asp Ile Ala Gln Asp
    3185            3190                3195 aaa ccc gat aag ccc acc tgg atc tcg gca gtt cgc tcc aat gcc              9639
Lys Pro Asp Lys Pro Thr Trp Ile Ser Ala Val Arg Ser Asn Ala
    3200            3205                3210 gaa cac tgc cca tca cta tcg gct ctc gac ctt gta cag ctt ggt              9684
Glu His Cys Pro Ser Leu Ser Ala Leu Asp Leu Val Gln Leu Gly
    3215            3220                3225 gag gag gca ggc ttc tgt gtg gag ctc agc tgg gct caa cag cga              9729
Glu Glu Ala Gly Phe Cys Val Glu Leu Ser Trp Ala Gln Gln Arg
    3230            3235                3240 tct cat cac gga gca atc gac gca gtc ttt cat cat tac cag ccc              9774
Ser His His Gly Ala Ile Asp Ala Val Phe His His Tyr Gln Pro
    3245            3250                3255
```

| | | | | | | | | | | | | | |
|---|---|---|---|---|---|---|---|---|---|---|---|---|---|
| gct | cga | gaa | gga | agc | cgt | gtt | ctg | ttt | cag | ttc | ccg | acc | gat acg | 9819 |
| Ala | Arg | Glu | Gly | Ser | Arg | Val | Leu | Phe | Gln | Phe | Pro | Thr | Asp Thr | |
| | 3260 | | | | 3265 | | | | 3270 | | | | | |
| tat | cga | cgc | caa | tcc | ggt | ccg | ctt | aca | aac | cga | ccc | ttg | cag cga | 9864 |
| Tyr | Arg | Arg | Gln | Ser | Gly | Pro | Leu | Thr | Asn | Arg | Pro | Leu | Gln Arg | |
| | 3275 | | | | 3280 | | | | 3285 | | | | | |
| att | cag | agc | cgg | cga | atg | gaa | aca | cag | gtt | aga | gaa | aag | cta cgg | 9909 |
| Ile | Gln | Ser | Arg | Arg | Met | Glu | Thr | Gln | Val | Arg | Glu | Lys | Leu Arg | |
| | 3290 | | | | 3295 | | | | 3300 | | | | | |
| gcc | gtt | ttg | cct | tca | tac | atg | att | cca | tcg | ctc | atc | gtg | ctg gtc | 9954 |
| Ala | Val | Leu | Pro | Ser | Tyr | Met | Ile | Pro | Ser | Leu | Ile | Val | Leu Val | |
| | 3305 | | | | 3310 | | | | 3315 | | | | | |
| gac | caa | atg | ccc | ctg | aac | ccc | aac | ggc | aaa | gtg | gat | agg | aag gcg | 9999 |
| Asp | Gln | Met | Pro | Leu | Asn | Pro | Asn | Gly | Lys | Val | Asp | Arg | Lys Ala | |
| | 3320 | | | | 3325 | | | | 3330 | | | | | |
| ttg | gaa | cga | cga | gcc | cag | gca | gtg | cta | cgg | gtc | gaa | aaa | cca act | 10044 |
| Leu | Glu | Arg | Arg | Ala | Gln | Ala | Val | Leu | Arg | Val | Glu | Lys | Pro Thr | |
| | 3335 | | | | 3340 | | | | 3345 | | | | | |
| tcc | gaa | cgt | gtt | ggt | gcc | cgt | aat | gag | act | gag | gct | gtg | ctt tgt | 10089 |
| Ser | Glu | Arg | Val | Gly | Ala | Arg | Asn | Glu | Thr | Glu | Ala | Val | Leu Cys | |
| | 3350 | | | | 3355 | | | | 3360 | | | | | |
| gag | gag | ttt | acc | gac | gtt | ctc | gga | ctt | gag | gtt | ggt | att | acg gat | 10134 |
| Glu | Glu | Phe | Thr | Asp | Val | Leu | Gly | Leu | Glu | Val | Gly | Ile | Thr Asp | |
| | 3365 | | | | 3370 | | | | 3375 | | | | | |
| aac | ttc | ttc | gac | ctc | ggt | ggg | cac | tcg | ctt | atg | gcg | acc | aaa ctc | 10179 |
| Asn | Phe | Phe | Asp | Leu | Gly | Gly | His | Ser | Leu | Met | Ala | Thr | Lys Leu | |
| | 3380 | | | | 3385 | | | | 3390 | | | | | |
| gcg | gcc | cgt | atc | agt | cga | cgc | ctt | gac | gcc | cgc | gtc | tct | gtt aaa | 10224 |
| Ala | Ala | Arg | Ile | Ser | Arg | Arg | Leu | Asp | Ala | Arg | Val | Ser | Val Lys | |
| | 3395 | | | | 3400 | | | | 3405 | | | | | |
| gat | gtc | ttt | gat | cag | cct | gtc | ata | gtc | gac | ctc | gcc | gcc | tcc att | 10269 |
| Asp | Val | Phe | Asp | Gln | Pro | Val | Ile | Val | Asp | Leu | Ala | Ala | Ser Ile | |
| | 3410 | | | | 3415 | | | | 3420 | | | | | |
| cgc | cgt | ggt | tcg | acc | cct | cac | aat | cct | atc | acc | cca | acc | gag tat | 10314 |
| Arg | Arg | Gly | Ser | Thr | Pro | His | Asn | Pro | Ile | Thr | Pro | Thr | Glu Tyr | |
| | 3425 | | | | 3430 | | | | 3435 | | | | | |
| tct | ggt | ccg | gta | gag | caa | tcg | ttt | gct | cag | ggc | cgt | ctc | tgg ttc | 10359 |
| Ser | Gly | Pro | Val | Glu | Gln | Ser | Phe | Ala | Gln | Gly | Arg | Leu | Trp Phe | |
| | 3440 | | | | 3445 | | | | 3450 | | | | | |
| tta | gac | cag | ttg | aat | ctc | ggt | gca | tct | tta | tat | ctc | atg | cct ctt | 10404 |
| Leu | Asp | Gln | Leu | Asn | Leu | Gly | Ala | Ser | Leu | Tyr | Leu | Met | Pro Leu | |
| | 3455 | | | | 3460 | | | | 3465 | | | | | |
| gcg | ttg | cgt | ttg | cgt | gga | cct | ctc | cgc | atc | gat | gct | ctc | aca gct | 10449 |
| Ala | Leu | Arg | Leu | Arg | Gly | Pro | Leu | Arg | Ile | Asp | Ala | Leu | Thr Ala | |
| | 3470 | | | | 3475 | | | | 3480 | | | | | |
| gcg | ctc | ttc | gca | ttg | gaa | cag | cga | cac | gag | act | ctc | cga | acc gtc | 10494 |
| Ala | Leu | Phe | Ala | Leu | Glu | Gln | Arg | His | Glu | Thr | Leu | Arg | Thr Val | |
| | 3485 | | | | 3490 | | | | 3495 | | | | | |
| ttc | aag | gag | caa | gat | ggc | gta | ggc | atc | caa | atc | att | caa | cct agc | 10539 |
| Phe | Lys | Glu | Gln | Asp | Gly | Val | Gly | Ile | Gln | Ile | Ile | Gln | Pro Ser | |
| | 3500 | | | | 3505 | | | | 3510 | | | | | |
| caa | aag | aag | aaa | ctc | aga | acc | att | gat | gta | tct | gca | ggc | gac ttt | 10584 |
| Gln | Lys | Lys | Lys | Leu | Arg | Thr | Ile | Asp | Val | Ser | Ala | Gly | Asp Phe | |
| | 3515 | | | | 3520 | | | | 3525 | | | | | |
| tcc | gag | gcg | ctg | cat | cac | gaa | cgc | act | gcc | cca | ttt | gat | ctc gca | 10629 |
| Ser | Glu | Ala | Leu | His | His | Glu | Arg | Thr | Ala | Pro | Phe | Asp | Leu Ala | |
| | 3530 | | | | 3535 | | | | 3540 | | | | | |
| tca | gag | ccg | ggc | ttc | aga | gtc | gcc | ctt | ctt | cag | ctt | gag | ccg tct | 10674 |
| Ser | Glu | Pro | Gly | Phe | Arg | Val | Ala | Leu | Leu | Gln | Leu | Glu | Pro Ser | |
| | 3545 | | | | 3550 | | | | 3555 | | | | | |

-continued

| | | | | | | | | | | | | |
|---|---|---|---|---|---|---|---|---|---|---|---|---|
| gat | cat | gtg | ctg | tct | atc | gtc | atg | cac | cat | atc | atc | tac gac ggc | 10719 |
| Asp | His | Val | Leu | Ser | Ile | Val | Met | His | His | Ile | Ile | Tyr Asp Gly | |
| | 3560 | | | | 3565 | | | | 3570 | | | | |
| tgg | tct | atc | gac | att | ttg | tgt | caa | gaa | ctg | ggc | cag | ttc tac gct | 10764 |
| Trp | Ser | Ile | Asp | Ile | Leu | Cys | Gln | Glu | Leu | Gly | Gln | Phe Tyr Ala | |
| | 3575 | | | | 3580 | | | | 3585 | | | | |
| gct | gca | atc | cag | ggc | cag | gat | cca | ttg | gga | caa | gtg | agc ccg ctc | 10809 |
| Ala | Ala | Ile | Gln | Gly | Gln | Asp | Pro | Leu | Gly | Gln | Val | Ser Pro Leu | |
| | 3590 | | | | 3595 | | | | 3600 | | | | |
| cca | att | caa | tac | cgt | gac | ttc | tct | gtc | tgg | caa | aag | caa cct gag | 10854 |
| Pro | Ile | Gln | Tyr | Arg | Asp | Phe | Ser | Val | Trp | Gln | Lys | Gln Pro Glu | |
| | 3605 | | | | 3610 | | | | 3615 | | | | |
| cag | gtc | gct | gag | cat | gag | cgg | cag | ctt | gcg | tac | tgg | atc gat cag | 10899 |
| Gln | Val | Ala | Glu | His | Glu | Arg | Gln | Leu | Ala | Tyr | Trp | Ile Asp Gln | |
| | 3620 | | | | 3625 | | | | 3630 | | | | |
| ttg | gcc | gat | agt | gct | ccc | gct | gag | ttc | ctt | gtc | gat | ctc cca cgc | 10944 |
| Leu | Ala | Asp | Ser | Ala | Pro | Ala | Glu | Phe | Leu | Val | Asp | Leu Pro Arg | |
| | 3635 | | | | 3640 | | | | 3645 | | | | |
| cca | ccc | gtc | ttg | tct | ggt | gat | gcc | gga | cta | gtc | cac | ctc act atc | 10989 |
| Pro | Pro | Val | Leu | Ser | Gly | Asp | Ala | Gly | Leu | Val | His | Leu Thr Ile | |
| | 3650 | | | | 3655 | | | | 3660 | | | | |
| gat | ggt | ccc | atc | tat | gac | cgc | ctg | aga | gcc | ttc | tgt | cga gtg cac | 11034 |
| Asp | Gly | Pro | Ile | Tyr | Asp | Arg | Leu | Arg | Ala | Phe | Cys | Arg Val His | |
| | 3665 | | | | 3670 | | | | 3675 | | | | |
| cag | acg | aca | act | ttt | gca | gtg | cta | cta | gca | gct | ttc | cgc gca acg | 11079 |
| Gln | Thr | Thr | Thr | Phe | Ala | Val | Leu | Leu | Ala | Ala | Phe | Arg Ala Thr | |
| | 3680 | | | | 3685 | | | | 3690 | | | | |
| cac | tat | cgt | ctt | aca | ggt | gcc | gaa | gat | gct | act | gtt | ggc aca cca | 11124 |
| His | Tyr | Arg | Leu | Thr | Gly | Ala | Glu | Asp | Ala | Thr | Val | Gly Thr Pro | |
| | 3695 | | | | 3700 | | | | 3705 | | | | |
| atc | gcc | aac | cgt | aac | cgg | ccg | gag | ctt | gaa | aac | ttg | gtc gga ttc | 11169 |
| Ile | Ala | Asn | Arg | Asn | Arg | Pro | Glu | Leu | Glu | Asn | Leu | Val Gly Phe | |
| | 3710 | | | | 3715 | | | | 3720 | | | | |
| ttc | gtc | aat | act | cag | tgt | atg | aga | att | agt | gtc | gga | gat gat gac | 11214 |
| Phe | Val | Asn | Thr | Gln | Cys | Met | Arg | Ile | Ser | Val | Gly | Asp Asp Asp | |
| | 3725 | | | | 3730 | | | | 3735 | | | | |
| acg | ttt | gag | cag | cta | gtg | cgc | cag | gtt | cga | tct | aca | gca acg gct | 11259 |
| Thr | Phe | Glu | Gln | Leu | Val | Arg | Gln | Val | Arg | Ser | Thr | Ala Thr Ala | |
| | 3740 | | | | 3745 | | | | 3750 | | | | |
| gca | ttt | gca | aac | caa | gac | gtt | cct | ttt | gaa | cgc | atc | gtg tca aca | 11304 |
| Ala | Phe | Ala | Asn | Gln | Asp | Val | Pro | Phe | Glu | Arg | Ile | Val Ser Thr | |
| | 3755 | | | | 3760 | | | | 3765 | | | | |
| ctc | ctg | ccg | ggc | tct | cgc | gat | acc | gcc | cgc | aat | cca | ctg gta cag | 11349 |
| Leu | Leu | Pro | Gly | Ser | Arg | Asp | Thr | Ala | Arg | Asn | Pro | Leu Val Gln | |
| | 3770 | | | | 3775 | | | | 3780 | | | | |
| ctc | atg | ttt | gct | gtc | cat | tct | ctc | aag | gac | ctt | ggc | aaa att cag | 11394 |
| Leu | Met | Phe | Ala | Val | His | Ser | Leu | Lys | Asp | Leu | Gly | Lys Ile Gln | |
| | 3785 | | | | 3790 | | | | 3795 | | | | |
| ttc | gag | ggt | ctc | gtg | ggc | gag | aca | att | ccc | acg | gct | tct ttc act | 11439 |
| Phe | Glu | Gly | Leu | Val | Gly | Glu | Thr | Ile | Pro | Thr | Ala | Ser Phe Thr | |
| | 3800 | | | | 3805 | | | | 3810 | | | | |
| cga | ttc | gac | gtc | gag | ttt | cat | ttg | ttc | cag | gaa | gtc | ggt cgt ctt | 11484 |
| Arg | Phe | Asp | Val | Glu | Phe | His | Leu | Phe | Gln | Glu | Val | Gly Arg Leu | |
| | 3815 | | | | 3820 | | | | 3825 | | | | |
| agc | gga | aat | gtg | ctc | ttc | tcg | act | gat | cta | ttt | gag | ccg gag act | 11529 |
| Ser | Gly | Asn | Val | Leu | Phe | Ser | Thr | Asp | Leu | Phe | Glu | Pro Glu Thr | |
| | 3830 | | | | 3835 | | | | 3840 | | | | |
| atc | cag | ggc | atg | gtc | tct | gtg | ttc | atg | gag | atc | ttg | cgc gga gct | 11574 |
| Ile | Gln | Gly | Met | Val | Ser | Val | Phe | Met | Glu | Ile | Leu | Arg Gly Ala | |

-continued

```
              3845                3850                3855
ctt gac cag cct cag atc ccc att gcc gtc cta ccg ctc aca gac                11619
Leu Asp Gln Pro Gln Ile Pro Ile Ala Val Leu Pro Leu Thr Asp
        3860                3865                3870 ggc ctc acg gag ctt cgc aac aga ggc ctg ctt gaa gtt gag cag                11664
Gly Leu Thr Glu Leu Arg Asn Arg Gly Leu Leu Glu Val Glu Gln
        3875                3880                3885 cct caa tat ccc cgc gac tcg agc gtc att gac gtg ttc cgc gct                11709
Pro Gln Tyr Pro Arg Asp Ser Ser Val Ile Asp Val Phe Arg Ala
        3890                3895                3900 cag gtc gtt gct tgc cca gat gca atc gct gtg aaa gat tcg acg                11754
Gln Val Val Ala Cys Pro Asp Ala Ile Ala Val Lys Asp Ser Thr
        3905                3910                3915 tcg cag ctc acc tat gcc caa ctt gat gag cag tcc gat gag gtg                11799
Ser Gln Leu Thr Tyr Ala Gln Leu Asp Glu Gln Ser Asp Glu Val
        3920                3925                3930 gct gta tgg cta cat caa cga aag ttg cca gcg gaa tcc ctg gtt                11844
Ala Val Trp Leu His Gln Arg Lys Leu Pro Ala Glu Ser Leu Val
        3935                3940                3945 gcc gtg cta gca cct aga tca tgc gag act atc att acc ttc ttc                11889
Ala Val Leu Ala Pro Arg Ser Cys Glu Thr Ile Ile Thr Phe Phe
        3950                3955                3960 ggt att ttg aag gct aat cta gcc tat ctt cca ctc gat att aac                11934
Gly Ile Leu Lys Ala Asn Leu Ala Tyr Leu Pro Leu Asp Ile Asn
        3965                3970                3975 gtc ccg gca gcc cgt att cag gca atc tta tcg tcc gtt gca ggg                11979
Val Pro Ala Ala Arg Ile Gln Ala Ile Leu Ser Ser Val Ala Gly
        3980                3985                3990 aag aaa atc ctc cta ctt ggt tct gat cag gct cag ccg gaa att                12024
Lys Lys Ile Leu Leu Leu Gly Ser Asp Gln Ala Gln Pro Glu Ile
        3995                4000                4005 cgg ctt gat gat gtt gaa ttt gta caa atc aat gaa acg att gac                12069
Arg Leu Asp Asp Val Glu Phe Val Gln Ile Asn Glu Thr Ile Asp
        4010                4015                4020 cac aat atg gcg aag gat aat act acc cgc tct gga ccc tta gct                12114
His Asn Met Ala Lys Asp Asn Thr Thr Arg Ser Gly Pro Leu Ala
        4025                4030                4035 aca agt ctt gct tat gtt atc ttc act tct gga tcc act ggc cag                12159
Thr Ser Leu Ala Tyr Val Ile Phe Thr Ser Gly Ser Thr Gly Gln
        4040                4045                4050 ccg aag ggc gtc aag gtg gaa cac cgc ggt att gtt cgc ctc gtc                12204
Pro Lys Gly Val Lys Val Glu His Arg Gly Ile Val Arg Leu Val
        4055                4060                4065 aag aat agc aac gtg gta gca aag atg cca gag gcg gca tgt gtt                12249
Lys Asn Ser Asn Val Val Ala Lys Met Pro Glu Ala Ala Cys Val
        4070                4075                4080 gca cac ctt tca aat ctc gcg ttt gac gcc gcg aca tgg gaa atc                12294
Ala His Leu Ser Asn Leu Ala Phe Asp Ala Ala Thr Trp Glu Ile
        4085                4090                4095 tac gct gca ctc ttg aat ggt ggc tcg ctc atc tgt atc gac tac                12339
Tyr Ala Ala Leu Leu Asn Gly Gly Ser Leu Ile Cys Ile Asp Tyr
        4100                4105                4110 ttc acc acg cta gac agc aag gtc ctc gag gca gtt ttc gag cga                12384
Phe Thr Thr Leu Asp Ser Lys Val Leu Glu Ala Val Phe Glu Arg
        4115                4120                4125 gaa caa atc cgt gca gcc atg ttc cca ccg gcg ctt ctg aaa caa                12429
Glu Gln Ile Arg Ala Ala Met Phe Pro Pro Ala Leu Leu Lys Gln
        4130                4135                4140 tgc cta ctc aat atc ccc acg acc atc agc gcg cta gat gtt atc                12474
```

```
        Cys Leu Leu Asn Ile Pro Thr Thr Ile Ser Ala Leu Asp Val Ile
            4145                4150                4155 ctc gct gct ggt gac cga ttt gat agg cgc gac gct att gcg gcg          12519
Leu Ala Ala Gly Asp Arg Phe Asp Arg Arg Asp Ala Ile Ala Ala
    4160                4165                4170 cag gcg ctt gtt gga ggt ggt gta tac aat gcc tac ggt cct acg          12564
Gln Ala Leu Val Gly Gly Gly Val Tyr Asn Ala Tyr Gly Pro Thr
    4175                4180                4185 gaa aat act acg ctt agc aca ata tac aac gtt gtg gat ggc gat          12609
Glu Asn Thr Thr Leu Ser Thr Ile Tyr Asn Val Val Asp Gly Asp
    4190                4195                4200 acc aac gtc aac ggt att cca atc ggg ctt cct gtc agc aac tct          12654
Thr Asn Val Asn Gly Ile Pro Ile Gly Leu Pro Val Ser Asn Ser
    4205                4210                4215 ggc gtg tat gtc atg gat ccc aac cag cag ctt gtc ccg ttg ggc          12699
Gly Val Tyr Val Met Asp Pro Asn Gln Gln Leu Val Pro Leu Gly
    4220                4225                4230 gtc atg gga gag ctt gtt gtg gtt ggc gat ggt gta gcc cga ggt          12744
Val Met Gly Glu Leu Val Val Val Gly Asp Gly Val Ala Arg Gly
    4235                4240                4245 tac act gat cca gct ctt gat gtt gat cgt ttc atc aag gtt gaa          12789
Tyr Thr Asp Pro Ala Leu Asp Val Asp Arg Phe Ile Lys Val Glu
    4250                4255                4260 atc gac ggc cag atc gta cga gcc tac cgc act ggt gac cgt gtt          12834
Ile Asp Gly Gln Ile Val Arg Ala Tyr Arg Thr Gly Asp Arg Val
    4265                4270                4275 cga cac cga ccc aag gac ggt cag att gag ttc ttt ggc cga atg          12879
Arg His Arg Pro Lys Asp Gly Gln Ile Glu Phe Phe Gly Arg Met
    4280                4285                4290 gat cag caa gtc aag att cga gga cat cgc att gaa ttg gct gag          12924
Asp Gln Gln Val Lys Ile Arg Gly His Arg Ile Glu Leu Ala Glu
    4295                4300                4305 gta gag cac gtc atc ctc gat aac agc tta gtc cag gac gct gca          12969
Val Glu His Val Ile Leu Asp Asn Ser Leu Val Gln Asp Ala Ala
    4310                4315                4320 gtc att gtc cac aag caa gct gac cag gag atc gaa atg atc gca          13014
Val Ile Val His Lys Gln Ala Asp Gln Glu Ile Glu Met Ile Ala
    4325                4330                4335 ttt gct ata gtc cga ggc gat aac gac agc aag cac cca gag aag          13059
Phe Ala Ile Val Arg Gly Asp Asn Asp Ser Lys His Pro Glu Lys
    4340                4345                4350 gat att cta gat cga gtg aag gct ttg ctt cca tca tac atg gtg          13104
Asp Ile Leu Asp Arg Val Lys Ala Leu Leu Pro Ser Tyr Met Val
    4355                4360                4365 cca gct caa atg gtg ctg ctt aac agc atg cct ctc aat gcc aac          13149
Pro Ala Gln Met Val Leu Leu Asn Ser Met Pro Leu Asn Ala Asn
    4370                4375                4380 ggc aag gtc gat cgc aaa gag ctt gct aag agg gcg ggg act gtg          13194
Gly Lys Val Asp Arg Lys Glu Leu Ala Lys Arg Ala Gly Thr Val
    4385                4390                4395 ccg cga agc gag atg gca tac gtc gct cca gag agg gtt ccg cct          13239
Pro Arg Ser Glu Met Ala Tyr Val Ala Pro Glu Arg Val Pro Pro
    4400                4405                4410 cgc aat gaa atc gaa aca att ctt tgc gaa gaa tac gcc gag gtc          13284
Arg Asn Glu Ile Glu Thr Ile Leu Cys Glu Glu Tyr Ala Glu Val
    4415                4420                4425 ctt ggc gtc gag gtt ggt gtc atg gac aac ttt ttc gat ctt gga          13329
Leu Gly Val Glu Val Gly Val Met Asp Asn Phe Phe Asp Leu Gly
    4430                4435                4440
```

```
ggg cac tct ctc atg gcg acc aag ctt gca gcc cgc gcc act cgt        13374
Gly His Ser Leu Met Ala Thr Lys Leu Ala Ala Arg Ala Thr Arg
    4445             4450             4455 cga ctt gat gca aag ttg tcc gtt aag gac att ttt gat tac cca        13419
Arg Leu Asp Ala Lys Leu Ser Val Lys Asp Ile Phe Asp Tyr Pro
    4460             4465             4470 att tta gcc aac ctt gca gca gcg gtt caa cga ggc tcg act cca        13464
Ile Leu Ala Asn Leu Ala Ala Ala Val Gln Arg Gly Ser Thr Pro
    4475             4480             4485 cat aat gcg att ctc gca acc aca tac tcc gga cca gtt gaa caa        13509
His Asn Ala Ile Leu Ala Thr Thr Tyr Ser Gly Pro Val Glu Gln
    4490             4495             4500 tca ttc gcc cag ggg cgc ctg tgg ttc ttg gac cag ctg aat gtt        13554
Ser Phe Ala Gln Gly Arg Leu Trp Phe Leu Asp Gln Leu Asn Val
    4505             4510             4515 ggc tcg aat tgg tac ctt cag cca att gcc ata cgc ata cgc gga        13599
Gly Ser Asn Trp Tyr Leu Gln Pro Ile Ala Ile Arg Ile Arg Gly
    4520             4525             4530 tca ctc aat att aac gcg ctc act acc gcg ctt cat gcc cta gaa        13644
Ser Leu Asn Ile Asn Ala Leu Thr Thr Ala Leu His Ala Leu Glu
    4535             4540             4545 caa cgt cac gag acg ttg cgc acc act ttt gag gaa gag gac ggc        13689
Gln Arg His Glu Thr Leu Arg Thr Thr Phe Glu Glu Glu Asp Gly
    4550             4555             4560 gtt ggt atg cag gtc gtc caa gaa tat gac cca ata gag ctc agg        13734
Val Gly Met Gln Val Val Gln Glu Tyr Asp Pro Ile Glu Leu Arg
    4565             4570             4575 ata atg gat att gct gcc gat tat gac ggc gat tat aca gaa gcg        13779
Ile Met Asp Ile Ala Ala Asp Tyr Asp Gly Asp Tyr Thr Glu Ala
    4580             4585             4590 ttg aag gga gag cag acg acc ccc ttc gat cta gag tcg gag cca        13824
Leu Lys Gly Glu Gln Thr Thr Pro Phe Asp Leu Glu Ser Glu Pro
    4595             4600             4605 gga tgg agg gta tcg ctg ctc cgt atg aac gac aac gat cat atc        13869
Gly Trp Arg Val Ser Leu Leu Arg Met Asn Asp Asn Asp His Ile
    4610             4615             4620 ttg tct ctg gtt cta cat cac atc atc tcc gat gga tgg tct gtc        13914
Leu Ser Leu Val Leu His His Ile Ile Ser Asp Gly Trp Ser Val
    4625             4630             4635 gac gtt cta cgc cag gag ttg aag caa ttc tat gcc gct gca ctc        13959
Asp Val Leu Arg Gln Glu Leu Lys Gln Phe Tyr Ala Ala Ala Leu
    4640             4645             4650 caa ggc ctg gat cct ctg tca ggg gct gat cca ctc ccc atc cag        14004
Gln Gly Leu Asp Pro Leu Ser Gly Ala Asp Pro Leu Pro Ile Gln
    4655             4660             4665 tac cgc gac ttc tct ctc tgg caa aag cag cca gag caa gtt gct        14049
Tyr Arg Asp Phe Ser Leu Trp Gln Lys Gln Pro Glu Gln Val Ala
    4670             4675             4680 gag cac gaa cga cag ctc aag tac tgg gtt gag cag ttg gct gac        14094
Glu His Glu Arg Gln Leu Lys Tyr Trp Val Glu Gln Leu Ala Asp
    4685             4690             4695 aat tcc cct gct acg ctt ctt gcg gac cgg cca cgt cca tct gtg        14139
Asn Ser Pro Ala Thr Leu Leu Ala Asp Arg Pro Arg Pro Ser Val
    4700             4705             4710 ctg tcg ggc caa gcc ggc tcg gtc ccg ctc tct atc gaa ggt cag        14184
Leu Ser Gly Gln Ala Gly Ser Val Pro Leu Ser Ile Glu Gly Gln
    4715             4720             4725 gtc tat gag aaa ctt cag gcc ttc tgc cga gct cat caa acg acc        14229
Val Tyr Glu Lys Leu Gln Ala Phe Cys Arg Ala His Gln Thr Thr
    4730             4735             4740
```

```
tcc ttt tcc gtt ttg ctc gct gcc ttc cga gct gct cac ttc cgc    14274
Ser Phe Ser Val Leu Leu Ala Ala Phe Arg Ala Ala His Phe Arg
    4745            4750            4755 ctg acg ggt gtt gac gac gcg acg att ggc ata ccg atc gcc aat    14319
Leu Thr Gly Val Asp Asp Ala Thr Ile Gly Ile Pro Ile Ala Asn
4760            4765            4770 cgt aat cga cct gag cta gag cac ctg atc ggc ttt ttc gtt aac    14364
Arg Asn Arg Pro Glu Leu Glu His Leu Ile Gly Phe Phe Val Asn
    4775            4780            4785 agg cag tgt atg cgg atc acg gtt ggg gaa gat gat acg ttc gaa    14409
Arg Gln Cys Met Arg Ile Thr Val Gly Glu Asp Asp Thr Phe Glu
    4790            4795            4800 tct ctt atc cgc cag gtt cac tca aca gcc act gca gcg tat gct    14454
Ser Leu Ile Arg Gln Val His Ser Thr Ala Thr Ala Ala Tyr Ala
    4805            4810            4815 aat caa gac gtg ccg ttc gag cga atc gta tcg tcc ctt ctt tct    14499
Asn Gln Asp Val Pro Phe Glu Arg Ile Val Ser Ser Leu Leu Ser
    4820            4825            4830 ggc tca aga gac aca tct cgt aat cca ctc gtc cag cta gta ttc    14544
Gly Ser Arg Asp Thr Ser Arg Asn Pro Leu Val Gln Leu Val Phe
    4835            4840            4845 gcc gtt cac tcc cag aag aac ctt ggc aag ttt gag ttg caa gac    14589
Ala Val His Ser Gln Lys Asn Leu Gly Lys Phe Glu Leu Gln Asp
    4850            4855            4860 ttg aca tct gag cca gtt gct gga gct atc tct act cga ttt gat    14634
Leu Thr Ser Glu Pro Val Ala Gly Ala Ile Ser Thr Arg Phe Asp
    4865            4870            4875 gcg gaa ttt cat cta ttc cag gaa gaa gag agg ttg aac ggt gtt    14679
Ala Glu Phe His Leu Phe Gln Glu Glu Glu Arg Leu Asn Gly Val
    4880            4885            4890 gtg tat tac gca acc gat ctg ttc gat gcg gag act atc caa ggg    14724
Val Tyr Tyr Ala Thr Asp Leu Phe Asp Ala Glu Thr Ile Gln Gly
    4895            4900            4905 gtg gtg tct gtt ttc caa gaa atc tta cgt cgc ggc ctc aac cat    14769
Val Val Ser Val Phe Gln Glu Ile Leu Arg Arg Gly Leu Asn His
    4910            4915            4920 cca cga acg ccg atc gca gct ctg tcg ctt acg gac ggg ctg gat    14814
Pro Arg Thr Pro Ile Ala Ala Leu Ser Leu Thr Asp Gly Leu Asp
    4925            4930            4935 aat ctt cgc aag atg aat ctg gtt cac ttc aag cgg act gat tat    14859
Asn Leu Arg Lys Met Asn Leu Val His Phe Lys Arg Thr Asp Tyr
    4940            4945            4950 ccc cgc gac tct agc atg gtc gac att ttc cgc gag caa gtc gct    14904
Pro Arg Asp Ser Ser Met Val Asp Ile Phe Arg Glu Gln Val Ala
    4955            4960            4965 acc tat ccg gac gtg att gct gtc aag gac tcg act tta cag ctg    14949
Thr Tyr Pro Asp Val Ile Ala Val Lys Asp Ser Thr Leu Gln Leu
    4970            4975            4980 acc tac gcg caa ctt gat caa caa tcc gat gag ata gcc acc tgg    14994
Thr Tyr Ala Gln Leu Asp Gln Gln Ser Asp Glu Ile Ala Thr Trp
    4985            4990            4995 ttg cga aac aaa aaa atg gcg cca gaa act ctg gtg ggt gtc ctt    15039
Leu Arg Asn Lys Lys Met Ala Pro Glu Thr Leu Val Gly Val Leu
5000            5005            5010 gct ccg cga tcg tgc cag act atc gta gcc ttc ctt ggt gtc ctc    15084
Ala Pro Arg Ser Cys Gln Thr Ile Val Ala Phe Leu Gly Val Leu
    5015            5020            5025 aag gcg aac cta gcc tat cta cct ctc gat gtc aat gcc ccg atg    15129
Lys Ala Asn Leu Ala Tyr Leu Pro Leu Asp Val Asn Ala Pro Met
```

```
                    5030                5035                5040
gcc cgc gtt gag aca atc atg tct tct gtg cca ggg agc aag ctg       15174
Ala Arg Val Glu Thr Ile Met Ser Ser Val Pro Gly Ser Lys Leu
        5045                5050                5055 ctt ctt cta ggt tct gat gtg cct gcc cag gag atc cag ctg cag       15219
Leu Leu Leu Gly Ser Asp Val Pro Ala Gln Glu Ile Gln Leu Gln
        5060                5065                5070 aat gtt gag ttg gtg cgt atc gaa gac acc ctc ggc cac gct gcc       15264
Asn Val Glu Leu Val Arg Ile Glu Asp Thr Leu Gly His Ala Ala
        5075                5080                5085 tct gcc ggt aca gcg aca aca gaa ccc tct cca acc agc cta gcg       15309
Ser Ala Gly Thr Ala Thr Thr Glu Pro Ser Pro Thr Ser Leu Ala
        5090                5095                5100 tac gtc ata ttc aca tct gga tcg acg ggt aag cca aag ggt gtg       15354
Tyr Val Ile Phe Thr Ser Gly Ser Thr Gly Lys Pro Lys Gly Val
        5105                5110                5115 atg gtc gag cat cga agc gtc att cgc ctc gtg aga aaa gaa agc       15399
Met Val Glu His Arg Ser Val Ile Arg Leu Val Arg Lys Glu Ser
        5120                5125                5130 aat tcc atg tcc aag atg tct tcc aga gct cgg gtt gcg cac ttg       15444
Asn Ser Met Ser Lys Met Ser Ser Arg Ala Arg Val Ala His Leu
        5135                5140                5145 act aac atc gcg ttc gac gtc tca gca tgg gag gta tat gct acg       15489
Thr Asn Ile Ala Phe Asp Val Ser Ala Trp Glu Val Tyr Ala Thr
        5150                5155                5160 ctt ctc aac gga ggg act ctg gtc tgt gtc gat tat ttc act tcg       15534
Leu Leu Asn Gly Gly Thr Leu Val Cys Val Asp Tyr Phe Thr Ser
        5165                5170                5175 ttc gat gct aaa gcc ctc ggt ctg ctg ttc gag cgg gag cag att       15579
Phe Asp Ala Lys Ala Leu Gly Leu Leu Phe Glu Arg Glu Gln Ile
        5180                5185                5190 act gcg gct atg atc acg cct acg ttg ctc aaa cag tgc atc act       15624
Thr Ala Ala Met Ile Thr Pro Thr Leu Leu Lys Gln Cys Ile Thr
        5195                5200                5205 att gta cca gaa gct ctc cgc aag ttg tcc gtt ctg tac acc ggt       15669
Ile Val Pro Glu Ala Leu Arg Lys Leu Ser Val Leu Tyr Thr Gly
        5210                5215                5220 ggc gat cgc ttt gat agg cgc gat gct atc gcg aca aaa gcg ctt       15714
Gly Asp Arg Phe Asp Arg Arg Asp Ala Ile Ala Thr Lys Ala Leu
        5225                5230                5235 gtc aag ggc cca gtt tac aat gca tgg ggc cct aca gaa acc aca       15759
Val Lys Gly Pro Val Tyr Asn Ala Trp Gly Pro Thr Glu Thr Thr
        5240                5245                5250 atc gtc agc aca atc tat gag ctt gcc gat gac gat cag ttc acc       15804
Ile Val Ser Thr Ile Tyr Glu Leu Ala Asp Asp Asp Gln Phe Thr
        5255                5260                5265 aat ggt gtg cct atc gga aag gct gtg agc aat tct tgg gcc tac       15849
Asn Gly Val Pro Ile Gly Lys Ala Val Ser Asn Ser Trp Ala Tyr
        5270                5275                5280 gtc atg gat ctc aat caa caa ctc gtt cca gtt ggt gtc atg gga       15894
Val Met Asp Leu Asn Gln Gln Leu Val Pro Val Gly Val Met Gly
        5285                5290                5295 gaa gct gtc gtt att gga gac ggc ctt gcc cga gga tat aca gat       15939
Glu Ala Val Val Ile Gly Asp Gly Leu Ala Arg Gly Tyr Thr Asp
        5300                5305                5310 ccc gcc ctg gat tgc aac cgc ttt gtg cat atc act atc gat ggc       15984
Pro Ala Leu Asp Cys Asn Arg Phe Val His Ile Thr Ile Asp Gly
        5315                5320                5325 aaa cgc gtg cgc gcc tat cga act ggt gac cgc gcg cgt tat cga       16029
```

|  |  |  |  |  |  |  |  |  |  |  |  |
|---|---|---|---|---|---|---|---|---|---|---|---|
| Lys | Arg | Val | Arg | Ala | Tyr | Arg | Thr | Gly | Asp | Arg | Ala | Arg | Tyr | Arg |
|  |  | 5330 |  |  |  | 5335 |  |  |  | 5340 |  |  |  |  |

```
cct aaa gat ggc gaa atc gaa ttc ttt ggg cgt atg gac cga cag       16074
Pro Lys Asp Gly Glu Ile Glu Phe Phe Gly Arg Met Asp Arg Gln
5345             5350                 5355 ctc aag att cgt ggt cat cgt att gag ccc gcc gag att gag cat       16119
Leu Lys Ile Arg Gly His Arg Ile Glu Pro Ala Glu Ile Glu His
5360             5365                 5370 gcc atg ctt ggc cac aat gac atc gtt gat gta gcc att gtc act       16164
Ala Met Leu Gly His Asn Asp Ile Val Asp Val Ala Ile Val Thr
5375             5380                 5385 cgc cat caa gat ggt gca ggc tta gaa atg gtt gcc ttt gtt aca       16209
Arg His Gln Asp Gly Ala Gly Leu Glu Met Val Ala Phe Val Thr
5390             5395                 5400 gcc cac act aac aag tct atc gaa cgc aat gaa gcc acc aat caa       16254
Ala His Thr Asn Lys Ser Ile Glu Arg Asn Glu Ala Thr Asn Gln
5405             5410                 5415 gta gct gga tgg ggg gac cac ttc gaa tcg agt aca tat gca gag       16299
Val Ala Gly Trp Gly Asp His Phe Glu Ser Ser Thr Tyr Ala Glu
5420             5425                 5430 ctc gac acc ctt gtc aag tct gat gtt ggc aag gac ttt gtc ggc       16344
Leu Asp Thr Leu Val Lys Ser Asp Val Gly Lys Asp Phe Val Gly
5435             5440                 5445 tgg acg aac atg tat gat ggc ggc gcg atc gat cag gcc gag atg       16389
Trp Thr Asn Met Tyr Asp Gly Gly Ala Ile Asp Gln Ala Glu Met
5450             5455                 5460 cag gaa tgg ctt gac gat acc ata cag acg att gtt gat ggt cag       16434
Gln Glu Trp Leu Asp Asp Thr Ile Gln Thr Ile Val Asp Gly Gln
5465             5470                 5475 cct gct ggt cat gtc ttt gag atc ggt act ggt acc ggt atg atc       16479
Pro Ala Gly His Val Phe Glu Ile Gly Thr Gly Thr Gly Met Ile
5480             5485                 5490 atg ttt ggt ctc ggg aaa cag gga ctg caa agc tac gtc ggc ctt       16524
Met Phe Gly Leu Gly Lys Gln Gly Leu Gln Ser Tyr Val Gly Leu
5495             5500                 5505 gag ccc tca acc tcg gcc act acg tac gtc aac agg aag atc aag       16569
Glu Pro Ser Thr Ser Ala Thr Thr Tyr Val Asn Arg Lys Ile Lys
5510             5515                 5520 acc gct cca acg gta gct ggc aaa gcc aag gta tat gtc ggc act       16614
Thr Ala Pro Thr Val Ala Gly Lys Ala Lys Val Tyr Val Gly Thr
5525             5530                 5535 gca atg gag gcg gct caa ctc aat gga ctc cat ccg gaa gtt gtc       16659
Ala Met Glu Ala Ala Gln Leu Asn Gly Leu His Pro Glu Val Val
5540             5545                 5550 gtc atc aac tct gtg gct caa tac ttc cct acg cca gaa tat ctc       16704
Val Ile Asn Ser Val Ala Gln Tyr Phe Pro Thr Pro Glu Tyr Leu
5555             5560                 5565 ctc gag gtc gtc ggt att ctc act cag atg cca ggt gtc aaa cgc       16749
Leu Glu Val Val Gly Ile Leu Thr Gln Met Pro Gly Val Lys Arg
5570             5575                 5580 ttg ttc ttt gga gac ata cga tcg tat gct act aac agg aaa ttc       16794
Leu Phe Phe Gly Asp Ile Arg Ser Tyr Ala Thr Asn Arg Lys Phe
5585             5590                 5595 ctt gca gcc aga gcc ctt cat atg cta ggg tcc aac gcg aag aaa       16839
Leu Ala Ala Arg Ala Leu His Met Leu Gly Ser Asn Ala Lys Lys
5600             5605                 5610 cat gac att cgc cgg aaa atg gct gag ttg gat gaa ttc gaa gaa       16884
His Asp Ile Arg Arg Lys Met Ala Glu Leu Asp Glu Phe Glu Glu
5615             5620                 5625
```

-continued

| | | | | | | | | | | | |
|---|---|---|---|---|---|---|---|---|---|---|---|
| gag | ttg | att | gtc | gat | cct | tct | ttc | ttc | act | ggt | ctg | gtc | agc | cga | 16929 |
| Glu | Leu | Ile | Val | Asp | Pro | Ser | Phe | Phe | Thr | Gly | Leu | Val | Ser | Arg | |
| | 5630 | | | | 5635 | | | | | 5640 | | | | | |

| ctg | cca | ggc | cag | gtc | aag | cat | gtg | gag | att | ctt | cca | aaa | caa | atg | 16974 |
| Leu | Pro | Gly | Gln | Val | Lys | His | Val | Glu | Ile | Leu | Pro | Lys | Gln | Met | |
| 5645 | | | | | 5650 | | | | | 5655 | | | | | |

| atc | gcc | aca | aat | gag | ctc | agc | gcg | tat | cgt | tat | gca | gcc | gtt | gtt | 17019 |
| Ile | Ala | Thr | Asn | Glu | Leu | Ser | Ala | Tyr | Arg | Tyr | Ala | Ala | Val | Val | |
| 5660 | | | | | 5665 | | | | | 5670 | | | | | |

| cat | cta | gct | ctt | ccc | gaa | gag | cag | cac | ata | gcg | aaa | atc | gaa | aag | 17064 |
| His | Leu | Ala | Leu | Pro | Glu | Glu | Gln | His | Ile | Ala | Lys | Ile | Glu | Lys | |
| 5675 | | | | 5680 | | | | | 5685 | | | | | | |

| ggc | gcc | tgg | gtc | gac | ttc | aca | gcc | acc | aag | atg | gat | cga | agc | gct | 17109 |
| Gly | Ala | Trp | Val | Asp | Phe | Thr | Ala | Thr | Lys | Met | Asp | Arg | Ser | Ala | |
| | 5690 | | | | 5695 | | | | | 5700 | | | | | |

| ctt | gtt | cat | cat | ctg | cag | agc | tcg | tca | aac | gct | gaa | att | gta | gct | 17154 |
| Leu | Val | His | His | Leu | Gln | Ser | Ser | Ser | Asn | Ala | Glu | Ile | Val | Ala | |
| 5705 | | | | | 5710 | | | | | 5715 | | | | | |

| atc | agt | aac | att | cca | ttc | agc | aaa | act | aat | ttc | gat | tgt | cat | ctt | 17199 |
| Ile | Ser | Asn | Ile | Pro | Phe | Ser | Lys | Thr | Asn | Phe | Asp | Cys | His | Leu | |
| 5720 | | | | | 5725 | | | | | 5730 | | | | | |

| ctc | gca | tct | ctg | gat | gag | gac | gaa | gaa | cac | tcg | ctt | gac | gga | tcc | 17244 |
| Leu | Ala | Ser | Leu | Asp | Glu | Asp | Glu | Glu | His | Ser | Leu | Asp | Gly | Ser | |
| 5735 | | | | | 5740 | | | | | 5745 | | | | | |

| gcc | tgg | atc | aaa | act | att | cat | tcc | agc | gcc | gaa | cag | tgt | cca | tcg | 17289 |
| Ala | Trp | Ile | Lys | Thr | Ile | His | Ser | Ser | Ala | Glu | Gln | Cys | Pro | Ser | |
| | 5750 | | | | 5755 | | | | | 5760 | | | | | |

| cta | tcc | gca | acc | gat | ctc | gtc | gaa | gtt | gct | aaa | gag | gtg | ggc | ttc | 17334 |
| Leu | Ser | Ala | Thr | Asp | Leu | Val | Glu | Val | Ala | Lys | Glu | Val | Gly | Phe | |
| 5765 | | | | | 5770 | | | | | 5775 | | | | | |

| cgt | gtc | gag | ctc | agc | tgg | gct | cgg | caa | aag | tct | caa | aac | ggt | gca | 17379 |
| Arg | Val | Glu | Leu | Ser | Trp | Ala | Arg | Gln | Lys | Ser | Gln | Asn | Gly | Ala | |
| | 5780 | | | | 5785 | | | | | 5790 | | | | | |

| ctt | gac | gct | atc | ttc | cac | caa | tac | caa | tct | ccc | aaa | gaa | ggt | agc | 17424 |
| Leu | Asp | Ala | Ile | Phe | His | Gln | Tyr | Gln | Ser | Pro | Lys | Glu | Gly | Ser | |
| 5795 | | | | | 5800 | | | | | 5805 | | | | | |

| cgt | gtt | cta | ata | cag | ttc | ccg | act | gac | gac | cag | ggt | cga | tcg | atg | 17469 |
| Arg | Val | Leu | Ile | Gln | Phe | Pro | Thr | Asp | Asp | Gln | Gly | Arg | Ser | Met | |
| 5810 | | | | | 5815 | | | | | 5820 | | | | | |

| gag | tct | ctt | acg | aac | cga | ccg | tta | cag | cga | gtt | cag | agc | cgc | cgg | 17514 |
| Glu | Ser | Leu | Thr | Asn | Arg | Pro | Leu | Gln | Arg | Val | Gln | Ser | Arg | Arg | |
| 5825 | | | | | 5830 | | | | | 5835 | | | | | |

| atc | gaa | aca | cag | att | cgt | gag | cga | cta | cag | gct | gtg | cta | cca | tca | 17559 |
| Ile | Glu | Thr | Gln | Ile | Arg | Glu | Arg | Leu | Gln | Ala | Val | Leu | Pro | Ser | |
| 5840 | | | | | 5845 | | | | | 5850 | | | | | |

| tac | atg | att | cca | gct | cgg | atc | gtg | gtg | cta | aat | gag | atg | cca | gtc | 17604 |
| Tyr | Met | Ile | Pro | Ala | Arg | Ile | Val | Val | Leu | Asn | Glu | Met | Pro | Val | |
| 5855 | | | | | 5860 | | | | | 5865 | | | | | |

| aat | gcc | aac | ggc | aaa | gtc | gac | cgc | aag | gag | ctg | acg | cgc | aga | gcg | 17649 |
| Asn | Ala | Asn | Gly | Lys | Val | Asp | Arg | Lys | Glu | Leu | Thr | Arg | Arg | Ala | |
| 5870 | | | | | 5875 | | | | | 5880 | | | | | |

| aag | gtg | gtc | cca | aga | atc | gaa | aca | gct | gcg | gag | cgt | att | caa | ccc | 17694 |
| Lys | Val | Val | Pro | Arg | Ile | Glu | Thr | Ala | Ala | Glu | Arg | Ile | Gln | Pro | |
| 5885 | | | | | 5890 | | | | | 5895 | | | | | |

| cga | aat | gaa | gtc | gaa | gcg | gtt | ctg | tgc | gag | gaa | ttc | agt | gaa | gtc | 17739 |
| Arg | Asn | Glu | Val | Glu | Ala | Val | Leu | Cys | Glu | Glu | Phe | Ser | Glu | Val | |
| 5900 | | | | | 5905 | | | | | 5910 | | | | | |

| ctc | ggc | gtc | gaa | gtt | ggt | gtc | acg | gac | aac | ttc | ttc | gat | ctt | ggt | 17784 |
| Leu | Gly | Val | Glu | Val | Gly | Val | Thr | Asp | Asn | Phe | Phe | Asp | Leu | Gly | |
| 5915 | | | | | 5920 | | | | | 5925 | | | | | |

| | | | | | | | | | | | | |
|---|---|---|---|---|---|---|---|---|---|---|---|---|
|gga|cac|tcg|ctc|atg|gct|acg|aag|ctg|gct|gca|cgt|act|ggg|cgc|17829|
|Gly|His|Ser|Leu|Met|Ala|Thr|Lys|Leu|Ala|Ala|Arg|Thr|Gly|Arg| |
| |5930| | | |5935| | | |5940| | | | | | |

| | | | | | | | | | | | | |
|---|---|---|---|---|---|---|---|---|---|---|---|---|
|cga|ctt|gat|gca|aag|gtg|tct|gtc|aaa|gac|gtt|ttc|gac|cac|cca|17874|
|Arg|Leu|Asp|Ala|Lys|Val|Ser|Val|Lys|Asp|Val|Phe|Asp|His|Pro| |
| |5945| | | |5950| | | |5955| | | | | | |

| | | | | | | | | | | | | |
|---|---|---|---|---|---|---|---|---|---|---|---|---|
|gta|cta|gcg|gat|ctt|gcc|gct|gct|att|cag|cga|ggc|tcg|act|ccc|17919|
|Val|Leu|Ala|Asp|Leu|Ala|Ala|Ala|Ile|Gln|Arg|Gly|Ser|Thr|Pro| |
| |5960| | | |5965| | | |5970| | | | | | |

| | | | | | | | | | | | | |
|---|---|---|---|---|---|---|---|---|---|---|---|---|
|cac|tcg|gcg|atc|gtt|act|act|gag|tac|tct|gga|cct|gta|gag|cag|17964|
|His|Ser|Ala|Ile|Val|Thr|Thr|Glu|Tyr|Ser|Gly|Pro|Val|Glu|Gln| |
| |5975| | | |5980| | | |5985| | | | | | |

| | | | | | | | | | | | | |
|---|---|---|---|---|---|---|---|---|---|---|---|---|
|tca|tac|gcc|cag|ggc|cgc|ctt|tgg|ttc|ctt|gaa|caa|ctc|aat|ttc|18009|
|Ser|Tyr|Ala|Gln|Gly|Arg|Leu|Trp|Phe|Leu|Glu|Gln|Leu|Asn|Phe| |
| |5990| | | |5995| | | |6000| | | | | | |

| | | | | | | | | | | | | |
|---|---|---|---|---|---|---|---|---|---|---|---|---|
|aag|gca|acg|tgg|tat|ctc|cta|ccg|ctt|gcg|gtg|cgg|att|cgt|ggg|18054|
|Lys|Ala|Thr|Trp|Tyr|Leu|Leu|Pro|Leu|Ala|Val|Arg|Ile|Arg|Gly| |
| |6005| | | |6010| | | |6015| | | | | | |

| | | | | | | | | | | | | |
|---|---|---|---|---|---|---|---|---|---|---|---|---|
|cca|ctc|aat|atc|aag|gcc|ctt|acc|acg|gcg|tta|cat|gcg|cta|gaa|18099|
|Pro|Leu|Asn|Ile|Lys|Ala|Leu|Thr|Thr|Ala|Leu|His|Ala|Leu|Glu| |
| |6020| | | |6025| | | |6030| | | | | | |

| | | | | | | | | | | | | |
|---|---|---|---|---|---|---|---|---|---|---|---|---|
|cag|cga|cat|gag|act|tta|aga|aca|aca|ttc|att|gag|cgg|gat|ggt|18144|
|Gln|Arg|His|Glu|Thr|Leu|Arg|Thr|Thr|Phe|Ile|Glu|Arg|Asp|Gly| |
| |6035| | | |6040| | | |6045| | | | | | |

| | | | | | | | | | | | | |
|---|---|---|---|---|---|---|---|---|---|---|---|---|
|gtg|ggc|aag|cag|gcc|gtt|cag|cca|ttt|cag|ccg|aag|gaa|ctc|gaa|18189|
|Val|Gly|Lys|Gln|Ala|Val|Gln|Pro|Phe|Gln|Pro|Lys|Glu|Leu|Glu| |
| |6050| | | |6055| | | |6060| | | | | | |

| | | | | | | | | | | | | |
|---|---|---|---|---|---|---|---|---|---|---|---|---|
|atc|gtc|gac|ata|gcg|gcc|gac|cac|cag|ggc|gac|tac|ctt|aaa|gtg|18234|
|Ile|Val|Asp|Ile|Ala|Ala|Asp|His|Gln|Gly|Asp|Tyr|Leu|Lys|Val| |
| |6065| | | |6070| | | |6075| | | | | | |

| | | | | | | | | | | | | |
|---|---|---|---|---|---|---|---|---|---|---|---|---|
|cta|cgt|gac|gag|cag|act|acc|atg|ttc|aat|cta|gca|act|cag|cct|18279|
|Leu|Arg|Asp|Glu|Gln|Thr|Thr|Met|Phe|Asn|Leu|Ala|Thr|Gln|Pro| |
| |6080| | | |6085| | | |6090| | | | | | |

| | | | | | | | | | | | | |
|---|---|---|---|---|---|---|---|---|---|---|---|---|
|ggt|tgg|agg|gtg|act|tta|cac|aga|gtg|gat|caa|aac|acg|cat|aat|18324|
|Gly|Trp|Arg|Val|Thr|Leu|His|Arg|Val|Asp|Gln|Asn|Thr|His|Asn| |
| |6095| | | |6100| | | |6105| | | | | | |

| | | | | | | | | | | | | |
|---|---|---|---|---|---|---|---|---|---|---|---|---|
|ctt|tcc|atc|gtc|atg|cac|cac|atc|att|tca|gac|ggc|tgg|tca|gtc|18369|
|Leu|Ser|Ile|Val|Met|His|His|Ile|Ile|Ser|Asp|Gly|Trp|Ser|Val| |
| |6110| | | |6115| | | |6120| | | | | | |

| | | | | | | | | | | | | |
|---|---|---|---|---|---|---|---|---|---|---|---|---|
|gat|gtt|ctg|cgc|cac|gag|ctg|agg|cag|ttc|tat|gct|gct|gcc|ctc|18414|
|Asp|Val|Leu|Arg|His|Glu|Leu|Arg|Gln|Phe|Tyr|Ala|Ala|Ala|Leu| |
| |6125| | | |6130| | | |6135| | | | | | |

| | | | | | | | | | | | | |
|---|---|---|---|---|---|---|---|---|---|---|---|---|
|cgg|ggt|cag|gat|ccc|ctc|gcg|cat|atc|agc|ccg|ctc|cca|att|caa|18459|
|Arg|Gly|Gln|Asp|Pro|Leu|Ala|His|Ile|Ser|Pro|Leu|Pro|Ile|Gln| |
| |6140| | | |6145| | | |6150| | | | | | |

| | | | | | | | | | | | | |
|---|---|---|---|---|---|---|---|---|---|---|---|---|
|tac|cgc|gac|ttc|tcg|ctc|tgg|caa|aag|cag|cca|gac|cag|atc|atc|18504|
|Tyr|Arg|Asp|Phe|Ser|Leu|Trp|Gln|Lys|Gln|Pro|Asp|Gln|Ile|Ile| |
| |6155| | | |6160| | | |6165| | | | | | |

| | | | | | | | | | | | | |
|---|---|---|---|---|---|---|---|---|---|---|---|---|
|gaa|cat|gca|aaa|caa|ctt|gag|tac|tgg|acc|aag|caa|ctg|gca|gac|18549|
|Glu|His|Ala|Lys|Gln|Leu|Glu|Tyr|Trp|Thr|Lys|Gln|Leu|Ala|Asp| |
| |6170| | | |6175| | | |6180| | | | | | |

| | | | | | | | | | | | | |
|---|---|---|---|---|---|---|---|---|---|---|---|---|
|agc|tcc|cca|gct|gag|ctc|cca|act|gat|tta|ccc|cgc|ccg|gcc|gta|18594|
|Ser|Ser|Pro|Ala|Glu|Leu|Pro|Thr|Asp|Leu|Pro|Arg|Pro|Ala|Val| |
| |6185| | | |6190| | | |6195| | | | | | |

| | | | | | | | | | | | | |
|---|---|---|---|---|---|---|---|---|---|---|---|---|
|ctg|tca|ggg|aaa|gct|ggc|gaa|gtg|gcc|ctt|tcc|gtc|aag|ggc|ccg|18639|
|Leu|Ser|Gly|Lys|Ala|Gly|Glu|Val|Ala|Leu|Ser|Val|Lys|Gly|Pro| |
| |6200| | | |6205| | | |6210| | | | | | |

| | | | | | | | | | | | | |
|---|---|---|---|---|---|---|---|---|---|---|---|---|
|cta|tat|gag|cgt|ctg|caa|gct|ttc|tgc|aag|act|cat|cag|aca|act|18684|
|Leu|Tyr|Glu|Arg|Leu|Gln|Ala|Phe|Cys|Lys|Thr|His|Gln|Thr|Thr| |

```
                  -continued
        6215            6220            6225 gcc ttc gcc aca ctc cta gca gcc ttc cgt gca aca cat cat cgc    18729
Ala Phe Ala Thr Leu Leu Ala Ala Phe Arg Ala Thr His His Arg
        6230            6235            6240 ctt aca gga gcc gaa gac gct acc atc ggc aca cct atc gcc aac    18774
Leu Thr Gly Ala Glu Asp Ala Thr Ile Gly Thr Pro Ile Ala Asn
        6245            6250            6255 cgc aac agg ccc gaa tta gag aac ctg att ggc ttc ttc gtg aat    18819
Arg Asn Arg Pro Glu Leu Glu Asn Leu Ile Gly Phe Phe Val Asn
        6260            6265            6270 gct cag tgt atg cgc att act atc gat gga gac gag act ttc gag    18864
Ala Gln Cys Met Arg Ile Thr Ile Asp Gly Asp Glu Thr Phe Glu
        6275            6280            6285 agt ctt ata cgt cag gtc cga gcc act gcg acg gct gcc atc gca    18909
Ser Leu Ile Arg Gln Val Arg Ala Thr Ala Thr Ala Ala Ile Ala
        6290            6295            6300 aat caa gat gtc ccc ttt gaa cgt atc gtg tct acc atg caa tct    18954
Asn Gln Asp Val Pro Phe Glu Arg Ile Val Ser Thr Met Gln Ser
        6305            6310            6315 acc tca cga gac acg tca agg aat ccg ctt gta cag ctc atg ttc    18999
Thr Ser Arg Asp Thr Ser Arg Asn Pro Leu Val Gln Leu Met Phe
        6320            6325            6330 gcc ctc cac tct caa cag gac ctc gga aaa atc caa cta gaa ggc    19044
Ala Leu His Ser Gln Gln Asp Leu Gly Lys Ile Gln Leu Glu Gly
        6335            6340            6345 tgc gaa acg gag cct att ccc cga gct gta cgc act cgc ttc gat    19089
Cys Glu Thr Glu Pro Ile Pro Arg Ala Val Arg Thr Arg Phe Asp
        6350            6355            6360 ctc gag ttc cat ctc tat caa gag caa ggg agc cta ggc ggc att    19134
Leu Glu Phe His Leu Tyr Gln Glu Gln Gly Ser Leu Gly Gly Ile
        6365            6370            6375 gtg tac ttt gcc acc gat ttg ttc gag cct gag agc att gag ggg    19179
Val Tyr Phe Ala Thr Asp Leu Phe Glu Pro Glu Ser Ile Glu Gly
        6380            6385            6390 atg gtt tcc att ttt aaa gaa atc ctc gct cga gct ctt gac caa    19224
Met Val Ser Ile Phe Lys Glu Ile Leu Ala Arg Ala Leu Asp Gln
        6395            6400            6405 ccc caa acc cca ctg gcg ctt cta ccg ctc acc gat ggg ctg gct    19269
Pro Gln Thr Pro Leu Ala Leu Leu Pro Leu Thr Asp Gly Leu Ala
        6410            6415            6420 gaa ctt cgc agg agg ggg ctg ctt gag att gaa agg ccc agc tat    19314
Glu Leu Arg Arg Arg Gly Leu Leu Glu Ile Glu Arg Pro Ser Tyr
        6425            6430            6435 cct cgc gag tcg agc gtt gtt gac gtc ttc tgt agc cag gta gcg    19359
Pro Arg Glu Ser Ser Val Val Asp Val Phe Cys Ser Gln Val Ala
        6440            6445            6450 gct tct ccc aac gca acc gct gtg aag gac tcg att tca cag ctc    19404
Ala Ser Pro Asn Ala Thr Ala Val Lys Asp Ser Ile Ser Gln Leu
        6455            6460            6465 act tac gct cag cta aat gag caa tct gac aag gtc gct gct tgg    19449
Thr Tyr Ala Gln Leu Asn Glu Gln Ser Asp Lys Val Ala Ala Trp
        6470            6475            6480 cta cac cag tgc aac ctt cca act gaa act ttg gtc gct gtg cta    19494
Leu His Gln Cys Asn Leu Pro Thr Glu Thr Leu Val Ala Val Leu
        6485            6490            6495 gcg cct cga tct tgc caa aca gtt gtg gcc ttc ttg ggt att ctg    19539
Ala Pro Arg Ser Cys Gln Thr Val Val Ala Phe Leu Gly Ile Leu
        6500            6505            6510 aag gcc aac cta gca tat ctt ccc cta gac gtc aat gtt ccg gca    19584
```

-continued

| | | | | | | | | | | | | | | |
|---|---|---|---|---|---|---|---|---|---|---|---|---|---|---|
| Lys | Ala | Asn | Leu | Ala | Tyr | Leu | Pro | Leu | Asp | Val | Asn | Val | Pro | Ala |
| 6515 | | | | | 6520 | | | | | 6525 | | | | |

| gct | cgc | att | gag | gca | att | ctc | tca | gaa | gtc | tct | ggc | cac | ata | ctt | 19629 |
|---|---|---|---|---|---|---|---|---|---|---|---|---|---|---|---|
| Ala | Arg | Ile | Glu | Ala | Ile | Leu | Ser | Glu | Val | Ser | Gly | His | Ile | Leu | |
| 6530 | | | | | 6535 | | | | | 6540 | | | | | |

| gtc | tta | ctt | gga | tct | cat | gtt | tct | gct | ccc | aag | att | gag | ctc | gct | 19674 |
|---|---|---|---|---|---|---|---|---|---|---|---|---|---|---|---|
| Val | Leu | Leu | Gly | Ser | His | Val | Ser | Ala | Pro | Lys | Ile | Glu | Leu | Ala | |
| 6545 | | | | | 6550 | | | | | 6555 | | | | | |

| gat | gtc | gaa | ttc | gtc | aaa | att | gac | aac | aca | gtc | gag | cac | aat | ttg | 19719 |
|---|---|---|---|---|---|---|---|---|---|---|---|---|---|---|---|
| Asp | Val | Glu | Phe | Val | Lys | Ile | Asp | Asn | Thr | Val | Glu | His | Asn | Leu | |
| 6560 | | | | | 6565 | | | | | 6570 | | | | | |

| ccg | ggc | cgc | att | gga | tct | gct | cca | tct | gcc | acg | agc | ctc | gcc | tat | 19764 |
|---|---|---|---|---|---|---|---|---|---|---|---|---|---|---|---|
| Pro | Gly | Arg | Ile | Gly | Ser | Ala | Pro | Ser | Ala | Thr | Ser | Leu | Ala | Tyr | |
| 6575 | | | | | 6580 | | | | | 6585 | | | | | |

| gtt | att | ttc | aca | tct | gga | tcg | act | ggc | aag | ccc | aaa | ggt | gtt | aag | 19809 |
|---|---|---|---|---|---|---|---|---|---|---|---|---|---|---|---|
| Val | Ile | Phe | Thr | Ser | Gly | Ser | Thr | Gly | Lys | Pro | Lys | Gly | Val | Lys | |
| 6590 | | | | | 6595 | | | | | 6600 | | | | | |

| gta | gag | cac | cgc | ggt | att | gtc | cgc | ctc | gtt | aaa | gag | agc | aat | gta | 19854 |
|---|---|---|---|---|---|---|---|---|---|---|---|---|---|---|---|
| Val | Glu | His | Arg | Gly | Ile | Val | Arg | Leu | Val | Lys | Glu | Ser | Asn | Val | |
| 6605 | | | | | 6610 | | | | | 6615 | | | | | |

| gta | gca | aaa | atg | cca | caa | gct | gcg | cgc | att | gct | cac | ttg | tca | aac | 19899 |
|---|---|---|---|---|---|---|---|---|---|---|---|---|---|---|---|
| Val | Ala | Lys | Met | Pro | Gln | Ala | Ala | Arg | Ile | Ala | His | Leu | Ser | Asn | |
| 6620 | | | | | 6625 | | | | | 6630 | | | | | |

| att | gcc | ttt | gac | gcg | gct | acg | tgg | gaa | tta | tat | gct | gcg | ttg | ctc | 19944 |
|---|---|---|---|---|---|---|---|---|---|---|---|---|---|---|---|
| Ile | Ala | Phe | Asp | Ala | Ala | Thr | Trp | Glu | Leu | Tyr | Ala | Ala | Leu | Leu | |
| 6635 | | | | | 6640 | | | | | 6645 | | | | | |

| aac | ggc | ggc | acc | ctc | gtc | tgt | atc | aac | tat | tta | acc | acg | ctg | gat | 19989 |
|---|---|---|---|---|---|---|---|---|---|---|---|---|---|---|---|
| Asn | Gly | Gly | Thr | Leu | Val | Cys | Ile | Asn | Tyr | Leu | Thr | Thr | Leu | Asp | |
| 6650 | | | | | 6655 | | | | | 6660 | | | | | |

| agt | aaa | gca | ctc | gag | gcc | gtg | ttt | gag | cag | gaa | aag | atc | caa | gcg | 20034 |
|---|---|---|---|---|---|---|---|---|---|---|---|---|---|---|---|
| Ser | Lys | Ala | Leu | Glu | Ala | Val | Phe | Glu | Gln | Glu | Lys | Ile | Gln | Ala | |
| 6665 | | | | | 6670 | | | | | 6675 | | | | | |

| gct | atg | ctt | cca | cca | gca | ctg | ctc | aaa | cag | tat | ttg | gtt | aac | att | 20079 |
|---|---|---|---|---|---|---|---|---|---|---|---|---|---|---|---|
| Ala | Met | Leu | Pro | Pro | Ala | Leu | Leu | Lys | Gln | Tyr | Leu | Val | Asn | Ile | |
| 6680 | | | | | 6685 | | | | | 6690 | | | | | |

| ccc | gca | gct | atc | ggt | gca | cta | gaa | gtg | gtc | ctt | gtc | gct | ggt | gac | 20124 |
|---|---|---|---|---|---|---|---|---|---|---|---|---|---|---|---|
| Pro | Ala | Ala | Ile | Gly | Ala | Leu | Glu | Val | Val | Leu | Val | Ala | Gly | Asp | |
| 6695 | | | | | 6700 | | | | | 6705 | | | | | |

| cgt | ttc | gat | cga | cgc | gat | gct | gca | gcc | acg | cag | gct | ctt | gtt | gga | 20169 |
|---|---|---|---|---|---|---|---|---|---|---|---|---|---|---|---|
| Arg | Phe | Asp | Arg | Arg | Asp | Ala | Ala | Ala | Thr | Gln | Ala | Leu | Val | Gly | |
| 6710 | | | | | 6715 | | | | | 6720 | | | | | |

| gca | ggc | gtg | tat | aac | gcc | tat | gga | ccg | acg | gag | aat | aca | aca | ctc | 20214 |
|---|---|---|---|---|---|---|---|---|---|---|---|---|---|---|---|
| Ala | Gly | Val | Tyr | Asn | Ala | Tyr | Gly | Pro | Thr | Glu | Asn | Thr | Thr | Leu | |
| 6725 | | | | | 6730 | | | | | 6735 | | | | | |

| agc | act | atc | tac | aat | gtc | gtt | cag | ggc | gat | gcc | aat | gtg | aat | ggc | 20259 |
|---|---|---|---|---|---|---|---|---|---|---|---|---|---|---|---|
| Ser | Thr | Ile | Tyr | Asn | Val | Val | Gln | Gly | Asp | Ala | Asn | Val | Asn | Gly | |
| 6740 | | | | | 6745 | | | | | 6750 | | | | | |

| gtc | ccg | att | gga | cgc | cct | gtc | agc | aac | tct | ggc | gcc | tac | atc | atg | 20304 |
|---|---|---|---|---|---|---|---|---|---|---|---|---|---|---|---|
| Val | Pro | Ile | Gly | Arg | Pro | Val | Ser | Asn | Ser | Gly | Ala | Tyr | Ile | Met | |
| 6755 | | | | | 6760 | | | | | 6765 | | | | | |

| aat | atg | aat | cag | gaa | ctc | gtt | cct | att | ggc | gtc | ata | ggc | gag | ctg | 20349 |
|---|---|---|---|---|---|---|---|---|---|---|---|---|---|---|---|
| Asn | Met | Asn | Gln | Glu | Leu | Val | Pro | Ile | Gly | Val | Ile | Gly | Glu | Leu | |
| 6770 | | | | | 6775 | | | | | 6780 | | | | | |

| gtc | gta | gta | gga | gac | ggt | gtc | gcc | cga | gga | tac | acc | gac | cca | gcc | 20394 |
|---|---|---|---|---|---|---|---|---|---|---|---|---|---|---|---|
| Val | Val | Val | Gly | Asp | Gly | Val | Ala | Arg | Gly | Tyr | Thr | Asp | Pro | Ala | |
| 6785 | | | | | 6790 | | | | | 6795 | | | | | |

| ttg | gac | gtc | aac | cgc | ttc | gtc | aac | gtc | act | att | gaa | ggc | caa | act | 20439 |
|---|---|---|---|---|---|---|---|---|---|---|---|---|---|---|---|
| Leu | Asp | Val | Asn | Arg | Phe | Val | Asn | Val | Thr | Ile | Glu | Gly | Gln | Thr | |
| 6800 | | | | | 6805 | | | | | 6810 | | | | | |

| | | | | | | | | | | | |
|---|---|---|---|---|---|---|---|---|---|---|---|
| atg | agg | gct | tat | agg | act | ggc | gat | cgt | gcc | cgc | tat | agg | ccc | aaa | 20484 |
| Met | Arg | Ala | Tyr | Arg | Thr | Gly | Asp | Arg | Ala | Arg | Tyr | Arg | Pro | Lys | |
| | 6815 | | | | 6820 | | | | 6825 | | | | | | |

| gac | gca | cag | att | gaa | ttc | ttt | ggc | cga | atg | gat | caa | cag | atc | aag | 20529 |
| Asp | Ala | Gln | Ile | Glu | Phe | Phe | Gly | Arg | Met | Asp | Gln | Gln | Ile | Lys | |
| 6830 | | | | 6835 | | | | | 6840 | | | | | | |

| att | cga | ggc | cat | cgt | att | gag | cca | gct | gag | gtc | gag | cat | gcg | ttg | 20574 |
| Ile | Arg | Gly | His | Arg | Ile | Glu | Pro | Ala | Glu | Val | Glu | His | Ala | Leu | |
| | 6845 | | | | 6850 | | | | 6855 | | | | | | |

| ctc | aac | aat | gac | ttg | ctt | cag | gac | gct | gca | gtc | att | atc | cga | aag | 20619 |
| Leu | Asn | Asn | Asp | Leu | Leu | Gln | Asp | Ala | Ala | Val | Ile | Ile | Arg | Lys | |
| 6860 | | | | 6865 | | | | | 6870 | | | | | | |

| caa | caa | aat | gat | gag | ctg | gag | atg | gtt | gct | ttt | gta | gaa | gca | aac | 20664 |
| Gln | Gln | Asn | Asp | Glu | Leu | Glu | Met | Val | Ala | Phe | Val | Glu | Ala | Asn | |
| | 6875 | | | | 6880 | | | | 6885 | | | | | | |

| agc | aat | aag | tcg | atc | gaa | caa | gag | gcg | agc | aac | caa | gta | gaa | gac | 20709 |
| Ser | Asn | Lys | Ser | Ile | Glu | Gln | Glu | Ala | Ser | Asn | Gln | Val | Glu | Asp | |
| 6890 | | | | 6895 | | | | | 6900 | | | | | | |

| tgg | ggc | gct | caa | ttc | gag | agc | aac | gtc | tac | gcc | gag | atc | gag | gca | 20754 |
| Trp | Gly | Ala | Gln | Phe | Glu | Ser | Asn | Val | Tyr | Ala | Glu | Ile | Glu | Ala | |
| | 6905 | | | | 6910 | | | | 6915 | | | | | | |

| atc | gat | gcc | tct | gct | gtt | ggt | aac | gac | ttc | atg | ggt | tgg | act | tcc | 20799 |
| Ile | Asp | Ala | Ser | Ala | Val | Gly | Asn | Asp | Phe | Met | Gly | Trp | Thr | Ser | |
| 6920 | | | | 6925 | | | | | 6930 | | | | | | |

| atg | tac | gac | ggc | agc | gcg | atc | gac | aag | gct | gag | atg | cag | gaa | tgg | 20844 |
| Met | Tyr | Asp | Gly | Ser | Ala | Ile | Asp | Lys | Ala | Glu | Met | Gln | Glu | Trp | |
| | 6935 | | | | 6940 | | | | 6945 | | | | | | |

| ctc | gat | gat | act | atg | cag | aca | ata | ctt | gat | ggt | cga | cca | gcc | ggc | 20889 |
| Leu | Asp | Asp | Thr | Met | Gln | Thr | Ile | Leu | Asp | Gly | Arg | Pro | Ala | Gly | |
| 6950 | | | | 6955 | | | | | 6960 | | | | | | |

| cgc | gtt | ctc | gaa | atc | ggc | act | ggc | acg | ggt | atg | atc | ctc | ttc | aat | 20934 |
| Arg | Val | Leu | Glu | Ile | Gly | Thr | Gly | Thr | Gly | Met | Ile | Leu | Phe | Asn | |
| | 6965 | | | | 6970 | | | | 6975 | | | | | | |

| ctt | ggt | gaa | ggg | tta | cag | agc | tat | gtc | ggt | ctc | gaa | cca | tct | acc | 20979 |
| Leu | Gly | Glu | Gly | Leu | Gln | Ser | Tyr | Val | Gly | Leu | Glu | Pro | Ser | Thr | |
| 6980 | | | | 6985 | | | | | 6990 | | | | | | |

| tcg | gcg | gct | gcg | ttc | gtc | aat | cgc | agg | att | cag | aca | ctt | cca | gct | 21024 |
| Ser | Ala | Ala | Ala | Phe | Val | Asn | Arg | Arg | Ile | Gln | Thr | Leu | Pro | Ala | |
| | 6995 | | | | 7000 | | | | 7005 | | | | | | |

| ttc | gct | ggt | aaa | gct | gaa | gtt | cac | gtg | ggt | aca | gcg | aca | gat | ata | 21069 |
| Phe | Ala | Gly | Lys | Ala | Glu | Val | His | Val | Gly | Thr | Ala | Thr | Asp | Ile | |
| 7010 | | | | 7015 | | | | | 7020 | | | | | | |

| agc | caa | ctt | caa | gat | ctc | cgc | ccg | gaa | gta | gtg | gtt | atc | aac | tcg | 21114 |
| Ser | Gln | Leu | Gln | Asp | Leu | Arg | Pro | Glu | Val | Val | Val | Ile | Asn | Ser | |
| | 7025 | | | | 7030 | | | | 7035 | | | | | | |

| gtg | gct | cag | tac | ttc | cca | tcg | cct | gag | tac | ttg | tct | aag | gtt | ttg | 21159 |
| Val | Ala | Gln | Tyr | Phe | Pro | Ser | Pro | Glu | Tyr | Leu | Ser | Lys | Val | Leu | |
| 7040 | | | | 7045 | | | | | 7050 | | | | | | |

| tac | gca | cta | gcc | caa | att | cct | ggc | gtc | aag | cgt | ttg | ttc | ttt | gga | 21204 |
| Tyr | Ala | Leu | Ala | Gln | Ile | Pro | Gly | Val | Lys | Arg | Leu | Phe | Phe | Gly | |
| | 7055 | | | | 7060 | | | | 7065 | | | | | | |

| gac | atg | cga | tct | tac | gcc | atc | aac | gac | cag | ttc | ctt | gca | gct | cgc | 21249 |
| Asp | Met | Arg | Ser | Tyr | Ala | Ile | Asn | Asp | Gln | Phe | Leu | Ala | Ala | Arg | |
| 7070 | | | | 7075 | | | | | 7080 | | | | | | |

| gcc | tta | cac | aac | ata | ggt | agc | aag | gct | act | aag | agc | gcc | att | cga | 21294 |
| Ala | Leu | His | Asn | Ile | Gly | Ser | Lys | Ala | Thr | Lys | Ser | Ala | Ile | Arg | |
| | 7085 | | | | 7090 | | | | 7095 | | | | | | |

| agc | aag | atg | gtc | gat | ctg | gaa | aac | tct | gag | gaa | gaa | ttg | ctc | gtc | 21339 |
| Ser | Lys | Met | Val | Asp | Leu | Glu | Asn | Ser | Glu | Glu | Glu | Leu | Leu | Val | |
| 7100 | | | | 7105 | | | | | 7110 | | | | | | |

```
gac cca acc ttc ttc acc aac cta gcg acc gag ctt cca gag gtt    21384
Asp Pro Thr Phe Phe Thr Asn Leu Ala Thr Glu Leu Pro Glu Val
    7115            7120            7125 gag cat gtt gag att ctg cca aaa cgc atg cag gct acc aac gaa    21429
Glu His Val Glu Ile Leu Pro Lys Arg Met Gln Ala Thr Asn Glu
7130            7135            7140 ctt agc gca tac cga tac gct gcg gtt gtt cat att cga gac cca    21474
Leu Ser Ala Tyr Arg Tyr Ala Ala Val Val His Ile Arg Asp Pro
    7145            7150            7155 gca agg cag gcg cag aca gtg cac acc att gat cct acc gct tgg    21519
Ala Arg Gln Ala Gln Thr Val His Thr Ile Asp Pro Thr Ala Trp
7160            7165            7170 atc gat ttt agc gca tct caa atg aat cgt act gct ctt gcc aac    21564
Ile Asp Phe Ser Ala Ser Gln Met Asn Arg Thr Ala Leu Ala Asn
    7175            7180            7185 ctc ttg caa aac tca gca gat gct gca gct atc gct gtc agc aac    21609
Leu Leu Gln Asn Ser Ala Asp Ala Ala Ala Ile Ala Val Ser Asn
7190            7195            7200 atc ccg tac agc aag acg atc ttg gcg cgc cac att gtt cag tcg    21654
Ile Pro Tyr Ser Lys Thr Ile Leu Ala Arg His Ile Val Gln Ser
    7205            7210            7215 ctt gat gac gat ctc aca gac agc gat gat cca caa gat gag ctt    21699
Leu Asp Asp Asp Leu Thr Asp Ser Asp Asp Pro Gln Asp Glu Leu
7220            7225            7230 gaa gga gct gct tgg atg tct gct atc cgg tcc aat atc aaa acc    21744
Glu Gly Ala Ala Trp Met Ser Ala Ile Arg Ser Asn Ile Lys Thr
    7235            7240            7245 tgt gca tcg ctg tcc gcc ttc gac ctt gcg caa ctt gcc cag gag    21789
Cys Ala Ser Leu Ser Ala Phe Asp Leu Ala Gln Leu Ala Gln Glu
7250            7255            7260 aaa ggc ttc cgt gtg gag ctt agt tgg gca aga caa cga acc cat    21834
Lys Gly Phe Arg Val Glu Leu Ser Trp Ala Arg Gln Arg Thr His
    7265            7270            7275 cat gga gct tta gac gct gtt ttc cat cat tac aag tct aac cag    21879
His Gly Ala Leu Asp Ala Val Phe His His Tyr Lys Ser Asn Gln
7280            7285            7290 gat ggt ggt cgt gtc ctg gtg cag ttc ccg act gat agt cga cct    21924
Asp Gly Gly Arg Val Leu Val Gln Phe Pro Thr Asp Ser Arg Pro
    7295            7300            7305 cgt cta tca gga caa ctc aca aac caa ccg ctg cag cgg cta cag    21969
Arg Leu Ser Gly Gln Leu Thr Asn Gln Pro Leu Gln Arg Leu Gln
7310            7315            7320 agt cga cga ttg gag gca cag att cga gat cag ctc agc gct tta    22014
Ser Arg Arg Leu Glu Ala Gln Ile Arg Asp Gln Leu Ser Ala Leu
    7325            7330            7335 ctt cca tct tac atg atc ccg tcg ctt atc gtg atg gtc gat gag    22059
Leu Pro Ser Tyr Met Ile Pro Ser Leu Ile Val Met Val Asp Glu
7340            7345            7350 atg ccc ttg aat gcc aat ggc aag gta gac agg aaa gcc cta gag    22104
Met Pro Leu Asn Ala Asn Gly Lys Val Asp Arg Lys Ala Leu Glu
    7355            7360            7365 cga agg gct cgc atg gtt cag aaa gtt gaa aag cca gct tct gag    22149
Arg Arg Ala Arg Met Val Gln Lys Val Glu Lys Pro Ala Ser Glu
7370            7375            7380 cga gtc ggt gca cgt aac gag atc gaa gcc gcg ctg tgc gaa gta    22194
Arg Val Gly Ala Arg Asn Glu Ile Glu Ala Ala Leu Cys Glu Val
    7385            7390            7395 ttc gta gat cta ctc ggc act gag gtc agc att act gac aac ttc    22239
Phe Val Asp Leu Leu Gly Thr Glu Val Ser Ile Thr Asp Asn Phe
```

-continued

| | | | | | | | | | | | | |
|---|---|---|---|---|---|---|---|---|---|---|---|---|
| | | 7400 | | | 7405 | | | 7410 | | | | |
| ttt | aat | ctt | ggc | ggt | cat | tcg | ctc | atg | gcc | aca | aaa | ttg gct gct | 22284 |
| Phe | Asn | Leu | Gly | Gly | His | Ser | Leu | Met | Ala | Thr | Lys | Leu Ala Ala | |
| | | 7415 | | | | 7420 | | | | 7425 | | | |
| cga | att | agc | aga | cgc | ctt | gac | gca | cgc | atc | tct | gtc | aag gat gtg | 22329 |
| Arg | Ile | Ser | Arg | Arg | Leu | Asp | Ala | Arg | Ile | Ser | Val | Lys Asp Val | |
| | | 7430 | | | | 7435 | | | | 7440 | | | |
| ttt | gac | tac | cct | gtt | ctc | gcc | gac | ctt | gcg | ggc | gcc | gtt cag cga | 22374 |
| Phe | Asp | Tyr | Pro | Val | Leu | Ala | Asp | Leu | Ala | Gly | Ala | Val Gln Arg | |
| | | 7445 | | | | 7450 | | | | 7455 | | | |
| ggc | tca | act | cca | cac | aac | cca | atc | gtc | gcg | acg | ccc | tac tca ggg | 22419 |
| Gly | Ser | Thr | Pro | His | Asn | Pro | Ile | Val | Ala | Thr | Pro | Tyr Ser Gly | |
| | | 7460 | | | | 7465 | | | | 7470 | | | |
| ccc | gtc | gag | cag | tcc | ttt | gct | cag | ggc | cgc | ctg | tgg | ttc ttg gac | 22464 |
| Pro | Val | Glu | Gln | Ser | Phe | Ala | Gln | Gly | Arg | Leu | Trp | Phe Leu Asp | |
| | | 7475 | | | | 7480 | | | | 7485 | | | |
| cag | ctt | aac | gcc | ggt | tcg | ctg | tgg | tac | atc | cag | cca | atc gcc gta | 22509 |
| Gln | Leu | Asn | Ala | Gly | Ser | Leu | Trp | Tyr | Ile | Gln | Pro | Ile Ala Val | |
| | | 7490 | | | | 7495 | | | | 7500 | | | |
| cgc | gta | cgc | ggt | tcg | ctc | aat | att | ggt | gcg | ctg | act | aca gca ctc | 22554 |
| Arg | Val | Arg | Gly | Ser | Leu | Asn | Ile | Gly | Ala | Leu | Thr | Thr Ala Leu | |
| | | 7505 | | | | 7510 | | | | 7515 | | | |
| aat | gcg | ctt | gag | aag | cgc | cac | gaa | ccg | ttg | cgc | acg | act ttc gaa | 22599 |
| Asn | Ala | Leu | Glu | Lys | Arg | His | Glu | Pro | Leu | Arg | Thr | Thr Phe Glu | |
| | | 7520 | | | | 7525 | | | | 7530 | | | |
| gag | cat | gac | ggc | att | ggt | gtg | caa | gtc | gtt | caa | ccg | cat cag ccg | 22644 |
| Glu | His | Asp | Gly | Ile | Gly | Val | Gln | Val | Val | Gln | Pro | His Gln Pro | |
| | | 7535 | | | | 7540 | | | | 7545 | | | |
| aag | aag | ctt | aga | att | gtc | gat | acg | gtg | gct | aac | tat | cag ggt gac | 22689 |
| Lys | Lys | Leu | Arg | Ile | Val | Asp | Thr | Val | Ala | Asn | Tyr | Gln Gly Asp | |
| | | 7550 | | | | 7555 | | | | 7560 | | | |
| ttc | atc | agg | gct | cta | cgg | aag | gag | cag | cag | act | cta | ttc aat ctc | 22734 |
| Phe | Ile | Arg | Ala | Leu | Arg | Lys | Glu | Gln | Gln | Thr | Leu | Phe Asn Leu | |
| | | 7565 | | | | 7570 | | | | 7575 | | | |
| gcg | acc | gag | cca | ggc | tgg | aga | gtg | tct | ctg | cta | cgc | att ggg gag | 22779 |
| Ala | Thr | Glu | Pro | Gly | Trp | Arg | Val | Ser | Leu | Leu | Arg | Ile Gly Glu | |
| | | 7580 | | | | 7585 | | | | 7590 | | | |
| gac | gac | aac | att | ctc | tcc | atc | gtc | atg | cac | cac | atc | att tca gac | 22824 |
| Asp | Asp | Asn | Ile | Leu | Ser | Ile | Val | Met | His | His | Ile | Ile Ser Asp | |
| | | 7595 | | | | 7600 | | | | 7605 | | | |
| ggt | tgg | tct | gtt | gac | atc | ttg | cgt | caa | gat | cta | aaa | cta ttc tat | 22869 |
| Gly | Trp | Ser | Val | Asp | Ile | Leu | Arg | Gln | Asp | Leu | Lys | Leu Phe Tyr | |
| | | 7610 | | | | 7615 | | | | 7620 | | | |
| gcc | gcc | gct | ctc | aaa | agc | cag | gag | ccg | caa | gta | gac | gcg ctc cca | 22914 |
| Ala | Ala | Ala | Leu | Lys | Ser | Gln | Glu | Pro | Gln | Val | Asp | Ala Leu Pro | |
| | | 7625 | | | | 7630 | | | | 7635 | | | |
| atc | caa | tat | cgt | gac | ttt | gcc | ttc | tgg | cag | aaa | cag | ccg gag cag | 22959 |
| Ile | Gln | Tyr | Arg | Asp | Phe | Ala | Phe | Trp | Gln | Lys | Gln | Pro Glu Gln | |
| | | 7640 | | | | 7645 | | | | 7650 | | | |
| gta | gct | gag | cac | cag | cga | caa | ctc | gac | tac | tgg | att | gaa caa ttg | 23004 |
| Val | Ala | Glu | His | Gln | Arg | Gln | Leu | Asp | Tyr | Trp | Ile | Glu Gln Leu | |
| | | 7655 | | | | 7660 | | | | 7665 | | | |
| aaa | gac | agc | aag | cct | gct | gag | ctt | atc | acc | gat | ttt | ccg cgg cca | 23049 |
| Lys | Asp | Ser | Lys | Pro | Ala | Glu | Leu | Ile | Thr | Asp | Phe | Pro Arg Pro | |
| | | 7670 | | | | 7675 | | | | 7680 | | | |
| gag | gtg | ctg | tct | ggc | act | gct | ggc | atc | gta | cag | ctt | gcc gtg gac | 23094 |
| Glu | Val | Leu | Ser | Gly | Thr | Ala | Gly | Ile | Val | Gln | Leu | Ala Val Asp | |
| | | 7685 | | | | 7690 | | | | 7695 | | | |
| ggc | caa | gtc | tac | gag | ggt | ctc | cgg | gct | ttc | tgc | aga | att cat caa | 23139 |

-continued

| | | | | | | | | | | | | |
|---|---|---|---|---|---|---|---|---|---|---|---|---|
| Gly | Gln | Val | Tyr | Glu | Gly | Leu | Arg | Ala | Phe | Cys | Arg | Ile | His | Gln |
| | | | 7700 | | | 7705 | | | | 7710 | | | |

| aca | acg | tcc | ttc | gtg | gta | ctt | ctt | gca | gcc | ttt | aga | gct | gcc | cat | 23184 |
| Thr | Thr | Ser | Phe | Val | Val | Leu | Leu | Ala | Ala | Phe | Arg | Ala | Ala | His | |
| | 7715 | | | 7720 | | | | 7725 | | | | | | | |

| tac | cgt | cta | aca | ggc | acc | gag | gac | gcg | aca | atc | ggt | tct | ccc | atc | 23229 |
| Tyr | Arg | Leu | Thr | Gly | Thr | Glu | Asp | Ala | Thr | Ile | Gly | Ser | Pro | Ile | |
| 7730 | | | | | 7735 | | | | | 7740 | | | | | |

| gcc | aac | cgg | aat | cgg | ccc | gaa | ctg | gag | agc | ctc | att | ggc | ttc | ttc | 23274 |
| Ala | Asn | Arg | Asn | Arg | Pro | Glu | Leu | Glu | Ser | Leu | Ile | Gly | Phe | Phe | |
| 7745 | | | | | 7750 | | | | | 7755 | | | | | |

| gtc | aat | acc | caa | tgt | atg | cgc | att | atg | gtc | gga | gag | gac | gac | aca | 23319 |
| Val | Asn | Thr | Gln | Cys | Met | Arg | Ile | Met | Val | Gly | Glu | Asp | Asp | Thr | |
| 7760 | | | | | 7765 | | | | | 7770 | | | | | |

| ttc | gaa | cga | ttg | gta | cag | cag | gtc | cga | tca | acg | aca | aca | gct | gca | 23364 |
| Phe | Glu | Arg | Leu | Val | Gln | Gln | Val | Arg | Ser | Thr | Thr | Thr | Ala | Ala | |
| 7775 | | | | | 7780 | | | | | 7785 | | | | | |

| ttt | gct | aac | cag | gac | gtt | ccc | ttc | gaa | cga | atc | gtt | tca | tcc | gtc | 23409 |
| Phe | Ala | Asn | Gln | Asp | Val | Pro | Phe | Glu | Arg | Ile | Val | Ser | Ser | Val | |
| 7790 | | | | | 7795 | | | | | 7800 | | | | | |

| cag | tca | acc | tca | aga | gat | gcc | tcc | cga | aac | cct | ttg | gta | cag | ctc | 23454 |
| Gln | Ser | Thr | Ser | Arg | Asp | Ala | Ser | Arg | Asn | Pro | Leu | Val | Gln | Leu | |
| 7805 | | | | | 7810 | | | | | 7815 | | | | | |

| atg | ttt | gca | ctt | cat | tca | cag | cag | ggt | atc | ggc | ctg | atg | gaa | ctc | 23499 |
| Met | Phe | Ala | Leu | His | Ser | Gln | Gln | Gly | Ile | Gly | Leu | Met | Glu | Leu | |
| 7820 | | | | | 7825 | | | | | 7830 | | | | | |

| gaa | ggt | gtt | gag | aca | gag | cca | att | gca | aga | gat | gta | tcg | acg | cgc | 23544 |
| Glu | Gly | Val | Glu | Thr | Glu | Pro | Ile | Ala | Arg | Asp | Val | Ser | Thr | Arg | |
| 7835 | | | | | 7840 | | | | | 7845 | | | | | |

| ttc | gac | atc | gag | ttc | cat | ctt | tac | cag | aag | gaa | gag | agc | tta | cac | 23589 |
| Phe | Asp | Ile | Glu | Phe | His | Leu | Tyr | Gln | Lys | Glu | Glu | Ser | Leu | His | |
| 7850 | | | | | 7855 | | | | | 7860 | | | | | |

| ggt | gtt | gtc | cac | ttt | gct | gcc | gac | ttg | ttc | gag | cct | gag | act | att | 23634 |
| Gly | Val | Val | His | Phe | Ala | Ala | Asp | Leu | Phe | Glu | Pro | Glu | Thr | Ile | |
| 7865 | | | | | 7870 | | | | | 7875 | | | | | |

| caa | ggc | ttg | gtc | tcc | gtc | ttc | cag | gaa | att | ctt | cgc | cga | gga | ctc | 23679 |
| Gln | Gly | Leu | Val | Ser | Val | Phe | Gln | Glu | Ile | Leu | Arg | Arg | Gly | Leu | |
| 7880 | | | | | 7885 | | | | | 7890 | | | | | |

| gag | aca | cct | cga | ttg | cca | atc | agc | att | ctg | cct | ctt | gat | aac | aac | 23724 |
| Glu | Thr | Pro | Arg | Leu | Pro | Ile | Ser | Ile | Leu | Pro | Leu | Asp | Asn | Asn | |
| 7895 | | | | | 7900 | | | | | 7905 | | | | | |

| att | ccg | gag | ctt | ctc | gtc | ggt | atg | ctc | gat | gtc | gac | act | cca | gag | 23769 |
| Ile | Pro | Glu | Leu | Leu | Val | Gly | Met | Leu | Asp | Val | Asp | Thr | Pro | Glu | |
| 7910 | | | | | 7915 | | | | | 7920 | | | | | |

| tat | cct | cgc | gat | tca | agc | gtg | gtt | gat | gtg | ttc | cgc | acc | caa | gtt | 23814 |
| Tyr | Pro | Arg | Asp | Ser | Ser | Val | Val | Asp | Val | Phe | Arg | Thr | Gln | Val | |
| 7925 | | | | | 7930 | | | | | 7935 | | | | | |

| gct | gcc | agc | ccg | gat | gcg | atc | gcc | gtt | aaa | gat | tca | act | tcg | cag | 23859 |
| Ala | Ala | Ser | Pro | Asp | Ala | Ile | Ala | Val | Lys | Asp | Ser | Thr | Ser | Gln | |
| 7940 | | | | | 7945 | | | | | 7950 | | | | | |

| ctc | acc | tac | gct | cag | ctt | gat | gaa | gaa | tcc | aac | aaa | gtg | gct | aca | 23904 |
| Leu | Thr | Tyr | Ala | Gln | Leu | Asp | Glu | Glu | Ser | Asn | Lys | Val | Ala | Thr | |
| 7955 | | | | | 7960 | | | | | 7965 | | | | | |

| tgg | ttg | agt | caa | agg | cag | ctg | gct | ccc | gaa | acg | ctg | gta | ggc | gtc | 23949 |
| Trp | Leu | Ser | Gln | Arg | Gln | Leu | Ala | Pro | Glu | Thr | Leu | Val | Gly | Val | |
| 7970 | | | | | 7975 | | | | | 7980 | | | | | |

| ctt | gcg | cct | aga | tcg | tgc | cca | aca | atc | gtt | aca | ttc | ttt | ggt | atc | 23994 |
| Leu | Ala | Pro | Arg | Ser | Cys | Pro | Thr | Ile | Val | Thr | Phe | Phe | Gly | Ile | |
| 7985 | | | | | 7990 | | | | | 7995 | | | | | |

| | | | | | | | | | | | | |
|---|---|---|---|---|---|---|---|---|---|---|---|---|
| ctc | aag | gcc | agt | ctg | gcg | tat | ctc | ccg | cta | gac | gtc | aac gta cca | 24039 |
| Leu | Lys | Ala | Ser | Leu | Ala | Tyr | Leu | Pro | Leu | Asp | Val | Asn Val Pro |
| | 8000 | | | | 8005 | | | | 8010 | | | |

```
ctc aag gcc agt ctg gcg tat ctc ccg cta gac gtc aac gta cca   24039
Leu Lys Ala Ser Leu Ala Tyr Leu Pro Leu Asp Val Asn Val Pro
    8000                8005                8010 tct gct cgt atc gag gcg atc ctc tcg gca gtc cct gac cat aag   24084
Ser Ala Arg Ile Glu Ala Ile Leu Ser Ala Val Pro Asp His Lys
    8015                8020                8025 ttg gtc ttc ctt ggt gct gac gtc ccc gat cca gag gct cca ctt   24129
Leu Val Phe Leu Gly Ala Asp Val Pro Asp Pro Glu Ala Pro Leu
    8030                8035                8040 gtc aac gtg gag ctg gtg cgg atc gac gac atc tta cgc caa agc   24174
Val Asn Val Glu Leu Val Arg Ile Asp Asp Ile Leu Arg Gln Ser
    8045                8050                8055 att cac gct tcg aat gca ggg ctt cta gca aat cac ccc tta gca   24219
Ile His Ala Ser Asn Ala Gly Leu Leu Ala Asn His Pro Leu Ala
    8060                8065                8070 act agt ctt gcc tac gtc atg ttt aca tct gga tct aca ggc aag   24264
Thr Ser Leu Ala Tyr Val Met Phe Thr Ser Gly Ser Thr Gly Lys
    8075                8080                8085 cct aag ggt gtc atg gtt gag cat cga agt att gta cgc ttg gta   24309
Pro Lys Gly Val Met Val Glu His Arg Ser Ile Val Arg Leu Val
    8090                8095                8100 aag gaa acg aac cta gtc cca gca gta gag gca gtt tcc tca gta   24354
Lys Glu Thr Asn Leu Val Pro Ala Val Glu Ala Val Ser Ser Val
    8105                8110                8115 gct cac atc tct aat gtt gct ttc gat gct gca act tgg gag ata   24399
Ala His Ile Ser Asn Val Ala Phe Asp Ala Ala Thr Trp Glu Ile
    8120                8125                8130 tac gct gcg ctc cta aat ggc gga act act gtt tgc att gat cac   24444
Tyr Ala Ala Leu Leu Asn Gly Gly Thr Thr Val Cys Ile Asp His
    8135                8140                8145 att act gtg ttg gat cct gct aaa cta gct ctc gtc ttc tca agc   24489
Ile Thr Val Leu Asp Pro Ala Lys Leu Ala Leu Val Phe Ser Ser
    8150                8155                8160 gag aag atc aaa gct gcg ttc ttc tca act gct ttg ctc aag cag   24534
Glu Lys Ile Lys Ala Ala Phe Phe Ser Thr Ala Leu Leu Lys Gln
    8165                8170                8175 cgg ctc tac gaa gag cca tct act atc act gga ctc gat ctt tta   24579
Arg Leu Tyr Glu Glu Pro Ser Thr Ile Thr Gly Leu Asp Leu Leu
    8180                8185                8190 tat gct ggc ggt gag aga atg agg cct caa gac gct ctt aag acg   24624
Tyr Ala Gly Gly Glu Arg Met Arg Pro Gln Asp Ala Leu Lys Thr
    8195                8200                8205 cga gaa cta gtt cgt ggt agc ttc tgc cac gtc tat ggg ccg aca   24669
Arg Glu Leu Val Arg Gly Ser Phe Cys His Val Tyr Gly Pro Thr
    8210                8215                8220 gaa aat aca aca ttc agc act gtc tat cct atg ggg gta gaa gaa   24714
Glu Asn Thr Thr Phe Ser Thr Val Tyr Pro Met Gly Val Glu Glu
    8225                8230                8235 cgc tgc gtc aac gga cta cct atc ggc cgc gca gtc agc cat tca   24759
Arg Cys Val Asn Gly Leu Pro Ile Gly Arg Ala Val Ser His Ser
    8240                8245                8250 ggc gca gtg atc atg gat gcc aat cag cgc ctc gtg ccg tta ggg   24804
Gly Ala Val Ile Met Asp Ala Asn Gln Arg Leu Val Pro Leu Gly
    8255                8260                8265 gtg atg ggc gaa ctt gtt gtc aca ggt gat ggt ctc gcc cga gga   24849
Val Met Gly Glu Leu Val Val Thr Gly Asp Gly Leu Ala Arg Gly
    8270                8275                8280 tac acc gat ccc gct ctg aat cgt gat cgc ttc gtg gaa gtc aat   24894
Tyr Thr Asp Pro Ala Leu Asn Arg Asp Arg Phe Val Glu Val Asn
    8285                8290                8295
```

```
atc cac ggt cag gtc ctg agg gca tat cgc aca ggc gac caa gcc    24939
Ile His Gly Gln Val Leu Arg Ala Tyr Arg Thr Gly Asp Gln Ala
    8300            8305            8310 cgc tat cga ccc aaa gat ggc cag att gag ttc tcc ggg cgt atg    24984
Arg Tyr Arg Pro Lys Asp Gly Gln Ile Glu Phe Ser Gly Arg Met
    8315            8320            8325 gac aga cag ctg aaa att cga ggc cat cgt atc gag cca gct gag    25029
Asp Arg Gln Leu Lys Ile Arg Gly His Arg Ile Glu Pro Ala Glu
    8330            8335            8340 gtc gag cac gcc ata ctt agc cac gac gat atc cga aac gca gtt    25074
Val Glu His Ala Ile Leu Ser His Asp Asp Ile Arg Asn Ala Val
    8345            8350            8355 gtg gtt act cga caa cag gaa ggc caa gat ctg gaa atg gtc gct    25119
Val Val Thr Arg Gln Gln Glu Gly Gln Asp Leu Glu Met Val Ala
    8360            8365            8370 ttc gtc tct act ccc aac gat caa acc gta gaa cgc gac gaa gct    25164
Phe Val Ser Thr Pro Asn Asp Gln Thr Val Glu Arg Asp Glu Ala
    8375            8380            8385 agg aat caa gtt gag gac tgg ggg gct caa ttc gag agc aac gtt    25209
Arg Asn Gln Val Glu Asp Trp Gly Ala Gln Phe Glu Ser Asn Val
    8390            8395            8400 tac gcc gag atc gag gag atc gac tcc tct gcc gtt ggg aat gac    25254
Tyr Ala Glu Ile Glu Glu Ile Asp Ser Ser Ala Val Gly Asn Asp
    8405            8410            8415 ttc atg ggc tgg acg tct atg tac gac ggt act gcg atc gat aaa    25299
Phe Met Gly Trp Thr Ser Met Tyr Asp Gly Thr Ala Ile Asp Lys
    8420            8425            8430 gca gag atg cag gag tgg ctc gac gat act atg aga acc ctc cat    25344
Ala Glu Met Gln Glu Trp Leu Asp Asp Thr Met Arg Thr Leu His
    8435            8440            8445 gac ggc cga gat cct ggc cac gtc ctc gaa gtt ggt aca ggc acg    25389
Asp Gly Arg Asp Pro Gly His Val Leu Glu Val Gly Thr Gly Thr
    8450            8455            8460 ggc atg atc cta ttc aat ctc ggc aag ggc ctg cag agc tac gtc    25434
Gly Met Ile Leu Phe Asn Leu Gly Lys Gly Leu Gln Ser Tyr Val
    8465            8470            8475 ggc ctc gag ccg tcg act tcg gca gct gca ttc gtc aat cgc aag    25479
Gly Leu Glu Pro Ser Thr Ser Ala Ala Ala Phe Val Asn Arg Lys
    8480            8485            8490 att gag act atc tca tca ttg gcg ggt aag gct aaa gtt gag att    25524
Ile Glu Thr Ile Ser Ser Leu Ala Gly Lys Ala Lys Val Glu Ile
    8495            8500            8505 ggc aca gca acc gac gta ggc cag ctc aag aac ctc cgc tcc gat    25569
Gly Thr Ala Thr Asp Val Gly Gln Leu Lys Asn Leu Arg Ser Asp
    8510            8515            8520 ttg gtc gtt att aat tcg gta gct caa tac ttc cct tcc ccc gag    25614
Leu Val Val Ile Asn Ser Val Ala Gln Tyr Phe Pro Ser Pro Glu
    8525            8530            8535 tat cta gtc gaa gca gta act gct cta gtc cac atc cca ggt gta    25659
Tyr Leu Val Glu Ala Val Thr Ala Leu Val His Ile Pro Gly Val
    8540            8545            8550 aaa cgc ttg ttc ttc ggc gac atg cga tcc tac gcc atg aat aag    25704
Lys Arg Leu Phe Phe Gly Asp Met Arg Ser Tyr Ala Met Asn Lys
    8555            8560            8565 cag ttc ctg gtt gct agg gct ctc cgt acg cta gga gcc aag gca    25749
Gln Phe Leu Val Ala Arg Ala Leu Arg Thr Leu Gly Ala Lys Ala
    8570            8575            8580 aac aag gac gat gtt cgc agg aag atg gtg gag cta gag gaa ttc    25794
Asn Lys Asp Asp Val Arg Arg Lys Met Val Glu Leu Glu Glu Phe
```

```
                 8585                8590                8595
gaa gag gaa cta ctc gtg gat cca gcc ttc ttc aca ggc ctc gca       25839
Glu Glu Glu Leu Leu Val Asp Pro Ala Phe Phe Thr Gly Leu Ala
        8600                8605                8610 aac tgg ctg tca gaa gtc gaa cat gtc gag att cta ccc aaa cag       25884
Asn Trp Leu Ser Glu Val Glu His Val Glu Ile Leu Pro Lys Gln
        8615                8620                8625 atg aca tct acc aac gag ctg agc tca tac cgt tat gca gcc atc       25929
Met Thr Ser Thr Asn Glu Leu Ser Ser Tyr Arg Tyr Ala Ala Ile
        8630                8635                8640 gta cac cta cgg ctt cca ggc cag gag gca caa cca gtc gtg aca       25974
Val His Leu Arg Leu Pro Gly Gln Glu Ala Gln Pro Val Val Thr
        8645                8650                8655 gtc aat caa gac gcc tgg gtt gac ttc gga gga tcc aag atg gat       26019
Val Asn Gln Asp Ala Trp Val Asp Phe Gly Gly Ser Lys Met Asp
        8660                8665                8670 cga cac gct ctt ctt cac cac cta caa agc tca cca aag gcc gaa       26064
Arg His Ala Leu Leu His His Leu Gln Ser Ser Pro Lys Ala Glu
        8675                8680                8685 act gta gcc atc agc aac atc ccc tat agc aag acg att tat gag       26109
Thr Val Ala Ile Ser Asn Ile Pro Tyr Ser Lys Thr Ile Tyr Glu
        8690                8695                8700 cgc cat gtc ctc gca tct ttg gat gac gat gaa gtc gag gac tcg       26154
Arg His Val Leu Ala Ser Leu Asp Asp Asp Glu Val Glu Asp Ser
        8705                8710                8715 tta gat ggg tca gca tgg cta tcg gct gtt cgc tct acc gcc gaa       26199
Leu Asp Gly Ser Ala Trp Leu Ser Ala Val Arg Ser Thr Ala Glu
        8720                8725                8730 cag tgc gcg tca ctc tcc gga gtc gac tta gtt caa atc gcc aag       26244
Gln Cys Ala Ser Leu Ser Gly Val Asp Leu Val Gln Ile Ala Lys
        8735                8740                8745 gag gcc ggc ttc cgc gtg gag ctc agc tgg gcg cga cag agg tct       26289
Glu Ala Gly Phe Arg Val Glu Leu Ser Trp Ala Arg Gln Arg Ser
        8750                8755                8760 cag aag ggt gga atc gac gcg gtc ttc cac cac tac gag tca gtg       26334
Gln Lys Gly Gly Ile Asp Ala Val Phe His His Tyr Glu Ser Val
        8765                8770                8775 cac gat gga gct cgc gtc atg gtc aag ttc ccg aca gat gat caa       26379
His Asp Gly Ala Arg Val Met Val Lys Phe Pro Thr Asp Asp Gln
        8780                8785                8790 ggc cga gcg ctc gat tcg ctt gcg aac agg ccg ctg caa cga ctc       26424
Gly Arg Ala Leu Asp Ser Leu Ala Asn Arg Pro Leu Gln Arg Leu
        8795                8800                8805 cag agt cga cga atc gag gtg caa att cgg gag cgg cta caa gct       26469
Gln Ser Arg Arg Ile Glu Val Gln Ile Arg Glu Arg Leu Gln Ala
        8810                8815                8820 gta ctg ccg tcc tat atg atg cca gtc cgc att gta gtc ttg gac       26514
Val Leu Pro Ser Tyr Met Met Pro Val Arg Ile Val Val Leu Asp
        8825                8830                8835 gag atg cct atg aat gcg aac ggc aag gtt gac aga aaa gtg ctt       26559
Glu Met Pro Met Asn Ala Asn Gly Lys Val Asp Arg Lys Val Leu
        8840                8845                8850 acc cgc aga gct aag atg att tcg agg gtc gag aca acc gct gaa       26604
Thr Arg Arg Ala Lys Met Ile Ser Arg Val Glu Thr Thr Ala Glu
        8855                8860                8865 cgc gtt ggg cct cgc aac gag ata gag gct ctc ctc tgt gag gag       26649
Arg Val Gly Pro Arg Asn Glu Ile Glu Ala Leu Leu Cys Glu Glu
        8870                8875                8880 ttt gct gaa gtg ctt ggt gtc gag gtt ggc att aat gac gac ttc       26694
```

```
                Phe Ala Glu Val Leu Gly Val Glu Val Gly Ile Asn Asp Asp Phe
                    8885            8890            8895 ttc gat ctt ggc gga cac tct ctc atg gcc acg aag ctt gca gct        26739
Phe Asp Leu Gly Gly His Ser Leu Met Ala Thr Lys Leu Ala Ala
    8900            8905            8910 cgc agt agc cgt cgc ttc gat gcg aag gtc tct gtc aaa gac gtg        26784
Arg Ser Ser Arg Arg Phe Asp Ala Lys Val Ser Val Lys Asp Val
    8915            8920            8925 ttt gat cat cct atc cta gcg gac cta gca gct tcg att cag cga        26829
Phe Asp His Pro Ile Leu Ala Asp Leu Ala Ala Ser Ile Gln Arg
    8930            8935            8940 ggc tca act cca cac aac ccc atc ctc gca aca caa tat agc ggg        26874
Gly Ser Thr Pro His Asn Pro Ile Leu Ala Thr Gln Tyr Ser Gly
    8945            8950            8955 cct gtg gag cag tct ttc gct cag ggt cgg ctg tgg ttc ctt gaa        26919
Pro Val Glu Gln Ser Phe Ala Gln Gly Arg Leu Trp Phe Leu Glu
    8960            8965            8970 cag ctg aac gtc agt tca aca tgg tat ctg caa cca atc gca gtg        26964
Gln Leu Asn Val Ser Ser Thr Trp Tyr Leu Gln Pro Ile Ala Val
    8975            8980            8985 cgt atg cgc gga ccg ctt aag att gag gcg ctc gcg gcg gcg ttt        27009
Arg Met Arg Gly Pro Leu Lys Ile Glu Ala Leu Ala Ala Ala Phe
    8990            8995            9000 cac gct ctg gag gag cgt cac gaa acc ctg cga acg acg ttt gaa        27054
His Ala Leu Glu Glu Arg His Glu Thr Leu Arg Thr Thr Phe Glu
    9005            9010            9015 gag cac gac ggc att ggt atg cag gtt gtt cag cca cat cgc ccc        27099
Glu His Asp Gly Ile Gly Met Gln Val Val Gln Pro His Arg Pro
    9020            9025            9030 aaa gaa ctc aga gtg att gat gta cag gct gag cat gat ggc gat        27144
Lys Glu Leu Arg Val Ile Asp Val Gln Ala Glu His Asp Gly Asp
    9035            9040            9045 tat act cag gct ctg cac aca gag caa aca act acg ttc aat tta        27189
Tyr Thr Gln Ala Leu His Thr Glu Gln Thr Thr Thr Phe Asn Leu
    9050            9055            9060 gaa acg gaa cca gga tgg agg gta tcg gtg ttt cgc ctg aac gaa        27234
Glu Thr Glu Pro Gly Trp Arg Val Ser Val Phe Arg Leu Asn Glu
    9065            9070            9075 gat gac aac atc ctc tct ata gtg atg cac cat atc atc tct gat        27279
Asp Asp Asn Ile Leu Ser Ile Val Met His His Ile Ile Ser Asp
    9080            9085            9090 ggt tgg tcg ttc gat atc ctg cgt aag gag atc aga gag ttt tac        27324
Gly Trp Ser Phe Asp Ile Leu Arg Lys Glu Ile Arg Glu Phe Tyr
    9095            9100            9105 aac gcc gcg ctc aag ggc aag gac ccc ttg gcg caa atg agc ccc        27369
Asn Ala Ala Leu Lys Gly Lys Asp Pro Leu Ala Gln Met Ser Pro
    9110            9115            9120 ttg cat atc caa tat cgc gac ttt tcc gtt tgg caa aag cag ctg        27414
Leu His Ile Gln Tyr Arg Asp Phe Ser Val Trp Gln Lys Gln Leu
    9125            9130            9135 aat cag atc acc gag cat aaa cgg cag ctt gat tac tgg acg aag        27459
Asn Gln Ile Thr Glu His Lys Arg Gln Leu Asp Tyr Trp Thr Lys
    9140            9145            9150 aac cta gcc gac aat act cca gcc gag ctc cca acc gat ctg cct        27504
Asn Leu Ala Asp Asn Thr Pro Ala Glu Leu Pro Thr Asp Leu Pro
    9155            9160            9165 cgg cca gcc gtt cta tcc ggt aag gct gga gtc atc cag ctc tct        27549
Arg Pro Ala Val Leu Ser Gly Lys Ala Gly Val Ile Gln Leu Ser
    9170            9175            9180
```

| | | | | | | | | | | | |
|---|---|---|---|---|---|---|---|---|---|---|---|
| att | aca | ggt | cca | gtc | tat | gat | cgt | ctc | cgc | gcg | ttc | tgc | cga | gtc | 27594 |
| Ile | Thr | Gly | Pro | Val | Tyr | Asp | Arg | Leu | Arg | Ala | Phe | Cys | Arg | Val | |
| | | 9185 | | | | 9190 | | | | | 9195 | | | | |
| cac | cag | acc | acc | tta | ttc | acg | gtg | ctc | ctc | act | gta | ttt | cga | gcc | 27639 |
| His | Gln | Thr | Thr | Leu | Phe | Thr | Val | Leu | Leu | Thr | Val | Phe | Arg | Ala | |
| | 9200 | | | | | 9205 | | | | | 9210 | | | | |
| acc | cac | tat | cgc | ctc | act | gga | gca | gag | gat | gct | acg | att | ggt | acg | 27684 |
| Thr | His | Tyr | Arg | Leu | Thr | Gly | Ala | Glu | Asp | Ala | Thr | Ile | Gly | Thr | |
| | 9215 | | | | | 9220 | | | | | 9225 | | | | |
| cct | atc | gct | aat | cgt | aac | aga | cca | gag | ctt | gag | aac | ttg | atc | ggg | 27729 |
| Pro | Ile | Ala | Asn | Arg | Asn | Arg | Pro | Glu | Leu | Glu | Asn | Leu | Ile | Gly | |
| | 9230 | | | | | 9235 | | | | | 9240 | | | | |
| ttt | ttt | gtt | aac | act | cag | tgc | atg | cgg | att | acc | gta | gaa | gag | gag | 27774 |
| Phe | Phe | Val | Asn | Thr | Gln | Cys | Met | Arg | Ile | Thr | Val | Glu | Glu | Glu | |
| | 9245 | | | | | 9250 | | | | | 9255 | | | | |
| gac | acg | ttc | gag | aca | ctc | atc | cac | cag | gtt | cgg | act | aca | act | aca | 27819 |
| Asp | Thr | Phe | Glu | Thr | Leu | Ile | His | Gln | Val | Arg | Thr | Thr | Thr | Thr | |
| | 9260 | | | | | 9265 | | | | | 9270 | | | | |
| gcc | gct | ttc | gcc | aac | caa | gac | gta | cct | ttt | gag | cga | att | gtg | tca | 27864 |
| Ala | Ala | Phe | Ala | Asn | Gln | Asp | Val | Pro | Phe | Glu | Arg | Ile | Val | Ser | |
| | 9275 | | | | | 9280 | | | | | 9285 | | | | |
| gcc | cta | ctc | cca | ggc | tcc | cga | gac | acg | tcc | cgc | aac | ccg | ctc | tct | 27909 |
| Ala | Leu | Leu | Pro | Gly | Ser | Arg | Asp | Thr | Ser | Arg | Asn | Pro | Leu | Ser | |
| | 9290 | | | | | 9295 | | | | | 9300 | | | | |
| cag | atc | atg | ttt | gcc | gta | cat | tct | cag | aaa | aac | atc | agc | aag | atc | 27954 |
| Gln | Ile | Met | Phe | Ala | Val | His | Ser | Gln | Lys | Asn | Ile | Ser | Lys | Ile | |
| | 9305 | | | | | 9310 | | | | | 9315 | | | | |
| gaa | ctg | gac | ggc | cta | gag | agc | gag | gcc | att | tca | cga | gcc | aca | tca | 27999 |
| Glu | Leu | Asp | Gly | Leu | Glu | Ser | Glu | Ala | Ile | Ser | Arg | Ala | Thr | Ser | |
| | 9320 | | | | | 9325 | | | | | 9330 | | | | |
| act | cgt | ttc | gat | cta | gag | ttc | cat | ctt | ttc | cag | gaa | gag | aag | ggc | 28044 |
| Thr | Arg | Phe | Asp | Leu | Glu | Phe | His | Leu | Phe | Gln | Glu | Glu | Lys | Gly | |
| | 9335 | | | | | 9340 | | | | | 9345 | | | | |
| cta | ggc | ggc | att | gta | ttg | ttt | gcg | gca | gat | ctg | ttc | gag | ccg | gag | 28089 |
| Leu | Gly | Gly | Ile | Val | Leu | Phe | Ala | Ala | Asp | Leu | Phe | Glu | Pro | Glu | |
| | 9350 | | | | | 9355 | | | | | 9360 | | | | |
| acg | atc | gac | agc | ctc | gtc | ttc | gtc | ttc | caa | gag | atc | ctc | cgc | cag | 28134 |
| Thr | Ile | Asp | Ser | Leu | Val | Phe | Val | Phe | Gln | Glu | Ile | Leu | Arg | Gln | |
| | 9365 | | | | | 9370 | | | | | 9375 | | | | |
| agt | ctc | gag | aca | ccc | aag | act | cca | att | gcg | gtc | ttg | cct | ctt | acc | 28179 |
| Ser | Leu | Glu | Thr | Pro | Lys | Thr | Pro | Ile | Ala | Val | Leu | Pro | Leu | Thr | |
| | 9380 | | | | | 9385 | | | | | 9390 | | | | |
| aat | ggt | att | gcg | cag | ctt | cgc | agc | atg | tgt | gtg | cta | gat | att | gag | 28224 |
| Asn | Gly | Ile | Ala | Gln | Leu | Arg | Ser | Met | Cys | Val | Leu | Asp | Ile | Glu | |
| | 9395 | | | | | 9400 | | | | | 9405 | | | | |
| aag | acc | gcc | tac | cct | caa | gac | tcc | agc | gtc | atc | gat | atc | ttc | cgc | 28269 |
| Lys | Thr | Ala | Tyr | Pro | Gln | Asp | Ser | Ser | Val | Ile | Asp | Ile | Phe | Arg | |
| | 9410 | | | | | 9415 | | | | | 9420 | | | | |
| cag | cag | gtt | gct | gcc | cgc | ccg | gat | gcc | acg | gcc | gtc | aca | gat | tct | 28314 |
| Gln | Gln | Val | Ala | Ala | Arg | Pro | Asp | Ala | Thr | Ala | Val | Thr | Asp | Ser | |
| | 9425 | | | | | 9430 | | | | | 9435 | | | | |
| acc | tct | cag | ctc | acc | tac | gca | caa | ctg | gat | ctc | cac | tct | gac | gag | 28359 |
| Thr | Ser | Gln | Leu | Thr | Tyr | Ala | Gln | Leu | Asp | Leu | His | Ser | Asp | Glu | |
| | 9440 | | | | | 9445 | | | | | 9450 | | | | |
| cta | gcc | agc | tgg | ctg | cgt | cag | aaa | aag | atg | gca | ccc | gag | act | ttg | 28404 |
| Leu | Ala | Ser | Trp | Leu | Arg | Gln | Lys | Lys | Met | Ala | Pro | Glu | Thr | Leu | |
| | 9455 | | | | | 9460 | | | | | 9465 | | | | |
| gtg | ggt | gtg | cta | gca | cca | cgg | tct | tgc | caa | acg | atc | gtt | acc | ttt | 28449 |
| Val | Gly | Val | Leu | Ala | Pro | Arg | Ser | Cys | Gln | Thr | Ile | Val | Thr | Phe | |
| | 9470 | | | | | 9475 | | | | | 9480 | | | | |

| | | | | | | | | | | | | |
|---|---|---|---|---|---|---|---|---|---|---|---|---|
| ctt | ggt | att | tta | aag | gcg | agc | tta | gcc | tat | tta | ccg | cta | gac | gtc | 28494 |
| Leu | Gly | Ile | Leu | Lys | Ala | Ser | Leu | Ala | Tyr | Leu | Pro | Leu | Asp | Val | |
| | 9485 | | | | 9490 | | | | | 9495 | | | | | |

```
ctt ggt att tta aag gcg agc tta gcc tat tta ccg cta gac gtc     28494
Leu Gly Ile Leu Lys Ala Ser Leu Ala Tyr Leu Pro Leu Asp Val
    9485            9490                9495 aaa gtg ccg gtt gcc cgc ata gag gcc att ttg tcg tcc att tca     28539
Lys Val Pro Val Ala Arg Ile Glu Ala Ile Leu Ser Ser Ile Ser
    9500            9505                9510 ggg cag aaa ctg att ctg ctt ggg cag gac gta cct gtc cca gaa     28584
Gly Gln Lys Leu Ile Leu Leu Gly Gln Asp Val Pro Val Pro Glu
    9515            9520                9525 atc cag ctc cca gac gtc gat gtc gta cca atc agt gaa atc tta     28629
Ile Gln Leu Pro Asp Val Asp Val Val Pro Ile Ser Glu Ile Leu
    9530            9535                9540 ggc cgc tct gtc cct tct cgt gct aca gat aag agt tta gga cca     28674
Gly Arg Ser Val Pro Ser Arg Ala Thr Asp Lys Ser Leu Gly Pro
    9545            9550                9555 ttg gca aga aat ctt gcg tat gtt ctg ttc aca tct gga tcc aca     28719
Leu Ala Arg Asn Leu Ala Tyr Val Leu Phe Thr Ser Gly Ser Thr
    9560            9565                9570 ggc aag ccc aag ggt gtc atg atc gag cac cgt agt att gtg cgc     28764
Gly Lys Pro Lys Gly Val Met Ile Glu His Arg Ser Ile Val Arg
    9575            9580                9585 ctt gtc aaa gag aca aat ctt atc tct aag cta cca aac gcg cct     28809
Leu Val Lys Glu Thr Asn Leu Ile Ser Lys Leu Pro Asn Ala Pro
    9590            9595                9600 cgc acg gca cat ctc acc aat ctc gtc ttt gac aac tct gca tgg     28854
Arg Thr Ala His Leu Thr Asn Leu Val Phe Asp Asn Ser Ala Trp
    9605            9610                9615 gaa att tac tcc acc ctt ctc aac ggg gga acg cta gtc tgc atc     28899
Glu Ile Tyr Ser Thr Leu Leu Asn Gly Gly Thr Leu Val Cys Ile
    9620            9625                9630 gac tat gcc acc gtt ctg gat agc aaa gcc ctc gag acc gtg ttc     28944
Asp Tyr Ala Thr Val Leu Asp Ser Lys Ala Leu Glu Thr Val Phe
    9635            9640                9645 aag gag caa cgc att cag aca tct ctg atg cct cct gcg cta ctt     28989
Lys Glu Gln Arg Ile Gln Thr Ser Leu Met Pro Pro Ala Leu Leu
    9650            9655                9660 aaa gag tgc tta gcc aac atg cct act atg ttc gat gac gta gag     29034
Lys Glu Cys Leu Ala Asn Met Pro Thr Met Phe Asp Asp Val Glu
    9665            9670                9675 gtg ctc tac gcg ctt gga gat cga ttc gac aaa cag gat gcc atg     29079
Val Leu Tyr Ala Leu Gly Asp Arg Phe Asp Lys Gln Asp Ala Met
    9680            9685                9690 aaa gcg cgc tcg ata gtc aag acc gcc gtc tac aac gcc tat ggt     29124
Lys Ala Arg Ser Ile Val Lys Thr Ala Val Tyr Asn Ala Tyr Gly
    9695            9700                9705 ccc acg gaa aac acg gtc atc agt act atc tac gag att gcc aag     29169
Pro Thr Glu Asn Thr Val Ile Ser Thr Ile Tyr Glu Ile Ala Lys
    9710            9715                9720 gac gat tcg ttc gtg aac ggt gtt ccc atc ggt cgg agc atc agc     29214
Asp Asp Ser Phe Val Asn Gly Val Pro Ile Gly Arg Ser Ile Ser
    9725            9730                9735 aac tcc gga gcc ttc atc atg gac tcc cgg caa cag ctc gtc ccc     29259
Asn Ser Gly Ala Phe Ile Met Asp Ser Arg Gln Gln Leu Val Pro
    9740            9745                9750 gtt ggc gtg cta ggc gag ctc gtc gtt tct ggc gat ggc ctt gcg     29304
Val Gly Val Leu Gly Glu Leu Val Val Ser Gly Asp Gly Leu Ala
    9755            9760                9765 aga gga tat act gat ccc aca ctg gat gta aat cgc ttc gtt gag     29349
Arg Gly Tyr Thr Asp Pro Thr Leu Asp Val Asn Arg Phe Val Glu
```

-continued

```
                    9770                9775                9780
gtg act gtt gat ggc caa cat gtt aga gta tac cgg acc ggt gat              29394
Val Thr Val Asp Gly Gln His Val Arg Val Tyr Arg Thr Gly Asp
        9785                9790                9795 cgc gta cgc ttc cgt cca aag gat ggt cag att gaa ttt ttt agt              29439
Arg Val Arg Phe Arg Pro Lys Asp Gly Gln Ile Glu Phe Phe Ser
        9800                9805                9810 cgc atg gat cag caa gtc aag att cga ggc cat cgt atc gag ccg              29484
Arg Met Asp Gln Gln Val Lys Ile Arg Gly His Arg Ile Glu Pro
        9815                9820                9825 gct gag gta gag cac gtt att ctc acc aac aag att atc cgt gat              29529
Ala Glu Val Glu His Val Ile Leu Thr Asn Lys Ile Ile Arg Asp
        9830                9835                9840 gcg gct gtt gca atc cgg cga cct gag ggt caa gaa cca gaa atg              29574
Ala Ala Val Ala Ile Arg Arg Pro Glu Gly Gln Glu Pro Glu Met
        9845                9850                9855 gtt gct ttc gtt act acc cat gaa aat act tct att gag aag cag              29619
Val Ala Phe Val Thr Thr His Glu Asn Thr Ser Ile Glu Lys Gln
        9860                9865                9870 tca gtc gag gaa ttc gca gca cgg atc gag aat gaa gtc cgt cgc              29664
Ser Val Glu Glu Phe Ala Ala Arg Ile Glu Asn Glu Val Arg Arg
        9875                9880                9885 tgg atc aag acc tta ctt ccg ctc tac atg gtt cct aca cag att              29709
Trp Ile Lys Thr Leu Leu Pro Leu Tyr Met Val Pro Thr Gln Ile
        9890                9895                9900 gtt gta ttg gat cga atg cct gtc aat gct aac ggt aag gtt gac              29754
Val Val Leu Asp Arg Met Pro Val Asn Ala Asn Gly Lys Val Asp
        9905                9910                9915 agg aaa gag ctc gcg caa aga gca caa acc cta cag aag agc gag              29799
Arg Lys Glu Leu Ala Gln Arg Ala Gln Thr Leu Gln Lys Ser Glu
        9920                9925                9930 gcc ggt tcc ctt cct tcc gtg aga gtt cct ccc acc aac gac atg              29844
Ala Gly Ser Leu Pro Ser Val Arg Val Pro Pro Thr Asn Asp Met
        9935                9940                9945 gag agg ata ttg tgc gaa gag ttt gcc gac gtt ctc ggc gtg gag              29889
Glu Arg Ile Leu Cys Glu Glu Phe Ala Asp Val Leu Gly Val Glu
        9950                9955                9960 gtc ggc att acc gac aac ttc ttc gac ttt gga gga cac tca ctc              29934
Val Gly Ile Thr Asp Asn Phe Phe Asp Phe Gly Gly His Ser Leu
        9965                9970                9975 atg gca acc aag ctc gca gcg cgt att agt cgc cgc gtg aac gcc              29979
Met Ala Thr Lys Leu Ala Ala Arg Ile Ser Arg Arg Val Asn Ala
        9980                9985                9990 cga gta tcc gtc aag agc gtt ttc gac cac ccc gtc ctt gtt gac              30024
Arg Val Ser Val Lys Ser Val Phe Asp His Pro Val Leu Val Asp
        9995                10000               10005 ctt gca tcc act att aaa caa gac tca atc atg cac aaa cct atc              30069
Leu Ala Ser Thr Ile Lys Gln Asp Ser Ile Met His Lys Pro Ile
        10010               10015               10020 cca cag acc gcc tac acc ggg ccc gtg gaa cag tcc ttt gcc caa              30114
Pro Gln Thr Ala Tyr Thr Gly Pro Val Glu Gln Ser Phe Ala Gln
        10025               10030               10035 ggc cgt ctc tgg ttc tta gac cag ctt aac ttc ggt gcc tcg tgg              30159
Gly Arg Leu Trp Phe Leu Asp Gln Leu Asn Phe Gly Ala Ser Trp
        10040               10045               10050 tac ctc atg cct ctc gcg cta cgc ttg caa gga tct ctt cac gtc              30204
Tyr Leu Met Pro Leu Ala Leu Arg Leu Gln Gly Ser Leu His Val
        10055               10060               10065 aag tcc ctc act act gcg ttg ttt gca cta gaa cag cgt cat gag              30249
```

```
                Lys Ser Leu Thr Thr Ala Leu Phe Ala Leu Glu Gln Arg His Glu
                    10070              10075              10080 acc ctg aga aca aca ttt gag gaa caa gat ggc gtg ggc atc caa       30294
Thr Leu Arg Thr Thr Phe Glu Glu Gln Asp Gly Val Gly Ile Gln
    10085              10090              10095 att gta cac cct gcc aac aag aaa gac ctt aga atc ctg gac gta       30339
Ile Val His Pro Ala Asn Lys Lys Asp Leu Arg Ile Leu Asp Val
    10100              10105              10110 tct aaa gag caa aac agc gac tat gct aaa gtc ctg cac aag gag       30384
Ser Lys Glu Gln Asn Ser Asp Tyr Ala Lys Val Leu His Lys Glu
    10115              10120              10125 cgc acg atc ccc att gat ctg act tcg gag cca ggt tgg agg gta       30429
Arg Thr Ile Pro Ile Asp Leu Thr Ser Glu Pro Gly Trp Arg Val
    10130              10135              10140 tcg ctc att cgc ttg ggc gaa gac gat cat atc ctc tcc atc gtc       30474
Ser Leu Ile Arg Leu Gly Glu Asp Asp His Ile Leu Ser Ile Val
    10145              10150              10155 atg cat cac att atc tca gat gga tgg tcc gtg gat gtt ctg cgc       30519
Met His His Ile Ile Ser Asp Gly Trp Ser Val Asp Val Leu Arg
    10160              10165              10170 caa gaa ctg aag caa ttc tat act gct gcg ctc aag ggt caa gat       30564
Gln Glu Leu Lys Gln Phe Tyr Thr Ala Ala Leu Lys Gly Gln Asp
    10175              10180              10185 cct ctg gcg cag att gac gct ctg cca atc caa tac cgc gac ttc       30609
Pro Leu Ala Gln Ile Asp Ala Leu Pro Ile Gln Tyr Arg Asp Phe
    10190              10195              10200 tca ttg tgg cag aag ttg cca gat caa gtt gct gag cac caa cga       30654
Ser Leu Trp Gln Lys Leu Pro Asp Gln Val Ala Glu His Gln Arg
    10205              10210              10215 cag ctc gag tac tgg gcc gag cag ttg gca gat aac act cca gcc       30699
Gln Leu Glu Tyr Trp Ala Glu Gln Leu Ala Asp Asn Thr Pro Ala
    10220              10225              10230 gag ctc ctg acc gat cta ccc cgg ccg gac gtc cta tct ggc aag       30744
Glu Leu Leu Thr Asp Leu Pro Arg Pro Asp Val Leu Ser Gly Lys
    10235              10240              10245 gct gga gcc gta caa ctc act atc gat ggt ccg gtg ttc gat cag       30789
Ala Gly Ala Val Gln Leu Thr Ile Asp Gly Pro Val Phe Asp Gln
    10250              10255              10260 ctc cag gcg ttc tgc cga gca cat cag aca aca atg ttc acg gtt       30834
Leu Gln Ala Phe Cys Arg Ala His Gln Thr Thr Met Phe Thr Val
    10265              10270              10275 ctg ctg gca gtc ttc cga aca act cat tac cgc ttg aca ggc gct       30879
Leu Leu Ala Val Phe Arg Thr Thr His Tyr Arg Leu Thr Gly Ala
    10280              10285              10290 act gac gcc act atc ggt acc ccg att gcc aac cgt aac agg ccg       30924
Thr Asp Ala Thr Ile Gly Thr Pro Ile Ala Asn Arg Asn Arg Pro
    10295              10300              10305 gaa ctt gaa aga ttg gtg ggc ttc ttc gtc aat act caa tgt atc       30969
Glu Leu Glu Arg Leu Val Gly Phe Phe Val Asn Thr Gln Cys Ile
    10310              10315              10320 agg atc acg gta gac gtg gag gat aca ttt gaa gca ttg gta cga       31014
Arg Ile Thr Val Asp Val Glu Asp Thr Phe Glu Ala Leu Val Arg
    10325              10330              10335 caa gtc cat tct acg tcg acg acg gcc ttt gcc aat cag gat gtt       31059
Gln Val His Ser Thr Ser Thr Thr Ala Phe Ala Asn Gln Asp Val
    10340              10345              10350 ccg ttc gag cga att gtg tcc aca att cta cca ggc tcg cga gac       31104
Pro Phe Glu Arg Ile Val Ser Thr Ile Leu Pro Gly Ser Arg Asp
    10355              10360              10365
```

```
gcc tcc cgg aat cct ctt gct caa ctc atg ttt gcc gtc cat tct   31149
Ala Ser Arg Asn Pro Leu Ala Gln Leu Met Phe Ala Val His Ser
        10370            10375           10380 cag agg gat atc agt aaa ttc cag ctt gaa ggc cta gac acg aag   31194
Gln Arg Asp Ile Ser Lys Phe Gln Leu Glu Gly Leu Asp Thr Lys
        10385           10390           10395 cct atc ccc acg gct gca tcc act cgc ttt gac att gag ttc cat   31239
Pro Ile Pro Thr Ala Ala Ser Thr Arg Phe Asp Ile Glu Phe His
        10400           10405           10410 atg ttt cag cag gca gaa cgc ctt tct gga agg gtt ctt ttc gca   31284
Met Phe Gln Gln Ala Glu Arg Leu Ser Gly Arg Val Leu Phe Ala
        10415           10420           10425 gag gat ctg ttc gaa cta gag act atc caa gga atg gtt gta atc   31329
Glu Asp Leu Phe Glu Leu Glu Thr Ile Gln Gly Met Val Val Ile
        10430           10435           10440 ttc aaa gag att ctc cga aga ggc ctt gaa acg cca cag acc cca   31374
Phe Lys Glu Ile Leu Arg Arg Gly Leu Glu Thr Pro Gln Thr Pro
        10445           10450           10455 ctt gcg gtt ctc cca ctc act gat ggg ctg gca cat ctt cgc agt   31419
Leu Ala Val Leu Pro Leu Thr Asp Gly Leu Ala His Leu Arg Ser
        10460           10465           10470 caa ggc cta ctt gag att gag agg cca gag tat ccg cgc gac tca   31464
Gln Gly Leu Leu Glu Ile Glu Arg Pro Glu Tyr Pro Arg Asp Ser
        10475           10480           10485 agc atg atc gac gtt ttc cgt gct cag gtt gcc gca tgc cct gac   31509
Ser Met Ile Asp Val Phe Arg Ala Gln Val Ala Ala Cys Pro Asp
        10490           10495           10500 gcg att gcg gtc aaa gac tcc acc tca cag ctt acc tac agt caa   31554
Ala Ile Ala Val Lys Asp Ser Thr Ser Gln Leu Thr Tyr Ser Gln
        10505           10510           10515 ctc gac gac caa tct gat aag atc act gcc tgg ctt ctc caa cgc   31599
Leu Asp Asp Gln Ser Asp Lys Ile Thr Ala Trp Leu Leu Gln Arg
        10520           10525           10530 aaa atc cca gct gag agt ttg gtt gct gta tac gct cca aga acg   31644
Lys Ile Pro Ala Glu Ser Leu Val Ala Val Tyr Ala Pro Arg Thr
        10535           10540           10545 tgt caa acc atc att aca ttc ttt ggt att ctc aag gct aat cta   31689
Cys Gln Thr Ile Ile Thr Phe Phe Gly Ile Leu Lys Ala Asn Leu
        10550           10555           10560 gcc tac ctt cca ttg gat atc aat gtc cca gcc gcc cgt att gag   31734
Ala Tyr Leu Pro Leu Asp Ile Asn Val Pro Ala Ala Arg Ile Glu
        10565           10570           10575 gca atc tta tca acc ata tct ggt cac aag cta gta ctg ctt ggg   31779
Ala Ile Leu Ser Thr Ile Ser Gly His Lys Leu Val Leu Leu Gly
        10580           10585           10590 tct caa gtc tcc gct cct gcg gta caa ttg aag gac gtc gaa tat   31824
Ser Gln Val Ser Ala Pro Ala Val Gln Leu Lys Asp Val Glu Tyr
        10595           10600           10605 gtt tgg att gat gaa gcc atg gct gag act gtt cgt aca tgc acc   31869
Val Trp Ile Asp Glu Ala Met Ala Glu Thr Val Arg Thr Cys Thr
        10610           10615           10620 agc ccc gaa cct tct gcc aca agt ctt gca tac gtc atc ttc aca   31914
Ser Pro Glu Pro Ser Ala Thr Ser Leu Ala Tyr Val Ile Phe Thr
        10625           10630           10635 tcc gga tct aca ggt cta ccc aag ggc gtc aag gtc gag cac cgt   31959
Ser Gly Ser Thr Gly Leu Pro Lys Gly Val Lys Val Glu His Arg
        10640           10645           10650 ggt gtc gta cgt ctc gtc aag cag agt aat gtg gta gca aag atg   32004
Gly Val Val Arg Leu Val Lys Gln Ser Asn Val Val Ala Lys Met
        10655           10660           10665
```

```
cct caa gca gca cgc gtt gcc cat cta tca aat atc gct ttc gac    32049
Pro Gln Ala Ala Arg Val Ala His Leu Ser Asn Ile Ala Phe Asp
    10670           10675           10680 gct gcc acg tgg gag atc tat gct gcg ctc ctt aac ggc ggc tct    32094
Ala Ala Thr Trp Glu Ile Tyr Ala Ala Leu Leu Asn Gly Gly Ser
    10685           10690           10695 ctc ata tgt att gac tat ttc act aca ttg gat agc aag gag ctt    32139
Leu Ile Cys Ile Asp Tyr Phe Thr Thr Leu Asp Ser Lys Glu Leu
    10700           10705           10710 gaa gcc gtg ttt gca cga gaa aaa atc caa gcg gcc atg ctt ccg    32184
Glu Ala Val Phe Ala Arg Glu Lys Ile Gln Ala Ala Met Leu Pro
    10715           10720           10725 ccg gcg ctg ctc aag cag tgt ttg gtc aac atc cct gcg act atc    32229
Pro Ala Leu Leu Lys Gln Cys Leu Val Asn Ile Pro Ala Thr Ile
    10730           10735           10740 agc gcc tta gac gtg gta ctt gca gcg ggc gac cgt ttc gac agg    32274
Ser Ala Leu Asp Val Val Leu Ala Ala Gly Asp Arg Phe Asp Arg
    10745           10750           10755 cgc gac gcg gcg gcg aca caa gcg ctc gtc gga ggc tgt gtc tac    32319
Arg Asp Ala Ala Ala Thr Gln Ala Leu Val Gly Gly Cys Val Tyr
    10760           10765           10770 aac gcg tac ggc ccc acc gag aac acg act ctc agt acc atc tac    32364
Asn Ala Tyr Gly Pro Thr Glu Asn Thr Thr Leu Ser Thr Ile Tyr
    10775           10780           10785 aat gtg gtc aaa ggc gat gcc aac gtc aac gga gtt cca atc ggt    32409
Asn Val Val Lys Gly Asp Ala Asn Val Asn Gly Val Pro Ile Gly
    10790           10795           10800 cgc cct gtt agc aac tca ggt gcc tac atc atg gat ccc aat caa    32454
Arg Pro Val Ser Asn Ser Gly Ala Tyr Ile Met Asp Pro Asn Gln
    10805           10810           10815 cag ctg gtc ccc aag ggt gtt atg gga gag ctt atc gtg gta gga    32499
Gln Leu Val Pro Lys Gly Val Met Gly Glu Leu Ile Val Val Gly
    10820           10825           10830 gac gga gtc gct cga gga tat acc gat cca gca cta gat gtc aat    32544
Asp Gly Val Ala Arg Gly Tyr Thr Asp Pro Ala Leu Asp Val Asn
    10835           10840           10845 cgt ttc att gag atc gcg att gat ggt gat cag gcg gtg cgc gcc    32589
Arg Phe Ile Glu Ile Ala Ile Asp Gly Asp Gln Ala Val Arg Ala
    10850           10855           10860 tat cga aca ggt gat cgc gct cgt tac cga cct aaa gac ggt caa    32634
Tyr Arg Thr Gly Asp Arg Ala Arg Tyr Arg Pro Lys Asp Gly Gln
    10865           10870           10875 atc gag ttc ttc ggc cgc atg gac caa caa atc aag att cgt ggc    32679
Ile Glu Phe Phe Gly Arg Met Asp Gln Gln Ile Lys Ile Arg Gly
    10880           10885           10890 cat cgt att gaa cca gcc gaa gtg gag cac gcc gta ctt gat aac    32724
His Arg Ile Glu Pro Ala Glu Val Glu His Ala Val Leu Asp Asn
    10895           10900           10905 agt atg gtg caa gat gct gcc gta att act cgc aag caa gat cag    32769
Ser Met Val Gln Asp Ala Ala Val Ile Thr Arg Lys Gln Asp Gln
    10910           10915           10920 gag cta gag atg atc gct ttt gtt act aca cgt agc gat aag gaa    32814
Glu Leu Glu Met Ile Ala Phe Val Thr Thr Arg Ser Asp Lys Glu
    10925           10930           10935 att gac aac gac gaa gcc agc aac caa gtc gaa gat tgg ggt aac    32859
Ile Asp Asn Asp Glu Ala Ser Asn Gln Val Glu Asp Trp Gly Asn
    10940           10945           10950 cag ttt gag agt aac ata tat gct gag atc gaa gag atc gat tcc    32904
Gln Phe Glu Ser Asn Ile Tyr Ala Glu Ile Glu Glu Ile Asp Ser
```

-continued

|     |     |     |     |     |      |
|-----|-----|-----|-----|-----|------|
| tct gcc att ggc aaa gac ttc atg ggc tgg acg tcc atg tac gac | | | | | 32949 |
| Ser Ala Ile Gly Lys Asp Phe Met Gly Trp Thr Ser Met Tyr Asp | | | | | |
| 10970 10975 10980 | | | | | |
| ggt agt gct atc gac aaa gac gaa atg cag gag tgg cta gac gac | | | | | 32994 |
| Gly Ser Ala Ile Asp Lys Asp Glu Met Gln Glu Trp Leu Asp Asp | | | | | |
| 10985 10990 10995 | | | | | |
| act atg agc aca ctg ctc gac ggt cga caa cca ggc cac gta ctc | | | | | 33039 |
| Thr Met Ser Thr Leu Leu Asp Gly Arg Gln Pro Gly His Val Leu | | | | | |
| 11000 11005 11010 | | | | | |
| gaa atc ggt act ggt act ggc atg atc ttg ttc aac cta gcc gag | | | | | 33084 |
| Glu Ile Gly Thr Gly Thr Gly Met Ile Leu Phe Asn Leu Ala Glu | | | | | |
| 11015 11020 11025 | | | | | |
| aga atg gga ttg aag agc tac gta ggc ctc gat ccc tcg gag aag | | | | | 33129 |
| Arg Met Gly Leu Lys Ser Tyr Val Gly Leu Asp Pro Ser Glu Lys | | | | | |
| 11030 11035 11040 | | | | | |
| gca acc tca ttc gtt aaa cag gcc atc aag tct cgc cca tct ctg | | | | | 33174 |
| Ala Thr Ser Phe Val Lys Gln Ala Ile Lys Ser Arg Pro Ser Leu | | | | | |
| 11045 11050 11055 | | | | | |
| gca ggc aag gct gag gtt cac gtc ggc aca gca aca gat gtg gct | | | | | 33219 |
| Ala Gly Lys Ala Glu Val His Val Gly Thr Ala Thr Asp Val Ala | | | | | |
| 11060 11065 11070 | | | | | |
| cga atg cga gat ctg cac ccc gaa gtg gtg gtt atc aat tcg gta | | | | | 33264 |
| Arg Met Arg Asp Leu His Pro Glu Val Val Val Ile Asn Ser Val | | | | | |
| 11075 11080 11085 | | | | | |
| gct caa tac ttt cca tcg cct gag tat ctg gcc gat gtc gtt ggc | | | | | 33309 |
| Ala Gln Tyr Phe Pro Ser Pro Glu Tyr Leu Ala Asp Val Val Gly | | | | | |
| 11090 11095 11100 | | | | | |
| gct ttg gtt cgc att cca ggc gtg aaa cga ctc ttc ttc ggc gac | | | | | 33354 |
| Ala Leu Val Arg Ile Pro Gly Val Lys Arg Leu Phe Phe Gly Asp | | | | | |
| 11105 11110 11115 | | | | | |
| ata cga tcc tac gct act aat aat cat ttc ctt gca gcc aga gcc | | | | | 33399 |
| Ile Arg Ser Tyr Ala Thr Asn Asn His Phe Leu Ala Ala Arg Ala | | | | | |
| 11120 11125 11130 | | | | | |
| cta cac aag cta gga gaa aag gca act agg gat act gta cga agc | | | | | 33444 |
| Leu His Lys Leu Gly Glu Lys Ala Thr Arg Asp Thr Val Arg Ser | | | | | |
| 11135 11140 11145 | | | | | |
| aaa atg gct gag ctc gaa ggc tac gag gag gaa ctg ctt gtc gac | | | | | 33489 |
| Lys Met Ala Glu Leu Glu Gly Tyr Glu Glu Glu Leu Leu Val Asp | | | | | |
| 11150 11155 11160 | | | | | |
| cca aca ttc ttc acc agt cta acg gcc aag ctt cac ggc cag gtc | | | | | 33534 |
| Pro Thr Phe Phe Thr Ser Leu Thr Ala Lys Leu His Gly Gln Val | | | | | |
| 11165 11170 11175 | | | | | |
| gag cac gtt gag atc cta cct aag cgt atg cag gcc acc aac gaa | | | | | 33579 |
| Glu His Val Glu Ile Leu Pro Lys Arg Met Gln Ala Thr Asn Glu | | | | | |
| 11180 11185 11190 | | | | | |
| ctc agc gca tac cga tac gcg gct ata gtc tac atc cgt gat cca | | | | | 33624 |
| Leu Ser Ala Tyr Arg Tyr Ala Ala Ile Val Tyr Ile Arg Asp Pro | | | | | |
| 11195 11200 11205 | | | | | |
| aaa cga gcg cag act gtg cag acg tcc aaa tcg gac gcc tgg gtc | | | | | 33669 |
| Lys Arg Ala Gln Thr Val Gln Thr Val Lys Ser Asp Ala Trp Val | | | | | |
| 11210 11215 11220 | | | | | |
| gat ttc agc acc tct caa atg gac cgc agt gtg ctc gtc agt ctc | | | | | 33714 |
| Asp Phe Ser Thr Ser Gln Met Asp Arg Ser Val Leu Val Ser Leu | | | | | |
| 11225 11230 11235 | | | | | |
| tta cag agc tca gat gct gaa gct atc gct gtc agc aat att ccc | | | | | 33759 |
| Leu Gln Ser Ser Asp Ala Glu Ala Ile Ala Val Ser Asn Ile Pro | | | | | |
| 11240 11245 11250 | | | | | |
| tac agc aag acg atc gtg gcg cgg cat atc gtt gag tca ctc agc | | | | | 33804 |

```
Tyr Ser Lys Thr Ile Val Ala   Arg His Ile Val Glu   Ser Leu Ser
    11255                 11260                 11265 gca gag gat tca caa gag atg   ctg gac ggc cct gct   tgg atc tca  33849
Ala Glu Asp Ser Gln Glu Met   Leu Asp Gly Pro Ala   Trp Ile Ser
    11270                 11275                 11280 gca gtc cgc tcc agc gct gaa   cag tgc gca tcc ttg   tct gcg atc  33894
Ala Val Arg Ser Ser Ala Glu   Gln Cys Ala Ser Leu   Ser Ala Ile
    11285                 11290                 11295 gac ctt gta cag gtt gct aaa   gag aac ggc ttc cga   gtg gag ctc  33939
Asp Leu Val Gln Val Ala Lys   Glu Asn Gly Phe Arg   Val Glu Leu
    11300                 11305                 11310 agc tgc gca cga cag cgg tct   cat aat gga gcg att   gat gcg gta  33984
Ser Cys Ala Arg Gln Arg Ser   His Asn Gly Ala Ile   Asp Ala Val
    11315                 11320                 11325 ttc cat cac tac aag cct gcg   caa gaa ggt agc cgt   gtc ttg cta  34029
Phe His His Tyr Lys Pro Ala   Gln Glu Gly Ser Arg   Val Leu Leu
    11330                 11335                 11340 caa ttt cca acc gac aat cac   atc cgg gca ggc tcg   ctt acg aac  34074
Gln Phe Pro Thr Asp Asn His   Ile Arg Ala Gly Ser   Leu Thr Asn
    11345                 11350                 11355 cga cca cta caa cgt ctc gag   agt cga agg gtg gag   aca aaa ctc  34119
Arg Pro Leu Gln Arg Leu Glu   Ser Arg Arg Val Glu   Thr Lys Leu
    11360                 11365                 11370 aag gaa cac ctt ttt agt gtg   ctt cca tcg tac atg   att cca tca  34164
Lys Glu His Leu Phe Ser Val   Leu Pro Ser Tyr Met   Ile Pro Ser
    11375                 11380                 11385 cat att gtg atg gtt gac cag   atg cct ctg aat gcg   aac ggc aag  34209
His Ile Val Met Val Asp Gln   Met Pro Leu Asn Ala   Asn Gly Lys
    11390                 11395                 11400 gtt gac cgg aaa gcc ctg gca   caa aga gct gaa gca   gtt ctc aag  34254
Val Asp Arg Lys Ala Leu Ala   Gln Arg Ala Glu Ala   Val Leu Lys
    11405                 11410                 11415 atc gag aaa cca gct tct gag   aga gtc agt gca cgg   aac gaa gtg  34299
Ile Glu Lys Pro Ala Ser Glu   Arg Val Ser Ala Arg   Asn Glu Val
    11420                 11425                 11430 gaa gct gta ctg tgt gaa gag   ttc acc gat gtc ctt   ggt gtg gag  34344
Glu Ala Val Leu Cys Glu Glu   Phe Thr Asp Val Leu   Gly Val Glu
    11435                 11440                 11445 gtc ggc att acc gac aac ttc   ttc gac ctg ggc gga   cac tcg ctc  34389
Val Gly Ile Thr Asp Asn Phe   Phe Asp Leu Gly Gly   His Ser Leu
    11450                 11455                 11460 atg gcc acc aaa ctc gca gcc   cgt atc agc aag cac   ctc gac gct  34434
Met Ala Thr Lys Leu Ala Ala   Arg Ile Ser Lys His   Leu Asp Ala
    11465                 11470                 11475 cgc gtc tct gtc aag gac gtt   ttt gat tac cct gtc   gtt gct gat  34479
Arg Val Ser Val Lys Asp Val   Phe Asp Tyr Pro Val   Val Ala Asp
    11480                 11485                 11490 cta gca gcg tca att gaa cga   aac tcg atc cct cat   aac ccc att  34524
Leu Ala Ala Ser Ile Glu Arg   Asn Ser Ile Pro His   Asn Pro Ile
    11495                 11500                 11505 ccc tcg acc aac tac tct gga   ccc gtg gag caa tct   ttc gcg caa  34569
Pro Ser Thr Asn Tyr Ser Gly   Pro Val Glu Gln Ser   Phe Ala Gln
    11510                 11515                 11520 ggc cga ctt tgg ttc ctg gat   caa ctg aat atg ggc   gta tcg gaa  34614
Gly Arg Leu Trp Phe Leu Asp   Gln Leu Asn Met Gly   Val Ser Glu
    11525                 11530                 11535 tta tat cta atg cct ctt gct   cta cgc ctg cgc gga   cct ctg cgc  34659
Leu Tyr Leu Met Pro Leu Ala   Leu Arg Leu Arg Gly   Pro Leu Arg
    11540                 11545                 11550
```

```
gtt gac gcc ttc gca gct gca     gta tct gct ctc gag     gca cgc cat      34704
Val Asp Ala Phe Ala Ala Ala     Val Ser Ala Leu Glu     Ala Arg His
        11555           11560                   11565 gaa act ctc cga aca acc ttc     atg gat cac gac ggt     gta ggc atg      34749
Glu Thr Leu Arg Thr Thr Phe     Met Asp His Asp Gly     Val Gly Met
        11570           11575                   11580 caa gtc att ctg ccc agt aac     agc aag aaa ctg aga     gtc att gac      34794
Gln Val Ile Leu Pro Ser Asn     Ser Lys Lys Leu Arg     Val Ile Asp
        11585           11590                   11595 gcg tcc gag aac gac tat ata     gac atc ctg cga cag     gaa cgg aca      34839
Ala Ser Glu Asn Asp Tyr Ile     Asp Ile Leu Arg Gln     Glu Arg Thr
        11600           11605                   11610 gct cca ttc aat ctc acg acc     gag cca ggg ttt agg     atc gcc ctc      34884
Ala Pro Phe Asn Leu Thr Thr     Glu Pro Gly Phe Arg     Ile Ala Leu
        11615           11620                   11625 ttg cag ctg ggt caa acc gac     ttc att ctg tca att     gtc atg cac      34929
Leu Gln Leu Gly Gln Thr Asp     Phe Ile Leu Ser Ile     Val Met His
        11630           11635                   11640 cat atc ata tat gac ggt tgg     tct att gat gtt cta     tgc aga gag      34974
His Ile Ile Tyr Asp Gly Trp     Ser Ile Asp Val Leu     Cys Arg Glu
        11645           11650                   11655 ctt ggc cga ttc tat agc gct     gca cta cag ggc cag     gat cca ttg      35019
Leu Gly Arg Phe Tyr Ser Ala     Ala Leu Gln Gly Gln     Asp Pro Leu
        11660           11665                   11670 gcg caa gtg agc cct ctg cct     atc cag tac cga gat     ttc tct atc      35064
Ala Gln Val Ser Pro Leu Pro     Ile Gln Tyr Arg Asp     Phe Ser Ile
        11675           11680                   11685 tgg caa aag cgg cca gag caa     gtg gcc gag cat gag     cgc cag cta      35109
Trp Gln Lys Arg Pro Glu Gln     Val Ala Glu His Glu     Arg Gln Leu
        11690           11695                   11700 caa tac tgg act gaa caa ctg     gca gat agc tct cca     gct gag ctt      35154
Gln Tyr Trp Thr Glu Gln Leu     Ala Asp Ser Ser Pro     Ala Glu Leu
        11705           11710                   11715 ctt acg gat cta ccc cgg cca     ttg gtg cca acc ggt     aag gcc ggt      35199
Leu Thr Asp Leu Pro Arg Pro     Leu Val Pro Thr Gly     Lys Ala Gly
        11720           11725                   11730 atc gtt caa ctc acg att gag     ggc gca gtc tac gag     cgc ctt cga      35244
Ile Val Gln Leu Thr Ile Glu     Gly Ala Val Tyr Glu     Arg Leu Arg
        11735           11740                   11745 gcc ttt tgc cgt gtt cat caa     acg acc tcg ttc gct     gta ctc ctc      35289
Ala Phe Cys Arg Val His Gln     Thr Thr Ser Phe Ala     Val Leu Leu
        11750           11755                   11760 gca gcc ttc cgt gcg acc cac     tac cgt ctc acg ggc     gct gag gat      35334
Ala Ala Phe Arg Ala Thr His     Tyr Arg Leu Thr Gly     Ala Glu Asp
        11765           11770                   11775 gct acc atc ggc tct cca att     gct aat cgt aac cgc     cca gaa cta      35379
Ala Thr Ile Gly Ser Pro Ile     Ala Asn Arg Asn Arg     Pro Glu Leu
        11780           11785                   11790 gaa agt ctg att ggc ttc ttt     gtc aat acc cag tgt     ata cgc gtg      35424
Glu Ser Leu Ile Gly Phe Phe     Val Asn Thr Gln Cys     Ile Arg Val
        11795           11800                   11805 aca atc aga gag gac gat acc     ttc gac aaa ttg gtg     cag caa gtc      35469
Thr Ile Arg Glu Asp Asp Thr     Phe Asp Lys Leu Val     Gln Gln Val
        11810           11815                   11820 cgg gca acg aca aca gcc gcg     cag gtc aac cag gat     gtc cca ttc      35514
Arg Ala Thr Thr Thr Ala Ala     Gln Val Asn Gln Asp     Val Pro Phe
        11825           11830                   11835 gaa cgc atc gtc tca gct ctg     atg cct ggc tca aga     gac acg tcc      35559
Glu Arg Ile Val Ser Ala Leu     Met Pro Gly Ser Arg     Asp Thr Ser
        11840           11845                   11850
```

```
cga aat cca cta gtg cag ctc agc ttt gct ctt cac tca cag cat    35604
Arg Asn Pro Leu Val Gln Leu Ser Phe Ala Leu His Ser Gln His
    11855             11860             11865 gac ctt gga aga atc gat ctc cag gat ctg aca gga gaa gct ctt    35649
Asp Leu Gly Arg Ile Asp Leu Gln Asp Leu Thr Gly Glu Ala Leu
    11870             11875             11880 ccc aca cca gtg ttc acc aga ctg gat gta gag ttc cat ctt ttc    35694
Pro Thr Pro Val Phe Thr Arg Leu Asp Val Glu Phe His Leu Phe
    11885             11890             11895 cag caa gct gag aag ttc ggt ggt agc gta ttt gca aca gac        35739
Gln Gln Ala Glu Lys Phe Gly Gly Ser Val Leu Phe Ala Thr Asp
    11900             11905             11910 ttg ttt gag ccg gag act att caa gga ctg gtc tcc gtc ttc cag    35784
Leu Phe Glu Pro Glu Thr Ile Gln Gly Leu Val Ser Val Phe Gln
    11915             11920             11925 gag gtc tta cgc cga gga ctt gag caa ccc caa acg cct att gca    35829
Glu Val Leu Arg Arg Gly Leu Glu Gln Pro Gln Thr Pro Ile Ala
    11930             11935             11940 gtt ctg ccc ctt gac aac gcg tcc gag gat ctt cgg agc atg ggt    35874
Val Leu Pro Leu Asp Asn Ala Ser Glu Asp Leu Arg Ser Met Gly
    11945             11950             11955 ctg ctt caa atg gag aga acc aac tat cca cgg gac tct agt gtg    35919
Leu Leu Gln Met Glu Arg Thr Asn Tyr Pro Arg Asp Ser Ser Val
    11960             11965             11970 gtt gat gtc ttc cgt gat cag gtg gca gcc aat cct aga gca ata    35964
Val Asp Val Phe Arg Asp Gln Val Ala Ala Asn Pro Arg Ala Ile
    11975             11980             11985 gcc gtc aag gat tca gtc tta gag ctg acc tac gct cag ctg gac    36009
Ala Val Lys Asp Ser Val Leu Glu Leu Thr Tyr Ala Gln Leu Asp
    11990             11995             12000 gag aaa tct gac cag ttg gct gcc tgg ctc tgc caa cat aac att    36054
Glu Lys Ser Asp Gln Leu Ala Ala Trp Leu Cys Gln His Asn Ile
    12005             12010             12015 ccg gca gag aca atc gtt ggc gtt ctg gct ccg aga tct tgc gag    36099
Pro Ala Glu Thr Ile Val Gly Val Leu Ala Pro Arg Ser Cys Glu
    12020             12025             12030 aca att att gcc ttc ctc gga atc ctc aag gcc aac ctc gca tac    36144
Thr Ile Ile Ala Phe Leu Gly Ile Leu Lys Ala Asn Leu Ala Tyr
    12035             12040             12045 ttg cca tta gac gat aat gtt cca gct gct cgc att gag act ata    36189
Leu Pro Leu Asp Asp Asn Val Pro Ala Ala Arg Ile Glu Thr Ile
    12050             12055             12060 ttg tca gca gtc cct ggc cac aca tta gtc cta ctc ggc tca cat    36234
Leu Ser Ala Val Pro Gly His Thr Leu Val Leu Leu Gly Ser His
    12065             12070             12075 gtg gct gct cca agc att gga tta gca gat gct gaa ttc gtt aat    36279
Val Ala Ala Pro Ser Ile Gly Leu Ala Asp Ala Glu Phe Val Asn
    12080             12085             12090 atc aat cat act tta ggc cac agt ttg caa ctc aac agc aca tgc    36324
Ile Asn His Thr Leu Gly His Ser Leu Gln Leu Asn Ser Thr Cys
    12095             12100             12105 gcc aag ttg cag ccc tcc gct aca agc ctt gca tat gtt atc ttt    36369
Ala Lys Leu Gln Pro Ser Ala Thr Ser Leu Ala Tyr Val Ile Phe
    12110             12115             12120 aca tct ggg tcg aca ggc aag cca aaa ggc gtt atg att gag cac    36414
Thr Ser Gly Ser Thr Gly Lys Pro Lys Gly Val Met Ile Glu His
    12125             12130             12135 aga agc att gtg cga ctt gtc aaa aac agc aat acc ctc gcc aag    36459
Arg Ser Ile Val Arg Leu Val Lys Asn Ser Asn Thr Leu Ala Lys
```

-continued

|  |  |  |  |  |  |  |  |  |  |  |  |  |
|---|---|---|---|---|---|---|---|---|---|---|---|---|
|  |  | 12140 |  |  | 12145 |  |  | 12150 |  |  |  |  |
| ctc<br>Leu | cca<br>Pro<br>12155 | cga<br>Arg | gcc<br>Ala | gct<br>Ala | cgt<br>Arg<br>12160 | gtc<br>Val | gct<br>Ala | cat<br>His | caa<br>Gln<br>12165 | ttc<br>Phe | aac<br>Asn | ctt<br>Leu | gcc<br>Ala | ttc<br>Phe | 36504 |
| gat<br>Asp | gca<br>Ala<br>12170 | gca<br>Ala | aac<br>Asn | tac<br>Tyr | gag<br>Glu<br>12175 | atc<br>Ile | tat<br>Tyr | ggt<br>Gly | aca<br>Thr<br>12180 | ctg<br>Leu | ctg<br>Leu | aat<br>Asn | ggg<br>Gly | ggt<br>Gly | 36549 |
| gcc<br>Ala | ctg<br>Leu<br>12185 | atc<br>Ile | tgt<br>Cys | gtc<br>Val | gat<br>Asp<br>12190 | tac<br>Tyr | tcc<br>Ser | acc<br>Thr | ctc<br>Leu<br>12195 | ttg<br>Leu | gac<br>Asp | att<br>Ile | gat<br>Asp | gct<br>Ala | 36594 |
| ctc<br>Leu | gtg<br>Val<br>12200 | gcc<br>Ala | atg<br>Met | ttc<br>Phe | aag<br>Lys<br>12205 | cga<br>Arg | gag<br>Glu | aaa<br>Lys | atc<br>Ile<br>12210 | acc<br>Thr | gca<br>Ala | tcc<br>Ser | tca<br>Ser | ctg<br>Leu | 36639 |
| tct<br>Ser | cct<br>Pro<br>12215 | ggt<br>Gly | ttg<br>Leu | ctc<br>Leu | aag<br>Lys<br>12220 | cag<br>Gln | tgt<br>Cys | gtg<br>Val | aac<br>Asn<br>12225 | agt<br>Ser | gca<br>Ala | ccc<br>Pro | gaa<br>Glu | atg<br>Met | 36684 |
| ctc<br>Leu | aag<br>Lys<br>12230 | gct<br>Ala | tta<br>Leu | cag<br>Gln | gtg<br>Val<br>12235 | atc<br>Ile | tac<br>Tyr | aca<br>Thr | ggt<br>Gly<br>12240 | gga<br>Gly | gac<br>Asp | cga<br>Arg | ctc<br>Leu | gat<br>Asp | 36729 |
| ggt<br>Gly | cgc<br>Arg<br>12245 | gat<br>Asp | gcc<br>Ala | att<br>Ile | gag<br>Glu<br>12250 | ttg<br>Leu | caa<br>Gln | gca<br>Ala | ctt<br>Leu<br>12255 | gtt<br>Val | ccc<br>Pro | gga<br>Gly | ggc<br>Gly | gtt<br>Val | 36774 |
| tac<br>Tyr | aac<br>Asn<br>12260 | atg<br>Met | tac<br>Tyr | gga<br>Gly | cct<br>Pro<br>12265 | acc<br>Thr | gaa<br>Glu | aac<br>Asn | aca<br>Thr<br>12270 | gtc<br>Val | atc<br>Ile | agc<br>Ser | acg<br>Thr | ctt<br>Leu | 36819 |
| tac<br>Tyr | aat<br>Asn<br>12275 | ctc<br>Leu | ggc<br>Gly | gac<br>Asp | aag<br>Lys<br>12280 | cat<br>His | tcg<br>Ser | tat<br>Tyr | gtg<br>Val<br>12285 | aat<br>Asn | ggc<br>Gly | gtt<br>Val | ccc<br>Pro | att<br>Ile | 36864 |
| gga<br>Gly | aca<br>Thr<br>12290 | acc<br>Thr | gtc<br>Val | agc<br>Ser | aat<br>Asn<br>12295 | tcg<br>Ser | gga<br>Gly | gcc<br>Ala | tac<br>Tyr<br>12300 | gtc<br>Val | atg<br>Met | gat<br>Asp | gcc<br>Ala | ctg<br>Leu | 36909 |
| caa<br>Gln | cag<br>Gln<br>12305 | ctc<br>Leu | gtc<br>Val | cct<br>Pro | gtc<br>Val<br>12310 | gga<br>Gly | gta<br>Val | atg<br>Met | gga<br>Gly<br>12315 | gag<br>Glu | ctc<br>Leu | gtc<br>Val | gtc<br>Val | act<br>Thr | 36954 |
| ggg<br>Gly | gat<br>Asp<br>12320 | gga<br>Gly | ctt<br>Leu | gct<br>Ala | cga<br>Arg<br>12325 | ggg<br>Gly | tac<br>Tyr | act<br>Thr | gat<br>Asp<br>12330 | ccg<br>Pro | gaa<br>Glu | cta<br>Leu | gac<br>Asp | cgc<br>Arg | 36999 |
| aac<br>Asn | cga<br>Arg<br>12335 | ttc<br>Phe | atc<br>Ile | aag<br>Lys | gtc<br>Val<br>12340 | aac<br>Asn | att<br>Ile | gat<br>Asp | ggt<br>Gly<br>12345 | cag<br>Gln | gtc<br>Val | gtc<br>Val | agg<br>Arg | gcg<br>Ala | 37044 |
| tac<br>Tyr | cga<br>Arg<br>12350 | aca<br>Thr | ggc<br>Gly | gat<br>Asp | cgc<br>Arg<br>12355 | gtc<br>Val | cgc<br>Arg | tac<br>Tyr | cga<br>Arg<br>12360 | aga<br>Arg | ata<br>Ile | gac<br>Asp | ggt<br>Gly | caa<br>Gln | 37089 |
| tta<br>Leu | gaa<br>Glu<br>12365 | ttc<br>Phe | ttc<br>Phe | ggg<br>Gly | cgc<br>Arg<br>12370 | atg<br>Met | gat<br>Asp | cag<br>Gln | caa<br>Gln<br>12375 | att<br>Ile | aag<br>Lys | att<br>Ile | cga<br>Arg | ggc<br>Gly | 37134 |
| ttc<br>Phe | cgt<br>Arg<br>12380 | atc<br>Ile | gag<br>Glu | acg<br>Thr | gcg<br>Ala<br>12385 | gaa<br>Glu | gtt<br>Val | gag<br>Glu | aac<br>Asn<br>12390 | gcc<br>Ala | atg<br>Met | ctc<br>Leu | agt<br>Ser | cac<br>His | 37179 |
| agc<br>Ser | gca<br>Ala<br>12395 | gtt<br>Val | cgc<br>Arg | aat<br>Asn | gct<br>Ala<br>12400 | gct<br>Ala | gtt<br>Val | gtc<br>Val | gtc<br>Val<br>12405 | cct<br>Pro | acc<br>Thr | caa<br>Gln | gac<br>Asp | att<br>Ile | 37224 |
| caa<br>Gln | gag<br>Glu<br>12410 | aag<br>Lys | gga<br>Gly | atg<br>Met | att<br>Ile<br>12415 | ggt<br>Gly | ttc<br>Phe | gtg<br>Val | gtg<br>Val<br>12420 | att<br>Ile | gaa<br>Glu | aac<br>Asn | aat<br>Asn | aca<br>Thr | 37269 |
| ccc<br>Pro | aag<br>Lys<br>12425 | aac<br>Asn | gag<br>Glu | gag<br>Glu | agc<br>Ser<br>12430 | aag<br>Lys | gaa<br>Glu | gaa<br>Glu | cac<br>His<br>12435 | ttg<br>Leu | cta<br>Leu | caa<br>Gln | act<br>Thr | gaa<br>Glu | 37314 |
| ttg<br>Leu | gcg<br>Ala | atc<br>Ile | ctc<br>Leu | aac<br>Asn | cgg<br>Arg | atg<br>Met | aag<br>Lys | agc<br>Ser | atc<br>Ile | ctt<br>Leu | cct<br>Pro | cct<br>Pro | tac<br>Tyr | atg<br>Met | 37359 |

|   |   |   |   |   |   |   |   |   |   |   |   |   |   |   |
|---|---|---|---|---|---|---|---|---|---|---|---|---|---|---|
|   | Leu | Ala | Ile | Leu | Asn | Arg | Met | Lys | Ser | Ile | Leu | Pro | Pro | Tyr | Met |
|   |   | 12440 |   |   |   | 12445 |   |   |   | 12450 |   |   |   |   |

```
ctc cca tct cgc atc atc atc ctt gat cag atg cct tcg aat ttc   37404
Leu Pro Ser Arg Ile Ile Ile Leu Asp Gln Met Pro Ser Asn Phe
    12455           12460              12465 aat gga aag gtc gat cgt aaa gag ctt gat cgc atg gct cag agc   37449
Asn Gly Lys Val Asp Arg Lys Glu Leu Asp Arg Met Ala Gln Ser
    12470           12475              12480 gta cct aga cag aag act acg gca ggg cgc ata gtt ccc cgc aat   37494
Val Pro Arg Gln Lys Thr Thr Ala Gly Arg Ile Val Pro Arg Asn
    12485           12490              12495 gaa ttg gaa gct tcg ctc tgt aag gag ttc gct gaa gtg ctc ggc   37539
Glu Leu Glu Ala Ser Leu Cys Lys Glu Phe Ala Glu Val Leu Gly
    12500           12505              12510 gtt gag gtc ggc atc act gac aat ttc ttc gac ctc ggt ggg cac   37584
Val Glu Val Gly Ile Thr Asp Asn Phe Phe Asp Leu Gly Gly His
    12515           12520              12525 tcg cta ctg gca acc aag ctc gca gct cgc att agc cgc agg ctg   37629
Ser Leu Leu Ala Thr Lys Leu Ala Ala Arg Ile Ser Arg Arg Leu
    12530           12535              12540 gat act cgc gtg tct gtt aaa gac gta ttc gat cag cct gtg ccc   37674
Asp Thr Arg Val Ser Val Lys Asp Val Phe Asp Gln Pro Val Pro
    12545           12550              12555 gca gat cta gca ctc aag gtt tcg tct tac atc tcc caa ggt cat   37719
Ala Asp Leu Ala Leu Lys Val Ser Ser Tyr Ile Ser Gln Gly His
    12560           12565              12570 gca atg gac aac gga acc ttg tcg aca acg aac agc atc ccc ttc   37764
Ala Met Asp Asn Gly Thr Leu Ser Thr Thr Asn Ser Ile Pro Phe
    12575           12580              12585 cag cta cta cat ttt gaa gat tcg cag aaa ttt atc gac cgc gac   37809
Gln Leu Leu His Phe Glu Asp Ser Gln Lys Phe Ile Asp Arg Asp
    12590           12595              12600 att gtc ccg caa ctt gct cat cag tca gct aaa att gtg gat gtc   37854
Ile Val Pro Gln Leu Ala His Gln Ser Ala Lys Ile Val Asp Val
    12605           12610              12615 tat cct gtt acg tgg ata cag aag cac ttc ctt gtt gat cca gca   37899
Tyr Pro Val Thr Trp Ile Gln Lys His Phe Leu Val Asp Pro Ala
    12620           12625              12630 aca gga ctt cca cgt aca cca tca ctc ttc ttt gtc gat ttc cca   37944
Thr Gly Leu Pro Arg Thr Pro Ser Leu Phe Phe Val Asp Phe Pro
    12635           12640              12645 gcc aac gct gac tgc gac aaa att tgc aat gcg agc cgg tct ctc   37989
Ala Asn Ala Asp Cys Asp Lys Ile Cys Asn Ala Ser Arg Ser Leu
    12650           12655              12660 att cag ctt ttc gat atc ttc agg act gtc ttt gtt cag gct gcc   38034
Ile Gln Leu Phe Asp Ile Phe Arg Thr Val Phe Val Gln Ala Ala
    12665           12670              12675 ggc aat ttt tac caa gtc gtt ctg gaa gag ctt gac ata ccc atc   38079
Gly Asn Phe Tyr Gln Val Val Leu Glu Glu Leu Asp Ile Pro Ile
    12680           12685              12690 tcg gtc atc gaa acc gaa gac atc agt act gca act cgc gtc ctg   38124
Ser Val Ile Glu Thr Glu Asp Ile Ser Thr Ala Thr Arg Val Leu
    12695           12700              12705 aag gaa cag gat caa caa aat ccg ctc caa ttc gga caa gga ttc   38169
Lys Glu Gln Asp Gln Gln Asn Pro Leu Gln Phe Gly Gln Gly Phe
    12710           12715              12720 tta cgc ttt gca gtc gtg aag acg agg tca gct gtg cgc ttg gta   38214
Leu Arg Phe Ala Val Val Lys Thr Arg Ser Ala Val Arg Leu Val
    12725           12730              12735
```

```
ctt cgc atc tct cat tgc ttg tac gat ggc ttg agt ttc gag cat    38259
Leu Arg Ile Ser His Cys Leu Tyr Asp Gly Leu Ser Phe Glu His
    12740            12745                12750 gtt gtg caa tca ctt cat gct ttg tat aat ggc gac cgc atc cca    38304
Val Val Gln Ser Leu His Ala Leu Tyr Asn Gly Asp Arg Ile Pro
    12755            12760                12765 aca cag ccc aag ttc gtt cag tat gtt cag cat ctg act gac agc    38349
Thr Gln Pro Lys Phe Val Gln Tyr Val Gln His Leu Thr Asp Ser
    12770            12775                12780 cgc aaa gaa ggt tac gat ttc tgg cta tct gtc ctg gag gag tcc    38394
Arg Lys Glu Gly Tyr Asp Phe Trp Leu Ser Val Leu Glu Glu Ser
    12785            12790                12795 tcg atg aca gtc gta gag act ggc cgt cgc gct caa caa cta tca    38439
Ser Met Thr Val Val Glu Thr Gly Arg Arg Ala Gln Gln Leu Ser
    12800            12805                12810 tca cct gag ggt gct tgg ttc gtc gag aag att atc aag gct gtt    38484
Ser Pro Glu Gly Ala Trp Phe Val Glu Lys Ile Ile Lys Ala Val
    12815            12820                12825 atc cca gcc aac tca gat ggt att acg cag gca aca gta ttt acc    38529
Ile Pro Ala Asn Ser Asp Gly Ile Thr Gln Ala Thr Val Phe Thr
    12830            12835                12840 act gct tcc acc atc ctg ctt gcc aga atg acc gga tca agc gac    38574
Thr Ala Ser Thr Ile Leu Leu Ala Arg Met Thr Gly Ser Ser Asp
    12845            12850                12855 atc acc ttc agc cga ctc gta tct ggg cgt caa tct ttg ccg atc    38619
Ile Thr Phe Ser Arg Leu Val Ser Gly Arg Gln Ser Leu Pro Ile
    12860            12865                12870 aat gac caa cat atc gtc ggc cct tgc aca aac atc gtc ccc gtt    38664
Asn Asp Gln His Ile Val Gly Pro Cys Thr Asn Ile Val Pro Val
    12875            12880                12885 cgt att cgc atg act gat ggc act aat gca aga gag ctt ctc ggc    38709
Arg Ile Arg Met Thr Asp Gly Thr Asn Ala Arg Glu Leu Leu Gly
    12890            12895                12900 atg gtg caa gac caa tac atc gac agc ttg cca ttt gaa acg cta    38754
Met Val Gln Asp Gln Tyr Ile Asp Ser Leu Pro Phe Glu Thr Leu
    12905            12910                12915 ggg ttc gat gac atc aag gag aac tgc act aaa tgg cca gcg tcg    38799
Gly Phe Asp Asp Ile Lys Glu Asn Cys Thr Lys Trp Pro Ala Ser
    12920            12925                12930 act acg aac tac ggc tgc tgc agc aca ttc cag aac ttc gag atg    38844
Thr Thr Asn Tyr Gly Cys Cys Ser Thr Phe Gln Asn Phe Glu Met
    12935            12940                12945 cag cct caa agt caa gtc cag gac gaa cgt gtt cga ttg gct ggt    38889
Gln Pro Gln Ser Gln Val Gln Asp Glu Arg Val Arg Leu Ala Gly
    12950            12955                12960 ttg aca aat ttc aaa gat gca gaa cta cta aat ggc gct acc gct    38934
Leu Thr Asn Phe Lys Asp Ala Glu Leu Leu Asn Gly Ala Thr Ala
    12965            12970                12975 aca aac aag aga gtt cta gat gac gta cca atg cat gag att gat    38979
Thr Asn Lys Arg Val Leu Asp Asp Val Pro Met His Glu Ile Asp
    12980            12985                12990 atg att gga atc cct gag ccg gat gga ctt cat gta cga gtt gtc    39024
Met Ile Gly Ile Pro Glu Pro Asp Gly Leu His Val Arg Val Val
    12995            13000                13005 ctt acc gct agc agg cag att ttc gag gag gag gtt gtg gac cgc    39069
Leu Thr Ala Ser Arg Gln Ile Phe Glu Glu Glu Val Val Asp Arg
    13010            13015                13020 atg cac gaa gag ttc tgc gat atc atc ttg ggt ttg aac aag atc    39114
Met His Glu Glu Phe Cys Asp Ile Ile Leu Gly Leu Asn Lys Ile
    13025            13030                13035
```

```
ttg caa    aaa tag                                              39126
Leu Gln    Lys
    13040
```

<210> SEQ ID NO 37
<211> LENGTH: 13041
<212> TYPE: PRT
<213> ORGANISM: Curvularia clavata

<400> SEQUENCE: 37

```
Met Ala Ser Asp Ile Asn Thr His Pro Glu Gly Ala Thr Lys Phe Trp
1               5                   10                  15

Gln Gln His Phe Asp Gly Leu Asn Ala Ser Val Phe Pro Ala Leu Ser
            20                  25                  30

Ser His Leu Thr Val Pro Arg Pro Asn Ala Gln Thr Ala His Arg Ile
        35                  40                  45

Ser Tyr Ser Thr Leu Ala Lys Gln Lys Trp Asp Asn Thr Ser Leu Cys
    50                  55                  60

Arg Ala Ala Leu Ala Ile Leu Leu Ala Arg Tyr Ser Asn Ala Ser Glu
65                  70                  75                  80

Ala Leu Phe Gly Val Leu Val Glu Gln Phe Leu Pro Ser Asn Gly Glu
                85                  90                  95

Gln Ala Ser Thr Glu Glu Ser Pro Gln Ser Ile Leu Pro Ile Arg Ile
            100                 105                 110

Arg Leu Asp Leu Glu Glu Ala Gly Leu Gly Leu Leu Gln Ala Ile Asn
        115                 120                 125

Thr Leu Asp Ala Ser Leu Arg Glu Trp Lys His Ile Gly Leu Asp Ala
    130                 135                 140

Ile Arg Gly Thr Gly Glu Tyr Gly Ser Ala Gly Cys Glu Phe Gln Thr
145                 150                 155                 160

Val Leu Ala Val Thr Thr Gly Lys Thr Pro Arg Thr His Arg Leu Ala
                165                 170                 175

Ser Cys Thr Asp Arg Ala Leu Leu Leu Asp Cys Arg Met Asp Asp Asp
            180                 185                 190

Ser Ala Thr Leu Leu Ala Arg Tyr Asp Pro Ser Val Ile Asp Asp Leu
        195                 200                 205

Gln Val Ala Arg Phe Leu Lys Gln Leu Gly His Val Ile Glu Gln Leu
    210                 215                 220

Arg Val Gln Ala Val Asp Leu Pro Leu Trp Glu Leu Gly Ile Val Thr
225                 230                 235                 240

Gln Glu Asp Ser Ala Glu Ile Gln Lys Trp Asn Ser Gln Gln Leu Gln
                245                 250                 255

Phe Ser Gln Glu Cys Ile His Asp Val Phe Ala Asn Arg Val Val Asp
            260                 265                 270

Thr Pro Gln Lys Ile Ala Val Ser Ala Trp Asn Gly Glu Leu Thr Phe
        275                 280                 285

Ala Glu Leu Asp Ser Phe Ser Ser Cys Leu Ala Gln His Ile Gln Ser
    290                 295                 300

Leu Glu Leu Gly Asp Ala Lys Ala Ile Pro Leu Cys Phe Glu Lys Ser
305                 310                 315                 320

Lys Trp Ala Ile Val Gly Met Leu Gly Val Leu Lys Ala Gly Arg Ala
                325                 330                 335

Phe Thr Leu Ile Asp Pro Ser Asn Pro Pro Ala Arg Ala Arg Gln Ile
            340                 345                 350
```

-continued

```
Cys Arg Gln Thr Ala Ala Thr Ile Ser Ile Ala Ser Pro Tyr Gln Cys
            355                 360                 365

Asp Met Met Arg Ala Leu Val Pro Asp Cys Ile Val Val Asp Asp Asp
    370                 375                 380

Phe Phe Lys Ser Leu Ala Phe Asp Thr Asp Gln Phe Gln Pro Thr Ala
385                 390                 395                 400

Thr Pro Gln Thr Leu Ala Tyr Ile Leu Phe Thr Ser Gly Ser Thr Gly
                405                 410                 415

Glu Pro Lys Gly Ser Met Met Glu His His Gly Phe Val Ser Cys Cys
            420                 425                 430

Leu Glu Phe Gly Ala Ala Leu Gly Ile Asn Ser Asn Thr Arg Ala Leu
        435                 440                 445

Gln Phe Ala Ser Tyr Ala Phe Gly Ala Cys Leu Leu Glu Ile Leu Thr
    450                 455                 460

Thr Leu Met His Gly Gly Thr Val Cys Ile Pro Ser Asp Asp Glu Arg
465                 470                 475                 480

Ile Asn Asp Ala Pro Gly Phe Ile Arg Arg Ala Asn Val Asn Trp Ala
                485                 490                 495

Ile Leu Thr Pro Ser Phe Ile Gly Ala Ile Gln Pro Thr Thr Val Pro
            500                 505                 510

Asn Leu Lys Thr Leu Val Leu Val Gly Glu Ala Met Pro Ser Asp Ile
        515                 520                 525

Arg Asp Val Trp Ala Ser His Val Gln Leu Lys Asn Ala Tyr Gly Gln
    530                 535                 540

Ser Glu Ser Ala Thr Ile Cys Ser Val Thr Glu Val Thr Pro Ala Thr
545                 550                 555                 560

Val Glu Ala His Asn Ile Gly His Ala Val Gly Ala Arg Phe Trp Ile
                565                 570                 575

Thr Asp Pro Asn Asn Pro Asn Lys Leu Ala Pro Ile Gly Cys Val Gly
            580                 585                 590

Glu Leu Leu Val Glu Ser Pro Gly Ile Ala Arg Gly Tyr Leu Ile Pro
        595                 600                 605

Leu Pro Ala Asp Ala Thr Pro Phe Ile Asp Thr Leu Pro Asp Trp Tyr
    610                 615                 620

Pro Arg Thr Gln Pro Leu Asp Asn Phe Lys Phe Tyr Arg Thr Gly Asp
625                 630                 635                 640

Leu Val Cys Tyr Arg Ser Asp Gly Thr Val Tyr Leu Gly Arg Arg
                645                 650                 655

Asp Ser Gln Ile Lys Ile Arg Gly Gln Arg Val Glu Ile Gly Glu Val
            660                 665                 670

Glu Thr Cys Leu Arg Gln Gln Leu Pro Ser Gln Leu Val Pro Val Val
        675                 680                 685

Glu Ala Val Ser Leu Ser Gly Met Ser Lys Ser Met Thr Leu Ile Ala
    690                 695                 700

Phe Leu Val Gly Glu Asn Thr Ile Leu Glu Glu Asp Val Tyr Val Leu
705                 710                 715                 720

Glu Gly Ser Ala Ala Gln Arg Ile Ser Ser Lys Leu Arg Gln Ile Val
                725                 730                 735

Pro Gly Tyr Cys Ile Pro Ser His Tyr Ile Arg Ile Asn His Leu Pro
            740                 745                 750

Thr Thr Ala Thr Gly Lys Cys Asp Arg Lys Ala Leu Arg Ala Ile Gly
        755                 760                 765

Thr Lys Leu Leu Arg Glu Ala Val Glu Gly Met Ala Ser Gln Glu Glu
```

-continued

```
                770                 775                 780
Gln Glu Ser Ala Ser Leu Met Thr Glu Gly Ile Thr Leu Glu Arg Ile
785                 790                 795                 800

Trp Phe Gln Ser Leu Gly Leu Lys Pro Asn Ser Thr Arg His Lys Ser
                805                 810                 815

Asn Phe Phe Asn Leu Gly Gly Asp Ser Ile Ala Ala Ile Arg Met Val
                820                 825                 830

Asn Met Ala Arg Ala Ala Gly Leu Leu Leu Ser Ile Ser Asp Ile Phe
                835                 840                 845

Gln Asn Pro Ser Leu Ala Gly Leu Ile Asn Val Met Gln Gln Ser Ser
850                 855                 860

Thr Ala Gln Asp Ala Ile Pro Ala Thr Glu Tyr Ser Gly Pro Val Glu
865                 870                 875                 880

Gln Ser Phe Ala Gln Gly Arg Leu Trp Phe Leu Asp Gln Leu Thr Thr
                885                 890                 895

Gly Ala Ser Trp Tyr Leu Met Pro Leu Ala Val Arg Ile His Gly Pro
                900                 905                 910

Leu Arg Val Gln Ala Leu Ser Ser Ala Leu His Ala Leu Glu Gln Arg
                915                 920                 925

His Glu Thr Leu Arg Thr Thr Phe Glu Gln Gln Asp Gly Met Gly Val
930                 935                 940

Gln Ile Val His Pro Ser Ser Lys Arg Glu Leu Arg Val Ile Asp Val
945                 950                 955                 960

Ser Gly Lys Gln Asn Gly Gly Tyr Asp Gln Val Leu Lys Arg Glu Gln
                965                 970                 975

Thr Thr Pro Ile Asp Leu Ala Lys Pro Gly Trp Arg Ala Ala Leu
                980                 985                 990

Leu Arg Val Gly Asp Asp Glu His Ile Leu Ser Ile Val Ile His His
                995                 1000                1005

Ile Ile Tyr Asp Gly Trp Ser Leu Gly Val Leu Arg Glu Glu Leu
        1010                1015                1020

Gly Asp Leu Tyr Ala Ala Ala Leu Arg Gly Pro Asp Pro Leu Ala
        1025                1030                1035

His Met Ala Pro Leu Pro Ile Gln Tyr Arg Asp Phe Ser Val Trp
        1040                1045                1050

Gln Lys Gln Pro Gln Gln Val Ala Gln His Gln Gln Gln Leu Val
        1055                1060                1065

Tyr Trp Thr Lys Gln Leu Glu Asp Ser Ala Pro Ala Glu Leu Leu
        1070                1075                1080

Thr Asp Phe Pro Arg Pro Ala Glu Leu Ser Gly Arg Ala Gly Glu
        1085                1090                1095

Val Arg Phe Thr Ile Glu Gly Ser Val Phe Asp Ser Leu Leu Ala
        1100                1105                1110

Phe Arg Arg Val His Gln Thr Thr Ser Phe Ala Val Leu Leu Ala
        1115                1120                1125

Val Phe Arg Ala Ala His Tyr Arg Leu Thr Gly Thr Glu Asp Ala
        1130                1135                1140

Thr Ile Gly Thr Pro Ile Ala Asn Arg Thr Arg Ala Glu Val Glu
        1145                1150                1155

Lys Leu Ile Gly Phe Phe Val Asn Thr Gln Cys Met Arg Ile Ala
        1160                1165                1170

Val Ala Asp Asp Asp Thr Phe Ala Ser Leu Val Ser Gln Val Trp
        1175                1180                1185
```

Ser Val Ala Thr Ala Ala Phe Glu His Gln Asp Val Pro Phe Glu
    1190            1195            1200

Arg Ile Val Ser Ala Leu Leu Pro Gly Ala Arg Asp Thr Ser Arg
    1205            1210            1215

Asn Pro Leu Ala Gln Leu Leu Phe Ala Leu His Leu Glu Gln Asp
    1220            1225            1230

Leu Asp Lys Ile Asn Leu Glu Gly Leu Ala Cys Glu Thr Val Pro
    1235            1240            1245

Thr Pro Met Ala Thr Arg Phe Asp Val Glu Phe His Leu Phe Gln
    1250            1255            1260

Glu Asp Asp Arg Leu Asn Gly Val Val Asn Phe Ser Thr Asp Leu
    1265            1270            1275

Phe Glu Pro Gln Thr Ile His Ser Leu Val Ser Val Phe Gln Glu
    1280            1285            1290

Ile Leu Arg Arg Gly Leu Asp Gln Pro Gln Thr Pro Ile Ala His
    1295            1300            1305

Leu Gln Leu Thr Asp Gly Leu Glu Glu Leu Arg Asn Ala Gly Leu
    1310            1315            1320

Leu Asp Ile Lys Arg Ile Asp Tyr Pro Arg Glu Ala Ser Val Val
    1325            1330            1335

Asp Met Phe Gln Lys Gln Val Ala Ala Cys Pro Asn Val Thr Ala
    1340            1345            1350

Val Lys Asp Ser Thr Ser Gln Leu Thr Tyr Ala Gln Leu Asp Gln
    1355            1360            1365

Glu Ser Asp Lys Ile Ala Val Trp Leu Arg Lys Arg Asn Ile Pro
    1370            1375            1380

Ala Glu Thr Leu Ile Ala Leu Leu Ala Pro Arg Ser Cys Asp Ser
    1385            1390            1395

Val Ala Ala Phe Leu Gly Ile Leu Lys Ala Asn Leu Ala Tyr Leu
    1400            1405            1410

Pro Leu Asp Val Asn Val Pro Ala Ala Arg Ile Glu Ala Ile Leu
    1415            1420            1425

Ser Thr Val Ala Gly His Lys Leu Val Leu Leu Gly Arg Asp Val
    1430            1435            1440

Pro Leu Leu Gly Thr Gln Leu Ala Asp Leu Glu Leu Val Arg Ile
    1445            1450            1455

Gly Glu Ala Leu Arg Gly Ser Ser Ser Gly Ser Val Ala Ala Asp
    1460            1465            1470

Lys Ala Ile Arg Pro Thr Ala Thr Ser Leu Ala Tyr Val Ile Phe
    1475            1480            1485

Thr Ser Gly Ser Thr Gly Gln Pro Lys Gly Ile Met Val Pro His
    1490            1495            1500

Arg Ser Leu Val Asn Val Ile Lys Gln Arg Pro Ala Tyr Gly Asn
    1505            1510            1515

Val Ala His Met Thr Asn Leu Ala Phe Asp Pro Ser Leu Phe Glu
    1520            1525            1530

Met Cys Thr Ala Leu Phe Asn Gly Asn Thr Leu Ile Cys Ile Asp
    1535            1540            1545

Thr Leu Val Ala Leu Asp Ala Thr Gln Leu Pro Thr Ile Phe Lys
    1550            1555            1560

Gln Glu Ala Ile Arg Val Ala Met Met Thr Pro Ala Leu Leu Thr
    1565            1570            1575

```
Arg Leu Leu Ala Gln Ala Thr Asp Ala Leu His Glu Leu Glu Ala
    1580            1585                1590
Leu Tyr Val Leu Gly Asp Arg Phe Pro Lys Asp Ala Ala Arg
    1595            1600            1605
Ala Ser Glu Leu Val Lys Thr Ala Val Tyr Asn Ala Tyr Gly Pro
    1610            1615            1620
Ser Glu Asn Ser Ile Cys Thr Thr Leu Phe His Ala Ala Thr Gly
    1625            1630            1635
Ala Met Cys Thr Asn Gly Val Pro Val Gly Arg Val Ile Asn Asn
    1640            1645            1650
Ser Gly Val Tyr Val Met Asp Pro Lys Gln Ser Leu Val Ser Tyr
    1655            1660            1665
Gly Val Met Gly Glu Leu Val Val Ala Gly Glu Gly Leu Ala Ile
    1670            1675            1680
Gly Tyr Thr Lys Pro Glu Leu Asn Glu Gly Arg Phe Leu Thr Leu
    1685            1690            1695
Thr Met Asp Gly Lys Pro Val Arg Ala Phe Arg Thr Gly Asp Arg
    1700            1705            1710
Val Arg Tyr Arg Pro Thr Asp Gly Gln Leu Glu Phe Phe Gly Arg
    1715            1720            1725
Met Asp Phe Gln Ile Lys Ile Arg Gly His Arg Val Glu Leu Ala
    1730            1735            1740
Glu Val Glu Arg Val Leu Asn Arg His Pro Ala Ile Lys Asp Ala
    1745            1750            1755
Ile Thr Leu Leu Arg Gln His Gly Ser Ser Ala Gln Asp Thr Glu
    1760            1765            1770
Leu Val Ser Phe Ile Val Leu Gly Glu Gln Lys Pro Val Lys Pro
    1775            1780            1785
His Arg Asn Ala Thr Asp His Gly Gly Met Glu Ile Glu Gln Leu
    1790            1795            1800
Asp Gln Lys Leu Glu Ala Asn Leu Arg Ala Met Met Gln Ala Thr
    1805            1810            1815
Leu Pro Ser Tyr Met Val Pro Ser Arg Ile Ile Val Leu Asp His
    1820            1825            1830
Met Pro Leu Asp Lys Asn Gly Lys Val Asp Arg Arg Gly Leu Thr
    1835            1840            1845
Gly Leu Thr Leu Ser Pro Ala Met Glu Thr Ser Ser Arg Val Val
    1850            1855            1860
Val Ala Ala Arg Asn Glu Ile Glu Ala Val Leu Cys Glu Glu Phe
    1865            1870            1875
Ala His Ile Leu Gly Val Glu Ile Gly Val Thr Asp Asn Phe Phe
    1880            1885            1890
Asp Leu Gly Gly His Ser Leu Met Ala Thr Thr Leu Ala Ala Arg
    1895            1900            1905
Leu Ala Arg Arg Leu Asn Ala Ser Ile Ser Val Lys Asp Val Phe
    1910            1915            1920
Asp Gln Pro Ile Val Ala Asn Leu Ala Ala Thr Ile Lys Arg Gly
    1925            1930            1935
Ser Thr Pro His Asn Ala Ile Pro Pro Thr Lys Tyr Ser Gly Pro
    1940            1945            1950
Val Glu Gln Ser Phe Ala Gln Gly Arg Leu Trp Phe Leu Asp Gln
    1955            1960            1965
Leu Asn Leu Gly Ala Ala Trp Tyr His Met Pro Leu Ala Val Arg
```

-continued

```
             1970                1975                1980
Leu Arg Gly Pro Leu His Leu Glu Ala Leu Thr Ala Ala Leu His
     1985                1990                1995
Ala Leu Glu Glu Arg His Glu Thr Leu Arg Thr Val Phe Glu Glu
     2000                2005                2010
Gln Asp Gly Val Gly Met Gln Ile Val Arg Pro Ser Ser Lys Thr
     2015                2020                2025
Pro Leu Arg Ile Ile Asp Val Ser Thr Lys Glu Arg Gly Tyr Ala
     2030                2035                2040
Glu Leu Leu Lys Gln Glu Gln Thr Thr Pro Phe Asp Leu Ala Thr
     2045                2050                2055
Glu Leu Gly Trp Arg Val Ala Leu Leu Arg Gln Gly Lys Asp Asp
     2060                2065                2070
His Ile Leu Ser Ile Val Ile His His Ile Ile Ser Asp Gly Trp
     2075                2080                2085
Ser Leu Asp Ile Leu Cys Glu Glu Leu Gly Gln Phe Tyr Ala Ala
     2090                2095                2100
Val Leu Arg Gly Gln Asp Pro Leu Ala Gln Ile Ser Pro Leu Pro
     2105                2110                2115
Ile Gln Tyr Arg Asp Phe Ser Leu Trp Gln Lys Gln Pro Glu Gln
     2120                2125                2130
Val Ala Glu His His Arg Gln Leu Glu Tyr Trp Thr Thr Gln Leu
     2135                2140                2145
Glu Gly Ser Val Pro Ala Glu Leu Leu Thr Asp Leu Pro Arg Pro
     2150                2155                2160
Thr Ile Gln Ser Gly Lys Ala Gly Val Ile Pro Ile Thr Val Asn
     2165                2170                2175
Gly Pro Val Tyr Glu Arg Leu Arg Ala Phe Ser Arg Ala His Gln
     2180                2185                2190
Thr Thr Ala Phe Ala Val Leu Leu Ala Ala Phe Arg Ala Thr His
     2195                2200                2205
Tyr Arg Leu Ser Gly Val Ala Asp Ala Thr Ile Gly Thr Pro Ile
     2210                2215                2220
Ala Asn Arg Asn Arg Pro Glu Leu Glu Asn Met Ile Gly Phe Phe
     2225                2230                2235
Val Asn Ala Gln Cys Met Arg Ile Thr Val Glu Gln Asp Asp Thr
     2240                2245                2250
Phe Glu Thr Leu Val Arg Gln Ile Arg Phe Thr Ala Thr Ala Ala
     2255                2260                2265
Phe Ala Asn Gln Asp Val Pro Phe Glu His Ile Val Ser Ala Leu
     2270                2275                2280
Met Pro Asp Ser Arg Asp Thr Ser Arg Asn Pro Leu Val Gln Leu
     2285                2290                2295
Met Phe Ala Leu His Ala Tyr Lys Asp Leu Gly Lys Ile Glu Leu
     2300                2305                2310
Glu Gly Tyr Val Ala Glu Pro Val His Thr Thr Leu Ser Thr Arg
     2315                2320                2325
Phe Asp Leu Glu Phe His Met Phe Gln Glu Thr Asn His Leu Ser
     2330                2335                2340
Gly Tyr Val Leu Tyr Ala Thr Asp Leu Phe Glu Pro Glu Ser Ile
     2345                2350                2355
Glu Gly Met Val Ser Ile Phe Lys Glu Ile Leu Ala Arg Ala Leu
     2360                2365                2370
```

```
Asp Gln Pro Gln Thr Pro Leu Ala Leu Leu Pro Leu Thr Asp Gly
    2375                2380                2385

Leu Ala Glu Leu Arg Arg Arg Gly Leu Leu Glu Ile Glu Arg Pro
    2390                2395                2400

Ser Tyr Pro Arg Glu Ser Ser Val Val Asp Val Phe Cys Ser Gln
    2405                2410                2415

Val Ala Ala Ser Pro Asn Ala Thr Ala Val Lys Asp Ser Ile Ser
    2420                2425                2430

Gln Leu Thr Tyr Ala Gln Leu Asn Glu Gln Ser Asp Lys Val Ala
    2435                2440                2445

Ala Trp Leu His Gln Cys Asn Leu Pro Thr Glu Thr Leu Val Ala
    2450                2455                2460

Val Leu Ala Pro Arg Ser Cys Gln Thr Val Val Ala Phe Leu Gly
    2465                2470                2475

Ile Leu Lys Ala Asn Leu Ala Tyr Leu Pro Leu Asp Val Asn Val
    2480                2485                2490

Pro Ala Ala Arg Ile Glu Ala Ile Leu Ser Glu Val Ser Gly His
    2495                2500                2505

Ile Leu Val Leu Leu Gly Ser His Val Ser Ala Pro Lys Ile Glu
    2510                2515                2520

Leu Ala Asp Val Glu Phe Val Lys Ile Asp Asn Thr Val Glu His
    2525                2530                2535

Asn Leu Pro Gly Arg Ile Gly Ser Ala Pro Ser Ala Thr Ser Leu
    2540                2545                2550

Ala Tyr Val Ile Phe Thr Ser Gly Ser Thr Gly Lys Pro Lys Gly
    2555                2560                2565

Val Lys Val Glu His Arg Gly Ile Val Arg Leu Val Lys Glu Ser
    2570                2575                2580

Asn Val Val Ala Lys Met Pro Gln Ala Ala Arg Ile Ala His Leu
    2585                2590                2595

Ser Asn Ile Ala Phe Asp Ala Ala Thr Trp Glu Leu Tyr Ala Ala
    2600                2605                2610

Leu Leu Asn Gly Gly Thr Leu Val Cys Ile Asn Tyr Leu Thr Thr
    2615                2620                2625

Leu Asp Ser Lys Ala Leu Glu Ala Val Phe Glu Gln Glu Lys Ile
    2630                2635                2640

Gln Ala Ala Met Leu Pro Pro Ala Leu Leu Lys Gln Tyr Leu Val
    2645                2650                2655

Asn Ile Pro Ala Ala Ile Gly Ala Leu Glu Val Val Leu Val Ala
    2660                2665                2670

Gly Asp Arg Phe Asp Arg Arg Asp Ala Ala Ala Thr Gln Ala Leu
    2675                2680                2685

Val Gly Ala Gly Val Tyr Asn Ala Tyr Gly Pro Thr Glu Asn Thr
    2690                2695                2700

Thr Leu Ser Thr Ile Tyr Asn Val Val Gln Gly Asp Ala Asn Val
    2705                2710                2715

Asn Gly Val Pro Ile Gly Arg Pro Val Ser Asn Ser Gly Ala Tyr
    2720                2725                2730

Ile Met Asn Met Asn Gln Glu Leu Val Pro Ile Gly Val Ile Gly
    2735                2740                2745

Glu Leu Val Val Val Gly Asp Gly Val Ala Arg Gly Tyr Thr Asp
    2750                2755                2760
```

```
Pro Ala Leu Asp Val Asn Arg Phe Val Asn Val Thr Ile Glu Gly
    2765            2770            2775

Gln Thr Met Arg Ala Tyr Arg Thr Gly Asp Arg Ala Arg Tyr Arg
    2780            2785            2790

Pro Lys Asp Ala Gln Ile Glu Phe Phe Gly Arg Met Asp Gln Gln
    2795            2800            2805

Ile Lys Ile Arg Gly His Arg Ile Glu Pro Ala Glu Val Glu His
    2810            2815            2820

Ala Leu Leu Asn Asn Asp Leu Leu Gln Asp Ala Ala Val Ile Ile
    2825            2830            2835

Arg Lys Gln Gln Asn Asp Glu Leu Glu Met Val Ala Phe Val Glu
    2840            2845            2850

Ala Asn Ser Asn Lys Ser Ile Glu Gln Glu Ala Ser Asn Gln Val
    2855            2860            2865

Glu Asp Trp Gly Ala Gln Phe Glu Ser Asn Val Tyr Ala Glu Ile
    2870            2875            2880

Glu Ala Ile Asp Ala Ser Ala Val Gly Asn Asp Phe Met Gly Trp
    2885            2890            2895

Thr Ser Met Tyr Asp Gly Ser Ala Ile Asp Lys Ala Glu Met Gln
    2900            2905            2910

Glu Trp Leu Asp Asp Thr Met Gln Thr Ile Leu Asp Gly Arg Pro
    2915            2920            2925

Ala Gly Arg Val Leu Glu Ile Gly Thr Gly Thr Gly Met Ile Leu
    2930            2935            2940

Phe Asn Leu Gly Glu Gly Leu Gln Ser Tyr Val Gly Leu Glu Pro
    2945            2950            2955

Ser Thr Ser Ala Ala Ala Phe Val Asn Arg Arg Ile Gln Thr Leu
    2960            2965            2970

Pro Ala Phe Ala Gly Lys Ala Glu Val His Val Gly Thr Ala Thr
    2975            2980            2985

Asp Ile Ser Gln Leu Gln Asp Leu Arg Pro Glu Val Val Val Ile
    2990            2995            3000

Asn Ser Val Ala Gln Tyr Phe Pro Ser Pro Glu Tyr Leu Ser Lys
    3005            3010            3015

Val Leu Tyr Ala Leu Ala Gln Ile Pro Gly Val Lys Arg Leu Phe
    3020            3025            3030

Phe Gly Asp Met Arg Ser Tyr Ala Ile Asn Asp Gln Phe Leu Ala
    3035            3040            3045

Ala Arg Ala Leu His Asn Ile Gly Ser Lys Ala Thr Lys Ser Ala
    3050            3055            3060

Ile Arg Ser Lys Met Val Asp Leu Glu Asn Ser Glu Glu Glu Leu
    3065            3070            3075

Leu Val Asp Pro Thr Phe Phe Thr Asn Leu Ala Thr Glu Leu Pro
    3080            3085            3090

Glu Val Glu His Val Glu Ile Leu Pro Lys Arg Met Gln Ala Thr
    3095            3100            3105

Asn Glu Leu Ser Ala Tyr Arg Tyr Ala Ala Val Val His Ile Arg
    3110            3115            3120

Asp Ser Ser Glu Arg Ala Gln Thr Val His Ala Ile Lys Ser Ser
    3125            3130            3135

Ala Trp Val Asp Phe Ser Lys Ser Gln Met Asp Arg Lys Ala Leu
    3140            3145            3150

Ile Ser Leu Leu Gln Ser Ser Val Asn Thr Glu Ala Val Ala Ile
```

```
            3155                3160                3165
Gly Asn Ile Pro Tyr Ser Lys Thr Ile Met Ala Arg His Val Val
        3170                3175                3180
Gln Ser Leu Asp Glu Asp Asn Ala Asp Lys Asp Ile Ala Gln Asp
        3185                3190                3195
Lys Pro Asp Lys Pro Thr Trp Ile Ser Ala Val Arg Ser Asn Ala
        3200                3205                3210
Glu His Cys Pro Ser Leu Ser Ala Leu Asp Leu Val Gln Leu Gly
        3215                3220                3225
Glu Glu Ala Gly Phe Cys Val Glu Leu Ser Trp Ala Gln Gln Arg
        3230                3235                3240
Ser His His Gly Ala Ile Asp Ala Val Phe His His Tyr Gln Pro
        3245                3250                3255
Ala Arg Glu Gly Ser Arg Val Leu Phe Gln Phe Pro Thr Asp Thr
        3260                3265                3270
Tyr Arg Arg Gln Ser Gly Pro Leu Thr Asn Arg Pro Leu Gln Arg
        3275                3280                3285
Ile Gln Ser Arg Arg Met Glu Thr Gln Val Arg Glu Lys Leu Arg
        3290                3295                3300
Ala Val Leu Pro Ser Tyr Met Ile Pro Ser Leu Ile Val Leu Val
        3305                3310                3315
Asp Gln Met Pro Leu Asn Pro Asn Gly Lys Val Asp Arg Lys Ala
        3320                3325                3330
Leu Glu Arg Arg Ala Gln Ala Val Leu Arg Val Glu Lys Pro Thr
        3335                3340                3345
Ser Glu Arg Val Gly Ala Arg Asn Glu Thr Glu Ala Val Leu Cys
        3350                3355                3360
Glu Glu Phe Thr Asp Val Leu Gly Leu Glu Val Gly Ile Thr Asp
        3365                3370                3375
Asn Phe Phe Asp Leu Gly Gly His Ser Leu Met Ala Thr Lys Leu
        3380                3385                3390
Ala Ala Arg Ile Ser Arg Arg Leu Asp Ala Arg Val Ser Val Lys
        3395                3400                3405
Asp Val Phe Asp Gln Pro Val Ile Val Asp Leu Ala Ala Ser Ile
        3410                3415                3420
Arg Arg Gly Ser Thr Pro His Asn Pro Ile Thr Pro Thr Glu Tyr
        3425                3430                3435
Ser Gly Pro Val Glu Gln Ser Phe Ala Gln Gly Arg Leu Trp Phe
        3440                3445                3450
Leu Asp Gln Leu Asn Leu Gly Ala Ser Leu Tyr Leu Met Pro Leu
        3455                3460                3465
Ala Leu Arg Leu Arg Gly Pro Leu Arg Ile Asp Ala Leu Thr Ala
        3470                3475                3480
Ala Leu Phe Ala Leu Glu Gln Arg His Glu Thr Leu Arg Thr Val
        3485                3490                3495
Phe Lys Glu Gln Asp Gly Val Gly Ile Gln Ile Ile Gln Pro Ser
        3500                3505                3510
Gln Lys Lys Lys Leu Arg Thr Ile Asp Val Ser Ala Gly Asp Phe
        3515                3520                3525
Ser Glu Ala Leu His His Glu Arg Thr Ala Pro Phe Asp Leu Ala
        3530                3535                3540
Ser Glu Pro Gly Phe Arg Val Ala Leu Leu Gln Leu Glu Pro Ser
        3545                3550                3555
```

-continued

Asp His Val Leu Ser Ile Val Met His His Ile Ile Tyr Asp Gly
3560                3565                3570

Trp Ser Ile Asp Ile Leu Cys Gln Glu Leu Gly Gln Phe Tyr Ala
3575                3580                3585

Ala Ala Ile Gln Gly Gln Asp Pro Leu Gly Gln Val Ser Pro Leu
3590                3595                3600

Pro Ile Gln Tyr Arg Asp Phe Ser Val Trp Gln Lys Gln Pro Glu
3605                3610                3615

Gln Val Ala Glu His Glu Arg Gln Leu Ala Tyr Trp Ile Asp Gln
3620                3625                3630

Leu Ala Asp Ser Ala Pro Ala Glu Phe Leu Val Asp Leu Pro Arg
3635                3640                3645

Pro Pro Val Leu Ser Gly Asp Ala Gly Leu Val His Leu Thr Ile
3650                3655                3660

Asp Gly Pro Ile Tyr Asp Arg Leu Arg Ala Phe Cys Arg Val His
3665                3670                3675

Gln Thr Thr Thr Phe Ala Val Leu Leu Ala Ala Phe Arg Ala Thr
3680                3685                3690

His Tyr Arg Leu Thr Gly Ala Glu Asp Ala Thr Val Gly Thr Pro
3695                3700                3705

Ile Ala Asn Arg Asn Arg Pro Glu Leu Glu Asn Leu Val Gly Phe
3710                3715                3720

Phe Val Asn Thr Gln Cys Met Arg Ile Ser Val Gly Asp Asp Asp
3725                3730                3735

Thr Phe Glu Gln Leu Val Arg Gln Val Arg Ser Thr Ala Thr Ala
3740                3745                3750

Ala Phe Ala Asn Gln Asp Val Pro Phe Glu Arg Ile Val Ser Thr
3755                3760                3765

Leu Leu Pro Gly Ser Arg Asp Thr Ala Arg Asn Pro Leu Val Gln
3770                3775                3780

Leu Met Phe Ala Val His Ser Leu Lys Asp Leu Gly Lys Ile Gln
3785                3790                3795

Phe Glu Gly Leu Val Gly Glu Thr Ile Pro Thr Ala Ser Phe Thr
3800                3805                3810

Arg Phe Asp Val Glu Phe His Leu Phe Gln Glu Val Gly Arg Leu
3815                3820                3825

Ser Gly Asn Val Leu Phe Ser Thr Asp Leu Phe Glu Pro Glu Thr
3830                3835                3840

Ile Gln Gly Met Val Ser Val Phe Met Glu Ile Leu Arg Gly Ala
3845                3850                3855

Leu Asp Gln Pro Gln Ile Pro Ile Ala Val Leu Pro Leu Thr Asp
3860                3865                3870

Gly Leu Thr Glu Leu Arg Asn Arg Gly Leu Leu Glu Val Glu Gln
3875                3880                3885

Pro Gln Tyr Pro Arg Asp Ser Ser Val Ile Asp Val Phe Arg Ala
3890                3895                3900

Gln Val Val Ala Cys Pro Asp Ala Ile Ala Val Lys Asp Ser Thr
3905                3910                3915

Ser Gln Leu Thr Tyr Ala Gln Leu Asp Glu Gln Ser Asp Glu Val
3920                3925                3930

Ala Val Trp Leu His Gln Arg Lys Leu Pro Ala Glu Ser Leu Val
3935                3940                3945

```
Ala Val Leu Ala Pro Arg Ser Cys Glu Thr Ile Ile Thr Phe Phe
3950                3955                3960

Gly Ile Leu Lys Ala Asn Leu Ala Tyr Leu Pro Leu Asp Ile Asn
3965                3970                3975

Val Pro Ala Ala Arg Ile Gln Ala Ile Leu Ser Ser Val Ala Gly
3980                3985                3990

Lys Lys Ile Leu Leu Leu Gly Ser Asp Gln Ala Gln Pro Glu Ile
3995                4000                4005

Arg Leu Asp Asp Val Glu Phe Val Gln Ile Asn Glu Thr Ile Asp
4010                4015                4020

His Asn Met Ala Lys Asp Asn Thr Thr Arg Ser Gly Pro Leu Ala
4025                4030                4035

Thr Ser Leu Ala Tyr Val Ile Phe Thr Ser Gly Ser Thr Gly Gln
4040                4045                4050

Pro Lys Gly Val Lys Val Glu His Arg Gly Ile Val Arg Leu Val
4055                4060                4065

Lys Asn Ser Asn Val Val Ala Lys Met Pro Glu Ala Ala Cys Val
4070                4075                4080

Ala His Leu Ser Asn Leu Ala Phe Asp Ala Ala Thr Trp Glu Ile
4085                4090                4095

Tyr Ala Ala Leu Leu Asn Gly Gly Ser Leu Ile Cys Ile Asp Tyr
4100                4105                4110

Phe Thr Thr Leu Asp Ser Lys Val Leu Glu Ala Val Phe Glu Arg
4115                4120                4125

Glu Gln Ile Arg Ala Ala Met Phe Pro Pro Ala Leu Leu Lys Gln
4130                4135                4140

Cys Leu Leu Asn Ile Pro Thr Thr Ile Ser Ala Leu Asp Val Ile
4145                4150                4155

Leu Ala Ala Gly Asp Arg Phe Asp Arg Arg Asp Ala Ile Ala Ala
4160                4165                4170

Gln Ala Leu Val Gly Gly Val Tyr Asn Ala Tyr Gly Pro Thr
4175                4180                4185

Glu Asn Thr Thr Leu Ser Thr Ile Tyr Asn Val Val Asp Gly Asp
4190                4195                4200

Thr Asn Val Asn Gly Ile Pro Ile Gly Leu Pro Val Ser Asn Ser
4205                4210                4215

Gly Val Tyr Val Met Asp Pro Asn Gln Gln Leu Val Pro Leu Gly
4220                4225                4230

Val Met Gly Glu Leu Val Val Val Gly Asp Gly Val Ala Arg Gly
4235                4240                4245

Tyr Thr Asp Pro Ala Leu Asp Val Asp Arg Phe Ile Lys Val Glu
4250                4255                4260

Ile Asp Gly Gln Ile Val Arg Ala Tyr Arg Thr Gly Asp Arg Val
4265                4270                4275

Arg His Arg Pro Lys Asp Gly Gln Ile Glu Phe Phe Gly Arg Met
4280                4285                4290

Asp Gln Gln Val Lys Ile Arg Gly His Arg Ile Glu Leu Ala Glu
4295                4300                4305

Val Glu His Val Ile Leu Asp Asn Ser Leu Val Gln Asp Ala Ala
4310                4315                4320

Val Ile Val His Lys Gln Ala Asp Gln Glu Ile Glu Met Ile Ala
4325                4330                4335

Phe Ala Ile Val Arg Gly Asp Asn Asp Ser Lys His Pro Glu Lys
```

-continued

```
            4340                4345                4350
Asp Ile Leu Asp Arg Val Lys Ala Leu Leu Pro Ser Tyr Met Val
    4355                4360                4365
Pro Ala Gln Met Val Leu Leu Asn Ser Met Pro Leu Asn Ala Asn
    4370                4375                4380
Gly Lys Val Asp Arg Lys Glu Leu Ala Lys Arg Ala Gly Thr Val
    4385                4390                4395
Pro Arg Ser Glu Met Ala Tyr Val Ala Pro Glu Arg Val Pro Pro
    4400                4405                4410
Arg Asn Glu Ile Glu Thr Ile Leu Cys Glu Glu Tyr Ala Glu Val
    4415                4420                4425
Leu Gly Val Glu Val Gly Val Met Asp Asn Phe Phe Asp Leu Gly
    4430                4435                4440
Gly His Ser Leu Met Ala Thr Lys Leu Ala Ala Arg Ala Thr Arg
    4445                4450                4455
Arg Leu Asp Ala Lys Leu Ser Val Lys Asp Ile Phe Asp Tyr Pro
    4460                4465                4470
Ile Leu Ala Asn Leu Ala Ala Ala Val Gln Arg Gly Ser Thr Pro
    4475                4480                4485
His Asn Ala Ile Leu Ala Thr Thr Tyr Ser Gly Pro Val Glu Gln
    4490                4495                4500
Ser Phe Ala Gln Gly Arg Leu Trp Phe Leu Asp Gln Leu Asn Val
    4505                4510                4515
Gly Ser Asn Trp Tyr Leu Gln Pro Ile Ala Ile Arg Ile Arg Gly
    4520                4525                4530
Ser Leu Asn Ile Asn Ala Leu Thr Thr Ala Leu His Ala Leu Glu
    4535                4540                4545
Gln Arg His Glu Thr Leu Arg Thr Thr Phe Glu Glu Glu Asp Gly
    4550                4555                4560
Val Gly Met Gln Val Val Gln Glu Tyr Asp Pro Ile Glu Leu Arg
    4565                4570                4575
Ile Met Asp Ile Ala Ala Asp Tyr Asp Gly Asp Tyr Thr Glu Ala
    4580                4585                4590
Leu Lys Gly Glu Gln Thr Thr Pro Phe Asp Leu Glu Ser Glu Pro
    4595                4600                4605
Gly Trp Arg Val Ser Leu Leu Arg Met Asn Asp Asn Asp His Ile
    4610                4615                4620
Leu Ser Leu Val Leu His His Ile Ile Ser Asp Gly Trp Ser Val
    4625                4630                4635
Asp Val Leu Arg Gln Glu Leu Lys Gln Phe Tyr Ala Ala Ala Leu
    4640                4645                4650
Gln Gly Leu Asp Pro Leu Ser Gly Ala Asp Pro Leu Pro Ile Gln
    4655                4660                4665
Tyr Arg Asp Phe Ser Leu Trp Gln Lys Gln Pro Glu Gln Val Ala
    4670                4675                4680
Glu His Glu Arg Gln Leu Lys Tyr Trp Val Glu Gln Leu Ala Asp
    4685                4690                4695
Asn Ser Pro Ala Thr Leu Leu Ala Asp Arg Pro Arg Pro Ser Val
    4700                4705                4710
Leu Ser Gly Gln Ala Gly Ser Val Pro Leu Ser Ile Glu Gly Gln
    4715                4720                4725
Val Tyr Glu Lys Leu Gln Ala Phe Cys Arg Ala His Gln Thr Thr
    4730                4735                4740
```

Ser Phe Ser Val Leu Leu Ala Ala Phe Arg Ala His Phe Arg
    4745            4750            4755

Leu Thr Gly Val Asp Asp Ala Thr Ile Gly Ile Pro Ile Ala Asn
    4760            4765            4770

Arg Asn Arg Pro Glu Leu Glu His Leu Ile Gly Phe Phe Val Asn
    4775            4780            4785

Arg Gln Cys Met Arg Ile Thr Val Gly Glu Asp Thr Phe Glu
    4790            4795            4800

Ser Leu Ile Arg Gln Val His Ser Thr Ala Thr Ala Ala Tyr Ala
    4805            4810            4815

Asn Gln Asp Val Pro Phe Glu Arg Ile Val Ser Ser Leu Leu Ser
    4820            4825            4830

Gly Ser Arg Asp Thr Ser Arg Asn Pro Leu Val Gln Leu Val Phe
    4835            4840            4845

Ala Val His Ser Gln Lys Asn Leu Gly Lys Phe Glu Leu Gln Asp
    4850            4855            4860

Leu Thr Ser Glu Pro Val Ala Gly Ala Ile Ser Thr Arg Phe Asp
    4865            4870            4875

Ala Glu Phe His Leu Phe Gln Glu Glu Glu Arg Leu Asn Gly Val
    4880            4885            4890

Val Tyr Tyr Ala Thr Asp Leu Phe Asp Ala Glu Thr Ile Gln Gly
    4895            4900            4905

Val Val Ser Val Phe Gln Glu Ile Leu Arg Arg Gly Leu Asn His
    4910            4915            4920

Pro Arg Thr Pro Ile Ala Ala Leu Ser Leu Thr Asp Gly Leu Asp
    4925            4930            4935

Asn Leu Arg Lys Met Asn Leu Val His Phe Lys Arg Thr Asp Tyr
    4940            4945            4950

Pro Arg Asp Ser Ser Met Val Asp Ile Phe Arg Glu Gln Val Ala
    4955            4960            4965

Thr Tyr Pro Asp Val Ile Ala Val Lys Asp Ser Thr Leu Gln Leu
    4970            4975            4980

Thr Tyr Ala Gln Leu Asp Gln Gln Ser Asp Glu Ile Ala Thr Trp
    4985            4990            4995

Leu Arg Asn Lys Lys Met Ala Pro Glu Thr Leu Val Gly Val Leu
    5000            5005            5010

Ala Pro Arg Ser Cys Gln Thr Ile Val Ala Phe Leu Gly Val Leu
    5015            5020            5025

Lys Ala Asn Leu Ala Tyr Leu Pro Leu Asp Val Asn Ala Pro Met
    5030            5035            5040

Ala Arg Val Glu Thr Ile Met Ser Ser Val Pro Gly Ser Lys Leu
    5045            5050            5055

Leu Leu Leu Gly Ser Asp Val Pro Ala Gln Glu Ile Gln Leu Gln
    5060            5065            5070

Asn Val Glu Leu Val Arg Ile Glu Asp Thr Leu Gly His Ala Ala
    5075            5080            5085

Ser Ala Gly Thr Ala Thr Thr Glu Pro Ser Pro Thr Ser Leu Ala
    5090            5095            5100

Tyr Val Ile Phe Thr Ser Gly Ser Thr Gly Lys Pro Lys Gly Val
    5105            5110            5115

Met Val Glu His Arg Ser Val Ile Arg Leu Val Arg Lys Glu Ser
    5120            5125            5130

```
Asn Ser Met Ser Lys Met Ser Ser Arg Ala Arg Val Ala His Leu
5135                5140                5145

Thr Asn Ile Ala Phe Asp Val Ser Ala Trp Glu Val Tyr Ala Thr
5150                5155                5160

Leu Leu Asn Gly Gly Thr Leu Val Cys Val Asp Tyr Phe Thr Ser
5165                5170                5175

Phe Asp Ala Lys Ala Leu Gly Leu Leu Phe Glu Arg Glu Gln Ile
5180                5185                5190

Thr Ala Ala Met Ile Thr Pro Thr Leu Leu Lys Gln Cys Ile Thr
5195                5200                5205

Ile Val Pro Glu Ala Leu Arg Lys Leu Ser Val Leu Tyr Thr Gly
5210                5215                5220

Gly Asp Arg Phe Asp Arg Arg Asp Ala Ile Ala Thr Lys Ala Leu
5225                5230                5235

Val Lys Gly Pro Val Tyr Asn Ala Trp Gly Pro Thr Glu Thr Thr
5240                5245                5250

Ile Val Ser Thr Ile Tyr Glu Leu Ala Asp Asp Gln Phe Thr
5255                5260                5265

Asn Gly Val Pro Ile Gly Lys Ala Val Ser Asn Ser Trp Ala Tyr
5270                5275                5280

Val Met Asp Leu Asn Gln Gln Leu Val Pro Val Gly Val Met Gly
5285                5290                5295

Glu Ala Val Val Ile Gly Asp Gly Leu Ala Arg Gly Tyr Thr Asp
5300                5305                5310

Pro Ala Leu Asp Cys Asn Arg Phe Val His Ile Thr Ile Asp Gly
5315                5320                5325

Lys Arg Val Arg Ala Tyr Arg Thr Gly Asp Arg Ala Arg Tyr Arg
5330                5335                5340

Pro Lys Asp Gly Glu Ile Glu Phe Phe Gly Arg Met Asp Arg Gln
5345                5350                5355

Leu Lys Ile Arg Gly His Arg Ile Glu Pro Ala Glu Ile Glu His
5360                5365                5370

Ala Met Leu Gly His Asn Asp Ile Val Asp Val Ala Ile Val Thr
5375                5380                5385

Arg His Gln Asp Gly Ala Gly Leu Glu Met Val Ala Phe Val Thr
5390                5395                5400

Ala His Thr Asn Lys Ser Ile Glu Arg Asn Glu Ala Thr Asn Gln
5405                5410                5415

Val Ala Gly Trp Gly Asp His Phe Glu Ser Ser Thr Tyr Ala Glu
5420                5425                5430

Leu Asp Thr Leu Val Lys Ser Asp Val Gly Lys Asp Phe Val Gly
5435                5440                5445

Trp Thr Asn Met Tyr Asp Gly Gly Ala Ile Asp Gln Ala Glu Met
5450                5455                5460

Gln Glu Trp Leu Asp Asp Thr Ile Gln Thr Ile Val Asp Gly Gln
5465                5470                5475

Pro Ala Gly His Val Phe Glu Ile Gly Thr Gly Thr Gly Met Ile
5480                5485                5490

Met Phe Gly Leu Gly Lys Gln Gly Leu Gln Ser Tyr Val Gly Leu
5495                5500                5505

Glu Pro Ser Thr Ser Ala Thr Thr Tyr Val Asn Arg Lys Ile Lys
5510                5515                5520

Thr Ala Pro Thr Val Ala Gly Lys Ala Lys Val Tyr Val Gly Thr
```

-continued

```
            5525                5530                5535

Ala Met Glu Ala Ala Gln Leu Asn Gly Leu His Pro Glu Val Val
        5540                5545                5550

Val Ile Asn Ser Val Ala Gln Tyr Phe Pro Thr Pro Glu Tyr Leu
        5555                5560                5565

Leu Glu Val Val Gly Ile Leu Thr Gln Met Pro Gly Val Lys Arg
        5570                5575                5580

Leu Phe Phe Gly Asp Ile Arg Ser Tyr Ala Thr Asn Arg Lys Phe
        5585                5590                5595

Leu Ala Ala Arg Ala Leu His Met Leu Gly Ser Asn Ala Lys Lys
        5600                5605                5610

His Asp Ile Arg Arg Lys Met Ala Glu Leu Asp Glu Phe Glu Glu
        5615                5620                5625

Glu Leu Ile Val Asp Pro Ser Phe Phe Thr Gly Leu Val Ser Arg
        5630                5635                5640

Leu Pro Gly Gln Val Lys His Val Glu Ile Leu Pro Lys Gln Met
        5645                5650                5655

Ile Ala Thr Asn Glu Leu Ser Ala Tyr Arg Tyr Ala Ala Val Val
        5660                5665                5670

His Leu Ala Leu Pro Glu Glu Gln His Ile Ala Lys Ile Glu Lys
        5675                5680                5685

Gly Ala Trp Val Asp Phe Thr Ala Thr Lys Met Asp Arg Ser Ala
        5690                5695                5700

Leu Val His His Leu Gln Ser Ser Ser Asn Ala Glu Ile Val Ala
        5705                5710                5715

Ile Ser Asn Ile Pro Phe Ser Lys Thr Asn Phe Asp Cys His Leu
        5720                5725                5730

Leu Ala Ser Leu Asp Glu Asp Glu Glu His Ser Leu Asp Gly Ser
        5735                5740                5745

Ala Trp Ile Lys Thr Ile His Ser Ser Ala Glu Gln Cys Pro Ser
        5750                5755                5760

Leu Ser Ala Thr Asp Leu Val Glu Val Ala Lys Glu Val Gly Phe
        5765                5770                5775

Arg Val Glu Leu Ser Trp Ala Arg Gln Lys Ser Gln Asn Gly Ala
        5780                5785                5790

Leu Asp Ala Ile Phe His Gln Tyr Gln Ser Pro Lys Glu Gly Ser
        5795                5800                5805

Arg Val Leu Ile Gln Phe Pro Thr Asp Asp Gln Gly Arg Ser Met
        5810                5815                5820

Glu Ser Leu Thr Asn Arg Pro Leu Gln Arg Val Gln Ser Arg Arg
        5825                5830                5835

Ile Glu Thr Gln Ile Arg Glu Arg Leu Gln Ala Val Leu Pro Ser
        5840                5845                5850

Tyr Met Ile Pro Ala Arg Ile Val Val Leu Asn Glu Met Pro Val
        5855                5860                5865

Asn Ala Asn Gly Lys Val Asp Arg Lys Glu Leu Thr Arg Arg Ala
        5870                5875                5880

Lys Val Val Pro Arg Ile Glu Thr Ala Ala Glu Arg Ile Gln Pro
        5885                5890                5895

Arg Asn Glu Val Glu Ala Val Leu Cys Glu Glu Phe Ser Glu Val
        5900                5905                5910

Leu Gly Val Glu Val Gly Val Thr Asp Asn Phe Phe Asp Leu Gly
        5915                5920                5925
```

-continued

Gly His Ser Leu Met Ala Thr Lys Leu Ala Ala Arg Thr Gly Arg
5930                5935                5940

Arg Leu Asp Ala Lys Val Ser Val Lys Asp Val Phe Asp His Pro
5945                5950                5955

Val Leu Ala Asp Leu Ala Ala Ala Ile Gln Arg Gly Ser Thr Pro
5960                5965                5970

His Ser Ala Ile Val Thr Thr Glu Tyr Ser Gly Pro Val Glu Gln
5975                5980                5985

Ser Tyr Ala Gln Gly Arg Leu Trp Phe Leu Glu Gln Leu Asn Phe
5990                5995                6000

Lys Ala Thr Trp Tyr Leu Leu Pro Leu Ala Val Arg Ile Arg Gly
6005                6010                6015

Pro Leu Asn Ile Lys Ala Leu Thr Thr Ala Leu His Ala Leu Glu
6020                6025                6030

Gln Arg His Glu Thr Leu Arg Thr Thr Phe Ile Glu Arg Asp Gly
6035                6040                6045

Val Gly Lys Gln Ala Val Gln Pro Phe Gln Pro Lys Glu Leu Glu
6050                6055                6060

Ile Val Asp Ile Ala Ala Asp His Gln Gly Asp Tyr Leu Lys Val
6065                6070                6075

Leu Arg Asp Glu Gln Thr Thr Met Phe Asn Leu Ala Thr Gln Pro
6080                6085                6090

Gly Trp Arg Val Thr Leu His Arg Val Asp Gln Asn Thr His Asn
6095                6100                6105

Leu Ser Ile Val Met His His Ile Ile Ser Asp Gly Trp Ser Val
6110                6115                6120

Asp Val Leu Arg His Glu Leu Arg Gln Phe Tyr Ala Ala Ala Leu
6125                6130                6135

Arg Gly Gln Asp Pro Leu Ala His Ile Ser Pro Leu Pro Ile Gln
6140                6145                6150

Tyr Arg Asp Phe Ser Leu Trp Gln Lys Gln Pro Asp Gln Ile Ile
6155                6160                6165

Glu His Ala Lys Gln Leu Glu Tyr Trp Thr Lys Gln Leu Ala Asp
6170                6175                6180

Ser Ser Pro Ala Glu Leu Pro Thr Asp Leu Pro Arg Pro Ala Val
6185                6190                6195

Leu Ser Gly Lys Ala Gly Glu Val Ala Leu Ser Val Lys Gly Pro
6200                6205                6210

Leu Tyr Glu Arg Leu Gln Ala Phe Cys Lys Thr His Gln Thr Thr
6215                6220                6225

Ala Phe Ala Thr Leu Leu Ala Ala Phe Arg Ala Thr His His Arg
6230                6235                6240

Leu Thr Gly Ala Glu Asp Ala Thr Ile Gly Thr Pro Ile Ala Asn
6245                6250                6255

Arg Asn Arg Pro Glu Leu Glu Asn Leu Ile Gly Phe Phe Val Asn
6260                6265                6270

Ala Gln Cys Met Arg Ile Thr Ile Asp Gly Asp Glu Thr Phe Glu
6275                6280                6285

Ser Leu Ile Arg Gln Val Arg Ala Thr Ala Thr Ala Ala Ile Ala
6290                6295                6300

Asn Gln Asp Val Pro Phe Glu Arg Ile Val Ser Thr Met Gln Ser
6305                6310                6315

```
Thr Ser Arg Asp Thr Ser Arg Asn Pro Leu Val Gln Leu Met Phe
    6320                6325                6330

Ala Leu His Ser Gln Gln Asp Leu Gly Lys Ile Gln Leu Glu Gly
    6335                6340                6345

Cys Glu Thr Glu Pro Ile Pro Arg Ala Val Arg Thr Arg Phe Asp
    6350                6355                6360

Leu Glu Phe His Leu Tyr Gln Glu Gln Gly Ser Leu Gly Gly Ile
    6365                6370                6375

Val Tyr Phe Ala Thr Asp Leu Phe Glu Pro Glu Ser Ile Glu Gly
    6380                6385                6390

Met Val Ser Ile Phe Lys Glu Ile Leu Ala Arg Ala Leu Asp Gln
    6395                6400                6405

Pro Gln Thr Pro Leu Ala Leu Leu Pro Leu Thr Asp Gly Leu Ala
    6410                6415                6420

Glu Leu Arg Arg Arg Gly Leu Leu Glu Ile Glu Arg Pro Ser Tyr
    6425                6430                6435

Pro Arg Glu Ser Ser Val Val Asp Val Phe Cys Ser Gln Val Ala
    6440                6445                6450

Ala Ser Pro Asn Ala Thr Ala Val Lys Asp Ser Ile Ser Gln Leu
    6455                6460                6465

Thr Tyr Ala Gln Leu Asn Glu Gln Ser Asp Lys Val Ala Ala Trp
    6470                6475                6480

Leu His Gln Cys Asn Leu Pro Thr Glu Thr Leu Val Ala Val Leu
    6485                6490                6495

Ala Pro Arg Ser Cys Gln Thr Val Val Ala Phe Leu Gly Ile Leu
    6500                6505                6510

Lys Ala Asn Leu Ala Tyr Leu Pro Leu Asp Val Asn Val Pro Ala
    6515                6520                6525

Ala Arg Ile Glu Ala Ile Leu Ser Glu Val Ser Gly His Ile Leu
    6530                6535                6540

Val Leu Leu Gly Ser His Val Ser Ala Pro Lys Ile Glu Leu Ala
    6545                6550                6555

Asp Val Glu Phe Val Lys Ile Asp Asn Thr Val Glu His Asn Leu
    6560                6565                6570

Pro Gly Arg Ile Gly Ser Ala Pro Ser Ala Thr Ser Leu Ala Tyr
    6575                6580                6585

Val Ile Phe Thr Ser Gly Ser Thr Gly Lys Pro Lys Gly Val Lys
    6590                6595                6600

Val Glu His Arg Gly Ile Val Arg Leu Val Lys Glu Ser Asn Val
    6605                6610                6615

Val Ala Lys Met Pro Gln Ala Ala Arg Ile Ala His Leu Ser Asn
    6620                6625                6630

Ile Ala Phe Asp Ala Ala Thr Trp Glu Leu Tyr Ala Ala Leu Leu
    6635                6640                6645

Asn Gly Gly Thr Leu Val Cys Ile Asn Tyr Leu Thr Thr Leu Asp
    6650                6655                6660

Ser Lys Ala Leu Glu Ala Val Phe Glu Gln Glu Lys Ile Gln Ala
    6665                6670                6675

Ala Met Leu Pro Pro Ala Leu Leu Lys Gln Tyr Leu Val Asn Ile
    6680                6685                6690

Pro Ala Ala Ile Gly Ala Leu Glu Val Val Leu Val Ala Gly Asp
    6695                6700                6705

Arg Phe Asp Arg Arg Asp Ala Ala Ala Thr Gln Ala Leu Val Gly
```

|  |  |  |  | 6710 |  |  |  | 6715 |  |  |  | 6720 |  |  |
|---|---|---|---|---|---|---|---|---|---|---|---|---|---|---|

Ala Gly Val Tyr Asn Ala Tyr Gly Pro Thr Glu Asn Thr Thr Leu
    6725                6730                6735

Ser Thr Ile Tyr Asn Val Val Gln Gly Asp Ala Asn Val Asn Gly
    6740                6745                6750

Val Pro Ile Gly Arg Pro Val Ser Asn Ser Gly Ala Tyr Ile Met
    6755                6760                6765

Asn Met Asn Gln Glu Leu Val Pro Ile Gly Val Ile Gly Glu Leu
    6770                6775                6780

Val Val Val Gly Asp Gly Val Ala Arg Gly Tyr Thr Asp Pro Ala
    6785                6790                6795

Leu Asp Val Asn Arg Phe Val Asn Val Thr Ile Glu Gly Gln Thr
    6800                6805                6810

Met Arg Ala Tyr Arg Thr Gly Asp Arg Ala Arg Tyr Arg Pro Lys
    6815                6820                6825

Asp Ala Gln Ile Glu Phe Phe Gly Arg Met Asp Gln Gln Ile Lys
    6830                6835                6840

Ile Arg Gly His Arg Ile Glu Pro Ala Glu Val Glu His Ala Leu
    6845                6850                6855

Leu Asn Asn Asp Leu Leu Gln Asp Ala Ala Val Ile Ile Arg Lys
    6860                6865                6870

Gln Gln Asn Asp Glu Leu Glu Met Val Ala Phe Val Glu Ala Asn
    6875                6880                6885

Ser Asn Lys Ser Ile Glu Gln Glu Ala Ser Asn Gln Val Glu Asp
    6890                6895                6900

Trp Gly Ala Gln Phe Glu Ser Asn Val Tyr Ala Glu Ile Glu Ala
    6905                6910                6915

Ile Asp Ala Ser Ala Val Gly Asn Asp Phe Met Gly Trp Thr Ser
    6920                6925                6930

Met Tyr Asp Gly Ser Ala Ile Asp Lys Ala Glu Met Gln Glu Trp
    6935                6940                6945

Leu Asp Asp Thr Met Gln Thr Ile Leu Asp Gly Arg Pro Ala Gly
    6950                6955                6960

Arg Val Leu Glu Ile Gly Thr Gly Thr Gly Met Ile Leu Phe Asn
    6965                6970                6975

Leu Gly Glu Gly Leu Gln Ser Tyr Val Gly Leu Glu Pro Ser Thr
    6980                6985                6990

Ser Ala Ala Ala Phe Val Asn Arg Arg Ile Gln Thr Leu Pro Ala
    6995                7000                7005

Phe Ala Gly Lys Ala Glu Val His Val Gly Thr Ala Thr Asp Ile
    7010                7015                7020

Ser Gln Leu Gln Asp Leu Arg Pro Glu Val Val Ile Asn Ser
    7025                7030                7035

Val Ala Gln Tyr Phe Pro Ser Pro Glu Tyr Leu Ser Lys Val Leu
    7040                7045                7050

Tyr Ala Leu Ala Gln Ile Pro Gly Val Lys Arg Leu Phe Phe Gly
    7055                7060                7065

Asp Met Arg Ser Tyr Ala Ile Asn Asp Gln Phe Leu Ala Ala Arg
    7070                7075                7080

Ala Leu His Asn Ile Gly Ser Lys Ala Thr Lys Ser Ala Ile Arg
    7085                7090                7095

Ser Lys Met Val Asp Leu Glu Asn Ser Glu Glu Glu Leu Leu Val
    7100                7105                7110

-continued

```
Asp Pro Thr Phe Phe Thr Asn Leu Ala Thr Glu Leu Pro Glu Val
7115                7120                7125

Glu His Val Glu Ile Leu Pro Lys Arg Met Gln Ala Thr Asn Glu
7130                7135                7140

Leu Ser Ala Tyr Arg Tyr Ala Ala Val Val His Ile Arg Asp Pro
7145                7150                7155

Ala Arg Gln Ala Gln Thr Val His Thr Ile Asp Pro Thr Ala Trp
7160                7165                7170

Ile Asp Phe Ser Ala Ser Gln Met Asn Arg Thr Ala Leu Ala Asn
7175                7180                7185

Leu Leu Gln Asn Ser Ala Asp Ala Ala Ile Ala Val Ser Asn
7190                7195                7200

Ile Pro Tyr Ser Lys Thr Ile Leu Ala Arg His Ile Val Gln Ser
7205                7210                7215

Leu Asp Asp Asp Leu Thr Asp Ser Asp Asp Pro Gln Asp Glu Leu
7220                7225                7230

Glu Gly Ala Ala Trp Met Ser Ala Ile Arg Ser Asn Ile Lys Thr
7235                7240                7245

Cys Ala Ser Leu Ser Ala Phe Asp Leu Ala Gln Leu Ala Gln Glu
7250                7255                7260

Lys Gly Phe Arg Val Glu Leu Ser Trp Ala Arg Gln Arg Thr His
7265                7270                7275

His Gly Ala Leu Asp Ala Val Phe His His Tyr Lys Ser Asn Gln
7280                7285                7290

Asp Gly Gly Arg Val Leu Val Gln Phe Pro Thr Asp Ser Arg Pro
7295                7300                7305

Arg Leu Ser Gly Gln Leu Thr Asn Gln Pro Leu Gln Arg Leu Gln
7310                7315                7320

Ser Arg Arg Leu Glu Ala Gln Ile Arg Asp Gln Leu Ser Ala Leu
7325                7330                7335

Leu Pro Ser Tyr Met Ile Pro Ser Leu Ile Val Met Val Asp Glu
7340                7345                7350

Met Pro Leu Asn Ala Asn Gly Lys Val Asp Arg Lys Ala Leu Glu
7355                7360                7365

Arg Arg Ala Arg Met Val Gln Lys Val Glu Lys Pro Ala Ser Glu
7370                7375                7380

Arg Val Gly Ala Arg Asn Glu Ile Glu Ala Ala Leu Cys Glu Val
7385                7390                7395

Phe Val Asp Leu Leu Gly Thr Glu Val Ser Ile Thr Asp Asn Phe
7400                7405                7410

Phe Asn Leu Gly Gly His Ser Leu Met Ala Thr Lys Leu Ala Ala
7415                7420                7425

Arg Ile Ser Arg Arg Leu Asp Ala Arg Ile Ser Val Lys Asp Val
7430                7435                7440

Phe Asp Tyr Pro Val Leu Ala Asp Leu Ala Gly Ala Val Gln Arg
7445                7450                7455

Gly Ser Thr Pro His Asn Pro Ile Val Ala Thr Pro Tyr Ser Gly
7460                7465                7470

Pro Val Glu Gln Ser Phe Ala Gln Gly Arg Leu Trp Phe Leu Asp
7475                7480                7485

Gln Leu Asn Ala Gly Ser Leu Trp Tyr Ile Gln Pro Ile Ala Val
7490                7495                7500
```

```
Arg Val Arg Gly Ser Leu Asn Ile Gly Ala Leu Thr Thr Ala Leu
    7505                7510                7515

Asn Ala Leu Glu Lys Arg His Glu Pro Leu Arg Thr Thr Phe Glu
    7520                7525                7530

Glu His Asp Gly Ile Gly Val Gln Val Val Gln Pro His Gln Pro
    7535                7540                7545

Lys Lys Leu Arg Ile Val Asp Thr Val Ala Asn Tyr Gln Gly Asp
    7550                7555                7560

Phe Ile Arg Ala Leu Arg Lys Glu Gln Gln Thr Leu Phe Asn Leu
    7565                7570                7575

Ala Thr Glu Pro Gly Trp Arg Val Ser Leu Leu Arg Ile Gly Glu
    7580                7585                7590

Asp Asp Asn Ile Leu Ser Ile Val Met His His Ile Ile Ser Asp
    7595                7600                7605

Gly Trp Ser Val Asp Ile Leu Arg Gln Asp Leu Lys Leu Phe Tyr
    7610                7615                7620

Ala Ala Ala Leu Lys Ser Gln Glu Pro Gln Val Asp Ala Leu Pro
    7625                7630                7635

Ile Gln Tyr Arg Asp Phe Ala Phe Trp Gln Lys Gln Pro Glu Gln
    7640                7645                7650

Val Ala Glu His Gln Arg Gln Leu Asp Tyr Trp Ile Glu Gln Leu
    7655                7660                7665

Lys Asp Ser Lys Pro Ala Glu Leu Ile Thr Asp Phe Pro Arg Pro
    7670                7675                7680

Glu Val Leu Ser Gly Thr Ala Gly Ile Val Gln Leu Ala Val Asp
    7685                7690                7695

Gly Gln Val Tyr Glu Gly Leu Arg Ala Phe Cys Arg Ile His Gln
    7700                7705                7710

Thr Thr Ser Phe Val Val Leu Leu Ala Ala Phe Arg Ala Ala His
    7715                7720                7725

Tyr Arg Leu Thr Gly Thr Glu Asp Ala Thr Ile Gly Ser Pro Ile
    7730                7735                7740

Ala Asn Arg Asn Arg Pro Glu Leu Glu Ser Leu Ile Gly Phe Phe
    7745                7750                7755

Val Asn Thr Gln Cys Met Arg Ile Met Val Gly Glu Asp Asp Thr
    7760                7765                7770

Phe Glu Arg Leu Val Gln Gln Val Arg Ser Thr Thr Thr Ala Ala
    7775                7780                7785

Phe Ala Asn Gln Asp Val Pro Phe Glu Arg Ile Val Ser Ser Val
    7790                7795                7800

Gln Ser Thr Ser Arg Asp Ala Ser Arg Asn Pro Leu Val Gln Leu
    7805                7810                7815

Met Phe Ala Leu His Ser Gln Gln Gly Ile Gly Leu Met Glu Leu
    7820                7825                7830

Glu Gly Val Glu Thr Glu Pro Ile Ala Arg Asp Val Ser Thr Arg
    7835                7840                7845

Phe Asp Ile Glu Phe His Leu Tyr Gln Lys Glu Glu Ser Leu His
    7850                7855                7860

Gly Val Val His Phe Ala Ala Asp Leu Phe Glu Pro Glu Thr Ile
    7865                7870                7875

Gln Gly Leu Val Ser Val Phe Gln Glu Ile Leu Arg Arg Gly Leu
    7880                7885                7890

Glu Thr Pro Arg Leu Pro Ile Ser Ile Leu Pro Leu Asp Asn Asn
```

```
            7895            7900            7905
Ile Pro Glu Leu Leu Val Gly Met Leu Asp Val Asp Thr Pro Glu
    7910            7915            7920

Tyr Pro Arg Asp Ser Ser Val Val Asp Val Phe Arg Thr Gln Val
    7925            7930            7935

Ala Ala Ser Pro Asp Ala Ile Ala Val Lys Asp Ser Thr Ser Gln
    7940            7945            7950

Leu Thr Tyr Ala Gln Leu Asp Glu Glu Ser Asn Lys Val Ala Thr
    7955            7960            7965

Trp Leu Ser Gln Arg Gln Leu Ala Pro Glu Thr Leu Val Gly Val
    7970            7975            7980

Leu Ala Pro Arg Ser Cys Pro Thr Ile Val Thr Phe Phe Gly Ile
    7985            7990            7995

Leu Lys Ala Ser Leu Ala Tyr Leu Pro Leu Asp Val Asn Val Pro
    8000            8005            8010

Ser Ala Arg Ile Glu Ala Ile Leu Ser Ala Val Pro Asp His Lys
    8015            8020            8025

Leu Val Phe Leu Gly Ala Asp Val Pro Asp Pro Glu Ala Pro Leu
    8030            8035            8040

Val Asn Val Glu Leu Val Arg Ile Asp Asp Ile Leu Arg Gln Ser
    8045            8050            8055

Ile His Ala Ser Asn Ala Gly Leu Leu Ala Asn His Pro Leu Ala
    8060            8065            8070

Thr Ser Leu Ala Tyr Val Met Phe Thr Ser Gly Ser Thr Gly Lys
    8075            8080            8085

Pro Lys Gly Val Met Val Glu His Arg Ser Ile Val Arg Leu Val
    8090            8095            8100

Lys Glu Thr Asn Leu Val Pro Ala Val Glu Ala Val Ser Ser Val
    8105            8110            8115

Ala His Ile Ser Asn Val Ala Phe Asp Ala Ala Thr Trp Glu Ile
    8120            8125            8130

Tyr Ala Ala Leu Leu Asn Gly Gly Thr Thr Val Cys Ile Asp His
    8135            8140            8145

Ile Thr Val Leu Asp Pro Ala Lys Leu Ala Leu Val Phe Ser Ser
    8150            8155            8160

Glu Lys Ile Lys Ala Ala Phe Phe Ser Thr Ala Leu Leu Lys Gln
    8165            8170            8175

Arg Leu Tyr Glu Glu Pro Ser Thr Ile Thr Gly Leu Asp Leu Leu
    8180            8185            8190

Tyr Ala Gly Gly Glu Arg Met Arg Pro Gln Asp Ala Leu Lys Thr
    8195            8200            8205

Arg Glu Leu Val Arg Gly Ser Phe Cys His Val Tyr Gly Pro Thr
    8210            8215            8220

Glu Asn Thr Thr Phe Ser Thr Val Tyr Pro Met Gly Val Glu Glu
    8225            8230            8235

Arg Cys Val Asn Gly Leu Pro Ile Gly Arg Ala Val Ser His Ser
    8240            8245            8250

Gly Ala Val Ile Met Asp Ala Asn Gln Arg Leu Val Pro Leu Gly
    8255            8260            8265

Val Met Gly Glu Leu Val Val Thr Gly Asp Gly Leu Ala Arg Gly
    8270            8275            8280

Tyr Thr Asp Pro Ala Leu Asn Arg Asp Arg Phe Val Glu Val Asn
    8285            8290            8295
```

```
Ile His Gly Gln Val Leu Arg Ala Tyr Arg Thr Gly Asp Gln Ala
    8300                8305                8310

Arg Tyr Arg Pro Lys Asp Gly Gln Ile Glu Phe Ser Gly Arg Met
    8315                8320                8325

Asp Arg Gln Leu Lys Ile Arg Gly His Arg Ile Glu Pro Ala Glu
    8330                8335                8340

Val Glu His Ala Ile Leu Ser His Asp Asp Ile Arg Asn Ala Val
    8345                8350                8355

Val Val Thr Arg Gln Gln Glu Gly Gln Asp Leu Glu Met Val Ala
    8360                8365                8370

Phe Val Ser Thr Pro Asn Asp Gln Thr Val Glu Arg Asp Glu Ala
    8375                8380                8385

Arg Asn Gln Val Glu Asp Trp Gly Ala Gln Phe Glu Ser Asn Val
    8390                8395                8400

Tyr Ala Glu Ile Glu Glu Ile Asp Ser Ser Ala Val Gly Asn Asp
    8405                8410                8415

Phe Met Gly Trp Thr Ser Met Tyr Asp Gly Thr Ala Ile Asp Lys
    8420                8425                8430

Ala Glu Met Gln Glu Trp Leu Asp Asp Thr Met Arg Thr Leu His
    8435                8440                8445

Asp Gly Arg Asp Pro Gly His Val Leu Glu Val Gly Thr Gly Thr
    8450                8455                8460

Gly Met Ile Leu Phe Asn Leu Gly Lys Gly Leu Gln Ser Tyr Val
    8465                8470                8475

Gly Leu Glu Pro Ser Thr Ser Ala Ala Ala Phe Val Asn Arg Lys
    8480                8485                8490

Ile Glu Thr Ile Ser Ser Leu Ala Gly Lys Ala Lys Val Glu Ile
    8495                8500                8505

Gly Thr Ala Thr Asp Val Gly Gln Leu Lys Asn Leu Arg Ser Asp
    8510                8515                8520

Leu Val Val Ile Asn Ser Val Ala Gln Tyr Phe Pro Ser Pro Glu
    8525                8530                8535

Tyr Leu Val Glu Ala Val Thr Ala Leu Val His Ile Pro Gly Val
    8540                8545                8550

Lys Arg Leu Phe Phe Gly Asp Met Arg Ser Tyr Ala Met Asn Lys
    8555                8560                8565

Gln Phe Leu Val Ala Arg Ala Leu Arg Thr Leu Gly Ala Lys Ala
    8570                8575                8580

Asn Lys Asp Asp Val Arg Arg Lys Met Val Glu Leu Glu Glu Phe
    8585                8590                8595

Glu Glu Glu Leu Leu Val Asp Pro Ala Phe Phe Thr Gly Leu Ala
    8600                8605                8610

Asn Trp Leu Ser Glu Val Glu His Val Glu Ile Leu Pro Lys Gln
    8615                8620                8625

Met Thr Ser Thr Asn Glu Leu Ser Ser Tyr Arg Tyr Ala Ala Ile
    8630                8635                8640

Val His Leu Arg Leu Pro Gly Gln Glu Ala Gln Pro Val Val Thr
    8645                8650                8655

Val Asn Gln Asp Ala Trp Val Asp Phe Gly Gly Ser Lys Met Asp
    8660                8665                8670

Arg His Ala Leu Leu His His Leu Gln Ser Ser Pro Lys Ala Glu
    8675                8680                8685
```

-continued

| | | | | | | | | | | | |
|---|---|---|---|---|---|---|---|---|---|---|---|
|Thr|Val|Ala|Ile|Ser|Asn|Ile|Pro|Tyr|Ser|Lys|Thr|Ile|Tyr|Glu
| | | |8690| | |8695| | | |8700| | | |

```
Thr Val Ala Ile Ser Asn Ile Pro Tyr Ser Lys Thr Ile Tyr Glu
        8690            8695            8700

Arg His Val Leu Ala Ser Leu Asp Asp Glu Val Glu Asp Ser
8705            8710            8715

Leu Asp Gly Ser Ala Trp Leu Ser Ala Val Arg Ser Thr Ala Glu
8720            8725            8730

Gln Cys Ala Ser Leu Ser Gly Val Asp Leu Val Gln Ile Ala Lys
8735            8740            8745

Glu Ala Gly Phe Arg Val Glu Leu Ser Trp Ala Arg Gln Arg Ser
8750            8755            8760

Gln Lys Gly Gly Ile Asp Ala Val Phe His His Tyr Glu Ser Val
8765            8770            8775

His Asp Gly Ala Arg Val Met Val Lys Phe Pro Thr Asp Asp Gln
8780            8785            8790

Gly Arg Ala Leu Asp Ser Leu Ala Asn Arg Pro Leu Gln Arg Leu
8795            8800            8805

Gln Ser Arg Arg Ile Glu Val Gln Ile Arg Glu Arg Leu Gln Ala
8810            8815            8820

Val Leu Pro Ser Tyr Met Met Pro Val Arg Ile Val Val Leu Asp
8825            8830            8835

Glu Met Pro Met Asn Ala Asn Gly Lys Val Asp Arg Lys Val Leu
8840            8845            8850

Thr Arg Arg Ala Lys Met Ile Ser Arg Val Glu Thr Thr Ala Glu
8855            8860            8865

Arg Val Gly Pro Arg Asn Glu Ile Glu Ala Leu Leu Cys Glu Glu
8870            8875            8880

Phe Ala Glu Val Leu Gly Val Glu Val Gly Ile Asn Asp Asp Phe
8885            8890            8895

Phe Asp Leu Gly Gly His Ser Leu Met Ala Thr Lys Leu Ala Ala
8900            8905            8910

Arg Ser Ser Arg Arg Phe Asp Ala Lys Val Ser Val Lys Asp Val
8915            8920            8925

Phe Asp His Pro Ile Leu Ala Asp Leu Ala Ala Ser Ile Gln Arg
8930            8935            8940

Gly Ser Thr Pro His Asn Pro Ile Leu Ala Thr Gln Tyr Ser Gly
8945            8950            8955

Pro Val Glu Gln Ser Phe Ala Gln Gly Arg Leu Trp Phe Leu Glu
8960            8965            8970

Gln Leu Asn Val Ser Ser Thr Trp Tyr Leu Gln Pro Ile Ala Val
8975            8980            8985

Arg Met Arg Gly Pro Leu Lys Ile Glu Ala Leu Ala Ala Ala Phe
8990            8995            9000

His Ala Leu Glu Glu Arg His Glu Thr Leu Arg Thr Thr Phe Glu
9005            9010            9015

Glu His Asp Gly Ile Gly Met Gln Val Val Gln Pro His Arg Pro
9020            9025            9030

Lys Glu Leu Arg Val Ile Asp Val Gln Ala Glu His Asp Gly Asp
9035            9040            9045

Tyr Thr Gln Ala Leu His Thr Glu Gln Thr Thr Thr Phe Asn Leu
9050            9055            9060

Glu Thr Glu Pro Gly Trp Arg Val Ser Val Phe Arg Leu Asn Glu
9065            9070            9075

Asp Asp Asn Ile Leu Ser Ile Val Met His His Ile Ile Ser Asp
```

-continued

```
            9080                9085                9090
Gly Trp Ser Phe Asp Ile Leu Arg Lys Glu Ile Arg Glu Phe Tyr
            9095                9100               9105
Asn Ala Ala Leu Lys Gly Lys Asp Pro Leu Ala Gln Met Ser Pro
            9110                9115               9120
Leu His Ile Gln Tyr Arg Asp Phe Ser Val Trp Gln Lys Gln Leu
            9125                9130               9135
Asn Gln Ile Thr Glu His Lys Arg Gln Leu Asp Tyr Trp Thr Lys
            9140                9145               9150
Asn Leu Ala Asp Asn Thr Pro Ala Glu Leu Pro Thr Asp Leu Pro
            9155                9160               9165
Arg Pro Ala Val Leu Ser Gly Lys Ala Gly Val Ile Gln Leu Ser
            9170                9175               9180
Ile Thr Gly Pro Val Tyr Asp Arg Leu Arg Ala Phe Cys Arg Val
            9185                9190               9195
His Gln Thr Thr Leu Phe Thr Val Leu Leu Thr Val Phe Arg Ala
            9200                9205               9210
Thr His Tyr Arg Leu Thr Gly Ala Glu Asp Ala Thr Ile Gly Thr
            9215                9220               9225
Pro Ile Ala Asn Arg Asn Arg Pro Glu Leu Glu Asn Leu Ile Gly
            9230                9235               9240
Phe Phe Val Asn Thr Gln Cys Met Arg Ile Thr Val Glu Glu Glu
            9245                9250               9255
Asp Thr Phe Glu Thr Leu Ile His Gln Val Arg Thr Thr Thr Thr
            9260                9265               9270
Ala Ala Phe Ala Asn Gln Asp Val Pro Phe Glu Arg Ile Val Ser
            9275                9280               9285
Ala Leu Leu Pro Gly Ser Arg Asp Thr Ser Arg Asn Pro Leu Ser
            9290                9295               9300
Gln Ile Met Phe Ala Val His Ser Gln Lys Asn Ile Ser Lys Ile
            9305                9310               9315
Glu Leu Asp Gly Leu Glu Ser Glu Ala Ile Ser Arg Ala Thr Ser
            9320                9325               9330
Thr Arg Phe Asp Leu Glu Phe His Leu Phe Gln Glu Glu Lys Gly
            9335                9340               9345
Leu Gly Gly Ile Val Leu Phe Ala Ala Asp Leu Phe Glu Pro Glu
            9350                9355               9360
Thr Ile Asp Ser Leu Val Phe Val Phe Gln Glu Ile Leu Arg Gln
            9365                9370               9375
Ser Leu Glu Thr Pro Lys Thr Pro Ile Ala Val Leu Pro Leu Thr
            9380                9385               9390
Asn Gly Ile Ala Gln Leu Arg Ser Met Cys Val Leu Asp Ile Glu
            9395                9400               9405
Lys Thr Ala Tyr Pro Gln Asp Ser Ser Val Ile Asp Ile Phe Arg
            9410                9415               9420
Gln Gln Val Ala Ala Arg Pro Asp Ala Thr Ala Val Thr Asp Ser
            9425                9430               9435
Thr Ser Gln Leu Thr Tyr Ala Gln Leu Asp Leu His Ser Asp Glu
            9440                9445               9450
Leu Ala Ser Trp Leu Arg Gln Lys Lys Met Ala Pro Glu Thr Leu
            9455                9460               9465
Val Gly Val Leu Ala Pro Arg Ser Cys Gln Thr Ile Val Thr Phe
            9470                9475               9480
```

```
Leu Gly Ile Leu Lys Ala Ser Leu Ala Tyr Leu Pro Leu Asp Val
    9485                9490                9495

Lys Val Pro Val Ala Arg Ile Glu Ala Ile Leu Ser Ser Ile Ser
    9500                9505                9510

Gly Gln Lys Leu Ile Leu Leu Gly Gln Asp Val Pro Val Pro Glu
    9515                9520                9525

Ile Gln Leu Pro Asp Val Asp Val Val Pro Ile Ser Glu Ile Leu
    9530                9535                9540

Gly Arg Ser Val Pro Ser Arg Ala Thr Asp Lys Ser Leu Gly Pro
    9545                9550                9555

Leu Ala Arg Asn Leu Ala Tyr Val Leu Phe Thr Ser Gly Ser Thr
    9560                9565                9570

Gly Lys Pro Lys Gly Val Met Ile Glu His Arg Ser Ile Val Arg
    9575                9580                9585

Leu Val Lys Glu Thr Asn Leu Ile Ser Lys Leu Pro Asn Ala Pro
    9590                9595                9600

Arg Thr Ala His Leu Thr Asn Leu Val Phe Asp Asn Ser Ala Trp
    9605                9610                9615

Glu Ile Tyr Ser Thr Leu Leu Asn Gly Gly Thr Leu Val Cys Ile
    9620                9625                9630

Asp Tyr Ala Thr Val Leu Asp Ser Lys Ala Leu Glu Thr Val Phe
    9635                9640                9645

Lys Glu Gln Arg Ile Gln Thr Ser Leu Met Pro Pro Ala Leu Leu
    9650                9655                9660

Lys Glu Cys Leu Ala Asn Met Pro Thr Met Phe Asp Asp Val Glu
    9665                9670                9675

Val Leu Tyr Ala Leu Gly Asp Arg Phe Asp Lys Gln Asp Ala Met
    9680                9685                9690

Lys Ala Arg Ser Ile Val Lys Thr Ala Val Tyr Asn Ala Tyr Gly
    9695                9700                9705

Pro Thr Glu Asn Thr Val Ile Ser Thr Ile Tyr Glu Ile Ala Lys
    9710                9715                9720

Asp Asp Ser Phe Val Asn Gly Val Pro Ile Gly Arg Ser Ile Ser
    9725                9730                9735

Asn Ser Gly Ala Phe Ile Met Asp Ser Arg Gln Gln Leu Val Pro
    9740                9745                9750

Val Gly Val Leu Gly Glu Leu Val Val Ser Gly Asp Gly Leu Ala
    9755                9760                9765

Arg Gly Tyr Thr Asp Pro Thr Leu Asp Val Asn Arg Phe Val Glu
    9770                9775                9780

Val Thr Val Asp Gly Gln His Val Arg Val Tyr Arg Thr Gly Asp
    9785                9790                9795

Arg Val Arg Phe Arg Pro Lys Asp Gly Gln Ile Glu Phe Phe Ser
    9800                9805                9810

Arg Met Asp Gln Gln Val Lys Ile Arg Gly His Arg Ile Glu Pro
    9815                9820                9825

Ala Glu Val Glu His Val Ile Leu Thr Asn Lys Ile Ile Arg Asp
    9830                9835                9840

Ala Ala Val Ala Ile Arg Arg Pro Glu Gly Gln Glu Pro Glu Met
    9845                9850                9855

Val Ala Phe Val Thr Thr His Glu Asn Thr Ser Ile Glu Lys Gln
    9860                9865                9870
```

```
Ser Val Glu Glu Phe Ala Ala Arg Ile Glu Asn Glu Val Arg Arg
    9875                9880                9885

Trp Ile Lys Thr Leu Leu Pro Leu Tyr Met Val Pro Thr Gln Ile
    9890                9895                9900

Val Val Leu Asp Arg Met Pro Val Asn Ala Asn Gly Lys Val Asp
    9905                9910                9915

Arg Lys Glu Leu Ala Gln Arg Ala Gln Thr Leu Gln Lys Ser Glu
    9920                9925                9930

Ala Gly Ser Leu Pro Ser Val Arg Val Pro Pro Thr Asn Asp Met
    9935                9940                9945

Glu Arg Ile Leu Cys Glu Glu Phe Ala Asp Val Leu Gly Val Glu
    9950                9955                9960

Val Gly Ile Thr Asp Asn Phe Phe Asp Phe Gly Gly His Ser Leu
    9965                9970                9975

Met Ala Thr Lys Leu Ala Ala Arg Ile Ser Arg Arg Val Asn Ala
    9980                9985                9990

Arg Val Ser Val Lys Ser Val Phe Asp His Pro Val Leu Val Asp
    9995                10000               10005

Leu Ala Ser Thr Ile Lys Gln Asp Ser Ile Met His Lys Pro Ile
    10010               10015               10020

Pro Gln Thr Ala Tyr Thr Gly Pro Val Glu Gln Ser Phe Ala Gln
    10025               10030               10035

Gly Arg Leu Trp Phe Leu Asp Gln Leu Asn Phe Gly Ala Ser Trp
    10040               10045               10050

Tyr Leu Met Pro Leu Ala Leu Arg Leu Gln Gly Ser Leu His Val
    10055               10060               10065

Lys Ser Leu Thr Thr Ala Leu Phe Ala Leu Glu Gln Arg His Glu
    10070               10075               10080

Thr Leu Arg Thr Thr Phe Glu Glu Gln Asp Gly Val Gly Ile Gln
    10085               10090               10095

Ile Val His Pro Ala Asn Lys Lys Asp Leu Arg Ile Leu Asp Val
    10100               10105               10110

Ser Lys Glu Gln Asn Ser Asp Tyr Ala Lys Val Leu His Lys Glu
    10115               10120               10125

Arg Thr Ile Pro Ile Asp Leu Thr Ser Glu Pro Gly Trp Arg Val
    10130               10135               10140

Ser Leu Ile Arg Leu Gly Glu Asp Asp His Ile Leu Ser Ile Val
    10145               10150               10155

Met His His Ile Ile Ser Asp Gly Trp Ser Val Asp Val Leu Arg
    10160               10165               10170

Gln Glu Leu Lys Gln Phe Tyr Thr Ala Ala Leu Lys Gly Gln Asp
    10175               10180               10185

Pro Leu Ala Gln Ile Asp Ala Leu Pro Ile Gln Tyr Arg Asp Phe
    10190               10195               10200

Ser Leu Trp Gln Lys Leu Pro Asp Gln Val Ala Glu His Gln Arg
    10205               10210               10215

Gln Leu Glu Tyr Trp Ala Glu Gln Leu Ala Asp Asn Thr Pro Ala
    10220               10225               10230

Glu Leu Leu Thr Asp Leu Pro Arg Pro Asp Val Leu Ser Gly Lys
    10235               10240               10245

Ala Gly Ala Val Gln Leu Thr Ile Asp Gly Pro Val Phe Asp Gln
    10250               10255               10260

Leu Gln Ala Phe Cys Arg Ala His Gln Thr Thr Met Phe Thr Val
```

```
            10265             10270             10275

Leu Leu Ala Val Phe Arg Thr  Thr His Tyr Arg Leu  Thr Gly Ala
    10280             10285             10290

Thr Asp Ala Thr Ile Gly Thr  Pro Ile Ala Asn Arg  Asn Arg Pro
    10295             10300             10305

Glu Leu Glu Arg Leu Val Gly  Phe Phe Val Asn Thr  Gln Cys Ile
    10310             10315             10320

Arg Ile Thr Val Asp Val Glu  Asp Thr Phe Glu Ala  Leu Val Arg
    10325             10330             10335

Gln Val His Ser Thr Ser Thr  Thr Ala Phe Ala Asn  Gln Asp Val
    10340             10345             10350

Pro Phe Glu Arg Ile Val Ser  Thr Ile Leu Pro Gly  Ser Arg Asp
    10355             10360             10365

Ala Ser Arg Asn Pro Leu Ala  Gln Leu Met Phe Ala  Val His Ser
    10370             10375             10380

Gln Arg Asp Ile Ser Lys Phe  Gln Leu Glu Gly Leu  Asp Thr Lys
    10385             10390             10395

Pro Ile Pro Thr Ala Ala Ser  Thr Arg Phe Asp Ile  Glu Phe His
    10400             10405             10410

Met Phe Gln Gln Ala Glu Arg  Leu Ser Gly Arg Val  Leu Phe Ala
    10415             10420             10425

Glu Asp Leu Phe Glu Leu Glu  Thr Ile Gln Gly Met  Val Val Ile
    10430             10435             10440

Phe Lys Glu Ile Leu Arg Arg  Gly Leu Glu Thr Pro  Gln Thr Pro
    10445             10450             10455

Leu Ala Val Leu Pro Leu Thr  Asp Gly Leu Ala His  Leu Arg Ser
    10460             10465             10470

Gln Gly Leu Leu Glu Ile Glu  Arg Pro Glu Tyr Pro  Arg Asp Ser
    10475             10480             10485

Ser Met Ile Asp Val Phe Arg  Ala Gln Val Ala Ala  Cys Pro Asp
    10490             10495             10500

Ala Ile Ala Val Lys Asp Ser  Thr Ser Gln Leu Thr  Tyr Ser Gln
    10505             10510             10515

Leu Asp Asp Gln Ser Asp Lys  Ile Thr Ala Trp Leu  Leu Gln Arg
    10520             10525             10530

Lys Ile Pro Ala Glu Ser Leu  Val Ala Val Tyr Ala  Pro Arg Thr
    10535             10540             10545

Cys Gln Thr Ile Ile Thr Phe  Phe Gly Ile Leu Lys  Ala Asn Leu
    10550             10555             10560

Ala Tyr Leu Pro Leu Asp Ile  Asn Val Pro Ala Ala  Arg Ile Glu
    10565             10570             10575

Ala Ile Leu Ser Thr Ile Ser  Gly His Lys Leu Val  Leu Leu Gly
    10580             10585             10590

Ser Gln Val Ser Ala Pro Ala  Val Gln Leu Lys Asp  Val Glu Tyr
    10595             10600             10605

Val Trp Ile Asp Glu Ala Met  Ala Glu Thr Val Arg  Thr Cys Thr
    10610             10615             10620

Ser Pro Glu Pro Ser Ala Thr  Ser Leu Ala Tyr Val  Ile Phe Thr
    10625             10630             10635

Ser Gly Ser Thr Gly Leu Pro  Lys Gly Val Lys Val  Glu His Arg
    10640             10645             10650

Gly Val Val Arg Leu Val Lys  Gln Ser Asn Val Val  Ala Lys Met
    10655             10660             10665
```

-continued

| | | | | | | | | | | |
|---|---|---|---|---|---|---|---|---|---|---|
| Pro | Gln 10670 | Ala | Ala | Arg 10675 | Val | Ala | His | Leu | Ser 10680 | Asn | Ile | Ala | Phe | Asp |
| Ala | Ala 10685 | Thr | Trp | Glu 10690 | Ile | Tyr | Ala | Ala | Leu 10695 | Leu | Asn | Gly | Gly | Ser |
| Leu | Ile 10700 | Cys | Ile | Asp 10705 | Tyr | Phe | Thr | Thr | Leu 10710 | Asp | Ser | Lys | Glu | Leu |
| Glu | Ala 10715 | Val | Phe | Ala 10720 | Arg | Glu | Lys | Ile | Gln 10725 | Ala | Ala | Met | Leu | Pro |
| Pro | Ala 10730 | Leu | Leu | Lys 10735 | Gln | Cys | Leu | Val | Asn 10740 | Ile | Pro | Ala | Thr | Ile |
| Ser | Ala 10745 | Leu | Asp | Val 10750 | Val | Leu | Ala | Ala | Gly 10755 | Asp | Arg | Phe | Asp | Arg |
| Arg | Asp 10760 | Ala | Ala | Ala 10765 | Thr | Gln | Ala | Leu | Val 10770 | Gly | Gly | Cys | Val | Tyr |
| Asn | Ala 10775 | Tyr | Gly | Pro 10780 | Thr | Glu | Asn | Thr | Thr 10785 | Leu | Ser | Thr | Ile | Tyr |
| Asn | Val 10790 | Val | Lys | Gly 10795 | Asp | Ala | Asn | Val | Asn 10800 | Gly | Val | Pro | Ile | Gly |
| Arg | Pro 10805 | Val | Ser | Asn 10810 | Ser | Gly | Ala | Tyr | Ile 10815 | Met | Asp | Pro | Asn | Gln |
| Gln | Leu 10820 | Val | Pro | Lys 10825 | Gly | Val | Met | Gly | Glu 10830 | Leu | Ile | Val | Val | Gly |
| Asp | Gly 10835 | Val | Ala | Arg 10840 | Gly | Tyr | Thr | Asp | Pro 10845 | Ala | Leu | Asp | Val | Asn |
| Arg | Phe 10850 | Ile | Glu | Ile 10855 | Ala | Ile | Asp | Gly | Asp 10860 | Gln | Ala | Val | Arg | Ala |
| Tyr | Arg 10865 | Thr | Gly | Asp 10870 | Arg | Ala | Arg | Tyr | Arg 10875 | Pro | Lys | Asp | Gly | Gln |
| Ile | Glu 10880 | Phe | Phe | Gly 10885 | Arg | Met | Asp | Gln | Gln 10890 | Ile | Lys | Ile | Arg | Gly |
| His | Arg 10895 | Ile | Glu | Pro 10900 | Ala | Glu | Val | Glu | His 10905 | Ala | Val | Leu | Asp | Asn |
| Ser | Met 10910 | Val | Gln | Asp 10915 | Ala | Ala | Val | Ile | Thr 10920 | Arg | Lys | Gln | Asp | Gln |
| Glu | Leu 10925 | Glu | Met | Ile 10930 | Ala | Phe | Val | Thr | Thr 10935 | Arg | Ser | Asp | Lys | Glu |
| Ile | Asp 10940 | Asn | Asp | Glu 10945 | Ala | Ser | Asn | Gln | Val 10950 | Glu | Asp | Trp | Gly | Asn |
| Gln | Phe 10955 | Glu | Ser | Asn 10960 | Ile | Tyr | Ala | Glu | Ile 10965 | Glu | Glu | Ile | Asp | Ser |
| Ser | Ala 10970 | Ile | Gly | Lys 10975 | Asp | Phe | Met | Gly | Trp 10980 | Thr | Ser | Met | Tyr | Asp |
| Gly | Ser 10985 | Ala | Ile | Asp 10990 | Lys | Asp | Glu | Met | Gln 10995 | Glu | Trp | Leu | Asp | Asp |
| Thr | Met 11000 | Ser | Thr | Leu 11005 | Leu | Asp | Gly | Arg | Gln 11010 | Pro | Gly | His | Val | Leu |
| Glu | Ile 11015 | Gly | Thr | Gly 11020 | Thr | Gly | Met | Ile | Leu 11025 | Phe | Asn | Leu | Ala | Glu |
| Arg | Met 11030 | Gly | Leu | Lys 11035 | Ser | Tyr | Val | Gly | Leu 11040 | Asp | Pro | Ser | Glu | Lys |
| Ala | Thr 11045 | Ser | Phe | Val 11050 | Lys | Gln | Ala | Ile | Lys 11055 | Ser | Arg | Pro | Ser | Leu |

```
Ala Gly Lys Ala Glu Val His Val Gly Thr Ala Thr Asp Val Ala
    11060               11065               11070

Arg Met Arg Asp Leu His Pro Glu Val Val Ile Asn Ser Val
    11075               11080               11085

Ala Gln Tyr Phe Pro Ser Pro Glu Tyr Leu Ala Asp Val Val Gly
    11090               11095               11100

Ala Leu Val Arg Ile Pro Gly Val Lys Arg Leu Phe Phe Gly Asp
    11105               11110               11115

Ile Arg Ser Tyr Ala Thr Asn Asn His Phe Leu Ala Ala Arg Ala
    11120               11125               11130

Leu His Lys Leu Gly Glu Lys Ala Thr Arg Asp Thr Val Arg Ser
    11135               11140               11145

Lys Met Ala Glu Leu Glu Gly Tyr Glu Glu Glu Leu Leu Val Asp
    11150               11155               11160

Pro Thr Phe Phe Thr Ser Leu Thr Ala Lys Leu His Gly Gln Val
    11165               11170               11175

Glu His Val Glu Ile Leu Pro Lys Arg Met Gln Ala Thr Asn Glu
    11180               11185               11190

Leu Ser Ala Tyr Arg Tyr Ala Ala Ile Val Tyr Ile Arg Asp Pro
    11195               11200               11205

Lys Arg Ala Gln Thr Val Gln Thr Val Lys Ser Asp Ala Trp Val
    11210               11215               11220

Asp Phe Ser Thr Ser Gln Met Asp Arg Ser Val Leu Val Ser Leu
    11225               11230               11235

Leu Gln Ser Ser Asp Ala Glu Ala Ile Ala Val Ser Asn Ile Pro
    11240               11245               11250

Tyr Ser Lys Thr Ile Val Ala Arg His Ile Val Glu Ser Leu Ser
    11255               11260               11265

Ala Glu Asp Ser Gln Glu Met Leu Asp Gly Pro Ala Trp Ile Ser
    11270               11275               11280

Ala Val Arg Ser Ser Ala Glu Gln Cys Ala Ser Leu Ser Ala Ile
    11285               11290               11295

Asp Leu Val Gln Val Ala Lys Glu Asn Gly Phe Arg Val Glu Leu
    11300               11305               11310

Ser Cys Ala Arg Gln Arg Ser His Asn Gly Ala Ile Asp Ala Val
    11315               11320               11325

Phe His His Tyr Lys Pro Ala Gln Glu Gly Ser Arg Val Leu Leu
    11330               11335               11340

Gln Phe Pro Thr Asp Asn His Ile Arg Ala Gly Ser Leu Thr Asn
    11345               11350               11355

Arg Pro Leu Gln Arg Leu Glu Ser Arg Arg Val Glu Thr Lys Leu
    11360               11365               11370

Lys Glu His Leu Phe Ser Val Leu Pro Ser Tyr Met Ile Pro Ser
    11375               11380               11385

His Ile Val Met Val Asp Gln Met Pro Leu Asn Ala Asn Gly Lys
    11390               11395               11400

Val Asp Arg Lys Ala Leu Ala Gln Arg Ala Glu Ala Val Leu Lys
    11405               11410               11415

Ile Glu Lys Pro Ala Ser Glu Arg Val Ser Ala Arg Asn Glu Val
    11420               11425               11430

Glu Ala Val Leu Cys Glu Glu Phe Thr Asp Val Leu Gly Val Glu
    11435               11440               11445

Val Gly Ile Thr Asp Asn Phe Phe Asp Leu Gly Gly His Ser Leu
```

```
            11450            11455              11460

Met Ala Thr Lys Leu Ala Ala Arg Ile Ser Lys His Leu Asp Ala
            11465            11470              11475

Arg Val Ser Val Lys Asp Val Phe Asp Tyr Pro Val Val Ala Asp
            11480            11485              11490

Leu Ala Ala Ser Ile Glu Arg Asn Ser Ile Pro His Asn Pro Ile
            11495            11500              11505

Pro Ser Thr Asn Tyr Ser Gly Pro Val Glu Gln Ser Phe Ala Gln
            11510            11515              11520

Gly Arg Leu Trp Phe Leu Asp Gln Leu Asn Met Gly Val Ser Glu
            11525            11530              11535

Leu Tyr Leu Met Pro Leu Ala Leu Arg Leu Arg Gly Pro Leu Arg
            11540            11545              11550

Val Asp Ala Phe Ala Ala Ala Val Ser Ala Leu Glu Ala Arg His
            11555            11560              11565

Glu Thr Leu Arg Thr Thr Phe Met Asp His Asp Gly Val Gly Met
            11570            11575              11580

Gln Val Ile Leu Pro Ser Asn Ser Lys Lys Leu Arg Val Ile Asp
            11585            11590              11595

Ala Ser Glu Asn Asp Tyr Ile Asp Ile Leu Arg Gln Glu Arg Thr
            11600            11605              11610

Ala Pro Phe Asn Leu Thr Thr Glu Pro Gly Phe Arg Ile Ala Leu
            11615            11620              11625

Leu Gln Leu Gly Gln Thr Asp Phe Ile Leu Ser Ile Val Met His
            11630            11635              11640

His Ile Ile Tyr Asp Gly Trp Ser Ile Asp Val Leu Cys Arg Glu
            11645            11650              11655

Leu Gly Arg Phe Tyr Ser Ala Ala Leu Gln Gly Gln Asp Pro Leu
            11660            11665              11670

Ala Gln Val Ser Pro Leu Pro Ile Gln Tyr Arg Asp Phe Ser Ile
            11675            11680              11685

Trp Gln Lys Arg Pro Glu Gln Val Ala Glu His Glu Arg Gln Leu
            11690            11695              11700

Gln Tyr Trp Thr Glu Gln Leu Ala Asp Ser Ser Pro Ala Glu Leu
            11705            11710              11715

Leu Thr Asp Leu Pro Arg Pro Leu Val Pro Thr Gly Lys Ala Gly
            11720            11725              11730

Ile Val Gln Leu Thr Ile Glu Gly Ala Val Tyr Glu Arg Leu Arg
            11735            11740              11745

Ala Phe Cys Arg Val His Gln Thr Thr Ser Phe Ala Val Leu Leu
            11750            11755              11760

Ala Ala Phe Arg Ala Thr His Tyr Arg Leu Thr Gly Ala Glu Asp
            11765            11770              11775

Ala Thr Ile Gly Ser Pro Ile Ala Asn Arg Asn Arg Pro Glu Leu
            11780            11785              11790

Glu Ser Leu Ile Gly Phe Phe Val Asn Thr Gln Cys Ile Arg Val
            11795            11800              11805

Thr Ile Arg Glu Asp Asp Thr Phe Asp Lys Leu Val Gln Gln Val
            11810            11815              11820

Arg Ala Thr Thr Thr Ala Ala Gln Val Asn Gln Asp Val Pro Phe
            11825            11830              11835

Glu Arg Ile Val Ser Ala Leu Met Pro Gly Ser Arg Asp Thr Ser
            11840            11845              11850
```

```
Arg  Asn  Pro  Leu  Val  Gln  Leu  Ser  Phe  Ala  Leu  His  Ser  Gln  His
     11855          11860               11865

Asp  Leu  Gly  Arg  Ile  Asp  Leu  Gln  Asp  Leu  Thr  Gly  Glu  Ala  Leu
     11870          11875               11880

Pro  Thr  Pro  Val  Phe  Thr  Arg  Leu  Asp  Val  Glu  Phe  His  Leu  Phe
     11885          11890               11895

Gln  Gln  Ala  Glu  Lys  Phe  Gly  Gly  Ser  Val  Leu  Phe  Ala  Thr  Asp
     11900          11905               11910

Leu  Phe  Glu  Pro  Glu  Thr  Ile  Gln  Gly  Leu  Val  Ser  Val  Phe  Gln
     11915          11920               11925

Glu  Val  Leu  Arg  Arg  Gly  Leu  Glu  Gln  Pro  Gln  Thr  Pro  Ile  Ala
     11930          11935               11940

Val  Leu  Pro  Leu  Asp  Asn  Ala  Ser  Glu  Asp  Leu  Arg  Ser  Met  Gly
     11945          11950               11955

Leu  Leu  Gln  Met  Glu  Arg  Thr  Asn  Tyr  Pro  Arg  Asp  Ser  Ser  Val
     11960          11965               11970

Val  Asp  Val  Phe  Arg  Asp  Gln  Val  Ala  Ala  Asn  Pro  Arg  Ala  Ile
     11975          11980               11985

Ala  Val  Lys  Asp  Ser  Val  Leu  Glu  Leu  Thr  Tyr  Ala  Gln  Leu  Asp
     11990          11995               12000

Glu  Lys  Ser  Asp  Gln  Leu  Ala  Ala  Trp  Leu  Cys  Gln  His  Asn  Ile
     12005          12010               12015

Pro  Ala  Glu  Thr  Ile  Val  Gly  Val  Leu  Ala  Pro  Arg  Ser  Cys  Glu
     12020          12025               12030

Thr  Ile  Ile  Ala  Phe  Leu  Gly  Ile  Leu  Lys  Ala  Asn  Leu  Ala  Tyr
     12035          12040               12045

Leu  Pro  Leu  Asp  Asp  Asn  Val  Pro  Ala  Ala  Arg  Ile  Glu  Thr  Ile
     12050          12055               12060

Leu  Ser  Ala  Val  Pro  Gly  His  Thr  Leu  Val  Leu  Leu  Gly  Ser  His
     12065          12070               12075

Val  Ala  Ala  Pro  Ser  Ile  Gly  Leu  Ala  Asp  Ala  Glu  Phe  Val  Asn
     12080          12085               12090

Ile  Asn  His  Thr  Leu  Gly  His  Ser  Leu  Gln  Leu  Asn  Ser  Thr  Cys
     12095          12100               12105

Ala  Lys  Leu  Gln  Pro  Ser  Ala  Thr  Ser  Leu  Ala  Tyr  Val  Ile  Phe
     12110          12115               12120

Thr  Ser  Gly  Ser  Thr  Gly  Lys  Pro  Lys  Gly  Val  Met  Ile  Glu  His
     12125          12130               12135

Arg  Ser  Ile  Val  Arg  Leu  Val  Lys  Asn  Ser  Asn  Thr  Leu  Ala  Lys
     12140          12145               12150

Leu  Pro  Arg  Ala  Ala  Arg  Val  Ala  His  Gln  Phe  Asn  Leu  Ala  Phe
     12155          12160               12165

Asp  Ala  Ala  Asn  Tyr  Glu  Ile  Tyr  Gly  Thr  Leu  Leu  Asn  Gly  Gly
     12170          12175               12180

Ala  Leu  Ile  Cys  Val  Asp  Tyr  Ser  Thr  Leu  Leu  Asp  Ile  Asp  Ala
     12185          12190               12195

Leu  Val  Ala  Met  Phe  Lys  Arg  Glu  Lys  Ile  Thr  Ala  Ser  Ser  Leu
     12200          12205               12210

Ser  Pro  Gly  Leu  Leu  Lys  Gln  Cys  Val  Asn  Ser  Ala  Pro  Glu  Met
     12215          12220               12225

Leu  Lys  Ala  Leu  Gln  Val  Ile  Tyr  Thr  Gly  Gly  Asp  Arg  Leu  Asp
     12230          12235               12240
```

-continued

| | | | | | | | | | | |
|---|---|---|---|---|---|---|---|---|---|---|
|Gly|Arg|Asp|Ala|Ile|Glu|Leu|Gln|Ala|Leu|Val|Pro|Gly|Gly|Val|
| |12245| | | |12250| | | |12255| | | | | |
|Tyr|Asn|Met|Tyr|Gly|Pro|Thr|Glu|Asn|Thr|Val|Ile|Ser|Thr|Leu|
| |12260| | | |12265| | | |12270| | | | | |
|Tyr|Asn|Leu|Gly|Asp|Lys|His|Ser|Tyr|Val|Asn|Gly|Val|Pro|Ile|
| |12275| | | |12280| | | |12285| | | | | |
|Gly|Thr|Thr|Val|Ser|Asn|Ser|Gly|Ala|Tyr|Val|Met|Asp|Ala|Leu|
| |12290| | | |12295| | | |12300| | | | | |
|Gln|Gln|Leu|Val|Pro|Val|Gly|Val|Met|Gly|Glu|Leu|Val|Val|Thr|
| |12305| | | |12310| | | |12315| | | | | |
|Gly|Asp|Gly|Leu|Ala|Arg|Gly|Tyr|Thr|Asp|Pro|Glu|Leu|Asp|Arg|
| |12320| | | |12325| | | |12330| | | | | |
|Asn|Arg|Phe|Ile|Lys|Val|Asn|Ile|Asp|Gly|Gln|Val|Val|Arg|Ala|
| |12335| | | |12340| | | |12345| | | | | |
|Tyr|Arg|Thr|Gly|Asp|Arg|Val|Arg|Tyr|Arg|Arg|Ile|Asp|Gly|Gln|
| |12350| | | |12355| | | |12360| | | | | |
|Leu|Glu|Phe|Phe|Gly|Arg|Met|Asp|Gln|Gln|Ile|Lys|Ile|Arg|Gly|
| |12365| | | |12370| | | |12375| | | | | |
|Phe|Arg|Ile|Glu|Thr|Ala|Glu|Val|Glu|Asn|Ala|Met|Leu|Ser|His|
| |12380| | | |12385| | | |12390| | | | | |
|Ser|Ala|Val|Arg|Asn|Ala|Ala|Val|Val|Val|Pro|Thr|Gln|Asp|Ile|
| |12395| | | |12400| | | |12405| | | | | |
|Gln|Glu|Lys|Gly|Met|Ile|Gly|Phe|Val|Val|Ile|Glu|Asn|Asn|Thr|
| |12410| | | |12415| | | |12420| | | | | |
|Pro|Lys|Asn|Glu|Glu|Ser|Lys|Glu|Glu|His|Leu|Leu|Gln|Thr|Glu|
| |12425| | | |12430| | | |12435| | | | | |
|Leu|Ala|Ile|Leu|Asn|Arg|Met|Lys|Ser|Ile|Leu|Pro|Pro|Tyr|Met|
| |12440| | | |12445| | | |12450| | | | | |
|Leu|Pro|Ser|Arg|Ile|Ile|Ile|Leu|Asp|Gln|Met|Pro|Ser|Asn|Phe|
| |12455| | | |12460| | | |12465| | | | | |
|Asn|Gly|Lys|Val|Asp|Arg|Lys|Glu|Leu|Asp|Arg|Met|Ala|Gln|Ser|
| |12470| | | |12475| | | |12480| | | | | |
|Val|Pro|Arg|Gln|Lys|Thr|Thr|Ala|Gly|Arg|Ile|Val|Pro|Arg|Asn|
| |12485| | | |12490| | | |12495| | | | | |
|Glu|Leu|Glu|Ala|Ser|Leu|Cys|Lys|Glu|Phe|Ala|Glu|Val|Leu|Gly|
| |12500| | | |12505| | | |12510| | | | | |
|Val|Glu|Val|Gly|Ile|Thr|Asp|Asn|Phe|Phe|Asp|Leu|Gly|Gly|His|
| |12515| | | |12520| | | |12525| | | | | |
|Ser|Leu|Leu|Ala|Thr|Lys|Leu|Ala|Ala|Arg|Ile|Ser|Arg|Arg|Leu|
| |12530| | | |12535| | | |12540| | | | | |
|Asp|Thr|Arg|Val|Ser|Val|Lys|Asp|Val|Phe|Asp|Gln|Pro|Val|Pro|
| |12545| | | |12550| | | |12555| | | | | |
|Ala|Asp|Leu|Ala|Leu|Lys|Val|Ser|Ser|Tyr|Ile|Ser|Gln|Gly|His|
| |12560| | | |12565| | | |12570| | | | | |
|Ala|Met|Asp|Asn|Gly|Thr|Leu|Ser|Thr|Thr|Asn|Ser|Ile|Pro|Phe|
| |12575| | | |12580| | | |12585| | | | | |
|Gln|Leu|Leu|His|Phe|Glu|Asp|Ser|Gln|Lys|Phe|Ile|Asp|Arg|Asp|
| |12590| | | |12595| | | |12600| | | | | |
|Ile|Val|Pro|Gln|Leu|Ala|His|Gln|Ser|Ala|Lys|Ile|Val|Asp|Val|
| |12605| | | |12610| | | |12615| | | | | |
|Tyr|Pro|Val|Thr|Trp|Ile|Gln|Lys|His|Phe|Leu|Val|Asp|Pro|Ala|
| |12620| | | |12625| | | |12630| | | | | |
|Thr|Gly|Leu|Pro|Arg|Thr|Pro|Ser|Leu|Phe|Phe|Val|Asp|Phe|Pro|

-continued

```
              12635                   12640                   12645
Ala  Asn  Ala  Asp  Cys  Asp  Lys  Ile  Cys  Asn  Ala  Ser  Arg  Ser  Leu
              12650                   12655                   12660
Ile  Gln  Leu  Phe  Asp  Ile  Phe  Arg  Thr  Val  Phe  Val  Gln  Ala  Ala
              12665                   12670                   12675
Gly  Asn  Phe  Tyr  Gln  Val  Val  Leu  Glu  Glu  Leu  Asp  Ile  Pro  Ile
              12680                   12685                   12690
Ser  Val  Ile  Glu  Thr  Glu  Asp  Ile  Ser  Thr  Ala  Thr  Arg  Val  Leu
              12695                   12700                   12705
Lys  Glu  Gln  Asp  Gln  Gln  Asn  Pro  Leu  Gln  Phe  Gly  Gln  Gly  Phe
              12710                   12715                   12720
Leu  Arg  Phe  Ala  Val  Val  Lys  Thr  Arg  Ser  Ala  Val  Arg  Leu  Val
              12725                   12730                   12735
Leu  Arg  Ile  Ser  His  Cys  Leu  Tyr  Asp  Gly  Leu  Ser  Phe  Glu  His
              12740                   12745                   12750
Val  Val  Gln  Ser  Leu  His  Ala  Leu  Tyr  Asn  Gly  Asp  Arg  Ile  Pro
              12755                   12760                   12765
Thr  Gln  Pro  Lys  Phe  Val  Gln  Tyr  Val  Gln  His  Leu  Thr  Asp  Ser
              12770                   12775                   12780
Arg  Lys  Glu  Gly  Tyr  Asp  Phe  Trp  Leu  Ser  Val  Leu  Glu  Glu  Ser
              12785                   12790                   12795
Ser  Met  Thr  Val  Val  Glu  Thr  Gly  Arg  Arg  Ala  Gln  Gln  Leu  Ser
              12800                   12805                   12810
Ser  Pro  Glu  Gly  Ala  Trp  Phe  Val  Glu  Lys  Ile  Ile  Lys  Ala  Val
              12815                   12820                   12825
Ile  Pro  Ala  Asn  Ser  Asp  Gly  Ile  Thr  Gln  Ala  Thr  Val  Phe  Thr
              12830                   12835                   12840
Thr  Ala  Ser  Thr  Ile  Leu  Leu  Ala  Arg  Met  Thr  Gly  Ser  Ser  Asp
              12845                   12850                   12855
Ile  Thr  Phe  Ser  Arg  Leu  Val  Ser  Gly  Arg  Gln  Ser  Leu  Pro  Ile
              12860                   12865                   12870
Asn  Asp  Gln  His  Ile  Val  Gly  Pro  Cys  Thr  Asn  Ile  Val  Pro  Val
              12875                   12880                   12885
Arg  Ile  Arg  Met  Thr  Asp  Gly  Thr  Asn  Ala  Arg  Glu  Leu  Leu  Gly
              12890                   12895                   12900
Met  Val  Gln  Asp  Gln  Tyr  Ile  Asp  Ser  Leu  Pro  Phe  Glu  Thr  Leu
              12905                   12910                   12915
Gly  Phe  Asp  Asp  Ile  Lys  Glu  Asn  Cys  Thr  Lys  Trp  Pro  Ala  Ser
              12920                   12925                   12930
Thr  Thr  Asn  Tyr  Gly  Cys  Cys  Ser  Thr  Phe  Gln  Asn  Phe  Glu  Met
              12935                   12940                   12945
Gln  Pro  Gln  Ser  Gln  Val  Gln  Asp  Glu  Arg  Val  Arg  Leu  Ala  Gly
              12950                   12955                   12960
Leu  Thr  Asn  Phe  Lys  Asp  Ala  Glu  Leu  Leu  Asn  Gly  Ala  Thr  Ala
              12965                   12970                   12975
Thr  Asn  Lys  Arg  Val  Leu  Asp  Asp  Val  Pro  Met  His  Glu  Ile  Asp
              12980                   12985                   12990
Met  Ile  Gly  Ile  Pro  Glu  Pro  Asp  Gly  Leu  His  Val  Arg  Val  Val
              12995                   13000                   13005
Leu  Thr  Ala  Ser  Arg  Gln  Ile  Phe  Glu  Glu  Glu  Val  Val  Asp  Arg
              13010                   13015                   13020
Met  His  Glu  Glu  Phe  Cys  Asp  Ile  Ile  Leu  Gly  Leu  Asn  Lys  Ile
              13025                   13030                   13035
```

```
Leu Gln  Lys
    130 40

<210> SEQ ID NO 38
<211> LENGTH: 1197
<212> TYPE: DNA
<213> ORGANISM: Curvularia clavata
<220> FEATURE:
<221> NAME/KEY: CDS
<222> LOCATION: (1)..(1197)

<400> SEQUENCE: 38 atg acc ttt gtc gag act gta gcc gtc ccg gac aat gag gag cgt cct      48
Met Thr Phe Val Glu Thr Val Ala Val Pro Asp Asn Glu Glu Arg Pro
1               5                  10                  15 tcg gct gga cac aat cgt cct gta gcc gac agc acc aag tgt ccc aac      96
Ser Ala Gly His Asn Arg Pro Val Ala Asp Ser Thr Lys Cys Pro Asn
            20                  25                  30 gcg agg gag atg aag gtt cag aat cgt gtc gcc caa agg aca cat cat     144
Ala Arg Glu Met Lys Val Gln Asn Arg Val Ala Gln Arg Thr His His
        35                  40                  45 cgc cgt tta aaa aca aag ctg gaa gtg cta cgg gaa aga ttg aaa gag     192
Arg Arg Leu Lys Thr Lys Leu Glu Val Leu Arg Glu Arg Leu Lys Glu
    50                  55                  60 cct gag aag caa gtt ggg gaa cct gcc agg gtc cag aca tcc acc tcc     240
Pro Glu Lys Gln Val Gly Glu Pro Ala Arg Val Gln Thr Ser Thr Ser
65                  70                  75                  80 acg ctg gtg tcg gat gcg gca acc agc ttg gca gat tcg atg tgc ttg     288
Thr Leu Val Ser Asp Ala Ala Thr Ser Leu Ala Asp Ser Met Cys Leu
                85                  90                  95 gtg cca gca gtg caa aat gac cag gcc atg gcg ttt gat ttc ctg atg     336
Val Pro Ala Val Gln Asn Asp Gln Ala Met Ala Phe Asp Phe Leu Met
            100                 105                 110 acg cca tca cct tct gtt ggt aat gat tgt cct tca aat gac ctg gaa     384
Thr Pro Ser Pro Ser Val Gly Asn Asp Cys Pro Ser Asn Asp Leu Glu
        115                 120                 125 acc atg cgc caa gct gcg tct gtt cat tcc aac acc tta ggc ggg gcc     432
Thr Met Arg Gln Ala Ala Ser Val His Ser Asn Thr Leu Gly Gly Ala
    130                 135                 140 ttc ccg cta aac agg tcg ccc tgt act gag aac atg acg ccc gaa tcg     480
Phe Pro Leu Asn Arg Ser Pro Cys Thr Glu Asn Met Thr Pro Glu Ser
145                 150                 155                 160 caa gtt agt tta tct acc gca cca tta tgt ttt act tct gtc gtc ccg     528
Gln Val Ser Leu Ser Thr Ala Pro Leu Cys Phe Thr Ser Val Val Pro
                165                 170                 175 gcg gag ttg gac atg gac gct ttc tgc acg ctt gac agc agt gat tgg     576
Ala Glu Leu Asp Met Asp Ala Phe Cys Thr Leu Asp Ser Ser Asp Trp
            180                 185                 190 tcg cgg ccg aat gaa gaa tct ctc cta cgt ttg gcc aat tat tct acc     624
Ser Arg Pro Asn Glu Glu Ser Leu Leu Arg Leu Ala Asn Tyr Ser Thr
        195                 200                 205 tct gtg tca cct aca aac gtt caa tgg ggc gta gat gag aat gct ccg     672
Ser Val Ser Pro Thr Asn Val Gln Trp Gly Val Asp Glu Asn Ala Pro
    210                 215                 220 ctc caa gat cgt gtg cgc tac atg agg gac caa gcc gtc gcc atg ggc     720
Leu Gln Asp Arg Val Arg Tyr Met Arg Asp Gln Ala Val Ala Met Gly
225                 230                 235                 240 ttc ggc tct ctc gat gac gtc gtc gag gcg cac tac aca cag aag ctt     768
Phe Gly Ser Leu Asp Asp Val Val Glu Ala His Tyr Thr Gln Lys Leu
                245                 250                 255
```

-continued

```
gag tgc acc agc cca tcg ttc caa gag cag cga ctg agt cgc aat cgg    816
Glu Cys Thr Ser Pro Ser Phe Gln Glu Gln Arg Leu Ser Arg Asn Arg
            260                 265                 270 cga ctg tcg cga ctg ttg agc acg ctg cac aat gca gcc aaa gac tgg    864
Arg Leu Ser Arg Leu Leu Ser Thr Leu His Asn Ala Ala Lys Asp Trp
275                 280                 285 tcg gag tgg gag cga cgc ggg ttg caa gag caa gtt acc caa ggt gcc    912
Ser Glu Trp Glu Arg Arg Gly Leu Gln Glu Gln Val Thr Gln Gly Ala
            290                 295                 300 gaa gac atc ttg gtc tcc gag cta aat tcg tac att aca cag cgc tcg    960
Glu Asp Ile Leu Val Ser Glu Leu Asn Ser Tyr Ile Thr Gln Arg Ser
305                 310                 315                 320 atg aac tca acg gac gac aaa atc atc acg ggc ggc ctc ctg gac gag   1008
Met Asn Ser Thr Asp Asp Lys Ile Ile Thr Gly Gly Leu Leu Asp Glu
                325                 330                 335 cag tct aga ctg agg cag gac gtg gaa gaa agg cgg aga ctc cag gac   1056
Gln Ser Arg Leu Arg Gln Asp Val Glu Glu Arg Arg Arg Leu Gln Asp
            340                 345                 350 agt ctc ccc aac cta ggt gcc ctc ctc acc act ctg ctg tca agg tcc   1104
Ser Leu Pro Asn Leu Gly Ala Leu Leu Thr Thr Leu Leu Ser Arg Ser
            355                 360                 365 aac gca ccc aac caa gac gcc cgt cga gac act gta ctc gcc atg atc   1152
Asn Ala Pro Asn Gln Asp Ala Arg Arg Asp Thr Val Leu Ala Met Ile
370                 375                 380 aag aca atg tgc ttt gat caa gac gag aac atg agt ata tca tag       1197
Lys Thr Met Cys Phe Asp Gln Asp Glu Asn Met Ser Ile Ser
385                 390                 395
```

<210> SEQ ID NO 39
<211> LENGTH: 398
<212> TYPE: PRT
<213> ORGANISM: Curvularia clavata

<400> SEQUENCE: 39

```
Met Thr Phe Val Glu Thr Val Ala Val Pro Asp Asn Glu Glu Arg Pro
1               5                   10                  15

Ser Ala Gly His Asn Arg Pro Val Ala Asp Ser Thr Lys Cys Pro Asn
            20                  25                  30

Ala Arg Glu Met Lys Val Gln Asn Arg Val Ala Gln Arg Thr His His
        35                  40                  45

Arg Arg Leu Lys Thr Lys Leu Glu Val Leu Arg Glu Arg Leu Lys Glu
    50                  55                  60

Pro Glu Lys Gln Val Gly Glu Pro Ala Arg Val Gln Thr Ser Thr Ser
65                  70                  75                  80

Thr Leu Val Ser Asp Ala Ala Thr Ser Leu Ala Asp Ser Met Cys Leu
                85                  90                  95

Val Pro Ala Val Gln Asn Asp Gln Ala Met Ala Phe Asp Phe Leu Met
            100                 105                 110

Thr Pro Ser Pro Ser Val Gly Asn Asp Cys Pro Ser Asn Asp Leu Glu
        115                 120                 125

Thr Met Arg Gln Ala Ala Ser Val His Ser Asn Thr Leu Gly Gly Ala
    130                 135                 140

Phe Pro Leu Asn Arg Ser Pro Cys Thr Glu Asn Met Thr Pro Glu Ser
145                 150                 155                 160

Gln Val Ser Leu Ser Thr Ala Pro Leu Cys Phe Thr Ser Val Val Pro
                165                 170                 175

Ala Glu Leu Asp Met Asp Ala Phe Cys Thr Leu Asp Ser Ser Asp Trp
            180                 185                 190
```

```
Ser Arg Pro Asn Glu Glu Ser Leu Leu Arg Leu Ala Asn Tyr Ser Thr
        195                 200                 205

Ser Val Ser Pro Thr Asn Val Gln Trp Gly Val Asp Glu Asn Ala Pro
    210                 215                 220

Leu Gln Asp Arg Val Arg Tyr Met Arg Asp Gln Ala Val Ala Met Gly
225                 230                 235                 240

Phe Gly Ser Leu Asp Asp Val Val Glu Ala His Tyr Thr Gln Lys Leu
                245                 250                 255

Glu Cys Thr Ser Pro Ser Phe Gln Glu Gln Arg Leu Ser Arg Asn Arg
                260                 265                 270

Arg Leu Ser Arg Leu Leu Ser Thr Leu His Asn Ala Ala Lys Asp Trp
            275                 280                 285

Ser Glu Trp Glu Arg Arg Gly Leu Gln Glu Gln Val Thr Gln Gly Ala
        290                 295                 300

Glu Asp Ile Leu Val Ser Glu Leu Asn Ser Tyr Ile Thr Gln Arg Ser
305                 310                 315                 320

Met Asn Ser Thr Asp Asp Lys Ile Ile Thr Gly Gly Leu Leu Asp Glu
                325                 330                 335

Gln Ser Arg Leu Arg Gln Asp Val Glu Glu Arg Arg Leu Gln Asp
                340                 345                 350

Ser Leu Pro Asn Leu Gly Ala Leu Leu Thr Thr Leu Leu Ser Arg Ser
            355                 360                 365

Asn Ala Pro Asn Gln Asp Ala Arg Arg Asp Thr Val Leu Ala Met Ile
        370                 375                 380

Lys Thr Met Cys Phe Asp Gln Asp Glu Asn Met Ser Ile Ser
385                 390                 395
```

```
<210> SEQ ID NO 40
<211> LENGTH: 1269
<212> TYPE: DNA
<213> ORGANISM: Curvularia clavata
<220> FEATURE:
<221> NAME/KEY: CDS
<222> LOCATION: (1)..(1269)

<400> SEQUENCE: 40
```

```
atg gac ccg aga cag tca cgg atc acg gag ctg gca ata gcc atc aaa    48
Met Asp Pro Arg Gln Ser Arg Ile Thr Glu Leu Ala Ile Ala Ile Lys
1               5                   10                  15 aag cag acg gaa aca ctg cag tca cta ttg gac agt ctc aaa gtt gcg    96
Lys Gln Thr Glu Thr Leu Gln Ser Leu Leu Asp Ser Leu Lys Val Ala
            20                  25                  30 acg cct tct ttt tct gta aac gcc aat cag gag ttg cct cgc aat gca   144
Thr Pro Ser Phe Ser Val Asn Ala Asn Gln Glu Leu Pro Arg Asn Ala
        35                  40                  45 gct gtt cag ctc gcg cag tcc tct atc ctc gac tcc tgt acg gaa ctg   192
Ala Val Gln Leu Ala Gln Ser Ser Ile Leu Asp Ser Cys Thr Glu Leu
    50                  55                  60 cag gat ttg gtc gaa ggc cct ctg gca cat gtt ggg cga ata atg agc   240
Gln Asp Leu Val Glu Gly Pro Leu Ala His Val Gly Arg Ile Met Ser
65                  70                  75                  80 cct cga gtt cat ata tcg tca gct ctg caa gct att gta cat ttc aat   288
Pro Arg Val His Ile Ser Ser Ala Leu Gln Ala Ile Val His Phe Asn
                85                  90                  95 ata gca gag aaa atc gca aaa cac gag act atc tca ttt ggc gag atc   336
Ile Ala Glu Lys Ile Ala Lys His Glu Thr Ile Ser Phe Gly Glu Ile
            100                 105                 110
```

```
gca aaa aga tgc aaa atg gac gta gat gat gtc aag cga att atg cga    384
Ala Lys Arg Cys Lys Met Asp Val Asp Asp Val Lys Arg Ile Met Arg
        115                 120                 125 tta gcc atc tcg tac cga atc ttc aaa gag tct cat atc gga ttt gta    432
Leu Ala Ile Ser Tyr Arg Ile Phe Lys Glu Ser His Ile Gly Phe Val
    130                 135                 140 aat cac acg gct agc tca ttc ttg att gcg gaa aac ctt ctt gtg agg    480
Asn His Thr Ala Ser Ser Phe Leu Ile Ala Glu Asn Leu Leu Val Arg
145                 150                 155                 160 caa tgg att agt ctt tgc tgt gat gag ttc ata cca gcg ggt tcg ttc    528
Gln Trp Ile Ser Leu Cys Cys Asp Glu Phe Ile Pro Ala Gly Ser Phe
                165                 170                 175 ctt gtt cct gcc atg aaa aaa tgg cct agc tct gaa gag cct aac gag    576
Leu Val Pro Ala Met Lys Lys Trp Pro Ser Ser Glu Glu Pro Asn Glu
            180                 185                 190 acc gcg ttt gcg ctg ctt cat aag gga gat agt cta tgg gaa gtc ctt    624
Thr Ala Phe Ala Leu Leu His Lys Gly Asp Ser Leu Trp Glu Val Leu
        195                 200                 205 aaa aag cag cct gaa aaa gct cag cgc ttt gct cac gga atg gag tac    672
Lys Lys Gln Pro Glu Lys Ala Gln Arg Phe Ala His Gly Met Glu Tyr
    210                 215                 220 atg cgg aca ctc ccg cca ttc gac atc aac cat ctg ttt acc tcg ttg    720
Met Arg Thr Leu Pro Pro Phe Asp Ile Asn His Leu Phe Thr Ser Leu
225                 230                 235                 240 aac tgg gag atc gac tgt gag atg gtt ttg gtg gac gtg ggc ggt tct    768
Asn Trp Glu Ile Asp Cys Glu Met Val Leu Val Asp Val Gly Gly Ser
                245                 250                 255 caa ggc tcc att gct gaa gct tta ctt cga aga cac ccg cga cta cga    816
Gln Gly Ser Ile Ala Glu Ala Leu Leu Arg Arg His Pro Arg Leu Arg
            260                 265                 270 tgt tac gtt caa gac ctt cca gag acc ttg agc aaa gcc gtc gtg ccc    864
Cys Tyr Val Gln Asp Leu Pro Glu Thr Leu Ser Lys Ala Val Val Pro
        275                 280                 285 aag gat ctc aag ggt cgt ctt gag ttc gta agc cac agc atg ttc aaa    912
Lys Asp Leu Lys Gly Arg Leu Glu Phe Val Ser His Ser Met Phe Lys
    290                 295                 300 gag cag cct ata aaa gcc gac gta tac ttg ctc agg tca att ttg cac    960
Glu Gln Pro Ile Lys Ala Asp Val Tyr Leu Leu Arg Ser Ile Leu His
305                 310                 315                 320 gac tgg tta gat gga tac gcc ctg caa atc atc cgg aac ctg att ccc   1008
Asp Trp Leu Asp Gly Tyr Ala Leu Gln Ile Ile Arg Asn Leu Ile Pro
                325                 330                 335 gct ctc gag gtt gga tcc aag gtg att ata aat gag atc tgt cta ccg   1056
Ala Leu Glu Val Gly Ser Lys Val Ile Ile Asn Glu Ile Cys Leu Pro
            340                 345                 350 gag cca aac gcc atc tca gca tat gag gca cag ctt att cgc ggg tac   1104
Glu Pro Asn Ala Ile Ser Ala Tyr Glu Ala Gln Leu Ile Arg Gly Tyr
        355                 360                 365 gat ctt tca atg aag caa caa ttt aat tcg aaa gag cga gat gtg cac   1152
Asp Leu Ser Met Lys Gln Gln Phe Asn Ser Lys Glu Arg Asp Val His
    370                 375                 380 gag tgg gaa act ctg ttc cga ctt gca gac aga cgg ttc aaa cta aat   1200
Glu Trp Glu Thr Leu Phe Arg Leu Ala Asp Arg Arg Phe Lys Leu Asn
385                 390                 395                 400 cgc atc gtc aat cca cca ggc tca ttc ctt gcc gtt cta gaa ttc gaa   1248
Arg Ile Val Asn Pro Pro Gly Ser Phe Leu Ala Val Leu Glu Phe Glu
                405                 410                 415 tgg caa ccc acc aca cca taa                                       1269
Trp Gln Pro Thr Thr Pro
            420
```

<210> SEQ ID NO 41
<211> LENGTH: 422
<212> TYPE: PRT
<213> ORGANISM: Curvularia clavata

<400> SEQUENCE: 41

```
Met Asp Pro Arg Gln Ser Arg Ile Thr Glu Leu Ala Ile Ala Ile Lys
1               5                   10                  15

Lys Gln Thr Glu Thr Leu Gln Ser Leu Leu Asp Ser Leu Lys Val Ala
            20                  25                  30

Thr Pro Ser Phe Ser Val Asn Ala Asn Gln Glu Leu Pro Arg Asn Ala
        35                  40                  45

Ala Val Gln Leu Ala Gln Ser Ser Ile Leu Asp Ser Cys Thr Glu Leu
    50                  55                  60

Gln Asp Leu Val Glu Gly Pro Leu Ala His Val Gly Arg Ile Met Ser
65                  70                  75                  80

Pro Arg Val His Ile Ser Ser Ala Leu Gln Ala Ile Val His Phe Asn
                85                  90                  95

Ile Ala Glu Lys Ile Ala Lys His Glu Thr Ile Ser Phe Gly Glu Ile
            100                 105                 110

Ala Lys Arg Cys Lys Met Asp Val Asp Val Lys Arg Ile Met Arg
        115                 120                 125

Leu Ala Ile Ser Tyr Arg Ile Phe Lys Glu Ser His Ile Gly Phe Val
    130                 135                 140

Asn His Thr Ala Ser Ser Phe Leu Ile Ala Glu Asn Leu Leu Val Arg
145                 150                 155                 160

Gln Trp Ile Ser Leu Cys Cys Asp Glu Phe Ile Pro Ala Gly Ser Phe
                165                 170                 175

Leu Val Pro Ala Met Lys Lys Trp Pro Ser Glu Glu Pro Asn Glu
            180                 185                 190

Thr Ala Phe Ala Leu Leu His Lys Gly Asp Ser Leu Trp Glu Val Leu
        195                 200                 205

Lys Lys Gln Pro Glu Lys Ala Gln Arg Phe Ala His Gly Met Glu Tyr
    210                 215                 220

Met Arg Thr Leu Pro Pro Phe Asp Ile Asn His Leu Phe Thr Ser Leu
225                 230                 235                 240

Asn Trp Glu Ile Asp Cys Glu Met Val Leu Val Asp Val Gly Gly Ser
                245                 250                 255

Gln Gly Ser Ile Ala Glu Ala Leu Leu Arg Arg His Pro Arg Leu Arg
            260                 265                 270

Cys Tyr Val Gln Asp Leu Pro Glu Thr Leu Ser Lys Ala Val Val Pro
        275                 280                 285

Lys Asp Leu Lys Gly Arg Leu Glu Phe Val Ser His Ser Met Phe Lys
    290                 295                 300

Glu Gln Pro Ile Lys Ala Asp Val Tyr Leu Leu Arg Ser Ile Leu His
305                 310                 315                 320

Asp Trp Leu Asp Gly Tyr Ala Leu Gln Ile Ile Arg Asn Leu Ile Pro
                325                 330                 335

Ala Leu Glu Val Gly Ser Lys Val Ile Ile Asn Glu Ile Cys Leu Pro
            340                 345                 350

Glu Pro Asn Ala Ile Ser Ala Tyr Glu Ala Gln Leu Ile Arg Gly Tyr
        355                 360                 365

Asp Leu Ser Met Lys Gln Gln Phe Asn Ser Lys Glu Arg Asp Val His
```

```
                  370                 375                 380
Glu Trp Glu Thr Leu Phe Arg Leu Ala Asp Arg Arg Phe Lys Leu Asn
385                 390                 395                 400

Arg Ile Val Asn Pro Pro Gly Ser Phe Leu Ala Val Leu Glu Phe Glu
                405                 410                 415

Trp Gln Pro Thr Thr Pro
            420

<210> SEQ ID NO 42
<211> LENGTH: 1617
<212> TYPE: DNA
<213> ORGANISM: Curvularia clavata
<220> FEATURE:
<221> NAME/KEY: CDS
<222> LOCATION: (1)..(1617)

<400> SEQUENCE: 42 atg act gaa ccc aca tgg aag aca gtt gca tcg gag aaa cag cag cag    48
Met Thr Glu Pro Thr Trp Lys Thr Val Ala Ser Glu Lys Gln Gln Gln
1               5                   10                  15 cgt gaa tcc aaa atc cct tca gaa tgg caa att ccg aag tcg tcg cat    96
Arg Glu Ser Lys Ile Pro Ser Glu Trp Gln Ile Pro Lys Ser Ser His
                20                  25                  30 cca gct ccc gaa gta acc ttt gtt caa gac ttc cca gcc aaa tcg gga   144
Pro Ala Pro Glu Val Thr Phe Val Gln Asp Phe Pro Ala Lys Ser Gly
            35                  40                  45 atg ttc acc aat cga gag ctg caa cta aca gcg gcg act gca tcg gat   192
Met Phe Thr Asn Arg Glu Leu Gln Leu Thr Ala Ala Thr Ala Ser Asp
        50                  55                  60 gta acg gcc aag atc tcc act ggc gaa tgg acg gcc gtg gag gtc acg   240
Val Thr Ala Lys Ile Ser Thr Gly Glu Trp Thr Ala Val Glu Val Thr
65                  70                  75                  80 act gct gtg tgc aag cga gct gcc gtg gct caa caa ttg ttg aat tgt   288
Thr Ala Val Cys Lys Arg Ala Ala Val Ala Gln Gln Leu Leu Asn Cys
                85                  90                  95 gta acg gag atc tgc ttt gat caa gct ata gca aga gcg aag gag ctt   336
Val Thr Glu Ile Cys Phe Asp Gln Ala Ile Ala Arg Ala Lys Glu Leu
                100                 105                 110 gac gcg tat ttt gaa aaa gaa gga aag acc gtg ggc cca ctc cac gga   384
Asp Ala Tyr Phe Glu Lys Glu Gly Lys Thr Val Gly Pro Leu His Gly
            115                 120                 125 tta cca att agc ttc aaa gac cag ttc aat gtc aaa ggc ttc gac tcc   432
Leu Pro Ile Ser Phe Lys Asp Gln Phe Asn Val Lys Gly Phe Asp Ser
        130                 135                 140 acc atc ggc tac tgc agt tat gct agc aag cca gca acg gca gac tca   480
Thr Ile Gly Tyr Cys Ser Tyr Ala Ser Lys Pro Ala Thr Ala Asp Ser
145                 150                 155                 160 act ctc gtc aag ctc ctg gtc aag gct ggg gca atc atc tat gtc aag   528
Thr Leu Val Lys Leu Leu Val Lys Ala Gly Ala Ile Ile Tyr Val Lys
                165                 170                 175 tcc aat gtt cct atc acg cta atg atg ggc gag tca ttc aac aac atc   576
Ser Asn Val Pro Ile Thr Leu Met Met Gly Glu Ser Phe Asn Asn Ile
                180                 185                 190 ttt gga cgc aca ctc aac ccc gcg aat cgg gag ttg acc aca gga ggc   624
Phe Gly Arg Thr Leu Asn Pro Arg Asn Arg Glu Leu Thr Thr Gly Gly
            195                 200                 205 tca tca ggc gga gaa gca gca ctg gtc acg ttc tgt gcc agc ttc ctc   672
Ser Ser Gly Gly Glu Ala Ala Leu Val Thr Phe Cys Ala Ser Phe Leu
        210                 215                 220 ggt gtg ggc acc gac atc ggt ggc agc ctt cgc ata cca tgc tca ttc   720
```

|  |  |
|---|---|
| Gly Val Gly Thr Asp Ile Gly Gly Ser Leu Arg Ile Pro Cys Ser Phe<br>225                          230                      235                    240 |  |
| acc ggg ctg tat ggg cta aga cca tcc cac ggc aga gtg tca tat caa<br>Thr Gly Leu Tyr Gly Leu Arg Pro Ser His Gly Arg Val Ser Tyr Gln<br>                      245                      250                      255 | 768 |
| cat gtg cag aac acc ttg ctc gga cag gaa gca gtc aga tca tgt gct<br>His Val Gln Asn Thr Leu Leu Gly Gln Glu Ala Val Arg Ser Cys Ala<br>              260                      265                      270 | 816 |
| gga ccc atg tgc cgt gca ccg gaa gat atc cgc ttg ttc atg tcg agt<br>Gly Pro Met Cys Arg Ala Pro Glu Asp Ile Arg Leu Phe Met Ser Ser<br>            275                      280                      285 | 864 |
| cta gct gcc cag cag ccc tgg ctt tgg gat ccc cag agt ctg cca ctc<br>Leu Ala Ala Gln Gln Pro Trp Leu Trp Asp Pro Gln Ser Leu Pro Leu<br>    290                      295                      300 | 912 |
| cca tgg cgg gcg gag gaa gag gtc tta ccg aag aag ttg tgt ttc ggt<br>Pro Trp Arg Ala Glu Glu Glu Val Leu Pro Lys Lys Leu Cys Phe Gly<br>305                          310                      315                    320 | 960 |
| ttt gct cta ggt gat ggc cat gta ggc ccg aaa aag tta aag caa gca<br>Phe Ala Leu Gly Asp Gly His Val Gly Pro Lys Lys Leu Lys Gln Ala<br>                      325                      330                      335 | 1008 |
| ggg cat gct gtc att aac ttc aat ctc aca gaa gga aaa gaa gta aat<br>Gly His Ala Val Ile Asn Phe Asn Leu Thr Glu Gly Lys Glu Val Asn<br>            340                      345                      350 | 1056 |
| gag atc atg aac aag atg ttc act gcg gat ggg ggt gcc gag ttt cag<br>Glu Ile Met Asn Lys Met Phe Thr Ala Asp Gly Gly Ala Glu Phe Gln<br>                355                      360                      365 | 1104 |
| cgc gac acc gat gcc acg ggc gag ccc ctg cca cct aca gta gaa tac<br>Arg Asp Thr Asp Ala Thr Gly Glu Pro Leu Pro Pro Thr Val Glu Tyr<br>    370                      375                      380 | 1152 |
| tgg ctc ggc cac agc tcg caa atc aaa gcc tca acc gta agc gag aca<br>Trp Leu Gly His Ser Ser Gln Ile Lys Ala Ser Thr Val Ser Glu Thr<br>385                          390                      395                    400 | 1200 |
| tgg aaa aat cag cac aag aag gcg ttg ctt gcg caa aag ttc cta gag<br>Trp Lys Asn Gln His Lys Lys Ala Leu Leu Ala Gln Lys Phe Leu Glu<br>                405                      410                      415 | 1248 |
| aag tgg caa gca acc aaa ggg cga acg ggc acg agt cgc cct atc gat<br>Lys Trp Gln Ala Thr Lys Gly Arg Thr Gly Thr Ser Arg Pro Ile Asp<br>            420                      425                      430 | 1296 |
| ggg ctg atc atg cca tcg acg cca ttt ccg gcc agt cgt cac ggc agc<br>Gly Leu Ile Met Pro Ser Thr Pro Phe Pro Ala Ser Arg His Gly Ser<br>                435                      440                      445 | 1344 |
| ggc tgg cca tgg cac ttt ggt gat ctc tct gcc cta cta gat ctg acc<br>Gly Trp Pro Trp His Phe Gly Asp Leu Ser Ala Leu Leu Asp Leu Thr<br>    450                      455                      460 | 1392 |
| acg ggc gtt ttc cca gtc acc cgg gtc aat ctg gag aaa gac gcc gtg<br>Thr Gly Val Phe Pro Val Thr Arg Val Asn Leu Glu Lys Asp Ala Val<br>465                          470                      475                    480 | 1440 |
| ccg ccg agc tgg acg ccc atg tct gtg aaa gac aag gag gcg atg gat<br>Pro Pro Ser Trp Thr Pro Met Ser Val Lys Asp Lys Glu Ala Met Asp<br>                485                      490                      495 | 1488 |
| tac tat gag aag cca gag aat cac gag aat gcc cta gtc ggc ctc caa<br>Tyr Tyr Glu Lys Pro Glu Asn His Glu Asn Ala Leu Val Gly Leu Gln<br>            500                      505                      510 | 1536 |
| ttg att ggt aga agg ttg gag gag gaa aag gta aca gct atg ctt acg<br>Leu Ile Gly Arg Arg Leu Glu Glu Glu Lys Val Thr Ala Met Leu Thr<br>                515                      520                      525 | 1584 |
| ctt att agg aat gtg ctt gaa gta gat tat taa<br>Leu Ile Arg Asn Val Leu Glu Val Asp Tyr<br>    530                      535 | 1617 |

<210> SEQ ID NO 43
<211> LENGTH: 538
<212> TYPE: PRT
<213> ORGANISM: Curvularia clavata

<400> SEQUENCE: 43

| | | | | | | | | | | | | | | |
|---|---|---|---|---|---|---|---|---|---|---|---|---|---|---|
| Met | Thr | Glu | Pro | Thr | Trp | Lys | Thr | Val | Ala | Ser | Glu | Lys | Gln | Gln |
| 1 | | | | 5 | | | | | 10 | | | | | 15 |
| Gln | Arg | Glu | Ser | Lys | Ile | Pro | Ser | Glu | Trp | Gln | Ile | Pro | Lys | Ser |
| | | | | 20 | | | | | 25 | | | | | 30 |
| Ser | His | Pro | Ala | Pro | Glu | Val | Thr | Phe | Val | Gln | Asp | Phe | Pro | Ala |
| | | | | 35 | | | | | 40 | | | | | 45 |
| Lys | Ser | Gly | Met | Phe | Thr | Asn | Arg | Glu | Leu | Gln | Leu | Thr | Ala | Ala |
| | | | 50 | | | | | 55 | | | | | 60 | |
| Thr | Ala | Ser | Asp | Val | Thr | Ala | Lys | Ile | Ser | Thr | Gly | Glu | Trp | Thr |
| 65 | | | | | 70 | | | | | 75 | | | | |
| Ala | Val | Glu | Val | Thr | Thr | Ala | Val | Cys | Lys | Arg | Ala | Ala | Val | Ala |
| | | | | 80 | | | | 85 | | | | | 90 | |
| Gln | Gln | Leu | Leu | Asn | Cys | Val | Thr | Glu | Ile | Cys | Phe | Asp | Gln | Ala |
| | | | | 95 | | | | | 100 | | | | | 105 |
| Ile | Ala | Arg | Ala | Lys | Glu | Leu | Asp | Ala | Tyr | Phe | Glu | Lys | Glu | Gly |
| | | | | 110 | | | | | 115 | | | | | 120 |
| Lys | Thr | Val | Gly | Pro | Leu | His | Gly | Leu | Pro | Ile | Ser | Phe | Lys | Asp |
| | | | | 125 | | | | | 130 | | | | | 135 |
| Gln | Phe | Asn | Val | Lys | Gly | Phe | Asp | Ser | Thr | Ile | Gly | Tyr | Cys | Ser |
| | | | | 140 | | | | | 145 | | | | | 150 |
| Tyr | Ala | Ser | Lys | Pro | Ala | Thr | Ala | Asp | Ser | Thr | Leu | Val | Lys | Leu |
| | | | | 155 | | | | | 160 | | | | 165 | |
| Leu | Val | Lys | Ala | Gly | Ala | Ile | Ile | Tyr | Val | Lys | Ser | Asn | Val | Pro |
| | | | | 170 | | | | | 175 | | | | | 180 |
| Ile | Thr | Leu | Met | Met | Gly | Glu | Ser | Phe | Asn | Asn | Ile | Phe | Gly | Arg |
| | | | | 185 | | | | | 190 | | | | | 195 |
| Thr | Leu | Asn | Pro | Arg | Asn | Arg | Glu | Leu | Thr | Thr | Gly | Gly | Ser | Ser |
| | | | | 200 | | | | | 205 | | | | | 210 |
| Gly | Gly | Glu | Ala | Ala | Leu | Val | Thr | Phe | Cys | Ala | Ser | Phe | Leu | Gly |
| | | | | 215 | | | | | 220 | | | | | 225 |
| Val | Gly | Thr | Asp | Ile | Gly | Gly | Ser | Leu | Arg | Ile | Pro | Cys | Ser | Phe |
| | | | 230 | | | | | 235 | | | | | 240 | |
| Thr | Gly | Leu | Tyr | Gly | Leu | Arg | Pro | Ser | His | Gly | Arg | Val | Ser | Tyr |
| | | | 245 | | | | | 250 | | | | | 255 | |
| Gln | His | Val | Gln | Asn | Thr | Leu | Leu | Gly | Gln | Glu | Ala | Val | Arg | Ser |
| | | | | 260 | | | | | 265 | | | | | 270 |
| Cys | Ala | Gly | Pro | Met | Cys | Arg | Ala | Pro | Glu | Asp | Ile | Arg | Leu | Phe |
| | | | 275 | | | | | 280 | | | | | 285 | |
| Met | Ser | Ser | Leu | Ala | Gln | Gln | Pro | Trp | Leu | Trp | Asp | Pro | Gln | Ser |
| | | | 290 | | | | | 295 | | | | | 300 | |
| Leu | Pro | Leu | Pro | Trp | Arg | Ala | Glu | Glu | Val | Leu | Pro | Lys | Lys | Leu |
| 305 | | | | | 310 | | | | | 315 | | | | |
| Cys | Phe | Gly | Phe | Ala | Leu | Gly | Asp | Gly | His | Val | Gly | Pro | Lys | Lys |
| | 320 | | | | | 325 | | | | | 330 | | | |
| Leu | Lys | Gln | Ala | Gly | His | Ala | Val | Ile | Asn | Phe | Asn | Leu | Thr | Glu |
| | | 335 | | | | | 340 | | | | | 345 | | |
| Gly | Lys | Glu | Val | Asn | Glu | Ile | Met | Asn | Lys | Met | Phe | Thr | Ala | Asp |
| | | | 350 | | | | | 355 | | | | | 360 | |
| Gly | Gly | Ala | Glu | Phe | Gln | Arg | Asp | Thr | Asp | Ala | Thr | Gly | Glu | Pro |
| | | | 365 | | | | | 370 | | | | | 375 | |
| Leu | Pro | Pro | Thr | Val | Glu | Tyr | | | | | | | | |
| | | | 380 | | | | | | | | | | | |

```
Trp Leu Gly His Ser Ser Gln Ile Lys Ala Ser Thr Val Ser Glu Thr
385                 390                 395                 400

Trp Lys Asn Gln His Lys Lys Ala Leu Leu Ala Gln Lys Phe Leu Glu
            405                 410                 415

Lys Trp Gln Ala Thr Lys Gly Arg Thr Gly Thr Ser Arg Pro Ile Asp
        420                 425                 430

Gly Leu Ile Met Pro Ser Thr Pro Phe Pro Ala Ser Arg His Gly Ser
    435                 440                 445

Gly Trp Pro Trp His Phe Gly Asp Leu Ser Ala Leu Leu Asp Leu Thr
450                 455                 460

Thr Gly Val Phe Pro Val Thr Arg Val Asn Leu Glu Lys Asp Ala Val
465                 470                 475                 480

Pro Pro Ser Trp Thr Pro Met Ser Val Lys Asp Lys Glu Ala Met Asp
                485                 490                 495

Tyr Tyr Glu Lys Pro Glu Asn His Glu Asn Ala Leu Val Gly Leu Gln
                500                 505                 510

Leu Ile Gly Arg Arg Leu Glu Glu Glu Lys Val Thr Ala Met Leu Thr
            515                 520                 525

Leu Ile Arg Asn Val Leu Glu Val Asp Tyr
    530                 535
```

```
<210> SEQ ID NO 44
<211> LENGTH: 2991
<212> TYPE: DNA
<213> ORGANISM: Curvularia clavata
<220> FEATURE:
<221> NAME/KEY: CDS
<222> LOCATION: (1)..(2991)

<400> SEQUENCE: 44
```

```
atg gcg ttg caa gag cgc cgt gcc gcg gtc aca agt tcc gat atc ctc      48
Met Ala Leu Gln Glu Arg Arg Ala Ala Val Thr Ser Ser Asp Ile Leu
1               5                   10                  15 tca gcg cat gct atc tcg tct ccc gcc ttg gcc gca gcg gcc atc aat      96
Ser Ala His Ala Ile Ser Ser Pro Ala Leu Ala Ala Ala Ala Ile Asn
            20                  25                  30 ttc gcc gcc agc ttc cat cga gat gcc cgc acc tgt tgc agc gct cat     144
Phe Ala Ala Ser Phe His Arg Asp Ala Arg Thr Cys Cys Ser Ala His
        35                  40                  45 gag cgt agc cag ctc cag aaa gtc tac cgc gac aag atc ctc gcc aac     192
Glu Arg Ser Gln Leu Gln Lys Val Tyr Arg Asp Lys Ile Leu Ala Asn
    50                  55                  60 gac aag ttt acg gcc aac att gct gct gcc ttc ctc tct gtc ctg ggc     240
Asp Lys Phe Thr Ala Asn Ile Ala Ala Ala Phe Leu Ser Val Leu Gly
65                  70                  75                  80 ccc aac gcc ggc cgt aac gat gca ggt gcc gag cgc gag cgc tgg ggc     288
Pro Asn Ala Gly Arg Asn Asp Ala Gly Ala Glu Arg Glu Arg Trp Gly
                85                  90                  95 gac ttt gac cgc ctg gcg cag cga ggc aag aac atg cgc gac cgc gag     336
Asp Phe Asp Arg Leu Ala Gln Arg Gly Lys Asn Met Arg Asp Arg Glu
            100                 105                 110 agc cag cat ttg caa cat cag tca ggc atc att gcc gcc tgg ggg cct     384
Ser Gln His Leu Gln His Gln Ser Gly Ile Ile Ala Ala Trp Gly Pro
        115                 120                 125 cga tgc ttc gag tac tac ggc tgg cat gtc ctg ccg ctg ccg ctg ctg     432
Arg Cys Phe Glu Tyr Tyr Gly Trp His Val Leu Pro Leu Pro Leu Leu
    130                 135                 140 cgt cag gtg cac gac ctt gcc gtg ctg ata cct agc tgg gac gac gcc     480
```

```
                Arg Gln Val His Asp Leu Ala Val Leu Ile Pro Ser Trp Asp Asp Ala
                145                 150                 155                 160 gtt gag ctg ctg aat tcc agg atg ctg ttg cgc cac gaa ctg cgt gtg                 528
Val Glu Leu Leu Asn Ser Arg Met Leu Leu Arg His Glu Leu Arg Val
                165                 170                 175 ctg cac ggc aac aac aag gcc ctc cga atc ggt gaa cac tct gcc gct                 576
Leu His Gly Asn Asn Lys Ala Leu Arg Ile Gly Glu His Ser Ala Ala
                180                 185                 190 tcc aaa gtt cag gac tca cgc tca cct gtt gag cgt acc gac atc gtg                 624
Ser Lys Val Gln Asp Ser Arg Ser Pro Val Glu Arg Thr Asp Ile Val
                195                 200                 205 gct gct ctc gac tgg gct cgt gcc aac gca act tcg gct gcg gca cgt                 672
Ala Ala Leu Asp Trp Ala Arg Ala Asn Ala Thr Ser Ala Ala Ala Arg
                210                 215                 220 caa gcg gtc aag gaa gcg gcg cag ggc atg aat ggg act ccg atc aac                 720
Gln Ala Val Lys Glu Ala Ala Gln Gly Met Asn Gly Thr Pro Ile Asn
225                 230                 235                 240 aca ttc ggt ttg aag cga gat tgc tat ggt atg gtc gta ccg tcg gtc                 768
Thr Phe Gly Leu Lys Arg Asp Cys Tyr Gly Met Val Val Pro Ser Val
                245                 250                 255 ggc ccc tac gat cct gat gga gat gat gac aat gat gaa gac gtt gtc                 816
Gly Pro Tyr Asp Pro Asp Gly Asp Asp Asp Asn Asp Glu Asp Val Val
                260                 265                 270 gat gtg tcc cct cgg cca gcg aag cac atc aaa ttg tca gcc gca gag                 864
Asp Val Ser Pro Arg Pro Ala Lys His Ile Lys Leu Ser Ala Ala Glu
                275                 280                 285 ccg ctt cgt ctg atg ttt cca ggt tca ttg agt cat gtc cag gct tgt                 912
Pro Leu Arg Leu Met Phe Pro Gly Ser Leu Ser His Val Gln Ala Cys
                290                 295                 300 caa aga cat gac act gac ggc gag aag gcc agt act gca ccc att cgt                 960
Gln Arg His Asp Thr Asp Gly Glu Lys Ala Ser Thr Ala Pro Ile Arg
305                 310                 315                 320 agt aac aaa ctg tcc cag tcc aaa cag cca gag cta gac aca gca gcc                 1008
Ser Asn Lys Leu Ser Gln Ser Lys Gln Pro Glu Leu Asp Thr Ala Ala
                325                 330                 335 gag agt ctt cgt acg agg cat att cac aat gaa cgc atc aac gag ccc                 1056
Glu Ser Leu Arg Thr Arg His Ile His Asn Glu Arg Ile Asn Glu Pro
                340                 345                 350 ctc gac gaa gtc tcg gac tgc agt cta tct ctc caa aca ata gcc gtg                 1104
Leu Asp Glu Val Ser Asp Cys Ser Leu Ser Leu Gln Thr Ile Ala Val
                355                 360                 365 gga gga ggg agc gct cag gag gaa acg cca gac caa gat gtg gaa cat                 1152
Gly Gly Gly Ser Ala Gln Glu Glu Thr Pro Asp Gln Asp Val Glu His
                370                 375                 380 gca cat cct gaa gtt gag ata aca tcc gcc ata agc agt gag ctt agg                 1200
Ala His Pro Glu Val Glu Ile Thr Ser Ala Ile Ser Ser Glu Leu Arg
385                 390                 395                 400 aag gta gac gag cgt acc gat ggt ata agg ata ggg cgt gtg att atg                 1248
Lys Val Asp Glu Arg Thr Asp Gly Ile Arg Ile Gly Arg Val Ile Met
                405                 410                 415 agg cgc agt cac tgt atg gta aga gaa cag gac aac cag act aac gag                 1296
Arg Arg Ser His Cys Met Val Arg Glu Gln Asp Asn Gln Thr Asn Glu
                420                 425                 430 gag ggg aca gga gaa gta cag tca cag cgg gac agg aga gcg agg gac                 1344
Glu Gly Thr Gly Glu Val Gln Ser Gln Arg Asp Arg Arg Ala Arg Asp
                435                 440                 445 ttg gga aag gat atg gag acg gat atg gat att gac agc cag ctg gag                 1392
Leu Gly Lys Asp Met Glu Thr Asp Met Asp Ile Asp Ser Gln Leu Glu
                450                 455                 460
```

```
gag atg ctg gac ata cat gct ctg gag gcg caa aga aat cac gaa gaa    1440
Glu Met Leu Asp Ile His Ala Leu Glu Ala Gln Arg Asn His Glu Glu
465                 470                 475                 480 atg tcg gat ggt gaa gat gtt gtt gca gga gtg gcg ggc ccg gga acg    1488
Met Ser Asp Gly Glu Asp Val Val Ala Gly Val Ala Gly Pro Gly Thr
            485                 490                 495 cca acg cac agg gcg gcg gaa gaa gga gga tgc aga gaa aaa gaa gca    1536
Pro Thr His Arg Ala Ala Glu Glu Gly Gly Cys Arg Glu Lys Glu Ala
        500                 505                 510 gag aat gcc aaa acg gat gag gag caa gtg cag gac aaa gca gct ctg    1584
Glu Asn Ala Lys Thr Asp Glu Glu Gln Val Gln Asp Lys Ala Ala Leu
    515                 520                 525 gat cag gcg gga aat act aat acg aat cga gag gta gaa aac gca gca    1632
Asp Gln Ala Gly Asn Thr Asn Thr Asn Arg Glu Val Glu Asn Ala Ala
530                 535                 540 cca aaa gcg cac agc caa gaa ggt gcc ctg cgt gca tcg cga acg ggc    1680
Pro Lys Ala His Ser Gln Glu Gly Ala Leu Arg Ala Ser Arg Thr Gly
545                 550                 555                 560 acg atc gtg gaa agg aca gtg gag tta cac tca acg cac tca att cat    1728
Thr Ile Val Glu Arg Thr Val Glu Leu His Ser Thr His Ser Ile His
            565                 570                 575 caa aga gcg agt gtg aat acg acg gct cca acc gtg gcg cga tca agc    1776
Gln Arg Ala Ser Val Asn Thr Thr Ala Pro Thr Val Ala Arg Ser Ser
        580                 585                 590 gat agc gac gac agc gat tca ctc cat tca ccc acg gcg ctt caa aat    1824
Asp Ser Asp Asp Ser Asp Ser Leu His Ser Pro Thr Ala Leu Gln Asn
    595                 600                 605 ctg caa gcc tat atc gat acc aga act cac caa ctc act caa gtg ctg    1872
Leu Gln Ala Tyr Ile Asp Thr Arg Thr His Gln Leu Thr Gln Val Leu
610                 615                 620 agc cag ctc aac tca aca cct gac gtc aga cac cac gct caa ctg cag    1920
Ser Gln Leu Asn Ser Thr Pro Asp Val Arg His His Ala Gln Leu Gln
625                 630                 635                 640 ctt gac tgg tta agt ccg caa cga tgg gcc agt gtc tac gtg gag cca    1968
Leu Asp Trp Leu Ser Pro Gln Arg Trp Ala Ser Val Tyr Val Glu Pro
            645                 650                 655 gaa cat cac atg ggc gcc act tcc tca gca tca tca gac agc gct gac    2016
Glu His His Met Gly Ala Thr Ser Ser Ala Ser Ser Asp Ser Ala Asp
        660                 665                 670 att tgg tgt ctg gac tgg gat acg ttc cac cag tat gct gac agc aac    2064
Ile Trp Cys Leu Asp Trp Asp Thr Phe His Gln Tyr Ala Asp Ser Asn
    675                 680                 685 cat gtc ttc cgg cgg cct gtt gtt atc aag caa aag ttc cag gac agc    2112
His Val Phe Arg Arg Pro Val Val Ile Lys Gln Lys Phe Gln Asp Ser
690                 695                 700 ggt atg tat gag gtt gac aga tac gtg gat atg ctg tgg cag cgc ttt    2160
Gly Met Tyr Glu Val Asp Arg Tyr Val Asp Met Leu Trp Gln Arg Phe
705                 710                 715                 720 ccg gag cag cat att gag gtc caa aac agc att aca ggc act agt cga    2208
Pro Glu Gln His Ile Glu Val Gln Asn Ser Ile Thr Gly Thr Ser Arg
            725                 730                 735 ttg atg agc atg gcc gag tat tgc tct acg gct ttg act gtt acg gag    2256
Leu Met Ser Met Ala Glu Tyr Cys Ser Thr Ala Leu Thr Val Thr Glu
        740                 745                 750 gct ggc acg agt ctg tct gac aat act acc tcc gtg agc aac gct gtt    2304
Ala Gly Thr Ser Leu Ser Asp Asn Thr Thr Ser Val Ser Asn Ala Val
    755                 760                 765 aac ctt cgc tgt ctg gct cgc gca gac gag ccg ctc ttg aca cgg ctc    2352
Asn Leu Arg Cys Leu Ala Arg Ala Asp Glu Pro Leu Leu Thr Arg Leu
770                 775                 780
```

-continued

```
gag cgc ttt caa ctg ctc tcg acg ctc gca tct cgc gtt gca ggc aca      2400
Glu Arg Phe Gln Leu Leu Ser Thr Leu Ala Ser Arg Val Ala Gly Thr
785                 790                 795                 800 att ggc agg acc gaa cat tct cca cct agc aat ctc gag agt ctc ctc      2448
Ile Gly Arg Thr Glu His Ser Pro Pro Ser Asn Leu Glu Ser Leu Leu
        805                 810                 815 gga ttc gac gcg ctc agc ttt gcc gac gcg ttt tca agc tca cat gcc      2496
Gly Phe Asp Ala Leu Ser Phe Ala Asp Ala Phe Ser Ser Ser His Ala
    820                 825                 830 aat ctc ttt ggc gga agt tgg gtg cgg tgc ctc gat ggc ctc aag att      2544
Asn Leu Phe Gly Gly Ser Trp Val Arg Cys Leu Asp Gly Leu Lys Ile
835                 840                 845 tat gcc atc gct gca gac tta gat gca gaa gac tgg cgg cgc ttc gca      2592
Tyr Ala Ile Ala Ala Asp Leu Asp Ala Glu Asp Trp Arg Arg Phe Ala
850                 855                 860 gat gaa gga tac aaa tgg tcg cct cga ggc aaa ggg cgc ttg atc gcc      2640
Asp Glu Gly Tyr Lys Trp Ser Pro Arg Gly Lys Gly Arg Leu Ile Ala
865                 870                 875                 880 cta gag gaa gac gat gtt ctg ttc att ccg cct ggc ctg cgg gcc ata      2688
Leu Glu Glu Asp Asp Val Leu Phe Ile Pro Pro Gly Leu Arg Ala Ile
            885                 890                 895 cat gcc agc ttc acg cca gag ccc tgt ttg atg gaa ggc ggt atg ctg      2736
His Ala Ser Phe Thr Pro Glu Pro Cys Leu Met Glu Gly Gly Met Leu
        900                 905                 910 tgg gac gaa tgc gcc atc cct gag atc tta gac gag ctg ctc tgg att      2784
Trp Asp Glu Cys Ala Ile Pro Glu Ile Leu Asp Glu Leu Leu Trp Ile
    915                 920                 925 gca cga cac cag gca ggc act gtc cag cct ctc gaa ttt cag ctt tca      2832
Ala Arg His Gln Ala Gly Thr Val Gln Pro Leu Glu Phe Gln Leu Ser
930                 935                 940 agt ctg att gat gcg ctg gag cag tgg ttg aat gag aat aac cac att      2880
Ser Leu Ile Asp Ala Leu Glu Gln Trp Leu Asn Glu Asn Asn His Ile
945                 950                 955                 960 aac cag tcg tcg cca tca cac act gca gct gaa gag cgt cag acg ctc      2928
Asn Gln Ser Ser Pro Ser His Thr Ala Ala Glu Glu Arg Gln Thr Leu
            965                 970                 975 aag gct agc att cag tcg ctt cgc gac tgt tta agc ggc aga tca gcg      2976
Lys Ala Ser Ile Gln Ser Leu Arg Asp Cys Leu Ser Gly Arg Ser Ala
        980                 985                 990 gct ttc cca tct tga                                                  2991
Ala Phe Pro Ser
    995

<210> SEQ ID NO 45
<211> LENGTH: 996
<212> TYPE: PRT
<213> ORGANISM: Curvularia clavata

<400> SEQUENCE: 45

Met Ala Leu Gln Glu Arg Arg Ala Ala Val Thr Ser Ser Asp Ile Leu
1               5                   10                  15

Ser Ala His Ala Ile Ser Ser Pro Ala Leu Ala Ala Ala Ala Ile Asn
            20                  25                  30

Phe Ala Ala Ser Phe His Arg Asp Ala Arg Thr Cys Cys Ser Ala His
        35                  40                  45

Glu Arg Ser Gln Leu Gln Lys Val Tyr Arg Asp Lys Ile Leu Ala Asn
    50                  55                  60

Asp Lys Phe Thr Ala Asn Ile Ala Ala Ala Phe Leu Ser Val Leu Gly
65                  70                  75                  80
```

-continued

```
Pro Asn Ala Gly Arg Asn Asp Ala Gly Ala Glu Arg Glu Arg Trp Gly
                85                  90                  95

Asp Phe Asp Arg Leu Ala Gln Arg Gly Lys Asn Met Arg Asp Arg Glu
            100                 105                 110

Ser Gln His Leu Gln His Gln Ser Gly Ile Ile Ala Ala Trp Gly Pro
        115                 120                 125

Arg Cys Phe Glu Tyr Tyr Gly Trp His Val Leu Pro Leu Pro Leu Leu
    130                 135                 140

Arg Gln Val His Asp Leu Ala Val Leu Ile Pro Ser Trp Asp Asp Ala
145                 150                 155                 160

Val Glu Leu Leu Asn Ser Arg Met Leu Leu Arg His Glu Leu Arg Val
                165                 170                 175

Leu His Gly Asn Asn Lys Ala Leu Arg Ile Gly Glu His Ser Ala Ala
            180                 185                 190

Ser Lys Val Gln Asp Ser Arg Ser Pro Val Glu Arg Thr Asp Ile Val
        195                 200                 205

Ala Ala Leu Asp Trp Ala Arg Ala Asn Ala Thr Ser Ala Ala Ala Arg
    210                 215                 220

Gln Ala Val Lys Glu Ala Ala Gln Gly Met Asn Gly Thr Pro Ile Asn
225                 230                 235                 240

Thr Phe Gly Leu Lys Arg Asp Cys Tyr Gly Met Val Val Pro Ser Val
                245                 250                 255

Gly Pro Tyr Asp Pro Asp Gly Asp Asp Asn Asp Glu Asp Val Val
            260                 265                 270

Asp Val Ser Pro Arg Pro Ala Lys His Ile Lys Leu Ser Ala Ala Glu
        275                 280                 285

Pro Leu Arg Leu Met Phe Pro Gly Ser Leu Ser His Val Gln Ala Cys
    290                 295                 300

Gln Arg His Asp Thr Asp Gly Glu Lys Ala Ser Thr Ala Pro Ile Arg
305                 310                 315                 320

Ser Asn Lys Leu Ser Gln Ser Lys Gln Pro Glu Leu Asp Thr Ala Ala
                325                 330                 335

Glu Ser Leu Arg Thr Arg His Ile His Asn Glu Arg Ile Asn Glu Pro
            340                 345                 350

Leu Asp Glu Val Ser Asp Cys Ser Leu Ser Leu Gln Thr Ile Ala Val
        355                 360                 365

Gly Gly Gly Ser Ala Gln Glu Thr Pro Asp Gln Asp Val Glu His
    370                 375                 380

Ala His Pro Glu Val Glu Ile Thr Ser Ala Ile Ser Ser Glu Leu Arg
385                 390                 395                 400

Lys Val Asp Glu Arg Thr Asp Gly Ile Arg Ile Gly Arg Val Ile Met
                405                 410                 415

Arg Arg Ser His Cys Met Val Arg Glu Gln Asp Asn Gln Thr Asn Glu
            420                 425                 430

Glu Gly Thr Gly Glu Val Gln Ser Gln Arg Asp Arg Arg Ala Arg Asp
        435                 440                 445

Leu Gly Lys Asp Met Glu Thr Asp Met Asp Ile Asp Ser Gln Leu Glu
    450                 455                 460

Glu Met Leu Asp Ile His Ala Leu Glu Ala Gln Arg Asn His Glu Glu
465                 470                 475                 480

Met Ser Asp Gly Glu Asp Val Val Ala Gly Val Ala Gly Pro Gly Thr
                485                 490                 495
```

-continued

```
Pro Thr His Arg Ala Ala Glu Glu Gly Gly Cys Arg Glu Lys Glu Ala
            500                 505                 510

Glu Asn Ala Lys Thr Asp Glu Glu Gln Val Gln Asp Lys Ala Ala Leu
        515                 520                 525

Asp Gln Ala Gly Asn Thr Asn Thr Asn Arg Glu Val Glu Asn Ala Ala
    530                 535                 540

Pro Lys Ala His Ser Gln Gly Ala Leu Arg Ala Ser Arg Thr Gly
545                 550                 555                 560

Thr Ile Val Glu Arg Thr Val Glu Leu His Ser Thr His Ser Ile His
                565                 570                 575

Gln Arg Ala Ser Val Asn Thr Thr Ala Pro Thr Val Arg Ser Ser
            580                 585                 590

Asp Ser Asp Asp Ser Asp Ser Leu His Ser Pro Thr Ala Leu Gln Asn
        595                 600                 605

Leu Gln Ala Tyr Ile Asp Thr Arg Thr His Gln Leu Thr Gln Val Leu
    610                 615                 620

Ser Gln Leu Asn Ser Thr Pro Asp Val Arg His His Ala Gln Leu Gln
625                 630                 635                 640

Leu Asp Trp Leu Ser Pro Gln Arg Trp Ala Ser Val Tyr Val Glu Pro
                645                 650                 655

Glu His His Met Gly Ala Thr Ser Ser Ala Ser Ser Asp Ser Ala Asp
            660                 665                 670

Ile Trp Cys Leu Asp Trp Asp Thr Phe His Gln Tyr Ala Asp Ser Asn
        675                 680                 685

His Val Phe Arg Arg Pro Val Val Ile Lys Gln Lys Phe Gln Asp Ser
    690                 695                 700

Gly Met Tyr Glu Val Asp Arg Tyr Val Asp Met Leu Trp Gln Arg Phe
705                 710                 715                 720

Pro Glu Gln His Ile Glu Val Gln Asn Ser Ile Thr Gly Thr Ser Arg
                725                 730                 735

Leu Met Ser Met Ala Glu Tyr Cys Ser Thr Ala Leu Thr Val Thr Glu
            740                 745                 750

Ala Gly Thr Ser Leu Ser Asp Asn Thr Thr Ser Val Ser Asn Ala Val
        755                 760                 765

Asn Leu Arg Cys Leu Ala Arg Ala Asp Glu Pro Leu Leu Thr Arg Leu
    770                 775                 780

Glu Arg Phe Gln Leu Leu Ser Thr Leu Ala Ser Arg Val Ala Gly Thr
785                 790                 795                 800

Ile Gly Arg Thr Glu His Ser Pro Pro Ser Asn Leu Glu Ser Leu Leu
                805                 810                 815

Gly Phe Asp Ala Leu Ser Phe Ala Asp Ala Phe Ser Ser Ser His Ala
            820                 825                 830

Asn Leu Phe Gly Gly Ser Trp Val Arg Cys Leu Asp Gly Leu Lys Ile
        835                 840                 845

Tyr Ala Ile Ala Ala Asp Leu Asp Ala Glu Asp Trp Arg Arg Phe Ala
    850                 855                 860

Asp Glu Gly Tyr Lys Trp Ser Pro Arg Gly Lys Gly Arg Leu Ile Ala
865                 870                 875                 880

Leu Glu Glu Asp Asp Val Leu Phe Ile Pro Pro Gly Leu Arg Ala Ile
                885                 890                 895

His Ala Ser Phe Thr Pro Glu Pro Cys Leu Met Glu Gly Gly Met Leu
            900                 905                 910

Trp Asp Glu Cys Ala Ile Pro Glu Ile Leu Asp Glu Leu Leu Trp Ile
```

```
                915                 920                 925
Ala Arg His Gln Ala Gly Thr Val Gln Pro Leu Glu Phe Gln Leu Ser
        930                 935                 940

Ser Leu Ile Asp Ala Leu Glu Gln Trp Leu Asn Glu Asn Asn His Ile
945                 950                 955                 960

Asn Gln Ser Ser Pro Ser His Thr Ala Ala Glu Glu Arg Gln Thr Leu
            965                 970                 975

Lys Ala Ser Ile Gln Ser Leu Arg Asp Cys Leu Ser Gly Arg Ser Ala
                980                 985                 990

Ala Phe Pro Ser
        995

<210> SEQ ID NO 46
<211> LENGTH: 234
<212> TYPE: DNA
<213> ORGANISM: Curvularia clavata
<220> FEATURE:
<221> NAME/KEY: CDS
<222> LOCATION: (1)..(234)

<400> SEQUENCE: 46 atg tca aac aag aag aac gag ggc ctt gag aag gga ggc aat ggg tcg      48
Met Ser Asn Lys Lys Asn Glu Gly Leu Glu Lys Gly Gly Asn Gly Ser
1               5                   10                  15 gct gag cac gag agc ttt ctg ccc aag tcg gcg ctt cac tac cgc gct      96
Ala Glu His Glu Ser Phe Leu Pro Lys Ser Ala Leu His Tyr Arg Ala
                20                  25                  30 cgc gtc gat ggc ggc aca agc ggc ctt ctt gcg cgg ctc gac aat agt     144
Arg Val Asp Gly Gly Thr Ser Gly Leu Leu Ala Arg Leu Asp Asn Ser
            35                  40                  45 ccc ggc gct gct gtc ttg gct tat tgc ttc tcc tcg gtc agc acc ctt     192
Pro Gly Ala Ala Val Leu Ala Tyr Cys Phe Ser Ser Val Ser Thr Leu
        50                  55                  60 gga tat gtt ccg gac tgc gag gat aac ctt tgc ggc tcc taa             234
Gly Tyr Val Pro Asp Cys Glu Asp Asn Leu Cys Gly Ser
65                  70                  75

<210> SEQ ID NO 47
<211> LENGTH: 77
<212> TYPE: PRT
<213> ORGANISM: Curvularia clavata

<400> SEQUENCE: 47

Met Ser Asn Lys Lys Asn Glu Gly Leu Glu Lys Gly Gly Asn Gly Ser
1               5                   10                  15

Ala Glu His Glu Ser Phe Leu Pro Lys Ser Ala Leu His Tyr Arg Ala
                20                  25                  30

Arg Val Asp Gly Gly Thr Ser Gly Leu Leu Ala Arg Leu Asp Asn Ser
            35                  40                  45

Pro Gly Ala Ala Val Leu Ala Tyr Cys Phe Ser Ser Val Ser Thr Leu
        50                  55                  60

Gly Tyr Val Pro Asp Cys Glu Asp Asn Leu Cys Gly Ser
65                  70                  75

<210> SEQ ID NO 48
<211> LENGTH: 4017
<212> TYPE: DNA
<213> ORGANISM: Curvularia clavata
<220> FEATURE:
<221> NAME/KEY: CDS
<222> LOCATION: (1)..(4017)
```

<400> SEQUENCE: 48

```
atg agt gct atc gag ctg ccg ccg ctg cgc tcg cgg tct gaa gaa gca      48
Met Ser Ala Ile Glu Leu Pro Pro Leu Arg Ser Arg Ser Glu Glu Ala
1               5                   10                  15 gcg agg gca gaa cac aat gcg cag aca ctc gca cac gaa aat gca aat      96
Ala Arg Ala Glu His Asn Ala Gln Thr Leu Ala His Glu Asn Ala Asn
            20                  25                  30 atc gcg ggc tat gat gag agc ccg gca gtc caa caa gtc gag acc gat     144
Ile Ala Gly Tyr Asp Glu Ser Pro Ala Val Gln Gln Val Glu Thr Asp
        35                  40                  45 gct cca gag act aaa gga gcc ccg cag gct tct ttc aag aat tac ttt     192
Ala Pro Glu Thr Lys Gly Ala Pro Gln Ala Ser Phe Lys Asn Tyr Phe
    50                  55                  60 cgt gtc ttt tca tat ggg aca aag ctt gac tac ttt tta att tcg cta     240
Arg Val Phe Ser Tyr Gly Thr Lys Leu Asp Tyr Phe Leu Ile Ser Leu
65                  70                  75                  80 tgt tgc ttt acg tct att gga gca ggt act gcg atg ccg ctg atg aac     288
Cys Cys Phe Thr Ser Ile Gly Ala Gly Thr Ala Met Pro Leu Met Asn
                85                  90                  95 att gtc ttt ggc aag ctc gta gga aat ttt aca gac tac ttc atc cca     336
Ile Val Phe Gly Lys Leu Val Gly Asn Phe Thr Asp Tyr Phe Ile Pro
            100                 105                 110 gga tca aat gtc acc cga caa gaa ttc gag gca gag att aac aaa cta     384
Gly Ser Asn Val Thr Arg Gln Glu Phe Glu Ala Glu Ile Asn Lys Leu
        115                 120                 125 gcc ctc tat atc ttc tac ctc ttc ata ggc aag ttt gcc atg tcg tac     432
Ala Leu Tyr Ile Phe Tyr Leu Phe Ile Gly Lys Phe Ala Met Ser Tyr
    130                 135                 140 att tcc atg ctc gca att cga atc agc ggt atg aga ata tcg gct gcg     480
Ile Ser Met Leu Ala Ile Arg Ile Ser Gly Met Arg Ile Ser Ala Ala
145                 150                 155                 160 ctt cgc ctg gca tac ctg cgt gca ctc ttc gcc cag cca gtg agc gtt     528
Leu Arg Leu Ala Tyr Leu Arg Ala Leu Phe Ala Gln Pro Val Ser Val
                165                 170                 175 atc gac acc gtc agt ccc ggc aag gtt gcc aat cgc atc acg acg tca     576
Ile Asp Thr Val Ser Pro Gly Lys Val Ala Asn Arg Ile Thr Thr Ser
            180                 185                 190 tcg aat atc gtc cag ctt gct atc tcg cag cat ttt gca acc ctg ttt     624
Ser Asn Ile Val Gln Leu Ala Ile Ser Gln His Phe Ala Thr Leu Phe
        195                 200                 205 cag tct ctt gcc ttc acc gtc gga tta tac gtg gtg gcg tta gta aaa     672
Gln Ser Leu Ala Phe Thr Val Gly Leu Tyr Val Val Ala Leu Val Lys
    210                 215                 220 ggg tgg aag ttg acg ctg atc gcc tcg acg ggt ctc cct ttc atc cta     720
Gly Trp Lys Leu Thr Leu Ile Ala Ser Thr Gly Leu Pro Phe Ile Leu
225                 230                 235                 240 atc gta tac ggc gcc atg ttc ccg ccc ttt ctc cgg atc cac cag atc     768
Ile Val Tyr Gly Ala Met Phe Pro Pro Phe Leu Arg Ile His Gln Ile
                245                 250                 255 acc gac aag ttc caa gag gaa gca tcg gct atg gcg tat gaa atg ttc     816
Thr Asp Lys Phe Gln Glu Glu Ala Ser Ala Met Ala Tyr Glu Met Phe
            260                 265                 270 tcc tcc att agg atg att gtc gcc ttt ggc acc gag tcg aga ctt gct     864
Ser Ser Ile Arg Met Ile Val Ala Phe Gly Thr Glu Ser Arg Leu Ala
        275                 280                 285 aag cag cac gga gtc atg ctc tcc aaa gct gca agc aat gag aaa aga     912
Lys Gln His Gly Val Met Leu Ser Lys Ala Ala Ser Asn Glu Lys Arg
    290                 295                 300
```

-continued

| | | |
|---|---|---|
| gct gcg ccg tta atg ggc ttg acc atg tct ccg gct atg gtg gcc atg<br>Ala Ala Pro Leu Met Gly Leu Thr Met Ser Pro Ala Met Val Ala Met<br>305                              310                          315                        320 | 960 |
| tac ggt atc ttc ggt atc acc ttc tgg ttc gga atc aag gaa tat aca<br>Tyr Gly Ile Phe Gly Ile Thr Phe Trp Phe Gly Ile Lys Glu Tyr Thr<br>325                           330                         335 | 1008 |
| aaa ggg aga atc tca agc gtc ggc gac atc acc gtt gtg ctc ttc tca<br>Lys Gly Arg Ile Ser Ser Val Gly Asp Ile Thr Val Val Leu Phe Ser<br>                  340                        345                        350 | 1056 |
| gtc atg atg gcc gta atg aat att ggg cga gtc gcg tct ccg att ata<br>Val Met Met Ala Val Met Asn Ile Gly Arg Val Ala Ser Pro Ile Ile<br>                355                        360                       365 | 1104 |
| tcc atc gca aaa gcc gcg act gct gcg acc gag ctc ttt gtc aca atc<br>Ser Ile Ala Lys Ala Ala Thr Ala Ala Thr Glu Leu Phe Val Thr Ile<br>370                              375                          380 | 1152 |
| gac gct tcg ttc cac gat aca tct ggt gtc atg gag ccc gag gtt aca<br>Asp Ala Ser Phe His Asp Thr Ser Gly Val Met Glu Pro Glu Val Thr<br>385                              390                          395                       400 | 1200 |
| ggt aat gct gct atc act ttc atc aat gtt gct ttt tcg tac ccc agc<br>Gly Asn Ala Ala Ile Thr Phe Ile Asn Val Ala Phe Ser Tyr Pro Ser<br>                          405                        410                       415 | 1248 |
| cgg ccg ggt gtc cca att ctc aag gga ctt gat ttg aca att act gct<br>Arg Pro Gly Val Pro Ile Leu Lys Gly Leu Asp Leu Thr Ile Thr Ala<br>                  420                        425                       430 | 1296 |
| ggc aaa gtc act gcc att gta ggt cca tcg ggg tcc ggg aaa agc acg<br>Gly Lys Val Thr Ala Ile Val Gly Pro Ser Gly Ser Gly Lys Ser Thr<br>                435                        440                       445 | 1344 |
| att gtt ggc ctt atc caa cga tgg tac gac ctt ctc ggc aca aca gct<br>Ile Val Gly Leu Ile Gln Arg Trp Tyr Asp Leu Leu Gly Thr Thr Ala<br>              450                        455                       460 | 1392 |
| act gct aag aaa atc gac gag aca gag att cct tca tca tcc act atg<br>Thr Ala Lys Lys Ile Asp Glu Thr Glu Ile Pro Ser Ser Ser Thr Met<br>465                              470                          475                       480 | 1440 |
| gcg tcc agc cca ata gaa gca gtc tat gac aat aca gac aag aaa tcc<br>Ala Ser Ser Pro Ile Glu Ala Val Tyr Asp Asn Thr Asp Lys Lys Ser<br>                          485                        490                       495 | 1488 |
| aaa aag ggg aag gcc ggg gaa gaa gaa gaa cca gaa caa gat ctc ggg<br>Lys Lys Gly Lys Ala Gly Glu Glu Glu Glu Pro Glu Gln Asp Leu Gly<br>                  500                        505                       510 | 1536 |
| cca aat acg tgc act ggc tcg ttg agt gtt ggt aga aca aat ctt cgt<br>Pro Asn Thr Cys Thr Gly Ser Leu Ser Val Gly Arg Thr Asn Leu Arg<br>              515                        520                       525 | 1584 |
| aat gtg gat gta agg tgg tgg cgt tcg caa atc ggc atg gtc cag cag<br>Asn Val Asp Val Arg Trp Trp Arg Ser Gln Ile Gly Met Val Gln Gln<br>530                              535                         540 | 1632 |
| gag cct ttc ctg ttc aat gat aca ata tac aac aat att gtg ttt gga<br>Glu Pro Phe Leu Phe Asn Asp Thr Ile Tyr Asn Asn Ile Val Phe Gly<br>545                              550                          555                       560 | 1680 |
| ctc tgc ggg acc cgt tat gaa gga ctg tcc aaa gat gaa aag aaa ata<br>Leu Cys Gly Thr Arg Tyr Glu Gly Leu Ser Lys Asp Glu Lys Lys Ile<br>                          565                        570                       575 | 1728 |
| atg gtc gat gag gcg tgt cgc gag gct tgc gcg gag gag ttt atc tcg<br>Met Val Asp Glu Ala Cys Arg Glu Ala Cys Ala Glu Glu Phe Ile Ser<br>                  580                        585                       590 | 1776 |
| cgg ctc cca caa ggg ttg gac acg ctt gtg ggc gag agc ggc atc aaa<br>Arg Leu Pro Gln Gly Leu Asp Thr Leu Val Gly Glu Ser Gly Ile Lys<br>              595                        600                       605 | 1824 |
| ctt tct ggt ggc cag cgt cag cgt atc gcc att gcc agg agt att atc<br>Leu Ser Gly Gly Gln Arg Gln Arg Ile Ala Ile Ala Arg Ser Ile Ile<br>610                              615                          620 | 1872 |

```
aaa cga ccg cct att ctc att cta gac gag gca acg agt gcc atc gat    1920
Lys Arg Pro Pro Ile Leu Ile Leu Asp Glu Ala Thr Ser Ala Ile Asp
625             630                 635                 640 gtc aga acg gag cga att gtt caa gaa gcg ctt gat cgt gtt tct aag    1968
Val Arg Thr Glu Arg Ile Val Gln Glu Ala Leu Asp Arg Val Ser Lys
                645                 650                 655 aac cgt acc acg att gtc atc gca cat cgc cta tcc aca atc aaa cgg    2016
Asn Arg Thr Thr Ile Val Ile Ala His Arg Leu Ser Thr Ile Lys Arg
            660                 665                 670 gcg gac agc ata gtc gtc tta cgg cag ggc cag ctg gtt gag caa ggc    2064
Ala Asp Ser Ile Val Val Leu Arg Gln Gly Gln Leu Val Glu Gln Gly
        675                 680                 685 acg cat gaa gag ctg ctg aaa aac gga gat ggg gtc tat tac ggc tta    2112
Thr His Glu Glu Leu Leu Lys Asn Gly Asp Gly Val Tyr Tyr Gly Leu
    690                 695                 700 gtt cat gcc caa gag ctg gaa atg gac gct gaa gac gat gat gac cac    2160
Val His Ala Gln Glu Leu Glu Met Asp Ala Glu Asp Asp Asp Asp His
705                 710                 715                 720 agc tca agc tta gag aac atc aaa atg aac gac act aag gag gac act    2208
Ser Ser Ser Leu Glu Asn Ile Lys Met Asn Asp Thr Lys Glu Asp Thr
                725                 730                 735 gct agt agc gga ttc gag gga cac gct tct aga gaa gat tca aca tat    2256
Ala Ser Ser Gly Phe Glu Gly His Ala Ser Arg Glu Asp Ser Thr Tyr
            740                 745                 750 cag aat gta ggt cta ctt cac agt ctc ggt cga ctt gtt gta gag caa    2304
Gln Asn Val Gly Leu Leu His Ser Leu Gly Arg Leu Val Val Glu Gln
        755                 760                 765 cgt cac cat tgg atc ctc tac agc gtt tgc tgc ata ggc ata ctc gga    2352
Arg His His Trp Ile Leu Tyr Ser Val Cys Cys Ile Gly Ile Leu Gly
    770                 775                 780 gcc ggc gca gtc tac cca ctc caa gcg tac att ttc gca agg att atc    2400
Ala Gly Ala Val Tyr Pro Leu Gln Ala Tyr Ile Phe Ala Arg Ile Ile
785                 790                 795                 800 aac gtc ttc aca ctt aca ggt ccc gag ctc gtc aaa caa ggc aac ttc    2448
Asn Val Phe Thr Leu Thr Gly Pro Glu Leu Val Lys Gln Gly Asn Phe
                805                 810                 815 tgg gca ggc atg ttc ggc gta ctt gcg ggt ggg gtt gga ctg tcg tac    2496
Trp Ala Gly Met Phe Gly Val Leu Ala Gly Gly Val Gly Leu Ser Tyr
            820                 825                 830 tat ctg ctt ggt gct gcc tca cat cta att tct gtc gaa tta aca cgc    2544
Tyr Leu Leu Gly Ala Ala Ser His Leu Ile Ser Val Glu Leu Thr Arg
        835                 840                 845 aag tat cga tca gaa tac ctc agc aac atg atc cga aaa cca atc ctc    2592
Lys Tyr Arg Ser Glu Tyr Leu Ser Asn Met Ile Arg Lys Pro Ile Leu
    850                 855                 860 ttt ttt gac gat aaa gtt cac agc cca ggc tct ctt acg tca aga ctg    2640
Phe Phe Asp Asp Lys Val His Ser Pro Gly Ser Leu Thr Ser Arg Leu
865                 870                 875                 880 agc tcg gac agt caa cag gtc cag cag ttg ttg tcg atg gag atg agc    2688
Ser Ser Asp Ser Gln Gln Val Gln Gln Leu Leu Ser Met Glu Met Ser
                885                 890                 895 atg gcg ctc att gcc tgc acc aac ctt ctc gga tgt aca att atc gcc    2736
Met Ala Leu Ile Ala Cys Thr Asn Leu Leu Gly Cys Thr Ile Ile Ala
            900                 905                 910 ttc gtt tac ggc tgg aag ctt tcc ctt gtt ggt tta ttt gct gcc ttg    2784
Phe Val Tyr Gly Trp Lys Leu Ser Leu Val Gly Leu Phe Ala Ala Leu
        915                 920                 925 cct ctc att ctt ggt gcc gga ctc gtg cgc acg cgt ctc gag ata caa    2832
Pro Leu Ile Leu Gly Ala Gly Leu Val Arg Thr Arg Leu Glu Ile Gln
```

-continued

| | | | | | | | | | | | | |
|---|---|---|---|---|---|---|---|---|---|---|---|---|
| | | 930 | | | 935 | | | 940 | | | | |
| ctc | gag | gct | gag | aac | gca | aaa | gtt | ttc | gag | aac | agc | agc cag ttt gcc | 2880 |
| Leu | Glu | Ala | Glu | Asn | Ala | Lys | Val | Phe | Glu | Asn | Ser | Ser Gln Phe Ala |
| 945 | | | | 950 | | | | 955 | | | | 960 |

```
ctc gag gct gag aac gca aaa gtt ttc gag aac agc agc cag ttt gcc    2880
Leu Glu Ala Glu Asn Ala Lys Val Phe Glu Asn Ser Ser Gln Phe Ala
945                 950                 955                 960 aca gaa gcg gtg gca ggt ttc cgc act gtg cta agt ctg ctc atg gag    2928
Thr Glu Ala Val Ala Gly Phe Arg Thr Val Leu Ser Leu Leu Met Glu
                965                 970                 975 ccg atg att aga agc cgc tac gac aag ttg ctc aag ggc cac gtt gtg    2976
Pro Met Ile Arg Ser Arg Tyr Asp Lys Leu Leu Lys Gly His Val Val
            980                 985                 990 gaa gct ttg gcc aag gca aaa tat ggt acc atc att ttc gct gca agt    3024
Glu Ala Leu Ala Lys Ala Lys Tyr Gly Thr Ile Ile Phe Ala Ala Ser
        995                 1000                1005 gac agt ctt gag ctt gca tgt atg tct ctg acc ttc tgg tac ggc        3069
Asp Ser Leu Glu Leu Ala Cys Met Ser Leu Thr Phe Trp Tyr Gly
    1010                1015                1020 gga aaa ctc ctt gcg tct cgt gaa tat gat ctc att cag ttc ttc        3114
Gly Lys Leu Leu Ala Ser Arg Glu Tyr Asp Leu Ile Gln Phe Phe
1025                1030                1035 att gtc tac acg gcc atc att caa ggc gct acg gca gca gga atc        3159
Ile Val Tyr Thr Ala Ile Ile Gln Gly Ala Thr Ala Ala Gly Ile
    1040                1045                1050 tgg ttc tct ttt act cca agc atg gct caa gcg aca ggt gct gca        3204
Trp Phe Ser Phe Thr Pro Ser Met Ala Gln Ala Thr Gly Ala Ala
1055                1060                1065 aac cga atc ctt agc atg cgg ccg aca tcg acg gat cca tca tct        3249
Asn Arg Ile Leu Ser Met Arg Pro Thr Ser Thr Asp Pro Ser Ser
1070                1075                1080 tac tcg cct ctt cca tgc tca gat gag gga gtg ggc att gaa ttt        3294
Tyr Ser Pro Leu Pro Cys Ser Asp Glu Gly Val Gly Ile Glu Phe
    1085                1090                1095 caa cac gtc tcc ttc aaa tac cag tct cga gac gtg ccc gtt ctt        3339
Gln His Val Ser Phe Lys Tyr Gln Ser Arg Asp Val Pro Val Leu
1100                1105                1110 tcc aac ctc aat ctg caa atc cta ccg ggt cag gtt gct gcg tta        3384
Ser Asn Leu Asn Leu Gln Ile Leu Pro Gly Gln Val Ala Ala Leu
1115                1120                1125 gta ggc agt agt ggc tgt ggt aaa tca aca aca ctg tct ctt ctc        3429
Val Gly Ser Ser Gly Cys Gly Lys Ser Thr Thr Leu Ser Leu Leu
1130                1135                1140 gaa cgc ttc tac gat gcg agt tcg ggc cat att cta tac aac ggg        3474
Glu Arg Phe Tyr Asp Ala Ser Ser Gly His Ile Leu Tyr Asn Gly
    1145                1150                1155 caa gac atc acc acg ttc agc ccg gca gag tac cgg aaa caa atg        3519
Gln Asp Ile Thr Thr Phe Ser Pro Ala Glu Tyr Arg Lys Gln Met
1160                1165                1170 agc ctg gtg agc caa gag ccc acg ctc tac caa ggc agc att cga        3564
Ser Leu Val Ser Gln Glu Pro Thr Leu Tyr Gln Gly Ser Ile Arg
1175                1180                1185 gaa aac ata tct ctg agt gta gag tct gca tcc gac gac gac atc        3609
Glu Asn Ile Ser Leu Ser Val Glu Ser Ala Ser Asp Asp Asp Ile
1190                1195                1200 aaa cag gcc tgc cgt gat gcg caa att cat gac ttc atc acc tcg        3654
Lys Gln Ala Cys Arg Asp Ala Gln Ile His Asp Phe Ile Thr Ser
1205                1210                1215 ctt cca gaa ggc tac gag acg cgc ttg gga ccg aaa gga atg tct        3699
Leu Pro Glu Gly Tyr Glu Thr Arg Leu Gly Pro Lys Gly Met Ser
    1220                1225                1230 ctc tca ggt ggt caa aga cag cga atc tct ctt gcc agg gcg ctg        3744
```

```
Leu Ser Gly Gly Gln Arg Gln Arg Ile Ser Leu Ala Arg Ala Leu
    1235                1240                1245 ttg cgc aaa cca aaa atc cta ctc ctc gat gaa gca acc agc tcg    3789
Leu Arg Lys Pro Lys Ile Leu Leu Leu Asp Glu Ala Thr Ser Ser
    1250                1255                1260 cta gat tca gag agc gag aaa tac gtc cag gaa gct atc gag cga    3834
Leu Asp Ser Glu Ser Glu Lys Tyr Val Gln Glu Ala Ile Glu Arg
    1265                1270                1275 gct gca agc gag ggt gac aga acc gtc ata att gtt gcg cat agg    3879
Ala Ala Ser Glu Gly Asp Arg Thr Val Ile Ile Val Ala His Arg
    1280                1285                1290 ctg gct aca att cag aag gcg gat gtt atc ttt gta ctg ggc agt    3924
Leu Ala Thr Ile Gln Lys Ala Asp Val Ile Phe Val Leu Gly Ser
    1295                1300                1305 gga aag gtg cta gag aag ggg gat cat cag gca ctg ctc cgg aaa    3969
Gly Lys Val Leu Glu Lys Gly Asp His Gln Ala Leu Leu Arg Lys
    1310                1315                1320 aag ggc gtg tac tgg cag atg tgt caa gcc cag gcc ctc aat cgc    4014
Lys Gly Val Tyr Trp Gln Met Cys Gln Ala Gln Ala Leu Asn Arg
    1325                1330                1335 tga                                                             4017
```

<210> SEQ ID NO 49
<211> LENGTH: 1338
<212> TYPE: PRT
<213> ORGANISM: Curvularia clavata

<400> SEQUENCE: 49

```
Met Ser Ala Ile Glu Leu Pro Pro Leu Arg Ser Arg Ser Glu Glu Ala
1               5                   10                  15

Ala Arg Ala Glu His Asn Ala Gln Thr Leu Ala His Glu Asn Ala Asn
            20                  25                  30

Ile Ala Gly Tyr Asp Glu Ser Pro Ala Val Gln Gln Val Glu Thr Asp
        35                  40                  45

Ala Pro Glu Thr Lys Gly Ala Pro Gln Ala Ser Phe Lys Asn Tyr Phe
    50                  55                  60

Arg Val Phe Ser Tyr Gly Thr Lys Leu Asp Tyr Phe Leu Ile Ser Leu
65                  70                  75                  80

Cys Cys Phe Thr Ser Ile Gly Ala Gly Thr Ala Met Pro Leu Met Asn
                85                  90                  95

Ile Val Phe Gly Lys Leu Val Gly Asn Phe Thr Asp Tyr Phe Ile Pro
            100                 105                 110

Gly Ser Asn Val Thr Arg Gln Glu Phe Glu Ala Glu Ile Asn Lys Leu
        115                 120                 125

Ala Leu Tyr Ile Phe Tyr Leu Phe Ile Gly Lys Phe Ala Met Ser Tyr
    130                 135                 140

Ile Ser Met Leu Ala Ile Arg Ile Ser Gly Met Arg Ile Ser Ala Ala
145                 150                 155                 160

Leu Arg Leu Ala Tyr Leu Arg Ala Leu Phe Ala Gln Pro Val Ser Val
                165                 170                 175

Ile Asp Thr Val Ser Pro Gly Lys Val Ala Asn Arg Ile Thr Thr Ser
            180                 185                 190

Ser Asn Ile Val Gln Leu Ala Ile Ser Gln His Phe Ala Thr Leu Phe
        195                 200                 205

Gln Ser Leu Ala Phe Thr Val Gly Leu Tyr Val Val Ala Leu Val Lys
    210                 215                 220
```

-continued

```
Gly Trp Lys Leu Thr Leu Ile Ala Ser Thr Gly Leu Pro Phe Ile Leu
225                 230                 235                 240

Ile Val Tyr Gly Ala Met Phe Pro Pro Phe Leu Arg Ile His Gln Ile
            245                 250                 255

Thr Asp Lys Phe Gln Glu Glu Ala Ser Ala Met Ala Tyr Glu Met Phe
        260                 265                 270

Ser Ser Ile Arg Met Ile Val Ala Phe Gly Thr Glu Ser Arg Leu Ala
    275                 280                 285

Lys Gln His Gly Val Met Leu Ser Lys Ala Ala Ser Asn Glu Lys Arg
290                 295                 300

Ala Ala Pro Leu Met Gly Leu Thr Met Ser Pro Ala Met Val Ala Met
305                 310                 315                 320

Tyr Gly Ile Phe Gly Ile Thr Phe Trp Phe Gly Ile Lys Glu Tyr Thr
            325                 330                 335

Lys Gly Arg Ile Ser Ser Val Gly Asp Ile Thr Val Val Leu Phe Ser
        340                 345                 350

Val Met Met Ala Val Met Asn Ile Gly Arg Val Ala Ser Pro Ile Ile
    355                 360                 365

Ser Ile Ala Lys Ala Ala Thr Ala Ala Thr Glu Leu Phe Val Thr Ile
370                 375                 380

Asp Ala Ser Phe His Asp Thr Ser Gly Val Met Glu Pro Glu Val Thr
385                 390                 395                 400

Gly Asn Ala Ala Ile Thr Phe Ile Asn Val Ala Phe Ser Tyr Pro Ser
            405                 410                 415

Arg Pro Gly Val Pro Ile Leu Lys Gly Leu Asp Leu Thr Ile Thr Ala
        420                 425                 430

Gly Lys Val Thr Ala Ile Val Gly Pro Ser Gly Ser Gly Lys Ser Thr
    435                 440                 445

Ile Val Gly Leu Ile Gln Arg Trp Tyr Asp Leu Leu Gly Thr Thr Ala
450                 455                 460

Thr Ala Lys Lys Ile Asp Glu Thr Glu Ile Pro Ser Ser Ser Thr Met
465                 470                 475                 480

Ala Ser Ser Pro Ile Glu Ala Val Tyr Asp Asn Thr Asp Lys Lys Ser
            485                 490                 495

Lys Lys Gly Lys Ala Gly Glu Glu Glu Pro Glu Gln Asp Leu Gly
        500                 505                 510

Pro Asn Thr Cys Thr Gly Ser Leu Ser Val Gly Arg Thr Asn Leu Arg
    515                 520                 525

Asn Val Asp Val Arg Trp Trp Arg Ser Gln Ile Gly Met Val Gln Gln
530                 535                 540

Glu Pro Phe Leu Phe Asn Asp Thr Ile Tyr Asn Asn Ile Val Phe Gly
545                 550                 555                 560

Leu Cys Gly Thr Arg Tyr Glu Gly Leu Ser Lys Asp Glu Lys Lys Ile
            565                 570                 575

Met Val Asp Glu Ala Cys Arg Glu Ala Cys Ala Glu Glu Phe Ile Ser
        580                 585                 590

Arg Leu Pro Gln Gly Leu Asp Thr Leu Val Gly Glu Ser Gly Ile Lys
    595                 600                 605

Leu Ser Gly Gly Gln Arg Gln Arg Ile Ala Ile Ala Arg Ser Ile Ile
610                 615                 620

Lys Arg Pro Pro Ile Leu Ile Leu Asp Glu Ala Thr Ser Ala Ile Asp
625                 630                 635                 640

Val Arg Thr Glu Arg Ile Val Gln Glu Ala Leu Asp Arg Val Ser Lys
```

```
                    645                 650                 655
Asn Arg Thr Thr Ile Val Ile Ala His Arg Leu Ser Thr Ile Lys Arg
                660                 665                 670

Ala Asp Ser Ile Val Val Leu Arg Gln Gly Gln Leu Val Glu Gln Gly
                675                 680                 685

Thr His Glu Glu Leu Leu Lys Asn Gly Asp Gly Val Tyr Tyr Gly Leu
                690                 695                 700

Val His Ala Gln Glu Leu Glu Met Asp Ala Glu Asp Asp Asp His
705                 710                 715                 720

Ser Ser Ser Leu Glu Asn Ile Lys Met Asn Asp Thr Lys Glu Asp Thr
                725                 730                 735

Ala Ser Ser Gly Phe Glu Gly His Ala Ser Arg Glu Asp Ser Thr Tyr
                740                 745                 750

Gln Asn Val Gly Leu Leu His Ser Leu Gly Arg Leu Val Val Glu Gln
                755                 760                 765

Arg His His Trp Ile Leu Tyr Ser Val Cys Cys Ile Gly Ile Leu Gly
                770                 775                 780

Ala Gly Ala Val Tyr Pro Leu Gln Ala Tyr Ile Phe Ala Arg Ile Ile
785                 790                 795                 800

Asn Val Phe Thr Leu Thr Gly Pro Glu Leu Val Lys Gln Gly Asn Phe
                805                 810                 815

Trp Ala Gly Met Phe Gly Val Leu Ala Gly Gly Val Gly Leu Ser Tyr
                820                 825                 830

Tyr Leu Leu Gly Ala Ala Ser His Leu Ile Ser Val Glu Leu Thr Arg
                835                 840                 845

Lys Tyr Arg Ser Glu Tyr Leu Ser Asn Met Ile Arg Lys Pro Ile Leu
                850                 855                 860

Phe Phe Asp Asp Lys Val His Ser Pro Gly Ser Leu Thr Ser Arg Leu
865                 870                 875                 880

Ser Ser Asp Ser Gln Gln Val Gln Gln Leu Leu Ser Met Glu Met Ser
                885                 890                 895

Met Ala Leu Ile Ala Cys Thr Asn Leu Leu Gly Cys Thr Ile Ile Ala
                900                 905                 910

Phe Val Tyr Gly Trp Lys Leu Ser Leu Val Gly Leu Phe Ala Ala Leu
                915                 920                 925

Pro Leu Ile Leu Gly Ala Gly Leu Val Arg Thr Arg Leu Glu Ile Gln
                930                 935                 940

Leu Glu Ala Glu Asn Ala Lys Val Phe Glu Asn Ser Ser Gln Phe Ala
945                 950                 955                 960

Thr Glu Ala Val Ala Gly Phe Arg Thr Val Leu Ser Leu Leu Met Glu
                965                 970                 975

Pro Met Ile Arg Ser Arg Tyr Asp Lys Leu Leu Lys Gly His Val Val
                980                 985                 990

Glu Ala Leu Ala Lys Ala Lys Tyr Gly Thr Ile Ile Phe Ala Ala Ser
                995                 1000                1005

Asp Ser Leu Glu Leu Ala Cys Met Ser Leu Thr Phe Trp Tyr Gly
                1010                1015                1020

Gly Lys Leu Leu Ala Ser Arg Glu Tyr Asp Leu Ile Gln Phe Phe
                1025                1030                1035

Ile Val Tyr Thr Ala Ile Ile Gln Gly Ala Thr Ala Ala Gly Ile
                1040                1045                1050

Trp Phe Ser Phe Thr Pro Ser Met Ala Gln Ala Thr Gly Ala Ala
                1055                1060                1065
```

```
Asn Arg Ile Leu Ser Met Arg Pro Thr Ser Thr Asp Pro Ser Ser
    1070            1075                1080

Tyr Ser Pro Leu Pro Cys Ser Asp Glu Gly Val Gly Ile Glu Phe
    1085            1090                1095

Gln His Val Ser Phe Lys Tyr Gln Ser Arg Asp Val Pro Val Leu
    1100            1105                1110

Ser Asn Leu Asn Leu Gln Ile Leu Pro Gly Gln Val Ala Ala Leu
    1115            1120                1125

Val Gly Ser Ser Gly Cys Gly Lys Ser Thr Thr Leu Ser Leu Leu
    1130            1135                1140

Glu Arg Phe Tyr Asp Ala Ser Ser Gly His Ile Leu Tyr Asn Gly
    1145            1150                1155

Gln Asp Ile Thr Thr Phe Ser Pro Ala Glu Tyr Arg Lys Gln Met
    1160            1165                1170

Ser Leu Val Ser Gln Glu Pro Thr Leu Tyr Gln Gly Ser Ile Arg
    1175            1180                1185

Glu Asn Ile Ser Leu Ser Val Glu Ser Ala Ser Asp Asp Ile
    1190            1195                1200

Lys Gln Ala Cys Arg Asp Ala Gln Ile His Asp Phe Ile Thr Ser
    1205            1210                1215

Leu Pro Glu Gly Tyr Glu Thr Arg Leu Gly Pro Lys Gly Met Ser
    1220            1225                1230

Leu Ser Gly Gly Gln Arg Gln Arg Ile Ser Leu Ala Arg Ala Leu
    1235            1240                1245

Leu Arg Lys Pro Lys Ile Leu Leu Leu Asp Glu Ala Thr Ser Ser
    1250            1255                1260

Leu Asp Ser Glu Ser Glu Lys Tyr Val Gln Glu Ala Ile Glu Arg
    1265            1270                1275

Ala Ala Ser Glu Gly Asp Arg Thr Val Ile Ile Val Ala His Arg
    1280            1285                1290

Leu Ala Thr Ile Gln Lys Ala Asp Val Ile Phe Val Leu Gly Ser
    1295            1300                1305

Gly Lys Val Leu Glu Lys Gly Asp His Gln Ala Leu Leu Arg Lys
    1310            1315                1320

Lys Gly Val Tyr Trp Gln Met Cys Gln Ala Gln Ala Leu Asn Arg
    1325            1330                1335

<210> SEQ ID NO 50
<211> LENGTH: 1047
<212> TYPE: DNA
<213> ORGANISM: Curvularia clavata
<220> FEATURE:
<221> NAME/KEY: CDS
<222> LOCATION: (1)..(1047)

<400> SEQUENCE: 50 atg aag ctc acc gtt ttc agt gca aaa ccc tac gat atc gaa tac ctg      48
Met Lys Leu Thr Val Phe Ser Ala Lys Pro Tyr Asp Ile Glu Tyr Leu
1               5                   10                  15 ggt ggc atc gct act aat caa aac tcc tcg cct gca att gag atc aac      96
Gly Gly Ile Ala Thr Asn Gln Asn Ser Ser Pro Ala Ile Glu Ile Asn
            20                  25                  30 ttc ctg cat gtc ccg ctc tcc agc gag acg gcc gcg ttc gcg aac ggc     144
Phe Leu His Val Pro Leu Ser Ser Glu Thr Ala Ala Phe Ala Asn Gly
        35                  40                  45 gct gat gcc gtc tgc gtc ttc gtt cac gat gtg ctt gac gcc aac gtc     192
```

```
                Ala Asp Ala Val Cys Val Phe Val His Asp Val Leu Asp Ala Asn Val
                    50                  55                  60 ctc cgc gaa cta tac gcc gcc ggc gtg cgc gcc att ctc ttc cgc tgc            240
Leu Arg Glu Leu Tyr Ala Ala Gly Val Arg Ala Ile Leu Phe Arg Cys
 65                  70                  75                  80 tca ggg tat aac aat att gac cta agg gag gct gag cgc tta ggc ttc            288
Ser Gly Tyr Asn Asn Ile Asp Leu Arg Glu Ala Glu Arg Leu Gly Phe
                     85                  90                  95 ttc gtc gcc aac gtc cct tcg tac tcg ccg gag gca gtc gcc gag ttc            336
Phe Val Ala Asn Val Pro Ser Tyr Ser Pro Glu Ala Val Ala Glu Phe
                100                 105                 110 gca gtc gcg ctc atc caa aca ctt aac cgg aag acg cac cgg gca tac            384
Ala Val Ala Leu Ile Gln Thr Leu Asn Arg Lys Thr His Arg Ala Tyr
            115                 120                 125 aac cgc gtg cgg gac ggc aat ttc aac ctc gac ggc cta ctc gga cga            432
Asn Arg Val Arg Asp Gly Asn Phe Asn Leu Asp Gly Leu Leu Gly Arg
        130                 135                 140 aca cta cac ggc aaa aca gtc ggc att gta ggg tca ggc cgg atc gga            480
Thr Leu His Gly Lys Thr Val Gly Ile Val Gly Ser Gly Arg Ile Gly
145                 150                 155                 160 ctc gcc atg gcg cag atc gtt cag ggc ttc gga tgc aag ctg ttg gca            528
Leu Ala Met Ala Gln Ile Val Gln Gly Phe Gly Cys Lys Leu Leu Ala
                165                 170                 175 tac gat cct cgg cct aca gaa gcc ttc aag aag tac ggc gaa tac gtg            576
Tyr Asp Pro Arg Pro Thr Glu Ala Phe Lys Lys Tyr Gly Glu Tyr Val
                180                 185                 190 gat ctc gat acg ctg ctg tca caa tgc gac att gta agc tta cac tgc            624
Asp Leu Asp Thr Leu Leu Ser Gln Cys Asp Ile Val Ser Leu His Cys
            195                 200                 205 ccg ctg atg gac tcg acg cag cac atc atc aac gac aca act gtc agc            672
Pro Leu Met Asp Ser Thr Gln His Ile Ile Asn Asp Thr Thr Val Ser
        210                 215                 220 aaa atg aag cgc ggc gcg atg ctc gtc aac acg tcg cgt ggc ggg ctg            720
Lys Met Lys Arg Gly Ala Met Leu Val Asn Thr Ser Arg Gly Gly Leu
225                 230                 235                 240 atc gac acg cag agc gtg atg aag gcg ctg aag agc aag cgt ctg ggc            768
Ile Asp Thr Gln Ser Val Met Lys Ala Leu Lys Ser Lys Arg Leu Gly
                245                 250                 255 ggg cta gcc ctc gac gtt tac gag ggc gag cgc gcg ctc ttc tac aaa            816
Gly Leu Ala Leu Asp Val Tyr Glu Gly Glu Arg Ala Leu Phe Tyr Lys
                260                 265                 270 gac cat tcg ggt gac atc atc cat gac gat ttg ctc atg cgc ctc acc            864
Asp His Ser Gly Asp Ile Ile His Asp Asp Leu Leu Met Arg Leu Thr
            275                 280                 285 acg ttt cac aac gtc gtt gtg tct ggc cac cag gcg tat ttc act gaa            912
Thr Phe His Asn Val Val Val Ser Gly His Gln Ala Tyr Phe Thr Glu
        290                 295                 300 gag gca ctc acg gaa att gcg gag tgt acg ctg agg aat ctg gat gat            960
Glu Ala Leu Thr Glu Ile Ala Glu Cys Thr Leu Arg Asn Leu Asp Asp
305                 310                 315                 320 tgg gcg aag gga gtg cca acg gcg aat gcg ctg gtg cag ggc agg aat           1008
Trp Ala Lys Gly Val Pro Thr Ala Asn Ala Leu Val Gln Gly Arg Asn
                325                 330                 335 tcg aat ggg agg agg gag cgg ggg ttg gcg cgg ctc tga                       1047
Ser Asn Gly Arg Arg Glu Arg Gly Leu Ala Arg Leu
                340                 345

<210> SEQ ID NO 51
<211> LENGTH: 348
<212> TYPE: PRT
```

<213> ORGANISM: Curvularia clavata

<400> SEQUENCE: 51

| Met | Lys | Leu | Thr | Val | Phe | Ser | Ala | Lys | Pro | Tyr | Asp | Ile | Glu | Tyr | Leu |
|---|---|---|---|---|---|---|---|---|---|---|---|---|---|---|---|
| 1 | | | | 5 | | | | | 10 | | | | | 15 | |

| Gly | Gly | Ile | Ala | Thr | Asn | Gln | Asn | Ser | Ser | Pro | Ala | Ile | Glu | Ile | Asn |
|---|---|---|---|---|---|---|---|---|---|---|---|---|---|---|---|
| | | | 20 | | | | | 25 | | | | | 30 | | |

| Phe | Leu | His | Val | Pro | Leu | Ser | Ser | Glu | Thr | Ala | Ala | Phe | Ala | Asn | Gly |
|---|---|---|---|---|---|---|---|---|---|---|---|---|---|---|---|
| | | | 35 | | | | | 40 | | | | | 45 | | |

| Ala | Asp | Ala | Val | Cys | Val | Phe | Val | His | Asp | Val | Leu | Asp | Ala | Asn | Val |
|---|---|---|---|---|---|---|---|---|---|---|---|---|---|---|---|
| | 50 | | | | | 55 | | | | | 60 | | | | |

| Leu | Arg | Glu | Leu | Tyr | Ala | Ala | Gly | Val | Arg | Ala | Ile | Leu | Phe | Arg | Cys |
|---|---|---|---|---|---|---|---|---|---|---|---|---|---|---|---|
| 65 | | | | | 70 | | | | | 75 | | | | | 80 |

| Ser | Gly | Tyr | Asn | Asn | Ile | Asp | Leu | Arg | Glu | Ala | Glu | Arg | Leu | Gly | Phe |
|---|---|---|---|---|---|---|---|---|---|---|---|---|---|---|---|
| | | | | 85 | | | | | 90 | | | | | 95 | |

| Phe | Val | Ala | Asn | Val | Pro | Ser | Tyr | Ser | Pro | Glu | Ala | Val | Ala | Glu | Phe |
|---|---|---|---|---|---|---|---|---|---|---|---|---|---|---|---|
| | | | 100 | | | | | 105 | | | | | 110 | | |

| Ala | Val | Ala | Leu | Ile | Gln | Thr | Leu | Asn | Arg | Lys | Thr | His | Arg | Ala | Tyr |
|---|---|---|---|---|---|---|---|---|---|---|---|---|---|---|---|
| | | | 115 | | | | | 120 | | | | | 125 | | |

| Asn | Arg | Val | Arg | Asp | Gly | Asn | Phe | Asn | Leu | Asp | Gly | Leu | Leu | Gly | Arg |
|---|---|---|---|---|---|---|---|---|---|---|---|---|---|---|---|
| | 130 | | | | | 135 | | | | | 140 | | | | |

| Thr | Leu | His | Gly | Lys | Thr | Val | Gly | Ile | Val | Gly | Ser | Gly | Arg | Ile | Gly |
|---|---|---|---|---|---|---|---|---|---|---|---|---|---|---|---|
| 145 | | | | | 150 | | | | | 155 | | | | | 160 |

| Leu | Ala | Met | Ala | Gln | Ile | Val | Gln | Gly | Phe | Gly | Cys | Lys | Leu | Leu | Ala |
|---|---|---|---|---|---|---|---|---|---|---|---|---|---|---|---|
| | | | | 165 | | | | | 170 | | | | | 175 | |

| Tyr | Asp | Pro | Arg | Pro | Thr | Glu | Ala | Phe | Lys | Lys | Tyr | Gly | Glu | Tyr | Val |
|---|---|---|---|---|---|---|---|---|---|---|---|---|---|---|---|
| | | | | 180 | | | | | 185 | | | | | 190 | |

| Asp | Leu | Asp | Thr | Leu | Leu | Ser | Gln | Cys | Asp | Ile | Val | Ser | Leu | His | Cys |
|---|---|---|---|---|---|---|---|---|---|---|---|---|---|---|---|
| | | | 195 | | | | | 200 | | | | | 205 | | |

| Pro | Leu | Met | Asp | Ser | Thr | Gln | His | Ile | Ile | Asn | Asp | Thr | Thr | Val | Ser |
|---|---|---|---|---|---|---|---|---|---|---|---|---|---|---|---|
| | 210 | | | | | 215 | | | | | 220 | | | | |

| Lys | Met | Lys | Arg | Gly | Ala | Met | Leu | Val | Asn | Thr | Ser | Arg | Gly | Gly | Leu |
|---|---|---|---|---|---|---|---|---|---|---|---|---|---|---|---|
| 225 | | | | | 230 | | | | | 235 | | | | | 240 |

| Ile | Asp | Thr | Gln | Ser | Val | Met | Lys | Ala | Leu | Lys | Ser | Lys | Arg | Leu | Gly |
|---|---|---|---|---|---|---|---|---|---|---|---|---|---|---|---|
| | | | | 245 | | | | | 250 | | | | | 255 | |

| Gly | Leu | Ala | Leu | Asp | Val | Tyr | Glu | Gly | Glu | Arg | Ala | Leu | Phe | Tyr | Lys |
|---|---|---|---|---|---|---|---|---|---|---|---|---|---|---|---|
| | | | 260 | | | | | 265 | | | | | 270 | | |

| Asp | His | Ser | Gly | Asp | Ile | Ile | His | Asp | Leu | Leu | Met | Arg | Leu | Thr |
|---|---|---|---|---|---|---|---|---|---|---|---|---|---|---|
| | | 275 | | | | | 280 | | | | | 285 | | |

| Thr | Phe | His | Asn | Val | Val | Ser | Gly | His | Gln | Ala | Tyr | Phe | Thr | Glu |
|---|---|---|---|---|---|---|---|---|---|---|---|---|---|---|
| | 290 | | | | | 295 | | | | | 300 | | | |

| Glu | Ala | Leu | Thr | Glu | Ile | Ala | Glu | Cys | Thr | Leu | Arg | Asn | Leu | Asp | Asp |
|---|---|---|---|---|---|---|---|---|---|---|---|---|---|---|---|
| 305 | | | | | 310 | | | | | 315 | | | | | 320 |

| Trp | Ala | Lys | Gly | Val | Pro | Thr | Ala | Asn | Ala | Leu | Val | Gln | Gly | Arg | Asn |
|---|---|---|---|---|---|---|---|---|---|---|---|---|---|---|---|
| | | | | 325 | | | | | 330 | | | | | 335 | |

| Ser | Asn | Gly | Arg | Arg | Glu | Arg | Gly | Leu | Ala | Arg | Leu |
|---|---|---|---|---|---|---|---|---|---|---|---|
| | | | 340 | | | | | 345 | | | |

<210> SEQ ID NO 52
<211> LENGTH: 936
<212> TYPE: DNA
<213> ORGANISM: Curvularia clavata
<220> FEATURE:
<221> NAME/KEY: CDS
<222> LOCATION: (1)..(936)

```
<400> SEQUENCE: 52 atg acg aaa agg gaa agc aac act cta gcg gtt ctc gga tgc ggt atg       48
Met Thr Lys Arg Glu Ser Asn Thr Leu Ala Val Leu Gly Cys Gly Met
1               5                  10                  15 gtt ttt ctt gta tca tta tta gat ctg gct aac aga ctg tta ggt gcg       96
Val Phe Leu Val Ser Leu Leu Asp Leu Ala Asn Arg Leu Leu Gly Ala
            20                  25                  30 ctt ggc acc gcc att ctc tca ggc ata ctt gct tct atg gca gat cag      144
Leu Gly Thr Ala Ile Leu Ser Gly Ile Leu Ala Ser Met Ala Asp Gln
        35                  40                  45 aca gcc gat gat tcg ggt cgc ctg ttt acg aat ttc act gcc tgt gtg      192
Thr Ala Asp Asp Ser Gly Arg Leu Phe Thr Asn Phe Thr Ala Cys Val
    50                  55                  60 cgt cgc aaa gag acc ggt gct gct gtt agt gat aag atc agt tcg cac      240
Arg Arg Lys Glu Thr Gly Ala Ala Val Ser Asp Lys Ile Ser Ser His
65                  70                  75                  80 gcc aat gca aac aaa gtc gag ata ttg aac aag gaa aat cta cgg ggc      288
Ala Asn Ala Asn Lys Val Glu Ile Leu Asn Lys Glu Asn Leu Arg Gly
                85                  90                  95 gtc aag caa gca gat gct gtt ctc tta gcc tgc caa acg cac cta tac      336
Val Lys Gln Ala Asp Ala Val Leu Leu Ala Cys Gln Thr His Leu Tyr
            100                 105                 110 aaa gct ctg ttc gac gag cca ggg atg cga gag gca ctg aag aag aaa      384
Lys Ala Leu Phe Asp Glu Pro Gly Met Arg Glu Ala Leu Lys Lys Lys
        115                 120                 125 ctg atc atc agc gtg ctg gct ggt gtt acc aca gca caa ctc gaa gca      432
Leu Ile Ile Ser Val Leu Ala Gly Val Thr Thr Ala Gln Leu Glu Ala
    130                 135                 140 gcg ctg ggg aat ggt gag gat tac ttt gta atc cga gct atg cca aat      480
Ala Leu Gly Asn Gly Glu Asp Tyr Phe Val Ile Arg Ala Met Pro Asn
145                 150                 155                 160 atc gca tgt ttt gta cga gat tct gca acc gtc atc gag aag cct cag      528
Ile Ala Cys Phe Val Arg Asp Ser Ala Thr Val Ile Glu Lys Pro Gln
                165                 170                 175 cga act ttc cca gag gca ttg ctt cac gtc acc gac acc gtc ttc aaa      576
Arg Thr Phe Pro Glu Ala Leu Leu His Val Thr Asp Thr Val Phe Lys
            180                 185                 190 gcc gtg ggc aac gtc ttt tac atc caa cca tct gcc tat gac ata tgt      624
Ala Val Gly Asn Val Phe Tyr Ile Gln Pro Ser Ala Tyr Asp Ile Cys
        195                 200                 205 act gct ctc tgt ggt tca tca ccc gca ttt ctt gca gta ttt att gac      672
Thr Ala Leu Cys Gly Ser Ser Pro Ala Phe Leu Ala Val Phe Ile Asp
    210                 215                 220 tct atg gtg gat ggt gcg gta gcc atg ggg cta agt cac aag gac gcg      720
Ser Met Val Asp Gly Ala Val Ala Met Gly Leu Ser His Lys Asp Ala
225                 230                 235                 240 gtc gac atg gcg gcc tgc aca atg agg gga gct gcc agt ttg gtg cta      768
Val Asp Met Ala Ala Cys Thr Met Arg Gly Ala Ala Ser Leu Val Leu
                245                 250                 255 gag agc ggc aat cct tgg acg ata cga cac cag gtg gcg tca cct gga      816
Glu Ser Gly Asn Pro Trp Thr Ile Arg His Gln Val Ala Ser Pro Gly
            260                 265                 270 ggc tcg acc atg cag ggt cta ctg gca ctt gaa caa gga aat gtg aga      864
Gly Ser Thr Met Gln Gly Leu Leu Ala Leu Glu Gln Gly Asn Val Arg
        275                 280                 285 tca acc atc tcc aac gcg ttg atg gtc gcc gcg aaa gaa gca aaa aag      912
Ser Thr Ile Ser Asn Ala Leu Met Val Ala Ala Lys Glu Ala Lys Lys
    290                 295                 300 ctg ggg tcg aaa gaa aac gcg tag                                      936
```

Leu Gly Ser Lys Glu Asn Ala
305                 310

<210> SEQ ID NO 53
<211> LENGTH: 311
<212> TYPE: PRT
<213> ORGANISM: Curvularia clavata

<400> SEQUENCE: 53

Met Thr Lys Arg Glu Ser Asn Thr Leu Ala Val Leu Gly Cys Gly Met
1               5                   10                  15

Val Phe Leu Val Ser Leu Leu Asp Leu Ala Asn Arg Leu Leu Gly Ala
            20                  25                  30

Leu Gly Thr Ala Ile Leu Ser Gly Ile Leu Ala Ser Met Ala Asp Gln
        35                  40                  45

Thr Ala Asp Asp Ser Gly Arg Leu Phe Thr Asn Phe Thr Ala Cys Val
    50                  55                  60

Arg Arg Lys Glu Thr Gly Ala Ala Val Ser Asp Lys Ile Ser Ser His
65                  70                  75                  80

Ala Asn Ala Asn Lys Val Glu Ile Leu Asn Lys Glu Asn Leu Arg Gly
                85                  90                  95

Val Lys Gln Ala Asp Ala Val Leu Leu Ala Cys Gln Thr His Leu Tyr
            100                 105                 110

Lys Ala Leu Phe Asp Glu Pro Gly Met Arg Glu Ala Leu Lys Lys Lys
        115                 120                 125

Leu Ile Ile Ser Val Leu Ala Gly Val Thr Thr Ala Gln Leu Glu Ala
    130                 135                 140

Ala Leu Gly Asn Gly Glu Asp Tyr Phe Val Ile Arg Ala Met Pro Asn
145                 150                 155                 160

Ile Ala Cys Phe Val Arg Asp Ser Ala Thr Val Ile Glu Lys Pro Gln
                165                 170                 175

Arg Thr Phe Pro Glu Ala Leu Leu His Val Thr Asp Thr Val Phe Lys
            180                 185                 190

Ala Val Gly Asn Val Phe Tyr Ile Gln Pro Ser Ala Tyr Asp Ile Cys
        195                 200                 205

Thr Ala Leu Cys Gly Ser Ser Pro Ala Phe Leu Ala Val Phe Ile Asp
    210                 215                 220

Ser Met Val Asp Gly Ala Val Ala Met Gly Leu Ser His Lys Asp Ala
225                 230                 235                 240

Val Asp Met Ala Ala Cys Thr Met Arg Gly Ala Ala Ser Leu Val Leu
                245                 250                 255

Glu Ser Gly Asn Pro Trp Thr Ile Arg His Gln Val Ala Ser Pro Gly
            260                 265                 270

Gly Ser Thr Met Gln Gly Leu Leu Ala Leu Glu Gln Gly Asn Val Arg
        275                 280                 285

Ser Thr Ile Ser Asn Ala Leu Met Val Ala Ala Lys Glu Ala Lys Lys
    290                 295                 300

Leu Gly Ser Lys Glu Asn Ala
305                 310

<210> SEQ ID NO 54
<211> LENGTH: 924
<212> TYPE: DNA
<213> ORGANISM: Curvularia clavata
<220> FEATURE:
<221> NAME/KEY: CDS
<222> LOCATION: (1)..(924)

<400> SEQUENCE: 54

```
atg gag agc gaa gac aat cca ttg agg ata caa acc ggc tcg ctc tgc      48
Met Glu Ser Glu Asp Asn Pro Leu Arg Ile Gln Thr Gly Ser Leu Cys
1               5                   10                  15 tca ttc caa cga ccg act ccg ctg gta ctc att cac gac tct agt ggc      96
Ser Phe Gln Arg Pro Thr Pro Leu Val Leu Ile His Asp Ser Ser Gly
            20                  25                  30 acg acc ttt agt tat ttc cgc ctg ggc agc ttg aac cgt gat gtc tgg     144
Thr Thr Phe Ser Tyr Phe Arg Leu Gly Ser Leu Asn Arg Asp Val Trp
        35                  40                  45 gct att cat gac cca cac ttt gat aaa agc acg ccg tgg aag ggc ggg     192
Ala Ile His Asp Pro His Phe Asp Lys Ser Thr Pro Trp Lys Gly Gly
    50                  55                  60 ttt ggc gag att gcc gag cac tac ata aaa ttg att gaa acg gca gga     240
Phe Gly Glu Ile Ala Glu His Tyr Ile Lys Leu Ile Glu Thr Ala Gly
65                  70                  75                  80 att cga ggt tcg atc ttg ctc gga gga tgg tcg ctc ggg ggt tat ctc     288
Ile Arg Gly Ser Ile Leu Leu Gly Gly Trp Ser Leu Gly Gly Tyr Leu
                85                  90                  95 gcg ctc acg att gct cac aaa tta acg gct atc aca aat cct acc ttc     336
Ala Leu Thr Ile Ala His Lys Leu Thr Ala Ile Thr Asn Pro Thr Phe
            100                 105                 110 tct gtc acc ggc atc ttg ctt gtt gac tct ccg tat cac acc cca atg     384
Ser Val Thr Gly Ile Leu Leu Val Asp Ser Pro Tyr His Thr Pro Met
        115                 120                 125 agt aag ctg cca cct cac gcc cca gat ccc aac ttt caa cac ctt ccg     432
Ser Lys Leu Pro Pro His Ala Pro Asp Pro Asn Phe Gln His Leu Pro
    130                 135                 140 gaa ctc gtc cgt aag tca ttc gag aat tac gat gtc ctt tta gac aga     480
Glu Leu Val Arg Lys Ser Phe Glu Asn Tyr Asp Val Leu Leu Asp Arg
145                 150                 155                 160 tgg gaa cta cct cca tgg acc gcg cct gct ttg gaa ggc aaa act ata     528
Trp Glu Leu Pro Pro Trp Thr Ala Pro Ala Leu Glu Gly Lys Thr Ile
                165                 170                 175 cgt tgt agc gcg ggt ggc aag acc ttc acg gta gca aac ggc agg atc     576
Arg Cys Ser Ala Gly Gly Lys Thr Phe Thr Val Ala Asn Gly Arg Ile
            180                 185                 190 cta tac aag ccc cta ggt aag ggc tgg gaa gat gtc aaa atg caa agc     624
Leu Tyr Lys Pro Leu Gly Lys Gly Trp Glu Asp Val Lys Met Gln Ser
        195                 200                 205 ttc gag cat ggc acc tct act ttg gaa cgc tac atc gaa tta ccc cca     672
Phe Glu His Gly Thr Ser Thr Leu Glu Arg Tyr Ile Glu Leu Pro Pro
    210                 215                 220 gca gct ctg atc aga tgc gct cag gcc ata cca act gat aca gat tcg     720
Ala Ala Leu Ile Arg Cys Ala Gln Ala Ile Pro Thr Asp Thr Asp Ser
225                 230                 235                 240 aaa atg ccg tgt ttc gta gat cga ttc cgt cac gag aca ctg cta ggt     768
Lys Met Pro Cys Phe Val Asp Arg Phe Arg His Glu Thr Leu Leu Gly
                245                 250                 255 tgg gat agt aat ttc ccc agt ttc atc aag gcc gcc gtg gac acg aac     816
Trp Asp Ser Asn Phe Pro Ser Phe Ile Lys Ala Ala Val Asp Thr Asn
            260                 265                 270 act cac cac ttc aac ata ttc gag tct cag aat ctc aaa cga tta acg     864
Thr His His Phe Asn Ile Phe Glu Ser Gln Asn Leu Lys Arg Leu Thr
        275                 280                 285 ata caa ttg aat gaa tgt cta gaa gtt cta gat agc tgt tgc ccg atg     912
Ile Gln Leu Asn Glu Cys Leu Glu Val Leu Asp Ser Cys Cys Pro Met
    290                 295                 300
```

```
gga tac tgc tga                                                        924
Gly Tyr Cys
305
```

<210> SEQ ID NO 55
<211> LENGTH: 307
<212> TYPE: PRT
<213> ORGANISM: Curvularia clavata

<400> SEQUENCE: 55

```
Met Glu Ser Glu Asp Asn Pro Leu Arg Ile Gln Thr Gly Ser Leu Cys
1               5                   10                  15

Ser Phe Gln Arg Pro Thr Pro Leu Val Leu Ile His Asp Ser Ser Gly
            20                  25                  30

Thr Thr Phe Ser Tyr Phe Arg Leu Gly Ser Leu Asn Arg Asp Val Trp
        35                  40                  45

Ala Ile His Asp Pro His Phe Asp Lys Ser Thr Pro Trp Lys Gly Gly
    50                  55                  60

Phe Gly Glu Ile Ala Glu His Tyr Ile Lys Leu Ile Glu Thr Ala Gly
65                  70                  75                  80

Ile Arg Gly Ser Ile Leu Leu Gly Gly Trp Ser Leu Gly Gly Tyr Leu
                85                  90                  95

Ala Leu Thr Ile Ala His Lys Leu Thr Ala Ile Thr Asn Pro Thr Phe
            100                 105                 110

Ser Val Thr Gly Ile Leu Leu Val Asp Ser Pro Tyr His Thr Pro Met
        115                 120                 125

Ser Lys Leu Pro Pro His Ala Pro Asp Pro Asn Phe Gln His Leu Pro
    130                 135                 140

Glu Leu Val Arg Lys Ser Phe Glu Asn Tyr Asp Val Leu Leu Asp Arg
145                 150                 155                 160

Trp Glu Leu Pro Pro Trp Thr Ala Pro Ala Leu Glu Gly Lys Thr Ile
                165                 170                 175

Arg Cys Ser Ala Gly Gly Lys Thr Phe Thr Val Ala Asn Gly Arg Ile
            180                 185                 190

Leu Tyr Lys Pro Leu Gly Lys Gly Trp Glu Asp Val Lys Met Gln Ser
        195                 200                 205

Phe Glu His Gly Thr Ser Thr Leu Glu Arg Tyr Ile Glu Leu Pro Pro
    210                 215                 220

Ala Ala Leu Ile Arg Cys Ala Gln Ala Ile Pro Thr Asp Thr Asp Ser
225                 230                 235                 240

Lys Met Pro Cys Phe Val Asp Arg Phe Arg His Glu Thr Leu Leu Gly
                245                 250                 255

Trp Asp Ser Asn Phe Pro Ser Phe Ile Lys Ala Ala Val Asp Thr Asn
            260                 265                 270

Thr His His Phe Asn Ile Phe Glu Ser Gln Asn Leu Lys Arg Leu Thr
        275                 280                 285

Ile Gln Leu Asn Glu Cys Leu Glu Val Leu Asp Ser Cys Cys Pro Met
    290                 295                 300

Gly Tyr Cys
305
```

<210> SEQ ID NO 56
<211> LENGTH: 33
<212> TYPE: DNA
<213> ORGANISM: Artificial
<220> FEATURE:
<223> OTHER INFORMATION: Synthetic DNA

<400> SEQUENCE: 56
cggtacccgg ggatctagtc tgttgattac tcg                                33

<210> SEQ ID NO 57
<211> LENGTH: 35
<212> TYPE: DNA
<213> ORGANISM: Artificial
<220> FEATURE:
<223> OTHER INFORMATION: Synthetic DNA

<400> SEQUENCE: 57
ctcgacaaag gtcattttga ctttgaatac cggtg                              35

<210> SEQ ID NO 58
<211> LENGTH: 22
<212> TYPE: DNA
<213> ORGANISM: Artificial
<220> FEATURE:
<223> OTHER INFORMATION: Synthetic DNA

<400> SEQUENCE: 58
gcagttgccg ttggaccaga gg                                            22

<210> SEQ ID NO 59
<211> LENGTH: 37
<212> TYPE: DNA
<213> ORGANISM: Artificial
<220> FEATURE:
<223> OTHER INFORMATION: Synthetic DNA

<400> SEQUENCE: 59
atagtcataa caagccgcga cactgtaata ttaaagc                            37

<210> SEQ ID NO 60
<211> LENGTH: 24
<212> TYPE: DNA
<213> ORGANISM: Artificial
<220> FEATURE:
<223> OTHER INFORMATION: Synthetic DNA

<400> SEQUENCE: 60
atgacctttg tcgagactgt agcc                                          24

<210> SEQ ID NO 61
<211> LENGTH: 39
<212> TYPE: DNA
<213> ORGANISM: Artificial
<220> FEATURE:
<223> OTHER INFORMATION: Synthetic DNA

<400> SEQUENCE: 61
tccaacggca actgcctatg atatactcat gttctcgtc                          39

<210> SEQ ID NO 62
<211> LENGTH: 35
<212> TYPE: DNA
<213> ORGANISM: Artificial
<220> FEATURE:
<223> OTHER INFORMATION: Synthetic DNA

<400> SEQUENCE: 62
cgactctaga ggatcctgat ggtcagatgg atctg                              35

<210> SEQ ID NO 63

```
<211> LENGTH: 28
<212> TYPE: DNA
<213> ORGANISM: Artificial
<220> FEATURE:
<223> OTHER INFORMATION: Synthetic DNA

<400> SEQUENCE: 63
gcttgttatg actatgtata catatgcg                                           28

<210> SEQ ID NO 64
<211> LENGTH: 21
<212> TYPE: DNA
<213> ORGANISM: Artificial
<220> FEATURE:
<223> OTHER INFORMATION: Synthetic DNA

<400> SEQUENCE: 64
gacagactct tcgtcgacgt c                                                  21

<210> SEQ ID NO 65
<211> LENGTH: 22
<212> TYPE: DNA
<213> ORGANISM: Artificial
<220> FEATURE:
<223> OTHER INFORMATION: Synthetic DNA

<400> SEQUENCE: 65
gttgtggttg gtgttcctga gg                                                 22

<210> SEQ ID NO 66
<211> LENGTH: 22
<212> TYPE: DNA
<213> ORGANISM: Artificial
<220> FEATURE:
<223> OTHER INFORMATION: Synthetic DNA

<400> SEQUENCE: 66
cactcgatct accaaatcga cg                                                 22

<210> SEQ ID NO 67
<211> LENGTH: 21
<212> TYPE: DNA
<213> ORGANISM: Artificial
<220> FEATURE:
<223> OTHER INFORMATION: Synthetic DNA

<400> SEQUENCE: 67
cctatccgga tatgcagtca c                                                  21

<210> SEQ ID NO 68
<211> LENGTH: 38
<212> TYPE: DNA
<213> ORGANISM: Artificial
<220> FEATURE:
<223> OTHER INFORMATION: Synthetic DNA

<400> SEQUENCE: 68
cggtacccgg ggatcctctg aagcggtcaa ggataacg                                38

<210> SEQ ID NO 69
<211> LENGTH: 37
<212> TYPE: DNA
<213> ORGANISM: Artificial
<220> FEATURE:
<223> OTHER INFORMATION: Synthetic DNA

<400> SEQUENCE: 69
```
atgaagcaga gcggcgagcc taagatatgc caggagg      37

<210> SEQ ID NO 70
<211> LENGTH: 37
<212> TYPE: DNA
<213> ORGANISM: Artificial
<220> FEATURE:
<223> OTHER INFORMATION: Synthetic DNA

<400> SEQUENCE: 70
ctagcaaccg tcatgccata gacgtggcac tcgaacg      37

<210> SEQ ID NO 71
<211> LENGTH: 38
<212> TYPE: DNA
<213> ORGANISM: Artificial
<220> FEATURE:
<223> OTHER INFORMATION: Synthetic DNA

<400> SEQUENCE: 71
cgactctaga ggatccgtct taaggatggt tcagctgc      38

<210> SEQ ID NO 72
<211> LENGTH: 20
<212> TYPE: DNA
<213> ORGANISM: Artificial
<220> FEATURE:
<223> OTHER INFORMATION: Synthetic DNA

<400> SEQUENCE: 72
catgacggtt gctagggtcg      20

<210> SEQ ID NO 73
<211> LENGTH: 20
<212> TYPE: DNA
<213> ORGANISM: Artificial
<220> FEATURE:
<223> OTHER INFORMATION: Synthetic DNA

<400> SEQUENCE: 73
gccgctctgc ttcattgctg      20

<210> SEQ ID NO 74
<211> LENGTH: 33
<212> TYPE: DNA
<213> ORGANISM: Artificial
<220> FEATURE:
<223> OTHER INFORMATION: Synthetic DNA

<400> SEQUENCE: 74
cggtacccgg ggatcgaccc attgcagctt gtg      33

<210> SEQ ID NO 75
<211> LENGTH: 37
<212> TYPE: DNA
<213> ORGANISM: Artificial
<220> FEATURE:
<223> OTHER INFORMATION: Synthetic DNA

<400> SEQUENCE: 75
atgaagcaga gcggcgtgca gtatggtgtc taaaacg      37

<210> SEQ ID NO 76
<211> LENGTH: 36
<212> TYPE: DNA

<213> ORGANISM: Artificial
<220> FEATURE:
<223> OTHER INFORMATION: Synthetic DNA

<400> SEQUENCE: 76
ctagcaaccg tcatggatga atgagcaccc tgttag    36

<210> SEQ ID NO 77
<211> LENGTH: 39
<212> TYPE: DNA
<213> ORGANISM: Artificial
<220> FEATURE:
<223> OTHER INFORMATION: Synthetic DNA

<400> SEQUENCE: 77
cgactctaga ggatcgtaca ttacaaaaac ctgttgcag    39

<210> SEQ ID NO 78
<211> LENGTH: 35
<212> TYPE: DNA
<213> ORGANISM: Artificial
<220> FEATURE:
<223> OTHER INFORMATION: Synthetic DNA

<400> SEQUENCE: 78
cggtacccgg ggatcgtccc acgtgcagct tcaac    35

<210> SEQ ID NO 79
<211> LENGTH: 35
<212> TYPE: DNA
<213> ORGANISM: Artificial
<220> FEATURE:
<223> OTHER INFORMATION: Synthetic DNA

<400> SEQUENCE: 79
atgaagcaga gcggccgtgg agtatcccag gatgg    35

<210> SEQ ID NO 80
<211> LENGTH: 35
<212> TYPE: DNA
<213> ORGANISM: Artificial
<220> FEATURE:
<223> OTHER INFORMATION: Synthetic DNA

<400> SEQUENCE: 80
ctagcaaccg tcatgccagc caaagggtat catgg    35

<210> SEQ ID NO 81
<211> LENGTH: 33
<212> TYPE: DNA
<213> ORGANISM: Artificial
<220> FEATURE:
<223> OTHER INFORMATION: Synthetic DNA

<400> SEQUENCE: 81
cgactctaga ggatctgagg gcagcgtagc ctg    33

<210> SEQ ID NO 82
<211> LENGTH: 37
<212> TYPE: DNA
<213> ORGANISM: Artificial
<220> FEATURE:
<223> OTHER INFORMATION: Synthetic DNA

<400> SEQUENCE: 82
cggtacccgg ggatcgtgga taaattcgta ccctttg    37

<210> SEQ ID NO 83
<211> LENGTH: 36
<212> TYPE: DNA
<213> ORGANISM: Artificial
<220> FEATURE:
<223> OTHER INFORMATION: Synthetic DNA

<400> SEQUENCE: 83
atgaagcaga gcggcctgat ctttgttgtg gtcgtg            36

<210> SEQ ID NO 84
<211> LENGTH: 35
<212> TYPE: DNA
<213> ORGANISM: Artificial
<220> FEATURE:
<223> OTHER INFORMATION: Synthetic DNA

<400> SEQUENCE: 84
ctagcaaccg tcatgcagtt tggcacttga gcatc            35

<210> SEQ ID NO 85
<211> LENGTH: 36
<212> TYPE: DNA
<213> ORGANISM: Artificial
<220> FEATURE:
<223> OTHER INFORMATION: Synthetic DNA

<400> SEQUENCE: 85
cgactctaga ggatccacgg aaaggaactc ctacag            36

<210> SEQ ID NO 86
<211> LENGTH: 34
<212> TYPE: DNA
<213> ORGANISM: Artificial
<220> FEATURE:
<223> OTHER INFORMATION: Synthetic DNA

<400> SEQUENCE: 86
cggtacccgg ggatcctctg ggaaaagcgg ttag            34

<210> SEQ ID NO 87
<211> LENGTH: 34
<212> TYPE: DNA
<213> ORGANISM: Artificial
<220> FEATURE:
<223> OTHER INFORMATION: Synthetic DNA

<400> SEQUENCE: 87
atgaagcaga gcggcgaaga accgagagcg agag            34

<210> SEQ ID NO 88
<211> LENGTH: 40
<212> TYPE: DNA
<213> ORGANISM: Artificial
<220> FEATURE:
<223> OTHER INFORMATION: Synthetic DNA

<400> SEQUENCE: 88
ctagcaaccg tcatgcttgc atctacctag atatttcacg            40

<210> SEQ ID NO 89
<211> LENGTH: 36
<212> TYPE: DNA
<213> ORGANISM: Artificial
<220> FEATURE:

<223> OTHER INFORMATION: Synthetic DNA

<400> SEQUENCE: 89
cgactctaga ggatccagag aatcagcaga gacacc                                    36

<210> SEQ ID NO 90
<211> LENGTH: 39
<212> TYPE: DNA
<213> ORGANISM: Artificial
<220> FEATURE:
<223> OTHER INFORMATION: Synthetic DNA

<400> SEQUENCE: 90
cggtacccgg ggatcccctg gtagttcagt ggaagtaag                                 39

<210> SEQ ID NO 91
<211> LENGTH: 34
<212> TYPE: DNA
<213> ORGANISM: Artificial
<220> FEATURE:
<223> OTHER INFORMATION: Synthetic DNA

<400> SEQUENCE: 91
atgaagcaga gcggctgata gaggtacggg ggtg                                      34

<210> SEQ ID NO 92
<211> LENGTH: 34
<212> TYPE: DNA
<213> ORGANISM: Artificial
<220> FEATURE:
<223> OTHER INFORMATION: Synthetic DNA

<400> SEQUENCE: 92
ctagcaaccg tcatgtgctt ggctgcttca aatc                                      34

<210> SEQ ID NO 93
<211> LENGTH: 39
<212> TYPE: DNA
<213> ORGANISM: Artificial
<220> FEATURE:
<223> OTHER INFORMATION: Synthetic DNA

<400> SEQUENCE: 93
cgactctaga ggatcctaat acttgtcgtc ccactgatg                                 39

<210> SEQ ID NO 94
<211> LENGTH: 34
<212> TYPE: DNA
<213> ORGANISM: Artificial
<220> FEATURE:
<223> OTHER INFORMATION: Synthetic DNA

<400> SEQUENCE: 94
cggtacccgg ggatcgcagt acatcgtcag ggtc                                      34

<210> SEQ ID NO 95
<211> LENGTH: 36
<212> TYPE: DNA
<213> ORGANISM: Artificial
<220> FEATURE:
<223> OTHER INFORMATION: Synthetic DNA

<400> SEQUENCE: 95
atgaagcaga gcggcgatga ataaggcgaa ggaaag                                    36

```
<210> SEQ ID NO 96
<211> LENGTH: 37
<212> TYPE: DNA
<213> ORGANISM: Artificial
<220> FEATURE:
<223> OTHER INFORMATION: Synthetic DNA

<400> SEQUENCE: 96
ctagcaaccg tcatgccctc tttttcttg ctgtctc                            37

<210> SEQ ID NO 97
<211> LENGTH: 35
<212> TYPE: DNA
<213> ORGANISM: Artificial
<220> FEATURE:
<223> OTHER INFORMATION: Synthetic DNA

<400> SEQUENCE: 97
cgactctaga ggatcgaagg aaggacggat actgg                             35

<210> SEQ ID NO 98
<211> LENGTH: 39
<212> TYPE: DNA
<213> ORGANISM: Artificial
<220> FEATURE:
<223> OTHER INFORMATION: Synthetic DNA

<400> SEQUENCE: 98
cggtacccgg ggatcgatga gcgtagaatt cgtaaaaag                         39

<210> SEQ ID NO 99
<211> LENGTH: 32
<212> TYPE: DNA
<213> ORGANISM: Artificial
<220> FEATURE:
<223> OTHER INFORMATION: Synthetic DNA

<400> SEQUENCE: 99
atgaagcaga gcggcgcgaa cgggcgtttt tc                                32

<210> SEQ ID NO 100
<211> LENGTH: 35
<212> TYPE: DNA
<213> ORGANISM: Artificial
<220> FEATURE:
<223> OTHER INFORMATION: Synthetic DNA

<400> SEQUENCE: 100
ctagcaaccg tcatggaagg aaggacggat actgg                             35

<210> SEQ ID NO 101
<211> LENGTH: 37
<212> TYPE: DNA
<213> ORGANISM: Artificial
<220> FEATURE:
<223> OTHER INFORMATION: Synthetic DNA

<400> SEQUENCE: 101
cgactctaga ggatcccctc tttttcttg ctgtctc                            37

<210> SEQ ID NO 102
<211> LENGTH: 40
<212> TYPE: DNA
<213> ORGANISM: Artificial
<220> FEATURE:
<223> OTHER INFORMATION: Synthetic DNA
```

<400> SEQUENCE: 102
cggtacccgg ggatcctcct tattttgcaa cttctgatac         40

<210> SEQ ID NO 103
<211> LENGTH: 37
<212> TYPE: DNA
<213> ORGANISM: Artificial
<220> FEATURE:
<223> OTHER INFORMATION: Synthetic DNA

<400> SEQUENCE: 103
atgaagcaga gcggccgtgt tgattttggt aattttg         37

<210> SEQ ID NO 104
<211> LENGTH: 39
<212> TYPE: DNA
<213> ORGANISM: Artificial
<220> FEATURE:
<223> OTHER INFORMATION: Synthetic DNA

<400> SEQUENCE: 104
ctagcaaccg tcatggatga gcgtagaatt cgtaaaaag         39

<210> SEQ ID NO 105
<211> LENGTH: 32
<212> TYPE: DNA
<213> ORGANISM: Artificial
<220> FEATURE:
<223> OTHER INFORMATION: Synthetic DNA

<400> SEQUENCE: 105
cgactctaga ggatcgcgaa cgggcgtttt tc         32

<210> SEQ ID NO 106
<211> LENGTH: 37
<212> TYPE: DNA
<213> ORGANISM: Artificial
<220> FEATURE:
<223> OTHER INFORMATION: Synthetic DNA

<400> SEQUENCE: 106
cggtacccgg ggatccgtgt tgattttggt aattttg         37

<210> SEQ ID NO 107
<211> LENGTH: 40
<212> TYPE: DNA
<213> ORGANISM: Artificial
<220> FEATURE:
<223> OTHER INFORMATION: Synthetic DNA

<400> SEQUENCE: 107
atgaagcaga gcggcctcct tattttgcaa cttctgatac         40

<210> SEQ ID NO 108
<211> LENGTH: 39
<212> TYPE: DNA
<213> ORGANISM: Artificial
<220> FEATURE:
<223> OTHER INFORMATION: Synthetic DNA

<400> SEQUENCE: 108
ctagcaaccg tcatgctagc agccataaga gacgtaacc         39

<210> SEQ ID NO 109
<211> LENGTH: 34

```
<212> TYPE: DNA
<213> ORGANISM: Artificial
<220> FEATURE:
<223> OTHER INFORMATION: Synthetic DNA

<400> SEQUENCE: 109
cgactctaga ggatcgtttt cattgcatgc tccg                         34

<210> SEQ ID NO 110
<211> LENGTH: 59
<212> TYPE: DNA
<213> ORGANISM: Artificial
<220> FEATURE:
<223> OTHER INFORMATION: Synthetic DNA

<400> SEQUENCE: 110
tcgacaagct tgcggccgcc acgtgactag tatggccagc gacatcaata ctcatccag   59

<210> SEQ ID NO 111
<211> LENGTH: 47
<212> TYPE: DNA
<213> ORGANISM: Artificial
<220> FEATURE:
<223> OTHER INFORMATION: Synthetic DNA

<400> SEQUENCE: 111
actagtcacg tggcggccgc ggcgcgccaa gatcgtcttg ctgtacg             47

<210> SEQ ID NO 112
<211> LENGTH: 41
<212> TYPE: DNA
<213> ORGANISM: Artificial
<220> FEATURE:
<223> OTHER INFORMATION: Synthetic DNA

<400> SEQUENCE: 112
gatgcgctag cggccgcgaa gtggtccttg tcgctggtga c                   41

<210> SEQ ID NO 113
<211> LENGTH: 28
<212> TYPE: DNA
<213> ORGANISM: Artificial
<220> FEATURE:
<223> OTHER INFORMATION: Synthetic DNA

<400> SEQUENCE: 113
tgccgttcgc attcataggc atctcgtc                                 28

<210> SEQ ID NO 114
<211> LENGTH: 25
<212> TYPE: DNA
<213> ORGANISM: Artificial
<220> FEATURE:
<223> OTHER INFORMATION: Synthetic DNA

<400> SEQUENCE: 114
tgaatgcgaa cggcaaggtt gacag                                    25

<210> SEQ ID NO 115
<211> LENGTH: 25
<212> TYPE: DNA
<213> ORGANISM: Artificial
<220> FEATURE:
<223> OTHER INFORMATION: Synthetic DNA

<400> SEQUENCE: 115
```

```
cttggttgct ggcttcgtcg ttgtc                                          25

<210> SEQ ID NO 116
<211> LENGTH: 25
<212> TYPE: DNA
<213> ORGANISM: Artificial
<220> FEATURE:
<223> OTHER INFORMATION: Synthetic DNA

<400> SEQUENCE: 116
aagccagcaa ccaagtcgaa gattg                                          25

<210> SEQ ID NO 117
<211> LENGTH: 43
<212> TYPE: DNA
<213> ORGANISM: Artificial
<220> FEATURE:
<223> OTHER INFORMATION: Synthetic DNA

<400> SEQUENCE: 117
gtcactagtg cggccgccta tttttgcaag atcttgttca aac                      43

<210> SEQ ID NO 118
<211> LENGTH: 29
<212> TYPE: DNA
<213> ORGANISM: Artificial
<220> FEATURE:
<223> OTHER INFORMATION: Synthetic DNA

<400> SEQUENCE: 118
ggactagtat gactgaaccc acatggaag                                      29

<210> SEQ ID NO 119
<211> LENGTH: 29
<212> TYPE: DNA
<213> ORGANISM: Artificial
<220> FEATURE:
<223> OTHER INFORMATION: Synthetic DNA

<400> SEQUENCE: 119
ggactagttt aataatctac ttcaagcac                                      29

<210> SEQ ID NO 120
<211> LENGTH: 33
<212> TYPE: DNA
<213> ORGANISM: Artificial
<220> FEATURE:
<223> OTHER INFORMATION: Synthetic DNA

<400> SEQUENCE: 120
ataagaatgc ggccgcatgg cgttgcaaga gcg                                 33

<210> SEQ ID NO 121
<211> LENGTH: 36
<212> TYPE: DNA
<213> ORGANISM: Artificial
<220> FEATURE:
<223> OTHER INFORMATION: Synthetic DNA

<400> SEQUENCE: 121
ataagaatgc ggccgctcaa gatgggaaag ccgctg                              36

<210> SEQ ID NO 122
<211> LENGTH: 28
<212> TYPE: DNA
<213> ORGANISM: Artificial
```

```
<220> FEATURE:
<223> OTHER INFORMATION: Synthetic DNA

<400> SEQUENCE: 122
ctagctagca tgagtgctat cgagctgc                                              28

<210> SEQ ID NO 123
<211> LENGTH: 28
<212> TYPE: DNA
<213> ORGANISM: Artificial
<220> FEATURE:
<223> OTHER INFORMATION: Synthetic DNA

<400> SEQUENCE: 123
ctagctagct cagcgattga gggcctgg                                              28

<210> SEQ ID NO 124
<211> LENGTH: 36
<212> TYPE: DNA
<213> ORGANISM: Artificial
<220> FEATURE:
<223> OTHER INFORMATION: Synthetic DNA

<400> SEQUENCE: 124
ataagaatgc ggccgcatga agctcaccgt tttcag                                     36

<210> SEQ ID NO 125
<211> LENGTH: 32
<212> TYPE: DNA
<213> ORGANISM: Artificial
<220> FEATURE:
<223> OTHER INFORMATION: Synthetic DNA

<400> SEQUENCE: 125
ataagaatgc ggccgctcag agccgcgcca ac                                         32

<210> SEQ ID NO 126
<211> LENGTH: 29
<212> TYPE: DNA
<213> ORGANISM: Artificial
<220> FEATURE:
<223> OTHER INFORMATION: Synthetic DNA

<400> SEQUENCE: 126
ggactagtat gacgaaaagg gaaagcaac                                             29

<210> SEQ ID NO 127
<211> LENGTH: 27
<212> TYPE: DNA
<213> ORGANISM: Artificial
<220> FEATURE:
<223> OTHER INFORMATION: Synthetic DNA

<400> SEQUENCE: 127
ggactagtct acgcgttttc tttcgac                                               27

<210> SEQ ID NO 128
<211> LENGTH: 29
<212> TYPE: DNA
<213> ORGANISM: Artificial
<220> FEATURE:
<223> OTHER INFORMATION: Synthetic DNA

<400> SEQUENCE: 128
ctagctagca tggagagcga agacaatcc                                             29
```

<210> SEQ ID NO 129
<211> LENGTH: 27
<212> TYPE: DNA
<213> ORGANISM: Artificial
<220> FEATURE:
<223> OTHER INFORMATION: Synthetic DNA

<400> SEQUENCE: 129
ctagctagct cagcagtatc ccatcgg                                27

<210> SEQ ID NO 130
<211> LENGTH: 36
<212> TYPE: DNA
<213> ORGANISM: Artificial
<220> FEATURE:
<223> OTHER INFORMATION: Synthetic DNA

<400> SEQUENCE: 130
atttgcggcc gcatggaccc gagacagtca cggatc                      36

<210> SEQ ID NO 131
<211> LENGTH: 36
<212> TYPE: DNA
<213> ORGANISM: Artificial
<220> FEATURE:
<223> OTHER INFORMATION: Synthetic DNA

<400> SEQUENCE: 131
atttgcggcc gcttatggtg tggtgggttg ccattc                      36

<210> SEQ ID NO 132
<211> LENGTH: 20
<212> TYPE: DNA
<213> ORGANISM: Artificial
<220> FEATURE:
<223> OTHER INFORMATION: Synthetic DNA

<400> SEQUENCE: 132
gacgccacga acgcatagac                                        20

<210> SEQ ID NO 133
<211> LENGTH: 21
<212> TYPE: DNA
<213> ORGANISM: Artificial
<220> FEATURE:
<223> OTHER INFORMATION: Synthetic DNA

<400> SEQUENCE: 133
ttcccagaga ggtagatcga c                                      21

<210> SEQ ID NO 134
<211> LENGTH: 20
<212> TYPE: DNA
<213> ORGANISM: Artificial
<220> FEATURE:
<223> OTHER INFORMATION: Synthetic DNA

<400> SEQUENCE: 134
gaccgttaca gcgagttcag                                        20

<210> SEQ ID NO 135
<211> LENGTH: 20
<212> TYPE: DNA
<213> ORGANISM: Artificial
<220> FEATURE:
<223> OTHER INFORMATION: Synthetic DNA

```
<400> SEQUENCE: 135
ctgaattcct cgcacagaac                                              20

<210> SEQ ID NO 136
<211> LENGTH: 20
<212> TYPE: DNA
<213> ORGANISM: Artificial
<220> FEATURE:
<223> OTHER INFORMATION: Synthetic DNA

<400> SEQUENCE: 136
gaagttgaga acgccatgct                                              20

<210> SEQ ID NO 137
<211> LENGTH: 20
<212> TYPE: DNA
<213> ORGANISM: Artificial
<220> FEATURE:
<223> OTHER INFORMATION: Synthetic DNA

<400> SEQUENCE: 137
gatgcgagat gggagcatgt                                              20

<210> SEQ ID NO 138
<211> LENGTH: 20
<212> TYPE: DNA
<213> ORGANISM: Artificial
<220> FEATURE:
<223> OTHER INFORMATION: Synthetic DNA

<400> SEQUENCE: 138
gccctactag atctgaccac                                              20

<210> SEQ ID NO 139
<211> LENGTH: 20
<212> TYPE: DNA
<213> ORGANISM: Artificial
<220> FEATURE:
<223> OTHER INFORMATION: Synthetic DNA

<400> SEQUENCE: 139
gctgttacct tttcctcctc                                              20

<210> SEQ ID NO 140
<211> LENGTH: 20
<212> TYPE: DNA
<213> ORGANISM: Artificial
<220> FEATURE:
<223> OTHER INFORMATION: Synthetic DNA

<400> SEQUENCE: 140
agatcttaga cgagctgctc                                              20

<210> SEQ ID NO 141
<211> LENGTH: 20
<212> TYPE: DNA
<213> ORGANISM: Artificial
<220> FEATURE:
<223> OTHER INFORMATION: Synthetic DNA

<400> SEQUENCE: 141
aaacagtcgc gaagcgactg                                              20

<210> SEQ ID NO 142
```

```
<211> LENGTH: 20
<212> TYPE: DNA
<213> ORGANISM: Artificial
<220> FEATURE:
<223> OTHER INFORMATION: Synthetic DNA

<400> SEQUENCE: 142
acgtccagga agctatcgag                                           20

<210> SEQ ID NO 143
<211> LENGTH: 20
<212> TYPE: DNA
<213> ORGANISM: Artificial
<220> FEATURE:
<223> OTHER INFORMATION: Synthetic DNA

<400> SEQUENCE: 143
attgagggcc tgggcttgac                                           20

<210> SEQ ID NO 144
<211> LENGTH: 20
<212> TYPE: DNA
<213> ORGANISM: Artificial
<220> FEATURE:
<223> OTHER INFORMATION: Synthetic DNA

<400> SEQUENCE: 144
gtgatgaagg cgctgaagag                                           20

<210> SEQ ID NO 145
<211> LENGTH: 20
<212> TYPE: DNA
<213> ORGANISM: Artificial
<220> FEATURE:
<223> OTHER INFORMATION: Synthetic DNA

<400> SEQUENCE: 145
ctccgcaatt tccgtgagtg                                           20

<210> SEQ ID NO 146
<211> LENGTH: 20
<212> TYPE: DNA
<213> ORGANISM: Artificial
<220> FEATURE:
<223> OTHER INFORMATION: Synthetic DNA

<400> SEQUENCE: 146
tgactctatg gtggatggtg                                           20

<210> SEQ ID NO 147
<211> LENGTH: 20
<212> TYPE: DNA
<213> ORGANISM: Artificial
<220> FEATURE:
<223> OTHER INFORMATION: Synthetic DNA

<400> SEQUENCE: 147
ccttgttcaa gtgccagtag                                           20

<210> SEQ ID NO 148
<211> LENGTH: 20
<212> TYPE: DNA
<213> ORGANISM: Artificial
<220> FEATURE:
<223> OTHER INFORMATION: Synthetic DNA

<400> SEQUENCE: 148
```

```
gattccgtca cgagacactg                                               20

<210> SEQ ID NO 149
<211> LENGTH: 20
<212> TYPE: DNA
<213> ORGANISM: Artificial
<220> FEATURE:
<223> OTHER INFORMATION: Synthetic DNA

<400> SEQUENCE: 149
agtatcccat cgggcaacag                                               20

<210> SEQ ID NO 150
<211> LENGTH: 18
<212> TYPE: DNA
<213> ORGANISM: Artificial
<220> FEATURE:
<223> OTHER INFORMATION: Synthetic DNA

<400> SEQUENCE: 150
acgttcaaga ccttccag                                                 18

<210> SEQ ID NO 151
<211> LENGTH: 18
<212> TYPE: DNA
<213> ORGANISM: Artificial
<220> FEATURE:
<223> OTHER INFORMATION: Synthetic DNA

<400> SEQUENCE: 151
gttccggatg atttgcag                                                 18
```

US 11,230,726 B2

GENE INVOLVED IN SYNTHESIS OF CYCLIC PEPTIDE COMPOUND, METHOD FOR PRODUCING CYCLIC PEPTIDE COMPOUND USING THE SAME, AND TRANSFORMANT COMPRISING THE SAME

TECHNICAL FIELD

The present invention relates to a novel gene involved in the synthesis of a cyclic peptide compound having bactericidal activity against fungi produced by a filamentous fungus of the *Curvularia* species, a method for producing a cyclic peptide compound using the gene involved in the synthesis of a cyclic peptide compound, and a transformant comprising the gene involved in the synthesis of a cyclic peptide compound.

BACKGROUND ART

A particular cyclic peptide compound that is known as "CAS143380-71-6" produced by a filamentous fungus of the *Curvularia* species (hereafter, referred to as "KK-1") is known to exert potent bactericidal activity against plant pathogenic bacteria, and, in particular, against fungi (JP H8-504165 A (1996)). While KK-1 shows potent bactericidal activity, commercial use thereof as an agricultural chemical has not yet been realized for the following reasons. For example, KK-1 has a complicated chemical structure, so that chemical synthesis thereof is difficult. Even if KK-1 could be chemically synthesized, in addition, a complicated chemical structure of KK-1 would disadvantageously increase the cost. While production of KK-1 is intended via culture of filamentous fungi of the *Curvularia* species, the amount of production may not be sufficient.

To date, pharmaceutical products and agricultural chemicals have been developed from secondary metabolites produced by microorganisms, including mycetes, actinomycetes, and bacteria. As a result of genome analysis of several types of mycetes, specifically, *Aspergillus*, which is the same filamentous fungus as the *Curvularia* species, the presence of a biosynthetic gene cluster involved in the biosynthesis of a variety of secondary metabolites, including polyketide compounds, nonribosomal peptides, terpenes, and alkaloyds, has been elucidated (Machida, M., et al., Nature, 2005, 438 (7071), pp. 1157-1161). According to the results of genome analysis and molecular biological research on filamentous fungi of recent years, the transcription level of secondary metabolite-biosynthesizing genes of filamentous fungi was found to be low by a general filamentous fungi culture technique (Georgianna, D. R. et al., Mol. Plant. Pathol., 11, 213, 2010).

In order to exert a potential ability to produce secondary metabolites, accordingly, so-called synthetic biology techniques aimed at synthesis of sufficient quantities of secondary metabolites through activation of a biosynthetic gene cluster (Brakhage, Fungal Genetics and Biology, 2011, 48 (1), pp. 15-22) and expression in adequate heterologs, such as budding yeast, have been attempted.

SUMMARY OF THE INVENTION

Objects to be Attained by the Invention

As with the case of secondary metabolites described above, KK-1 produced by a filamentous fungus of the *Curvularia* species may also be produced via synthetic biology techniques. However, the genome of a filamentous fungus of the *Curvularia* species has not been substantially elucidated, and the gene cluster involved in the production of KK-1 has not been identified.

Under the above circumstances, it is an object of the present invention to identify a gene cluster involved in the biosynthesis of KK-1 produced by a filamentous fungus of the *Curvularia* species to provide a system for synthesizing KK-1.

Means for Attaining the Objects

The present inventors have conducted concentrated studies in order to attain the above objects. As a result, they succeeded in identifying a plurality of nonribosomal peptide synthetase (NRPS) genes from the genome of *Curvularia clavata* and identifying a NRPS gene involved in the synthesis of KK-1 and a gene cluster including such NRPS gene from among the identified NRPS genes. This has led to the completion of the present invention.

The present invention encompasses the following.

(1) A gene involved in the synthesis of a cyclic peptide compound, wherein the gene encodes a protein having activity of synthesizing a nonribosomal peptide of a cyclic peptide compound produced by a filamentous fungus of the *Curvularia* species, and comprising successively from the N terminus the modules described below:

a first module comprising successively from the N terminus a first adenylation domain comprising the amino acid sequence as shown in SEQ ID NO: 1 or an amino acid sequence having 70% or higher identity to the amino acid sequence as shown in SEQ ID NO: 1 and a first peptidyl carrier protein domain comprising the amino acid sequence as shown in SEQ ID NO: 2 or an amino acid sequence having 70% or higher identity to the amino acid sequence as shown in SEQ ID NO: 2;

a second module comprising successively from the N terminus a first condensation domain comprising the amino acid sequence as shown in SEQ ID NO: 3 or an amino acid sequence having 70% or higher identity to the amino acid sequence as shown in SEQ ID NO: 3, a second adenylation domain comprising the amino acid sequence as shown in SEQ ID NO: 4 or an amino acid sequence having 70% or higher identity to the amino acid sequence as shown in SEQ ID NO: 4, and a second peptidyl carrier protein domain comprising the amino acid sequence as shown in SEQ ID NO: 5 or an amino acid sequence having 70% or higher identity to the amino acid sequence as shown in SEQ ID NO: 5;

a third module comprising successively from the N terminus a second condensation domain comprising the amino acid sequence as shown in SEQ ID NO: 6 or an amino acid sequence having 70% or higher identity to the amino acid sequence as shown in SEQ ID NO: 6, a third adenylation domain comprising the amino acid sequence as shown in SEQ ID NO: 7 or an amino acid sequence having 70% or higher identity to the amino acid sequence as shown in SEQ ID NO: 7, a first N-methyl transferase domain comprising the amino acid sequence as shown in SEQ ID NO: 8 or an amino acid sequence having 70% or higher identity to the amino acid sequence as shown in SEQ ID NO: 8, and a third peptidyl carrier protein domain comprising the amino acid sequence as shown in SEQ ID NO: 9 or an amino acid sequence having 70% or higher identity to the amino acid sequence as shown in SEQ ID NO: 9;

a fourth module comprising successively from the N terminus a third condensation domain comprising the amino acid sequence as shown in SEQ ID NO: 10 or an amino acid sequence having 70% or higher identity to the amino acid sequence as shown in SEQ ID NO: 10, a fourth adenylation domain comprising the amino acid sequence as shown in SEQ ID NO: 11 or an amino acid sequence having 70% or higher identity to the amino acid sequence as shown in SEQ ID NO: 11, and a fourth peptidyl carrier protein domain comprising the amino acid sequence as shown in SEQ ID NO: 12 or an amino acid sequence having 70% or higher identity to the amino acid sequence as shown in SEQ ID NO: 12;

a fifth module comprising successively from the N terminus a fourth condensation domain comprising the amino acid sequence as shown in SEQ ID NO: 13 or an amino acid sequence having 70% or higher identity to the amino acid sequence as shown in SEQ ID NO: 13, a fifth adenylation domain comprising the amino acid sequence as shown in SEQ ID NO: 14 or an amino acid sequence having 70% or higher identity to the amino acid sequence as shown in SEQ ID NO: 14, a second N-methyl transferase domain comprising the amino acid sequence as shown in SEQ ID NO: 15 or an amino acid sequence having 70% or higher identity to the amino acid sequence as shown in SEQ ID NO: 15, and a fifth peptidyl carrier protein domain comprising the amino acid sequence as shown in SEQ ID NO: 16 or an amino acid sequence having 70% or higher identity to the amino acid sequence as shown in SEQ ID NO: 16;

a sixth module comprising successively from the N terminus a fifth condensation domain comprising the amino acid sequence as shown in SEQ ID NO: 17 or an amino acid sequence having 70% or higher identity to the amino acid sequence as shown in SEQ ID NO: 17, a sixth adenylation domain comprising the amino acid sequence as shown in SEQ ID NO: 18 or an amino acid sequence having 70% or higher identity to the amino acid sequence as shown in SEQ ID NO: 18, a third N-methyl transferase domain comprising the amino acid sequence as shown in SEQ ID NO: 19 or an amino acid sequence having 70% or higher identity to the amino acid sequence as shown in SEQ ID NO: 19, and a sixth peptidyl carrier protein domain comprising the amino acid sequence as shown in SEQ ID NO: 20 or an amino acid sequence having 70% or higher identity to the amino acid sequence as shown in SEQ ID NO: 20;

a seventh module comprising successively from the N terminus a sixth condensation domain comprising the amino acid sequence as shown in SEQ ID NO: 21 or an amino acid sequence having 70% or higher identity to the amino acid sequence as shown in SEQ ID NO: 21, a seventh adenylation domain comprising the amino acid sequence as shown in SEQ ID NO: 22 or an amino acid sequence having 70% or higher identity to the amino acid sequence as shown in SEQ ID NO: 22, a fourth N-methyl transferase domain comprising the amino acid sequence as shown in SEQ ID NO: 23 or an amino acid sequence having 70% or higher identity to the amino acid sequence as shown in SEQ ID NO: 23, and a seventh peptidyl carrier protein domain comprising the amino acid sequence as shown in SEQ ID NO: 24 or an amino acid sequence having 70% or higher identity to the amino acid sequence as shown in SEQ ID NO: 24;

an eighth module comprising successively from the N terminus a seventh condensation domain comprising the amino acid sequence as shown in SEQ ID NO: 25 or an amino acid sequence having 70% or higher identity to the amino acid sequence as shown in SEQ ID NO: 25, an eighth adenylation domain comprising the amino acid sequence as shown in SEQ ID NO: 26 or an amino acid sequence having 70% or higher identity to the amino acid sequence as shown in SEQ ID NO: 26, and an eighth peptidyl carrier protein domain comprising the amino acid sequence as shown in SEQ ID NO: 27 or an amino acid sequence having 70% or higher identity to the amino acid sequence as shown in SEQ ID NO: 27;

a ninth module comprising successively from the N terminus an eighth condensation domain comprising the amino acid sequence as shown in SEQ ID NO: 28 or an amino acid sequence having 70% or higher identity to the amino acid sequence as shown in SEQ ID NO: 28, a ninth adenylation domain comprising the amino acid sequence as shown in SEQ ID NO: 29 or an amino acid sequence having 70% or higher identity to the amino acid sequence as shown in SEQ ID NO: 29, a fifth N-methyl transferase domain comprising the amino acid sequence as shown in SEQ ID NO: 30 or an amino acid sequence having 70% or higher identity to the amino acid sequence as shown in SEQ ID NO: 30, and a ninth peptidyl carrier protein domain comprising the amino acid sequence as shown in SEQ ID NO: 31 or an amino acid sequence having 70% or higher identity to the amino acid sequence as shown in SEQ ID NO: 31; and a tenth module comprising successively from the N terminus a ninth condensation domain comprising the amino acid sequence as shown in SEQ ID NO: 32 or an amino acid sequence having 70% or higher identity to the amino acid sequence as shown in SEQ ID NO: 32, a tenth adenylation domain comprising the amino acid sequence as shown in SEQ ID NO: 33 or an amino acid sequence having 70% or higher identity to the amino acid sequence as shown in SEQ ID NO: 33, a tenth peptidyl carrier protein domain comprising the amino acid sequence as shown in SEQ ID NO: 34 or an amino acid sequence having 70% or higher identity to the amino acid sequence as shown in SEQ ID NO: 34, and a tenth condensation domain comprising the amino acid sequence as shown in SEQ ID NO: 35 or an amino acid sequence having 70% or higher identity to the amino acid sequence as shown in SEQ ID NO: 35.

(2) The gene involved in the synthesis of a cyclic peptide compound according to (1), wherein the protein is any of the proteins (a) to (c) below:

(a) a protein comprising the amino acid sequence as shown in SEQ ID NO: 37;

(b) a protein comprising an amino acid sequence having 70% or higher identity to the amino acid sequence as shown in SEQ ID NO: 37 and having activity of synthesizing a nonribosomal peptide of a cyclic peptide compound produced by a filamentous fungus of the *Curvularia* species; and (c) a protein encoded by a polynucleotide hybridizing under stringent conditions to a complementary strand of the nucleotide sequence as shown in SEQ ID NO: 36 and having activity of synthesizing a nonribosomal peptide of a cyclic peptide compound produced by a filamentous fungus of the *Curvularia* species.

(3) The gene involved in the synthesis of a cyclic peptide compound according to (1), which is derived from a filamentous fungus of the *Curvularia* species.

(4) The gene involved in the synthesis of a cyclic peptide compound according to (3), wherein the filamentous fungus is *Curvularia clavata*.

(5) A gene involved in the synthesis of a cyclic peptide compound encoding any of proteins (a) to (c) below:

(a) a protein comprising the amino acid sequence as shown in SEQ ID NO: 39;

(b) a protein comprising an amino acid sequence having 70% or higher identity to the amino acid sequence as shown in SEQ ID NO: 39 and having transcription factor activity; and (c) a protein encoded by a polynucleotide hybridizing under stringent conditions to a complementary strand of the nucleotide sequence as shown in SEQ ID NO: 38 and having transcription factor activity.

(6) The gene involved in the synthesis of a cyclic peptide compound according to (5), which is derived from a filamentous fungus of the *Curvularia* species.

(7) The gene involved in the synthesis of a cyclic peptide compound according to (6), wherein the filamentous fungus is *Curvularia clavata*.

(8) A method for producing a cyclic peptide compound, wherein the compound is produced by a filamentous fungus of the *Curvularia* species, comprising:

a step of culturing a transformant into which the gene involved in the synthesis of a cyclic peptide compound according to any of (1) to (4) and a group of genes involved in the production of a cyclic peptide compound in a filamentous fungus of the *Curvularia* species; and a step of collecting the cyclic peptide compound from the cultured transformant and/or culture solution.

(9) The method for producing a cyclic peptide compound according to (8), wherein the group of genes includes genes [1] to [7] below:

[1] a gene encoding a protein comprising the amino acid sequence as shown in SEQ ID NO: 41 or an amino acid sequence having 70% or higher identity to the amino acid sequence as shown in SEQ ID NO: 41;

[2] a gene encoding a protein comprising the amino acid sequence as shown in SEQ ID NO: 43 or an amino acid sequence having 70% or higher identity to the amino acid sequence as shown in SEQ ID NO: 43;

[3] a gene encoding a protein comprising the amino acid sequence as shown in SEQ ID NO: 45 or an amino acid sequence having 70% or higher identity to the amino acid sequence as shown in SEQ ID NO: 45;

[4] a gene encoding a protein comprising the amino acid sequence as shown in SEQ ID NO: 47 or an amino acid sequence having 70% or higher identity to the amino acid sequence as shown in SEQ ID NO: 47;

[5] a gene encoding a protein comprising the amino acid sequence as shown in SEQ ID NO: 49 or an amino acid sequence having 70% or higher identity to the amino acid sequence as shown in SEQ ID NO: 49;

[6] a gene encoding a protein comprising the amino acid sequence as shown in SEQ ID NO: 51 or an amino acid sequence having 70% or higher identity to the amino acid sequence as shown in SEQ ID NO: 51; and

[7] a gene encoding a protein comprising the amino acid sequence as shown in SEQ ID NO: 53 or an amino acid sequence having 70% or higher identity to the amino acid sequence as shown in SEQ ID NO: 53.

(10) The method for producing a cyclic peptide compound according to (8), wherein the transformant is obtained by using *Aspergillus oryzae* as a host.

(11) A transformant into which the gene involved in the synthesis of a cyclic peptide compound according to any of (1) to (4) and a group of genes involved in the production of a cyclic peptide compound in a filamentous fungus of the *Curvularia* species have been introduced.

(12) The transformant according to (11), wherein the group of genes includes genes [1] to [7] below:

[1] a gene encoding a protein comprising the amino acid sequence as shown in SEQ ID NO: 41 or an amino acid sequence having 70% or higher identity to the amino acid sequence as shown in SEQ ID NO: 41;

[2] a gene encoding a protein comprising the amino acid sequence as shown in SEQ ID NO: 43 or an amino acid sequence having 70% or higher identity to the amino acid sequence as shown in SEQ ID NO: 43;

[3] a gene encoding a protein comprising the amino acid sequence as shown in SEQ ID NO: 45 or an amino acid sequence having 70% or higher identity to the amino acid sequence as shown in SEQ ID NO: 45;

[4] a gene encoding a protein comprising the amino acid sequence as shown in SEQ ID NO: 47 or an amino acid sequence having 70% or higher identity to the amino acid sequence as shown in SEQ ID NO: 47;

[5] a gene encoding a protein comprising the amino acid sequence as shown in SEQ ID NO: 49 or an amino acid sequence having 70% or higher identity to the amino acid sequence as shown in SEQ ID NO: 49;

[6] a gene encoding a protein comprising the amino acid sequence as shown in SEQ ID NO: 51 or an amino acid sequence having 70% or higher identity to the amino acid sequence as shown in SEQ ID NO: 51; and

[7] a gene encoding a protein comprising the amino acid sequence as shown in SEQ ID NO: 53 or an amino acid sequence having 70% or higher identity to the amino acid sequence as shown in SEQ ID NO: 53.

(13) The transformant according to (11), which is obtained by using *Aspergillus oryzae* as a host.

(14) A filamentous fungus of the *Curvularia* species comprising the gene involved in the synthesis of a cyclic peptide compound according to any of (1) to (4) above.

(15) The filamentous fungus of the *Curvularia* species according to (14), which is *Curvularia clavata*.

(16) The filamentous fungus of the *Curvularia* species according to (14), which is under Accession Number NITE BP-02399.

Effects of the Invention

The present invention can provide a gene encoding a nonribosomal peptide synthetase involved in the synthesis of a cyclic peptide compound produced by a filamentous fungus of the *Curvularia* species and a group of genes involved in the synthesis of other cyclic peptide compounds. With the use of the gene involved in the synthesis of a cyclic peptide compound according to the present invention, a system for synthesizing a cyclic peptide compound produced by a filamentous fungus of the *Curvularia* species can be constructed, and such cyclic peptide compound can be produced with high efficiency.

BRIEF DESCRIPTION OF THE DRAWINGS

FIG. 3-1 shows the results of antiSMASH analysis of the NRPS domain structure deduced in the examples using the InterProScan and antiSMASH programs.

FIG. 3-2 shows the results of antiSMASH analysis of the NRPS domain structure deduced in the examples using the InterProScan and antiSMASH programs.

FIG. 4 shows the results of blastp search of the genes located upstream and downstream of the NRPS gene (TRAF01000135000001_J3G).

FIG. 24 schematically shows a scheme for simultaneously introducing three types of vectors carrying 7 genes after the front half portion and the rear half portion of the NRPS gene are introduced in two steps.

FIG. 26 shows characteristic diagrams demonstrating the results of LC/MS analysis of KK-1 in *Aspergillus oryzae* into which the KK-1 biosynthetic gene cluster had been introduced and the results of antibacterial activity test against the *Aspergillus oryzae*.

EMBODIMENTS FOR CARRYING OUT THE INVENTION

Figure 1:
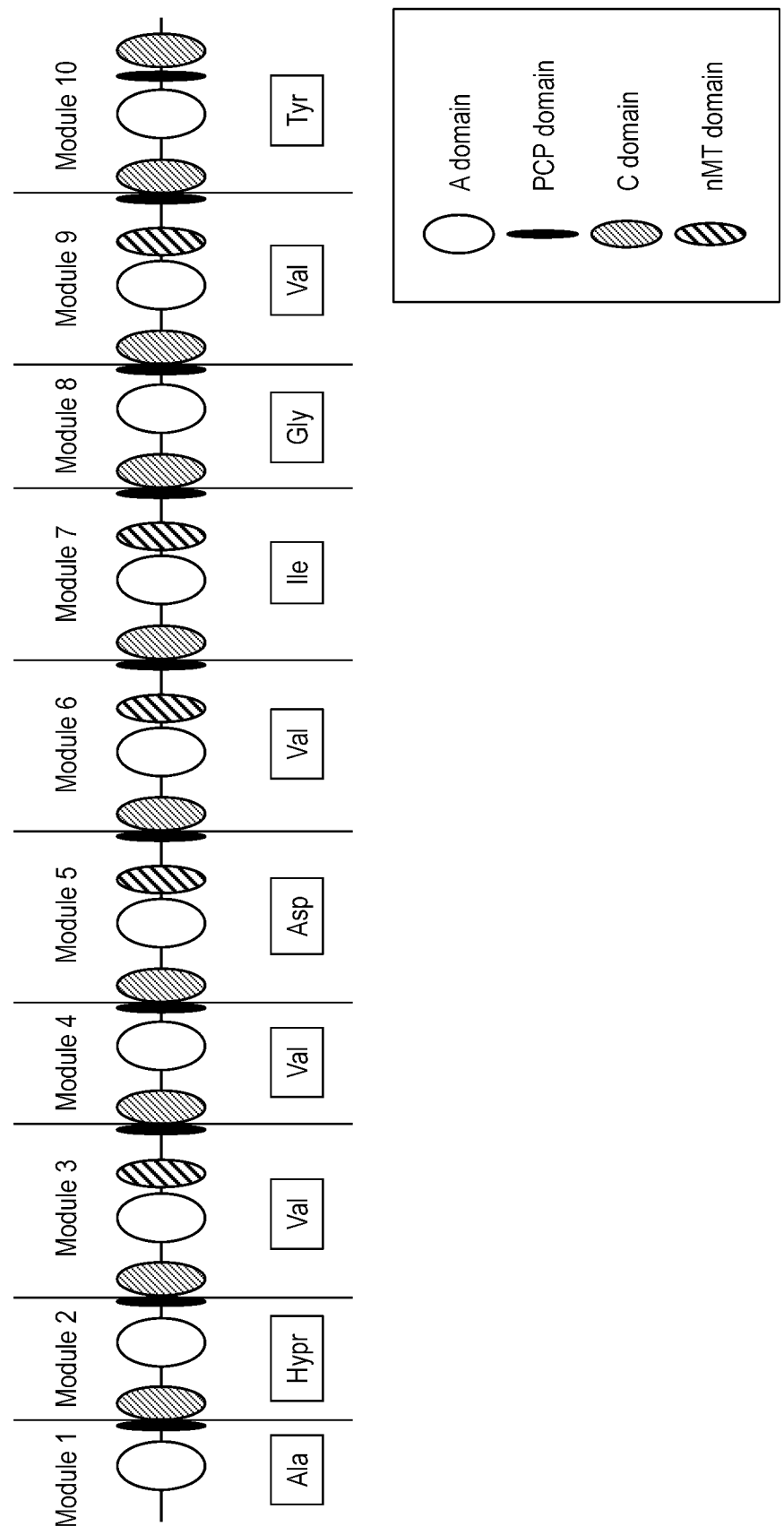
FIG. 1 schematically shows module structures and domain structures of the gene involved in the synthesis of a cyclic peptide compound according to the present invention.

Hereafter, the present invention is described in detail.

According to the present invention, the term "the gene involved in the synthesis of a cyclic peptide compound" refers to each gene included in the group of genes (i.e., a gene cluster) involved in the synthesis of a cyclic peptide compound produced by a filamentous fungus of the *Curvularia* species. Such cyclic peptide compound is represented by the chemical formula shown below, as disclosed in JP H8-504165 A (1996) (or WO 93/12659):

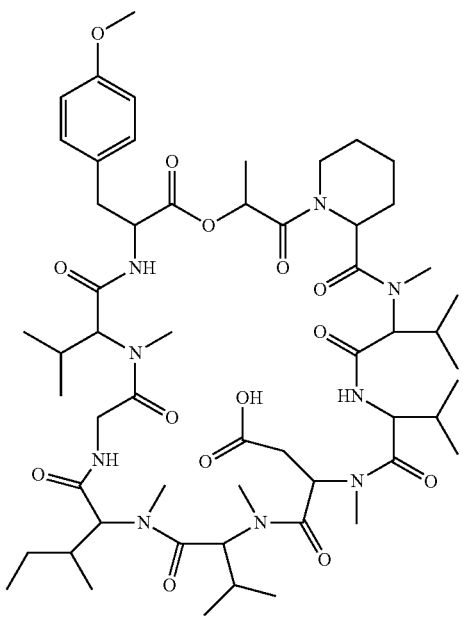 [SMILES: CCC(C)C1C(=O)NCC(=O)N(C)C(C(C)C)C(=O)NC(Cc2ccc(OC)cc2)C(=O)OC(C)C(=O)N2CCCCC2C(=O)N(C)C(C(C)C)C(=O)NC(C(C)C)C(=O)N(C)C(CC(=O)O)C(=O)N(C)C(C(C)C)C(=O)N1C]

wherein each amino acid residue and lactate residue can independently be in an L-form or D-form.

The name of the cyclic peptide compound (hereafter, it is occasionally referred to as "KK-1") is Tyrosine, N—[N—[N—[N—[N—[N—[N-[1-(2-hydroxy-1-oxopropyl)-2-piperidinyl]carbonyl]-N-methylvalyl]valyl]-N-methyl-a-aspartyl]-N-methylvalyl]-N-methylisoleucyl]glycyl]-N-methylvalyl]-O-methyl-, d2-lactone (9CI).

A representative example of a filamentous fungus of the *Curvularia* species producing such cyclic peptide compound is *Curvularia clavata* and other examples include *C. affinis, C. brachyspora, C. caricae-papayae, C. eragrostidis* (*Cochliobolus eragrostidis*), *C. fallax, C. geniculata* (*Cochliobolus geniculatus*), *C. harveyi, C. lunata* (*Cochliobolus lunatus*), *C. ovoidea, C. pallescens, C. penniseti, C. prasadii, C. protuberata, C. senegalensis, C. trifolii,* and *C. tuberculata* (*Cochliobolus tuberculatus*). An example of *Curvularia clavata* is the *Curvularia clavata* BAUA-2787 strain provided by Akita Konno Co., Ltd. The *Curvularia clavata* BAUA-2787 strain was deposited at Patent Microorganisms Depositary (NPMD), National Institute of Technology and Evaluation (NITE), #122, 2-5-8 Kazusakamatari, Kisarazu-shi, Chiba 292-0818 Japan as of Dec. 28, 2016 under the accession number NITE BP-02399.

As described in the examples below, a group of genes involved in the synthesis of the cyclic peptide compound can be defined as a group of genes including 10 types of genes, and preferably 9 types of genes.

These 10 types of genes are the O-methyltransferase gene, the nonribosomal peptide synthetase gene (the NRPS gene), the amidase gene, genes whose functions remain unknown (2 types), the transcription factor gene, the pmd1 gene encoding the leptomycin B-tolerant protein, the pyroline-5-carboxylate reductase-like gene, and the α/β hydrolase gene. Among such 10 types of genes, in particular, the O-methyltransferase gene, the nonribosomal peptide synthetase gene (the NRPS gene), the amidase gene, a gene whose functions remain unknown (1 type), the transcription factor gene, the pmd1 gene encoding the leptomycin B-tolerant protein, the pyroline-5-carboxylate reductase-like gene, and the α/β hydrolase gene can be defined as a group of genes that are strongly involved in the synthesis of a cyclic peptide compound.

[NRPS Genes]

Among the group of genes described above, the NRPS gene encodes NRPS having functions of forming a basic backbone of the cyclic peptide compound. Specifically, such NRPS forms a peptide backbone composed of 10 amino acids; that is, alanine (Ala)-pipecolic acid (Pip)-valine (Val)-valine-aspartic acid (Asp)-valine-isoleucine (Ile)-glycine (Gly)-valine-tyrosine (Tyr). More specifically, such NRPS has activity of forming peptide bonds between a carboxyl group of alanine and an amino group of pipecolic acid; between a carboxyl group of the pipecolic acid and an amino group of valine; between a carboxyl group of the valine and an amino group of valine; between a carboxyl group of the valine and an amino group of aspartic acid; between a carboxyl group of the aspartic acid and an amino group of valine; between a carboxyl group of the valine and an amino group of isoleucine; between a carboxyl group of the isoleucine and an amino group of glycine; between a carboxyl group of the glycine and an amino group of valine; between a carboxyl group of the valine and an amino group of tyrosine; and between a carboxyl group of the tyrosine and an amino group of the above alanine. Also, the NRPS has activity of methylating peptide bonds between pipecolic acid and valine; between valine and aspartic acid; between aspartic acid and valine; between valine and isoleucine; and between glycine and valine The NRPS comprises 10 modules corresponding to 10 amino acids constituting the basic peptide backbone describe above (i.e., alanine-pipecolic acid-valine-valine-aspartic acid-valine-isoleucine-glycine-valine-tyrosine). Each module comprises an adenylation domain (an A domain) that incorporates a target amino acid and binds adenosine monophosphate (AMP) to the amino acid, so as to synthesize aminoacyl AMP. Also, each module comprises a peptidyl carrier protein (PCP) domain having phosphopantetheine that binds the aminoacyl AMP with the aid of thioester formed between the serine site of phosphopantetheine and the aminoacyl AMP. In addition, each module comprises a condensation domain (a C domain) that forms a peptide bond between aminoacyl AMPs bound to the adjacent PCP domain. Further, some modules comprise an N-methyltransferase (nMT) domain that methylates a formed peptide bond.

As shown in FIG. 1, NRPS having the activity described above is composed of the first to the tenth modules. The positions of the modules in NRPS correspond to the positions of amino acids constituting the synthesized peptide backbone. Also, the positions of modules comprising the nMT domains correspond to the positions of N-methylated peptide bonds.

The first module comprises successively from the N terminus a first A domain comprising the amino acid sequence as shown in SEQ ID NO: 1 and a first PCP domain comprising the amino acid sequence as shown in SEQ ID NO: 2. In the first module, amino acid sequences constituting the first A domain and the first PCP domain are not limited to the amino acid sequences as shown in SEQ ID NOs: 1 and 2, respectively. Amino acid sequences having identity of 70% or higher, preferably 80% or higher, more preferably 90% or higher, further preferably 95% or higher, and most preferably 97% or higher to the amino acid sequences as shown in SEQ ID NOs: 1 and 2 may be sufficient if such sequences function as the A domain and the PCP domain, respectively.

The second module comprises successively from the N terminus a first C domain comprising the amino acid sequence as shown in SEQ ID NO: 3, a second A domain comprising the amino acid sequence as shown in SEQ ID NO: 4, and a second PCP domain comprising the amino acid sequence as shown in SEQ ID NO: 5. In the second module, amino acid sequences constituting the first C domain, the second A domain, and the second PCP domain are not limited to the amino acid sequences as shown in SEQ ID NOs: 3, 4, and 5, respectively. Amino acid sequences having identity of 70% or higher, preferably 80% or higher, more preferably 90% or higher, further preferably 95% or higher, and most preferably 97% or higher to the amino acid sequences as shown in SEQ ID NOs: 3, 4, and 5 may be sufficient if such sequences function as the C domain, the A domain, and the PCP domain, respectively.

The third module comprises successively from the N terminus a second C domain comprising the amino acid sequence as shown in SEQ ID NO: 6, a third A domain comprising the amino acid sequence as shown in SEQ ID NO: 7, a first nMT domain comprising the amino acid sequence as shown in SEQ ID NO: 8, and a third PCP domain comprising the amino acid sequence as shown in SEQ ID NO: 9. In the third module, amino acid sequences constituting the second C domain, the third A domain, the first nMT domain, and the third PCP domain are not limited to the amino acid sequences as shown in SEQ ID NOs: 6, 7, 8, and 9, respectively. Amino acid sequences having identity of 70% or higher, preferably 80% or higher, more preferably 90% or higher, further preferably 95% or higher, and most preferably 97% or higher to the amino acid sequences as shown in SEQ ID NO: 6, 7, 8, and 9 may be sufficient if such sequences function as the C domain, the A domain, the nMT domain, and the PCP domain, respectively.

The fourth module comprises successively from the N terminus a third C domain comprising the amino acid sequence as shown in SEQ ID NO: 10, a fourth A domain comprising the amino acid sequence as shown in SEQ ID NO: 11, and a fourth PCP domain comprising the amino acid sequence as shown in SEQ ID NO: 12. In the fourth module, amino acid sequences constituting the third C domain, the fourth A domain, and the fourth PCP domain are not limited to the amino acid sequences as shown in SEQ ID NO: 10, 11, and 12, respectively. Amino acid sequences having identity of 70% or higher, preferably 80% or higher, more preferably 90% or higher, further preferably 95% or higher, and most preferably 97% or higher to the amino acid sequences as shown in SEQ ID NOs: 10, 11, and 12 may be sufficient if such sequences function as the C domain, the A domain, and the PCP domain, respectively.

The fifth module comprises successively from the N terminus a fourth C domain comprising the amino acid sequence as shown in SEQ ID NO: 13, a fifth A domain comprising the amino acid sequence as shown in SEQ ID NO: 14, a second nMT domain comprising the amino acid sequence as shown in SEQ ID NO: 15, and a fifth PCP domain comprising the amino acid sequence as shown in SEQ ID NO: 16. In the fifth module, amino acid sequences constituting the fourth C domain, the fifth A domain, the second nMT domain, and the fifth PCP domain are not limited to the amino acid sequences as shown in SEQ ID NOs: 13, 14, 15, and 16, respectively. Amino acid sequences having identity of 70% or higher, preferably 80% or higher, more preferably 90% or higher, further preferably 95% or higher, and most preferably 97% or higher to the amino acid sequences as shown in SEQ ID NOs: 13, 14, 15, and 16 may be sufficient if such sequences function as the C domain, the A domain, the nMT domain, and the PCP domain, respectively.

The sixth module comprises successively from the N terminus a fifth C domain comprising the amino acid sequence as shown in SEQ ID NO: 17, a sixth A domain comprising the amino acid sequence as shown in SEQ ID NO: 18, a third nMT domain comprising the amino acid sequence as shown in SEQ ID NO: 19, and a sixth PCP domain comprising the amino acid sequence as shown in SEQ ID NO: 20. In the sixth module, amino acid sequences constituting the fifth C domain, the sixth A domain, the third nMT domain, and the sixth PCP domain are not limited to the amino acid sequences as shown in SEQ ID NOs: 17, 18, 19, and 20, respectively. Amino acid sequences having identity of 70% or higher, preferably 80% or higher, more preferably 90% or higher, further preferably 95% or higher, and most preferably 97% or higher to the amino acid sequences as shown in SEQ ID NOs: 17, 18, 19, and 20 may be sufficient if such sequences function as the C domain, the A domain, the nMT domain, and the PCP domain, respectively.

The seventh module comprises successively from the N terminus a sixth C domain comprising the amino acid sequence as shown in SEQ ID NO: 21, a seventh A domain comprising the amino acid sequence as shown in SEQ ID NO: 22, a fourth nMT domain comprising the amino acid sequence as shown in SEQ ID NO: 23, and a seventh PCP domain comprising the amino acid sequence as shown in SEQ ID NO: 24. In the seventh module, amino acid sequences constituting the sixth C domain, the seventh A domain, the fourth nMT domain, and the seventh PCP domain are not limited to the amino acid sequences as shown in SEQ ID NOs: 21, 22, 23, and 24, respectively. Amino acid sequences having identity of 70% or higher, preferably 80% or higher, more preferably 90% or higher, further preferably 95% or higher, and most preferably 97% or higher to the amino acid sequences as shown in SEQ ID NOs: 21, 22, 23, and 24 may be sufficient if such sequences function as the C domain, the A domain, the nMT domain, and the PCP domain, respectively.

The eighth module comprises successively from the N terminus a seventh C domain comprising the amino acid sequence as shown in SEQ ID NO: 25, an eighth A domain comprising the amino acid sequence as shown in SEQ ID NO: 26, and an eighth PCP domain comprising the amino acid sequence as shown in SEQ ID NO: 27. In the eighth module, amino acid sequences constituting the seventh C domain, the eighth A domain, and the eighth PCP domain are not limited to the amino acid sequences as shown in SEQ ID NOs: 25, 26, and 27, respectively. Amino acid sequences having identity of 70% or higher, preferably 80% or higher, more preferably 90% or higher, further preferably 95% or higher, and most preferably 97% or higher to the amino acid sequences as shown in SEQ ID NOs: 25, 26, and 27 may be sufficient if such sequences function as the C domain, the A domain, and the PCP domain, respectively.

The ninth module comprises successively from the N terminus an eighth C domain comprising the amino acid sequence as shown in SEQ ID NO: 28, a ninth A domain comprising the amino acid sequence as shown in SEQ ID NO: 29, a fifth nMT domain comprising the amino acid sequence as shown in SEQ ID NO: 30, and a ninth PCP domain comprising the amino acid sequence as shown in SEQ ID NO: 31. In the ninth module, amino acid sequences constituting the eighth C domain, the ninth A domain, the fifth nMT domain, and the ninth PCP domain are not limited to the amino acid sequences as shown in SEQ ID NOs: 28, 29, 30, and 31, respectively. Amino acid sequences having identity of 70% or higher, preferably 80% or higher, more preferably 90% or higher, further preferably 95% or higher, and most preferably 97% or higher to the amino acid sequences as shown in SEQ ID NOs: 28, 29, 30, and 31 may be sufficient if such sequences function as the C domain, the A domain, the nMT domain, and the PCP domain, respectively.

The tenth module comprises successively from the N terminus a ninth C domain comprising the amino acid sequence as shown in SEQ ID NO: 32, a tenth A domain comprising the amino acid sequence as shown in SEQ ID NO: 33, a tenth PCP domain comprising the amino acid sequence as shown in SEQ ID NO: 34, and a tenth C domain comprising the amino acid sequence as shown in SEQ ID NO: 35. In the tenth module, amino acid sequences constituting the ninth C domain, the tenth A domain, the tenth PCP domain, and the tenth C domain are not limited to the amino acid sequences as shown in SEQ ID NOs: 32, 33, 34, and 35, respectively. Amino acid sequences having identity of 70% or higher, preferably 80% or higher, more preferably 90% or higher, further preferably 95% or higher, and most preferably 97% or higher to the amino acid sequences as shown in SEQ ID NOs: 32, 33, 34, and 35 may be sufficient if such sequences function as the C domain, the A domain, the PCP domain, and the C domain, respectively.

When the first A domain does not comprise the amino acid sequence as shown in SEQ ID NO: 1, whether or not it can function as the A domain corresponding to alanine can be evaluated in the manner described below. At the outset, a mutant NRPS gene is designed to encode a first mutant A domain that is designed to comprise a sequence different from the amino acid sequence as shown in SEQ ID NO: 1. The resulting mutant NRPS gene is allowed to express in an adequate host, and whether or not a compound comprising a basic peptide backbone of the cyclic peptide compound is synthesized in the host and in metabolites in the culture supernatant is inspected. When a compound comprising a basic peptide backbone of the cyclic peptide compound is synthesized in the metabolite, the designed first mutant A domain can be evaluated as functioning as the A domain corresponding to alanine. When the second to the tenth A domains comprise amino acid sequences different from the amino acid sequences as shown in SEQ ID NOs: 4, 7, 11, 14, 18, 22, 26, 29, and 33, respectively, whether or not such domains can function as the A domains can be evaluated in the same manner.

When the first PCP domain does not comprise the amino acid sequence as shown in SEQ ID NO: 2, whether or not it can function as the PCP domain can be evaluated in the manner described below. At the outset, a mutant NRPS gene is designed to encode a first mutant PCP domain that is designed to comprise a sequence different from the amino acid sequence as shown in SEQ ID NO: 2. The resulting mutant NRPS gene is allowed to express in an adequate host, and whether or not a compound comprising a basic peptide backbone of the cyclic peptide compound is synthesized in the host or in metabolites in the culture supernatant is inspected. When a compound comprising a basic peptide backbone of the cyclic peptide compound is synthesized in the metabolite, the designed first mutant PCP domain can be evaluated as functioning as the PCP domain. When the second to the tenth PCP domains comprise amino acid sequences different from the amino acid sequences as shown in SEQ ID NOs: 5, 9, 12, 16, 20, 24, 27, 31, and 34, respectively, whether or not such domains can each function as the PCP domain can be evaluated in the same manner.

When the first C domain does not comprise the amino acid sequence as shown in SEQ ID NO: 3, whether or not it can function as the C domain can be evaluated in the manner described below. At the outset, a mutant NRPS gene is designed to encode a first mutant C domain that is designed to comprise a sequence different from the amino acid sequence as shown in SEQ ID NO: 3. The resulting mutant NRPS gene is allowed to express in an adequate host, and whether or not a compound comprising a basic peptide backbone of the cyclic peptide compound is synthesized in the host or in metabolites in the culture supernatant is inspected. When a compound comprising a basic peptide backbone of the cyclic peptide compound is synthesized in the metabolite, the designed first mutant C domain can be evaluated as functioning as the C domain. When the second to the tenth C domains comprise amino acid sequences different from the amino acid sequences as shown in SEQ ID NOs: 6, 10, 13, 17, 21, 25, 28, 32, and 35, respectively, whether or not such domains can function as the C domains can be evaluated in the same manner.

When the first nMT domain does not comprise the amino acid sequence as shown in SEQ ID NO: 8, whether or not it can function as the nMT domain can be evaluated in the manner described below. At the outset, a mutant NRPS gene is designed to encode the first mutant nMT domain that is designed to comprise a sequence different from the amino acid sequence as shown in SEQ ID NO: 8. The resulting mutant NRPS gene is allowed to express in an adequate host, and whether or not a compound comprising a basic peptide backbone of the cyclic peptide compound is synthesized in the host or in metabolites in the culture supernatant is inspected. When a compound comprising a basic peptide backbone of the cyclic peptide compound is synthesized in the metabolite, the designed first mutant nMT domain can be evaluated as functioning as the nMT domain. When the second to the fifth nMT domains comprise amino acid sequences different from the amino acid sequences as shown in SEQ ID NOs: 15, 19, 23, and 30, respectively, whether or not such domains can function as the nMT domains can be evaluated in the same manner.

As described above, NRPS that synthesizes the basic peptide backbone of the cyclic peptide compound can be defined with the first module to the tenth module. For example, SEQ ID NO: 37 shows the amino acid sequence of NRPS derived from *Curvularia clavata* and having activity of synthesizing a basic peptide backbone of the cyclic peptide compound, and SEQ ID NO: 36 shows the nucleotide sequence of a coding region corresponding to the amino acid sequence as shown in SEQ ID NO: 37.

Accordingly, the NRPS gene of the present invention comprises the first module to the tenth module defined by the amino acid sequences as shown in SEQ ID NOs: 1 to 35, and it may encode a protein comprising an amino acid sequence having identity of 70% or higher, preferably 80% or higher, more preferably 90% or higher, further preferably 95% or higher, and most preferably 97% or higher to the amino acid sequence as shown in SEQ ID NO: 37 and having activity of synthesizing a basic peptide backbone of the cyclic peptide compound. The value of identity between amino acid sequences can be calculated based on default setting using the BLASTN or BLASTX program equipped with the BLAST algorithm. Specifically, the value of identity is determined by calculating the number of amino acid residues that completely match the others when a pairwise alignment analysis is conducted for a pair of amino acid sequences and then determining the proportion of the number of such residues in all the amino acid residues compared.

The NRPS gene of the present invention may comprise the first module to the tenth module defined by the amino acid sequences as shown in SEQ ID NOs: 1 to 35, and it may encode a protein comprising an amino acid sequence derived from the amino acid sequence as shown in SEQ ID NO: 37 by substitution, deletion, addition, or insertion of 1 or several amino acids and having activity of synthesizing a basic peptide backbone in the cyclic peptide compound. The term "several" used herein refers to, for example, 2 to 1300, preferably 2 to 1000, more preferably 2 to 700, still more preferably 2 to 500, further preferably 2 to 250, more further preferably 2 to 100, and still further preferably 2 to 50, respectively.

In addition, the NRPS gene of the present invention may comprise the first module to the tenth module defined by the amino acid sequences as shown in SEQ ID NOs: 1 to 35, it may hybridize under stringent conditions to all or a part of a complementary strand of DNA comprising the nucleotide sequence as shown in SEQ ID NO: 36, and it may encode a protein having activity of synthesizing a basic peptide backbone of the cyclic peptide compound. Under "stringent conditions," a so-called specific hybrid is formed, but a non-specific hybrid is not formed. For example, such conditions can be adequately determined with reference to the Molecular Cloning: A Laboratory Manual (Third Edition). Specifically, stringency can be set based on the temperature and the concentration of salts contained in a solution for southern hybridization, and the temperature and the concentration of salts contained in a solution for a washing step of southern hybridization. Under stringent conditions, more precisely, sodium concentration is, for example, the sodium concentration of 25 to 500 mM, and preferably 25 to 300 mM, and the temperature is 42° C. to 68° C., and preferably 42° C. to 65° C. Further specifically, sodium concentration is 5×SSC (83 mM NaCl, 83 mM sodium citrate), and the temperature is 42° C.

The NRPS gene of the present invention is not limited to the gene encoding a protein comprising the first module to the tenth module defined by the amino acid sequences as shown in SEQ ID NOs: 1 to 35. As described above, SEQ ID NO: 37 shows the amino acid sequence of NRPS derived from *Curvularia clavata* and having activity of synthesizing a basic peptide backbone of the cyclic peptide compound, and SEQ ID NO: 36 shows the nucleotide sequence of a coding region corresponding to the amino acid sequence as shown in SEQ ID NO: 37. The NRPS gene of the present invention can also be defined by SEQ ID NOs: 36 and 37.

Specifically, the NRPS gene of the present invention can be a gene encoding the protein comprising the amino acid sequence as shown in SEQ ID NO: 37.

The NRPS gene of the present invention may be a gene that encodes a protein comprising an amino acid sequence having identity of 70% or higher, preferably 80% or higher, more preferably 90% or higher, further preferably 95% or higher, and most preferably 97% or higher to the amino acid sequence as shown in SEQ ID NO: 37 and having activity of synthesizing a basic peptide backbone of the cyclic peptide compound. The value of identity between amino acid sequences can be calculated based on default setting using the BLASTN or BLASTX program equipped with the BLAST algorithm as described above. Specifically, the value of identity is determined by calculating the number of amino acid residues that completely match the others when a pairwise alignment analysis is conducted for a pair of amino acid sequences and then determining the proportion of the number of such residues in all the amino acid residues compared.

With the use of known databases storing nucleotide sequence information, genes that satisfy the conditions such as a high coverage, a low E-value, and a high value of identity with the nucleotide sequence as shown in SEQ ID NO: 36 can be identified with regard to the NRPS gene of the present invention. The genes to be identified are expected to show a coverage of 90% or higher, preferably 95% or higher, and more preferably 99% or higher. Also, the genes to be identified are expected to show an E-value of 1.0e-5 or lower, preferably 1.0e-15 or lower, and more preferably 0.0. Further, the genes to be identified are expected to show a value of identity of 70% or higher, preferably 75% or higher, and more preferably 80% or higher. The gene identified to satisfy such conditions is highly likely to be homologous to the NRPS gene comprising the nucleotide sequence as shown in SEQ ID NO: 36, and such gene can be identified as a gene encoding a protein having activity of synthesizing a basic peptide backbone of the cyclic peptide compound as with the NRPS gene comprising the nucleotide sequence as shown in SEQ ID NO: 36.

Whether or not the identified gene encodes a protein having activity of synthesizing a basic peptide backbone of the cyclic peptide compound may be determined by obtaining microorganisms comprising such gene and examining the ability thereof to synthesize the cyclic peptide compound. The ability of the obtained microorganisms to synthesize the cyclic peptide compound can be examined by culturing the microorganisms and inspecting whether or not the cultured cells or the culture supernatant contains the cyclic peptide compound.

If the nucleotide sequence of the NRPS gene of the present invention is identified, the NRPS gene of interest can be prepared via chemical synthesis, PCR using the genomic DNA as a template, or hybridization involving the use of a DNA fragment comprising such nucleotide sequence as a probe. A gene comprising a nucleotide sequence different from SEQ ID NO: 36 or a gene encoding an amino acid sequence different from SEQ ID NO: 37 can be synthesized by subjecting a polynucleotide comprising the nucleotide sequence as shown in SEQ ID NO: 36 to site-directed mutagenesis. A mutation can be introduced into a polynucleotide comprising the nucleotide sequence as shown in SEQ ID NO: 36 by known techniques, such as the Kunkel's method or the Gapped duplex method, or techniques in accordance therewith. For example, mutagenesis can be carried out using a mutagenesis kit using site-directed mutagenesis (e.g., Mutant-K (Takara Bio Inc.) and Mutant-G (Takara Bio Inc.)) or a LA PCR in vitro Mutagenesis series kit (Takara Bio Inc.).

In particular, the NRPS gene of the present invention can be isolated from microorganisms known to produce the cyclic peptide compound. An example is the NRPS gene (i.e., the NRPS gene encoding the amino acid sequence as shown in SEQ ID NO: 37) isolated from *Curvularia clavata*.

The NRPS gene of the present invention is highly likely to be isolated from a filamentous fungus of the *Curvularia* species other than *Curvularia clavata* with the use of the nucleotide sequence as shown in SEQ ID NO: 36. Specifically, hybridization may be carried out with the use of a polynucleotide comprising continuous nucleotides that constitutes a part of the nucleotide sequence as shown in SEQ ID NO: 36 as a probe, so that the NRPS gene of the present invention can be isolated from the genome of a filamentous fungus of the *Curvularia* species other than *Curvularia clavata* or from cDNA derived from a transcription product. A filamentous fungus of the *Curvularia* species other than *Curvularia clavata* may or may not produce the cyclic peptide compound because a filamentous fungus of the *Curvularia* species that does not produce the cyclic peptide compound may comprise the NRPS gene of the present invention.

Examples of filamentous fungi of the *Curvularia* species other than *Curvularia clavata* include *C. affinis*, *C. brachyspora*, *C. caricae-papayae*, *C. eragrostidis* (*Cochliobolus eragrostidis* (Teleomorph)), *C. fallax*, *C. geniculata* (*Cochliobolus geniculatus* (Teleomorph)), *C. harveyi*, *C. lunata* (*Cochliobolus lunatus* (Teleomorph)), *C. ovoidea*, *C. pallescens*, *C. penniseti*, *C. prasadii*, *C. protuberata*, *C. senegalensis*, *C. trifolii*, and *C. tuberculata* (*Cochliobolus tuberculatus* (Teleomorph)).

[Filamentous Fungi of the *Curvularia* Species]

The filamentous fungus of the *Curvularia* species of the present invention comprises the NRPS gene described above. The NRPS gene of the present invention is highly likely to be isolated from a filamentous fungus of the *Curvularia* species other than *Curvularia clavata*, as described above. That is, the filamentous fungi of the *Curvularia* species of the present invention are not limited to *Curvularia clavata*, and examples thereof include *C. affinis*, *C. brachyspora*, *C. caricae-papayae*, *C. eragrostidis* (*Cochliobolus eragrostidis*), *C. fallax*, *C. geniculata* (*Cochliobolus geniculatus*), *C. harveyi*, *C. lunata* (*Cochliobolus lunatus*), *C. ovoidea*, *C. pallescens*, *C. penniseti*, *C. prasadii*, *C. protuberata*, *C. senegalensis*, *C. trifolii*, and *C. tuberculata* (*Cochliobolus tuberculatus*) producing cyclic peptide compounds.

The filamentous fungus of the *Curvularia* species of the present invention is particularly preferably *Curvularia clavata*. A specific example of the filamentous fungus of the *Curvularia* species of the present invention is the *Curvularia clavata* BAUA-2787 strain provided by Akita Konno Co., Ltd. The *Curvularia clavata* BAUA-2787 strain was deposited at Patent Microorganisms Depositary (NPMD), National Institute of Technology and Evaluation (NITE), #122, 2-5-8 Kazusakamatari, Kisarazu-shi, Chiba 292-0818 Japan as of Dec. 28, 2016 under the accession number NITE BP-02399.

[Transcription Factor Gene]

Transcription factor genes included in the group of genes involved in the synthesis of the cyclic peptide compound encode proteins capable of positively regulating the expression of the genes included in such group of genes at the level of transcription. An example of the transcription factor gene of the present invention is derived from *Curvularia clavata*. SEQ ID NO: 39 shows the amino acid sequence of a protein having transcription enhancing activity on a gene included in the group of genes involved in the synthesis of the cyclic peptide compound, and SEQ ID NO: 38 shows the nucleotide sequence of a coding region corresponding to such amino acid sequence. The transcription factor gene of the present invention can be defined with SEQ ID NOs: 38 and 39.

Specifically, the transcription factor gene of the present invention can be a gene encoding the protein comprising the amino acid sequence as shown in SEQ ID NO: 39.

The transcription factor gene of the present invention may be a gene encoding a protein comprising an amino acid sequence having identity of 70% or higher, preferably 80% or higher, more preferably 90% or higher, further preferably 95% or higher, and most preferably 97% or higher to the amino acid sequence as shown in SEQ ID NO: 39 and having the transcription enhancing activity described above. The value of identity between amino acid sequences can be calculated based on default setting using the BLASTN or BLASTX program equipped with the BLAST algorithm, as described above. Specifically, the value of identity is determined by calculating the number of amino acid residues that completely match the others when a pairwise alignment analysis is conducted for a pair of amino acid sequences and then determining the proportion of the number of such residues in all the amino acid residues compared.

The transcription factor gene of the present invention may encode a protein comprising an amino acid sequence derived from the amino acid sequence as shown in SEQ ID NO: 39 by substitution, deletion, addition, or insertion of 1 or several amino acids and having the transcription enhancing activity. The term "several" used herein refers to, for example, 2 to 40, preferably 2 to 30, more preferably 2 to 20, further preferably 2 to 10, and still further preferably 2 to 5, as described above.

The transcription factor gene of the present invention may hybridize under stringent conditions to all or a part of a complementary strand of DNA comprising the nucleotide sequence as shown in SEQ ID NO: 38 and encode a protein having the transcription enhancing activity. Under "stringent conditions," a so-called specific hybrid is formed, but a non-specific hybrid is not formed. For example, such conditions can be adequately determined with reference to the Molecular Cloning: A Laboratory Manual (Third Edition). Specifically, stringency can be set based on the temperature and the concentration of salts contained in a solution for southern hybridization, and the temperature and the concentration of salts contained in a solution for a washing step of southern hybridization. Under stringent conditions, more precisely, sodium concentration is, for example, 25 to 500 mM, and preferably 25 to 300 mM, and the temperature is 42° C. to 68° C., and preferably 42° C. to 65° C. Further specifically, sodium concentration is 5×SSC (83 mM NaCl, 83 mM sodium citrate), and the temperature is 42° C.

As described above, whether or not a gene comprising a nucleotide sequence different from SEQ ID NO: 38 or a gene encoding an amino acid sequence different from SEQ ID NO: 39 encodes a protein having the transcription enhancing activity can be determined by introducing the gene of interest into a host that produces the cyclic peptide compound (e.g., *Curvularia clavata*) in an expressible manner and examining the expression levels of the group of genes involved in the synthesis of the cyclic peptide compound in such host at the level of transcription.

If the nucleotide sequence of the transcription factor gene of the present invention is identified, the transcription factor gene of interest can be prepared via chemical synthesis, PCR using the genomic DNA as a template, or hybridization involving the use of a DNA fragment comprising such nucleotide sequence as a probe. A gene comprising a nucleotide sequence different from SEQ ID NO: 38 or a gene encoding an amino acid sequence different from SEQ ID NO: 39 can be synthesized by subjecting a polynucleotide comprising the nucleotide sequence as shown in SEQ ID NO: 38 to site-directed mutagenesis. A mutation can be introduced into a polynucleotide comprising the nucleotide sequence as shown in SEQ ID NO: 38 by known techniques, such as the Kunkel's method or the Gapped duplex method, or techniques in accordance therewith. For example, mutagenesis can be carried out using a mutagenesis kit using site-directed mutagenesis (e.g., Mutant-K (Takara Bio Inc.) and Mutant-G (Takara Bio Inc.)) or a LA PCR in vitro Mutagenesis series kit (Takara Bio Inc.).

In particular, the transcription factor gene of the present invention can be isolated from microorganisms known to produce the cyclic peptide compound. An example is the transcription factor gene (i.e., the transcription factor gene encoding the amino acid sequence as shown in SEQ ID NO: 39) isolated from *Curvularia clavata*.

The transcription factor gene of the present invention is highly likely to be isolated from a filamentous fungus of the *Curvularia* species other than *Curvularia clavata* with the use of the nucleotide sequence as shown in SEQ ID NO: 38. Specifically, hybridization may be carried out with the use of a polynucleotide comprising continuous nucleotides that constitutes a part of the nucleotide sequence as shown in SEQ ID NO: 38 as a probe, so that the transcription factor gene of the present invention can be isolated from the genome of a filamentous fungus of the *Curvularia* species other than *Curvularia clavata* or from cDNA derived from a transcription product. A filamentous fungus of the *Curvularia* species other than *Curvularia clavata* may or may not produce the cyclic peptide compound because a filamentous fungus of the *Curvularia* species that does not produce the NRPS gene of the present invention may comprise the NRPS gene of the present invention.

Examples of filamentous fungi of the *Curvularia* species other than *Curvularia clavata* include *C. affinis*, *C. brachyspora*, *C. caricae-papayae*, *C. eragrostidis* (*Cochliobolus eragrostidis* (Teleomorph)), *C. fallax*, *C. geniculata* (*Cochliobolus geniculatus* (Teleomorph)), *C. harveyi*, *C. lunata* (*Cochliobolus lunatus* (Teleomorph)), *C. ovoidea*, *C. pallescens*, *C. penniseti*, *C. prasadii*, *C. protuberata*, *C. senegalensis*, *C. trifolii*, and *C. tuberculata* (*Cochliobolus tuberculatus* (Teleomorph)).

[Transformant]

Among the genes involved in the synthesis of a cyclic peptide compound of the present invention, the NRPS gene is introduced into a host in an expressible manner, so that a transformant capable of synthesizing a compound comprising a basic peptide backbone of the cyclic peptide compound can be prepared. Also, genes capable of synthesizing a cyclic peptide compound other than the NRPS gene are introduced into a host in combination with the NRPS gene in an expressible manner, so that a transformant capable of synthesizing the cyclic peptide compound can be prepared.

When preparing a transformant capable of synthesizing the cyclic peptide compound, the transcription factor gene described above may or may not be introduced as a gene involved in the synthesis of a cyclic peptide compound other than the NRPS gene. For example, the NRPS gene and other genes may be introduced into a host in a position located downstream of a constitutive expression promoter capable of functioning in a host. Thus, such NRPS gene and other genes can be induced to be constitutively expressed. In such a case, genes involved in the synthesis of a cyclic peptide compound can be expressed without the introduction of the transcription factor gene, and the cyclic peptide compound can be prepared.

Any organisms and, in particular, any microorganisms, can serve as hosts without particular limitation. Examples of microorganisms that can be used as hosts include, but are not particularly limited to: bacteria of *Escherichia* such as *Escherichia coli, Coryncbacterium* such as *Corynebacterium glutamicum, Bacillus* such as *Bacillus subtilis, Pseudomonas* such as *Pseudomonas putida*, and *Rhizobium* such as *Rhizobium meliloti*; and mycetes including yeast and filamentous fungi, such as *Saccharomyces cerevisiae, Schizosaccharomyces pombe*, and *Pichia pastoris*.

When bacteria such as *E. coli* are hosts, the expression vector is preferably capable of autonomous replication in the bacteria, and it is preferably composed of a promoter, a ribosome-binding sequence, the gene described above, and a transcription terminator sequence. The expression vector may comprise a gene regulating promoter activity.

Any promoter may be used, provided that it can express a gene of interest in an *E. coli* or other host. For example, *E. coli*-derived promoters, such as trp promoter, lac promoter, PL promoter, and PR promoter, and phage-derived promoters, such as T7 promoter, may be used. An artificially designed or modified promoter, such as tac promoter, may also be used.

A method for introducing an expression vector is not particularly limited, provided that DNA is introduced into bacteria by such method. Examples include a method involving the use of calcium ions (Cohen, S. N., et al., Proc. Natl. Acad. Sci., U.S.A., 69: 2110-2114, 1972) and electroporation.

Examples of yeasts that can be used as hosts include, but are not particularly limited to, yeasts of *Candida* such as *Candida Shehatae*, yeasts of *Pichia* such as *Pichia stipites*, yeasts of *Pachysolen* such as *Pachysolen tannophilus*, yeasts of *Saccharomyces* such as *Saccharomyces cerevisiae*, and yeasts of *Schizosaccharomyces* such as *Schizosaccharomyces pombe*, with *Saccharomyces cerevisiae* being preferable.

The expression levels of the NRPS gene and other genes are intensified with the use of an adequate promoter having high transcription activity. Examples of promoters that can be used include, but are not particularly limited to, the glyceraldehyde-3-phosphate dehydrogenase (TDH3) gene promoter, the 3-phosphoglycerate kinase (PGK1) gene promoter, and the hyperosmolarity-responsive 7 (HOR7) gene promoter. In particular, the pyruvate decarboxylase (PDC1) gene promoter is preferable because of a high capacity for achieving high-level expression of the target downstream genes. Alternatively, gal1 promoter, gal10 promoter, heat shock protein promoter, MFα1 promoter, PHO5 promoter, GAP promoter, ADH promoter, AOX1 promoter, or the like may be used to allow forced expression of downstream genes.

Examples of filamentous fungi that can be used as hosts include, but are not particularly limited to: filamentous fungi of *Aspergillus*, such as *Aspergillus nidulans, Aspergillus niger, Aspergillus oryzae, Aspergillus sojae*, and *Aspergillus glaucus*; filamentous fungi of *Trichoderma*, such as *Trichoderma reesei* and *Trichoderma viride*; filamentous fungi of *Rhizomucor*, such as *Rhizomucor pusillus* and *Rhizomucor miehei*; filamentous fungi of *Penicillium*, such as *Penicillium notatum* and *Penicillium chrysogenum*; filamentous fungi of *Rhizopus*, such as *Rhizopus oryzae; Acremonium cellulolyticus; Humicola grisea*; and *Thermoaseus aurantiacus*. Specifically, hosts are preferably filamentous fungi of *Aspergillus* and particularly preferably *Aspergillus oryzae*.

The NRPS gene and other genes can be expressed in filamentous fungi with the use of, for example, α-amylase (amyB) gene promoter, α-glucosidase (agdA) gene promoter, glucoamylase (glaA) gene promoter, tryptophan biosynthesizing (trpC) gene promoter, alcohol dehydrogenase (alcA) gene promoter, translation elongation factor (tef1) promoter, triose-phosphate isomerase (tpiA) gene promoter, glyceraldehyde-3-phosphate dehydrogenase (gpdA) gene promoter, enolase (enoA) promoter, pyruvate carboxylase (pdcA) promoter, or cellobiohydrolase (cbh1) gene promoter.

Any conventional techniques known to transform yeasts and filamentous fungi can be employed as methods for introducing the genes described above. Specific examples thereof include transformation, transfection, conjugation, the protoplast method, the spheroplast method, electroporation, lipofection, and the lithium acetate method.

[Production of Cyclic Peptide Compound]

With the use of the transformant described above, the target cyclic peptide compound can be produced.

Among the genes involved in the synthesis of a cyclic peptide compound of the present invention, specifically, a transformant into which the NRPS gene has been introduced in an expressible manner is used. Thus, a compound comprising a basic peptide backbone of the cyclic peptide compound can be produced. For example, the cyclic peptide compound can be produced from a compound obtained via chemical synthesis. With the use of a transformant into which the NRPS gene and other genes have been introduced in an expressible manner, in addition, the cyclic peptide compound can be produced.

The cyclic peptide compound synthesized in a transformant or a compound comprising a basic peptide backbone thereof can be extracted from the culture supernatant by separating cells with the use of a centrifuge, Miracloth, or the like and adding an organic solvent such as ethyl acetate. The compound can be extracted from cells by releasing the compound extracellularly via physical disruption (e.g., homogenization, glass bead crushing, or freezing-thawing) or chemical disruption (e.g., treatment with a solvent, acid, base, osmotic pressure, or enzyme) and adding an organic solvent such as ethyl acetate. The extracted cyclic peptide compound or a compound comprising the basic peptide backbone thereof can be purified via a known purification technique (e.g., column chromatography or salt sedimentation). Such techniques can be employed in adequate combination, according to need.

The cyclic peptide compound produced as described above can be used as an antibacterial agent having bactericidal activity against, for example, plant pathogenic bacteria and, in particular, against fungi. When the cyclic peptide compound is used as an antibacterial agent, more specifically, such compound may be used in that state. In general, a solid carrier, liquid carrier, surfactant, or other adjuvant may be mixed with such compound to prepare an agent of any dosage form, such as an emulsion, EW agent, liquid preparation, suspension, wettable powder, granule wettable powder, powder, DL powder, microgranule powder, microgranule powder F, granule, tablet, oil, aero sol, flowable agent, dry flowable agent, or microcapsule.

Examples of solid carriers include animal- or plant-derived powders, such as starch, active carbon, soybean flour, wheat flour, wood flour, fish meal, and powdered milk, and inorganic powders, such as talc, kaolin, bentonite, calcium carbonate, zeolite, diatomaceous earth, white carbon, clay, alumina, ammonium sulfate, and urea.

Examples of liquid carriers include: water; an alcohol, such as isopropyl alcohol and ethylene glycol; a ketone, such as cyclohexane and methyl ethyl ketone; an ether, such as dioxane and tetrahydrofuran; an aliphatic hydrocarbon, such as kerosine and light oil; an aromatic hydrocarbon, such as xylene, trimethylbenzene, tetramethylbenzene, methylnaphthalin, and solvent naphtha; a halogenated hydrocarbon, such as chlorobenzene; an acid amide, such as dimethylacetamide; an ester, such as glycerin fatty acid ester; a nitrile, such as acetonitrile; and a sulfur-containing compound, such as dimethyl sulfoxide.

Examples of surfactants include metal salt of alkyl benzene sulfonic acid, metal salt of dinaphthylmethane disulfonic acid, alcohole-sulfate ester salt, alkyl aryl sulfonic acid salt, lignin sulfonic acid salt, polyoxyethylene glycol ether, polyoxyethylene alkyl aryl ether, and polyoxyethylene sorbitan monoalkylate.

Examples of other adjuvants that can be used include fixing agents or thickeners, such as carboxy methyl cellulose, gum Arabic, sodium alginate, guar gum, gum tragacanth, and polyvinyl alcohol, defoaming agents, such as metal soap, agents for improving physical properties, such as fatty acid, alkyl phosphate, silicone, and paraffin, and coloring agents.

Various types of formulations of antibacterial agents or diluents thereof can generally be applied in accordance with a common technique. Specifically, application thereof can be carried out by means of, for example, dispersion (e.g., spraying, misting, atomizing, dusting, granule application, water surface application, and in-box application), soil application (e.g., inclusion and affusion), surface application (e.g., coating, powder-coating, and covering), soaking, bait poisoning, and smoke application. Also, so-called ultra-high concentration and small-dose spraying can be employed. In such a case, active ingredient content can be 100%.

In an antibacterial agent comprising, as an active ingredient, the cyclic peptide compound, in addition, the cyclic peptide compound is sufficiently effective as an active ingredient by itself. According to need, the antibacterial agent can be mixed with or used in combination with, for example, another fertilizer or an agricultural chemical, such as an insecticide, miticide, nematicide, another antibacterial agent, anti-viral agent, attractant, herbicide, or plant growth regulator. In such a case, the effects thereof can occasionally be particularly high. Examples of plant pathogenic bacteria on which KK-1 itself exerts control effects include, but are not particularly limited to; gray molds (*Botrytis cinerea*), powdery mildew (*Blumeria graminis*), blast disease (*Magnaporthe oryzae*), and *Rhizoctonia solani* (*Thanatephorus cucumeris* (Frank) Donk).

EXAMPLES

Hereafter, the present invention is described in greater detail with reference to the examples, although the technical scope of the present invention is not limited to the following examples.

Example 1

[Genomic Analysis of *Curvularia clavata*]

Conidiospores of the *C. clavata* BAUA-2787 strain provided by Akita Konno Co., Ltd. were inoculated into 200 ml of CM liquid medium (a 500-ml triangular flask), and culture was conducted at 26° C. and 130 rpm for 48 hours. The cultured cells were harvested with the use of Miracloth, a spatula was pressed against the cells for dehydration, the dehydrated cells were introduced into a mortar, which had been cooled to −20° C. in advance, and liquid nitrogen was injected thereinto for freezing. The frozen cells were quickly fractured with the use of a pestle to result in a powder state, and genomic DNA was then extracted using the DNeasy Plant Maxi Kit.

Genomic analysis was performed using two types of next-generation sequencers (5500 xl SOLiD (life technologies) and MiSeq (illumina)). A library was prepared from genomic DNA of the *C. clavata* strain using the 5500 SOLiD Mate-Paired Library Kit (for 5500 xl SOLiD) and the Nextera DNA Sample Prep Kit (MiSeq), and genomic analysis was then conducted using the next-generation sequencers.

[Search of the NRPS Gene of *C. clavata*]

Figure 2:
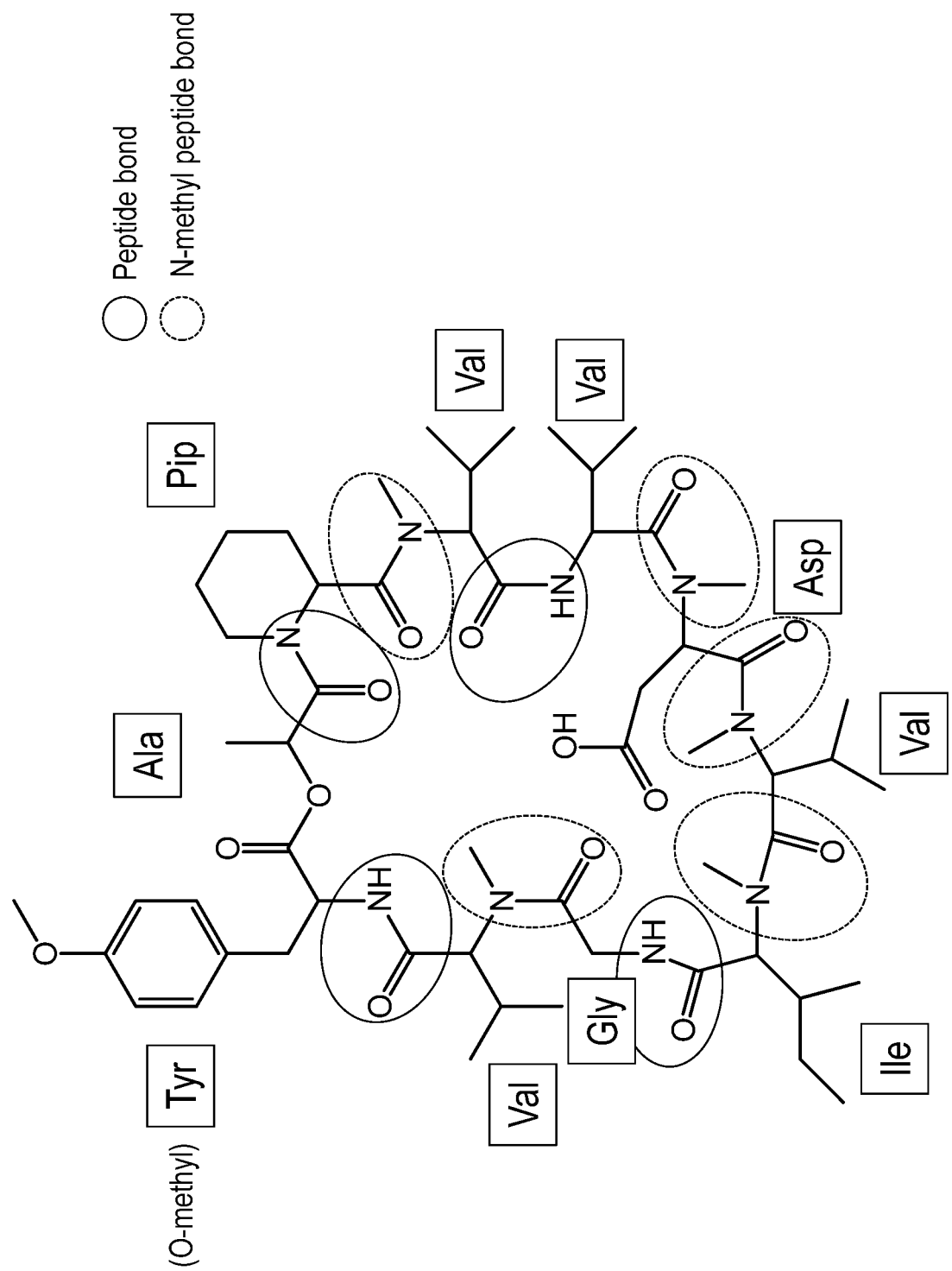
FIG. 2 shows the structure of the cyclic peptide compound produced by the *C. clavata* BAUA-2787 strain.

As shown in FIG. 2, a cyclic peptide produced by the *C. clavata* BAUA-2787 strain (hereafter, it is referred to as "KK-1") comprises 10 amino acids in which 5 out of 9 peptide bonds are N-methylated and the tyrosine (Tyr) residues in the molecules are O-methylated. In this example, the nonribosomal peptide synthetase (NRPS) gene synthesizing the basic backbone of the KK-1 was searched.

At the outset, the NRPS gene biosynthesizing the peptide basic backbone was deduced on the basis of the genome sequence information of the *C. clavata* BAUA-2787 strain, so as to deduce the KK-1 biosynthetic gene cluster.

NRPS is an enzyme that synthesizes a peptide by linking amino acids without the aid of ribosomes, and it has module structures consistent with the number and the order of the amino acid residues constituting the resulting peptide. Accordingly, NRPS comprising the module structures and the domain structures consistent with the structural features of the compound can be deduced to be NRPS biosynthesizing the peptide backbone of the compound.

Since the sequence of the gene of the *C. clavata* BAUA-2787 strain and that of a protein encoded thereby were deduced based on the genomic analysis of the *C. clavata* BAUA-2787 strain, all the genes that were deduced to encode NRPS in the *C. clavata* genome were searched. On the basis of the structural features of the putative protein, genes biosynthesizing the peptide basic backbone of KK-1 were then deduced.

At the outset, all the NRPS genes of *C. clavata* were retrieved by homology search with NRPS of *Cochliobolus heterostrophus* as related filamentous fungi. In *C. heterostrophus*, 12 NRPS genes (i.e., NPS1 to NPS12) have been found. As a result of inspection of the domain structures of these 12 NRPS genes, NPS7 was found to be a hybrid NRPS with PKS (polyketide synthase), and NPS10 and NPS12 were found to be NRPS-like proteins without C domains. Thus, the amino acid sequences of NPS1 to NPS6, NPS8, NPS9, and NPS11 excluding the 3 NRPS genes indicated above were subjected to blastp search as query sequences on the amino acid sequence database of the putative proteins of *C. clavata*. On the basis of the report such that a filamentous fungus comprise about 10 NRPS genes (e.g., *C. heterostrophus* comprises 12 NRPS genes and *Aspergillus fumigatus* comprises 14 NRPS genes), the top 20 genes matched with the query genes were extracted, and the 24 genes indicated below were identified; that is, TRAF01000140000154, TRAF01000135000001, TRAF01000070000001, TRAF01000068000001, TRAF01000108000067, TRAF01000130000847, TRAF01000117000049, TRAF01000117000050, TRAF01000099000028, TRAF01000088000002, TRAF01000082000001, TRAF01000081000001, TRAF01000117000368, TRAF01000142000376, TRAF01000109000032, TRAF01000142000383, TRAF01000136000233, TRAF01000100000101, TRAF01000061000021, TRAF01000108000142, TRAF01000139000099, TRAF01000140000122, TRAF01000117000201, and TRAF01000136000219.

The gene sequence of *C. clavata* (CDS) has been predicted using a dedicated program on the basis of the genomic DNA sequence analyzed using a next-generation sequencer. However, such CDS prediction is often erroneous. Because of the presence of the intron, in particular, the 5'- and 3'-sequences of CDS are deleted, and a sequence that is shorter than the actual CDS is often predicted. In order to more accurately predict CDS, accordingly, it is necessary to thoroughly examine the sequences one by one with the use of, for example, information concerning sequences in the vicinity of the genomic region where the gene of interest is located. Thus, the genomic DNA sequence from a position 3,000-bp upstream of the putative initiation codon to a position 3,000-bp downstream of the putative termination codon of the 24 identified genes were subjected to blastx search as query sequences on the GenBank database. As a result, a region exhibiting a homology to a known protein sequence was identified, and the initiation codon and the termination codon of the gene of interest were deduced. On the basis of homology to the known protein sequence, the position of the intron was also indicated. Accordingly, the site of the intron was predicted in accordance with the GU-AG rule, and CDS was deduced more accurately.

While TRAF01000117000049 and TRAF01000117000050 were deduced to be different genes, these genes were found to be a single gene (such single gene is designated as "TRAF01000117000049-50") as a result of the search. Since the genomic DNA sequence in the vicinity of the gene subjected to the search could not be sufficiently identified, some genes were determined to lack the 5'-side (the initiation codon could not be detected) or the 3'-side (the termination codon could not be detected). Such genes are indicated below.

TRAF01000135000001 (5'-deleted)
TRAF01000070000001 (5'-deleted and 3'-deleted)
TRAF01000068000001 (3'-deleted)
TRAF01000088000002 (3'-deleted)
TRAF01000082000001 (5'-deleted)
TRAF01000081000001 (3'-deleted)
TRAF01000117000368 (5'-deleted)

These sequences were analyzed in greater detail. As a result, the completely identical 2,285-bp sequences were detected at the 3'-terminus of TRAF01000068000001, the 5'-terminus and the 3'-terminus of TRAF01000070000001, and the 5'-terminus of TRAF01000135000001. That is, these 3 genes were deduced to be a single gene composed of TRAF01000068000001, TRAF01000070000001, and TRAF01000135000001 sequentially linked to each other (such single gene is designated as "TRAF01000135000001_J3G").

Also, the completely identical 2,959-bp sequences were detected at the 3'-termini of TRAF01000088000002 and TRAF01000081000001 and at the 5'-termini of TRAF01000082000001 and TRAF01000117000368. That is, these 4 genes were deduced to be 2 genes. While these genes may be linked to each other in any of the 4 combinations shown below, the correct combination could not be determined on the basis of sequence information:

1) TRAF01000088000002 and TRAF01000082000001;
2) TRAF01000088000002 and TRAF01000117000368;
3) TRAF01000081000001 and TRAF01000082000001; and
4) TRAF01000081000001 and TRAF01000117000368.

Figures 1, 3:
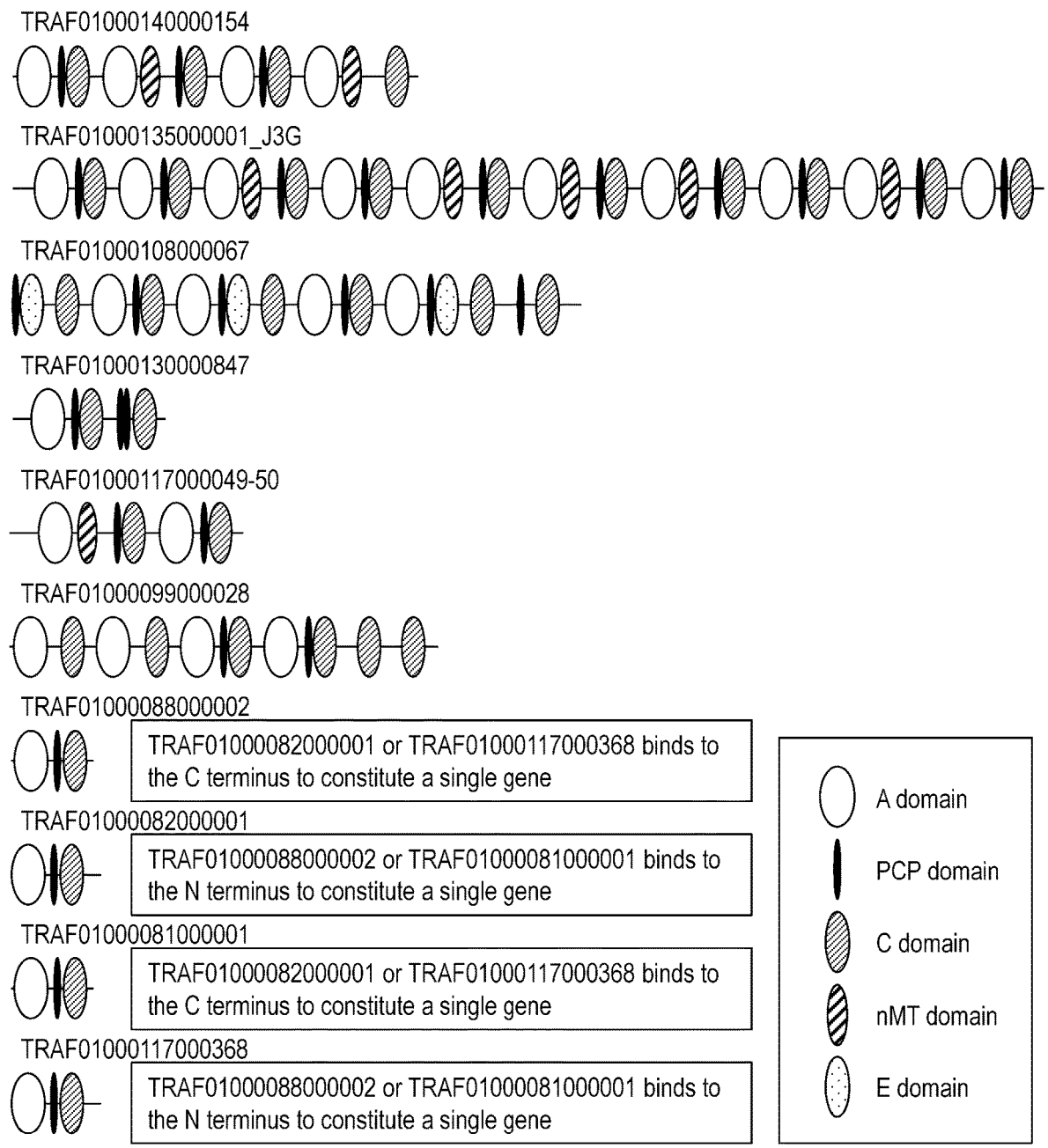
Figures 2, 3:
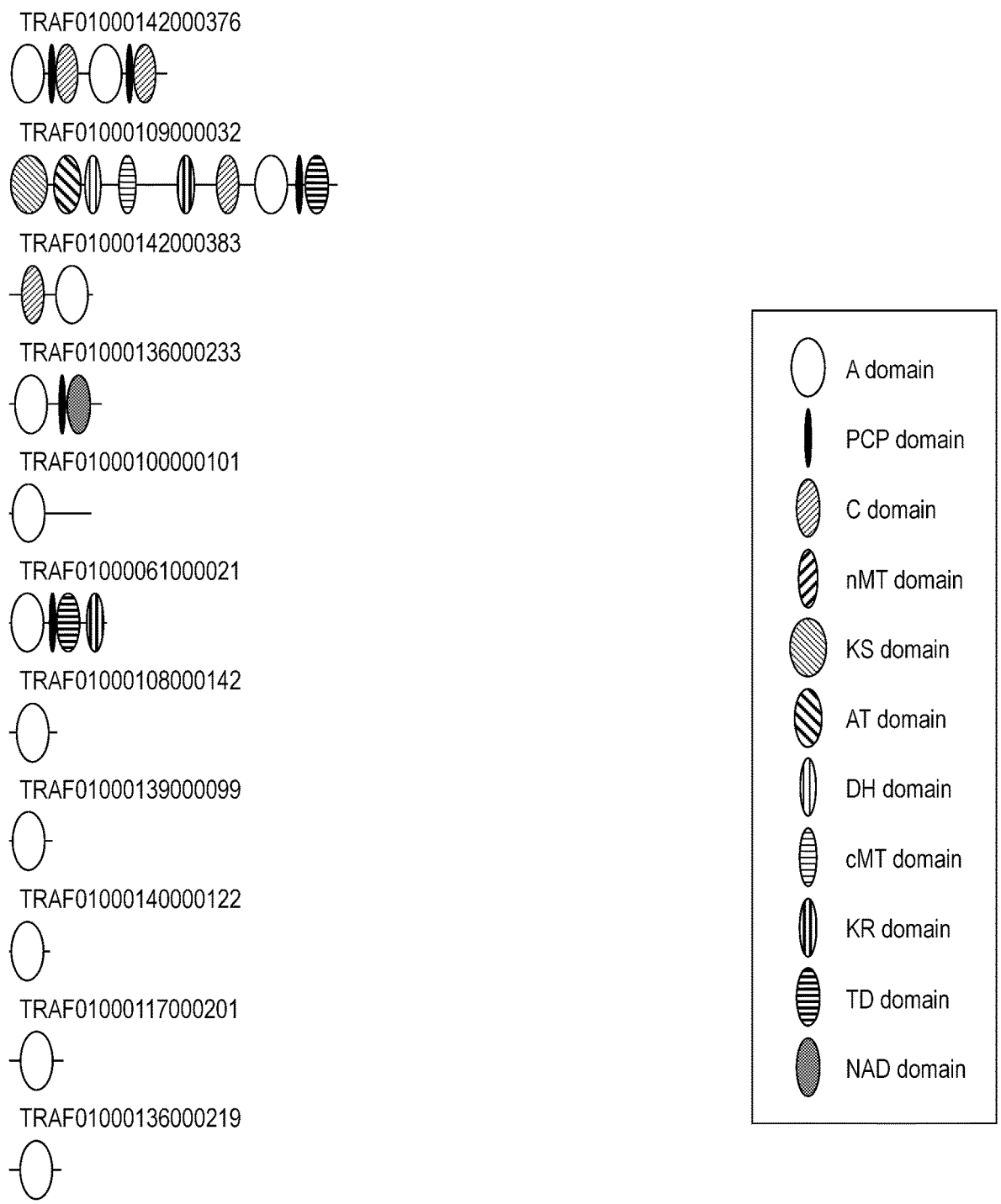

Subsequently, the domain structures of proteins encoded by the genes subjected to CDS prediction were predicted using the InterProScan and antiSMASH programs. The results of antiSMASH analysis are shown in FIGS. 3-1 and 3-2. The genes comprising the A domain, the PCP domain, and the C domain necessary for NRPS functions are the following 14 genes: TRAF01000135000001_J3G, TRAF01000108000067, TRAF01000130000847, TRAF01000117000049, TRAF01000117000050, TRAF01000099000028, TRAF01000088000002, TRAF01000082000001, TRAF01000081000001, TRAF01000117000368, TRAF01000142000376, TRAF01000109000032, and TRAF01000142000383. As described above, 4 of these genes (i.e., TRAF01000088000002, TRAF01000082000001, TRAF01000081000001, and TRAF01000117000368) each result from segmentation of 2 genes. This indicates that the *C. clavata* BAUA-2787 strain comprises 12 NRPS genes. In TRAF01000142000383, only the A domain and the C domain were detected via antiSMASH analysis. As a result of InterProScan analysis, however, a PCP domain-like sequence was detected at the N-terminal side. Accordingly, TRAF01000142000383 was deduced to be NRPS. Since TRAF01000109000032 comprises a typical polyketide synthase (PKS) domain at the N-terminal side, it was considered to be a PKS-NRPS hybrid.

[Deduction of NRPS Involved in Biosynthesis of KK-1]

The *C. clavata* BAUA-2787 strain was considered to comprise 12 NRPS genes. Thus, genes biosynthesizing the basic peptide backbone of KK-1 were searched from among such 12 genes. As shown in FIG. 2, KK-1 comprises a cyclic peptide of 10 amino acids as a basic backbone. A peptide bond is not formed between Tyr and Ala, but an ester bond is formed due to some sort of modification. A peptide biosynthesized by NRPS comprises amino acids, the number of which is consistent with that of biosynthetic NRPS modules. Thus, NRPS biosynthesizing the KK-1 basic peptide backbone comprising 10 amino acids is considered to comprise 10 modules (i.e., 10 A domains). As a result of inspection of the number of the A domains in 12 putative NRPS genes of *C. clavata*, only TRAF01000135000001_J3G was found to comprise 10 A domains. This indicates that the gene is NRPS involved in the biosynthesis of KK-1 (FIG. 3-1).

In the domain structure of TRAF01000135000001_J3G, as shown in FIG. 1, there are 5 N-methyl transferase domains (nMT domains) that N-methylate peptide bonds and such domains are located in the third module, the fifth module, the sixth module, the seventh module, and the ninth module. The position of each module in NRPS is consistent with the position of the amino acids constituting the biosynthesized peptide. Also, the position of the module comprising the nMT domain is consistent with the position of the N-methylated peptide bond. If the first module of TRAF01000135000001_J3G is hypothesized to correspond to the Ala residue of KK-1, the position of the module comprising the nMT domain is completely consistent with the position of the N-methylated peptide bond. This strongly suggests that TRAF01000135000001_J3G is NRPS that biosynthesizes the basic peptide backbone of KK-1.

It was further deduced that a peptide (Ala-Pip-(N-methyl)Val-Val-(N-methyl)Asp-(N-methyl)Val-(N-methyl)Ile-Gly-(N-methyl)Val-Tyr) was first synthesized by TRAF01000135000001_J3G, and cyclization and modification were then performed. In the case of well-known bacteria-derived NRPS, the TE domain is known to involve in the cyclization. In the case of filamentous fungi, in contrast, many NRPSs lack the TE domains but comprise the C domains. In recent years, the C domains have been found to involve in the peptide cyclization in filamentous fungi.

Also, TRAF01000135000001_J3G comprises the C domain at the C terminus of the tenth module, and the C domain may be involved in the cyclization. It is also deduced that the basic peptide backbone is biosynthesized by TRAF01000135000001_J3G, the resultant is modified with various enzymes, and KK-1 is then biosynthesized. The modifying enzyme genes are considered to form a gene cluster in the genome of the C. clavata BAUA-2787 strain together with TRAF01000135000001_J3G.

Domains in the first module to the tenth module constituting the deduced NRPSs, SEQ ID NOs of amino acid sequences thereof, and other information are summarized in Table 1 below.

TABLE 1

| Module | Domain | Amino acid sequence | SEQ ID NO: |
|---|---|---|---|
| First module | A | 286 to 678 | 1 |
|  | PCP | 795 to 863 | 2 |
| Second module | C | 877 to 1174 | 3 |
|  | A | 1361 to 1758 | 4 |
|  | PCP | 1870 to 1938 | 5 |
| Third module | C | 1952 to 2248 | 6 |
|  | A | 2435 to 2836 | 7 |
|  | nMT | 2903 to 3126 | 8 |
|  | PCP | 3358 to 3426 | 9 |
| Fourth module | C | 3440 to 3734 | 10 |
|  | A | 3921 to 4324 | 11 |
|  | PCP | 4417 to 4485 | 12 |
| Fifth module | C | 4499 to 4796 | 13 |
|  | A | 4983 to 5385 | 14 |
|  | nMT | 5454 to 5677 | 15 |
|  | PCP | 5902 to 5970 | 16 |
| Sixth module | C | 5984 to 6281 | 17 |
|  | A | 6468 to 6869 | 18 |
|  | nMT | 6936 to 7157 | 19 |
|  | PCP | 7391 to 7459 | 20 |
| Seventh module | C | 7473 to 7767 | 21 |
|  | A | 7954 to 8359 | 22 |
|  | nMT | 8427 to 8647 | 23 |
|  | PCP | 8876 to 8944 | 24 |
| Eighth module | C | 8958 to 9255 | 25 |
|  | A | 9442 to 9846 | 26 |
|  | PCP | 9948 to 10016 | 27 |
| Ninth module | C | 10030 to 10328 | 28 |
|  | A | 10514 to 10916 | 29 |
|  | nMT | 10983 to 11207 | 30 |
|  | PCP | 11433 to 11501 | 31 |

TABLE 1-continued

| Module | Domain | Amino acid sequence | SEQ ID NO: |
|---|---|---|---|
| Tenth module | C | 11515 to 11810 | 32 |
|  | A | 11997 to 12401 | 33 |
|  | PCP | 12500 to 12566 | 34 |
|  | C | 12616 to 12892 | 35 |

In Table 1, the numerical ranges in the "Amino acid sequence" column indicate the positions of the amino acid residues in the full-length amino acid sequence of the deduced NRPS (SEQ ID NO: 37).

[Deduction of KK-1 Biosynthetic Gene Cluster]

As described above, TRAF01000135000001_J3G was deduced to be the NRPS gene constituting the KK-1 basic peptide backbone. It was thus considered that a group of genes constituting the KK-1 biosynthetic gene cluster was present in a region including this NRPS (TRAF01000135000001_J3G). Among the genes located in the vicinity of such NRPS, accordingly, deduction of a group of genes constituting the biosynthetic gene cluster was attempted based on the amino acid sequences of proteins encoded by such genes and functions deduced based on the amino acid sequences. Since TRAF01000135000001_J3G is composed of three sequences that were separate sequences at the time of genome sequencing and gene prediction, the sequence constituted by linking these separate sequences was used for prediction of the gene cluster described below.

Figure 5:
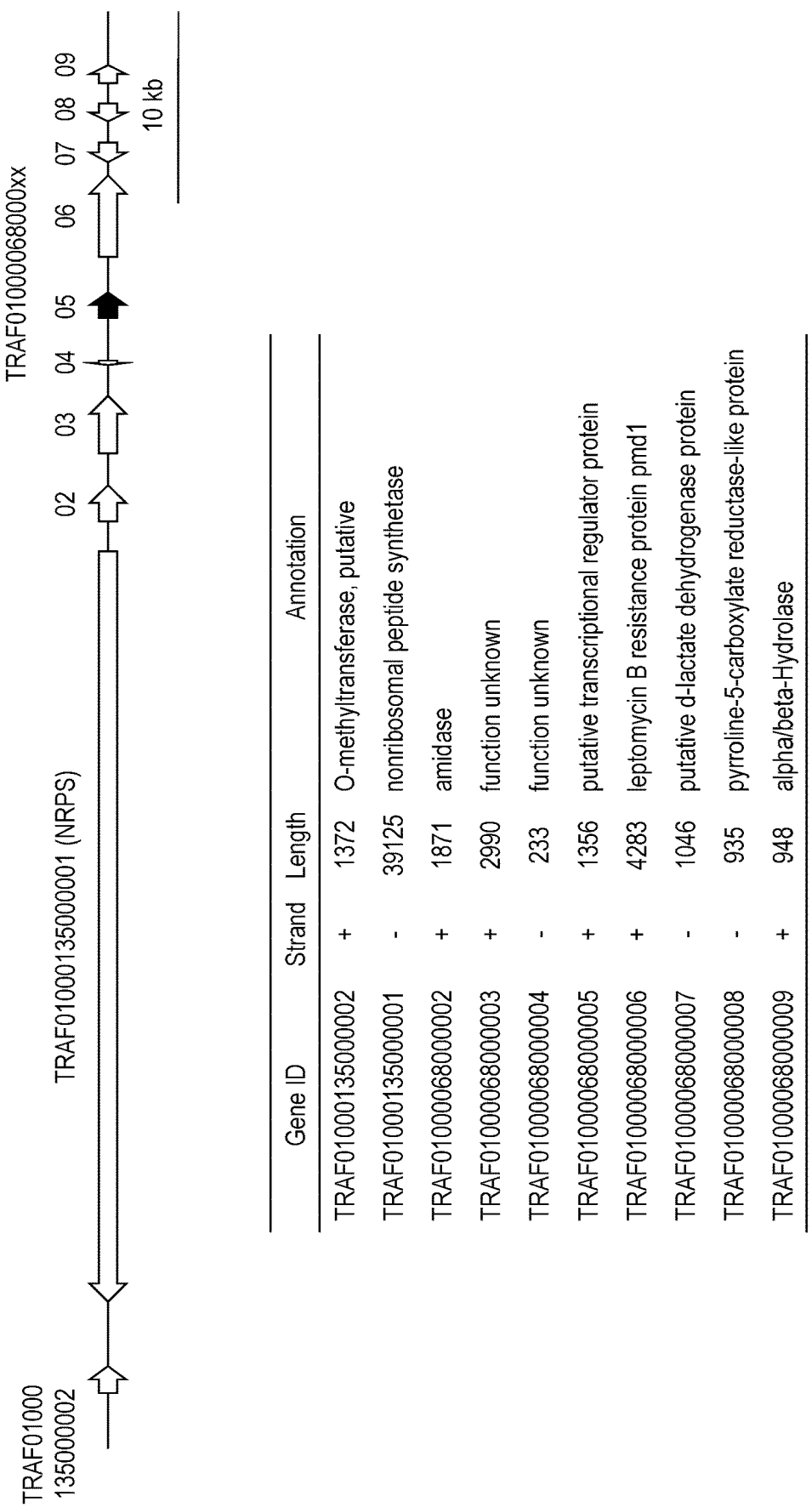
FIG. 5 shows a region deduced as the KK-1 biosynthetic gene cluster.

At the outset, 14 genes were extracted from the upstream region and the downstream region of the NRPS gene (TRAF01000135000001_J3G), respectively, and these genes were then annotated on the basis of the results of blastp search on the GenBank database. The results are shown in FIG. 4. On the basis of the annotation, a region including genes that may be involved in the secondary metabolism (i.e., a region from TRAF01000135000002 to TRAF01000068000009) was deduced to constitute the KK-1 biosynthetic gene cluster. FIG. 5 schematically shows the structure of the putative biosynthetic gene cluster. The cluster size was approximately 75 kb and the majority thereof was occupied by the NRPS genes. Concerning the functions of genes constituting the cluster, TRAF01000135000002 was annotated with "O-methyltransferase," and TRAF01000135000002 was thus considered to be involved in O-methylation of the tyrosine (Tyr) residue in the KK-1 molecule. TRAF01000068000006 that is annotated with "pmd1" encoding the leptomycin B-tolerant protein is an ABC transporter in view of protein functions, and it may be involved in efflux of KK-1 to the outside of the cells. Also, the transcription factor gene (TRAF01000068000005) was present in the cluster. In general, expression of genes constituting the biosynthetic gene cluster is often regulated in common by the transcription factor existing in the cluster. In the gene cluster, TRAF01000068000005 was deduced to regulate the transcription of all the genes constituting the cluster. By regulating the expression of this transcription factor, accordingly, the expression of the gene cluster may be regulated, and such gene may be critical if high-level KK-1 production is intended.

[Deduction of KK-1 Biosynthetic Gene Cluster Based on Gene Expression Information]

When deducing the KK-1 biosynthetic gene cluster, cluster detection was also carried out in accordance with a bioinformatics technique using the MIDDAS-M algorithm (Umemura, M. et. al., Plos one, 8 (5), e63673, 2013).

According to MIDDAS-M, a gene cluster is detected based on the gene expression information. When detecting the biosynthetic gene cluster of the secondary metabolite, extensive gene expression information in the production host under the condition in which a substance of interest is produced is compared with that under the condition in which a substance of interest is not produced, and a group of genes expressing under the former condition is detected as a cluster. By arranging the genes in the order of the genome positions along the horizontal axis and plotting the scores (the expression levels) along the vertical axis, a region in which genes exhibiting fluctuation in expression levels aggregate is detected as a peak.

Figure 6:
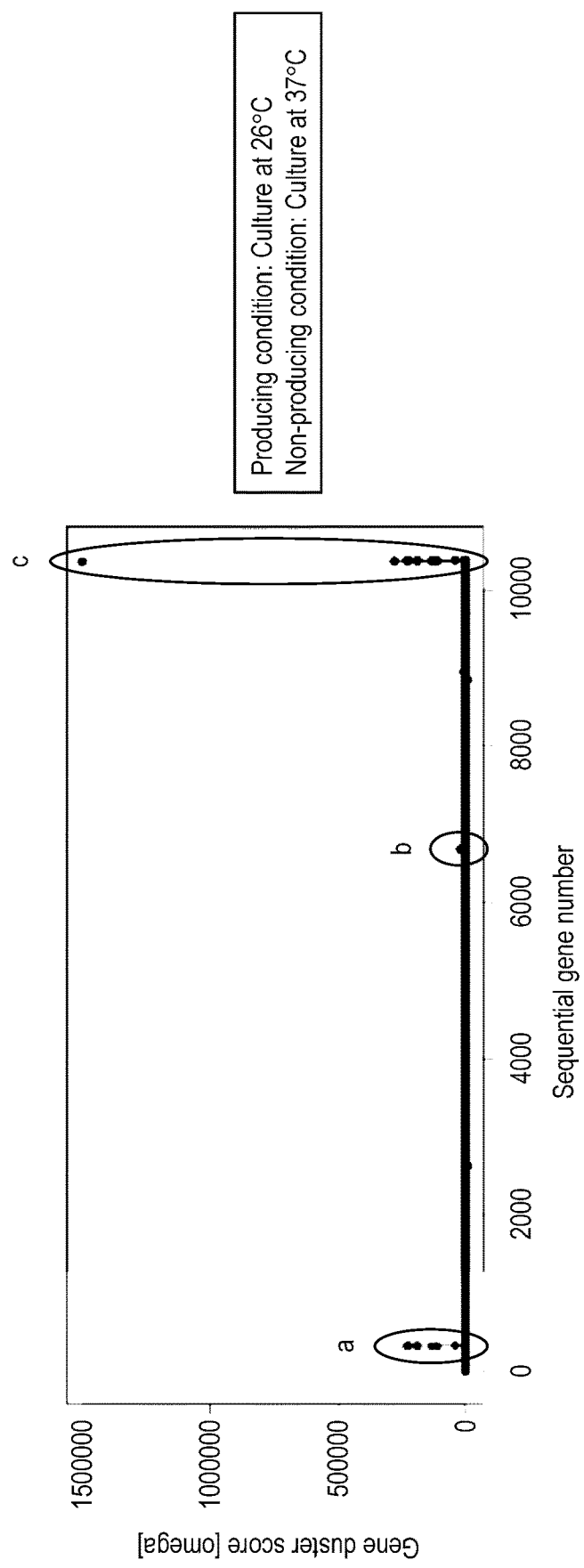
FIG. 6 shows a characteristic diagram demonstrating the results of MIDDAS-M cluster detection based on gene expression under KK-1-producing and non-producing conditions.

When the C. clavata BAUA-2786 strain is subjected to CM liquid culture, KK-1 production is not observed if the culture temperature is raised to 37° C. Accordingly, general culture temperature of 26° C. was designated as "Producing conditions," and that of 37° C. was designated as "Non-producing conditions." Under such conditions, C. clavata gene expression was extensively analyzed via RNA-seq using the next-generation DNA sequencer, and cluster detection was carried out via MIDDAS-M. As a result, as shown in FIG. 6, the group of genes identical to the gene cluster deduced based on the sequence information was detected (a and b in FIG. 6). Two peaks were detected because such gene cluster was fragmented when the initial genome sequence data was attained, as described above. The putative cluster sequence manually linked was bound to the end of the genome sequence (the right end on the horizontal axis) was simultaneously subjected to the MIDDAS-M-based analysis. As a result, genes in the region of interest were detected at a significant level (c in FIG. 6).

The results strongly suggest that the gene cluster including 10 genes deduced on the basis of gene sequence information may be involved in biosynthesis of KK-1. Concerning the 10 genes included in the putative gene cluster, the nucleotide sequences and the amino acid sequences of the coding regions are summarized in the table below.

TABLE 2

| Gene ID | Nucleotide sequence | Amino acid sequence |
| --- | --- | --- |
| TRAF01000135000002 | SEQ ID NO: 40 | SEQ ID NO: 41 |
| TRAF01000135000001_J3G | SEQ ID NO: 36 | SEQ ID NO: 37 |
| TRAF01000068000002 | SEQ ID NO: 42 | SEQ ID NO: 43 |
| TRAF01000068000003 | SEQ ID NO: 44 | SEQ ID NO: 45 |
| TRAF01000068000004 | SEQ ID NO: 46 | SEQ ID NO: 47 |
| TRAF01000068000005 | SEQ ID NO: 38 | SEQ ID NO: 39 |
| TRAF01000068000006 | SEQ ID NO: 48 | SEQ ID NO: 49 |
| TRAF01000068000007 | SEQ ID NO: 50 | SEQ ID NO: 51 |
| TRAF01000068000008 | SEQ ID NO: 52 | SEQ ID NO: 53 |
| TRAF01000068000009 | SEQ ID NO: 54 | SEQ ID NO: 55 |

Example 2

In this example, functions of the transcription factor genes among the group of genes included in the KK-1 biosynthetic gene cluster deduced in Example 1 were analyzed. In this example, the gene encoding the transcription factor denoted as "TRAF01000068000005" in Example 1 is denoted as "TF068-005."

[Analysis Using Transcription Factor High-Expression Strain]

Figure 7:
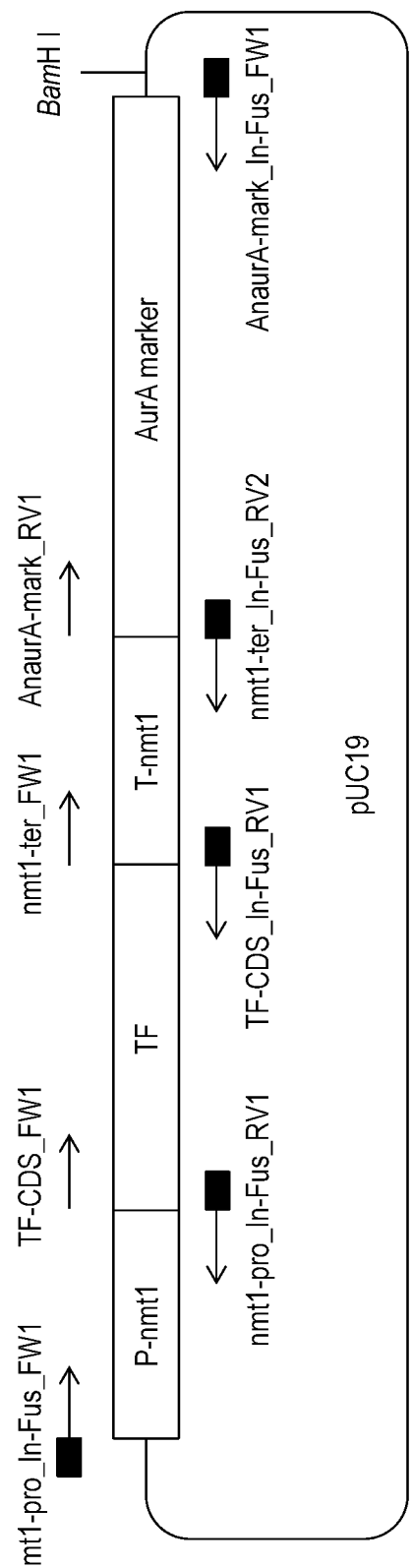
FIG. 7 schematically shows a construct achieving high-level expression of a transcription factor gene (the TF068-005 gene).

1) Construction of TF068-005 High Expression Construct (FIG. 7)

FIG. 7 schematically shows a construct achieving high-level expression of the TF068-005 gene. In this construct, a region from the initiation codon to a position 1,000-bp upstream therefrom of the Ccnmt1 (TRAF01000124000183) gene of the C. clavata BAUA-2787 strain was designated as the promoter, a 355-bp downstream region of the Ccnmt1 gene was designated as the terminator, and the Aureobasidin A (AurA)-tolerant gene was used as the selection marker. The promoter and the terminator of the Ccnmt1 gene were amplified via PCR using C. clavata genomic DNA as a template, the Aureobasidin A (AurA)-tolerant gene was amplified via PCR using the pAUR316 plasmid (TaKaRa) as a template, and the TF068-005 gene was amplified via PCR using C. clavata cDNA as a template.

Subsequently, the in-fusion reaction was carried out with linear pUC19 of the In-Fusion HD Cloning Kit (Clontech) to prepare a target plasmid (pUC-Pnmt1-TF-Tnmt1-aurA). The primers and the reaction conditions employed are shown below.

```
nmt1-pro_In-Fus_FW1:
                                        (SEQ ID NO: 56)
5'-cggtacccggggatcTAGTCTGTTGATTACTCG-3' nmt1-pro_In-Fus_RV1:
                                        (SEQ ID NO: 57)
5'-ctcgacaaaggtcatTTTGACTTTGAATACCGGTG-3' nmt1-ter_FW1:
                                        (SEQ ID NO: 58)
5'-GCAGTTGCCGTTGGACCAGAGG-3' nmt1-ter_In-Fus_RV2:
                                        (SEQ ID NO: 59)
5'-atagtcataacaagcCGCGACACTGTAATATTAAAGC-3'

TF-CDS_FW1:
                                        (SEQ ID NO: 60)
5'-ATGACCTTTGTCGAGACTGTAGCC-3'

TF-CDS_In-Fus_RV1:
                                        (SEQ ID NO: 61)
5'-TCCAACGGCAACTGCCTATGATATACTCATGTTCTCGTC-3'
```

PCR was carried out with the use of Phusion Hot Start II High-Fidelity DNA Polymerase (Thermo Fisher Scientific). The temperature conditions were: initial denaturation at 98° C. for 30 seconds; a cycle of denaturation at 98° C. for 10 seconds, annealing at 60° C. for 30 seconds, and extension at 72° C. for 30 seconds repeated 30 times; and final extension at 72° C. for 7 minutes.

```
AnaurA-mark_In-Fus_FW1:
                                        (SEQ ID NO: 62)
5'-cgactctagaggatcCTGATGGTCAGATGGATCTG-3'

AnaurA-mark_RV1:
                                        (SEQ ID NO: 63)
5'-GCTTGTTATGACTATGTATACATATGCG-3'
```

PCR was carried out with the use of Phusion Hot Start II High-Fidelity DNA Polymerase (Thermo Fisher Scientific). The temperature conditions were: initial denaturation at 98° C. for 30 seconds; a cycle of denaturation at 98° C. for 10 seconds, annealing at 60° C. for 30 seconds, and extension at 72° C. for 2 minutes repeated 30 times; and final extension at 72° C. for 7 minutes.

2) Transformation of C. Clavata BAUA-2787 Strain

A spore suspension of the C. clavata BAUA-2787 strain was inoculated into 100 ml of CM medium (a 300-ml triangular flask), shake culture was carried out at 30° C. for 40 hours, mycelial threads were collected via filtration using a glass strainer (11G1), the collected mycelial threads were washed with sterilized water, and a spatula or the like was pressed against the washed mycelial threads for thorough dehydration. The cells were added to 10 ml of a solution for protoplast formation (an YL composition) to prepare a suspension, and the suspension was moderately shaken at 30° C. for 3 hours to form protoplasts. The resultant was filtered through Miracloth, the filtrate was centrifuged at 1,500×g for 5 minutes, and protoplasts were collected, followed by washing two times with 0.8 M NaCl. The protoplasts were suspended in Solution 1 (0.8 M NaCl, 10 mM $CaCl_2$, 10 mM Tris-HCl (pH 8.0)) at $2×10^8$/ml, 0.2 vol. of Solution 2 (40% (w/v) PEG4000, 50 mM $CaCl_2$, 50 mM Tris-HCl (pH8.0)) was moderately mixed therewith to prepare a protoplast suspension, pUC-Pnmt1-TF-Tnmt1-aurA (7.8 μg/20 μl) was added to 0.2 ml of the protoplast suspension, and the mixture was then allowed to stand in ice for 10 minutes. Solution 2 (1 ml) was moderately mixed therewith to prepare a suspension, and the suspension was then allowed to stand at room temperature for 15 minutes. Solution 1 (10 ml) was moderately mixed therewith to prepare a suspension, the protoplasts were collected via centrifugation, the supernatant was removed as much as possible, and the protoplasts were then suspended in 1 ml of Solution 1. The protoplast suspension (0.2 ml each) was applied to each of the 5 CM+1.2 M sucrose+10 μg/ml AbA selection plates, 6 to 7 ml (per 90-mm (φ) petri dish) of CM+1.2 M sucrose+10 μg/ml AbA soft agar (1%) selection medium was quickly overlaid thereto to homogeneously disperse the protoplasts, and culture was then conducted at 26° C. for 6 days.

C. clavata transformation involving the use of the pUC-Pnmt1-TF-Tnmt1-aurA plasmid was carried out in two ways (i.e., transformation with the use of the cyclic plasmid and transformation with the use of the linear plasmid cleaved with the BamHI restriction enzyme at one site).

3) Culture Conditions for TF068-005 High-Expression Strain

The TF068-005 high-expression strain was cultured in three different conditions as described below, and RNA preparation and KK-1 production were inspected.

"Culture 1"

Conidiospores of wild-type strains and TF068-005 high-expression strains were inoculated into 100 ml of CM medium (a 500-ml triangular flask), and shake culture was carried out at 26° C. and 160 rpm for 72 hours.

"Culture 2"

Conidiospores of wild-type strains and TF068-005 high-expression strains were inoculated into 30 ml of K1 medium (a 100-ml baffled triangular flask), preculture was carried out at 26° C. and 200 rpm for 72 hours, 500 μl of the culture solution was transferred to a CM medium in which glucose content was 5% (a 500-ml baffled triangular flask), and the main culture was then carried out at 26° C. and 130 rpm.

"Culture 3"

To a 50-ml Falcon tube, 2.5 g of brown rice and 2 ml of water were introduced, and the Falcon tube was introduced into an autoclave. Conidiospores of wild-type strains and TF068-005 high-expression strains were inoculated thereinto, and stationary culture was then carried out at 26° C. for 8 days.

4) RNA-Seq Analysis of TF068-005 High-Expression Strains

The cells subjected to liquid culture was frozen with liquid nitrogen, the product was grounded with the use of a pestle in a mortar, and total RNA was then prepared using ISOGEN (Nippon Gene). An RNA-Seq library was prepared from the total RNA using the Truseq RNA Sample Prep Kit v2, and the library was then applied to the next-generation sequencer (MiSeq) (Paired-End, Read Length 75). The obtained sequence data were mapped against the C. clavata genomic sequence using the TopHat program.

5) KK-1 Extraction and Quantification

In liquid culture, 15 ml of ethyl acetate was directly added to a 30-ml culture system, shake culture was carried out at 130 rpm for 1 hour, and centrifugation was then carried out at 4,700×g for 15 minutes. The supernatant was collected, subjected to centrifugal condensation, and then designated as an extracellular fraction. Subsequently, 15 ml of acetone was added to an aqueous layer after ethyl acetate was collected, and the mixture was vortex-stirred, followed by centrifugation at 4,700×g for 15 minutes. The supernatant was collected via decantation and acetone was removed via centrifugal condensation. Ethyl acetate (15 ml) was added thereto, followed by centrifugation at 4,700×g for 15 minutes. The ethyl acetate layer was collected in a 50-ml tube, and the product of centrifugal condensation was designated as an intracellular fraction.

In solid culture, 25 ml of 80% acetone was added to the culture system, followed by vortex-stirring. Acetone was removed via centrifugal condensation, and 10 ml of ethyl acetate was added, followed by vortex-stirring. The ethyl acetate layer was collected via centrifugation, and the product of spin-column purification was then designated as a sample.

KK-1 quantification was carried out via UPLC under the following conditions.

Apparatus: ACQUITY UPLC I-Class System (Waters)
Column: Acquity UPLC BEH C18, 2.1×100 mm
Solvent: Gradient 50%-98% Acetonitrile+0.1% Formic Acid 3 min)
Flow rate: 0.6 ml/min
Detection wavelength: 273 nm

[Results and Discussion]

In this example, the promoter and the terminator of the nmt-1 gene homolog (TRAF01000124000183; Ccnmt1) detected as the high-level expression gene in C. clavata were used to prepare a construct that allows high-level expression of the transcription factor (pUC-Pnmt1-TF-Tnmt1-aurA) (FIG. 7). C. clavata transformation involving the use of the plasmid was carried out in two ways (i.e., transformation with the use of the cyclic plasmid and transformation with the use of the linear plasmid cleaved at one site). The resulting strain into which the plasmid had been introduced linearly (i.e., ox_TF_1) and the strain into which the plasmid had been introduced cyclically (i.e., (ox_TF_2) were subjected to RNA-seq analysis and evaluation in terms of KK-1 productivity.

Figure 8:
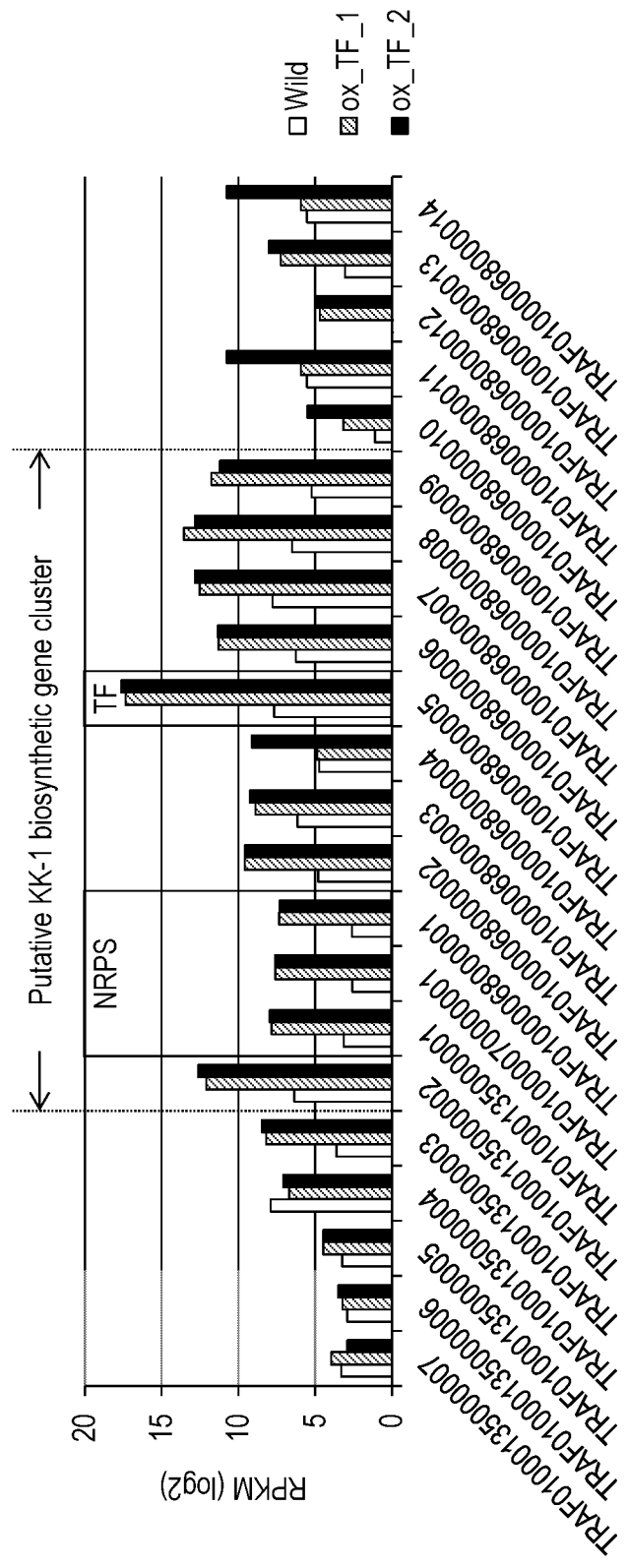
FIG. 8 shows a characteristic diagram demonstrating the results of inspection of the transcription level of genes constituting the KK-1 biosynthetic gene cluster when wild-type strains and strains achieving high-level expression of transcription factor genes are cultured under "Culture 1" conditions.

At the outset, conidiospores of wild-type strains and TF068-005 high-expression strains (ox_TF_1 and ox_TF_2) were subjected to shake culture in CM liquid medium at 26° C. and 160 rpm for 72 hours and then subjected to RNA-seq analysis ("Culture 1"). FIG. 8 shows the results of inspection of the transcription level of the genes constituting the KK-1 biosynthetic gene cluster. As shown in FIG. 8, the gene expression level in the TF068-005 high-expression strains was approximately 8 times greater than that in wild-type strains. There were no difference in transcription levels between the ox_TF_1 strain and the ox_TF_2 strain.

Figure 9:
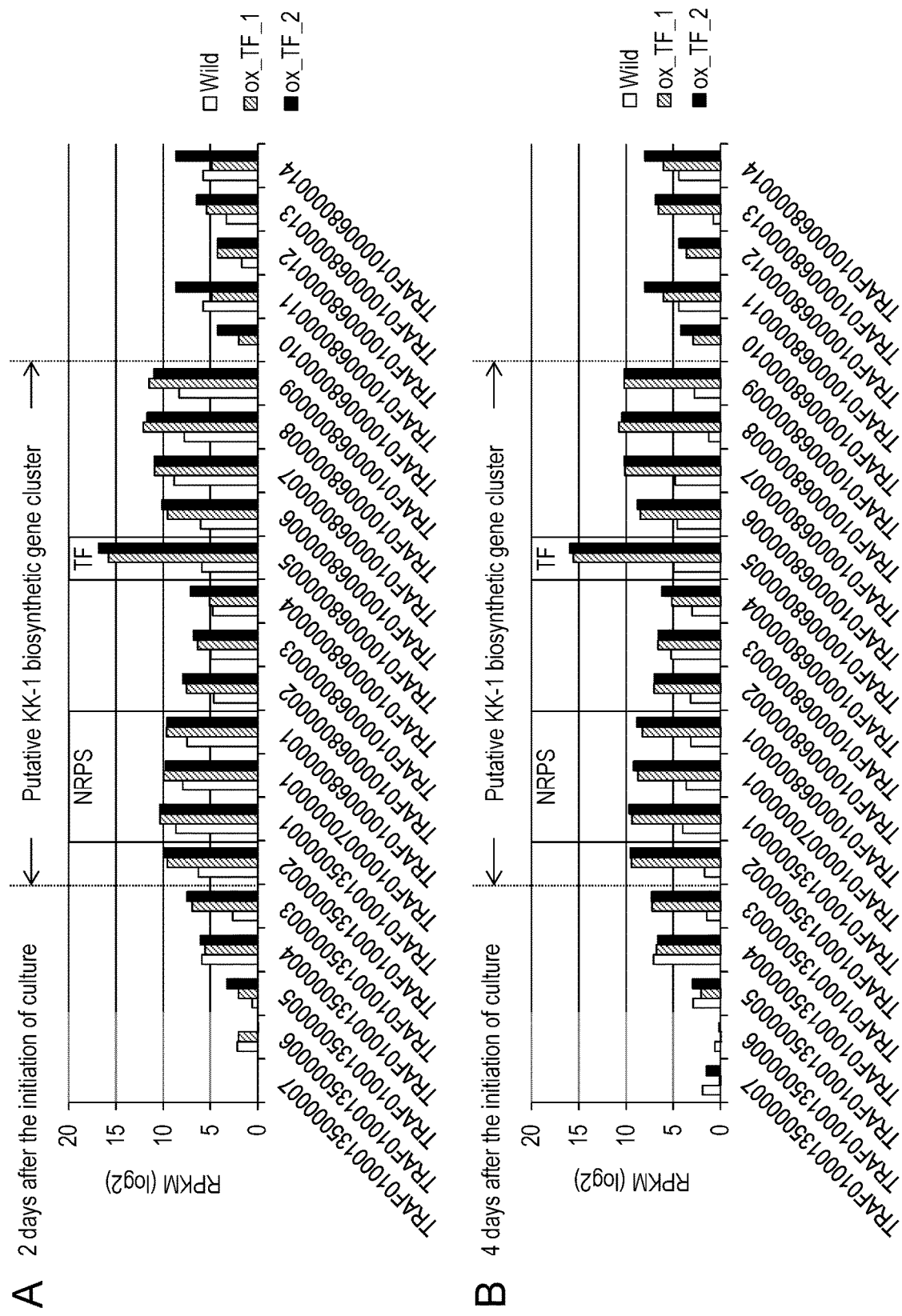
FIG. 9 shows characteristic diagrams demonstrating the results of inspection of the transcription level of genes constituting the KK-1 biosynthetic gene cluster when wild-type strains and strains achieving high-level expression of transcription factor genes are cultured under "Culture 2" conditions.

Accordingly, KK-1 productivity in the TF068-005 high-expression strains was to be inspected, and RNA-seq analysis was carried out simultaneously. In this case, preculture was carried out in K1 medium containing soybean flour and the main culture was then carried out in CM medium, so as to stabilize the shape of the cells at the time of liquid culture ("Culture 2"). FIG. 9 shows the results of RNA-seq analysis of the gene transcription levels 2 days and 4 days after the initiation of the main culture. As shown in FIG. 9, the transcription level of the genes constituting the KK-1 biosynthetic gene cluster in the TF068-005 high-expression strains was significantly higher than that in wild-type strain. Also, a difference in the expression levels compared with wild-type strains 4 days after the initiation of the main culture was greater than that 2 days after the initiation of the main culture.

Figure 10:
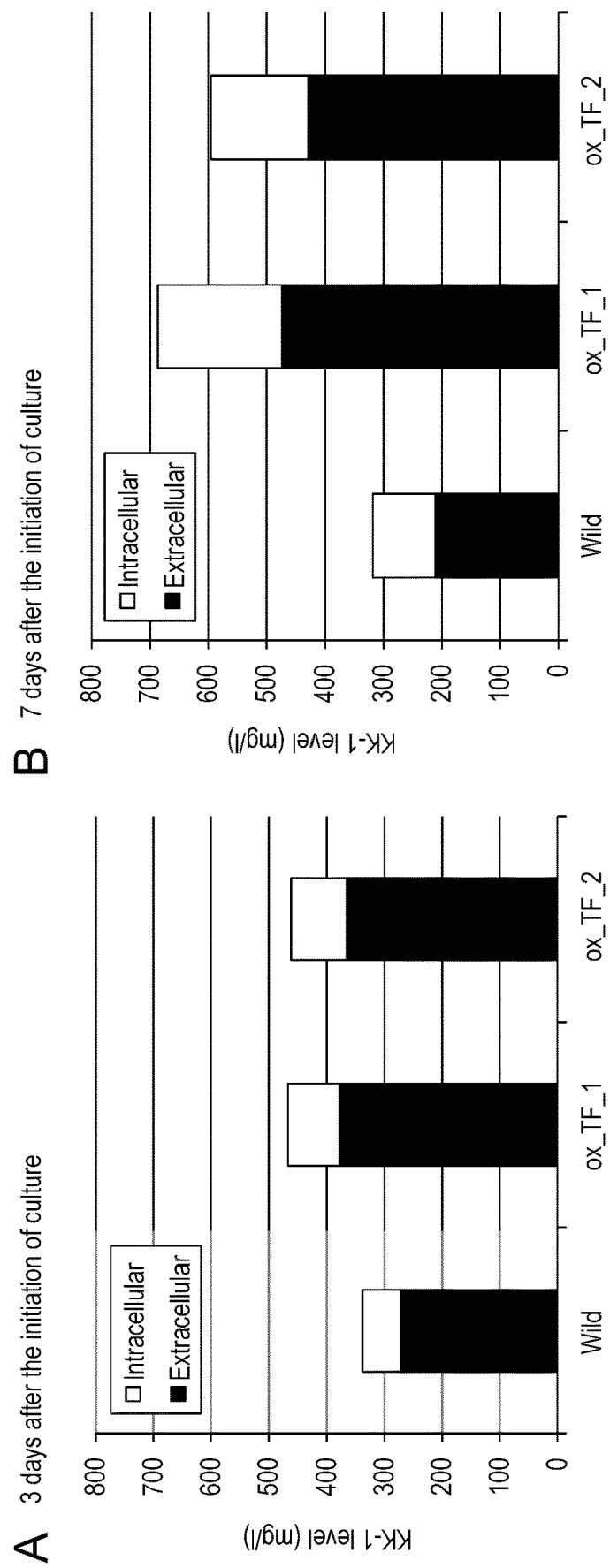
FIG. 10 shows characteristic diagrams demonstrating the results of inspection of the levels of KK-1 production of wild-type strains and strains achieving high-level expression of transcription factor genes outside and inside the cells at 3 days and 7 days after the initiation of culture.

Subsequently, the KK-1 production level was inspected extracellularly and intracellularly 3 days and 7 days after the initiation of the main culture. FIG. 10 shows the results thereof. As shown in FIG. 10, the total amount of KK-1 in the culture system (a total of the extracellular production level and the intracellular production level) became greater in the TF068-005 high-expression strains both on 3 days and 7 days after the initiation of culture, and it was approximately two times greater than that of wild-type strains 7 days after the initiation of culture. On the basis of the results shown in FIG. 10, approximately 20% to 30% of the total amount of KK-1 may be accumulated in the cells.

Figure 11:
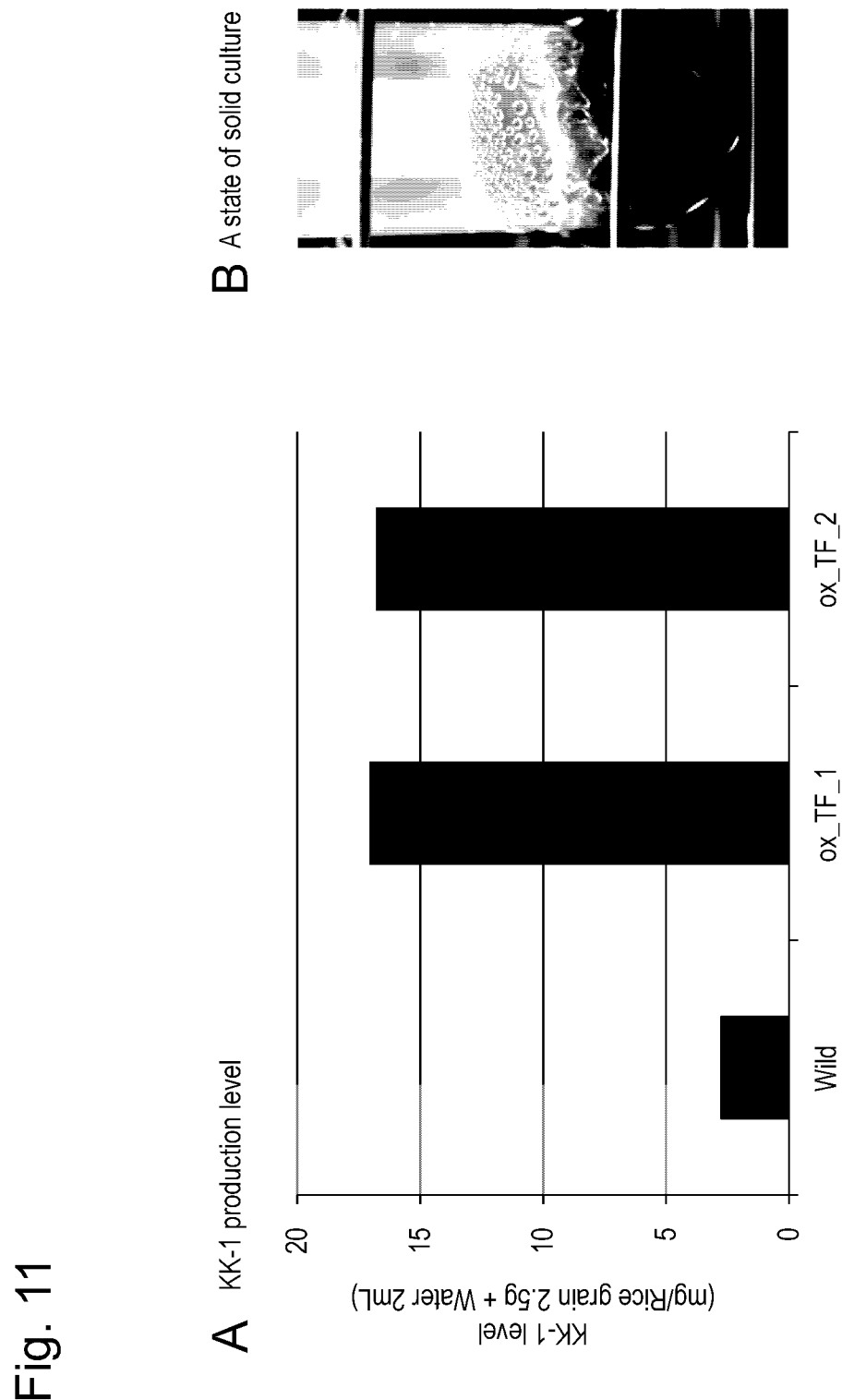
FIG. 11 shows characteristic diagrams demonstrating the results of inspection of the KK-1 production level when wild-type strains and strains achieving high-level expression of transcription factor genes are cultured under "Culture 3" conditions and a state of the solid culture thereof.

Further, FIG. 11 shows the results of inspection of KK-1 productivity under solid culture conditions involving the use of brown rice ("Culture 3"). FIG. 11 also shows a photograph demonstrating solid-culture of the TF068-005 high-expression strains. As shown in FIG. 11, KK-1 productivity in the TF068-005 high-expression strains was approximately 6 times greater than that in wild-type strains as a result of solid culture.

The results demonstrate that high-level expression of the TF068-005 gene results in elevated expression levels of the genes included in the putative gene cluster. Accordingly, the TF068-005 gene was identified as a transcription factor capable of positively regulating the expression level of particular genes at the level of transcription. In addition, KK-1 productivity was improved as a result of high-level expression of the TF068-005 gene encoding the transcription factor. Accordingly, a group of genes whose expression levels had been elevated by regulating the transcription factor was found to constitute a gene cluster involved in KK-1 production.

[Analysis Using Transcription Factor-Deleted Strain]

Figure 12:
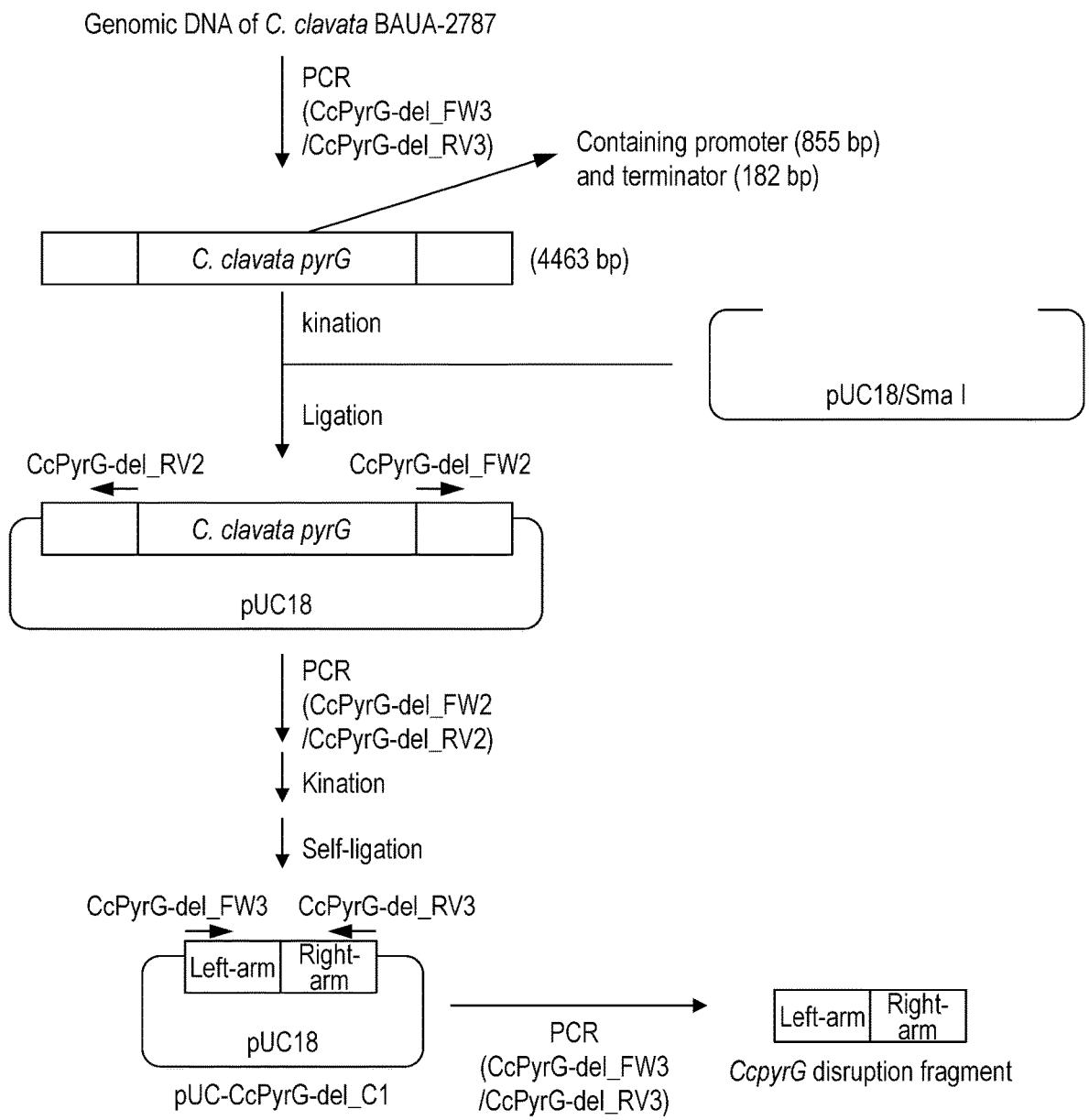
FIG. 12 schematically shows constitution of a plasmid for CcpyrG gene deletion.

1) Construction of Plasmid for CcpyrG Gene Deletion (FIG. 12)

FIG. 12 demonstrates a scheme for constructing a plasmid used for deleting the pyrG gene in the *C. clavata* BAUA-2787 strain (the CcpyrG gene). Since pyrG gene-deleted strain cannot convert 5-fluoroorotic acid (5-FOA) into 5-fluorouridine phosphoric acid (a thymine biosynthetase inhibitor), it can grow in a medium containing 5-FOA.

As shown in FIG. 12, at the outset, PCR was carried out with the use of genomic DNA of the *C. clavata* BAUA-2787 strain as a template and the set of primers shown below, so as to amplify a region from 2,005-bp upstream of the initiation codon to 1,261-bp downstream of the termination codon of the CcpyrG gene.

```
CcPyrG-del_FW3:
                              (SEQ ID NO: 64)
5'-GACAGACTCTTCGTCGACGTC-3'

CcPyrG-del_RV3:
                              (SEQ ID NO: 65)
5'-GTTGTGGTTGGTGTTCCTGAGG-3'
```

PCR was carried out with the use of Phusion Hot Start II High-Fidelity DNA Polymerase (Thermo Fisher Scientific). The temperature conditions were: initial denaturation at 98° C. for 3 minutes; a cycle of denaturation at 98° C. for 10 seconds, annealing at 60° C. for 30 seconds, and extension at 72° C. for 2.5 minutes repeated 30 times; and final extension at 72° C. for 7 minutes.

Subsequently, the terminus of a DNA fragment (4,463-bp) containing the amplified CcpyrG gene was phosphorylated with T4 polynucleotide kinase (TOYOBO). After pUC18 was digested with SmaI, it was dephosphorylated with *E. coli* alkaline phosphatase (TOYOBO), and the resultant was ligated to the DNA fragment containing the phosphorylated CcpyrG gene. Subsequently, a pUC18 region including the upstream and downstream regions of the CcpyrG gene was amplified via PCR using the set of primers shown below, so as to delete a region including the CcpyrG gene.

```
cPyrG-del_FW2:
                              (SEQ ID NO: 66)
5'-CACTCGATCTACCAAATCGACG-3' cPyrG-del_RV2:
                              (SEQ ID NO: 67)
5'-CCTATCCGGATATGCAGTCAC-3'
```

PCR was carried out with the use of Phusion Hot Start II High-Fidelity DNA Polymerase. The temperature conditions were: initial denaturation at 98° C. for 3 minutes; a cycle of denaturation at 98° C. for 10 seconds, annealing at 60° C. for 30 seconds, and extension at 72° C. for 3 minutes repeated 30 times; and final extension at 72° C. for 7 minutes.

Subsequently, the resulting PCR fragment was phosphorylated with T4 polynucleotide kinase and self-ligated, to construct a target CcpyrG gene-deleted construct (pUC-CcPyrG-del_C1).

2) Transformation Via CcpyrG Gene Deletion of *C. Clavata* BAUA-2787 Strain

An amplified fragment obtained via PCR with the use of pUC-CcPyrG-del_C1 as a template and the set of primers (CcPyrG-del_FW3 and CcPyrG-del_RV3) was used for CcpyrG gene deletion. PCR was carried out with the use of Phusion Hot Start II High-Fidelity DNA Polymerase. The temperature conditions were: initial denaturation at 98° C. for 30 seconds; a cycle of denaturation at 98° C. for 10 seconds, annealing at 63° C. for 30 seconds, and extension at 72° C. for 30 seconds repeated 35 times; and final extension at 72° C. for 5 minutes.

The *C. clavata* BAUA-2787 strain was transformed basically in accordance with the procedure described in the section [Analysis using transcription factor high-expression strain] above, except that CM+1 mg/ml 5-FOA+0.2% uridine+0.02% uracil was used as the selection medium.

Figure 13:
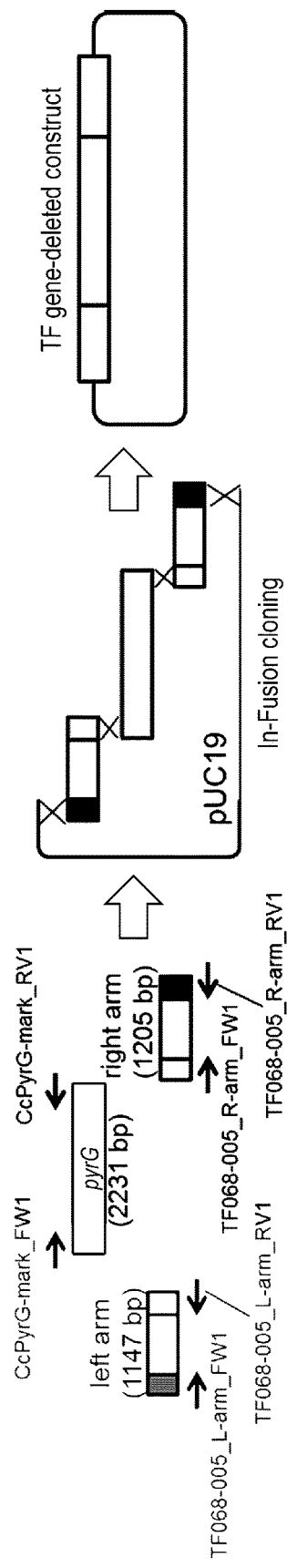
FIG. 13 schematically shows a construct for deleting a transcription factor gene (the TF068-005 gene).

3) Construction of TF068-005 Gene-Deleted Construct (FIG. 13)

FIG. 13 shows a scheme for constructing the TF068-005 gene-deleted construct that was found to encode a transcription factor as described above.

Figure 14:
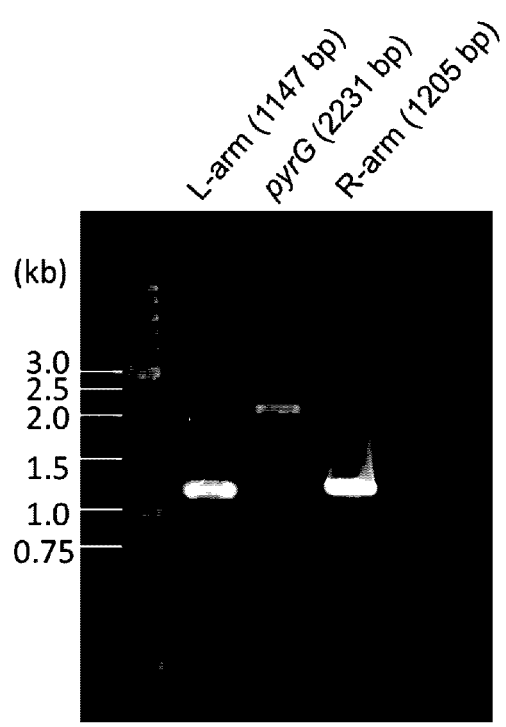
FIG. 14 shows an electrophoretic pattern of the upstream region of the TF068-005 gene amplified via PCR, the downstream region thereof, and the selection marker gene pyrG.

As shown in FIG. 13, the left arm (1,147 bp) was first amplified using the genome of the *C. clavata* BAUA-2787 strain as a template and primers complementary to the upstream region of the TF068-005 gene (i.e., TF068-005_L-arm_FW1 and TF068-005_L-arm_RV1). Also, the right arm (1,205 bp) was amplified using the primers complementary to the downstream region of the TF068-005 gene (i.e., TF068-005_R-arm_FW1 and TF068-005_R-arm_RV1). In addition, the selection marker gene (pyrG, 2,231 bp) was amplified with the use of the primers (i.e., CcPyrG-mark_FW1 and the cPyrG-mark_RV1). FIG. 14 shows an electrophoretic photograph of the amplified fragments.

In accordance with the protocol of the In-Fusion HD cloning Kit (Clontech), subsequently, the left arm, the pyrG marker, and the right arm amplified via PCR as described above were successively introduced into the linear pUC19 plasmid vector included in the kit. The resultant was introduced into the *E. coli* JM109 strain, and the plasmid was prepared from 3 clones of the transformant, followed by sequencing.

The sequences of the primers used for amplification of DNA fragments are shown below.

```
TF068-005_L-arm_FW1:
                                    (SEQ ID NO: 68)
5'-CGGTACCCGGGGATCCTCTGAAGCGGTCAAGGATAACG-3'

TF068-005_L-arm_RV1:
                                    (SEQ ID NO: 69)
5'-ATGAAGCAGAGCGGCGAGCCTAAGATATGCCAGGAGG-3'

TF068-005_R-arm_FW1:
                                    (SEQ ID NO: 70)
5'-CTAGCAACCGTCATGCCATAGACGTGGCACTCGAACG-3'

TF068-005_R-arm_RV1:
                                    (SEQ ID NO: 71)
5'-CGACTCTAGAGGATCCGTCTTAAGGATGGTTCAGCTGC-3'

CcPyrG-mark_FW1:
                                    (SEQ ID NO: 72)
5'-CATGACGGTTGCTAGGGTCG-3'

CcPyrG-mark_RV1:
                                    (SEQ ID NO: 73)
5'-GCCGCTCTGCTTCATTGCTG-3'
```

Figure 15:
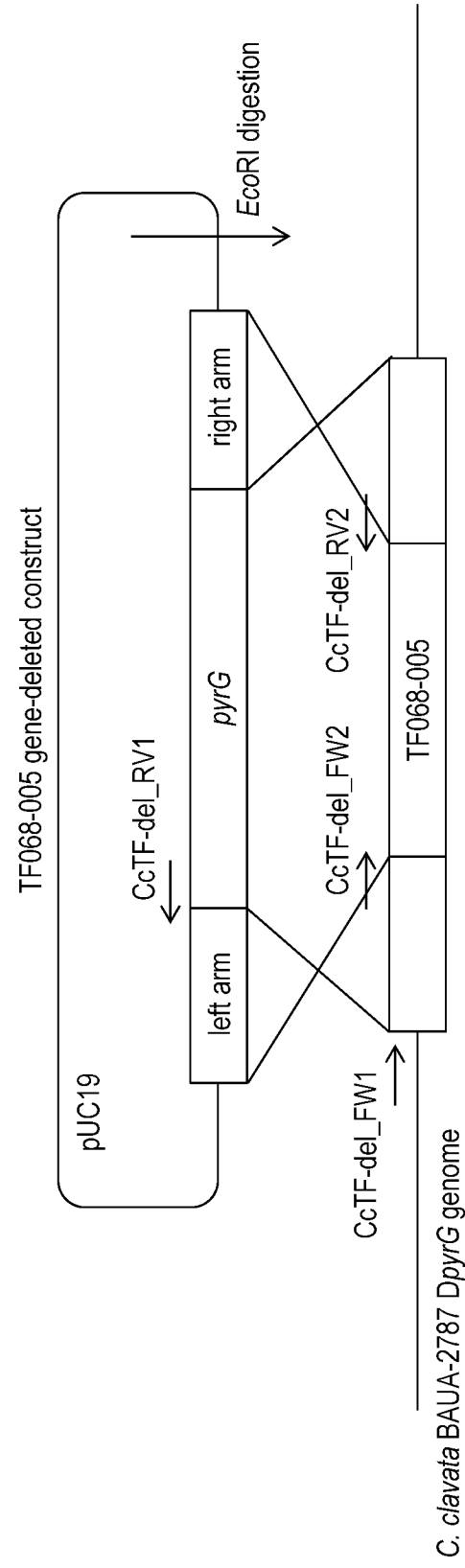
FIG. 15 schematically shows a method for transforming the CcpyrG gene-deleted strain with the aid of the TF068-005 gene-deleted construct.

(The underlined portions are 15-bp overlap sequences for the in-fusion reaction.) 4) Transformation with TF068-005 gene-deleted construct (FIG. 15)

FIG. 15 schematically shows the method for transforming the CcpyrG gene-deleted strain of the *C. clavata* BAUA-2787 strain prepared in 2) above with the TF068-005 gene-deleted construct. At the outset, the TF068-005 gene-deleted construct was linearized via digestion with the EcoRI restriction enzyme (TaKaRa) and purified with Ethachinimate (Nippon Gene, Co. Ltd.). Subsequently, the linearized construct was introduced into the *C. clavata* BAUA-2787 pyrG gene-deleted strain for transformation. Transformation was carried out basically in accordance with the protocol described in the section [Analysis using transcription factor high-expression strain]. However, the *C. clavata* BAUA-2787 pyrG gene-deleted strain was cultured in the CM+5 mM uridine+5 mM uracil medium, and the transformant was selected using MM agar medium (1% glucose, 0.6% NaNO$_3$, 0.052% KCl, 0.052% MgSO$_4$.7H$_2$O, 0.152% KH$_2$PO$_4$, and Hutner's trace elements (pH 6.5)).

5) Antibacterial Activity Test on TF068-005 Gene-Deleted Strain

The conidiospore suspension of the TF068-005 gene-deleted strain prepared in the manner described above was inoculated into 100 ml of CM medium, and culture was conducted at 26° C. and 130 rpm for 72 hours. The culture solution was filtered through Miracloth to remove the cells, sterilized through a 0.22-μm filter, and allowed to impregnate a paper disc. The paper disc and mycelial threads of gray mold (*Botrytis cinerea*) cut with agar medium were placed on a PDA medium at the interval of approximately 2.5 cm, and dual culture was then carried out at 26° C. for 3 days. A culture solution of a wild-type strain (i.e., the *C. clavata* BAUA-2787 strain) was used as a positive control, and CM medium in which cells were not cultured was used as a negative control.

6) Preparation of Total RNA of Transcription Factor Gene (TF068-005)-Deleted Strain The conidiospore suspension of the TF068-005 gene-deleted strain and that of wild-type strains were inoculated into 30 ml of CM medium, and shake culture was conducted at 26° C. and 130 rpm for 72 hours. Subsequently, the culture solution was filtered through Miracloth to collect the cells. A fraction (0.8 g) of the cells was frozen in liquid nitrogen and then grounded in a mortar using a pestle. The cells were suspended in 10 ml of ISOGEN (Nippon Gene Co., Ltd.), the resulting suspension was allowed to stand for 10 minutes, 2 ml of chloroform was added thereto, and the mixture was vortex-stirred, followed by centrifugation at 4,700×g for 10 minutes. The aqueous layer was collected, 5 ml of isopropanol was added, and the mixture was vortex-stirred, followed by centrifugation at 4,700×g for 10 minutes. The supernatant was discarded, the remnant was washed with the addition of 5 ml of 75% ethanol, centrifugation was carried out at 4,700×g for 10 minutes, the supernatant was discarded again, and RNA pellets were dissolved in 200 μl of nuclease-free water. The resulting RNA solution was purified again with the use of the RNeasy Plant Mini Kit (QIAGEN).

7) RNA-Seq Analysis of Transcription Factor Gene (TF068-005)-Deleted Strain

A library for RNA-Seq was prepared from total RNA prepared in the manner described above using the Truseq RNA Sample Prep Kit v2 (Illumina) and then applied to the next-generation sequencer (MiSeq) (paired-end; read length 75). The sequence data were mapped against the genome sequence of *C. clavata* using the TopHat program.

8) KK-1 Extraction and Quantification in Transcription Factor Gene-Deleted Strain and Wild-Type Strain The conidiospore suspension of the TF068-005 gene-deleted strain and that of wild-type strains were inoculated into 30 ml of CM medium, and shake culture was conducted at 26° C. and 130 rpm for 10 days. Ethyl acetate (15 ml) was added to the culture solution, and shake culture was carried out for 1 hour, followed by centrifugation at 4,700×g for 15 minutes. The ethyl acetate layer was collected, dehydrated to dryness, and then designated as the extracellular fraction. Subsequently, 10 ml of acetone was added to the aqueous layer after the ethyl acetate layer was collected, the mixture was vortex-stirred, and acetone was removed via centrifugal condensation. Ethyl acetate (15 ml) was added thereto, and the mixture was vortex-stirred, followed by centrifugation at 4,700×g for 10 minutes. The ethyl acetate layer was collected, subjected to centrifugal condensation, and then designated as the intracellular fraction. The resulting extract was dissolved in ethyl acetate again and then subjected to LC/MS analysis.

<LC>
Apparatus: ACQUITY UPLC I-Class system (Waters)
Column: Acquity UPLC BEH C18 2.1×100 mm
Mobile phase: DW+0.1% formic acid/acetonitrile+0.1% formic acid=50/50 (0.5 min)→2/98 (3.4 min)
Gradient: 50%-98% acetonitrile+0.1% formic acid (0.5-3.4 min)
Flow rate: 0.6 ml/min
Detection wavelength: 273 nm
<MS>
Apparatus: Xevo G2 QTof (Waters)
Ionization condition: Negative
<Results and Discussion>

Figure 16:
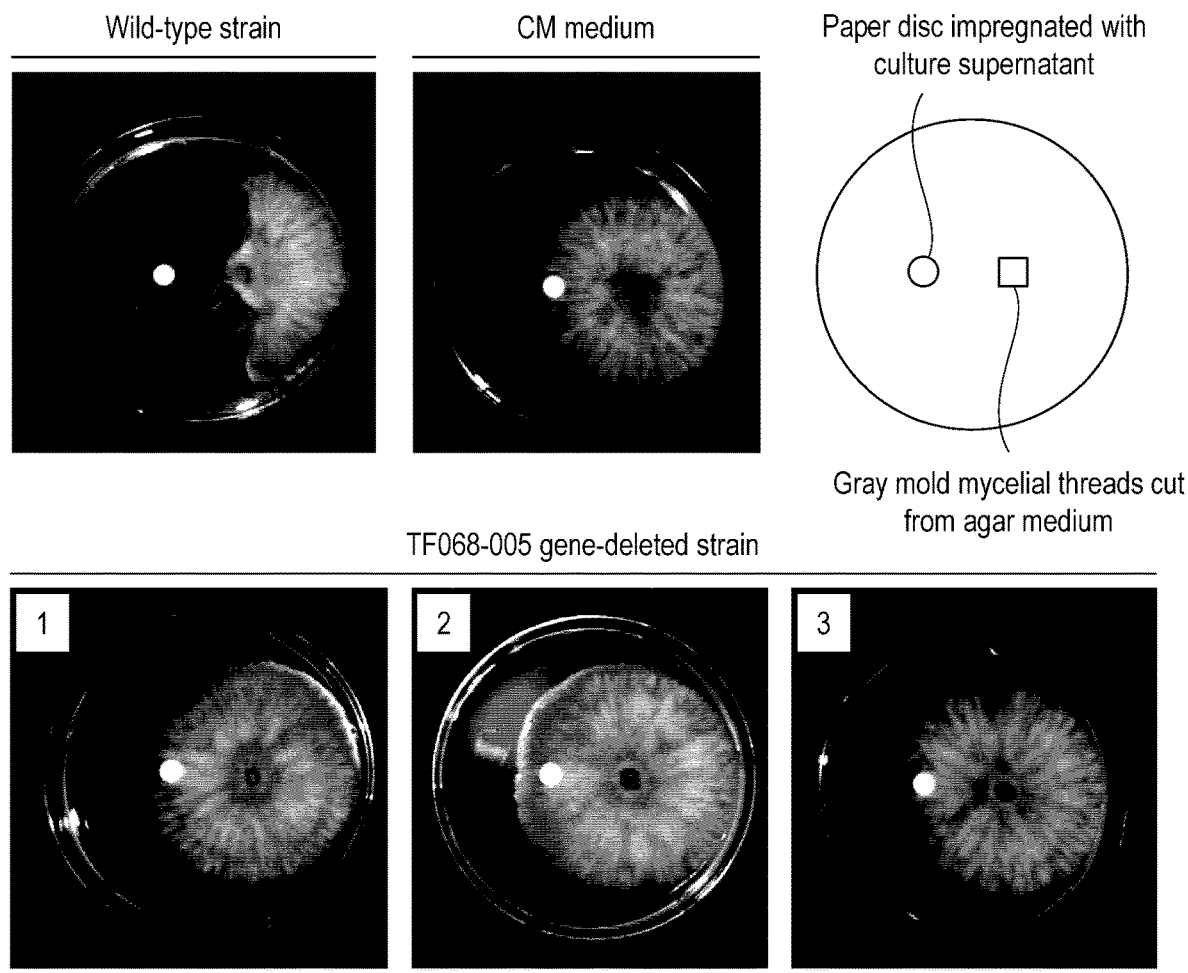
FIG. 16 shows characteristic diagrams showing the results of antibacterial activity tests performed on the transcription factor gene (the TF068-005 gene)-deleted strains and wild-type strains.

In this example, 5 strains in which TF068-005 gene deletion and nuclear purification had been observed were obtained, and antibacterial activity of the culture supernatant of these strains was inspected. FIG. 16 shows the results of the antibacterial activity test described above. FIG. 16 shows the results of the antibacterial activity test concerning 3 stains among the 5 TF068-005 gene-deleted strains obtained. As shown in FIG. 16, mycelial threads extension of gray mold toward the paper disc side was inhibited in a positive control sample (a culture solution of wild-type strains); however, inhibitory activity was not detected in the culture solution of the TF068-005 gene-deleted strain and the results similar to those concerning the negative control (a culture solution by itself) were obtained. It was thus considered that KK-1 productivity would be significantly lowered in the TF068-005 gene-deleted strain and that the TF068-005 gene would be deeply involved in the biosynthesis of KK-1.

Figure 17:
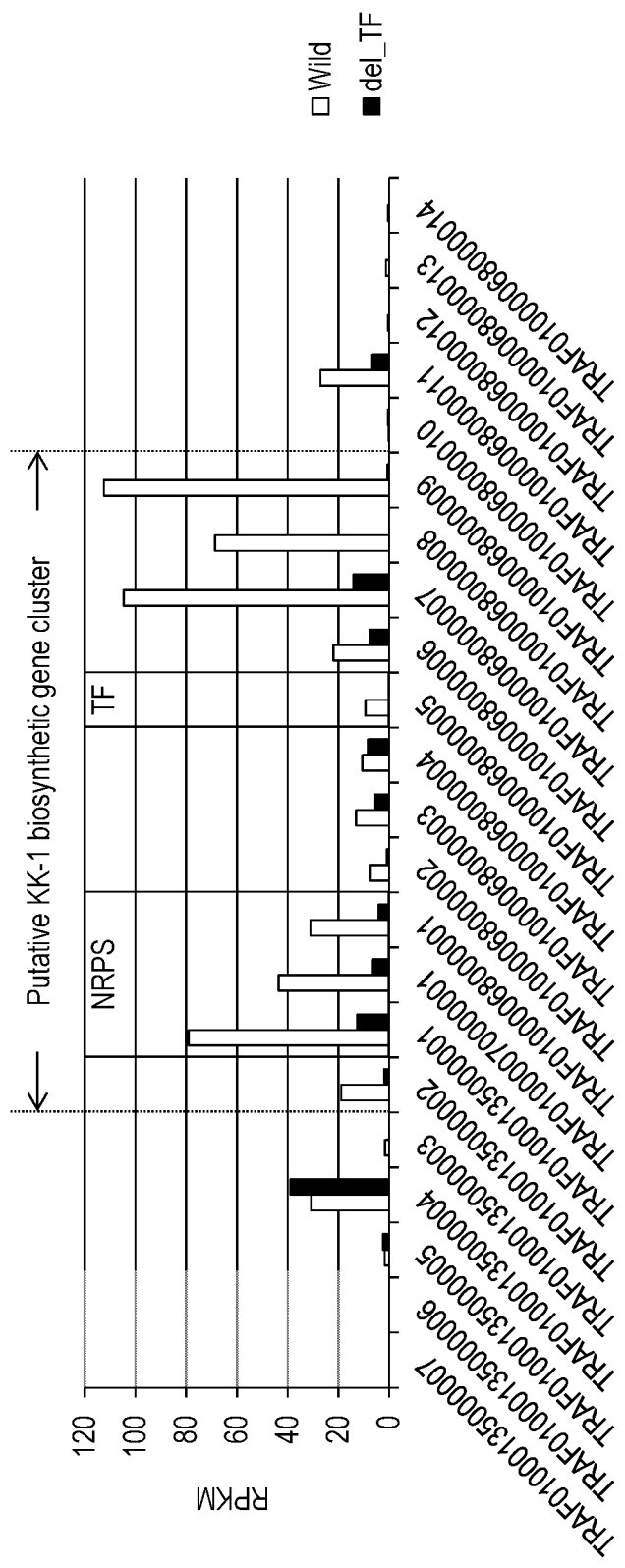
FIG. 17 shows characteristic diagrams showing the results of comprehensive gene expression analysis (RNA-seq) performed on the transcription factor gene (the TF068-005 gene)-deleted strain.

The TF068-005 gene-deleted strain was subjected to extensive gene expression analysis (RNA-seq) and analysis of KK-1 production level. In extensive gene expression analysis (RNA-seq), two TF068-005 gene-deleted strains were analyzed in comparison with wild-type strains. FIG. 17 shows the results of analysis. In FIG. 17, "del_TF" indicates the results concerning the TF068-005 gene-deleted strain. In the chart shown in FIG. 17, also, "RPKM" on the vertical axis indicates "reads per kilobase of exon per million mapped sequence reads," which are values obtained by normalizing the number of mapped sequences (lead sequences) with the total number of leads and the sequence length of the transcription product.

As shown in FIG. 17, the expression levels of the genes included in the putative biosynthetic cluster in the TF068-005 gene-deleted strain are significantly lower than those in wild-type strains. In contrast, the expression levels of the group of genes in the vicinity of the cluster (i.e., the outside of the cluster) was found to be equivalent to that in wild-type strains, except for the TRAF01000068000011 gene. On the basis of the annotated information, the TRAF01000068000011 gene is deduced to be a nucleotide-sugar transporter involved in transportation of a sugar nucleotide synthesized in a cytosol or nucleus to an endoplasmic reticulum or Golgi apparatus. Because of the absence of a sugar nucleotide in the KK-1 structure, the gene of interest was considered less likely to be involved in biosynthesis.

Figure 18:
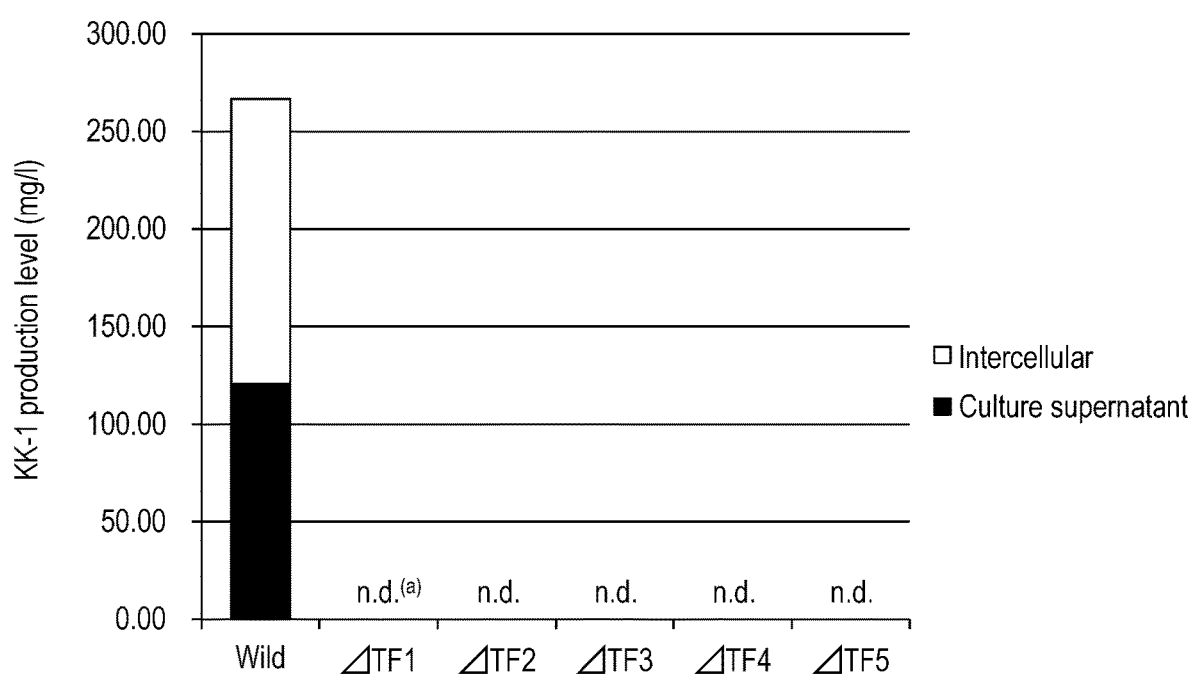
FIG. 18 shows a characteristic diagram showing the results of analysis of the KK-1 production level performed on the transcription factor gene (the TF068-005 gene)-deleted strain.

FIG. 18 shows the results of KK-1 production levels in the 5 TF068-005 gene-deleted strains analyzed via LC/MS. As shown in FIG. 18, KK-1 was not detected in the culture supernatant or in the cells in any of the 5 TF068-005 gene-deleted strains.

On the basis of the results concerning the TF068-005 gene-deleted strains and a significant increase in gene expression levels and KK-1 production levels in TF068-005 high-expression strains, it was found that the putative gene cluster would play a key role in KK-1 biosynthesis and the TF068-005 gene regulates transcription of the genes constituting the KK-1 biosynthetic gene cluster.

Example 3

In this example, gene-deleted strains of the genes included in the KK-1 biosynthetic gene cluster deduced in Example 1 were prepared and functions of the genes were analyzed.

Figure 19:
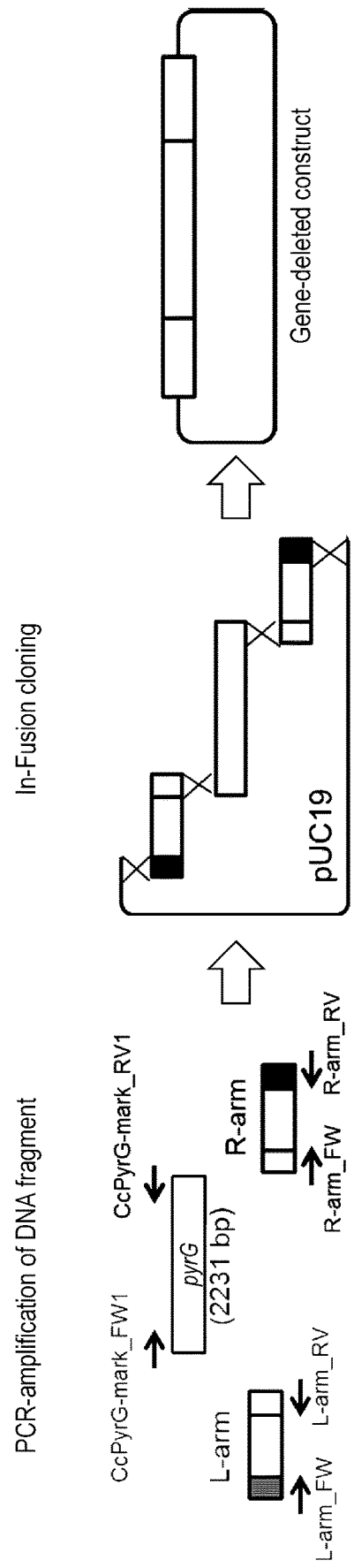
FIG. 19 schematically shows a gene-deleted construct prepared for each gene included in the KK-1 biosynthetic gene cluster.

1) Construction of Cluster Gene-Deleted Construct (FIG. 19)

Except for the TRAF01000068000005 (i.e., the transcription factor gene) examined in Example 2, an upstream region of about 1,000 bp and a downstream region of about 1,000 bp of each gene included in the KK-1 biosynthetic gene cluster were designated as L-arm and R-arm, respectively, and both gene-fragments were obtained via PCR using genomic DNA of the C. clavata BAUA-2787 strain as a template. Also, the pyrG gene serving as a transformant selection marker was amplified via PCR. Subsequently, L-arm, the pyrG gene, and R-arm amplified via PCR were successively ligated to each other, and the resulting fragment was inserted into pUC19 using the In-Fusion Cloning Kit (Clontech), so as to prepare a gene-deleted construct (FIG. 19).

The sequences of the primers used for PCR amplification of DNA fragments constituting each construct and PCR conditions are described below. The 15-bp overlap sequences to be subjected to the in-fusion reaction are underlined.

For amplification of pyrG selection marker (the primers used in Example 2)

```
CcPyrG-mark_FW1:
                                          (SEQ ID NO: 72)
5'-CATGACGGTTGCTAGGGTCG-3'

CcPyrG-mark_RV1:
                                          (SEQ ID NO: 73)
5'-GCCGCTCTGCTTCATTGCTG-3'
```

For amplification of L-arm (982 bp) of TRAF01000135000002-deleted construct

```
TRAF135-002_del_L-arm_FW:
                                          (SEQ ID NO: 74)
5'-CGGTACCCGGGGATCGACCCATTGCAGCTTGTG-3'

TRAF135-002_del_L-arm_RV:
                                          (SEQ ID NO: 75)
5'-ATGAAGCAGAGCGGCGTGCAGTATGGTGTCTAAAACG-3'
```

For amplification of R-arm (950 bp) of TRAF01000135000002-deleted construct

```
TRAF135-002_del_R-arm_FW:
                                          (SEQ ID NO: 76)
5'-CTAGCAACCGTCATGGATGAATGAGCACCCTGTTAG-3'

TRAF135-002_del_R-arm_RV:
                                          (SEQ ID NO: 77)
5'-CGACTCTAGAGGATCGTACATTACAAAAACCTGTTGCAG-3'
```

For amplification of L-arm (1,000 bp) of TRAF01000135000001-deleted construct

```
TRAF135-001_del_L-arm_FW:
                                          (SEQ ID NO: 78)
5'-CGGTACCCGGGGATCGTCCCACGTGCAGCTTCAAC-3'

TRAF135-001_del_L-arm_RV:
                                          (SEQ ID NO: 79)
5'-ATGAAGCAGAGCGGCCGTGGAGTATCCCAGGATGG-3'
```

For amplification of R-arm (982 bp) of TRAF01000135000001-deleted construct

```
TRAF135-001_del_R-arm_FW:
                                          (SEQ ID NO: 80)
5'-CTAGCAACCGTCATGCCAGCCAAAGGGTATCATGG-3'

TRAF135-001_del_R-arm_RV:
                                          (SEQ ID NO: 81)
5'-CGACTCTAGAGGATCTGAGGGCAGCGTAGCCTG-3'
```

For amplification of L-arm (992 bp) of TRAF01000068000002-deleted construct

```
TRAF068-002_del_L-arm_FW:
                               (SEQ ID NO: 82)
5'-CGGTACCCGGGGATCGTGGATAAATTCGTACCCTTTG-3'

TRAF068-002_del_L-arm_RV:
                               (SEQ ID NO: 83)
5'-ATGAAGCAGAGCGGCCTGATCTTTGTTGTGGTCGTG-3'
```

For amplification of R-arm (1,014 bp) of TRAF01000068000002-deleted construct

```
TRAF068-002_del_R-arm_FW:
                               (SEQ ID NO: 84)
5'-CTAGCAACCGTCATGCAGTTTGGCACTTGAGCATC-3'

TRAF068-002_del_R-arm_RV:
                               (SEQ ID NO: 85)
5'-CGACTCTAGAGGATCCACGGAAAGGAACTCCTACAG-3'
```

For amplification of L-arm (912 bp) of TRAF01000068000003-deleted construct

```
TRAF068-003_del_L-arm_FW:
                               (SEQ ID NO: 86)
5'-CGGTACCCGGGGATCCTCTGGGAAAAGCGGTTAG-3'

TRAF068-003_del_L-arm_RV:
                               (SEQ ID NO: 87)
5'-ATGAAGCAGAGCGGCGAAGAACCGAGAGCGAGAG-3'
```

For amplification of R-arm (995 bp) of TRAF01000068000003-deleted construct

```
TRAF068-003_del_R-arm_FW:
                               (SEQ ID NO: 88)
5'-CTAGCAACCGTCATGCTTGCATCTACCTAGATATTTCACG-3'

TRAF068-003_del_R-arm_RV:
                               (SEQ ID NO: 89)
5'-CGACTCTAGAGGATCCAGAGAATCAGCAGAGACACC-3'
```

For amplification of L-arm (991 bp) of TRAF01000068000004-deleted construct

```
TRAF068-004_del_L-arm_FW:
                               (SEQ ID NO: 90)
5'-CGGTACCCGGGGATCCCCTGGTAGTTCAGTGGAAGTAAG-3'

TRAF068-004_del_L-arm_RV:
                               (SEQ ID NO: 91)
5'-ATGAAGCAGAGCGGCTGATAGAGGTACGGGGGTG-3'
```

For amplification of R-arm (1,003 bp) of TRAF01000068000004-deleted construct

```
TRAF068-004_del_R-arm_FW:
                               (SEQ ID NO: 92)
5'-CTAGCAACCGTCATGTGCTTGGCTGCTTCAAATC-3'

TRAF068-004_del_R-arm_RV:
                               (SEQ ID NO: 93)
5'-CGACTCTAGAGGATCCTAATACTTGTCGTCCCACTGATG-3'
```

For amplification of L-arm (993 bp) of TRAF01000068000006-deleted construct

```
TRAF068-006_del_L-arm_FW:
                               (SEQ ID NO: 94)
5'-CGGTACCCGGGGATCGCAGTACATCGTCAGGGTC-3'

TRAF068-006_del_L-arm_RV:
                               (SEQ ID NO: 95)
5'-ATGAAGCAGAGCGGCGATGAATAAGGCGAAGGAAAG-3'
```

For amplification of R-arm (579 bp) of TRAF01000068000006-deleted construct

```
TRAF068-006_del_R-arm_FW:
                               (SEQ ID NO: 96)
5'-CTAGCAACCGTCATGCCCTCTTTTTTCTTGCTGTCTC-3'

TRAF068-006_del_R-arm_RV:
                               (SEQ ID NO: 97)
5'-CGACTCTAGAGGATCGAAGGAAGGACGGATACTGG-3'
```

For amplification of L-arm (769 bp) of TRAF01000068000007-deleted construct

```
TRAF068-007_del_L-arm_FW:
                               (SEQ ID NO: 98)
5'-CGGTACCCGGGGATCGATGAGCGTAGAATTCGTAAAAAG-3'

TRAF068-007_del_L-arm_RV:
                               (SEQ ID NO: 99)
5'-ATGAAGCAGAGCGGCGCGAACGGGCGTTTTTC-3'
```

For amplification of R-arm (579 bp) of TRAF01000068000007-deleted construct

```
TRAF068-007_del_R-arm_FW:
                               (SEQ ID NO: 100)
5'-CTAGCAACCGTCATGGAAGGAAGGACGGATACTGG-3'

TRAF068-007_del_R-arm_RV:
                               (SEQ ID NO: 101)
5'-CGACTCTAGAGGATCCCCTCTTTTTTCTTGCTGTCTC-3'
```

For amplification of L-arm (716 bp) of TRAF01000068000008-deleted construct

```
TRAF068-008_del_L-arm_FW:
                               (SEQ ID NO: 102)
5'-CGGTACCCGGGGATCCTCCTTATTTTGCAACTTCTGATAC-3'

TRAF068-008_del_L-arm_RV:
                               (SEQ ID NO: 103)
5'-ATGAAGCAGAGCGGCCGTGTTGATTTTGGTAATTTTG-3'
```

For amplification of R-arm (769 bp) of TRAF01000068000008-deleted construct

```
TRAF068-008_del_R-arm_FW:
                               (SEQ ID NO: 104)
5'-CTAGCAACCGTCATGGATGAGCGTAGAATTCGTAAAAAG-3'

TRAF068-008_del_R-arm_RV:
                               (SEQ ID NO: 105)
5'-CGACTCTAGAGGATCGCGAACGGGCGTTTTTC-3'
```

For amplification of L-arm (716 bp) of TRAF01000068000009-deleted construct

```
TRAF068-009_del_L-arm_FW:
                                (SEQ ID NO: 106)
5'-CGGTACCCGGGGATCCGTGTTGATTTTGGTAATTTTG-3'

TRAF068-009_del_L-arm_RV:
                                (SEQ ID NO: 107)
5'-ATGAAGCAGAGCGGCCTCCTTATTTTGCAACTTCTGATAC-3'
```

For amplification of R-arm (989 bp) of TRAF01000068000009-deleted construct

```
TRAF068-009_del_R-arm_FW:
                                (SEQ ID NO: 108)
5'-CTAGCAACCGTCATGCTAGCAGCCATAAGAGACGTAACC-3'

TRAF068-009_del_R-arm_RV:
                                (SEQ ID NO: 109)
5'-CGACTCTAGAGGATCGTTTTCATTGCATGCTCCG-3'
```

PCR Conditions

PCR was carried out with the use of the Phusion High-Fidelity DNA Polymerase (Thermo Fisher Scientific). The temperature conditions were: initial denaturation at 98° C. for 30 seconds; a cycle of denaturation at 98° C. for 10 seconds, annealing at 60° C. for 30 seconds, and extension at 72° C. for 45 seconds repeated 30 times; and final extension at 72° C. for 5 minutes.

2) Transformation of *C. Clavata* pyrG-Deleted Strain

Figure 20:
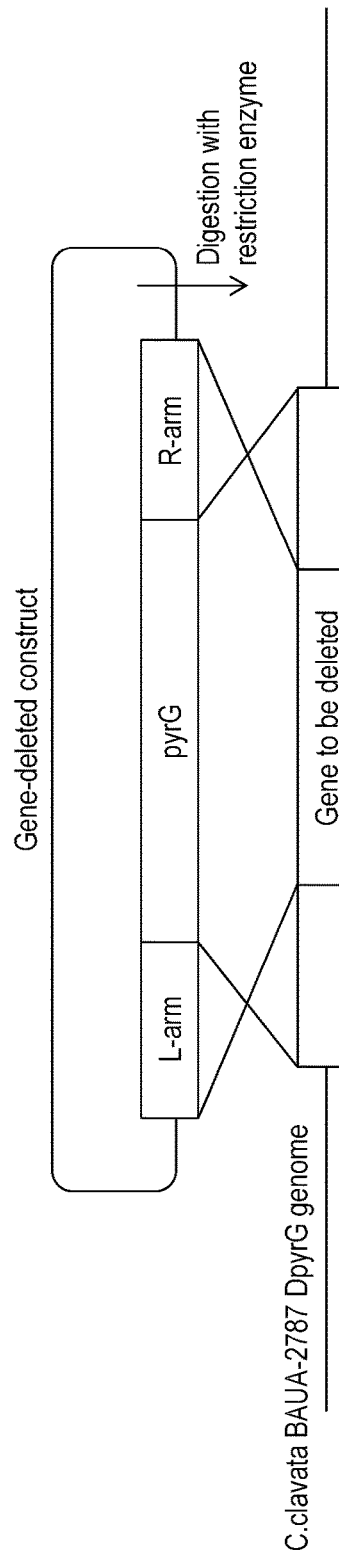
FIG. 20 schematically shows a method for transforming the CcpyrG gene-deleted strain with a gene-deleted construct prepared for each gene included in the KK-1 biosynthetic gene cluster.

FIG. 20A schematically shows a method for transforming the CcpyrG gene-deleted strain of the *C. clavata* BAUA-2787 strain prepared in Example 2 2) with a relevant gene-deleted construct. The resulting gene-deleted construct was linearized with a given restriction enzyme (shown in FIG. 20B). Subsequently, the linearized construct was introduced into the *C. clavata* BAUA-2787 pyrG gene-deleted strain in accordance with the protocol described in the section [Analysis using transcription factor high-expression strain] in Example 2. When culturing the host *C. clavata* BAUA-2787 pyrG gene-deleted strain, liquid CM medium supplemented with 5 mM uridine and uracil was used, and transformant selection was carried out in MM agar medium.

3) Culture of Cluster Gene-Deleted Strain

The conidiospore suspension of the gene-deleted strains obtained in 2) above was inoculated into 30 ml of KM medium (a 100-ml baffled triangular flask), shake culture was conducted at 26° C. and 130 rpm for 3 days, and the product was designated as a "preculture solution." Subsequently, 300 μl of the preculture solution was inoculated into 30 ml of the CM medium (a 100-ml baffled triangular flask), and shake culture was then conducted at 26° C. and 130 rpm for 7 days.

4) Extraction and Analysis of Metabolite in the Culture System

Ethyl acetate (15 ml) was added to the culture solution obtained in 3) above, shake culture was carried out at 130 rpm for 1 hour, and centrifugation was then carried out at 4,200×g for 15 minutes. The ethyl acetate layer was collected, subjected to centrifugal condensation, and then designated as an extracellular fraction. Subsequently, 10 ml of acetone was added to an aqueous layer after the ethyl acetate layer was collected, the mixture was vortex-stirred, and acetone was removed via centrifugal condensation. Ethyl acetate (15 ml) was added thereto, and the mixture was vortex-stirred, followed by centrifugation at 4,200×g for 10 minutes. The ethyl acetate layer was collected, subjected to centrifugal condensation, and then designated as an intracellular fraction. After the extracellular fraction was dissolved in 500 μl of ethyl acetate in combination with the intracellular fraction, 1 μl of the extract was subjected to LC/MS analysis.

Conditions for LC/MS Analysis

<LC>

Apparatus: ACQUITY UPLC I-Class System (Waters)

Column: Acquity UPLC BEH C18, 2.1×100 mm

Mobile phase: DW/MeCN=50/50 (0.5 min)→2/98 (3.4 min) (each solvent contains 0.1% formic acid)

Flow rate: 0.6 ml/min

Detection wavelength: 273 nm

<MS>

Apparatus: Xevo G2 QTof (Waters)

Ionization condition: Negative

<Results and Discussion>

Figure 21:
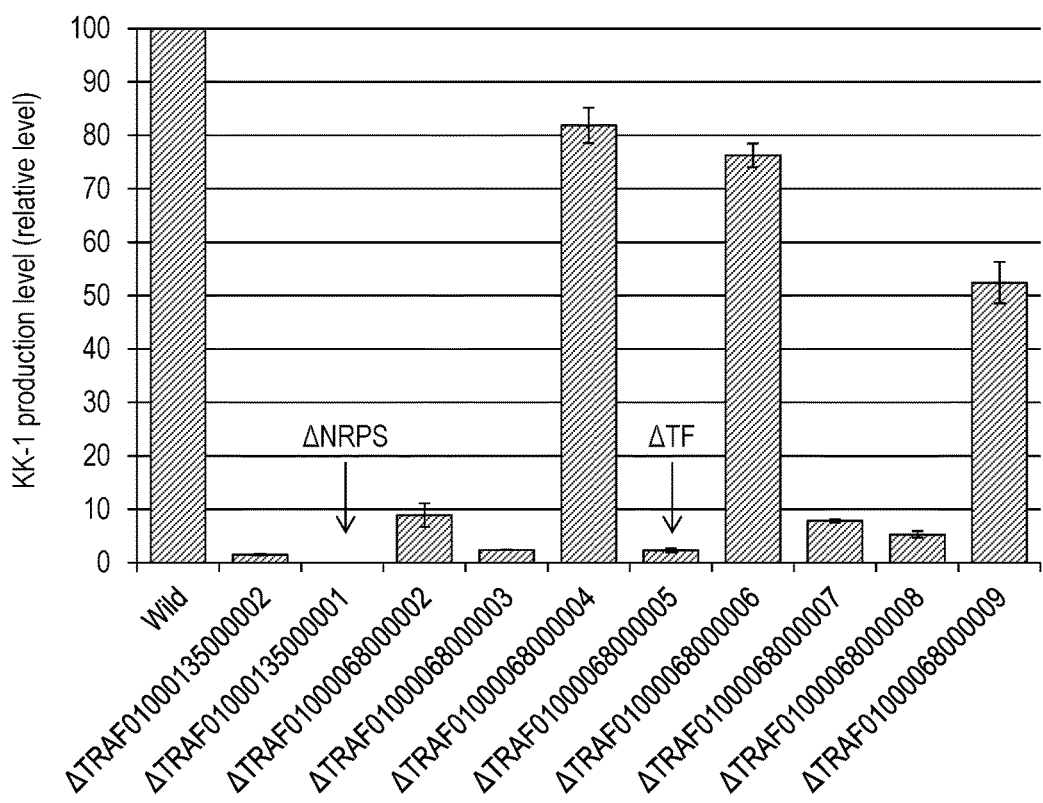
FIG. 21 shows a characteristic diagram showing the results of inspection of KK-1 productivity of gene-deleted strains and transcription factor gene-deleted strains.

The gene-deleted strains prepared in this example and the transcription factor gene-deleted strains prepared in Example 2 were inspected in terms of KK-1 productivity. The results are shown in FIG. 21. In FIG. 21, the KK-1 production level of each strain (i.e., the amount relative to a wild-type strain) is indicated in terms of "mean±standard error (n=2)." As shown in FIG. 21, KK-1 production was completely quenched in a strain in which the NRPS (TRAF01000135000001) gene biosynthesizing a cyclic peptide in a basic backbone had been deleted. This indicates that such gene is essential for biosynthesis of KK-1.

As shown in FIG. 21, also, the KK-1 production levels of strains lacking 5 types of genes (i.e., TRAF01000135000002, TRAF01000068000002, TRAF01000068000003, TRAF01000068000007, and TRAF01000068000008) among the group of genes included in the gene cluster were significantly lower than those in wild-type strains. Accordingly, these genes were considered to be deeply involved in KK-1 production at the time of, for example, modification of the cyclic peptide backbone biosynthesized by NRPS.

In the strains lacking 3 types of genes (i.e., TRAF01000068000004, TRAF01000068000006, and TRAF01000068000009), as shown in FIG. 21, the KK-1 production levels were lower than those in wild-type strains, although a range of fluctuation was smaller than the 5 types of genes described above. This indicates that these 3 types of genes are also involved in KK-1 production. In fact, a protein encoded by TRAF01000068000006 is deduced to be an ABC transporter, and it is considered to be involved in efflux of KK-1 produced in the cells toward the outside of the cells. Regarding TRAF01000068000009 annotated as "α/β hydrolase," a gene encoding thioesterase that hydrolyzes an erroneously incorporated substrate is included in the lankamycin biosynthetic cluster, which is a polyketide antibiotics produced by *Actinomycetes*, i.e., *Streptomyces rochei* 7434AN4. Accordingly, such gene was considered to function in the same manner. Since TRAF01000068000004 is as small as 8.1 kDa and there is no protein similar thereto, it may not have particular functions.

Example 4

In this example, the KK-1 biosynthetic gene cluster subjected to function analysis in Examples 1 to 3 was introduced into *Aspergillus oryzae*, and heterologous production of KK-1 in *Aspergillus oryzae* was examined.

1) *Aspergillus oryzae* Strain and Medium (*A. oryzae* Strain and Growth Medium)

As parent *Aspergillus oryzae* (*A. oryzae*) strains into which the KK-1 biosynthetic gene cluster was to be introduced, the NS4 ΔadeA strains (sC-, niaD-, ΔligD::sC, ΔadeA::ptrA) were used. General growth and conidiospore formation were implemented in the Czapek-dox (CD) minimal medium satisfying auxotrophy of the strains (0.6% NaNO₃, 0.052% KCl, 0.152% KH₂PO₄, 0.0001% FeSO₄.7H₂O, 0.00088% ZnSO₄.7H₂O, 0.00004% CuSO₄.5H₂O, 0.000015% MnSO₄.4H₂O, 0.00001% Na₂B₄O₇.10H₂O, 0.000005% (NH₄)₆Mo₇O₂₄.4H₂O, 0.059% MgSO₄.7H₂O, and 2% glucose). Specifically, a medium supplemented with 70 mM sodium glutamate instead of NaNO₃ as a nitrogen source (CDE) or a medium prepared by supplementing CDE with 0.01% adenine (CDEA) was used. YPM medium (1% yeast extract, 2% polypeptone, 2% maltose) was used to induce expression of the gene introduced with the aid of the *Aspergillus oryzae* amyB promoter, and YPM medium was also used to evaluate KK-1 productivity.

Figure 22:
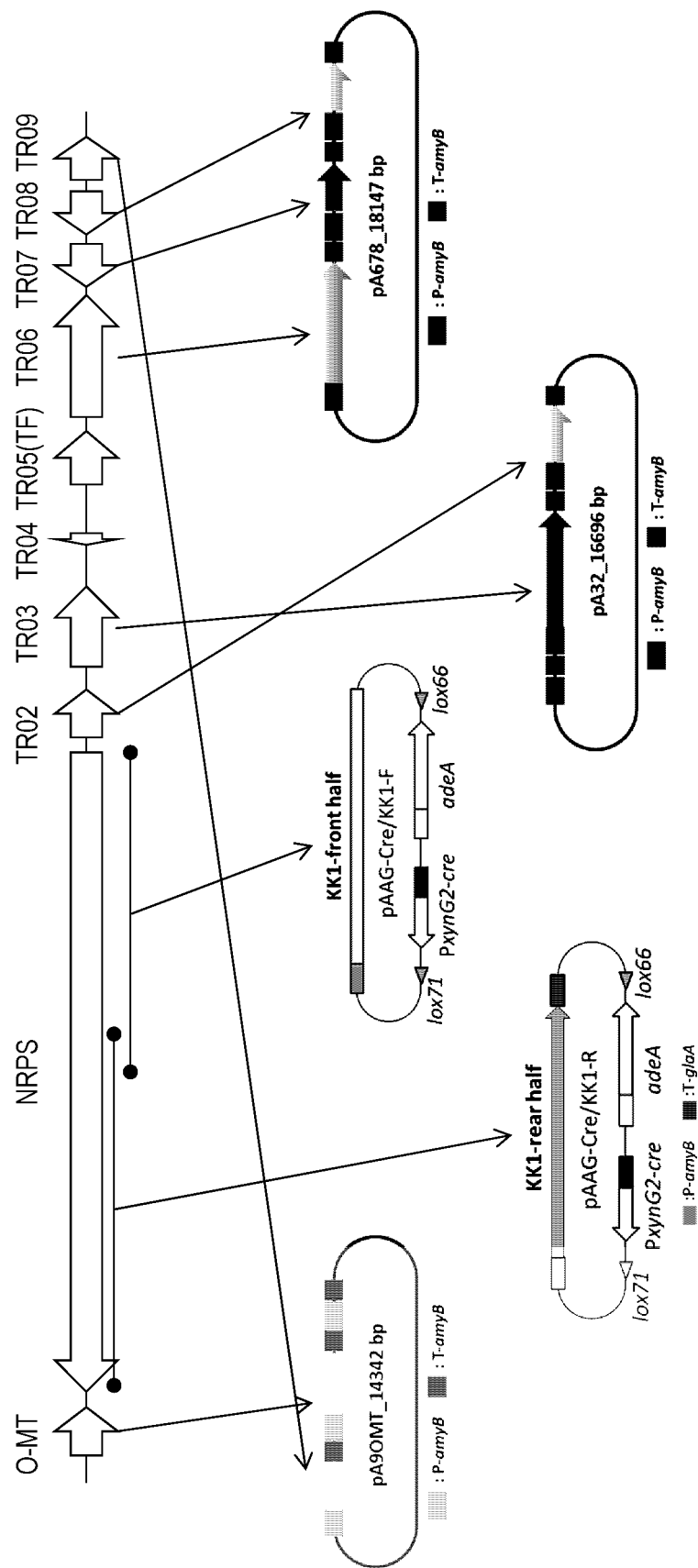
FIG. 22 schematically shows a scheme for constructing a vector used when introducing the KK-1 biosynthetic gene cluster.

2) Construction of Vector for Separate Introduction of NRPS Gene (FIG. 22)

FIG. 22 schematically shows a scheme for constructing a vector used when introducing the KK-1 biosynthetic gene cluster. Among the genes included in the KK-1 biosynthetic gene cluster, as shown in FIG. 22, the NRPS gene was divided into two fragments and introduced into *Aspergillus oryzae*. Specifically, a 39-kb gene (full-length) was divided into a front half portion (about 20 kb) and a rear half portion (about 20 kb) and separately subcloned into a plasmid vector, and the resultants were then introduced into *Aspergillus oryzae*. Thereafter, a transformant, the both fragments of which had been ligated to each other in *Aspergillus oryzae*, were selected. As a plasmid vector, pAAG-Cre whose marker could be reused via expression of endogenous Cre recombinase was used.

At the outset, PCR was carried out with the use of the primers (NRPS-fh-F and NRPS-fh-R) to amplify the gene of the front half portion. PCR was carried out with the use of genomic DNA of the *C. clavata* BAUA-2787 strain as a template and PrimeSTAR GXL DNA Polymerase (Takara) as an enzyme in accordance with the manufacturer's instructions. The PCR product was ligated to the EcoRV-cleavage site of pZErO-2 (Invitrogen). The front half portion of the NRPS gene was cleaved from the plasmid with NotI and ligated to the corresponding site of pAAG-Cre. A plasmid in which the PamyB promoter for *Aspergillus oryzae* and the NRPS gene had been ligated in the correct orientation was selected and designated as the vector for introduction of the front half of the NRPS gene (pAAG-Cre/KK1-F).

It was difficult to subject the gene of the rear half portion of the NRPS gene to cloning via PCR amplification through a single procedure. Thus, the portion was further divided into three fragments, the fragments were separately amplified, and the amplified fragments were then ligated to each other via in-fusion cloning. First of all, the fragments A, B, and C of the rear half portion were amplified via PCR. The fragment A of the rear half portion was amplified with the use of primers NRPS-rh-IF-Fa and NRPS-rh-IF-Ra, the fragment B was amplified with the use of primers NRPS-rh-IF-Fb and NRPS-rh-IF-Rb, and the fragment C was amplified with the use of primers NRPS-rh-IF-Fc and NRPS-rh-IF-Rc. These fragments were each ligated to the NotI-digested pAAG-Cre via in-fusion cloning, and the plasmid ligated in the correct orientation was designated as the vector for introduction of the rear half of the NRPS gene (pAAG-Cre/NRPSrh).

In-fusion cloning was carried out with the use of the In-Fusion HD Cloning kit (Clontech) in accordance with the manufacturer's instructions. The gene sequences of the vector for introduction of the front half of the NRPS gene and the vector for introduction of the rear half thereof were inspected to confirm that no variation would occur in NRPS.

The sequences of the primers used are shown below.

```
NRPS-fh-F:
                                        (SEQ ID NO: 110)
TCGACAAGCTTGCGGCCGCCACGTGACTAGTATGGCCAGCGACATCAATA

CTCATCCAG

NRPS-fh-R:
                                        (SEQ ID NO: 111)
ACTAGTCACGTGGCGGCCGCGGCGCGCCAAGATCGTCTTGCTGTACG

NRPS-rh-IF-Fa:
                                        (SEQ ID NO: 112)
GATGCGCTAGCGGCCGCGAAGTGGTCCTTGTCGCTGGTGAC

NRPS-rh-IF-Ra:
                                        (SEQ ID NO: 113)
TGCCGTTCGCATTCATAGGCATCTCGTC

NRPS-rh-IF-Fb:
                                        (SEQ ID NO: 114)
TGAATGCGAACGGCAAGGTTGACAG

NRPS-rh-IF-Rb:
                                        (SEQ ID NO: 115)
CTTGGTTGCTGGCTTCGTCGTTGTC

NRPS-rh-IF-Fc:
                                        (SEQ ID NO: 116)
AAGCCAGCAACCAAGTCGAAGATTG

NRPS-rh-IF-Rc:
                                        (SEQ ID NO: 117)
GTCACTAGTGCGGCCGCCTATTTTTGCAAGATCTTGTTCAAAC
```

3) Construction of Vector for Cluster Gene Introduction (FIG. 22)

Among the genes included in the KK-1 biosynthetic gene cluster, as described in Example 2, TRAF01000068000004 is not essential for biosynthesis of KK-1. Since TRAF01000068000005 is a transcription factor that regulates cluster gene expression, when all genes are to be regulated by a promoter for *Aspergillus oryzae*, accordingly, this gene may not be necessary. In order to introduce 7 genes except for the NRPS gene and these 2 genes into *Aspergillus oryzae*, as shown in FIG. 22, a gene introduction vector carrying such genes was constructed.

As a plasmid carrying the genes of interest, pA3AXPC capable of simultaneously carrying 3 genes at most and regulating all genes with the amyB promoter was selected (pA3AXPC can be provided by Professor Katsuya Gomi, Laboratory of Bioindustrial Genomics, Tohoku University). The plasmid carries the Cre-loxP marker recycling system utilizing Cre recombinase and loxP sequences, and it is a vector suitable for gene introduction at multiple stages.

At the outset, PCR was carried out using cDNA of the *C. clavata* BAUA-2787 strain as a template to amplify the genes. The TRAF01000068000002 gene was amplified with the use of the set of primers TR02-SpeI-F and TR02-SpeI-R, and the TRAF01000068000003 gene was amplified with the use of the set of primers TR03-NotI-F and TR03-NotI-R. The amplified fragments were ligated to the EcoRV cleavage site of pZErO-2 (referred to as pZTR02 and pZTR03, respectively). Thereafter, the TRAF01000068000002 gene was cleaved from pZTR02 via digestion with SpeI, and the TRAF01000068000003 gene was cleaved from pZTR03 via digestion with NotI. The cleaved TRAF01000068000002 (SpeI) and TRAF01000068000003 (NotI) genes were successively introduced into the SpeI site and the NotI site of pA3AXPC. A plasmid into which these genes had been inserted in the correct orientation was designated as pATR0203.

Subsequently, the TRAF01000068000006 gene was amplified with the use of the set of primers TR06-NheI-F and TR06-NheI-R, the TRAF01000068000007 gene was amplified with the use of the set of primers TR07-NotI-F and TR07-NotI-R, and the TRAF01000068000009 gene was amplified with the use of the set of primers TR08-SpeI-F and TR08-SpeI-R. The PCR-amplified fragments were ligated to the EcoRV cleavage site of pZErO-2 (the resultants are referred to as pZTR06, pZTR07, and pZTR08, respectively). Thereafter, the TRAF01000068000006 gene was cleaved from pZTR06 via digestion with NheI, the TRAF01000068000007 gene was cleaved from pZTR07 via digestion with NotI, and the TRAF01000068000008 gene was cleaved from pZTR08 via digestion with SpeI. The cleaved TRAF01000068000006 (NheI), TRAF01000068000008 (SpeI), and TRAF01000068000007 (NotI) genes were successively introduced into the NheI site, the SpeI site, and the NotI site of pA3AXPC, respectively. A plasmid into which these genes had been inserted in the correct orientation was designated as pATR678.

In the end, the TRAF01000068000009 gene was amplified with the use of the set of primers TR09-NheI-F and TR09-NheI-R, and the TRAF01000135000002 gene was amplified with the use of the set of primers OMT-NotI-F and OMT-NotI-R. The PCR-amplified fragments were ligated to the EcoRV cleavage site of pZErO-2 (the resultants are referred to as pZTR09 and pZOMT, respectively). Thereafter, the TRAF01000068000009 gene was cleaved from pZTR09 via digestion with NheI, and the TRAF01000135000001 gene was cleaved from pZOMT via digestion with NotI. The cleaved TRAF01000068000009 (NheI) and TRAF01000135000001OMT (NotI) genes were successively introduced into the NheI site and the NotI site of pA3AXPC, respectively. A plasmid into which these genes had been inserted in the correct orientation was designated as pATR09OMT.

The sequences of the primers used are shown below.

```
TR02-SpeI-F:
                                     (SEQ ID NO: 118)
GGACTAGTATGACTGAACCCACATGGAAG

TR02-SpeI-R:
                                     (SEQ ID NO: 119)
GGACTAGTTTAATAATCTACTTCAAGCAC

TR03-NotI-F:
                                     (SEQ ID NO: 120)
ATAAGAATGCGGCCGCATGGCGTTGCAAGAGCG

TR03-NotI-R:
                                     (SEQ ID NO: 121)
ATAAGAATGCGGCCGCTCAAGATGGGAAAGCCGCTG

TR06-NheI-F:
                                     (SEQ ID NO: 122)
CTAGCTAGCATGAGTGCTATCGAGCTGC

TR06-NheI-R:
                                     (SEQ ID NO: 123)
CTAGCTAGCTCAGCGATTGAGGGCCTGG

TR07-NotI-F:
                                     (SEQ ID NO: 124)
ATAAGAATGCGGCCGCATGAAGCTCACCGTTTTCAG

TR07-NotI-R:
                                     (SEQ ID NO: 125)
ATAAGAATGCGGCCGCTCAGAGCCGCGCCAAC

TR08-SpeI-F:
                                     (SEQ ID NO: 126)
GGACTAGTATGACGAAAAGGGAAAGCAAC

TR08-SpeI-R:
                                     (SEQ ID NO: 127)
GGACTAGTCTACGCGTTTTCTTTCGAC

TR09-NheI-F:
                                     (SEQ ID NO: 128)
CTAGCTAGCATGGAGAGCGAAGACAATCC

TR09-NheI-R:
                                     (SEQ ID NO: 129)
CTAGCTAGCTCAGCAGTATCCCATCGG

OMT-NotI-F:
                                     (SEQ ID NO: 130)
ATTTGCGGCCGCATGGACCCGAGACAGTCACGGATC

OMT-NotI-R:
                                     (SEQ ID NO: 131)
ATTTGCGGCCGCTTATGGTGTGGTGGGTTGCCATTC
```

4) Method of Gene Introduction into *Aspergillus oryzae*

Transformation of *Aspergillus oryzae* using various plasmids prepared in 3) above was carried out by the protoplast-PEG method. Conidiospores ($1 \times 10^7$ cells) of the parent strain (the NS4 ΔadeA strain) were inoculated into 100 ml of YPD liquid medium (1% yeast extract, 2% polypeptone, and 2% glucose) in a 200-ml triangular flask, shake culture was carried out at 30° C. and 160 rpm for 20 hours, and the resulting mycelial threads were collected through Miracloth (CALIBIOCHEM). The collected mycelial threads were washed with sterilized water, and a dry-heat-sterilized spatula was pressed against the cells for dehydration. The collected mycelial threads were introduced into a 50-ml tube, and 25 ml of a solution for protoplast preparation (the solution composed of 10 mg/ml lysing enzymes (Sigma), 5 mg/ml Cellulase Onozuka (Yakult Pharmaceutical Ind. Co., Ltd.), 2.5 mg/ml Yatalase (TAKARA) in 0.8 M NaCl, and 10 mM phosphate buffer (pH 6.0)), which had been filtered through a 0.20-μm filter, was added to prepare a suspension. Shake culture was conducted at 30° C. and 83 rpm for 3 hours to digest the cell wall. Thus, protoplasts were prepared. After the reaction, undigested cells were filtered through sterilized Miracloth, and the filtrate was centrifuged at 4° C. and 2,500×g for 5 minutes to collect protoplasts. The collected protoplasts were washed with 10 ml of 0.8 M NaCl and recentrifuged at 4° C. and 2,500×g for 5 minutes, and the precipitated protoplasts were then collected. Solution I (Sol. I) (0.8 M NaCl, 10 mM $CaCl_2$, 10 mM Tris-HCl (pH 8.0)) was added to prepare a suspension while adjusting the protoplast density to $2 \times 10^8$ cells/ml, Solution II (Sol. II) (40% (w/v) PEG4000, 50 mM $CaCl_2$, 50 mM Tris-HCl (pH 8.0)) in an amount one-fifth the amount of the suspension was added, and the resultant was then thoroughly mixed. A protoplast solution (240 μl) was fractionated into a 15-ml tube, 5 μg to 20 μg of the DNA solution was added thereto, the resultant was thoroughly mixed, and the mixture was then allowed to stand in ice for 30 minutes. Subsequently, 1 ml of Sol. II was added thereto, the resultant was thoroughly mixed, and the mixture was allowed to stand at room temperature for 20 minutes. Sol. I (10 ml) was added thereto, the resultant was thoroughly mixed, and the mixture was centrifuged at room temperature and 2,500×g for 5 minutes, the supernatant was removed, and 300 µl of Sol. I was added thereto. The protoplasts were homogeneously suspended, the suspension was dispersed in CDE selection agar medium containing 0.8 M NaCl, and 5 ml of soft agar medium (0.6% (w/v) agar) of the same composition that had been heated to 55° C. was poured thereinto from the circumference thereof to overlay the soft agar medium to quickly and homogeneously suspend the protoplasts. Thereafter, culture was continued at 30° C. until colonies were formed.

5) Marker Recycling in *Aspergillus oryzae*

Marker recycling in *Aspergillus oryzae* was carried out in accordance with the method described below. Specifically, the adeA selection marker and Cre recombinase were located between the mutant loxP sequences (lox66 and lox71), Cre recombinase was allowed to express so as to cause a looping out between the loxP sequences, and the adeA selection marker was then removed. The expression of Cre recombinase can be induced with a xylose-inducible promoter. Specifically, the cells comprising the aforementioned system incorporated therein are inoculated into a medium comprising xylose as a carbon source, and Cre recombinase is expressed. Thus, the cells from which the adeA selection marker has been removed can be obtained. In cells from which the adeA selection marker has been removed, adenine-requiring properties are restored. Thus, a gene recombinant can be selected using the adeA selection marker again.

Figure 23:
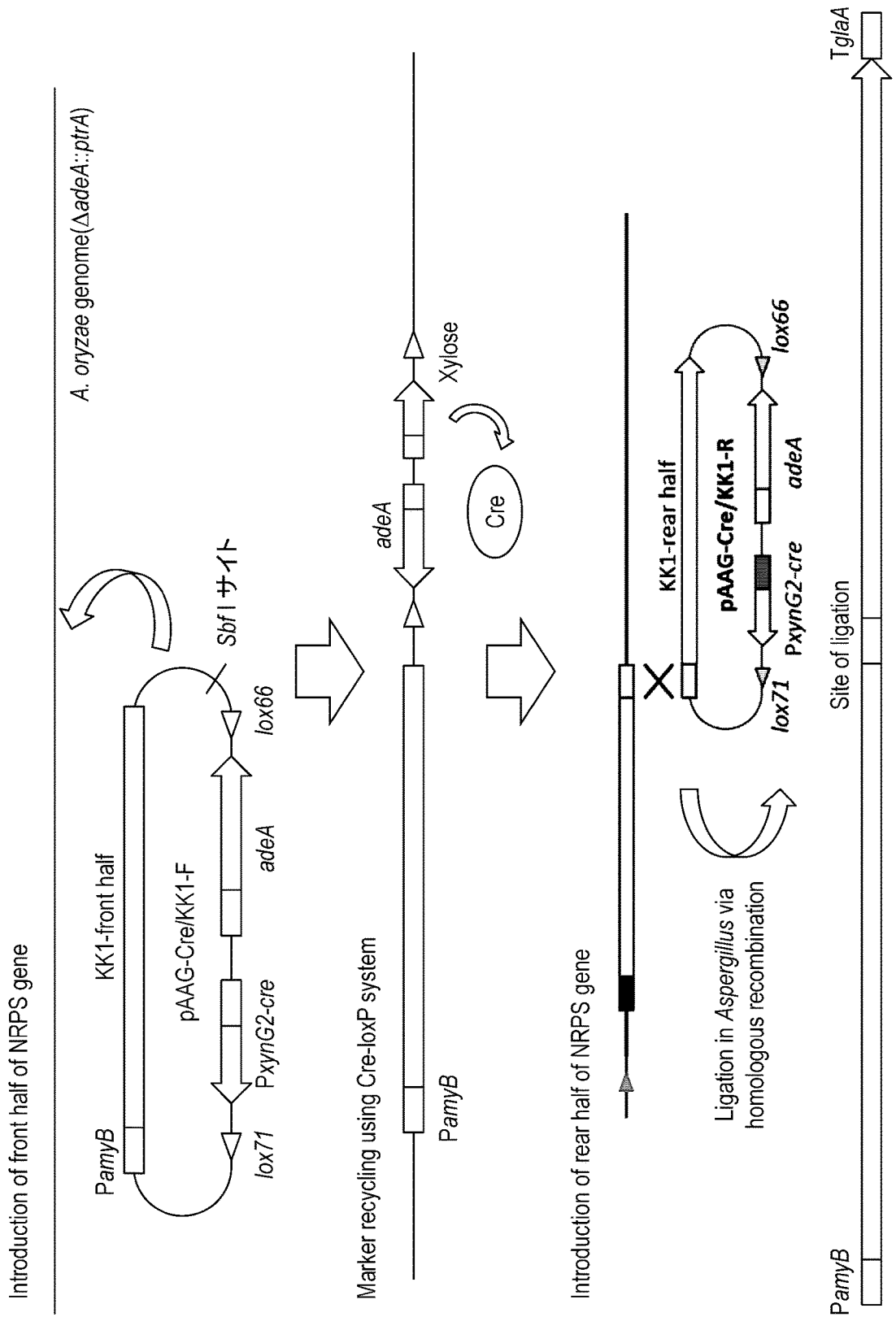
FIG. 23 schematically shows a scheme for introducing the front half portion and the rear half portion of the NRPS gene using the Cre-loxP system in two steps.

6) Reconstruction of KK-1 NRPS Gene in *Aspergillus oryzae* (FIG. 23)

FIG. 23 schematically shows a scheme for introducing a front half portion and a rear half portion of the NRPS gene with the use of the Cre-loxP system at two stages. As shown in FIG. 23, the pAAG-Cre/NRPSfh vector carrying the front half portion of the NRPS gene was first introduced into *Aspergillus oryzae*. Introduction of the vector into the resulting transformant was inspected via PCR. In order to introduce the rear half portion into the strain, Cre-loxP-mediated marker recycling was performed. In order to express Cre recombinase in the vector (regulated by the xynG2 promoter), cells were allowed to grow in a xylose-containing CDE medium supplemented with adenine (i.e., CDEAX medium). Among the grown cells, reddish colonies indicating deletion of the adeA gene as a marker were selected. The selected colonies were subjected to nuclear purification to confirm that such cells could not grow in an adenine-free medium.

In order to introduce the rear half portion of NRPS into the marker-recycled strain, subsequently, the strain was subjected to transformation by introducing pAAG-Cre/NRPSrh. Among the auxotrophy-restored strains, strains in which the front and rear half portions had been connected were selected via PCR. DNAs were extracted from the final candidate strains, and whether or not the full-length sequence had been connected was examined via PCR. As a result, introduction of the full-length NRPS gene was confirmed.

Subsequently, whether or not the site of connection had been correctly recombined via homologous recombination was inspected by determining the sequence of the site of connection. As a result, no mutations or shifts were observed at the site of connection. These results demonstrate that the NRPS gene was correctly reconstructed in *Aspergillus oryzae*.

In order to introduce other genes in the cluster into the strain, Cre-loxP-mediated marker recycling was carried out. After restoration of adenine-requiring properties was confirmed, strains in which nuclear purification had been observed were designated as parent strains subjected to all instances of gene introduction below.

7) High-Level Expression of Essential Genes in the Cluster in *Aspergillus oryzae*

The pATR0203, pATR678, and pATR09OMT plasmids carrying genes in the cluster prepared in 3) above were successively and repeatedly subjected to marker recycling and introduced into *Aspergillus oryzae*. In the strains into which all plasmids had been introduced, however, deletion of the TRAF01000068000009 gene was observed. Also, partial deletion of the NRPS gene from the strain of this lineage was found. In addition, the presence or absence of gene deletion was inspected in strains of other lineages. As a result, gene deletion was observed repeatedly. These results indicate that a looping out may have occurred between adjacent promoter sequences at the time of marker recycling or transformation. In order to redesign a strategy of introduction and minimize the number of procedures of marker recycling or transformation, as shown in FIG. 24, 3 types of vectors carrying 7 genes were to be simultaneously introduced. As a result, strains in which introduction of all the genes had been confirmed were obtained.

Figure 25:
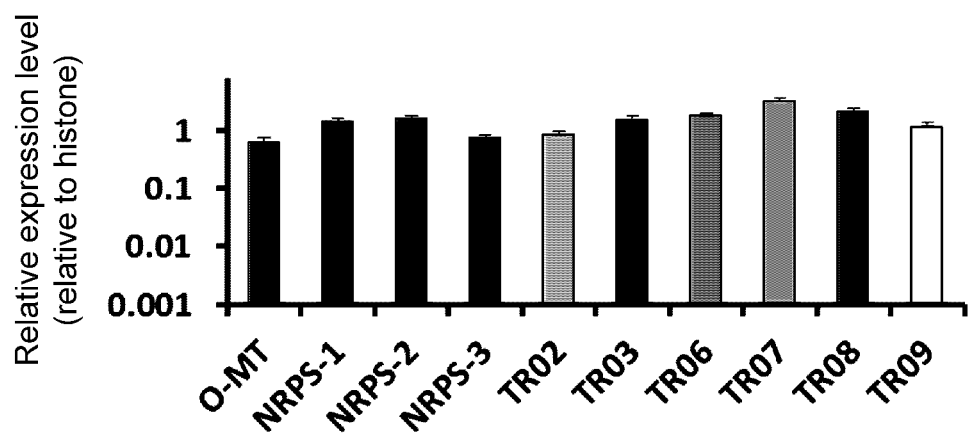
FIG. 25 shows a characteristic diagram demonstrating the results of analysis via quantitative real-time PCR of the expression levels of the introduced genes in *Aspergillus oryzae* into which the KK-1 biosynthetic gene cluster had been introduced.

8) Transcription Analysis (FIG. 25)

Subsequently, the transformed *Aspergillus oryzae* into which the KK-1 biosynthetic gene cluster prepared in the manner described above had been introduced was analyzed in respect of expression of the genes introduced. After the cells were shake-cultured in YMP medium (the medium containing 2% maltose as a promoter-derived substrate) for 24 hours, the culture solution was filtered through Miracloth to collect the cells. The cells were immediately frozen with liquid nitrogen and quickly disrupted in liquid nitrogen with the use of a pestle in a mortar. The disrupted cells were transferred to a 1.5-ml Eppendorf tube and RNA was extracted in accordance with the protocol of the RNeasy Plant Mini Kit (QIAGEN). In order to avoid DNA inclusion, DNase treatment was also carried out in an ion column in accordance with the protocol included in the kit. In the end, total RNA was obtained through elution with 50 µl of RNase-free water two times.

Subsequently, cDNA was synthesized from the obtained total RNA. cDNA was synthesized using the high-capacity cDNA Reverse Transcription Kit (Applied Biosystem) by the method in accordance with the protocol included in the kit. Total RNA in an amount equivalent to 4 µg was used for the 40-µl reaction system to synthesize cDNA from mRNA. The reverse transcription reaction was carried out by preincubation at 25° C. for 10 minutes, and reverse transcription at 37° C. for 120 minutes, followed by heating at 85° C. for 5 seconds to terminate the reaction. cDNA obtained was stored at −20° C. before use.

Quantitative real-time PCR (qRT-PCR) was carried out with the use of THUNDERBIRD SYBR qRCR Mix (TOYOBO) in a 20-µl reaction system in accordance with the instructions. The mixed solution contains 400 ng-equivalent cDNA synthesized in reverse transcription. Each sample was subjected to measurement three times. PCR was carried out with the use of the MiniOpticon real-time PCR detection system (BioRad) and analytical software (BioRad CFX Manager 2.1). The relative expression intensity was determined as a ratio of the expression level of each gene relative to the expression level of the internal standard gene (histone H2B) measured under the same conditions.

The sets of primers used are shown below.

```
For TRAF01000135000001 gene
NRPS-RT1-F:
                              (SEQ ID NO: 132)
GACGCCACGAACGCATAGAC

NRPS-RT1-R:
                              (SEQ ID NO: 133)
TTCCCAGAGAGGTAGATCGAC

For TRAF01000135000001 gene
NRPS-RT2-F:
                              (SEQ ID NO: 134)
GACCGTTACAGCGAGTTCAG

NRPS-RT2-R:
                              (SEQ ID NO: 135)
CTGAATTCCTCGCACAGAAC

For TRAF01000135000001 gene
NRPS-RT3-F:
                              (SEQ ID NO: 136)
GAAGTTGAGAACGCCATGCT

NRPS-RT3-R:
                              (SEQ ID NO: 137)
GATGCGAGATGGGAGCATGT

For TRAF01000068000002 gene
TR02-RT-F:
                              (SEQ ID NO: 138)
GCCCTACTAGATCTGACCAC

TR02-RT-R:
                              (SEQ ID NO: 139)
GCTGTTACCTTTTCCTCCTC

For TRAF01000068000003 gene
TR03-RT-F:
                              (SEQ ID NO: 140)
AGATCTTAGACGAGCTGCTC

TR03-RT-R:
                              (SEQ ID NO: 141)
AAACAGTCGCGAAGCGACTG

For TRAF01000068000006 gene
TR06-RT-F:
                              (SEQ ID NO: 142)
ACGTCCAGGAAGCTATCGAG

TR06-RT-R:
                              (SEQ ID NO: 143)
ATTGAGGGCCTGGGCTTGAC

For TRAF01000068000007 gene
TR07-RT-F:
                              (SEQ ID NO: 144)
GTGATGAAGGCGCTGAAGAG

TR07-RT-R:
                              (SEQ ID NO: 145)
CTCCGCAATTTCCGTGAGTG

For TRAF01000068000008 gene
TR08-RT-F:
                              (SEQ ID NO: 146)
TGACTCTATGGTGGATGGTG

TR08-RT-R:
                              (SEQ ID NO: 147)
CCTTGTTCAAGTGCCAGTAG

For TRAF01000068000009 gene
TR09-RT-F:
                              (SEQ ID NO: 148)
GATTCCGTCACGAGACACTG

TR09-RT-R:
                              (SEQ ID NO: 149)
AGTATCCCATCGGGCAACAG

For TRAF01000135000002 gene
OMT-RT-F:
                              (SEQ ID NO: 150)
ACGTTCAAGACCTTCCAG

OMT-RT-R:
                              (SEQ ID NO: 151)
GTTCCGGATGATTTGCAG
```

FIG. 25 shows the results of quantitative real-time PCR. In FIG. 25, O-MT indicates the TRAF01000135000002 gene, NRPS-1 to NRPS-3 each indicate the TRAF01000135000001 gene (the NRPS gene of Example 1), TR02 indicates the TRAF01000068000002 gene, TR03 indicates the TRAF01000068000003 gene, TR06 indicates the TRAF01000068000006 gene, TR07 indicates the TRAF01000068000007 gene, TR08 indicates the TRAF01000068000008 gene, and TR09 indicates the TRAF01000068000009 gene. As shown in FIG. 25, the expression level of all the introduced genes was equivalent to that of histone, and high-level expression of all the genes necessary for KK-1 biosynthesis was achieved in *Aspergillus oryzae* into which the gene cluster had been introduced.

9) Evaluation of KK-1 Productivity

Transformed *Aspergillus oryzae* into which the KK-1 biosynthetic gene cluster prepared in the manner described above had been introduced was evaluated in terms of KK-1 productivity.

Transformed *Aspergillus oryzae* prepared in this example is designed to be capable of regulating all the introduced genes with the PamyB promoter. When maltose is used as a carbon source, accordingly, all the genes can be induced to express. At the outset, a conidiospore suspension of the transformed *Aspergillus oryzae* prepared in this example was inoculated into 100-ml of YPM (2% maltose) or CM (2% maltose) medium, and shake culture was performed at 26° C. and 140 rpm for 5 days. Subsequently, the cultured cells and the culture solution were extracted with acetone/ethyl acetate, and the extract was solidified to dryness via condensation. The resultant was dissolved in acetonitrile and then subjected to LC/MS analysis. The conditions for LC/MS analysis were in accordance with the conditions for evaluation of KK-1 production in *Curvularia* sp. Also, the antibacterial activity of the extract was evaluated in terms of the growth inhibitory effects on gray mold as the target of evaluation in terms of antibacterial activity. At the outset, the extract was allowed to impregnate the paper disc (thin, φ6 mm), the paper disc and the mycelial threads of gray mold (*Botrytis cinerea*) cut with agar medium were placed on CM agar medium, and dual culture was carried out. Subsequently, antibacterial activity was evaluated on the basis of an extent of gray mold colony extension toward the paper disc.

FIG. 26 shows the results. FIG. 26A shows the results of LC/MS analysis and FIG. 26B shows the results of antibacterial activity test. As shown in FIG. 26A, the peak completely consistent with the retention time and the molecular weight of the KK-1 sample was detected in the extract derived from the transformed *Aspergillus oryzae* prepared in this example. As shown in FIG. 26B, in addition, inhibitory activity on extension of gray mold mycelial threads was observed in the extract. The results described above demonstrate that the transformed *Aspergillus oryzae* prepared in this example results from introduction of the KK-1 biosynthetic gene cluster identified in *C. clavata* in a functional manner and that KK-1 heterologs can be produced.

The invention claimed is:

1. A method for producing a cyclic peptide compound, the method comprising:
   a step of culturing a transformant transformed with a gene, wherein the gene is involved in the production of the cyclic peptide compound in the transformant; and
   a step of collecting the cyclic peptide compound from the cultured transformant and/or culture solution,
   wherein the gene encodes a nonribosomal peptide synthetase (NRPS) having nonribosomal peptide synthase activity comprising, successively from the N terminus, the modules described below:
   a first module comprising successively from the N terminus a first adenylation domain comprising the amino acid sequence as shown in SEQ ID NO: 1 or an amino acid sequence having 90% or higher identity to the amino acid sequence as shown in SEQ ID NO: 1 and a first peptidyl carrier protein domain comprising the amino acid sequence as shown in SEQ ID NO: 2 or an amino acid sequence having 90% or higher identity to the amino acid sequence as shown in SEQ ID NO: 2;
   a second module comprising successively from the N terminus a first condensation domain comprising the amino acid sequence as shown in SEQ ID NO: 3 or an amino acid sequence having 90% or higher identity to the amino acid sequence as shown in SEQ ID NO: 3, a second adenylation domain comprising the amino acid sequence as shown in SEQ ID NO: 4 or an amino acid sequence having 90% or higher identity to the amino acid sequence as shown in SEQ ID NO: 4, and a second peptidyl carrier protein domain comprising the amino acid sequence as shown in SEQ ID NO: 5 or an amino acid sequence having 90% or higher identity to the amino acid sequence as shown in SEQ ID NO: 5;
   a third module comprising successively from the N terminus a second condensation domain comprising the amino acid sequence as shown in SEQ ID NO: 6 or an amino acid sequence having 90% or higher identity to the amino acid sequence as shown in SEQ ID NO: 6, a third adenylation domain comprising the amino acid sequence as shown in SEQ ID NO: 7 or an amino acid sequence having 90% or higher identity to the amino acid sequence as shown in SEQ ID NO: 7, a first N-methyl transferase domain comprising the amino acid sequence as shown in SEQ ID NO: 8 or an amino acid sequence having 90% or higher identity to the amino acid sequence as shown in SEQ ID NO: 8, and a third peptidyl carrier protein domain comprising the amino acid sequence as shown in SEQ ID NO: 9 or an amino acid sequence having 90% or higher identity to the amino acid sequence as shown in SEQ ID NO: 9;
   a fourth module comprising successively from the N terminus a third condensation domain comprising the amino acid sequence as shown in SEQ ID NO: 10 or an amino acid sequence having 90% or higher identity to the amino acid sequence as shown in SEQ ID NO: 10, a fourth adenylation domain comprising the amino acid sequence as shown in SEQ ID NO: 11 or an amino acid sequence having 90% or higher identity to the amino acid sequence as shown in SEQ ID NO: 11, and a fourth peptidyl carrier protein domain comprising the amino acid sequence as shown in SEQ ID NO: 12 or an amino acid sequence having 90% or higher identity to the amino acid sequence as shown in SEQ ID NO: 12;

a fifth module comprising successively from the N terminus a fourth condensation domain comprising the amino acid sequence as shown in SEQ ID NO: 13 or an amino acid sequence having 90% or higher identity to the amino acid sequence as shown in SEQ ID NO: 13, a fifth adenylation domain comprising the amino acid sequence as shown in SEQ ID NO: 14 or an amino acid sequence having 90% or higher identity to the amino acid sequence as shown in SEQ ID NO: 14, a second N-methyl transferase domain comprising the amino acid sequence as shown in SEQ ID NO: 15 or an amino acid sequence having 90% or higher identity to the amino acid sequence as shown in SEQ ID NO: 15, and a fifth peptidyl carrier protein domain comprising the amino acid sequence as shown in SEQ ID NO: 16 or an amino acid sequence having 90% or higher identity to the amino acid sequence as shown in SEQ ID NO: 16;

a sixth module comprising successively from the N terminus a fifth condensation domain comprising the amino acid sequence as shown in SEQ ID NO: 17 or an amino acid sequence having 90% or higher identity to the amino acid sequence as shown in SEQ ID NO: 17, a sixth adenylation domain comprising the amino acid sequence as shown in SEQ ID NO: 18 or an amino acid sequence having 90% or higher identity to the amino acid sequence as shown in SEQ ID NO: 18, a third N-methyl transferase domain comprising the amino acid sequence as shown in SEQ ID NO: 19 or an amino acid sequence having 90% or higher identity to the amino acid sequence as shown in SEQ ID NO: 19, and a sixth peptidyl carrier protein domain comprising the amino acid sequence as shown in SEQ ID NO: 20 or an amino acid sequence having 90% or higher identity to the amino acid sequence as shown in SEQ ID NO: 20;

a seventh module comprising successively from the N terminus a sixth condensation domain comprising the amino acid sequence as shown in SEQ ID NO: 21 or an amino acid sequence having 90% or higher identity to the amino acid sequence as shown in SEQ ID NO: 21, a seventh adenylation domain comprising the amino acid sequence as shown in SEQ ID NO: 22 or an amino acid sequence having 90% or higher identity to the amino acid sequence as shown in SEQ ID NO: 22, a fourth N-methyl transferase domain comprising the amino acid sequence as shown in SEQ ID NO: 23 or an amino acid sequence having 90% or higher identity to the amino acid sequence as shown in SEQ ID NO: 23, and a seventh peptidyl carrier protein domain comprising the amino acid sequence as shown in SEQ ID NO: 24 or an amino acid sequence having 90% or higher identity to the amino acid sequence as shown in SEQ ID NO: 24;

an eighth module comprising successively from the N terminus a seventh condensation domain comprising the amino acid sequence as shown in SEQ ID NO: 25 or an amino acid sequence having 90% or higher identity to the amino acid sequence as shown in SEQ ID NO: 25, an eighth adenylation domain comprising the amino acid sequence as shown in SEQ ID NO: 26 or an amino acid sequence having 90% or higher identity to the amino acid sequence as shown in SEQ ID NO: 26, and an eighth peptidyl carrier protein domain comprising the amino acid sequence as shown in SEQ ID NO: 27 or an amino acid sequence having 90% or higher identity to the amino acid sequence as shown in SEQ ID NO: 27;

a ninth module comprising successively from the N terminus an eighth condensation domain comprising the amino acid sequence as shown in SEQ ID NO: 28 or an amino acid sequence having 90% or higher identity to the amino acid sequence as shown in SEQ ID NO: 28, a ninth adenylation domain comprising the amino acid sequence as shown in SEQ ID NO: 29 or an amino acid sequence having 90% or higher identity to the amino acid sequence as shown in SEQ ID NO: 29, a fifth N-methyl transferase domain comprising the amino acid sequence as shown in SEQ ID NO: 30 or an amino acid sequence having 90% or higher identity to the amino acid sequence as shown in SEQ ID NO: 30, and a ninth peptidyl carrier protein domain comprising the amino acid sequence as shown in SEQ ID NO: 31 or an amino acid sequence having 90% or higher identity to the amino acid sequence as shown in SEQ ID NO: 31; and a tenth module comprising successively from the N terminus a ninth condensation domain comprising the amino acid sequence as shown in SEQ ID NO: 32 or an amino acid sequence having 90% or higher identity to the amino acid sequence as shown in SEQ ID NO: 32, a tenth adenylation domain comprising the amino acid sequence as shown in SEQ ID NO: 33 or an amino acid sequence having 90% or higher identity to the amino acid sequence as shown in SEQ ID NO: 33, a tenth peptidyl carrier protein domain comprising the amino acid sequence as shown in SEQ ID NO: 34 or an amino acid sequence having 90% or higher identity to the amino acid sequence as shown in SEQ ID NO: 34, and a tenth condensation domain comprising the amino acid sequence as shown in SEQ ID NO: 35 or an amino acid sequence having 90% or higher identity to the amino acid sequence as shown in SEQ ID NO: 35.

2. The method for producing a cyclic peptide compound according to claim 1, wherein the transformant is further transformed with the following genes [1], [2], [3], [6] and [7] among genes [1] to [7] below:

[1] a gene encoding a protein comprising the amino acid sequence as shown in SEQ ID NO: 41 or an amino acid sequence having 90% or higher identity to the amino acid sequence as shown in SEQ ID NO: 41;

[2] a gene encoding a protein comprising the amino acid sequence as shown in SEQ ID NO: 43 or an amino acid sequence having 90% or higher identity to the amino acid sequence as shown in SEQ ID NO: 43;

[3] a gene encoding a protein comprising the amino acid sequence as shown in SEQ ID NO: 45 or an amino acid sequence having 90% or higher identity to the amino acid sequence as shown in SEQ ID NO: 45;

[4] a gene encoding a protein comprising the amino acid sequence as shown in SEQ ID NO: 47 or an amino acid sequence having 90% or higher identity to the amino acid sequence as shown in SEQ ID NO: 47;

[5] a gene encoding a protein comprising the amino acid sequence as shown in SEQ ID NO: 49 or an amino acid sequence having 90% or higher identity to the amino acid sequence as shown in SEQ ID NO: 49;

[6] a gene encoding a protein comprising the amino acid sequence as shown in SEQ ID NO: 51 or an amino acid sequence having 90% or higher identity to the amino acid sequence as shown in SEQ ID NO: 51; and

[7] a gene encoding a protein comprising the amino acid sequence as shown in SEQ ID NO: 53 or an amino acid sequence having 90% or higher identity to the amino acid sequence as shown in SEQ ID NO: 53.

3. The method for producing a cyclic peptide compound according to claim 1, wherein the transformant is an *Aspergillus oryzae* host.

4. The method for producing a cyclic peptide compound according to claim 1, wherein the NRPS is a protein (a) or (b) below:
  (a) a protein comprising the amino acid sequence as shown in SEQ ID NO: 37;
  (b) a protein comprising an amino acid sequence having 90% or higher identity to the amino acid sequence as shown in SEQ ID NO: 37 and having a nonribosomal peptide synthesizing activity.

5. The method for producing a cyclic peptide compound according to claim 2, wherein the transformant is further transformed with genes [4] and [5] among genes [1] to [7] of claim 2.

6. The method for producing a cyclic peptide compound according to claim 1, wherein the transformant is further transformed with genes [1], [2], [3], [6] and [7] among genes [1] to [7] below:
  [1] a gene encoding a protein comprising the amino acid sequence as shown in SEQ ID NO: 41;
  [2] a gene encoding a protein comprising the amino acid sequence as shown in SEQ ID NO: 43;
  [3] a gene encoding a protein comprising the amino acid sequence as shown in SEQ ID NO: 45;
  [4] a gene encoding a protein comprising the amino acid sequence as shown in SEQ ID NO: 47;
  [5] a gene encoding a protein comprising the amino acid sequence as shown in SEQ ID NO: 49;
  [6] a gene encoding a protein comprising the amino acid sequence as shown in SEQ ID NO: 51; and
  [7] a gene encoding a protein comprising the amino acid sequence as shown in SEQ ID NO: 53.

7. The method for producing a cyclic peptide compound according to claim 6, wherein the transformant is further transformed with genes [4] and [5] among genes [1] to [7] of claim 6.

8. A method for producing a cyclic peptide compound, the method comprising:
  a step of culturing a transformant transformed with a gene being involved in the production of the cyclic peptide compound in the transformant; and
  a step of collecting the cyclic peptide compound from the cultured transformant and/or culture solution,
  wherein the gene encodes a nonribosomal peptide synthetase (NRPS); and
  wherein the NRPS is
  a protein comprising the amino acid sequence as shown in SEQ ID NO: 37.

9. A method for producing a cyclic peptide compound, the method comprising:
  a step of culturing a transformant transformed with a gene being involved in the production of the cyclic peptide compound in the transformant; and
  a step of collecting the cyclic peptide compound from the cultured transformant and/or culture solution,
  wherein the gene encodes a nonribosomal peptide synthetase (NRPS); and
  wherein the NRPS is
  a protein comprising an amino acid sequence having 90% or higher identity to the amino acid sequence as shown in SEQ ID NO: 37 and having a nonribosomal peptide synthesizing activity.

* * * * *